(12) United States Patent
Shoda et al.

(10) Patent No.: US 7,470,807 B2
(45) Date of Patent: *Dec. 30, 2008

(54) SUBSTITUTED ARYLALKANOIC ACID DERIVATIVES AND USE THEREOF

(75) Inventors: Motoshi Shoda, Mishima (JP); Hiroshi Kuriyama, Fuji (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/568,185

(22) PCT Filed: Aug. 13, 2004

(86) PCT No.: PCT/JP2004/011952

§ 371 (c)(1),
(2), (4) Date: Jan. 22, 2007

(87) PCT Pub. No.: WO2005/016862

PCT Pub. Date: Feb. 24, 2005

(65) Prior Publication Data

US 2007/0213333 A1     Sep. 13, 2007

Related U.S. Application Data

(60) Provisional application No. 60/495,734, filed on Aug. 18, 2003.

(30) Foreign Application Priority Data

Aug. 14, 2003   (JP)   ............................. 2003-293590

(51) Int. Cl.
*C07C 69/76* (2006.01)
*C07C 62/00* (2006.01)
*C07C 233/00* (2006.01)
(52) U.S. Cl. ...................... 560/56; 562/466; 564/172
(58) Field of Classification Search .............. 560/56; 562/466; 564/172
See application file for complete search history.

(56) References Cited

U.S. PATENT DOCUMENTS

| | | | |
|---|---|---|---|
| 3,816,443 A | 6/1974 | Dorn, Jr. | |
| 4,873,259 A | 10/1989 | Summers, Jr. et al. | |
| 5,136,090 A | 8/1992 | Suzuki et al. | |
| 5,155,259 A | 10/1992 | Suzuki et al. | |
| 5,232,948 A | 8/1993 | Huang et al. | |
| 5,391,817 A | 2/1995 | Springer et al. | |
| 5,462,954 A | 10/1995 | Baker et al. | |
| 5,482,941 A | 1/1996 | Terrett | |
| 5,994,379 A | 11/1999 | Bayly et al. | |
| 6,069,156 A | 5/2000 | Oku et al. | |
| 6,147,100 A | 11/2000 | Seno et al. | |
| 6,200,980 B1 | 3/2001 | Piazza et al. | |
| 6,261,840 B1 * | 7/2001 | Cowsert et al. | ............ 435/375 |
| 6,376,546 B1 | 4/2002 | Shoda et al. | |
| 6,602,857 B1 * | 8/2003 | Cowsert et al. | ............... 514/44 |
| 6,867,320 B2 * | 3/2005 | Shoda et al. | ................. 560/56 |
| 2003/0083361 A1 | 5/2003 | Luengo et al. | |
| 2004/0044258 A1 | 3/2004 | Shoda et al. | |
| 2005/0032787 A1 | 2/2005 | Giannessi et al. | |

FOREIGN PATENT DOCUMENTS

| | | |
|---|---|---|
| CA | 2061538 | 8/1993 |
| DE | 2046992 A1 | 3/1972 |
| EP | 0 486 022 A2 | 5/1992 |
| GB | 1379526 A | 1/1975 |
| JP | 39-6668 B1 | 5/1964 |
| JP | 50-58087 A | 5/1975 |
| WO | WO-93/07149 | 4/1993 |
| WO | WO-93/12095 A | 6/1993 |
| WO | WO-95/17183 | 6/1995 |

(Continued)

OTHER PUBLICATIONS

Tamura Y. et al., J. Med. Chem., 1977, vol. 20, No. 5, pp. 709-714.

(Continued)

*Primary Examiner*—Rei-tsang Shiao
*Assistant Examiner*—Susannah Chung
(74) *Attorney, Agent, or Firm*—Birch, Stewart, Kolasch & Birch, LLP

(57) ABSTRACT

A compound represented by the formula (I):

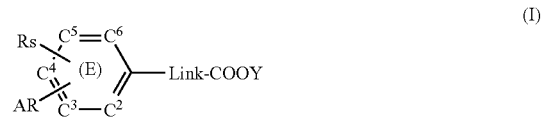

[In the formula, Link represents a saturated or unsaturated straight hydrocarbon chain having 1 to 3 carbon atoms, $C^2$ to $C^6$ in the aromatic ring (E) independently represent a ring-constituting carbon atom, one of the ring-constituting carbon atoms may be replaced with V, V represents nitrogen atom, or carbon atom substituted with Zx, Zx represents a saturated alkyl group having 1 to 4 carbon atoms and the like, Rs represents -D-Rx etc., D represents a single bond, oxygen atom and the like, Rx represents a saturated alkyl group having 3 to 8 carbon atoms and the like, AR represents a partially unsaturated or completely unsaturated condensed bicyclic carbon ring or a heterocyclic ring, and Y represents hydrogen atom, a lower alkyl group having 1 to 4 carbon atoms and the like] or a salt thereof. A compound having prostaglandin production-suppressing action and leukotriene production-suppressing action is provided.

36 Claims, No Drawings

FOREIGN PATENT DOCUMENTS

| | | |
|---|---|---|
| WO | WO-96/32379 A1 | 10/1996 |
| WO | WO-00/35886 | 6/2000 |
| WO | WO-01/39773 A1 | 6/2001 |
| WO | WO-01/53268 A2 | 7/2001 |
| WO | WO-01/55111 A1 | 8/2001 |
| WO | WO-02/28853 A1 | 4/2002 |
| WO | WO-03/070686 A1 | 8/2003 |
| WO | WO-03/70686 A1 | 8/2003 |

OTHER PUBLICATIONS

N. P. Buu-Hoi et al., "Acides arylacethydroxamiques anti-inflammatoires et analgesiques", Chimica Therapeutica, Societe d'etudes de chimie therapeutique, vol. 2, No. 1, (1967), pp. 39-48.

Tamura Y. et al., J. Med Chem., 1977, vol. 20, No. 5, pp. 709-714.

* cited by examiner

SUBSTITUTED ARYLALKANOIC ACID DERIVATIVES AND USE THEREOF

This National Phase PCT application claims priority under 35 U.S.C. 119(e) on U.S. Provisional Application No(s). 60/495,734 filed on Aug. 18, 2003 and under 35 U.S.C. 119(a) on Patent Application No(s). 2003-293590 filed in Japan on Aug. 14, 2003, all of which are hereby incorporated by reference.

FIELD OF THE INVENTION

The present invention relates to a novel substituted arylalkanoic acid derivative. More specifically, the present invention relates to a substituted arylalkanoic acid derivative having an action as a medicament and a synthetic intermediate of said compound.

BACKGROUND ART

Various kinds of prostaglandins and various kinds of leukotrienes are produced in the bodies of mammals in response to variety of stimuli such as inflammatory stimuli and physical stimuli.

Both of prostaglandins and leukotrienes are metabolites of arachidonic acid, and they are physiologically active substances referred to as lipid mediators, and they cause various physiological responses of mammals by binding to receptors expressed on surfaces of various cells or in the cells.

Arachidonic acid is produced from a phospholipid as a substrate, such as phosphatidylcholine which is a cell membrane component, with the aid of an enzymatic activity of phospholipase $A_2$ ($PLA_2$).

Arachidonic acid produced by the action of $PLA_2$ is converted into prostaglandin (PG) $H_2$ with the aid of an enzymatic activity of constitutive type cyclooxygenase (COX) 1 or inducible type COX-2, and further converted into $PGE_2$, $PGD_2$, $PGF_2\alpha$, $PGI_2$, thromboxane (TX) $A_2$ and the like with the aid of each synthetic enzyme. Further, arachidonic acid is also metabolized by the action of 5-lipoxygenase (5-LO) and thereby converted to leukotriene (LT) $A_4$, and further converted to $LTB_4$, $LTC_4$, $LTD_4$, $LTE_4$ and the like by the enzymatic activities of $LTA_4$ hydrolase, $LTC_4$ synthase, glutathione S-transferase and the like [Goodman & Gilman, Pharmacological Basis of Therapeutics, 9th edition, p. 801, 1999 (Hirokawa Shoten); Funk, C. D., SCIENCE, vol. 294, p. 1871, 2001].

Prostaglandins bind to each specific receptor to cause inflammatory reactions such as fervescence, enhancement of vascular permeability, vasodilation, swelling and pain, bronchial smooth muscle contraction, platelet aggregation, tumor cell proliferation, enhancement of bone resorption, nerve cell degeneration and the like, and thus play important roles in expression of symptoms or pathological formation for various diseases.

Leukotrienes are physiologically active substances which bind to each specific receptor to cause inflammatory reactions such as excessive accumulation of leucocytes and enhancement of vascular permeability, smooth muscle contraction, mucus secretion, proliferation of tumor cells and the like, and thus play important roles in expression of symptoms or pathological formation for various diseases.

Although inflammatory reactions themselves are essential reactions for living bodies to survive when they face pathogenic substances and affections, they are sometimes excessively caused or continue without any reason for providing evident benefit under certain situations or in certain diseases [Goodman & Gilman, Pharmacological Basis of Therapeutics, 9th edition, p. 827, 1999 (Hirokawa Shoten)]. The condition of living body referred to in this specification wherein an acute or chronic inflammatory reaction is observed means a condition that an excessive or unbeneficial acute or temporary inflammatory reaction or chronic and persistent inflammatory reaction is caused. Further, an inflammatory reaction refers to a series of events caused by stimuli, for example, physical hazards such as heat, infective substances, ischemia, antigen/antibody reaction and the like, and it is accompanied by flare, swelling, hyperalgesia, algesic onset and the like as well-known macroscopic clinical symptoms. It is known that, as histological mechanisms for these reactions, vasodilation, enhancement of vascular permeability, infiltration of leucocytes and phagocytes, histological decomposition and fibrosing and the like are caused [Goodman & Gilman, Pharmacological Basis of Therapeutics, 9th edition, p. 827, 1999 (Hirokawa Shoten)]. It is known that many of these histological reactions are caused by prostaglandins and/or leukotrienes, and prostaglandins and/or leukotrienes plays important roles in inflammatory reactions.

For example, it was reported that, in a pathological tissue of rheumatoid arthritis, which is an autoimmune and chronic inflammatory disease, expression of COX-2 and production of $PGE_2$ and $TXA_2$ as well as expression of 5-LO and production of $LTB_4$ were observed (Bonnet et al., Prostaglandins, 1995, vol. 50, p. 127), and in a mouse deficient in FLAP, which is a protein required for activation of 5-LO, symptom of collagen-induced arthritis, which is a pathological model of chronic rheumatoid arthritis, was milder compared with that in a wild-type mouse (Griffiths et al., J. Exp. Med., 1997, vol. 185, p. 1123), and thus it has been suggested that prostaglandins and leukotrienes play important roles in the pathological formation of chronic rheumatoid arthritis.

It was reported that, in a pathological tissue of bronchial asthma, one of chronic allergic diseases, excessive production of $PGD_2$ and $TXA_2$ as well as excessive production of $LTC_4$ and $LTD_4$ were observed (Wenzel et al., Am Rev. Respir. Dis., 1990, vol. 142, p. 112), and an airway hypersensitive reaction, which is a pathological model of bronchial asthma, was unlikely to occur in a $PGD_2$ receptor-deficient mouse (Matsuoka et al., SCIENCE, vol. 287, p. 2013, 2000). Thus, it has been demonstrated that roles of prostaglandins and leukotrienes are important in bronchial asthma.

In a cerebral tissue after ischemic reperfusion, expression of COX-2 increased, and concentrations of $PGE_2$ and $TXA_2$ increased, whereas activity of 5-LO increased, and production amount of $LTC_4$ increased (Ohtsuki et al., Am. J. Physiol., 1995, vol. 268, p. 1249). Thus, it is known that prostaglandins and leukotrienes play important roles in formation of infarct that is accepted as an ischemic reperfusion injury.

It has been revealed that, in a pathological tissue of Alzheimer's disease, one of the diseases with neurodegeneration, the COX activity and 5-LO activity increased, prostaglandins and leukotrienes cause formation of the β-amyloid protein, one of the pathogenic substances of Alzheimer's disease, and further cause degeneration of nerve cells (Sugaya et al., Jpn. J. Pharmacol., 2000, vol. 82, p. 85), and thus it is believed that prostaglandins and leukotrienes play important roles in the formation of neurodegenerative diseases such as Alzheimer's disease.

Furthermore, for example, it was reported that, in a pathological tissue of colon cancer, COX and 5-LO were expressed, and amounts of production of prostaglandins and leukotrienes were increased (Dreyling et al., Biochim. Biophys. Acta., 1986, vol. 878, p. 184), and leukotriene caused increase in colon cancer cells (Qiao et al., Biochim. Biophys. Acta, 1995, vol. 1258, p. 215; Hong et al., Cancer Res., 1999, vol. 59, p. 2223). Thus, it is believed that prostaglandins and leukotrienes play important roles also in tissues of large bowel cancer.

Involvement of prostaglandins and/or leukotrienes in diseases and pathological conditions is not limited to those diseases exemplified above, and it has been demonstrated that prostaglandins and/or leukotrienes are involved in variety of conditions, various diseases, or various pathological conditions where acute or chronic inflammatory reactions are observed and their roles are important.

For the above reason, various prostaglandin production suppressors or leukotriene production suppressors are used as agents for prophylactic or therapeutic treatment of conditions, various diseases or pathological conditions where an acute or chronic inflammatory reaction is recognized. Various non-steroidal anti-inflammatory drugs (NSAIDS) as medicaments having a prostaglandin production-suppressing action are available and used as therapeutic agents for chronic rheumatoid arthritis and osteoarthritis, antiphlogistic-analgesic agents for injury and the like, prophylactic agents for cerebral infarction or myocardial infarction, prophylactic agents for colon polyposis and the like. However, the class of NSAIDS suppress only production of prostaglandins, and as a result, they increase amounts of production of leukotrienes, and exhibit side effects such as asthmatic attack and gastrointestinal injury as well as renal disturbance. Furthermore, a difference between an effective dose and a dose inducing the side effects is small in these NSAIDS, and no satisfactory agent is available from a viewpoint of therapeutic effect. A 5-LO inhibitor is available which is described in European Patent No. 279263 as a medicament having a leukotriene production-suppressing action, and the inhibitor is known as a prophylactic agent for asthma. However, since the agent causes side effects such as hepatic disorder, its dosage is limited, and the agent is not satisfactory also from a viewpoint of therapeutic effect. Since steroid agents suppress production of both of prostaglandins and leukotrienes, they are used as prophylactic agents or therapeutic agents for conditions of living bodies, various diseases and pathological conditions where various acute or chronic inflammatory reactions are observed. However, their actions are not limited to the lipid mediator production-suppressing action, and they exhibit severe side effects such as induction and exacerbation of infectious diseases due to the immunosuppression action, growth retardation due to normal cell antiproliferative activity, anetoderma and peptic ulcer. Therefore, their uses are limited.

Furthermore, for the above reasons, it is considered that compounds, that suppress the production of both of prostaglandins and leukotrienes and have reduced side effect, are effective as therapeutic agents or prophylactic agents for such conditions of living bodies, diseases or pathological conditions in mammals as described above, and methods of using such compounds together with medicaments available at present are more effective therapeutic or prophylactic methods. Therefore, development of compounds suppressing the production of both of prostaglandins and leukotrienes, and manufacture of pharmaceutical preparations thereof are strongly desired.

As compounds structurally similar to the compounds of the present invention, for example, biphenyl-5-alkanoic acid derivatives and use thereof are described in WO99/19291. However, the moiety of these compounds that corresponds to "AR" included in the formula (I) of the compounds of the present invention is phenyl group, and thus structural features of the above compounds are different. Further, biaryl phospholipase $A^2$ inhibitors are described in U.S. Pat. No. 5,391,817 [Japanese Patent Unexamined Publication (Kokai) No. 7-22399]. However, the moiety of these compounds that corresponds to "AR" included in the formula (I) of the compounds of the present invention is only defined to be phenyl group, and thus the structural features of the above compounds are different. Bicyclic heterocyclic compounds are described in WO00/35886 as protease inhibitors. However, the substituents of these compounds on the moiety that corresponds to "AR" included in the formula (I) of the compounds of the present invention are different, and further, the publication is completely silent about whether or not the compounds described in the above patent document have any prostaglandin production-suppressing action or leukotriene production-suppressing action.

[Patent document 1] WO99/19291
[Patent document 2] U.S. Pat. No. 5,391,817
[Patent document 3] WO00/35886

DISCLOSURE OF THE INVENTION

An object of the present invention is to provide a novel compound having superior prostaglandin production-suppressing action and leukotriene production-suppressing action. Another object of the present invention is to provide a compound for prophylactic and/or therapeutic treatment of various inflammatory diseases, autoimmune diseases, allergic diseases, pain and fibrosis in mammals caused by lipid mediators. A further object of the present invention is to provide a pharmaceutical composition containing such a compound. A still further object of the present invention is to provide an intermediate for the production of the compound. These objects and other objects as well as advantages of the present invention will be apparent for those skilled in the art from the following descriptions.

In order to achieve the aforementioned objects, the inventors of the present invention conducted various researches. As a result, they found that the substituted arylalkanoic acid derivatives represented by the following general formula, which are novel compounds, had superior prostaglandin production-suppressing action and leukotriene production-suppressing action, and thus accomplished the present invention.

The present invention is embodied by, for example, those described in the following (1) to (191).

(1) A compound represented by the formula (I):

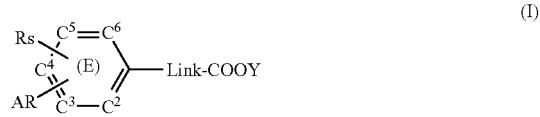

[In the formula, Link represents a saturated or unsaturated straight hydrocarbon chain having 1 to 3 carbon atoms.

$C^2$, $C^3$, $C^4$, $C^5$, and $C^6$ in the aromatic ring (E) independently represent a ring-constituting carbon atom. One of the ring-constituting carbon atoms to which Rs and AR do not bind may be replaced with V.

V represents nitrogen atom, or carbon atom substituted with Zx. Zx represents a linear or branched saturated alkyl group having 1 to 4 carbon atoms, fluorine atom, chlorine atom, bromine atom, nitro group, —$OR^9$, or —$N(Rn^1)(Rn^2)$. $R^9$ represents hydrogen atom, a lower alkyl group having 1 to 4 carbon atoms, or -$A^6$-Qp, wherein $A^6$ represents a single bond or methylene, Qp represents phenyl group, and the phenyl group may be substituted with one of $T^1$ or two or more of the same or different $T^1$. $T^1$ represents a linear or branched saturated alkyl group having 1 to 4 carbon atoms, hydroxyl group, fluorine atom, chlorine atom, bromine atom, trifluoromethyl group, nitro group, an alkoxy group having 1 to 4 carbon atoms, or a mono- or dialkylamino group having 1 to 4 carbon atoms. $Rn^1$ represents hydrogen atom or a linear or branched saturated alkyl group having 1 to 4 carbon atoms, $Rn^2$ has the same meaning as $Rn^1$, or represents —$COR^{23}$ or —$SO_2R^{24}$, or binds to $Rn^1$ to form a 3- to 6-membered ring together with the nitrogen atom to which they bind to form a saturated nitrogen-containing cycloalkyl group or morpholino group. $R^{23}$ represents hydrogen atom, a lower alkyl group having 1 to 4 carbon atoms, a lower alkoxy group having 1 to 4 carbon atoms, —O-$A^6$-Qp, or —$N(R^{25})(R^{26})$. $R^{25}$ represents hydrogen atom, or a linear or branched saturated alkyl group having 1 to 4 carbon atoms. $R^{26}$ has the same meaning as $R^{25}$, or binds to $R^{25}$ to form a 3- to 6-membered ring together with the nitrogen atom to which they bind to form a saturated nitrogen-containing cycloalkyl group or morpholino group. $R^{24}$ represents a lower alkyl group having 1 to 4 carbon atoms, amino group, or a mono- or dialkylamino group having 1 to 4 carbon atoms.

Rs represents -D-Rx or —N(Ry)(Rz).

D represents a single bond, oxygen atom, sulfur atom, —S(O)—, —S(O)$_2$—, or —C(O)—.

Rx represents a linear or branched saturated alkyl group having 3 to 8 carbon atoms, or represents Ra represented by the following formula:

$$R^1(CH_2)_k— \quad (Ra)$$

Rb represented by the following formula:

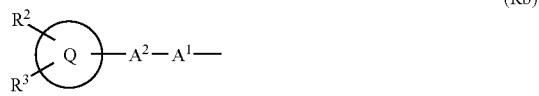

(Rb)

or Rc represented by the following formula:

(Rc)

k in Ra represents 0 or an integer of 1 to 3. $R^1$ represents a saturated cyclic alkyl group having 3 to 7 carbon atoms, or a condensed saturated cyclic alkyl group having 6 to 8 carbon atoms, and $R^1$ may be substituted with one of lower alkyl group having 1 to 4 carbon atoms or two or more of the same or different lower alkyl groups having 1 to 4 carbon atoms. Q in Rb represents a partially unsaturated or completely unsaturated monocyclic or condensed bicyclic carbon ring or a heterocyclic ring (q), and binds to $A^2$ at an arbitrary position. The heterocyclic ring (q) contains the same or different 1 to 4 ring-constituting heteroatoms selected from the group consisting of nitrogen atom, oxygen atom, and sulfur atom. $A^1$ represents a single bond or an alkylene (a) having 1 to 3 carbon atoms, and the alkylene (a) may be substituted with a lower alkyl group having 1 to 4 carbon atoms or phenyl group.

$A^2$ represents a single bond, oxygen atom, sulfur atom, —S(O)—, —S(O)$_2$—, or —N($R^4$)— (provided that when $A^2$ represents oxygen atom, sulfur atom, —S(O)—, —S(O)$_2$— or —N($R^4$)—, $A^1$ represents ethylene or trimethylene). $R^2$ and $R^3$ independently represent hydrogen atom, a linear or branched saturated alkyl group having 1 to 4 carbon atoms, oxo group, thioxo group, fluorine atom, chlorine atom, bromine atom, trifluoromethyl group, —$OR^5$, —$N(R^6)(R^{6'})$, —$NHCOR^7$, —$NHSO_2R^8$, or -$A^6$-Qa, or they bind to each other to represent methylenedioxy group. Qa represents a partially unsaturated or completely unsaturated monocyclic or condensed bicyclic carbon ring or a heterocyclic ring (qa), binds to $A^6$ at an arbitrary position on the ring, and may be substituted with one of $T^1$ or two or more of the same or different $T^1$. The heterocyclic ring (qa) contains the same or different 1 to 4 ring-constituting heteroatoms selected from the group consisting of nitrogen atom, oxygen atom, and sulfur atom. $R^4$ and $R^6$ independently represent hydrogen atom or a lower alkyl group having 1 to 4 carbon atoms. $R^5$ and $R^7$ independently represent hydrogen atom, a lower alkyl group having 1 to 4 carbon atoms, or -$A^6$-Qa. $R^8$ represents a lower alkyl group having 1 to 4 carbon atoms. $R^{6'}$ has the same meaning as $R^6$, or binds to $R^6$ to form a 3- to 6-membered ring together with the nitrogen atom to which they bind to represent a saturated nitrogen-containing cycloalkyl group or morpholino group. p in Rc represents an integer of 2 to 4. $A^4$ represents a single bond, methylene, or ethylene. $A^5$ represents —C(O)—, —C(S)—, or —S(O)$_2$—. Rd represents hydrogen atom, an alkyl group having 1 to 8 carbon atoms, or Qa. Re represents an alkyl group having 1 to 8 carbon atoms, -$A^6$-Qa, —$(CH_2)_iR^{14}$, —$OR^{28}$, —$SR^{28}$, or —$N(R^{29})(R^{30})$. i represents an integer of 1 to 3, $R^{14}$ represents hydroxyl group, an alkoxy group having 1 to 4 carbon atoms, carboxyl group, or an N,N-dialkylcarbamoyl group having 1 to 4 carbon atoms. $R^{28}$ represents an alkyl group having 1 to 8 carbon atoms, or -$A^6$-Qa. $R^{29}$ represents an alkyl group having 1 to 8 carbon atoms, an alkoxycarbonyl group having 1 to 4 carbon atoms, or -$A^6$-Qa. $R^{30}$ represents hydrogen atom or a lower alkyl group having 1 to 4 carbon atoms, or binds to $R^{29}$ to form a 3- to 6-membered ring together with the nitrogen atom to which they bind to represent a saturated nitrogen-containing cycloalkyl group or morpholino group.

Rz has the same meaning as Rx, or Rz represents methyl group, ethyl group, or -$A^5$-Re. Ry represents hydrogen atom, an alkyl group having 1 to 8 carbon atoms, or -$A^6$-Qp, or Ry may bind to Rz to form, together with a nitrogen atom to which they bind, a saturated or unsaturated 3 to 7-membered nitrogen-containing cyclic group, wherein said nitrogen-containing cyclic group may optionally be substituted with one or two lower alkyl groups having 1 to 4 carbon atoms wherein said two alkyl groups may be the same or different.

AR represents a partially unsaturated or completely unsaturated condensed bicyclic carbon ring or a heterocyclic ring (ar), and may be substituted with one of Xa or two or more of the same or different Xa. The heterocyclic ring (ar) contains the same or different 1 to 4 ring-constituting heteroatoms selected from the group consisting of nitrogen atom, oxygen atom, and sulfur atom. Xa represents a linear or branched saturated alkyl group having 1 to 4 carbon atoms, a saturated cyclic alkyl group having 3 to 7 carbon atoms, oxo group, thioxo group, fluorine atom, chlorine atom, trifluoromethyl group, —$(CH_2)_iR^{14}$, —$OR^{10}$, —$N(R^{11})(R^{12})$, —$SO_2R^{13}$, or —$COR^{27}$. $R^{10}$ represents hydrogen atom, a lower alkyl group having 1 to 4 carbon atoms, or —$(CH_2)_iR^{14}$. $R^{11}$ represents hydrogen atom or a lower alkyl group having 1 to 4 carbon atoms. $R^{12}$ represents hydrogen atom, a lower alkyl group having 1 to 4 carbon atoms, a hydroxyalkyl group having 2 to 4 carbon atoms, —$COR^{15}$, or —$SO_2R^{16}$, or binds to $R^{11}$ to form a 3- to 6-membered ring together with the nitrogen atom to which they bind to represent a saturated nitrogen-containing cycloalkyl group or morpholino group. $R^{15}$ represents a lower alkyl group having 1 to 4 carbon atoms, a hydroxyalkyl group having 2 to 4 carbon atoms, amino group, a mono- or dialkylamino group having 1 to 4 carbon atoms, or -$A^6$-Qa. $R^{13}$ and $R^{16}$ independently represent a lower alkyl group having 1 to 4 carbon atoms, amino group, or a mono- or dialkylamino group having 1 to 4 carbon atoms. $R^{27}$ represents hydrogen atom, hydroxyl group, an alkoxy group having 1 to 4 carbon atoms, a lower alkyl group having 1 to 4 carbon atoms, amino group, or a mono- or dialkylamino group having 1 to 4 carbon atoms.

Y represents hydrogen atom, a lower alkyl group having 1 to 4 carbon atoms, —$(CH_2)_mN(R^{18})(R^{19})$, or —$C(R^{20})_2OC(O)A^3R^{21}$. Symbol m represents an integer of 2 or 3. $R^{18}$ is the same as $R^{19}$, or binds to $R^{19}$ to form a 3- to 6-membered ring together with the nitrogen atom to which they bind to represent a saturated nitrogen-containing cycloalkyl group or morpholino group. $R^{19}$ represents methyl group, ethyl group, or propyl group. $R^{20}$ represents hydrogen atom, methyl group, ethyl group, or propyl group. $R^{21}$ represents a lower alkyl group having 1 to 4 carbon atoms, a cyclic saturated alkyl group having 3 to 6 carbon atoms, or phenyl group, and $A^3$ represents a single bond, or oxygen atom. This compound may sometimes be hereinafter referred to simply as "Compound (I)" of the present invention."] or a salt thereof.

(1-2) The compound or salt thereof according to (1), wherein, in the formula (I), Link is —$(CH_2)_n$—, n is an integer of 1 to 3, Rz has the same meaning as that of Rx or represents -$A^5$-Re when Rs is —N(Ry)(Rz), and Ry is hydrogen atom, an alkyl group having 1 to 8 carbon atoms, or $A^6$-Qp, or Ry binds to Rz to form, together with a nitrogen atom to which they bind, a saturated or unsaturated 3 to 7-membered nitrogen-containing cyclic group.

(2) The compound or salt thereof according to (1) or (1-2) mentioned above, wherein, in the formula (I), AR binds to any atom among $C^2$ and $C^3$ in the aromatic ring (E).

(3) The compound or salt thereof according to any one of (1) to (2) mentioned above, wherein, in the formula (I), n is an integer of 2 (the description of "according to any one of (1) to (2)" includes (1-2) mentioned above, and the same or similar description should be construed in the same manner hereinafter in the specification).

(4) The compound or salt thereof according to any one of (1) to (3) mentioned above, wherein, in the formula (I), AR is a residue of naphthalene, benzofuran, benzo[b]thiophene, indole, benzothiazole, dihydro-3H-benzothiazole, quinoline, dihydro-1H-quinoline, benzo[d]isothiazole, 1H-indazole, benzo[c]isothiazole, 2H-indazole, imidazo[1,2-a]pyridine, 1H-pyrrolo[2,3-b]pyridine, isoquinoline, dihydro-2H-isoquinoline, cinnoline, quinazoline, quinoxaline, 1H-benzimidazole, benzoxazole, 1H-pyrrolo[3,2-b]pyridine, benzo[1,2,5]thiadiazole, 1H-benzotriazole, 1,3-dihydropyrrolo[2,3-b]pyridine, 1,3-dihydrobenzimidazole, dihydro-3H-benzoxazole, phthalazine, [1,8]naphthalidine, [1,5]naphthalidine, 1H-pyrrolo[3,2-c]pyridine, 1H-pyrrolo[2,3-c]pyridine, 1H-pyrazolo[4,3-b]pyridine, 1H-pyrazolo[4,3-c]pyridine, 1H-pyrazolo[3,4-c]pyridine, 1H-pyrazolo[3,4-b]pyridine, [1,2,4]triazolo[4,3-a]pyridine, thieno[3,2-c]pyridine, thieno[3,2-b]pyridine, 1H-thieno[3,2-c]pyrazole, benzo[d]isoxazole, benzo[c]isoxazole, indolizine, 1,3-dihydroindole, 1H-pyrazolo[3,4-d]thiazole, 2H-isoindole, [1,2,4]triazolo[1,5-a]pyrimidine, 1H-pyrazolo[3,4-b]pyrazine, 1H-imidazo[4,5-b]pyrazine, 7H-purine, or 4H-chromene (the aforementioned residue may be substituted with one of Xa or two or more of the same or different Xa).

(5) The compound or salt thereof according to any one of (1) to (3) mentioned above, wherein, in the formula (I), AR is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 1H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa).

(6) The compound or salt thereof according to any one of (1) to (3) mentioned above, wherein, in the formula (I), AR is a residue of naphthalene, benzofuran, benzo[b]thiophene, indole, benzothiazole, dihydro-3H-benzothiazole, quinoline, dihydro-1H-quinoline, benzo[d]isothiazole, 1H-indazole, benzo[c]isothiazole, 2H-indazole, imidazo[1,2-a]pyridine, 1H-pyrrolo[2,3-b]pyridine, isoquinoline, or dihydro-2H-isoquinoline (the aforementioned residue may be substituted with one of Xa or two or more of the same or different Xa).

(7) The compound or salt thereof according to any one of (1) to (3) mentioned above, wherein, in the formula (I), AR is a residue of cinnoline, quinazoline, quinoxaline, 1H-benzimidazole, benzoxazole, 1H-pyrrolo[3,2-b]pyridine, benzo[1,2,5]thiadiazole, 1H-benzotriazole, 1,3-dihydropyrrolo[2,3-b]pyridine, 1,3-dihydrobenzimidazole, dihydro-3H-benzoxazole, phthalazine, [1,8]naphthalidine, [1,5]naphthalidine, 1H-pyrrolo[3,2-c]pyridine, 1H-pyrrolo[2,3-c]pyridine, 1H-pyrazolo[4,3-b]pyridine, 1H-pyrazolo[4,3-c]pyridine, 1H-pyrazolo[3,4-c]pyridine, 1H-pyrazolo[3,4-b]pyridine, [1,2,4]triazolo[4,3-a]pyridine, thieno[3,2-c]pyridine, thieno[3,2-b]pyridine, 1H-thieno[3,2-c]pyrazole, benzo[d]isoxazole, benzo[c]isoxazole, indolizine, 1,3-dihydroindole, 1H-pyrazolo[3,4-d]thiazole, 1H-pyrazolo[3,4-d]thiazole, 2H-isoindole, [1,2,4]triazolo[1,5-a]pyrimidine, 1H-pyrazolo[3,4-b]pyrazine, 1H-imidazo[4,5-b]pyrazine, 7H-purine, or 4H-chromene (the aforementioned residue may have one of Xa or two or more of the same or different Xa).

(8) The compound or salt thereof according to any one of (1) to (7) mentioned above, wherein, in the formula (I), Rs is -D-Rx or —N(Ry)(Rz), D is a single bond, oxygen atom, sulfur atom, —S(O)—, —S(O)$_2$—, or —C(O)—, Rx is a linear or branched saturated alkyl group having 3 to 8 carbon atoms, or Ra, Rb, or Rc, k in Ra is 0 or an integer of 1 to 3, $R^1$ is a saturated cyclic alkyl group having 3 to 7 carbon atoms or a condensed saturated cyclic alkyl group having 6 to 8 carbon atoms, $R^1$ may be substituted with one of lower alkyl group having 1 to 4 carbon atoms or two or more of the same or different lower alkyl groups having 1 to 4 carbon atoms, Q in Rb is phenyl group, thienyl group, furyl group, pyrrolyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, tetrahydronaphthyl group, indanyl group, indenyl group, quinolyl group, isoquinolyl group, indolyl group, benzofuryl group, benzothienyl group, benzimidazolyl group, benzoxazolyl group, benzothiazolyl group, indazolyl group, 4H-chromenyl group, dihydrobenzodioxyl group, benzoisoxazolyl group, pyrrolopyridinyl group, pyrazolopyridinyl group, triazolopyridinyl group, thienopyridinyl group, thienopyrazolyl group, 1,3-dihydrobenzimidazole group, dihydro-3H-benzoxazole group, or dihydro-3H-benzothiazole group (the aforementioned groups binds to $A^2$ at an arbitrary position), $A^1$ is a single bond or an alkylene (a) having 1 to 3 carbon atoms, the alkylene (a) may be substituted with a lower alkyl group having 1 to 4 carbon atoms or phenyl group, $A^2$ is a single bond, oxygen atom, sulfur atom, —S(O)—, —S(O)$_2$—, or —N($R^4$)— (provided that when $A^2$ represents oxygen atom, sulfur atom, —S(O)—, —S(O)$_2$—, or —N($R^4$)—, $A^1$ represents ethylene or trimethylene), $R^2$ and $R^3$ independently represent hydrogen atom, a linear or branched saturated alkyl group having 1 to 4 carbon atoms, oxo group, thioxo group, fluorine atom, chlorine atom, bromine atom, trifluoromethyl group, —$OR^6$, —N($R^6$)($R^{6'}$), —$NHCOR^7$, —$NHSO_2R^8$, or -$A^6$-Qa, or they bind to each other to represent methylenedioxy group, Qa is phenyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, indanyl group, indenyl group, quinolyl group, isoquinolyl group, indolyl group, benzofuryl group, benzothienyl group, benzimidazolyl group, benzoxazolyl group, benzothiazolyl group, or indazolyl group (these groups may be substituted with one of $T^1$ or two or more of the same or different $T^1$, and bind to $A^6$ at an arbitrary position on the ring), $R^4$ and $R^6$ independently represent hydrogen atom or a lower alkyl group having 1 to 4 carbon atoms, $R^5$ and $R^7$ independently represent hydrogen atom, a lower alkyl group having 1 to 4 carbon atoms, or -$A^6$-Qa, $R^8$ is a lower alkyl group having 1 to 4 carbon atoms, $R^{6'}$ has the same meaning as $R^6$, or binds to $R^6$ to form a 3- to 6-membered ring together with the nitrogen atom to which they bind to form a saturated nitrogen-containing cycloalkyl group or morpholino group, p in Rc is an integer of 2 to 4, $A^4$ is a single bond or methylene or ethylene, $A^5$ is —C(O)—, —C(S)—, or —S(O)$_2$—, Rd is hydrogen atom, an alkyl group having 1 to 8 carbon atoms, or Qa, Re is an alkyl group having 1 to 8 carbon atoms, -$A^6$-Qa, —(CH$_2$)$_i$$R^{14}$, —$OR^{28}$, —$SR^{28}$, or N($R^{29}$)($R^{30}$), i is an integer of 1 to 3, $R^{14}$ is hydroxyl group, an alkoxy group having 1 to 4 carbon atoms, carboxyl group, or an N,N-dialkylcarbamoyl group having 1 to 4 carbon atoms, $R^{28}$ is an alkyl group having 1 to 8 carbon atoms or -$A^6$-Qa, $R^{29}$ is an alkyl group having 1 to 8 carbon atoms, an alkoxycarbonyl group having 1 to 4 carbon atoms, or -$A^6$-Qa group, $R^{30}$ is hydrogen atom or a lower alkyl group having 1 to 4 carbon atoms, or binds to $R^{29}$ to form a 3- to 6-membered ring together with the nitrogen atom to which they bind to form a saturated nitrogen-containing cycloalkyl group or morpholino group, Rz has the same meaning as Rx, or is -$A^5$-Re, and Ry is hydrogen atom, an alkyl group having 1 to 8 carbon atoms, or -$A^6$-Qp, or binds to Rz to form a saturated or unsaturated nitrogen-containing cyclic substituent having 3 to 7 atoms together with nitrogen atom to which they binds.

(9) The compound or salt thereof according to any one of (1) to (8) mentioned above, wherein, in the formula (I), among $C^2$, $C^3$, $C^4$, $C^5$, and $C^6$ in the aromatic ring (E), one ring-constituting atom to which Rs or AR does not bind is replaced with nitrogen atom.

(10) The compound or salt thereof according to any one of (1) to (8) mentioned above, wherein, in the formula (I), among $C^2$, $C^3$, $C^4$, $C^5$, or $C^6$ in the aromatic ring (E), one ring-constituting atom to which Rs or AR does not bind is replaced with —N($Rn^1$)($Rn^2$) (provided that one of $Rn^1$ and $Rn^2$ represents a substituent other than hydrogen atom).

(11) The compound or salt thereof according to (1) or (10) mentioned above, wherein, in the formula (I), Rs is —O—Rx.

(12) The compound or salt thereof according to any one of (1) to (11) mentioned above, wherein, in the formula (I), Rs is —O—Rc.

(13) The compound or salt thereof according to any one of (1) to (10) mentioned above, wherein, in the formula (I), Rs is —N(Ry)(Rz).

(14) The compound or salt thereof according to any one of (1) to (10) mentioned above, wherein, in the formula (I), Rs is -D-Rx, and D is a single bond, sulfur atom, —S(O)—, —S(O)$_2$—, or —C(O)—.

(15) The compound or salt thereof according to any one of (1) to (10) mentioned above, wherein, in the formula (I), Rs is —S—Rx.

(16) The compound or salt thereof according to (1-2) mentioned above, wherein, in the formula (I), AR binds at the position of $C^2$ in the aromatic ring (E), and Rs binds to one of the ring-constituting carbon atoms $C^3$, $C^4$, and $C^5$.

(17) The compound or salt thereof according to (16) mentioned above, wherein, in the formula (I), Rs is —O—Rx, and no ring-constituting carbon atom in the aromatic ring (E) is replaced with V.

(18) The compound or salt thereof according to (16) or (17) mentioned above, wherein, in the formula (I), n is an integer of 2, and Y is hydrogen atom or a lower alkyl group having 1 to 4 carbon atoms.

(19) The compound or salt thereof according to (4) mentioned above, wherein, in the formula (I), Link is —(CH$_2$)$_n$—, n is an integer of 2, AR binds at the position of $C^2$ in the aromatic ring (E), Rs binds to one of ring-constituting carbon atoms $C^3$, $C^4$ and $C^5$, Rs is —O—Rx, Y is hydrogen atom or a lower alkyl group having 1 to 4 carbon atoms, and all of $C^2$, $C^3$, $C^4$, $C^5$, and $C^6$ in the aromatic ring (E) are not replaced with V.

(20) The compound or salt thereof according to (5) mentioned above, wherein, in the formula (I), Link is —(CH$_2$)$_n$—, n is an integer of 2, AR binds at the position of $C^2$ in the aromatic ring (E), Rs binds to one of ring-constituting carbon atoms $C^3$, $C^4$ and $C^5$, Rs is —O—Rx, Y is hydrogen atom or a lower alkyl group having 1 to 4 carbon atoms, and all of $C^2$, $C^3$, $C^4$, $C^5$, and $C^6$ in the aromatic ring (E) are not replaced with V.

(21) The compound or salt thereof according to any one of (16) to (20) mentioned above, wherein, in the formula (I), Xa which may substitute on AR is methyl group, ethyl group, propyl group, hydroxyethyl group, carboxymethyl group, hydroxyl group, methoxy group, 2-hydroxyethyloxy group, amino group, methylamino group, dimethylamino group, carboxyl group, carbamoyl group, acetyl group, methanesulfonyl group, sulfamoyl group, or N,N-dimethylsulfamoyl group.

(22) The compound or salt thereof according to any one of (16) to (21) mentioned above, wherein, in the formula (I), Rs is —O—Rx, Rx is butyl group, isobutyl group, 2-ethylbutyl group, cyclopentyl group, cyclohexyl group, cycloheptyl group, cyclopentylmethyl group, or cyclohexylmethyl group, or Rb (provided that Q in Rb is phenyl group or indan-2-yl group), $A^1$ is a single bond, a methylene group substituted with methyl group or ethyl group, or unsubstituted methylene group, or an ethylene group substituted with methyl group or ethyl group, or unsubstituted ethylene group, $A^2$ is a single bond, oxygen atom, sulfur atom, —N(methyl)-, or —N(ethyl)- (provided that when $A^2$ represents oxygen atom, sulfur atom, —N(methyl)-, or —N(ethyl)-, $A^1$ represents ethylene), and $R^2$ and $R^3$ independently represent hydrogen atom, methyl group, fluorine atom, chlorine atom, trifluoromethyl group, methoxy group, or dimethylamino group (provided that when Q is phenyl group, $A^1$ is a single bond or unsubstituted methylene, and $A^2$ is a single bond, one of $R^2$ and $R^3$ is a substituent other than hydrogen atom).

(23) The compound or salt thereof according to any one of (16) to (22) mentioned above, wherein, in the formula (I), Rx-D- binds at the position of $C^3$ in the aromatic ring (E).

(24) The compound or salt thereof according to any one of (16) to (22) mentioned above, wherein, in the formula (I), Rx-D- binds at the position of $C^4$ in the aromatic ring (E).

(25) The compound or salt thereof according to any one of (16) to (22) mentioned above, wherein, in the formula (I), Rx-D- binds at the position of $C^5$ in the aromatic ring (E).

(26) The compound or salt thereof according to (1-2) mentioned above, wherein, in the formula (I), n is an integer of 1 to 3, AR binds to $C^2$, Rs binds to one of the ring-constituting carbon atoms $C^3$, $C^4$, and $C^5$, a ring-constituting atom among $C^3$, $C^4$, and $C^5$ to which Rs does not bind may be replaced with V, V is nitrogen atom or carbon atom substituted with Zx, Zx is fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, or N,N-dimethylsulfamoylamino group, Rs is -D-Rx or —N(Ry)(Rz), D is oxygen atom or sulfur atom, Rx is butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or Rb or Rc, Q in Rb is phenyl group, thienyl group, furyl group, pyridyl group, oxazolyl group, naphthyl group, tetrahydronaphthyl group, indanyl group, indolyl group, or dihydrobenzodioxyl group, and $A^2$ is a single bond, oxygen atom, sulfur atom, —N(methyl)-, or —N(ethyl)- (provided that when $A^2$ is oxygen atom, sulfur atom, —N(methyl)-, or —N(ethyl)-, $A^1$ represents ethylene). $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q is phenyl group, $A^1$ is a single bond or unsubstituted methylene, and $A^2$ is a single bond, one of $R^2$ and $R^3$ is a substituent other than hydrogen atom). Symbol p in Rc is an integer of 2 or 3, $A^4$ is a single bond or methylene, $A^5$ is —C(O)—, —C(S)—, or —S(O)$_2$—, Rd is hydrogen atom, or methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, or pyridin-4-yl group, Re is methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen 3-yl)amino group, pyrrolidino group, piperidino group, morpholino group, methyloxycarbonylamino group, or ethyloxycarbonylamino group, Rz is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, or (morpholino-4-yl)carbonyl group, Ry is hydrogen atom, methyl group, ethyl group, or isobutyl group, or binds to Rz to form pyrrolidino group, piperidino group, piperazino group, morpholino group, pyrrol-1-yl group, imidazol-1-yl group, or pyrazol-1-yl group together with nitrogen atom to which they binds, AR is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]

thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa), Xa is oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl) amino group, methanesulfonyl group, sulfamoyl group, N-methylsulfamoyl group, N,N-dimethylsulfamoyl group, carboxyl group, acetyl group, carbamoyl group, or N,N-dimethylcarbamoyl group, and Y is hydrogen atom, methyl group or ethyl group.

(27) The compound or salt thereof according to (1-2) mentioned above, wherein, in the formula (I), n is an integer of 2, $C^2$ is carbon atom to which AR binds, $C^3$ is carbon atom to which Rs binds, $C^4$ may be replaced with V, $C^5$ and $C^6$ are unsubstituted ring-constituting carbon atoms, V is nitrogen atom, or carbon atom substituted with Zx, Zx is fluorine atom, methyl group, hydroxyl group, amino group, N-methylamino group, or N,N-dimethylamino group, Rs is —O—Rx, Rx is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl) ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl) ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl) ethyl group, 2-[2-(trifluoromethyl)phenyl]ethyl group, 2-[3-(trifluoromethyl)phenyl]ethyl group, 2-[4-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino) ethyl group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino) naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

(28) The compound or salt thereof according to (1-2) mentioned above, wherein, in the formula (I), n is an integer of 2, $C^2$ is carbon atom to which AR binds, $C^4$ is carbon atom to which Rs binds, $C^5$ may be replaced with V, $C^3$ and $C^6$ represents an unsubstituted ring-constituting carbon atom, V is nitrogen atom, or carbon atom substituted with Zx, Zx is fluorine atom, methyl group, hydroxyl group, amino group, N-methylamino group, or N,N-dimethylamino group, Rs is —O—Rx, Rx is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl) ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino)ethyl group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

(29) The compound or salt thereof according to (1-2) mentioned above, wherein, in the formula (I), AR binds to $C^3$ in the aromatic ring (E), and Rs binds to $C^5$ or $C^6$ in the aromatic ring (E).

(30) The compound or salt thereof according to (29) mentioned above, wherein, in the formula (I), Rs is —O—Rx, and all of $C^2$, $C^3$, $C^4$, $C^5$, and $C^6$ in the aromatic ring (E) are not replaced with V.

(31) The compound or salt thereof according to (29) or (30) mentioned above, wherein, in the formula (I), n is an integer of 2, and Y is hydrogen atom or a lower alkyl group having 1 to 4 carbon atoms.

(32) The compound or salt thereof according to (4) mentioned above, wherein, in the formula (I), Link is —$(CH_2)_n$—, n is an integer of 2, AR binds to $C^3$ in the aromatic ring (E), Rs binds to the ring-constituting carbon atom $C^5$ or $C^6$ in the aromatic ring (E), Rs is —O—Rx, Y is hydrogen atom or a lower alkyl group having 1 to 4 carbon atoms, and all of $C^2$, $C^3$, $C^4$, $C^5$, and $C^6$ in the aromatic ring (E) are not replaced with V.

(33) The compound or salt thereof according to (5) mentioned above, wherein, in the formula (I), n is an integer of 2, AR binds to $C^3$ in the aromatic ring (E), Rs binds to the ring-constituting carbon atom $C^5$ or $C^6$ in the aromatic ring (E), Rs is —O—Rx, Y is hydrogen atom or a lower alkyl group having 1 to 4 carbon atoms, and all of $C^2$, $C^3$, $C^4$, $C^5$, and $C^6$ in the aromatic ring (E) are not replaced with V.

(34) The compound or salt thereof according to any one of (29) to (33) mentioned above, wherein, in the formula (I), Xa which may substitute on AR is methyl group, ethyl group, propyl group, hydroxyethyl group, carboxymethyl group, hydroxyl group, methoxy group, 2-hydroxyethyloxy group, amino group, methylamino group, dimethylamino group, carboxyl group, carbamoyl group, acetyl group, methanesulfonyl group, sulfamoyl group, or N,N-dimethylsulfamoyl group.

(35) The compound or salt thereof according to any one of (29) to (34) mentioned above, wherein, in the formula (I), Rs is —O—Rx, Rx is butyl group, isobutyl group, 2-ethylbutyl group, cyclopentyl group, cyclohexyl group, cycloheptyl group, cyclopentylmethyl group, or cyclohexylmethyl group, or Rb (provided that Q in Rb is phenyl group or indan-2-yl group), $A^1$ is a single bond, or methylene group substituted with methyl group or ethyl group or unsubstituted methylene group, or ethylene group substituted with methyl group or ethyl group or unsubstituted ethylene group, $A^2$ is a single bond, oxygen atom, sulfur atom, —N(methyl)-, or —N(ethyl)- (provided that when $A^2$ is oxygen atom, sulfur atom, —N(methyl)-, or —N(ethyl)-, $A^1$ is ethylene), and $R^2$ and $R^3$ independently represent hydrogen atom, methyl group, fluorine atom, chlorine atom, trifluoromethyl group, methoxy group, or dimethylamino group (provided that when Q is phenyl group, $A^1$ is a single bond or unsubstituted methylene, and $A^2$ is a single bond, one of $R^2$ and $R^3$ is a substituent other than hydrogen atom).

(36) The compound or salt thereof according to any one of (29) to (35) mentioned above, wherein, in the formula (I), Rs binds at the position of $C^5$ in the aromatic ring (E).

(37) The compound or salt thereof according to any one of (29) to (35) mentioned above, wherein, in the formula (I), Rs binds at the position of $C^6$ in the aromatic ring (E).

(38) The compound or salt thereof according to (1-2) mentioned above, wherein, in the formula (I), n is an integer of 2, $C^3$ is carbon atom to which AR binds, $C^5$ is carbon atom to which Rs binds, $C^2$, $C^4$ and $C^6$ are unsubstituted ring-constituting carbon atoms, Rs is —O—Rx, Rx is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenylethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino)ethyl group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

(39) The compound or salt thereof according to (1-2) mentioned above, wherein, in the formula (I), AR binds to $C^3$ in the aromatic ring (E), Rs binds to $C^4$ in the aromatic ring (E), and $C^6$ is replaced with V.

(40) The compound or salt thereof according to (39) mentioned above, wherein, in the formula (I), n is an integer of 2, V is carbon atom substituted with Zx, Rs is —O—Rx, and Y is hydrogen atom or a lower alkyl group having 1 to 4 carbon atoms.

(41) The compound or salt thereof according to (4) mentioned above, wherein, in the formula (I), Link is —$(CH_2)_n$—, n is an integer of 2, AR binds to $C^3$ in the aromatic ring (E), Rs binds to $C^4$ in the aromatic ring (E), $C^6$ is carbon atom substituted with Zx, Rs is —O—Rx, and Y is hydrogen atom or a lower alkyl group having 1 to 4 carbon atoms.

(42) The compound or salt thereof according to (5) mentioned above, wherein, in the formula (I), Link is —$(CH_2)_n$—, n is an integer of 2, AR binds to $C^3$ in the aromatic ring (E), Rs binds to $C^4$ in the aromatic ring (E), $C^6$ is carbon atom substituted with Zx, Rs is —O—Rx, and Y is hydrogen atom or a lower alkyl group having 1 to 4 carbon atoms.

(43) The compound or salt thereof according to any one of (39) to (42) mentioned above, wherein, in the formula (I), Xa which may substitute on AR is methyl group, ethyl group, propyl group, hydroxyethyl group, carboxymethyl group, hydroxyl group, methoxy group, 2-hydroxyethyloxy group, amino group, methylamino group, dimethylamino group, carboxyl group, carbamoyl group, acetyl group, methanesulfonyl group, sulfamoyl group, or N,N-dimethylsulfamoyl group.

(44) The compound or salt thereof according to any one of (39) to (43) mentioned above, wherein, in the formula (I), Rs is —O—Rx, Rx is butyl group, isobutyl group, 2-ethylbutyl group, cyclopentyl group, cyclohexyl group, cycloheptyl group, cyclopentylmethyl group, or cyclohexylmethyl group, or Rb (provided that Q in Rb is phenyl group or indan-2-yl group), $A^1$ is a single bond, or methylene group substituted with methyl group or ethyl group or unsubstituted methylene group, or ethylene group substituted with methyl group or ethyl group or unsubstituted ethylene group, $A^2$ is a single bond, oxygen atom, sulfur atom, —N(methyl)-, or —N(ethyl)- (provided that when $A^2$ is oxygen atom, sulfur atom, —N(methyl)-, or —N(ethyl)-, $A^1$ is ethylene), $R^2$ and $R^3$ independently represent hydrogen atom, methyl group, fluorine atom, chlorine atom, trifluoromethyl group, methoxy group, or dimethylamino group (provided that when Q is phenyl group, $A^1$ is a single bond or unsubstituted methylene, and $A^2$ is a single bond, one of $R^2$ and $R^3$ is a substituent other than hydrogen atom).

(45) The compound or salt thereof according to (1-2) mentioned above, wherein, in the formula (I), n is an integer of 2, $C^3$ is carbon atom to which AR binds, $C^4$ is carbon atom to which Rs binds, $C^6$ is carbon atom substituted with Zx, $C^2$ and $C^5$ are unsubstituted ring-constituting carbon atoms, Zx is fluorine atom, methyl group, hydroxyl group, amino group, N-methylamino group, or N,N-dimethylamino group, Rs is —O—Rx, Rx is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino)ethyl group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]

thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

(46) The compound or salt thereof according to (1-2) mentioned above, wherein, in the formula (I), AR binds to $C^3$ in the aromatic ring (E), Rs binds to $C^4$ in the aromatic ring (E), $C^5$ is nitrogen atom, and $C^2$ and $C^6$ are unsubstituted ring-constituting carbon atoms.

(47) The compound or salt thereof according to (46) mentioned above, wherein, in the formula (I), n is an integer of 2, D is oxygen atom, and Y is hydrogen atom or a lower alkyl group having 1 to 4 carbon atoms.

(48) The compound or salt thereof according to (4) mentioned above, wherein, in the formula (I), Link is —$(CH_2)_n$—, n is an integer of 2, AR binds to $C^3$ in the aromatic ring (E), Rs binds to $C^4$ in the aromatic ring (E), $C^5$ is nitrogen atom, $C^2$ and $C^6$ are unsubstituted ring-constituting carbon atoms, Rs is —O—Rx, and Y is hydrogen atom or a lower alkyl group having 1 to 4 carbon atoms.

(49) The compound or salt thereof according to (5) mentioned above, wherein, in the formula (I), Link is —$(CH_2)_n$—, n is an integer of 2, AR binds to $C^3$ in the aromatic ring (E), Rs binds to $C^4$ in the aromatic ring (1), $C^5$ is nitrogen atom, $C^2$ and $C^6$ are unsubstituted ring-constituting carbon atoms, Rs is —O—Rx, and Y is hydrogen atom or a lower alkyl group having 1 to 4 carbon atoms.

(50) The compound or salt thereof according to any one of (46) to (49) mentioned above, wherein, in the formula (I), Xa which may substitute on AR is methyl group, ethyl group, propyl group, hydroxyethyl group, carboxymethyl group, hydroxyl group, methoxy group, 2-hydroxyethyloxy group, amino group, methylamino group, dimethylamino group, carboxyl group, carbamoyl group, acetyl group, methanesulfonyl group, sulfamoyl group, or N,N-dimethylsulfamoyl group.

(51) The compound or salt thereof according to any one of (46) to (50) mentioned above, wherein, in the formula (I), Rs is —O—Rx, Rx is butyl group, isobutyl group, 2-ethylbutyl group, cyclopentyl group, cyclohexyl group, cycloheptyl group, cyclopentylmethyl group, or cyclohexylmethyl group, or Rb (provided that Q in Rb is phenyl group or indan-2-yl group), $A^1$ is a single bond, or methylene group substituted with methyl group or ethyl group or unsubstituted methylene group, or ethylene group substituted with methyl group or ethyl group or unsubstituted ethylene group, $A^2$ is a single bond, oxygen atom, sulfur atom, —N(methyl)- or —N(ethyl)- (provided that when $A^2$ is oxygen atom, sulfur atom, —N(methyl)-, or —N(ethyl)-, $A^1$ is ethylene), and $R^2$ and $R^3$ independently represent hydrogen atom, methyl group, fluorine atom, chlorine atom, trifluoromethyl group, methoxy group, or dimethylamino group (provided that when Q is phenyl group, $A^1$ is a single bond or unsubstituted methylene, and $A^2$ is a single bond, one of $R^2$ and $R^3$ is a substituent other than hydrogen atom).

(52) The compound or salt thereof according to (1-2) mentioned above, wherein, in the formula (I), n is an integer of 2, $C^3$ is carbon atom to which AR binds, $C^4$ is carbon atom to which Rs binds, $C^5$ is nitrogen atom, $C^2$ and $C^6$ are unsubstituted ring-constituting carbon atoms, Rs is —O—Rx, Rx is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino)ethyl group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

(53) The compound or salt thereof according to (1-2) mentioned above, wherein, in the formula (I), AR binds to $C^3$ in the aromatic ring (E), Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, Rs is -D-Rx, and D is a single bond, sulfur atom, —S(O)—, —S(O)$_2$—, or —C(O)—.

(53-2) The compound of salt thereof according to (1-2) mentioned above, wherein, in the formula (I), A binds to $C^3$ in the aromatic ring (E), Rs binds to $C^4$ in the aromatic ring (E), $C^5$ is nitrogen atom, $C^2$ and $C^6$ are unsubstituted ring-constituting carbon atoms, Rs is -D-Rx, and D is a single bond, sulfur atom, —S(O)—, —S(O)$_2$—, or —C(O)—.

(53-3) The compound or salt thereof according to (53) or (53-2) mentioned above, wherein, in the formula (I), Rs is -D-Rx and D is single bond.

(54) The compound or salt thereof according to any one of (53) to (53-3) mentioned above, wherein, in the formula (I), n is an integer of 2, and Y is hydrogen atom or a lower alkyl group having 1 to 4 carbon atoms.

(55) The compound or salt thereof according to (4) mentioned above, wherein, in the formula (I), Link is —(CH$_2$)$_n$—, n is an integer of 2, AR binds to $C^3$ in the aromatic ring (E), Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, Rs is -D-Rx, D is a single bond, sulfur atom, —S(O)—, —S(O)$_2$—, or —C(O)—, and Y is hydrogen atom or a lower alkyl group having 1 to 4 carbon atoms.

(55-2) The compound or a salt thereof according to (4) mentioned above, wherein, in the formula (I), Link is —(CH$_2$)$_n$—, n is an integer of 2, AR binds to $C^3$ in the aromatic ring (E), Rs binds to $C^4$ in the aromatic ring (E), $C^5$ may be replaced with V, $C^2$ and $C^6$ are unsubstituted ring-constituting carbon atoms, Rs is -D-Rx, D is a single bond, and Y is hydrogen atom or a lower alkyl group having 1 to 4 carbon atoms.

(56) The compound or salt thereof according to (5) mentioned above, wherein, in the formula (I), Link is —(CH$_2$)$_n$—, n is an integer of 2, AR binds to $C^3$ in the aromatic ring (E), Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, Rs is -D-Rx, D is a single bond, sulfur atom, —S(O)—, —S(O)$_2$—, or —C(O)—, and Y is hydrogen atom or a lower alkyl group having 1 to 4 carbon atoms.

(56-2) The compound or a salt thereof according to (5) mentioned above, wherein, in the formula (I), Link is —(CH$_2$)$_n$—, n is an integer of 2, AR binds to $C^3$ in the aromatic ring (E), Rs binds to $C^4$ in the aromatic ring (E), $C^5$ may be replaced with V, $C^2$ and $C^6$ are unsubstituted ring-constituting carbon atoms, Rs is -D-Rx, D is a single bond, and Y is hydrogen atom or a lower alkyl group having 1 to 4 carbon atoms.

(57) The compound or salt thereof according to any one of (53) to (56-2) mentioned above, wherein, in the formula (I), Xa which may substitute on AR is methyl group, ethyl group, propyl group, hydroxyethyl group, carboxymethyl group, hydroxyl group, methoxy group, 2-hydroxyethyloxy group, amino group, methylamino group, dimethylamino group, carboxyl group, carbamoyl group, acetyl group, methanesulfonyl group, sulfamoyl group, or N,N-dimethylsulfamoyl group.

(58) The compound or salt thereof according to any one of (53) to (57) mentioned above, wherein, in the formula (I), Rs is -D-Rx, Rx is butyl group, isobutyl group, 2-ethylbutyl group, cyclopentyl group, cyclohexyl group, cycloheptyl group, cyclopentylmethyl group, or cyclohexylmethyl group, or Rb (provided that Q in Rb is phenyl group or indan-2-yl group), $A^1$ is a single bond, or methylene group substituted with methyl group or ethyl group or unsubstituted methylene group, or ethylene group substituted with methyl group or ethyl group or unsubstituted ethylene group, $A^2$ is a single bond, oxygen atom, sulfur atom, —N(methyl)-, or —N(ethyl)- (provided that when $A^2$ represents oxygen atom, sulfur atom, —N(methyl)- or —N(ethyl)-, $A^1$ represents ethylene), and $R^2$ and $R^3$ independently represent hydrogen atom, methyl group, fluorine atom, chlorine atom, trifluoromethyl group, methoxy group, or dimethylamino group (provided that when Q is phenyl group, $A^1$ is a single bond or unsubstituted methylene, and $A^2$ is a single bond, one of $R^2$ and $R^3$ is a substituent other than hydrogen atom).

(58-2) The compound or salt thereof according to (1-2) mentioned above, wherein, in the formula (I), n is an integer of 1 to 3, AR binds to $C^8$ in the aromatic ring (E), Rs binds to $C^4$ in the aromatic ring (E), $C^5$ may be replaced with V, $C^2$ and $C^6$ are unsubstituted ring-constituting carbon atoms, V is nitrogen atom or V is carbon atom substituted with Zx, Zx is any one of fluorine atom, methyl group, hydroxyl group, amino group, N-methylamino group, or N,N-dimethylamino group, Rs is -D-Rx, D is a single bond, Rx is butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or Rx is Rb or Rc (provided that Q in Rb is phenyl group, thienyl group, furyl group, pyridyl group, oxazolyl group, naphthyl group, tetrahydronaphthyl group, indanyl group, indolyl group, or dihydrobenzodioxyl group), $A^2$ is a single bond, oxygen atom, sulfur atom, —N(methyl)-, or —N(ethyl)- (provided that when $A^2$ represents oxygen atom, sulfur atom, —N(methyl)- or —N(ethyl)-, $A^1$ represents ethylene), $R^2$ and $R^3$ independently represent hydrogen atom, methyl group, fluorine atom, chlorine atom, trifluoromethyl group, methoxy group, dimethylamino group, acetylamino group, or methylsulfonylamino group, (provided that when Q is phenyl group, $A^1$ is a single bond or unsubstituted methylene, and $A^2$ is a single bond, one of $R^2$ and $R^3$ is a substituent other than hydrogen atom). p in Rc is an integer of 2 or 3, $A^4$ is a single bond or methylene, $A^5$ is —C(O)—, —C(S)—, or —S(O)$_2$—, Rd is hydrogen atom, or methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, or pyridin-4-yl group, Re is methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, or ethyloxycarbonylamino group, AR is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa), Xa is oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, or N,N-dimethylcarbamoyl group, and Y is hydrogen atom, methyl group, or ethyl group.

(58-3) The compound or salt thereof according to (1-2) mentioned above, wherein, in the formula (I), n is an integer of 2, AR binds to $C^3$ in the aromatic ring (E), Rs binds to $C^4$ in the aromatic ring (E), $C^5$ may be replaced with V, $C^2$ and $C^6$ are unsubstituted ring-constituting carbon atoms, V is nitrogen atom or V is carbon atom substituted with Zx, Zx is any one of fluorine atom, methyl group, hydroxyl group, amino group, N-methylamino group, or N,N-dimethylamino group, Rs is -D-Rx, D is a single bond, Rx is butyl group, isobutyl group, 2-ethylbutyl group, cyclopentyl group, cyclohexyl group, cycloheptyl group, cyclopentylmethyl group, cyclohexylmethyl group, phenyl group, 2-methylphenyl group, 3-methylphenyl group, 4-methylphenyl group, 2,3-dimethylphenyl group, 3,5-dimethylphenyl group, 2-methoxyphenyl group, 3-methoxyphenyl group, 4-methoxyphenyl group, 2-fluorophenyl group, 3-fluorophenyl group, 4-fluorophenyl group, 2-chlorophenyl group, 3-chlorophenyl group, 4-chlorophenyl group, 2,3-difluorophenyl group, 2,4-difluorophenyl group, 2,5-difluorophenyl group, 3,4-difluorophenyl group, 2,3-dichlorophenyl group, 2,4-dichlorophenyl group, 2,5-dichlorophenyl group, 2,6-dichlorophenyl group, 3,4-dichlorophenyl group, 3,5-dichlorophenyl group, 2-trifluoromethylphenyl group, 3-trifluoromethylphenyl group, 4-trifluoromethylphenyl group, 4-(N,N-dimethylamino)phenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, furan-2-yl group, furan-3-yl group, thiophen-2-yl group, thiophen-3-yl group, pyridin-2-yl group, pyridin-3-yl group, pyridin-4-yl group, naphthalen-1-yl group, naphthalen-2-yl group, 1H-indol-5-yl group, 1-methyl-1H-indol-5-yl group, 1H-indazol-5-yl group, 1-methyl-1H-indazol-5-yl group, biphenyl-2-yl group, biphenyl 3-yl group, biphenyl-4-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino)ethyl group;

AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

(58-4) The compound or salt thereof according to (1-2) mentioned above, wherein, in the formula (I), n is an integer of 2, AR binds to $C^3$ in the aromatic ring (E), Rs binds to $C^4$ in the aromatic ring (E), $C^5$ may be replaced with V, $C^2$ and $C^6$ are unsubstituted ring-constituting carbon atoms, V is nitrogen atom or V is carbon atom substituted with Zx, Zx is any one of fluorine atom, methyl group, hydroxyl group, amino group, N-methylamino group, or N,N-dimethylamino group, Rs is -D-Rx, D is a single bond, Rx is phenyl group, 2-methylphenyl group, 3-methylphenyl group, 4-methylphenyl group, 2,3-dimethylphenyl group, 3,5-dimethylphenyl group, 2-methoxyphenyl group, 3-methoxyphenyl group, 4-methoxyphenyl group, 2-fluorophenyl group, 3-fluorophenyl group, 4-fluorophenyl group, 2-chlorophenyl group, 3-chlorophenyl group, 4-chlorophenyl group, 2,3-difluorophenyl group, 2,4-difluorophenyl group, 2,5-difluorophenyl group, 3,4-difluorophenyl group, 2,3-dichlorophenyl group, 2,4-dichlorophenyl group, 2,5-dichlorophenyl group, 2,6-dichlorophenyl group, 3,4-dichlorophenyl group, 3,5-dichlorophenyl group, 2-trifluoromethylphenyl group, 3-trifluoromethylphenyl group, 4-trifluoromethylphenyl group, 4-(N,N-dimethylamino)phenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, furan-2-yl group, furan-3-yl group, thiophen-2-yl group, thiophen-3-yl group, pyridin-2-yl group, pyridin-3-yl group, pyridin-4-yl group, naphthalen-1-yl group, naphthalen-2-yl group, 1H-indol-5-yl group, 1-methyl-1H-indol-5-yl group, 1H-indazol-5-yl group, or 1-methyl-1H-indazol-5-yl group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

(58-5) The compound or salt thereof according to (1-2) mentioned above, wherein, in the formula (I), n is an integer of 2, AR binds to $C^3$ in the aromatic ring (E), Rs binds to $C^4$ in the aromatic ring (E), $C^2$, $C^5$, and $C^6$ are unsubstituted ring-constituting carbon atoms, Rs is -D-Rx, D is a single bond, Rx is phenyl group, 2-methylphenyl group, 3-methylphenyl group, 4-methylphenyl group, 2,3-dimethylphenyl group, 3,5-dimethylphenyl group, 2-methoxyphenyl group, 3-methoxyphenyl group, 4-methoxyphenyl group, 2-fluorophenyl group, 3-fluorophenyl group, 4-fluorophenyl group, 2-chlorophenyl group, 3-chlorophenyl group, 4-chlorophenyl group, 2,3-difluorophenyl group, 2,4-difluorophenyl group, 2,5-difluorophenyl group, 3,4-difluorophenyl group, 2,3-dichlorophenyl group, 2,4-dichlorophenyl group, 2,5-dichlorophenyl group, 2,6-dichlorophenyl group, 3,4-dichlorophenyl group, 3,5-dichlorophenyl group, 2-trifluoromethylphenyl group, 3-trifluoromethylphenyl group, 4-trifluoromethylphenyl group, 4-(N,N-dimethylamino)phenyl group, indan-2-yl group, furan-2-yl group, furan-3-yl group, thiophen-2-yl group, thiophen-3-yl group, pyridin-2-yl group, pyridin-3-yl group, pyridin-4-yl group, naphthalen-1-yl group, naphthalen-2-yl group, 1H-indol-5-yl group, 1-methyl-1H-indol-5-yl group, 1H-indazol-5-yl group, or 1-methyl-1H-indazol-5-yl group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl 1H-indazol-5-yl group, 1-propyl-1H-indazol-5-yl group, 1-(2-hydroxyethyl)-1H-indazol-5-yl group, 3-hydroxy-1H-indazol-5-yl group; 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

(59) The compound or salt thereof according to (1-2) mentioned above, wherein, in the formula (I), n is an integer of 1 to 3, $C^3$ is carbon atom to which AR binds, $C^4$ is carbon atom to which Rs binds, $C^5$ may be replaced with V, $C^2$ and $C^6$ are unsubstituted ring-constituting carbon atoms, V is nitrogen atom, or carbon atom substituted with Zx, Zx is fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, or N,N-dimethylsulfamoylamino group, Rs is —S—Rx, Rx is butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or Rb or Rc, Q in Rb is phenyl group, thienyl group, furyl group, pyridyl group, oxazolyl group, naphthyl group, tetrahydronaphthyl group, indanyl group, indolyl group, or dihydrobenzodioxyl group, $A^2$ is a single bond, oxygen atom, sulfur atom, —N(methyl)-, or —N(ethyl)- (provided that when $A^2$ is oxygen atom, sulfur atom, —N(methyl)-, or —N(ethyl)-, $A^1$ is ethylene), $R^2$ and $R^9$ independently represent hydrogen atom, methyl group, fluorine atom, chlorine atom, trifluoromethyl group, methoxy group, dimethylamino group, acetylamino group, or methylsulfonylamino group (provided that when Q is phenyl group, $A^1$ is a single bond or unsubstituted methylene, and $A^2$ is a single bond, one of $R^2$ and $R^3$ is a substituent other than hydrogen atom), p in Rc is an integer of 2 or 3, $A^4$ is a single bond or methylene, $A^5$ is —C(O)—, —C(S)—, or —S(O)$_2$—, Rd is hydrogen atom, or methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, or pyridin-4-yl group, Re is methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, or ethyloxycarbonylamino group, AR is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa), Xa is oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl) amino group, methanesulfonyl group, sulfamoyl group, N-methylsulfamoyl group, N,N-dimethylsulfamoyl group, carboxyl group, acetyl group, carbamoyl group, or N,N-dimethylcarbamoyl group, and Y is hydrogen atom, methyl group, or ethyl group.

(59-2) The compound or salt thereof according to (1) mentioned above, wherein, in the formula (I), AR binds to $C^5$ in the aromatic ring (E), Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, and Rs is —N(Ry)(Rz).

(59-3) The compound or salt thereof according to (1) mentioned above, wherein, in the formula (I), AR binds to $C^3$ in the aromatic ring (E), Rs binds to $C^4$ in the aromatic ring (E), $C^5$ is nitrogen atom, $C^2$ and $C^6$ are unsubstituted ring-constituting carbon atoms, and Rs is —N(Ry)(Rz).

(60) The compound or salt thereof according to (59-2) or (59-3) mentioned above, wherein, in the formula (I), Link is —$(CH_2)_n$—, n is an integer of 2, and Y is hydrogen atom or a lower alkyl group having 1 to 4 carbon atoms.

(61) The compound or salt thereof according to (4) mentioned above, wherein, in the formula (I), Link is —$(CH_2)_n$—, n is an integer of 2, AR binds to $C^3$ in the aromatic ring (E), Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, Rs is —N(Ry)(Rz), and Y is hydrogen atom or a lower alkyl group having 1 to 4 carbon atoms.

(61-2) The compound or salt thereof according to (4) mentioned above, wherein, in the formula (I), Link is —$(CH_2)_n$—, n is an integer of 2, AR binds to $C^3$ in the aromatic ring (E), Rs binds to $C^4$ in the aromatic ring (E), $C^5$ is nitrogen atom, $C^2$ and $C^6$ are unsubstituted ring-constituting carbon atoms, Rs is —N(Ry)(Rz), and Y is hydrogen atom or a lower alkyl group having 1 to 4 carbon atoms.

(62) The compound or salt thereof according to (5) mentioned above, wherein, in the formula (I), Link is —$(CH_2)_n$—, n is an integer of 2, AR binds to $C^3$ in the aromatic ring (E), Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, Rs is —N(Ry)(Rz), and Y is hydrogen atom or a lower alkyl group having 1 to 4 carbon atoms.

(62-2) The compound or salt thereof according to (5) mentioned above, wherein, in the formula (I), Link is —$(CH_2)_n$—, n is an integer of 2, AR binds to $C^3$ in the aromatic ring (E), Rs binds to $C^4$ in the aromatic ring (E), $C^5$ is nitrogen atom, $C^2$ and $C^6$ are unsubstituted ring-constituting carbon atoms, Rs is —N(Ry)(Rz), and Y is hydrogen atom or a lower alkyl group having 1 to 4 carbon atoms.

(63) The compound or salt thereof according to any one of (59-2) to (62-2) mentioned above, wherein, in the formula (I), Xa which may substitute on AR is methyl group, ethyl group, propyl group, hydroxyethyl group, carboxymethyl group, hydroxyl group, methoxy group, 2-hydroxyethyloxy group, amino group, methylamino group, dimethylamino group, carboxyl group, carbamoyl group, acetyl group, methanesulfonyl group, sulfamoyl group, or N,N-dimethylsulfamoyl group.

(64) The compound or salt thereof according to (1-2) mentioned above, wherein, in the formula (I), n is an integer of 1 to 3, $C^3$ is carbon atom to which AR binds, $C^4$ is carbon atom to which Rs binds, $C^2$, $C^5$, and $C^6$ are unsubstituted ring-constituting carbon atoms, Rs is —N(Ry)(Rz), Rz is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, or (morpholino-4-yl)carbonyl group, Ry is hydrogen atom, methyl group, ethyl group or isobutyl group, or binds to Rz to form pyrrolidino group, piperidino group, piperazino group, morpholino group, pyrrol-1-yl group, imidazol-1-yl group, or pyrazol-1-yl group together with the nitrogen atom to which they bind, AR is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (these groups may be substituted with one of Xa or two or more of the same or different Xa), Xa represents oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl) amino group, methanesulfonyl group, sulfamoyl group, N-methylsulfamoyl group, N,N-dimethylsulfamoyl group, carboxyl group, acetyl group, carbamoyl group, or N,N-dimethylcarbamoyl group, and Y is hydrogen atom, methyl group, or ethyl group.

(65) The compound or salt thereof according to (1-2) mentioned above, wherein, in the formula (I), n is an integer of 2, $C^3$ is carbon atom to which AR binds, $C^4$ is carbon atom, to which Rs binds, $C^2$, $C^5$ and $C^6$ are unsubstituted ring-constituting carbon atoms, Rs is —N(Ry)(Rz), Rz is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino) ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, or (morpholino-4-yl)carbonyl group, Ry is hydrogen atom, methyl group, ethyl group or isobutyl group, or binds to Rz to form pyrrolidino group, piperidino group, or morpholino group together with the nitrogen atom to which they bind, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino) naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b] thiophen-5-yl group, 2-methylbenzo[b]thiophen-5-yl group, 3-methylbenzo[b]thiophen-5-yl group, 2,3-dimethylbenzo [b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group; 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1 (2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

(65-2) The compound or salt thereof according to (1-2) mentioned above, wherein, in the formula (I), Link is —(CH$_2$)$_n$—, n is an integer of 2, $C^3$ is carbon atom to which AR binds, $C^4$ is carbon atom to which Rs binds, $C^2$, $C^5$ and $C^6$ are unsubstituted ring-constituting carbon atoms, Rs is —N(Ry)(Rz), and the group represented by —N(Ry)(Rz) is N,N-dimethylamino group, N-ethyl-N-methylamino group, N,N-diethylamino group, N-methyl-N-propylamino group, N-ethyl-N-propylamino group, N-isopropyl-N-methylamino group, N-ethyl-N-isopropylamino group, N-butylamino group, —N-butyl-N-methylamino group, N-butyl-N-ethylamino group, N-isobutylamino group, N-isobutyl-N-methylamino group, N-ethyl-N-isobutylamino group, N-(2-ethylbutyl)amino group, N-(2-ethylbutyl)-N-methylamino group, N-cyclopentylamino group, N-cyclopentyl-N-methylamino group, N-cyclohexylamino group, N-cyclohexyl-N-methylamino group, N-cycloheptylamino group, N-(cyclopentylmethyl)amino group, N-(cyclopentylmethyl)-N-methylamino group, N-(cyclohexylmethyl)amino group, N-(cyclohexylmethyl)-N-methylamino group, N-(2-methylphenyl)amino group, N-(4-methylphenyl)amino group, N-(2-fluorophenyl)amino group, N-(3-fluorophenyl)amino group, N-(4-fluorophenyl)amino group, N-(2-chlorophenyl)amino group, N-(3-chlorophenyl)amino group, N-(4-chlorophenyl)amino group, N-(indan-2-yl)amino group, N-(1-phenylethyl)amino group, N-[1-(2-fluorophenyl)ethyl]amino group, N-[1-(3-fluorophenyl)ethyl]amino group, N-[1-(4-fluorophenyl)ethyl]amino group, N-[1-(2-chlorophenyl)ethyl]amino group, N-[1-(3-chlorophenyl)ethyl]amino group, N-[1-(4-chlorophenyl)ethyl]amino group, N-(2-methylphenylmethyl)amino group, N-methyl-N-(2-methylphenylmethyl)amino group, N-(3-methylphenylmethyl)amino group, N-methyl-N-(3-methylphenylmethyl)amino group, N-(4-methylphenylmethyl)amino group, N-methyl-N-(4-methylphenylmethyl)amino group, N-(2-fluorophenylmethyl)amino group, N-(2-fluorophenylmethyl)-N-methylamino group, N-(3-fluorophenylmethyl)amino group, N-(3-fluorophenylmethyl)-N-methylamino group, N-(4-fluorophenylmethyl)amino group, N-(4-fluorophenylmethyl)-N-methylamino group, N-(2-chlorophenylmethyl)amino group, N-(2-chlorophenylmethyl)-N-methylamino group, N-(3-chlorophenylmethyl)amino group, N-(3-chlorophenylmethyl)-N-methylamino group, N-(4-chlorophenylmethyl)amino group, N-(4-chlorophenylmethyl)-N-methylamino group, N-(2,3-difluorophenylmethyl)amino group, N-(2,3-difluorophenylmethyl)-N-methylamino group, N-(2,4-difluorophenylmethyl)amino group, N-(2,4-difluorophenylmethyl)-N-methylamino group, N-(2,5-difluorophenylmethyl)amino group, N-(2,5-difluorophenylmethyl)-N-methylamino group, N-(3,4-difluorophenylmethyl)amino group, N-(3,4-difluorophenylmethyl)-N-methylamino group, N-(3,5-difluorophenylmethyl)amino group, N-(3,5-difluorophenylmethyl)-N-methylamino group, N-(2,3-dichlorophenylmethyl)amino group, N-(2,3-dichlorophenylmethyl)-N-methylamino group, N-(2,4-dichlorophenylmethyl)amino group, N-(2,4-dichlorophenylmethyl)-N-methylamino group, N-(2,5-dichlorophenylmethyl)amino group, N-(2,5-dichlorophenylmethyl)-N-methylamino group, N-(2,6-dichlorophenylmethyl)amino group, N-(2,6-dichlorophenylmethyl)-N-methylamino group, N-(3,4-dichlorophenylmethyl)amino group, N-(3,4-dichlorophenylmethyl)-N-methylamino group, N-(3,5-dichlorophenylmethyl)amino group, N-(3,5-dichlorophenylmethyl)-N-methylamino group, N-[2-(trifluoromethyl)phenylmethyl]amino group, N-methyl-N-[2-(trifluoromethyl)phenylmethyl]amino group, N-[3-(trifluoromethyl)phenylmethyl]amino group, N-methyl-N-[3-(trifluoromethyl)phenylmethyl]amino group, N-[4-(trifluoromethyl)phenylmethyl]amino group, N-methyl-N-[4-(trifluoromethyl)phenylmethyl]amino group, 1-pyrrolidino group, 1-(4-methylpiperidino) group, 1-homopiperidino group, or 4-morpholino group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-6-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

(65-3) The compound or salt thereof according to (1) mentioned above, wherein, in the formula (I), Link is —$(CH_2)_n$—, n is an integer of 2, $C^3$ is carbon atom to which AR binds, $C^4$ is carbon atom to which Rs binds, $C^5$ is nitrogen atom, $C^2$ and $C^6$ are unsubstituted ring-constituting carbon atoms, Rs is —N(Ry)(Rz), and the group represented by —N(Ry)(Rz) is N,N-dimethylamino group, N-ethyl-N-methylamino group, N,N-diethylamino group, N-methyl-N-propylamino group, N-ethyl-N-propylamino group, N-isopropyl-N-methylamino group, N-ethyl-N-isopropylamino group, N-butylamino group, N-butyl-N-methylamino group, N-butyl-N-ethylamino group, N-isobutylamino group, N-isobutyl-N-methylamino group, N-ethyl-N-isobutylamino group, N-(2-ethylbutyl)amino group, N-(2-ethylbutyl)-N-methylamino group, N-cyclopentylamino group, N-cyclopentyl-N-methylamino group, N-cyclohexylamino group, N-cyclohexyl-N-methylamino group, N-cycloheptylamino group, N-(cyclopentylmethyl)amino group, N-(cyclopentylmethyl)-N-methylamino group, N-(cyclohexylmethyl)amino group, N-(cyclohexylmethyl)-N-methylamino group, N-(2-methylphenyl)amino group, N-(4-methylphenyl)amino group, N-(2-fluorophenyl)amino group, N-(3-fluorophenyl)amino group, N-(4-fluorophenyl)amino group, N-(2-chlorophenyl)amino group, N-(3-chlorophenyl)amino group, N-(4-chlorophenyl)amino group, N-(indan-2-yl)amino group, N-(1-phenylethyl)amino group, N-[1-(2-fluorophenyl)ethyl]amino group, N-[1-(3-fluorophenyl)ethyl]amino group, N-[1-(4-fluorophenyl)ethyl]amino group, N-[1-(2-chlorophenyl)ethyl]amino group, N-[1-(3-chlorophenyl)ethyl]amino group, N-[1-(4-chlorophenyl)ethyl]amino group, N-(2-methylphenylmethyl)amino group, N-methyl-N-(2-methylphenylmethyl)amino group, N-(3-methylphenylmethyl)amino group, N-methyl-N-(3-methylphenylmethyl)amino group, N-(4-methylphenylmethyl)amino group, N-methyl-N-(4-methylphenylmethyl)amino group, N-(2-fluorophenylmethyl)amino group, N-(2-fluorophenylmethyl)-N-methylamino group, N-(3-fluorophenylmethyl)amino group, N-(3-fluorophenylmethyl)-N-methylamino group, N-(4-fluorophenylmethyl)amino group, N-(4-fluorophenylmethyl)-N-methylamino group, N-(2-chlorophenylmethyl)amino group, N-(2-chlorophenylmethyl)-N-methylamino group, N-(3-chlorophenylmethyl)amino group, N-(3-chlorophenylmethyl)-N-methylamino group, N-(4-chlorophenylmethyl)amino group, N-(4-chlorophenylmethyl)-N-methylamino group, N-(2,3-difluorophenylmethyl)amino group, N-(2,3-difluorophenylmethyl)-N-methylamino group, N-(2,4-difluorophenylmethyl)amino group, N-(2,4-difluorophenylmethyl)-N-methylamino group, N-(2,5-difluorophenylmethyl)amino group, N-(2,5-difluorophenylmethyl)-N-methylamino group, N-(3,4-difluorophenylmethyl)amino group, N-(3,4-difluorophenylmethyl)-N-methylamino group, N-(3,5-difluorophenylmethyl)amino group, N-(3,5-difluorophenylmethyl)-N-methylamino group, N-(2,3-dichlorophenylmethyl)amino group, N-(2,3-dichlorophenylmethyl)-N-methylamino group, N-(2,4-dichlorophenylmethyl)amino group, N-(2,4-dichlorophenylmethyl)-N-methylamino group, N-(2,5-dichlorophenylmethyl)amino group, N-(2,5-dichlorophenylmethyl)-N-methylamino group, N-(2,6-dichlorophenylmethyl)amino group, N-(2,6-dichlorophenylmethyl)-N-methylamino group, N-(3,4-dichlorophenylmethyl)amino group, N-(3,4-dichlorophenylmethyl)-N-methylamino group, N-(3,5-dichlorophenylmethyl)amino group, N-(3,5-dichlorophenylmethyl)-N-methylamino group, N-[2-(trifluoromethyl)phenylmethyl]amino group, N-methyl-N-[2-(trifluoromethyl)phenylmethyl]amino group, N-[3-(trifluoromethyl)phenylmethyl]amino group, N-methyl-N-[3-(trifluoromethyl)phenylmethyl]amino group, N-[4-(trifluoromethyl)phenylmethyl]amino group, N-methyl-N-[4-(trifluoromethyl)phenylmethyl]amino group, 1-pyrrolidino group, 1-(4-methylpiperidino) group, 1-homopiperidino group, or 4-morpholino group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

(66) The compound or salt thereof according to (1-2) mentioned above, wherein, in the formula (I), n is an integer of 2, AR binds to $C^3$ in the aromatic ring (E), Rs binds to $C^4$ in the aromatic ring (E), $C^5$ is carbon atom substituted with —N($Rn^1$)($Rn^2$) (provided that one of $Rn^1$ and $Rn^2$ is a substituent other than hydrogen atom), $C^2$ and $C^6$ are unsubsti-

(67) The compound or salt thereof according to (4) mentioned above, wherein, in the formula (I), Link is —$(CH_2)_n$—, n is an integer of 2, AR binds to $C^3$ in the aromatic ring (E), Rs binds to $C^4$ in the aromatic ring (E), $C^5$ is carbon atom substituted with —$N(Rn^1)(Rn^2)$ (provided that one of $Rn^1$ and $Rn^2$ is a substituent other than hydrogen atom), $C^2$ and $C^6$ are unsubstituted ring-constituting carbon atoms, Rs is —O—Rx, and Y is hydrogen atom or a lower alkyl group having 1 to 4 carbon atoms.

(68) The compound or salt thereof according to (5) mentioned above, wherein, in the formula (I), Link is —$(CH_2)_n$—, n is an integer of 2, AR binds to $C^3$ in the aromatic ring (E), Rs binds to $C^4$ in the aromatic ring (E), $C^5$ is carbon atom substituted with —$N(Rn^1)(Rn^2)$ (provided that one of $Rn^1$ and $Rn^2$ is a substituent other than hydrogen atom), $C^2$ and $C^6$ are unsubstituted ring-constituting carbon atoms, Rs is —O—Rx, and Y is hydrogen atom or a lower alkyl group having 1 to 4 carbon atoms.

(69) The compound or salt thereof according to any one of (66) to (68) mentioned above, wherein, in the formula (I), Xa which may substitute on AR is methyl group, ethyl group, propyl group, hydroxyethyl group, carboxymethyl group, hydroxyl group, methoxy group, 2-hydroxyethyloxy group, amino group, methylamino group, dimethylamino group, carboxyl group, carbamoyl group, acetyl group, methanesulfonyl group, sulfamoyl group, or N,N-dimethylsulfamoyl group.

(70) The compound or salt thereof according to any one of (66) to (69) mentioned above, wherein, in the formula (I), Rs is —O—Rx, Rx is a group selected from butyl group, isobutyl group, 2-ethylbutyl group, cyclopentyl group, cyclohexyl group, cycloheptyl group, cyclopentylmethyl group, and cyclohexylmethyl group, or Rb (provided that Q in Rb is phenyl group or indan-2-yl group), $A^1$ is a single bond, or methylene group substituted with methyl group or ethyl group or unsubstituted methylene group, or ethylene group substituted with methyl group or ethyl group or unsubstituted ethylene group, $A^2$ represents a single bond, oxygen atom, sulfur atom, —N(methyl)-, or —N(ethyl)- (provided that when $A^2$ is oxygen atom, sulfur atom, —N(methyl)-, or —N(ethyl)-, $A^1$ is ethylene), and $R^2$ and $R^3$ independently represent hydrogen atom, methyl group, fluorine atom, chlorine atom, trifluoromethyl group, methoxy group, or dimethylamino group (provided that when Q is phenyl group, $A^1$ is a single bond or unsubstituted methylene, and $A^2$ is a single bond, one of $R^2$ and $R^3$ is a substituent other than hydrogen atom).

(71) The compound or salt thereof according to (1-2) mentioned above, wherein, in the formula (I), n is an integer of 2, $C^3$ is carbon atom to which AR binds, $C^4$ is carbon atom to which Rs binds, $C^5$ is carbon atom substituted with Zx, $C^2$ and $C^6$ are unsubstituted ring-constituting carbon atoms, Zx is N-methylamino group, N-ethylamino group, N-propylamino group, N-isopropylamino group, N,N-dimethylamino group, N,N-diethylamino group, formylamino group, acetylamino group, carbamoylamino group, mesylamino group, or N,N-dimethylsulfamoylamino group, Rs is —O—Rx, Rx is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl) ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl) ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl) ethyl group, 2-[2-(trifluoromethyl)phenyl]ethyl group, 2-[3-(trifluoromethyl)phenyl]ethyl group, 2-[4-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino) ethyl group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino) naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b] thiophen-5-yl group, 2-methylbenzo[b]thiophen-5-yl group, 3-methylbenzo[b]thiophen-5-yl group, 2,3-dimethylbenzo [b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

(72) The compound or salt thereof according to (1-2) mentioned above, wherein, in the formula (I), n is an integer of 2, AR binds to $C^3$ in the aromatic ring (E), Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, Rs is -D-Rc, D is oxygen atom or sulfur atom, and Y is hydrogen atom or a lower alkyl group having 1 to 4 carbon atoms.

(73) The compound or salt thereof according to (4) mentioned above, wherein, in the formula (I), Link is —$(CH_2)_n$—, n is an integer of 2, AR binds to $C^3$ in the aromatic ring (E), Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, Rs is —O—Rc, and Y is hydrogen atom or a lower alkyl group having 1 to 4 carbon atoms.

(74) The compound or salt thereof according to (5) mentioned above, wherein, in the formula (I), Link is —$(CH_2)_n$—, n is an integer of 2, AR binds to $C^3$ in the aromatic ring (E), Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, Rs is —O—Rc, and Y is hydrogen atom or a lower alkyl group having 1 to 4 carbon atoms.

(75) The compound or salt thereof according to any one of (72) to (74) mentioned above, wherein, in the formula (I), Xa which may substitute on AR is methyl group, ethyl group, propyl group, hydroxyethyl group, carboxymethyl group, hydroxyl group, methoxy group, 2-hydroxyethyloxy group, amino group, methylamino group, dimethylamino group, carboxyl group, carbamoyl group, acetyl group, methanesulfonyl group, sulfamoyl group, or N,N-dimethylsulfamoyl group.

(76) The compound or salt thereof according to (1-2) mentioned above, wherein, in the formula (I), n is an integer of 1 to 3, $C^3$ is carbon atom to which AR binds, $C^4$ is carbon atom to which Rs binds, $C^5$ may be replaced with V, $C^2$ and $C^6$ are unsubstituted ring-constituting carbon atoms, V is nitrogen atom, or carbon atom substituted with Zx, Zx is fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, or N,N-dimethylsulfamoylamino group, Rs is -D-Rc, D is oxygen atom or sulfur atom, p in Rc is an integer of 2 or 3, $A^4$ is a single bond or methylene, $A^5$ is —C(O)—, —C(S)—, or —S(O)$_2$—, Rd is hydrogen atom, or methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, or pyridin-4-yl group, Re is methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, or ethyloxycarbonylamino group, AR is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo [3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa), Xa is oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl) amino group, methanesulfonyl group, sulfamoyl group, N-methylsulfamoyl group, N,N-dimethylsulfamoyl group, carboxyl group, acetyl group, carbamoyl group, or N,N-dimethylcarbamoyl group, and Y is hydrogen atom, methyl group, or ethyl group.

(77) The compound or salt thereof according to (1-2) mentioned above, wherein, in the formula (I), n is an integer of 2, $C^3$ is carbon atom to which AR binds, $C^4$ is carbon atom to which Rs binds, $C^5$ may be replaced with V, $C^2$ and $C^6$ are unsubstituted ring-constituting carbon atoms, V is nitrogen atom, or carbon atom substituted with Zx, Zx is fluorine atom, chlorine atom, bromine atom, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, or N,N-dimethylsulfamoylamino group, Rs is —O—Rc, p in Rc is an integer of 2, $A^4$ is a single bond or methylene, $A^5$ is —C(O)—, —C(S)—, or —S(O)$_2$—, Rd is methyl group, ethyl group, propyl group, isopropyl group, butyl group, isobutyl group, cyclopropyl group, cyclopentyl group, cyclohexyl group, phenyl group, 4-methylphenyl group, 4-chlorophenyl group, 4-fluorophenyl group, benzyl group, 4-chlorophenylmethyl group, or 4-fluorophenylmethyl group, Re is isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, pyrrolidino group, piperidino group, or morpholino group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino) naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

(78) The compound or salt thereof according to (7) mentioned above, wherein, in the formula (I), Link is —$(CH_2)_n$—, n is an integer of 2, AR binds to $C^8$ in the aromatic ring (E), Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, Rs is —O—Rx, and Y is hydrogen atom or a lower alkyl group having 1 to 4 carbon atoms.

(79) The compound or salt thereof according to (78) mentioned above, wherein, in the formula (I), Xa which may substitute on AR is methyl group, ethyl group, propyl group, hydroxyethyl group, carboxymethyl group, hydroxyl group, methoxy group, 2-hydroxyethyloxy group, amino group, methylamino group, dimethylamino group, carboxyl group, carbamoyl group, acetyl group, methanesulfonyl group, sulfamoyl group, or N,N-dimethylsulfamoyl group.

(80) The compound or salt thereof according to (78) or (79) mentioned above, wherein, in the formula (I), Rs is —O—Rx, Rx is butyl group, isobutyl group, 2-ethylbutyl group, cyclopentyl group, cyclohexyl group, cycloheptyl group, cyclopentylmethyl group, or cyclohexylmethyl group, or Rb (provided that Q in Rb is phenyl group or indan-2-yl group), $A^1$ is a single bond, or methylene group substituted with methyl group or ethyl group or unsubstituted methylene group, or ethylene group substituted with methyl group or ethyl group or unsubstituted ethylene group, $A^2$ is a single bond, oxygen atom, sulfur atom, —N(methyl)-, or —N(ethyl)- (provided that when $A^2$ is oxygen atom, sulfur atom, —N(methyl)-, or —N(ethyl)-, $A^1$ is ethylene), and $R^2$ and $R^3$ independently represent hydrogen atom, methyl group, fluorine atom, chlorine atom, trifluoromethyl group, methoxy group, or dimethylamino group (provided that when Q is phenyl group, $A^1$ is a single bond or unsubstituted methylene, and $A^2$ is a single bond, one of $R^2$ and $R^3$ is a substituent other than hydrogen atom).

(81) The compound or salt thereof according to (1-2) mentioned above, wherein, in the formula (I), n is an integer of 1 to 3, $C^3$ is carbon atom to which AR binds, $C^4$ is carbon atom to which Rs binds, $C^5$ may be replaced with V, $C^2$ and $C^6$ are unsubstituted ring-constituting carbon atoms, V is nitrogen atom, or carbon atom substituted with Zx, Zx is fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, or N,N-dimethylsulfamoylamino group, Rs is —O—Rx, Rx is butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or Rb or Rc, Q in Rb is phenyl group, thienyl group, furyl group, pyridyl group, oxazolyl group, naphthyl group, tetrahydronaphthyl group, indanyl group, indolyl group, or dihydrobenzodioxyl group, $A^2$ is a single bond, oxygen atom, sulfur atom, —N(methyl)-, or —N(ethyl)- (provided that when $A^2$ is oxygen atom, sulfur atom, —N(methyl)-, or —N(ethyl)-, $A^1$ is ethylene), $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q is phenyl group, $A^1$ is a single bond or unsubstituted methylene, and $A^2$ is a single bond, one of $R^2$ and $R^3$ is a substituent other than hydrogen atom), p in Rc is an integer of 2 or 3, $A^4$ is a single bond or methylene, $A^5$ is —C(O)—, —C(S)—, or —S(O)$_2$—, Rd is hydrogen atom, or methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, or pyridin-4-yl group, Re is methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, or ethyloxycarbonylamino group, AR is cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-5-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa), Xa is oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, or N,N-dimethylcarbamoyl group, and Y is hydrogen atom, methyl group, or ethyl group.

(82) The compound or salt thereof according to (6) mentioned above, wherein, in the formula (I), Link is —$(CH_2)_n$—, AR binds to $C^3$ in the aromatic ring (E), Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, Rs is —O—Rx, and Rx is a linear or branched saturated alkyl group having 3 to 8 carbon atoms, or Ra or Rb.

(83) The compound or salt thereof according to (82) mentioned above, wherein, in the formula (I), Zx is fluorine atom, chlorine atom, nitro group, amino group, methyl group, or $OR^9$.

(84) The compound or salt thereof according to (1-2) mentioned above, wherein, in the formula (I), n is an integer of 1 to 3, AR binds to $C^3$, Rs binds to one of the ring-constituting atoms $C^4$, $C^5$, and $C^6$, a ring-constituting carbon atom to which Rs does not bind among $C^4$, $C^5$, and $C^6$ may be replaced with V, V is nitrogen atom or carbon atom substituted with Zx, Zx is fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, or N,N-dimethylsulfamoylamino group, Rs is -D-Rx or —N(Ry)(Rz), D is oxygen atom or sulfur atom, Rx is butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or Rb or Rc, Q in Rb is phenyl group, thienyl group, furyl group, pyridyl group, oxazolyl group, naphthyl group, tetrahydronaphthyl group, indanyl group, indolyl group, or dihydrobenzodioxyl group, $A^2$ is a single bind, oxygen atom, sulfur atom, —N(methyl)-, or —N(ethyl)- (provided that when $A^2$ is oxygen atom, sulfur atom, —N(methyl)-, or —N(ethyl)-, $A^1$ is ethylene), $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q is phenyl group, $A^1$ is a single bind or unsubstituted methylene, and $A^2$ is a single bind, one of $R^2$ and $R^3$ is a substituent other than hydrogen atom), p in Rc is an integer of 2 or 3, $A^4$ is a single bind or methylene, $A^5$ is —C(O)—, —C(S)—, or —$S(O)_2$—, Rd is hydrogen atom, or methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, or pyridin-4-yl group, Re is methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group or ethyloxycarbonylamino group, Rz is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, or (morpholino-4-yl)carbonyl group, Ry is hydrogen atom, methyl group, ethyl group or isobutyl group, or binds to Rz to form pyrrolidino group, piperidino group, piperazino group, morpholino group, pyrrol-1-yl group, imidazol-1-yl group, or pyrazol-1-yl group together with the nitrogen atom, AR is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa), Xa is oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, or N,N-dimethylcarbamoyl group, and Y is hydrogen atom, methyl group, or ethyl group.

(85) A medicament containing a compound represented by the aforementioned formula (I) or a pharmacologically acceptable salt thereof as an active ingredient.

(86) An agent for suppressing production of a prostaglandin and/or leukotriene, which contains a compound represented by the aforementioned formula (I) or a pharmacologically acceptable salt thereof as an active ingredient.

(87) The medicament according to (85) for prophylactic and/or therapeutic treatment of a disease caused by production of a prostaglandin and/or leukotriene.

(88) The medicament according to (85) for prophylactic and/or therapeutic treatment of an inflammatory disease of a mammal.

(89) The medicament according to (85) for prophylactic and/or therapeutic treatment of an autoimmune disease of a mammal.

(90) The medicament according to (85) for prophylactic and/or therapeutic treatment of an allergic disease of a mammal.

(91) The medicament according to (85) for defervescence and/or pain relief of a mammal.

(92) A pharmaceutical composition for prophylactic and/or therapeutic treatment of a condition of living body of a mammal exhibiting an acute or chronic inflammatory reaction, which comprises a prophylactically and/or therapeutically effective amount of a compound represented by the aforementioned formula (I) or a pharmacologically acceptable salt thereof and a pharmaceutically acceptable carrier.

(93) A method for prophylactic and/or therapeutic treatment of a condition of living body of a mammal exhibiting an acute or chronic inflammatory reaction, which comprises administering a prophylactically and/or therapeutically effective amount of a compound represented by the aforementioned formula (I) or a pharmacologically acceptable salt thereof to the mammal.

(94) A compound represented by the following formula (II):

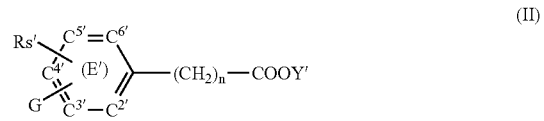

(II)

[In the formula, each of $C^{2'}$, $C^{3'}$, $C^{4'}$, $C^{5'}$, and $C^{6'}$ in the aromatic ring (E') represents a ring-constituting carbon atom, any one of them to which Rs' and G does not bind may be replaced with V', V' represents nitrogen atom, or carbon atom substituted with Zx', Zx' has the same meaning as Zx mentioned above, provided that when Zx contains hydroxyl group, the hydroxyl group may be protected with $Rp^1$, and when Zx contains amino group, the amino group may be protected with $Rp^2$, Rs' represents -D-Rx' or —N(Ry')(Rz'), -D-Rx' and —N(Ry')(Rz') have the same meanings as -D-Rx and —N(Ry)(Rz), respectively, provided that when -D-Rx or —N(Ry)(Rz) contains hydroxyl group, the hydroxyl group may be protected with $Rp^1$, when -D-Rx or —N(Ry)(Rz) contains amino group, the amino group may be protected with $Rp^2$, G represents chlorine atom, bromine atom, iodine atom, mesylate group, triflate group, or an arenesulfonate group of which aromatic portion may be substituted with one of $T^1$ or two or more of the same or different $T^1$, and Y' represents a lower alkyl group having 1 to 4 carbon atoms].

(95) The compound according to (94) mentioned above, wherein, in the formula (II), G binds to the ring-constituting carbon atom $C^{2'}$ or $C^{8'}$ in the aromatic ring (E').

(96) The compound according to (94) or (95) mentioned above, wherein, in the formula (II), n is an integer of 2.

(97) The compound according to any one of (94) to (96) mentioned above, wherein, in the formula (II), Rs' is —O—Rx'.

(98) The compound according to any one of (94) to (97) mentioned above, wherein, in the formula (II), Rs' is -D-Rx' or —N(Ry')(Rz'), D is a single bind, oxygen atom, sulfur atom, —S(O)—, —S(O)$_2$—, or —C(O)—, Rx' is a linear or branched saturated alkyl group having 3 to 8 carbon atoms, or Ra, Rb, or Rc, k in Ra is 0 or an integer of 1 to 3, $R^1$ is a saturated cyclic alkyl group having 3 to 7 carbon atoms or a condensed saturated cyclic alkyl group having 6 to 8 carbon atoms, $R^1$ may be substituted with one of lower alkyl group having 1 to 4 carbon atoms or two or more of the same or different lower alkyl groups having 1 to 4 carbon atoms, Q in Rb is phenyl group, thienyl group, furyl group, pyrrolyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, tetrahydronaphthyl group, indanyl group, indenyl group, quinolyl group, isoquinolyl group, indolyl group, benzofuryl group, benzothienyl group, benzimidazolyl group, benzoxazolyl group, benzothiazolyl group, indazolyl group, 4H-chromenyl group, dihydrobenzodioxyl group, benzoisoxazolyl group, pyrrolopyridinyl group, pyrazolopyridinyl group, triazolopyridinyl group, thienopyridinyl group, thienopyrazolyl group, 1,3-dihydrobenzimidazole group, dihydro-3H-benzoxazole group, or dihydro-3H-benzothiazole group, which binds to $A^2$ at an arbitrary position on the ring, $A^1$ is a single bind or an alkylene (a) having 1 to 3 carbon atoms, the alkylene (a) may be substituted with a lower alkyl group having 1 to 4 carbon atoms or phenyl group, $A^2$ is a single bind, oxygen atom, sulfur atom, —S(O)—, —S(O)$_2$—, or —N(R$^4$)— (provided that when $A^2$ is oxygen atom, sulfur atom, —S(O)—, —S(O)$_2$—, or —N(R$^4$)—, $A^1$ is ethylene or trimethylene), $R^2$ and $R^3$ independently represent hydrogen atom, a linear or branched saturated alkyl group having 1 to 4 carbon atoms, oxo group, thioxo group, fluorine atom, chlorine atom, bromine atom, trifluoromethyl group, —OR$^5$, —N(R$^6$)(R$^{6'}$), —NHCOR$^7$, —NHSO$_2$R$^8$, or -A$^6$-Qa, or they bind to each other to form methylenedioxy group, Qa may be substituted with one of T$^1$ or two or more of the same or different T$^1$, and is phenyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, indanyl group, indenyl group, quinolyl group, isoquinolyl group, indolyl group, benzofuryl group, benzothienyl group, benzimidazolyl group, benzoxazolyl group, benzothiazolyl group, or indazolyl group, which binds to A$^6$ at an arbitrary position on the ring, $R^4$ and $R^6$ independently represent hydrogen atom or a lower alkyl group having 1 to 4 carbon atoms, $R^5$ and $R^7$ independently represent hydrogen atom or a lower alkyl group having 1 to 4 carbon atoms, or -A$^6$-Qa, $R^8$ represents a lower alkyl group having 1 to 4 carbon atoms, $R^{6'}$ has the same meaning as $R^6$, or binds to $R^6$ to form a 3- to 6-membered ring of a cycloalkyl group or morpholino group together with the nitrogen atom to which they bind, p in Rc is an integer of 2 to 4, $A^4$ is a single bind or methylene or ethylene, $A^5$ is —C(O)—, —C(S)—, or —S(O)$_2$—, Rd is hydrogen atom, an alkyl group having 1 to 8 carbon atoms, or Qa, Re is an alkyl group having 1 to 8 carbon atoms, -A$^6$-Qa, —(CH$_2$)$_i$R$^{14}$, —OR$^{28}$, —SR$^{28}$, or —N(R$^{29}$)(R$^{30}$), i is an integer of 1 to 3, $R^{14}$ is hydroxyl group, an alkoxy group having 1 to 4 carbon atoms, carboxyl group, or an N,N-dialkylcarbamoyl group having 1 to 4 carbon atoms, $R^{28}$ is an alkyl group having 1 to 8 carbon atoms or -A$^6$-Qa, $R^{29}$ is an alkyl group having 1 to 8 carbon atoms, an alkoxycarbonyl group having 1 to 4 carbon atoms, or -A$^6$-Qa, $R^{30}$ represents hydrogen atom or a lower alkyl group having 1 to 4 carbon atoms, or binds to $R^{29}$ to form a 3- to 6-membered ring of nitrogen-containing cycloalkyl group or morpholino group together with the nitrogen atom to which they bind, Rz' has the same meaning as Rx', or represents -A$^5$-Re, Ry' represents hydrogen atom, an alkyl group having 1 to 8 carbon atoms, or -A$^6$-Qp, or binds to Rz' to form a saturated or unsaturated nitrogen-containing cyclic substituent having 3 to 7 atoms together with the nitrogen atom to which they bind, when -D-Rx' or —N(Ry')(Rz') contains hydroxyl group, the hydroxyl group may be protected with Rp$^1$, and when -D-Rx' or —N(Ry')(Rz') contains amino group, the amino group may be protected with Rp$^2$.

(99) The compound according to (94) mentioned above, wherein, in the formula (II), n is an integer of 1 to 3, G binds to C$^{3'}$, Rs' binds to one of the ring-constituting carbon atoms C$^{4'}$, C$^{5'}$, and C$^{6'}$, a ring-constituting carbon atom to which Rs' does not bind among C$^{4'}$, C$^{5'}$, and C$^{6'}$ may be replaced with V', V' is nitrogen atom or carbon atom substituted with Zx', Zx' is fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, or N,N-dimethylsulfamoylamino group, provided that when Zx' contains hydroxyl group, the hydroxyl group may be protected with Rp$^1$, and when Zx' contains amino group, the amino group may be protected with Rp$^2$, Rs' is -D-Rx' or —N(Ry')(Rz'), D is oxygen atom or sulfur atom, Rx' is butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or Rb or Rc, Q in Rb is phenyl group, thienyl group, furyl group, pyridyl group, oxazolyl group, naphthyl group, tetrahydronaphthyl group, indanyl group, indolyl group, or dihydrobenzodioxyl group, $A^2$ is a single bind, oxygen atom, sulfur atom, —N(methyl)-, or —N(ethyl)- (provided that when $A^2$ is oxygen atom, sulfur atom, —N(methyl)-, or —N(ethyl)-, $A^1$ is ethylene), $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q is phenyl group, $A^1$ is a single bind or unsubstituted methylene, and $A^2$ is a single bind, one of $R^2$ and $R^3$ is a substituent other than hydrogen atom), p in Rc is an integer of 2 or 3, $A^4$ is a single bind or methylene, $A^5$ is —C(O)—, —C(S)—, or —S(O)$_2$—, Rd is hydrogen atom, or methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, or pyridin-4-yl group, Re is methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2- yl)amino group, N-(pyridin-3-yl)amino group, N-(pyridin-4-yl)amino group, N-(furan-2-yl)amino group, N-(furan-3-yl) amino group, N-(thiophen-2-yl)amino group, N-(thiophen-3-yl)amino group, pyrrolidino group, piperidino group, morpholino group, methyloxycarbonylamino group or ethyloxycarbonylamino group, Rz is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, or (morpholino-4-yl)carbonyl group, Ry is hydrogen atom, methyl group, ethyl group or isobutyl group, or binds to Rz to form pyrrolidino group, piperidino group, piperazino group, morpholino group, pyrrol-1-yl group, imidazol-1-yl group, or pyrazol-1-yl group together with the nitrogen atom to which they binds, provided that when -D-Rx' or —N(Ry')(Rz') contains hydroxyl group, the hydroxyl group may be protected with $Rp^1$, and when -D-Rx' or —N(Ry')(Rz') contains amino group, the amino group may be protected with $Rp^2$, G is chlorine atom, bromine atom, iodine atom, or triflate group, and Y' is methyl group or ethyl group.

(100) The compound according to any one of (94) to (96) mentioned above, wherein, in the formula (II), Rs' is —N(Ry')(Rz').

(101) The compound according to any one of (94) to (96) mentioned above, wherein, in the formula (II), Rs' is -D-Rx', and D is sulfur atom, —S(O)—, —S(O)$_2$— or —C(O)—.

(102) The compound according to (94) mentioned above, wherein, in the formula (II), G binds at the position of $C^{2'}$ in the aromatic ring (E'), Rs' binds to one of the ring-constituting carbon atoms $C^{3'}$, $C^{4'}$ and $C^{5'}$, and all of $C^{2'}$, $C^{3'}$, $C^{4'}$, $C^{5'}$ and $C^{6'}$ in the aromatic ring (E') are not replaced with V'.

(103) The compound according to (94) mentioned above, wherein, in the formula (II), n is an integer of 1 to 3, G binds to $C^{2'}$, Rs' binds to one of the ring-constituting carbon atoms $C^{4'}$, $C^{5'}$, and $C^{6'}$, a ring-constituting carbon atom to which Rs' does not bind among $C^{3'}$, $C^{4'}$, and $C^{5'}$ may be replaced with V', V' is nitrogen atom, or carbon atom substituted with Zx', Zx' is fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, or N,N-dimethylsulfamoylamino group, provided that when Zx' contains hydroxyl group, the hydroxyl group may be protected with $Rp^1$, and when Zx' contains amino group, the amino group may be protected with $Rp^2$, Rs' is -D-Rx' or —N(Ry')(Rz'), D is oxygen atom or sulfur atom, Rx' is butyl group, isobutyl group, 2-ethylbutyl group, cyclopentyl group, cyclohexyl group, cycloheptyl group, cyclopentylmethyl group, cyclohexylmethyl group, 2-cyclopentylethyl group, 2-cyclohexylethyl group, or Rb or Rc, Q in Rb is phenyl group, thienyl group, furyl group, pyridyl group, oxazolyl group, naphthyl group, tetrahydronaphthyl group, indanyl group, indolyl group, or dihydrobenzodioxyl group, $A^2$ is a single bind, oxygen atom, sulfur atom, —N(methyl)-, or —N(ethyl)- (provided that when $A^2$ is oxygen atom, sulfur atom, —N(methyl)-, or —N(ethyl)-, $A^1$ is ethylene), $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q is phenyl group, $A^1$ is a single bind or unsubstituted methylene, and $A^2$ is a single bind, one of $R^2$ and $R^3$ is a substituent other than hydrogen atom), p in Rc is an integer of 2 or 3, $A^4$ is a single bind or methylene, $A^5$ is —C(O)—, —C(S)—, or —S(O)$_2$—, Rd is hydrogen atom, or methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, or pyridin-4-yl group, Re is methyl group, ethyl group, propyl group, isopropyl group, butyl group, isobutyl group, t-butyl group, cyclopropyl group, cyclopentyl group, cyclohexyl group, cyclopentylethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl) amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl) amino group, N-(thiophen-2-yl)amino group, N-(thiophen-3-yl)amino group, pyrrolidino group, piperidino group, morpholino group, methyloxycarbonylamino group, or ethyloxycarbonylamino group, Rz is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl) ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group; 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl) ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl) ethyl group, 2-[2-(trifluoromethyl)phenyl]ethyl group, 2-[3-(trifluoromethyl)phenyl]ethyl group, 2-[4-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino) ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, or (morpholino-4-yl)carbonyl group, Ry is hydrogen atom, methyl group, ethyl group or isobutyl group, or binds to Rz to form pyrrolidino group, piperidino group, piperazino group, morpholino group, pyrrol-1-yl group, imidazol-1-yl group, or pyrazol-1-yl group together with the nitrogen atom, provided that when -D-Rx' or —N(Ry')(Rz') contains hydroxyl group, the hydroxyl group may be protected with $Rp^1$, and when -D-Rx' or —N(Ry')(Rz') contains amino group, the amino group may be protected with $Rp^2$, G is chlorine atom, bromine atom, iodine atom, or triflate group, and Y' is methyl group or ethyl group.

(104) The compound according to (102) or (103) mentioned above, wherein, in the formula (II), n is an integer of 2, Rs' binds to $C^{3'}$ in the aromatic ring (E'), Rs' is —O—Rx', and Y' is methyl group or ethyl group.

(105) The compound according to (94) mentioned above, wherein, in the formula (II), n is an integer of 2, $C^{2'}$ is a ring-constituting carbon atom to which G binds, $C^{3'}$ is a ring-constituting carbon atom to which Rs' binds, $C^{4'}$ may be replaced with V', $C^{5'}$ and $C^{6'}$ are unsubstituted ring-constituting carbon atoms, V' is nitrogen atom, or carbon atom substituted with Zx', Zx' is fluorine atom, methyl group, hydroxyl group, amino group, N-methylamino group, or N,N-dimethylamino group, provided that when Zx' contains hydroxyl group, the hydroxyl group may be protected with $Rp^1$, and when Zx' contains amino group, the amino group may be protected with $Rp^2$, Rs' is —O—Rx', Rx' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl) ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl) ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl) ethyl group, 2-[2-(trifluoromethyl)phenyl]ethyl group, 2-[3-(trifluoromethyl)phenyl]ethyl group, 2-[4-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino) ethyl group, G is bromine atom or iodine atom, and Y' is methyl group or ethyl group.

(106) The compound according to (102) or (103) mentioned above, wherein, in the formula (II), n is an integer of 2, Rs' binds at the position of $C^{4'}$ in the aromatic ring (E'), Rs' is —O—Rx', and Y' is methyl group or ethyl group.

(107) The compound according to (94) mentioned above, wherein, in the formula (II), n is an integer of 2, $C^{2'}$ is a ring-constituting carbon atom to which G binds, $C^{4'}$ is a ring-constituting carbon atom to which Rs' binds, $C^{5'}$ may be replaced with V', $C^{3'}$ and $C^{6'}$ are unsubstituted ring-constituting carbon atoms, V' is nitrogen atom, or carbon atom substituted with Zx', Zx' is fluorine atom, methyl group, hydroxyl group, amino group, N-methylamino group, or N,N-dimethylamino group, provided that when Zx' contains hydroxyl group, the hydroxyl group may be protected with $Rp^1$, and when Zx' contains amino group, the amino group may be protected with $Rp^2$, Rs' is —O—Rx', Rx' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl) ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl) ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)

ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino)ethyl group, G is bromine atom or iodine atom, and Y' is methyl group or ethyl group.

(108) The compound according to (102) or (103) mentioned above, wherein, in the formula (II), n is an integer of 2, Rs' binds at the position of $C^{5'}$ in the aromatic ring (E'), Rs' is —O—Rx', and Y' is methyl group or ethyl group.

(109) The compound according to (94) mentioned above, wherein, in the formula (II), G binds to $C^{3'}$ in the aromatic ring (E'), Rs' binds to $C^{5'}$ or $C^{6'}$ in the aromatic ring (E'), and all of $C^{2'}$, $C^{3'}$, $C^{4'}$, $C^{5'}$ and $C^{6'}$ in the aromatic ring (E') are not replaced with V'.

(110) The compound according to (109) mentioned above, wherein, in the formula (II), n is an integer of 2, Rs' binds to $C^{5'}$ in the aromatic ring (E'), and Rs' is —O—Rx'.

(111) The compound according to (94) mentioned above, wherein, in the formula (II), n is an integer of 2, $C^{8'}$ is carbon atom to which G binds, $C^{5'}$ is carbon atom to which Rs' binds, $C^{2'}$, $C^{4'}$, and $C^{6'}$ are unsubstituted ring-constituting carbon atoms, Rs' is —O—Rx', Rx' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group or 2-(N-ethyl-N-phenylamino)ethyl group, G is bromine atom or iodine atom, and Y' is methyl group or ethyl group.

(112) The compound according to (109) mentioned above, wherein, in the formula (II), n is an integer of 2, Rs' binds to $C^{6'}$ in the aromatic ring (E'), and Rs' is —O—Rx'.

(113) The compound according to (94) mentioned above, wherein, in the formula (II), G binds to $C^{3'}$ in the aromatic ring (E'), Rs' binds to $C^{4'}$ in the aromatic ring (E'), and $C^{6'}$ is V'.

(114) The compound according to (113) mentioned above, wherein, in the formula (II), n is an integer of 2, V' is carbon atom substituted with Zx', and Rs' is —O—Rx'.

(115) The compound according to (94) mentioned above, wherein, in the formula (II), n is an integer of 2, $C^{8'}$ is carbon atom to which G binds, $C^{4'}$ is a carbon atom to which Rs' binds, $C^{6'}$ is carbon atom substituted with Zx', $C^{2'}$ and $C^{5'}$ are unsubstituted ring-constituting carbon atoms, Zx' is fluorine atom, methyl group, hydroxyl group, amino group, N-methylamino group, or N,N-dimethylamino group, provided that when Zx' contains hydroxyl group, the hydroxyl group may be protected with $Rp^1$, and when Zx' contains amino group, the amino group may be protected with $Rp^2$, Rs' is —O—Rx', Rx' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl) ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl) ethyl group, 2-[2-(trifluoromethyl)phenyl]ethyl group, 2-[3-(trifluoromethyl)phenyl]ethyl group, 2-[4-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino) ethyl group, G is bromine atom or iodine atom, and Y' is methyl group or ethyl group.

(116) The compound according to (94) mentioned above, wherein, in the formula (II), G binds to $C^{3\prime}$ in the aromatic ring (E'), Rs' binds to $C^{4\prime}$ in the aromatic ring (E'), $C^{5\prime}$ is nitrogen atom, and $C^{2\prime}$ and $C^{6\prime}$ are unsubstituted ring-constituting carbon atoms.

(117) The compound according to (116) mentioned above, wherein, in the formula (II), n is an integer of 2, and Rs' is —O—Rx'.

(118) The compound according to (94) mentioned above, wherein, in the formula (II), n is an integer of 2, $C^{3\prime}$ is carbon atom to which G binds, $C^{4\prime}$ is carbon atom to which Rs' binds, $C^{5\prime}$ is nitrogen atom, $C^{2\prime}$ and $C^{6\prime}$ are unsubstituted ring-constituting carbon atoms, Rs' is —O—Rx', Rx' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl) ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl) ethyl group, 2-(3-methylphenyl)ethyl group, 2-(4-methylphenyl) ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl) ethyl group, 2-[2-(trifluoromethyl)phenyl]ethyl group, 2-[3-(trifluoromethyl)phenyl]ethyl group, 2-[4-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino) ethyl group, G is bromine atom or iodine atom, and Y' is methyl group or ethyl group.

(119) The compound according to (94) mentioned above, wherein, in the formula (II), G binds to $C^{3\prime}$ in the aromatic ring (E'), Rs' binds to $C^{4\prime}$ in the aromatic ring (E'), $C^{5\prime}$ is a ring-constituting carbon atom substituted with Zx', or an unsubstituted ring-constituting carbon atom, $C^{2\prime}$ and $C^{6\prime}$ are unsubstituted ring-constituting carbon atoms, Rs' is -D-Rx', and D is a single bind, sulfur atom, —S(O)—, —S(O)$_2$—, or —C(O)—.

(120) The compound according to (94) mentioned above, wherein, in the formula (II), n is an integer of 2, $C^{3\prime}$ is carbon atom to which G binds, $C^{4\prime}$ is a carbon atom to which Rs' binds, $C^{5\prime}$ is a ring-constituting carbon atom substituted with Zx', or an unsubstituted ring-constituting carbon atom, $C^{2\prime}$ and $C^{6\prime}$ are unsubstituted ring-constituting carbon atoms, Zx' is fluorine atom, methyl group, hydroxyl group, amino group, N-methylamino group, or N,N-dimethylamino group, provided that when Zx' contains hydroxyl group, the hydroxyl group may be protected with $Rp^1$, and when Zx' contains amino group, the amino group may be protected with $Rp^2$, Rs' is —S-Rx', Rx' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl) ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl) ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl) ethyl group, 2-[2-(trifluoromethyl)phenyl]ethyl group, 2-[3-(trifluoromethyl)phenyl]ethyl group, 2-[4-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino) ethyl group, G is bromine atom or iodine atom, and Y' is methyl group or ethyl group.

(121) The compound according to (94) mentioned above, wherein, in the formula (II), G binds to $C^{3\prime}$ in the aromatic ring (E'), Rs' binds to $C^{4\prime}$ in the aromatic ring (E'), $C^{5\prime}$ is a ring-constituting carbon atom substituted with Zx', or an unsubstituted ring-constituting carbon atom, $C^{2\prime}$ and $C^{6\prime}$ are unsubstituted ring-constituting carbon atoms, and Rs' is —N(Ry')(Rz').

(122) The compound according to (94) mentioned above, wherein, in the formula (II), n is an integer of 2, $C^{3\prime}$ is carbon atom to which G binds, $C^{4\prime}$ is a carbon atom to which Rs' binds, $C^{5\prime}$ is a ring-constituting carbon atom substituted with Zx', or an unsubstituted ring-constituting carbon atom, $C^{2\prime}$ and $C^{6\prime}$ are unsubstituted ring-constituting carbon atoms, Zx' is fluorine atom, methyl group, hydroxyl group, amino group, N-methylamino group, or N,N-dimethylamino group, provided that when Zx' contains hydroxyl group, the hydroxyl group may be protected with $Rp^1$, and when Zx' contains amino group, the amino group may be protected with $Rp^2$, Rs' is —N(Ry')(Rz'), Rz' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl) ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl) ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl) ethyl group, 2-[2-(trifluoromethyl)phenyl]ethyl group, 2-[3-(trifluoromethyl)phenyl]ethyl group, 2-[4-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino) ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, or (morpholino-4-yl)carbonyl group, Ry' is hydrogen atom, methyl group, ethyl group or isobutyl group, or binds to Rz' to form pyrrolidino group, piperidino group, or morpholino group together with nitrogen atom to which they binds, provided that when —N(Ry')(Rz') contains hydroxyl group, the hydroxyl group may be protected with $Rp^1$, and when —N(Ry')(Rz') contains amino group, the amino group may be protected with $Rp^2$, G is bromine atom or iodine atom, and Y' is methyl group or ethyl group.

(123) The compound according to (94) mentioned above, wherein, in the formula (II), n is an integer of 2, G binds to $C^{3\prime}$ in the aromatic ring (E'), Rs' binds to $C^{4\prime}$ in the aromatic ring (E'), $C^{5\prime}$ is carbon atom substituted with —N($Rn^1$)($Rn^2$)

group (provided that one of $Rn^1$ and $Rn^2$ is a substituent other than hydrogen atom), $C^{2'}$ and $C^{6'}$ are unsubstituted ring-constituting carbon atoms, and Rs' is —O—Rx'.

(124) The compound according to (94) mentioned above, wherein, in the formula (II), n is an integer of 2, $C^{3'}$ is carbon atom to which G binds, $C^{4'}$ is carbon atom to which Rs' binds, $C^{5'}$ is carbon atom substituted with Zx', $C^{2'}$ and $C^{6'}$ are unsubstituted ring-constituting carbon atoms, Zx' is N-methylamino group, N-ethylamino group, N-propylamino group, N-isopropylamino group, N,N-dimethylamino group, N,N-diethylamino group, formylamino group, acetylamino group, carbamoylamino group, mesylamino group, or N,N-dimethylsulfamoylamino group, provided that when Zx' contains amino group, the amino group may be protected with $Rp^2$, Rs' is —O—Rx', Rx' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl) ethyl group, 1 (3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl) ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl) ethyl group, 2-[2-(trifluoromethyl)phenyl]ethyl group, 2-[3-(trifluoromethyl)phenyl]ethyl group, 2-[4-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino) ethyl group, G is bromine atom or iodine atom, and Y' is methyl group or ethyl group.

(125) The compound according to (94) mentioned above, wherein, in the formula (II), G binds to $C^{3'}$ in the aromatic ring (E'), Rs' binds to $C^{4'}$ in the aromatic ring (E'), $C^{5'}$ is a ring-constituting carbon atom substituted with Zx', or an unsubstituted ring-constituting carbon atom, $C^{2'}$ and $C^{6'}$ are unsubstituted ring-constituting carbon atoms, Rs' is -D-Rx', and Rx' has the same meaning as Rc, provided that when Rc contains hydroxyl group, the hydroxyl group may be protected with $Rp^1$, and when Rc contains amino group, the amino group may be protected with $Rp^2$.

(126) The compound according to (94) mentioned above, wherein, in the formula (II), n is an integer of 2, $C^{3'}$ is carbon atom to which G binds, $C^{4'}$ is a carbon atom to which Rs' binds, $C^{5'}$ is a ring-constituting carbon atom substituted with Zx', or an unsubstituted ring-constituting carbon atom, $C^{2'}$ and $C^{6'}$ are unsubstituted ring-constituting carbon atoms, Zx' is fluorine atom, methyl group, hydroxyl group, amino group, N-methylamino group, or N,N-dimethylamino group, provided that when Zx' contains hydroxyl group, the hydroxyl group may be protected with $Rp^1$, and when Zx' contains amino group, the amino group may be protected with $Rp^2$, Rs' is —O—Rx', Rx' has the same meaning as Rc, provided that when Rc contains hydroxyl group, the hydroxyl group may be protected with $Rp^1$, p in Rc is an integer of 2, $A^4$ is a single bond or methylene, $A^5$ is —C(O)—, —C(S)—, or —S(O)$_2$—, Rd is methyl group, ethyl group, propyl group, isopropyl group, butyl group, isobutyl group, cyclopropyl group, cyclopentyl group, cyclohexyl group, phenyl group, 4-methylphenyl group, 4-chlorophenyl group, 4-fluorophenyl group, benzyl group, 4-chlorophenylmethyl group, or 4-fluorophenylmethyl group, Re is isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, pyrrolidino group, piperidino group, or morpholino group, G is bromine atom or iodine atom, and Y' is methyl group or ethyl group.

(127) The compound according to (94) mentioned above, wherein, in the formula (II), G binds to $C^{3'}$ in the aromatic ring (E'), Rs' binds to $C^4$ in the aromatic ring (E'), $C^{5'}$ is a ring-constituting carbon atom substituted with Zx', or an unsubstituted ring-constituting carbon atom, $C^{2'}$ and $C^{6'}$ are unsubstituted ring-constituting carbon atoms, Rs' is —O—Rx', and Rx' is a linear or branched saturated alkyl group having 3 to 8 carbon atoms, or Ra or Rb.

(128) The compound according to (94) mentioned above, wherein, in the formula (II), n is an integer of 2, G binds to $C^{3\prime}$ in the aromatic ring (E'), Rs' binds to $C^{4\prime}$ in the aromatic ring (E'), $C^{5\prime}$ is carbon atom substituted with nitro group, $C^{2\prime}$ and $C^{6\prime}$ are unsubstituted ring-constituting carbon atoms, and Rs' is —O—Rx'.

(129) A compound represented by the following formula (III):

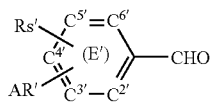

(III)

[In the formula, $C^{2\prime}$, $C^{3\prime}$, $C^{4\prime}$, $C^{5\prime}$ and $C^{6\prime}$ in the aromatic ring (E') represent a ring-constituting carbon atom, any one of these atoms to which Rs' and AR' does not bind may be replaced with V', and AR' has the same meaning as that of AR, provided that when AR contains hydroxyl group, the hydroxyl group may be protected with $Rp^1$, and when AR contains amino group, the amino group may be protected with $Rp^2$.].

(130) The compound according to (129) mentioned above, wherein, in the formula (III), AR' binds to the atom of $C^{2\prime}$ or $C^{3\prime}$ in the aromatic ring (E').

(131) The compound according to (129) or (130) mentioned above, wherein, in the formula (III), AR' is a residue of naphthalene, benzofuran, benzo[b]thiophene, indole, benzothiazole, dihydro-3H-benzothiazole, quinoline, dihydro-1H-quinoline, benzo[d]isothiazole, 1H-indazole, benzo[c]isothiazole, 2H-indazole, imidazo[1,2-a]pyridine, 1H-pyrrolo[2,3-b]pyridine, isoquinoline, dihydro-2H-isoquinoline, cinnoline, quinazoline, quinoxaline, 1H-benzimidazole, benzoxazole, 1H-pyrrolo[3,2-b]pyridine, benzo[1,2,5]thiadiazole, 1H-benzotriazole, 1,3-dihydropyrrolo[2,3-b]pyridine, 1,3-dihydrobenzimidazole, dihydro-3H-benzoxazole, phthalazine, [1,8]naphthalidine, [1,5]naphthalidine, 1H-pyrrolo[3,2-c]pyridine, 1H-pyrrolo[2,3-c]pyridine, 1H-pyrazolo[4,3-b]pyridine, 1H-pyrazolo[4,3-c]pyridine, 1H-pyrazolo[3,4-c]pyridine, 1H-pyrazolo[3,4-b]pyridine, [1,2,4]triazolo[4,3-a]pyridine, thieno[3,2-c]pyridine, thieno[3,2-b]pyridine, 1H-thieno[3,2-c]pyrazole, benzo[d]isoxazole, benzo[c]isoxazole, indolizine, 1,3-dihydroindole, 1H-pyrazolo[3,4-d]thiazole, 2H-isoindole, [1,2,4]triazolo[1,5-a]pyrimidine, 1H-pyrazolo[3,4-b]pyrazine, 1H-imidazo[4,5-b]pyrazine, 7H-purine, or 4H-chromene (the aforementioned residue may be substituted with one of Xa or two or more of the same or different Xa, when AR' contains hydroxyl group, the hydroxyl group may be protected with $Rp^1$, and when AR' contains amino group, the amino group may be protected with $Rp^2$).

(132) The compound according to (129) or (130) mentioned above, wherein, in the formula (III), AR' is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,6]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa, when AR' contains hydroxyl group, the hydroxyl group may be protected with $Rp^1$, and when AR' contains amino group, the amino group may be protected with $Rp^2$).

(133) The compound according to (129) or (130) mentioned above, wherein, in the formula (III), AR' is a residue of naphthalene, benzofuran, benzo[b]thiophene, indole, benzothiazole, dihydro-3H-benzothiazole, quinoline, dihydro-1H-quinoline, benzo[d]isothiazole, 1H-indazole, benzo[c]isothiazole, 2H-indazole, imidazo[1,2-a]pyridine, 1H-pyrrolo[2,3-b]pyridine, isoquinoline, or dihydro-2H-isoquinoline (the aforementioned residue may be substituted with one of Xa or two or more of the same or different Xa, when AR' contains hydroxyl group, the hydroxyl group may be protected with $Rp^1$, and when AR' contains amino group, the amino group may be protected with $Rp^2$).

(134) The compound according to (129) or (130) mentioned above, wherein, in the formula (III), AR' is a residue of cinnoline, quinazoline, quinoxaline, 1H-benzimidazole, benzoxazole, 1H-pyrrolo[3,2-b]pyridine, benzo[1,2,5]thiadiazole, 1H-benzotriazole, 1,3-dihydropyrrolo[2,3-b]pyridine, 1,3-dihydrobenzimidazole, dihydro-3H-benzoxazole, phthalazine, [1,8]naphthalidine, [1,5]naphthalidine, 1H-pyrrolo[3,2-c]pyridine, 1H-pyrrolo[2,3-c]pyridine, 1H-pyrazolo[4,3-b]pyridine, 1H-pyrazolo[4,3-c]pyridine, 1H-pyrazolo[3,4-c]pyridine, 1H-pyrazolo[3,4-b]pyridine, [1,2,4]triazolo[4,3-a]pyridine, thieno[3,2-c]pyridine, thieno[3,2-b]pyridine, 1H-thieno[3,2-c]pyrazole, benzo[d]isoxazole, benzo[c]isoxazole, indolizine, 1,3-dihydroindole, 1H-pyrazolo[3,4-d]thiazole, 2H-isoindole, [1,2,4]triazolo[1,5-a]pyrimidine, 1H-pyrazolo[3,4-b]pyrazine, 1H-imidazo[4,5-b]pyrazine, 7H-purine, or 4H-chromene (the aforementioned residue may be substituted with one of Xa or two or more of the same or different Xa, when AR' contains hydroxyl group, the hydroxyl group may be protected with $Rp^1$, and when AR' contains amino group, the amino group may be protected with $Rp^2$).

(135) The compound according to any one of (129) to (134) mentioned above, wherein, in the formula (III), Rs' is —O—Rx'.

(136) The compound according to any one of (129) to (135) mentioned above, wherein, in the formula (III), Rs' is -D-Rx' or —N(Ry')(Rz'), D is a single bind, oxygen atom, sulfur atom, —S(O)—, —S(O)$_2$—, or —C(O)—, Rx' is a linear or branched saturated alkyl group having 3 to 8 carbon atoms, or Ra, Rb, or Rc, k in Ra is 0 or an integer of 1 to 3, R' is a saturated cyclic alkyl group having 3 to 7 carbon atoms or a condensed saturated cyclic alkyl group having 6 to 8 carbon atoms, $R^1$ may be substituted with one of lower alkyl group having 1 to 4 carbon atoms or two or more of the same or different lower alkyl groups having 1 to 4 carbon atoms, Q in Rb is phenyl group, thienyl group, furyl group, pyrrolyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, tetrahydronaphthyl group, indanyl group, indenyl group, quinolyl group, isoquinolyl group, indolyl group, benzofuryl group, benzothienyl group, benzimidazolyl group, benzoxazolyl group, benzothiazolyl group, indazolyl group, 4H-chromenyl group, dihydrobenzodioxyl group, benzoisoxazolyl group, pyrrolopyridinyl group, pyrazolopyridinyl group, triazolopyridinyl group, thienopyridinyl group, thienopyrazolyl group, 1,3-dihydrobenzimidazole group, dihydro-3H-benzoxazole group, or dihydro-3H-benzothiazole group, which binds to $A^2$ at an arbitrary position on the ring, $A^1$ is a single bind or an alkylene (a) having 1 to 3 carbon atoms, the alkylene (a) may be substituted with a lower alkyl group having 1 to 4 carbon atoms or phenyl group may be substituted with, $A^2$ is a single bind, oxygen atom, sulfur atom, —S(O)—, —S(O)$_2$—, or —N($R^4$)— (provided that when $A^2$ is oxygen atom, sulfur atom, —S(O)—, —S(O)$_2$—, or —N($R^4$)—, $A^1$ is ethylene or trimethylene), $R^2$ and $R^3$ independently represent hydrogen atom, a linear or branched saturated alkyl group having 1 to 4 carbon atoms, oxo group, thioxo group, fluorine atom, chlorine atom, bromine atom, trifluoromethyl group, —$OR^5$, —N($R^6$)($R^{6'}$), —$NHCOR^7$, —$NHSO_2R^8$, or -$A^6$-Qa, or they binds to each other to form methylenedioxy group, Qa is phenyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, indanyl group, indenyl group, quinolyl group, isoquinolyl group, indolyl group, benzofuryl group, benzothienyl group, benzimidazolyl group, benzoxazolyl group, benzothiazolyl group, or indazolyl group, which may be substituted with one of $T^1$ or two or more of the same or different $T^1$, and binds to $A^6$ at an arbitrary position on the ring, $R^4$ and $R^6$ independently represent hydrogen atom or a lower alkyl group having 1 to 4 carbon atoms, $R^5$ and $R^7$ independently represent hydrogen atom, a lower alkyl group having 1 to 4 carbon atoms, or -$A^6$-Qa, $R^8$ is a lower alkyl group having 1 to 4 carbon atoms, $R^{6'}$ has the same meaning as $R^6$, or binds to $R^6$ to form a 3- to 6-membered ring together with the nitrogen atom to which they bind to form a saturated nitrogen-containing alkyl group or morpholino group, p in Rc is an integer of 2 to 4, $A^4$ is a single bond or methylene or ethylene, $A^5$ is —C(O)—, —C(S)—, or —S(O)$_2$—, Rd is hydrogen atom, an alkyl group having 1 to 8 carbon atoms, or Qa, Re is an alkyl group having 1 to 8 carbon atoms, -$A^6$-Qa, —(CH$_2$)$_i R^{14}$, —$OR^{23}$, —$SR^{28}$, or —N($R^{29}$)($R^{30}$), i is an integer of 1 to 3, $R^{14}$ is hydroxyl group, an alkoxy group having 1 to 4 carbon atoms, carboxyl group, or an N,N-dialkylcarbamoyl group having 1 to 4 carbon atoms, $R^{28}$ is an alkyl group having 1 to 8 carbon atoms or -$A^6$-Qa, $R^{29}$ is an alkyl group having 1 to 8 carbon atoms, an alkoxycarbonyl group having 1 to 4 carbon atoms, or -$A^6$-Qa, $R^{30}$ is hydrogen atom or a lower alkyl group having 1 to 4 carbon atoms, or binds to $R^{29}$ to form a 3- to 6-membered ring together with the nitrogen atom to which they bind to form a saturated nitrogen-containing alkyl group or morpholino group, Rz' has the same meaning as Rx', or represents -$A^5$-Re, Ry' is hydrogen atom, an alkyl group having 1 to 8 carbon atoms, or -$A^6$-Qp, or binds to Rz' to form a saturated or unsaturated nitrogen-containing cyclic substituent having 3 to 7 atoms, when -D-Rx' or —N(Ry')(Rz') contains hydroxyl group, the hydroxyl group may be protected with $Rp^1$, and when -D-Rx' or —N(Ry')(Rz') contains amino group, the amino group may be protected with $Rp^2$.

(137) The compound according to any one of (129) to (136) mentioned above, wherein, in the formula (III), Rs' is —N(Ry')(Rz').

(138) The compound according to any one of (129) to (136) mentioned above, wherein, in the formula (III), Rs' is -D-Rx', D is sulfur atom, —S(O)—, —S(O)$_2$—, or —C(O)—.

(139) The compound according to (129) mentioned above, wherein, in the formula (III), AR' binds at the position of $C^{2'}$ in the aromatic ring (E'), and Rs' binds to one of the ring-constituting carbon atoms $C^{3'}$, $C^{4'}$, and $C^{5'}$.

(140) The compound according to (129) mentioned above, wherein, in the formula (III), AR' binds to $C^{2'}$, Rs' binds to any one of the atoms $C^{3'}$, $C^{4'}$, and $C^{5'}$, a ring-constituting carbon atom to which Rs' does not bind among $C^{3'}$, $C^{4'}$, and $C^{5'}$ may be replaced with V', V' is nitrogen atom, or carbon atom substituted with Zx', Zx' is one kind of group selected from the group consisting of fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, and N,N-dimethylsulfamoylamino group, provided that when Zx' contains hydroxyl group, the hydroxyl group may be protected with $Rp^1$, and when Zx' contains amino group, the amino group may be protected with $Rp^2$, Rs' is -D-Rx' or —N(Ry')(Rz'), D is oxygen atom or sulfur atom, Rx' is butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or Rb or Rc, Q in Rb is phenyl group, thienyl group, furyl group, pyridyl group, oxazolyl group, naphthyl group, tetrahydronaphthyl group, indanyl group, indolyl group, or dihydrobenzodioxyl group, $A^2$ is a single bind, oxygen atom, sulfur atom, —N(methyl)-, or —N(ethyl)- (provided that when $A^2$ is oxygen atom, sulfur atom, —N(methyl)-, or —N(ethyl)-, $A^1$ is ethylene), $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q is phenyl group, $A^1$ is a single bind or unsubstituted methylene, and $A^2$ is a single bind, one of $R^2$ and $R^3$ is a substituent other than hydrogen atom), p in Rc is an integer of 2 or 3, $A^4$ is a single bind or methylene, $A^5$ is —C(O)—, —C(S)—, or —S(O)$_2$—, Rd is hydrogen atom, or methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, or pyridin-4-yl group, Re is methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, or ethyloxycarbonylamino group, Rz' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, or (morpholino-4-yl)carbonyl group, Ry' is hydrogen atom, methyl group, ethyl group or isobutyl group, or binds to Rz' to form pyrrolidino group, piperidino group, piperazino group, morpholino group, pyrrol-1-yl group, imidazol-1-yl group or pyrazol-1-yl group together with the nitrogen atom, provided that when -D-Rx' or —N(Ry')(Rz') contains hydroxyl group, the hydroxyl group may be protected with $Rp^1$, and when -D-Rx' or —N(Ry')(Rz') contains amino group, the amino group may be protected with $Rp^2$, AR' is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa), and Xa is oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, or N,N-dimethylcarbamoyl group, provided that when AR' contains hydroxyl group, the hydroxyl group may be protected with $Rp^1$, and when AR' contains amino group, the amino group may be protected with $Rp^2$.

(141) The compound according to (139) or (140) mentioned above, wherein, in the formula (III), Rs' is —O—Rx', and all of $C^{2'}$, $C^{3'}$, $C^{4'}$, $C^{5'}$ and $C^{6'}$ in the aromatic ring (E') are not replaced with V'.

(142) The compound according to (131) mentioned above, wherein, in the formula (III), AR' binds at the position of $C^{2'}$ in the aromatic ring (E'), Rs' binds to one of the ring-constituting carbon atoms $C^{3'}$, $C^{4'}$, and $C^{5'}$, Rs' is —O—Rx', and all of $C^{2'}$, $C^{3'}$, $C^{4'}$, $C^{5'}$ and $C^{6'}$ in the aromatic ring (E') are not replaced with V.

(143) The compound according to (132) mentioned above, wherein, in the formula (III), AR' binds at the position of $C^{2'}$ in the aromatic ring (E'), Rs' binds to one of the ring-constituting carbon atoms $C^{8'}$, $C^{4'}$, and $C^{5'}$, Rs' is —O—Rx', and all of $C^{2'}$, $C^{3'}$, $C^{4'}$, $C^{5'}$ and $C^{6'}$ in the aromatic ring (E') are not replaced with V.

(144) The compound according to any one of (139) to (143) mentioned above, wherein, in the formula (III), Rs' binds to $C^{3'}$.

(145) The compound according to (129) mentioned above, wherein, in the formula (III), $C^{2'}$ is carbon atom to which AR' binds, $C^{3'}$ is carbon atom to which Rs' binds, $C^{4'}$ may be replaced with V', $C^{5'}$ and $C^{6'}$ are unsubstituted ring-constituting carbon atoms, V' is nitrogen atom, or carbon atom substituted with Zx', Zx' is fluorine atom, methyl group, hydroxyl group, amino group, N-methylamino group, or N,N-dimethylamino group, provided that when Zx' contains hydroxyl group, the hydroxyl group may be protected with $Rp^1$, and when Zx' contains amino group, the amino group may be protected with $Rp^2$, Rs' is —O—Rx', Rx' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl) ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino) ethyl group, and AR' is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino) naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group; 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group (the aforementioned groups may be substituted with one of Xa or two or more of the same or different Xa), provided that when AR' contains hydroxyl group, the hydroxyl group may be protected with $Rp^1$, and when AR' contains amino group, the amino group may be protected with $Rp^2$.

(146) The compound according to (139) to (143) mentioned above, wherein, in the formula (III), Rs' binds to $C^{4'}$.

(147) The compound according to (129) mentioned above, wherein, in the formula (III), $C^{2'}$ is carbon atom to which AR' binds, $C^{4'}$ is carbon atom to which Rs' binds, $C^{5'}$ may be replaced with V', $C^{3'}$ and $C^{6'}$ are unsubstituted ring-constituting carbon atoms, V' is nitrogen atom, or carbon atom substituted with Zx', Zx' is fluorine atom, methyl group, hydroxyl group, amino group, N-methylamino group, or N,N-dimethylamino group, provided that when Zx' contains hydroxyl group, the hydroxyl group may be protected with $Rp^1$, and when Zx' contains amino group, the amino group may be protected with $Rp^2$, Rs' is —O—Rx', Rx' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino)ethyl group, and AR' is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group; 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, provided that when AR' contains hydroxyl group, the hydroxyl group may be protected with $Rp^1$, and when AR' contains amino group, the amino group may be protected with $Rp^2$.

(148) The compound according to any one of (139) to (143) mentioned above, wherein, in the formula (III), Rs' binds to $C^{5'}$.

(149) The compound according to (129) mentioned above, wherein, in the formula (III), AR' binds to $C^{3'}$ in the aromatic ring (E'), Rs' binds to the atom $C^{5'}$ or $C^{6'}$ in the aromatic ring (E').

(150) The compound according to (149) mentioned above, wherein, in the formula (III), Rs' is —O—Rx', and all of $C^{2'}$, $C^{3'}$, $C^{4'}$, $C^{5'}$ and $C^{6'}$ in the aromatic ring (E') are not replaced with V.

(151) The compound according to (131) mentioned above, wherein, in the formula (III), AR' binds to $C^{3'}$ in the aromatic ring (E'), Rs' binds to the atom $C^{5'}$ or $C^{6'}$ in the aromatic ring (E'), Rs' is —O—Rx', and all of $C^{2'}$, $C^{3'}$, $C^{4'}$, $C^{5'}$ and $C^{6'}$ in the aromatic ring (E') are not replaced with V.

(152) The compound according to (132) mentioned above, wherein, in the formula (III), AR' binds to $C^{3'}$ in the aromatic ring (E'), Rs' binds to the atom $C^{5'}$ or $C^{6'}$ in the aromatic ring (E'), Rs' is —O—Rx', and all of $C^{2'}$, $C^{3'}$, $C^{4'}$, $C^{5'}$ and $C^{6'}$ in the aromatic ring (E') are not replaced with V.

(153) The compound according to any one of (149) to (152) mentioned above, wherein, in the formula (III), Rs' binds to $C^{5'}$.

(154) The compound according to (129) mentioned above, wherein, in the formula (III), $C^{3'}$ is carbon atom to which AR' binds, $C^{5'}$ is carbon atom to which Rs' binds, $C^{2'}$, $C^{4'}$, and $C^{6'}$ are unsubstituted ring-constituting carbon atoms, Rs' is —O—Rx', Rx' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl) ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl) ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl) ethyl group, 2-[2-(trifluoromethyl)phenyl]ethyl group, 2-[3-(trifluoromethyl)phenyl]ethyl group, 2-[4-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino) ethyl group, and AR' is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino) naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b] thiophen-5-yl group, 2-methylbenzo[b]thiophen-5-yl group, 3-methylbenzo[b]thiophen-5-yl group, 2,3-dimethylbenzo [b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo [2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, provided that when AR' contains hydroxyl group, the hydroxyl group may be protected with $Rp^1$, and when AR' contains amino group, the amino group may be protected with $Rp^2$.

(155) The compound according to any one of (149) to (152) mentioned above, wherein, in the formula (III), Rs' binds to $C^{6'}$.

(156) The compound according to (129) mentioned above, wherein, in the formula (III), AR' binds to $C^{3'}$ in the aromatic ring (E'), Rs' binds to $C^{4'}$ in the aromatic ring (E'), and $C^{6'}$ is V'.

(157) The compound according to (131) mentioned above, wherein, in the formula (III), AR' binds to $C^{3'}$ in the aromatic ring (E'), Rs' binds to $C^{4'}$ in the aromatic ring (E'), $C^{6'}$ is carbon atom substituted with Zx, $C^{2'}$ and $C^{5'}$ are unsubstituted carbon atoms, and Rs' is —O—Rx'.

(158) The compound according to (132) mentioned above, wherein, in the formula (III), AR' binds to $C^{3'}$ in the aromatic ring (E'), Rs' binds to $C^{4'}$ in the aromatic ring (E'), $C^{6'}$ is carbon atom substituted with Zx, $C^{2'}$ and $C^{6'}$ are unsubstituted ring-constituting carbon atoms, and Rs' is —O—Rx'.

(159) The compound according to (129) mentioned above, wherein, in the formula (III), $C^{3'}$ is carbon atom to which AR' binds, $C^{4'}$ is a carbon atom to which Rs' binds, $C^{6'}$ is carbon atom substituted with Zx', $C^{2'}$ and $C^{6'}$ are unsubstituted ring-constituting carbon atoms, Zx' is fluorine atom, methyl group, hydroxyl group, amino group, N-methylamino group, or N,N-dimethylamino group, provided that when Zx' contains hydroxyl group, the hydroxyl group may be protected with $Rp^1$, and when Zx' contains amino group, the amino group may be protected with $Rp^2$, Rs' is —O—Rx', Rx' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl) ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino)ethyl group, and AR' is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, provided that when Ar' contains hydroxyl group, the hydroxyl group may be protected with $Rp^1$, and when AR' contains amino group, the amino group may be protected with $Rp^2$.

(160) The compound according to (129) mentioned above, wherein, in the formula (III), AR' binds to $C^{3'}$ in the aromatic ring (E'), Rs' binds to $C^{4'}$ in the aromatic ring (E'), $C^{5'}$ is nitrogen atom, $C^{2'}$ and $C^{6'}$ are unsubstituted ring-constituting carbon atoms, and Rs' is —O—Rx'.

(161) The compound according to (131) mentioned above, wherein, in the formula (III), AR' binds to $C^{3'}$ in the aromatic ring (E'), Rs' binds to $C^{4'}$ in the aromatic ring (E'), $C^{5'}$ is nitrogen atom, $C^{2'}$ and $C^{6'}$ are unsubstituted ring-constituting carbon atoms, and Rs' is —O—Rx'.

(162) The compound according to (132) mentioned above, wherein, in the formula (III), AR' binds to $C^{3'}$ in the aromatic ring (E'), Rs' binds to $C^{4'}$ in the aromatic ring (E'), $C^{5'}$ is nitrogen atom, $C^{2'}$ and $C^{6'}$ are unsubstituted ring-constituting carbon atoms, and Rs' is —O—Rx'.

(163) The compound according to (129) mentioned above, wherein, in the formula (III), $C^{3'}$ is carbon atom to which AR' binds, $C^{4'}$ is carbon atom to which Rs' binds, $C^{5'}$ is nitrogen atom, $C^{2'}$ and $C^{6'}$ are unsubstituted ring-constituting carbon atoms, Rs' is —O—Rx', Rx' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino)ethyl group, and AR' is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, provided that when AR' contains hydroxyl group, the hydroxyl group may be protected with $Rp^1$, and when AR' contains amino group, the amino group may be protected with $Rp^2$.

(164) The compound according to (129) mentioned above, wherein, in the formula (III), AR' binds to $C^{3'}$ in the aromatic ring (E'), Rs' binds to $C^{4'}$ in the aromatic ring (E'), $C^{5'}$ is a ring-constituting carbon atom substituted with Zx', or an unsubstituted ring-constituting carbon atom, $C^{2'}$ and $C^{6'}$ are unsubstituted ring-constituting carbon atoms, Rs' is -D-Rx', D is a single bind, sulfur atom, —S(O)—, —S(O)$_2$—, or —C(O)—.

(165) The compound according to (131) mentioned above, wherein, in the formula (III), AR' binds to $C^{3'}$ in the aromatic ring (E'), Rs' binds to $C^{4'}$ in the aromatic ring (E'), $C^5$ is a ring-constituting carbon atom substituted with Zx', or an unsubstituted ring-constituting carbon atom, $C^{2'}$ and $C^{6'}$ are unsubstituted ring-constituting carbon atoms, Rs' is -D-Rx', and D is a single bind, sulfur atom, —S(O)—, —S(O)$_2$—, or —C(O)—.

(166) The compound according to (132) mentioned above, wherein, in the formula (III), AR' binds to $C^{3'}$ in the aromatic ring (E'), Rs' binds to $C^{4'}$ in the aromatic ring (E'), $C^{5'}$ is a ring-constituting carbon atom substituted with Zx', or an unsubstituted ring-constituting carbon atom, $C^{2'}$ and $C^{6'}$ are unsubstituted ring-constituting carbon atoms, Rs' is -D-Rx', and D is a single bind, sulfur atom, —S(O)—, —S(O)$_2$—, or —C(O)—.

(167) The compound according to (129) mentioned above, wherein, in the formula (III), AR' binds to $C^{3'}$ in the aromatic ring (E'), Rs' binds to $C^{4'}$ in the aromatic ring (E'), $C^{5'}$ is a ring-constituting carbon atom substituted with Zx', or an unsubstituted ring-constituting carbon atom, $C^{2'}$ and $C^{6'}$ are unsubstituted ring-constituting carbon atoms, and Rs' is —N(Ry')(Rz').

(168) The compound according to (131) mentioned above, wherein, in the formula (III), AR' binds to $C^{3'}$ in the aromatic ring (E'), Rs' binds to $C^{4'}$ in the aromatic ring (E'), $C^5$ is a ring-constituting carbon atom substituted with Zx', or an unsubstituted ring-constituting carbon atom, $C^{2'}$ and $C^{6'}$ are unsubstituted ring-constituting carbon atoms, and Rs' is —N(Ry')(Rz').

(169) The compound according to (132) mentioned above, wherein, in the formula (III), AR' binds to $C^{9'}$ in the aromatic ring (E'), Rs' binds to $C^{4'}$ in the aromatic ring (E'), $C^{5'}$ is a ring-constituting carbon atom substituted with Zx', or an unsubstituted ring-constituting carbon atom, $C^{2'}$ and $C^{6'}$ are unsubstituted ring-constituting carbon atoms, and Rs' is —N(Ry')(Rz').

(170) The compound according to (129) mentioned above, wherein, in the formula (III), AR' binds to $C^{3'}$ in the aromatic ring (E'), Rs' binds to $C^{4'}$ in the aromatic ring (E'), $C^5$ is carbon atom substituted with —N(Rn$^1$)(Rn$^2$) (provided that one of Rn$^1$ and Rn$^2$ is a substituent other than hydrogen atom), $C^{2'}$ and $C^{6'}$ are unsubstituted ring-constituting carbon atoms, and Rs' is —O—Rx'.

(171) The compound according to (131) mentioned above, wherein, in the formula (III), AR' binds to $C^{3'}$ in the aromatic ring (E'), Rs' binds to $C^{4'}$ in the aromatic ring (E'), $C^{5'}$ is carbon atom substituted with —N(Rn$^1$)(Rn$^2$) (provided that one of Rn$^1$ and Rn$^2$ is a substituent other than hydrogen atom), $C^{2'}$ and $C^{6'}$ are unsubstituted ring-constituting carbon atoms, and Rs' is —O—Rx'.

(172) The compound according to (123) mentioned above, wherein, in the formula (III), AR' binds to $C^{3'}$ in the aromatic ring (E'), Rs' binds to $C^{4'}$ in the aromatic ring (E'), $C^{5'}$ is carbon atom substituted with —N(Rn$^1$)(Rn$^2$) (provided that one of Rn$^1$ and Rn$^2$ is a substituent other than hydrogen atom), $C^{2'}$ and $C^{6'}$ are unsubstituted ring-constituting carbon atoms, and Rs' is —O—Rx'.

(173) The compound according to (129) mentioned above, wherein, in the formula (III), $C^{3'}$ is carbon atom to which AR' binds, $C^{4'}$ is carbon atom to which Rs' binds, $C^{5'}$ is carbon atom substituted with Zx', $C^{2'}$ and $C^{6'}$ are unsubstituted ring-constituting carbon atoms, Zx' is N-methylamino group, N-ethylamino group, N-propylamino group, N-isopropylamino group, N,N-dimethylamino group, N,N-diethylamino group, formylamino group, acetylamino group, carbamoylamino group, mesylamino group, or N,N-dimethylsulfamoylamino group, provided that when Zx' contains amino group, the amino group may be protected with $Rp^2$, Rs' is —O—Rx', Rx' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino)ethyl group, and AR' is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, iso quinolin-6-yl group, 1-oxo-1,2-dihydroisoquinolin-6-yl group, cinnolin-6-yl group, or benzoxazol-5-yl group, provided that when AR' contains hydroxyl group, the hydroxyl group may be protected with $Rp^1$, and when AR' contains amino group, the amino group may be protected with $Rp^2$.

(174) The compound according to (129) mentioned above, wherein, in the formula (III), AR' binds to $C^{3'}$ in the aromatic ring (E'), Rs' binds to $C^{4'}$ in the aromatic ring (E'), $C^{5'}$ is a ring-constituting carbon atom substituted with Zx', or an unsubstituted ring-constituting carbon atom, $C^{2'}$ and $C^{6'}$ are unsubstituted ring-constituting carbon atoms, Rs' is -D-Rx', and Rx' has the same meaning as Rc, provided that when Rc contains hydroxyl group, the hydroxyl group may be protected with $Rp^1$, and when Rc contains amino group, the amino group may be protected with $Rp^2$.

(175) The compound according to (131) mentioned above, wherein, in the formula (III), AR' binds to $C^{8'}$ in the aromatic ring (E'), Rs' binds to $C^{4'}$ in the aromatic ring (E'), $C^{5'}$ is a ring-constituting carbon atom substituted with Zx', or an unsubstituted ring-constituting carbon atom, $C^{2'}$ and $C^{6'}$ are unsubstituted ring-constituting carbon atoms, Rs' is -D-Rx', and Rx' has the same meaning as Rc, provided that when Rc contains hydroxyl group, the hydroxyl group may be protected with $Rp^1$, and when Rc contains amino group, the amino group may be protected with $Rp^2$.

(176) The compound according to (132) mentioned above, wherein, in the formula (III), AR' binds to $C^{3'}$ in the aromatic ring (E'), Rs' binds to $C^{4'}$ in the aromatic ring (E'), $C^{5'}$ is a ring-constituting carbon atom substituted with Zx', or an unsubstituted ring-constituting carbon atom, $C^{2'}$ and $C^{6'}$ are unsubstituted ring-constituting carbon atoms, Rs' is -D-Rx', and Rx' has the same meaning as Rc, provided that when Rc contains hydroxyl group, the hydroxyl group may be protected with $Rp^1$, and when Rc contains amino group, the amino group may be protected with $Rp^2$.

(177) The compound according to (129) mentioned above, wherein, in the formula (III), $C^{3'}$ is carbon atom to which AR' binds, $C^{4'}$ is a carbon atom to which Rs' binds, $C^{5'}$ is a ring-constituting carbon atom substituted with Zx', or an unsubstituted ring-constituting carbon atom, $C^{2\prime}$ and $C^{6\prime}$ are unsubstituted ring-constituting carbon atoms, Zx' is fluorine atom, methyl group, hydroxyl group, amino group, N-methylamino group, or N,N-dimethylamino group, provided that when Zx' contains hydroxyl group, the hydroxyl group may be protected with $Rp^1$, and when Zx' contains amino group, the amino group may be protected with $Rp^2$, Rs' is —O—Rx', Rx' has the same meaning as Rc, provided that when Rc contains hydroxyl group, the hydroxyl group may be protected with $Rp^1$, p in Rc is an integer of 2, $A^4$ is a single bind or methylene, $A^5$ is —C(O)—, —C(S)—, or —S(O)$_2$—, Rd is methyl group, ethyl group, propyl group, isopropyl group, butyl group, isobutyl group, cyclopropyl group, cyclopentyl group, cyclohexyl group, phenyl group, 4-methylphenyl group, 4-chlorophenyl group, 4-fluorophenyl group, benzyl group, 4-chlorophenylmethyl group, or 4-fluorophenylmethyl group, Re is isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, pyrrolidino group, piperidino group, or morpholino group, and AR' is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino) naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-6-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-6-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, provided that when AR' contains hydroxyl group, the hydroxyl group may be protected with $Rp^1$, and when AR' contains amino group, the amino group may be protected with $Rp^2$.

(178) The compound according to (129) mentioned above, wherein, in the formula (III), AR' binds to $C^{3\prime}$, Rs' binds to any one of the atoms $C^{4\prime}$, $C^{5\prime}$, and $C^{6\prime}$, a ring-constituting carbon atom to which Rs' does not bind among $C^{4\prime}$, $C^{5\prime}$, and $C^{6\prime}$ may be replaced with V', V' is nitrogen atom, or carbon atom substituted with Zx', Zx' is fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, or N,N-dimethylsulfamoylamino group, provided that when Zx' contains hydroxyl group, the hydroxyl group may be protected with $Rp^1$, and when Zx' contains amino group, the amino group may be protected with $Rp^2$, Rs' is -D-Rx' or —N(Ry')(Rz'), D is oxygen atom or sulfur atom, Rx' is butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or Rb or Rc, Q in Rb is phenyl group, thienyl group, furyl group, pyridyl group, oxazolyl group, naphthyl group, tetrahydronaphthyl group, indanyl group, indolyl group, or dihydrobenzodioxyl group, $A^2$ is a single bind, oxygen atom, sulfur atom, —N(methyl)-, or —N(ethyl)- (provided that when $A^2$ is oxygen atom, sulfur atom, —N(methyl)-, or —N(ethyl)-, $A^1$ is ethylene), $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q is phenyl group, $A^1$ is a single bind or unsubstituted methylene, and $A^2$ is a single bind, one of $R^2$ and $R^3$ is a substituent other than hydrogen atom), p in Rc is an integer of 2 or 3, $A^4$ is a single bind or methylene, $A^5$ is —C(O)—, —C(S)—, or —S(O)$_2$—, Rd is hydrogen atom, or methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, or pyridin-4-yl group, Re is methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan- 3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group or ethyloxycarbonylamino group, Rz' is butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, or (morpholino-4-yl)carbonyl group, Ry' is hydrogen atom, methyl group, ethyl group or isobutyl group, or binds to Rz' to form pyrrolidino group, piperidino group, piperazino group, morpholino group, pyrrol-1-yl group, imidazol-1-yl group, or pyrazol-1-yl group together with the nitrogen atom, provided that when -D-Rx' or —N(Ry')(Rz') contains hydroxyl group, the hydroxyl group may be protected with $Rp^1$, and when the substituent -D-Rx' or —N(Ry')(Rz') contains amino group, the amino group may be protected with $Rp^2$, AR' is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa), and Xa is oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, or N,N-dimethylcarbamoyl group, provided that when AR' contains hydroxyl group, the hydroxyl group may be protected with $Rp^1$, and when AR' contains amino group, the amino group may be protected with $Rp^2$.

(179) The compound according to (119) mentioned above, wherein, in the formula (III), AR' binds to $C^{3\prime}$ in the aromatic ring (E'), Rs' binds to $C^{4\prime}$ in the aromatic ring (E'), $C^{5\prime}$ is a ring-constituting carbon atom substituted with Zx', or an unsubstituted ring-constituting carbon atom, $C^{2\prime}$ and $C^{6\prime}$ are unsubstituted ring-constituting carbon atoms, and Rs' is —O—Rx'.

(180) The compound according to (131) mentioned above, wherein, in the formula (III), AR' binds to $C^{3\prime}$ in the aromatic ring (E'), Rs' binds to $C^{4\prime}$ in the aromatic ring (E'), $C^{5\prime}$ is a ring-constituting carbon atom substituted with Zx, or an unsubstituted ring-constituting carbon atom, $C^{2\prime}$ and $C^{6\prime}$ are unsubstituted ring-constituting carbon atoms, and D is oxygen atom.

(181) The compound according to (132) mentioned above, wherein, in the formula (III), AR' binds to $C^{3\prime}$ in the aromatic ring (E'), Rs' binds to $C^{4\prime}$ in the aromatic ring (E'), $C^{5\prime}$ is a ring-constituting carbon atom substituted with Zx', or an unsubstituted ring-constituting carbon atom, $C^{2\prime}$ and $C^{6\prime}$ are unsubstituted ring-constituting carbon atoms, and Rs' is —O—Rx'.

(182) The compound according to (129) mentioned above, wherein, in the formula (III), AR' binds to $C^{3\prime}$ in the aromatic ring (E'), Rs' binds to $C^{4\prime}$ in the aromatic ring (E'), $C^{5\prime}$ is carbon atom substituted with nitro group, $C^{2\prime}$ and $C^{6\prime}$ are unsubstituted ring-constituting carbon atoms, and Rs' is —O—Rx'.

(183) The compound according to (131) mentioned above, wherein, in the formula (III), AR' binds to $C^{3\prime}$ in the aromatic ring (E'), Rs' binds to $C^{4\prime}$ in the aromatic ring (E'), $C^{5\prime}$ is carbon atom substituted with nitro group, $C^{2\prime}$ and $C^{6\prime}$ are unsubstituted ring-constituting carbon atoms, and Rs' is —O—Rx'.

(184) The compound according to (132) mentioned above, wherein, in the formula (III), AR' binds to $C^{3\prime}$ in the aromatic ring (E'), Rs' binds to $C^{4\prime}$ in the aromatic ring (E'), $C^{5\prime}$ is carbon atom substituted with nitro group, $C^{2\prime}$ and $C^{6\prime}$ are unsubstituted ring-constituting carbon atoms, and Rs' is —O—Rx'.

(185) An agent for prophylactic and/or therapeutic treatment of fibrosis, which contains a type 4 $PLA_2$ inhibitor as an active ingredient.

(186) An agent for prophylactic and/or therapeutic treatment of pulmonary fibrosis, which contains a type 4 $PLA_2$ inhibitor as an active ingredient.

(187) The prophylactic and/or therapeutic agent according to (186), wherein the pulmonary fibrosis is drug-induced pulmonary fibrosis.

(188) The prophylactic and/or therapeutic agent according to (187), wherein the drug-induced pulmonary fibrosis is a disease induced by one or more kinds of medicaments among methotrexate, sodium aurothiomalate, auranofin, D-penicillamine, bucillamine, actarit, salazosulfapyridine, cyclophosphamide, Taxol, etoposide, cisplatin, vincristine, vinblastine, irinotecan, gefitinib, and bleomycin.

(189) The prophylactic and/or therapeutic agent according to (187), wherein the drug-induced pulmonary fibrosis is a disease induced by one or more kinds of medicaments among methotrexate and bleomycin.

(190) The prophylactic and/or therapeutic agent according to (186), wherein the type 4 $PLA_2$ inhibitor is a compound represented by the formula (I) or a pharmacologically acceptable salt thereof.

(191) The prophylactic and/or therapeutic agent according to (186), wherein the type 4 $PLA_2$ inhibitor is an inhibitor selected from the group consisting of 4-(1-benzhydryl-6-chloro-1H-indol-3-ylmethyl)-3-methoxybenzoic acid, 4-{4-[2-(2-[bis(4-chlorophenyl)methoxy]ethylsulfonyl)ethoxy]phenyl}-1,1,1-trifluoro-2-butanone, N-{1-[2-(2,4-difluorobenzoyl)benzoyl]-4-tritylsulfanylpyrrolidin-2-ylmethyl}-4-(2,4-dioxothiazolidin-5-ylidenemethyl)benzoic acid amide, 4-methyl-2-oxo-5-(5,6,7,8-tetrahydronaphthalen-2-yl)oxazolidine-3-carbonxylic acid (6-methoxytetrahydropyran-2-yl)amide, 4-methyl-2-oxo-5-(4-methylphenyl)thiazolidine-3-carbonxylic acid (tetrahydropyran-2-yl) amide, 4-[3-(4-decyloxyphenyloxy)-2-oxopropyloxy]benzoic acid, and 1-{2-[4-(carboxymethyl)phenoxy]ethyl}-3-dodecanoylindole-2-carbonxylic acid.

The compound (I) of the present invention or a pharmaceutically acceptable salt thereof has an action of suppressing the production of both of prostaglandins and leukotrienes, and said compound has characteristic features that, when administered to a human or animal, the compound exerts superior prophylactic and/or therapeutic effect on diseases or pathological conditions in which a prostaglandin and/or leukotriene is involved, and the compound has extremely low toxicity. The compounds (II) and (III) of the present invention are synthetic intermediates useful for the production of the compound (I) of the present invention. Furthermore, it was confirmed that a type 4 $PLA_2$ inhibitor is useful as a prophylactic and/or therapeutic agent for fibrosis, in particular, pulmonary fibrosis, especially drug-induced pulmonary fibrosis, which was induced as a side effect of a medicament.

BEST MODE FOR CARRYING OUT THE INVENTION

In the present specification, carbon atom may sometimes be represented simply by "C", hydrogen atom by "H", oxygen atom by "O", sulfur atom by "S", and nitrogen atom by "N".

Examples of Link in the aforementioned general formula (I) include a saturated straight hydrocarbon chain having 1 to 3 carbon atoms or an unsaturated straight hydrocarbon chain having 2 or 3 carbon atoms. In the present invention, the straight chain of the saturated straight hydrocarbon chain is preferably unsubstituted. The straight chain of the unsaturated straight hydrocarbon chain is also preferably unsubstituted. As the saturated straight hydrocarbon chain, —$(CH_2)_n$— is preferred. Symbol n is an integer of 1 to 3. When n is 1, 2 or 3, the desired action is most characteristically exhibited. Methylene where n is 1, ethylene where n is 2 and trimethylene where n is 3 are preferred, and ethylene where n is 2 is particularly preferred.

The unsaturated hydrocarbon chain having 2 or 3 carbon atoms means a hydrocarbon chain which contains an unsaturated bond as a double bond or a triple bond among the carbon-carbon bonds. As the unsaturated hydrocarbon chain, an unsaturated hydrocarbon chain containing a double bond is preferred. When the chain contains one or more double bonds, the number of the double bond may preferably one. Specific examples include ethenylene which has two carbon atoms and contains one double bond, as well as ethynylene which has two carbon atoms and contains one triple bond, propen-3-yl which has three carbon atoms and contains one double bond, and propyn-3-yl which has three carbon atoms and contains one triple bond.

$C^2$, $C^3$, $C^4$, $C^5$ and $C^6$ in the aromatic ring (E) in the formula (I) each represent a ring-constituting carbon atom. The ring-constituting carbon atoms form the aromatic ring (E), and accordingly, they are represented as C or CH. Among them, any one of ring-constituting carbon atoms to which Rs or Ar does not bind may be replaced with V. The aforementioned expression "to be replaced with" means that any one of the ring-constituting carbon atoms $C^2$, $C^3$, $C^4$, $C^5$ and $C^6$ is replaced with V, and thus V may sometimes be a ring-constituting component. Rs and AR each bind to any of the ring-constituting carbon atoms $C^2$, $C^3$, $C^4$, $C^5$ or $C^6$ in the aromatic ring (E), and this means that, for example, when AR binds to $C^2$, Rs binds to any of the ring-constituting carbon atoms $C^3$, $C^4$, $C^5$ and $C^6$, when AR binds to $C^3$, Rs binds to any of the ring-constituting carbon atoms $C^2$, $C^4$, $C^5$ and $C^6$, and when AR bind to $C^4$, Rs binds to the ring-constituting carbon atom $C^2$ or $C^3$. Preferred examples of these combinations of substitution positions include a compound wherein AR binds to $C^2$, and Rs binds to any of the atoms $C^3$, $C^4$, and $C^5$, and particularly preferred examples include a compound wherein AR binds to $C^2$, and Rs binds to $C^3$ or $C^4$. Preferred examples also include a compound wherein AR binds to $C^3$, and Rs binds to any of the atoms $C^4$, $C^5$, and $C^6$, and particularly preferred examples also include a compound wherein AR binds to $C^3$, and Rs binds to the atom $C^4$ or $C^5$. A still more preferred example is a compound wherein AR binds to $C^3$, and Rs binds to $C^4$.

One of the atoms $C^2$, $C^3$, $C^4$, $C^5$ and $C^6$ to which Rs and AR do not bind may be replaced with V. For example, when AR binds to $C^2$, and Rs binds to $C^3$, one of the ring-constituting carbon atoms $C^4$, $C^5$, and $C^6$ may be replaced with V. As another example, it is meant that when AR binds to $C^3$, and Rs binds to $C^4$, one of the atoms $C^2$, $C^5$, and $C^6$ may be replaced with V. Among them combinations and other combinations, preferred examples are a compound wherein AR binds to $C^2$, Rs binds to $C^3$, and $C^4$ is replaced with V; a compound wherein AR binds to $C^2$, Rs binds to $C^4$, and $C^5$ is replaced with V; a compound wherein AR binds to $C^2$, Rs binds to $C^5$, and $C^4$ is replaced with V; a compound wherein AR binds to $C^3$, Rs binds to $C^4$, and $C^5$ is replaced with V; a compound wherein AR binds to $C^3$, Rs binds to $C^4$, and $C^6$ is replaced with V; a compound wherein AR binds to $C^3$, Rs binds to $C^5$, and $C^4$ is replaced with V; a compound wherein AR binds to $C^3$, Rs binds to $C^6$, and $C^5$ is replaced with V, and the like. Furthermore, particularly preferred examples include a compound wherein AR binds to $C^3$, Rs binds to $C^4$, and $C^3$ is replaced with V; and a compound wherein AR binds to $C^3$, Rs binds to $C^4$, and $C^6$ is replaced with V, and an particularly preferred example is a compound wherein AR binds to $C^3$, Rs binds to $C^4$, and $C^5$ is replaced with V.

V represents nitrogen atom, or carbon atom substituted with Zx. Namely, when V represent nitrogen atom, the aromatic ring (E) in the formula (I) represents a pyridine ring. When V represent carbon atom substituted with Zx, the aromatic ring (E) is a benzene ring having Zx. Both of the compounds are particularly preferred. Furthermore, a compound wherein AR binds to $C^3$, Rs binds to $C^4$, $C^5$ is V replaced with V, and this V represents nitrogen atom is particularly preferred.

Zx is defined as a linear or branched saturated alkyl group having 1 to 4 carbon atoms, fluorine atom, chlorine atom, bromine atom, nitro group, —$OR^9$, or —$N(Rn^1)(Rn^2)$.

Among them, fluorine atom, chlorine atom, bromine atom, and nitro group are preferred examples, and fluorine atom is particularly preferred.

As for Zx, examples of the linear or branched saturated alkyl group having 1 to 4 carbon atoms include methyl group, ethyl group, propyl group, isopropyl group, butyl group, isobutyl group, t-butyl group and the like, and among them, methyl group is particularly preferred.

$R^9$ represents hydrogen atom, a lower alkyl group having 1 to 4 carbon atoms, or -$A^6$-Qp. Among them, hydrogen atom is a particularly preferred example. Preferred examples of the lower alkyl group having 1 to 4 carbon atoms include methyl group, ethyl group, propyl group, isopropyl group, butyl group, isobutyl group, t-butyl group, and the like, and methyl group is particularly preferred.

$A^6$ in -$A^6$-Qp represents a single bond or methylene, and Qp represents a phenyl group which may be substituted with one of $T^1$ or two or more of the same or different $T^1$. The substituent $T^1$ is a linear or branched saturated alkyl group having 1 to 4 carbon atoms, hydroxyl group, fluorine atom, chlorine atom, bromine atom, trifluoromethyl group, nitro group, an alkoxy group having 1 to 4 carbon atoms, or a mono- or dialkylamino group having 1 to 4 carbon atoms. Specific examples of -$A^6$-Qp include phenyl group, methylphenyl group, chlorophenyl group, benzyl group, methylbenzyl group, chlorobenzyl group, dichlorobenzyl group, fluorobenzyl group, trifluoromethylbenzyl group, nitrobenzyl group, methoxyphenyl group, N-methylaminobenzyl group, N,N-dimethylaminobenzyl group, and the like.

Preferred examples of —$OR^9$ include hydroxyl group, methoxy group, and the like, and hydroxyl group is particularly preferred.

$Rn^1$ represents hydrogen atom or a linear or branched saturated alkyl group having 1 to 4 carbon atoms, and hydrogen atom is particularly preferred. Examples of the linear or branched saturated alkyl group having 1 to 4 carbon atoms include methyl group, ethyl group, propyl group, isopropyl group, butyl group, isobutyl group, or t-butyl group, and the like. Among them, methyl group, ethyl group, propyl group, isopropyl group, and the like are preferred examples, and methyl group is particularly preferred.

$Rn^2$ has the same meaning as $Rn^1$, or represents a —$COR^{23}$ group or a —$SO_2R^{24}$ group, or binds to $Rn^1$ to form a 3- to 6-membered ring together with the nitrogen atom to which they bind to form a saturated nitrogen-containing cycloalkyl group or morpholino group.

$R^{23}$ represents hydrogen atom, a lower alkyl group having 1 to 4 carbon atoms, a lower alkoxy group having 1 to 4 carbon atoms, —O-$A^6$-Qp, or —$N(R^{25})(R^{26})$. $R^{25}$ represents hydrogen atom, or a linear or branched saturated alkyl group having 1 to 4 carbon atoms. $R^{26}$ has the same meaning as $R^{25}$, or binds to $R^{25}$ to form a 3- to 6-membered ring together with the nitrogen atom to which they bind to represent a saturated nitrogen-containing cycloalkyl group or morpholino group. Examples of the compound wherein $R^{26}$ "binds to $R^{25}$ to form a 3- to 6-membered ring together with the nitrogen atom to which they bind to represent a saturated nitrogen-containing cycloalkyl group or morpholino group" include, for example, a compound wherein a cyclic aminoalkyl group containing nitrogen atom such as pyrrolidino group, piperazino group and morpholino group is formed.

Specific examples of —$COR^{23}$ include formyl group, acetyl group, t-butyloxycarbonyl group, phenyloxycarbonyl group, benzyloxycarbonyl group, carbamoyl group, N-methylcarbamoyl group, N,N-dimethylcarbamoyl group, piperidine-1-carbonyl group, morpholine-4-carbonyl group, and the like, and preferred examples include formyl group, acetyl group, carbamoyl group, and the like. In the aforementioned formulas, as represented by $A^6$ and Qp, for example, the same symbols may sometimes be used simultaneously at different positions. These symbols are used to mean the same class of groups of substituents. However, because each substituent is independently chosen from each other, the same symbols do not mean that an identical substituent should be necessarily chosen, and as a result, selection of the same or different kind of substituent is not prohibited.

$R^{24}$ represents a lower alkyl group having 1 to 4 carbon atoms, amino group, or a mono- or dialkylamino group having 1 to 4 carbon atoms. Specific examples of —$SO_2R^{24}$ include mesyl group, sulfamoyl group, N-methylsulfamoyl group, N,N-dimethylsulfamoyl group, and the like, and preferred examples include mesyl group, N,N-dimethylsulfamoyl group, and the like.

Specific examples of —$N(Rn^1)(Rn^2)$ include amino group, N-methylamino group, N-ethylamino group, N-propylamino group, N-isopropylamino group, N,N-dimethylamino group, N,N-diethylamino group, piperidino group, pyrrolidino group, morpholino group, formylamino group, acetylamino group, t-butyloxycarbonylamino group, phenyloxycarbonylamino group, benzyloxycarbonylamino group, carbamoylamino group, N-methylcarbamoylamino group, N,N-dimethylcarbamoylamino group, piperidine-1-carbonylamino group, morpholine-4-carbonylamino group, mesylamino group, sulfamoylamino group, N-methylsulfamoylamino group, N,N-dimethylsulfamoylamino group, and the like. Among them, preferred examples include amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, N,N-dimethylsulfamoylamino group, and the like, and amino group, N-methylamino group, and N,N-dimethylamino group are particularly preferred.

Therefore, preferred examples of Zx include fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, N,N-dimethylsulfamoylamino group, and the like, and particularly preferred examples include fluorine atom, methyl group, hydroxyl group, amino group, N-methylamino group, N,N-dimethylamino group, and the like.

In the formula (I), Rs is defined to represent -D-Rx or —N(Ry)(Rz).

D is defined to represent a single bond, oxygen atom, sulfur atom, —S(O)—, —S(O)$_2$—, or —C(O)—. Among them, oxygen atom and sulfur atom are preferred, and oxygen atom is particularly preferred. Another preferred examples include the compounds wherein D represent a single bond.

Rx represents a linear or branched saturated alkyl group having 3 to 8 carbon atoms, or represents Ra, Rb, or Rc mentioned above.

As for Rx, examples of the linear or branched saturated alkyl group having 3 to 8 carbon atoms include, for example, propyl group, isopropyl group, butyl group, isobutyl group, 1-methylpropyl group, t-butyl group, pentyl group, isopentyl group, 2-methylbutyl group, 2,2-dimethylpropyl group, hexyl group, 4-methylpentyl group, 2,3-dimethylbutyl group, 2-ethylbutyl group, heptyl group, octyl group, and the like, and butyl group, isobutyl group, and 2-ethylbutyl group are particularly preferred.

As for Rx, $R^1$ of Ra is defined to be a saturated cyclic alkyl group having 3 to 7 carbon atoms substituted with a lower alkyl group having 1 to 4 carbon atoms or an unsubstituted saturated cyclic alkyl group having 3 to 7 carbon atoms, or a condensed saturated cyclic alkyl group having 6 to 8 carbon atoms substituted with a lower alkyl group having 1 to 4 carbon atoms or an unsubstituted condensed saturated cyclic alkyl group having 6 to 8 carbon atoms. As for $R^1$, examples of the saturated cyclic alkyl group having 3 to 7 carbon atoms include cyclopropyl group, cyclobutyl group, cyclopentyl group, cyclohexyl group, cycloheptyl group, and the like, and cyclopentyl group, cyclohexyl group, and cycloheptyl group are particularly preferred. As for $R^1$, examples of the condensed saturated cyclic alkyl group having 6 to 8 carbon atoms group include bicyclo[2,2,1]heptyl group, bicyclo[2,2,2]octyl group, and the like.

Examples of the lower alkyl group having 1 to 4 carbon atoms substituting on $R^1$ include methyl group, ethyl group, propyl group, isopropyl group, butyl group, isobutyl group, t-butyl group, and the like. Examples of $R^1$ substituted with a lower alkyl group having 1 to 4 carbon atoms include methylcyclopentyl group, methylcyclohexyl group, methylbicyclo[2,2,1]heptyl group, and the like.

Symbol k is defined to be 0 or an integer of 1 to 3. A single bond where k is 0, methylene where k is 1, and ethylene where k is 2 are preferred, and a bond where k is 0, and methylene where k is 1 are particularly preferred.

Examples of Ra include cyclopropyl group, cyclobutyl group, cyclopentyl group, cyclohexyl group, cycloheptyl group, cyclopropylmethyl group, cyclobutylmethyl group, cyclopentylmethyl group, cyclohexylmethyl group, cycloheptylmethyl group, 2-cyclopentylethyl group, 2-cyclohexylethyl group, 3-cyclohexylpropyl group, 2-methylcyclopentyl group, 3-methylcyclopentyl group, 3,4-dimethylcyclopentyl group, 4-methylcyclohexyl group, 4,4-dimethylcyclohexyl group, 4-ethylcyclohexyl group, 4-methylcyclohexylmethyl group, bicyclo[2,2,1]heptane-2-methyl group, bicyclo[2,2,2]octane-2-methyl group, 3-methylbicyclo[2,2,1]heptane-2-methyl group, bicyclo[2,2,1]hept-1-ylmethyl group, bicyclo[2,2,2]oct-1-ylmethyl group, and the like. Cyclopentyl group, cyclohexyl group, cycloheptyl group, cyclopentylmethyl group, cyclohexylmethyl group, 2-cyclopentylethyl group, 2-cyclohexylethyl group are preferred, and cyclopentyl group, cyclohexyl group, cycloheptyl group, cyclopentylmethyl group, cyclohexylmethyl group are particularly preferred.

As for Rx, $A^2$ in Rb is defined to be a single bond, oxygen atom, sulfur atom, —S(O)—, —S(O)$_2$—, or —N(R$^4$)—. $R^4$ is defined to be a lower alkyl group having 1 to 4 carbon atoms. Preferred examples are methyl group, ethyl group, propyl group, isopropyl group, butyl group, isobutyl group, t-butyl group, and the like, and methyl group and ethyl group are particularly preferred examples. Therefore, particularly preferred examples of $A^2$ include a single bond, oxygen atom, sulfur atom, —N(methyl)-, and —N(ethyl)-.

$A^1$ is defined to be a single bond or an alkylene (a) having 1 to 3 carbon atoms, i.e., methylene, ethylene or trimethylene. However, when $A^2$ represents oxygen atom, sulfur atom, —S(O)—, —S(O)$_2$— or —N(R$^4$)—, $A^1$ is ethylene or trimethylene. Further, the alkylene (a) may be substituted with a lower alkyl group having 1 to 4 carbon atoms or phenyl group. Examples of the lower alkyl group having 1 to 4 carbon atoms for the above compound include methyl group, ethyl group, propyl group, isopropyl group, butyl group, isobutyl group, t-butyl group, and the like, and methyl group, and ethyl group are preferred examples. Specific examples of $A^1$ include methylene, methylmethylene, ethylmethylene, phenylmethylene, ethylene, methylethylene, dimethylethylene, ethylethylene, phenylethylene, trimethylene, methyltrimethylene, and the like. Among them, when $A^2$ represents a single bond, $A^1$ is most preferably a single bond, or methylene, methylmethylene, or ethylene. Further, when $A^2$ represents oxygen atom, sulfur atom, —S(O)—, —S(O)$_2$— or —N(R$^4$)—, $A^1$ is most preferably ethylene.

Q in Rb is defined to be a residue of a partially unsaturated or completely unsaturated monocyclic or condensed bicyclic carbon ring or heterocyclic ring (q), and the heterocyclic ring (q) means a ring containing 1 to 4 the same or different ring-constituting heteroatoms selected from the group consisting of nitrogen atom, oxygen atom, and sulfur atom. The term "residue" means a monovalent group formed by eliminating hydrogen atom bonding to a ring-constituting atom. The residue of monocyclic carbon ring or heterocyclic ring is a partially unsaturated or completely unsaturated substituent having 5 to 7 atoms, and examples include, for example, phenyl group, thienyl group, furyl group, pyrrolyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, and the like. Among them, phenyl group, thienyl group, furyl group, pyridyl group, and oxazolyl group are preferred examples, and phenyl group is particularly preferred.

The condensed bicyclic carbon ring or heterocyclic ring is a partially unsaturated or completely unsaturated ring having 8 to 11 atoms, and examples of residue thereof include, for example, naphthyl group, tetrahydronaphthyl group, indanyl group, indenyl group, quinolyl group, isoquinolyl group, indolyl group, benzofuryl group, benzothienyl group, benzimidazolyl group, benzoxazolyl group, benzothiazolyl group, indazolyl group, 4H-chromenyl group, dihydrobenzodioxyl group, benzoisoxazolyl group, pyrrolopyridinyl group, pyrazolopyridinyl group, triazolopyridinyl group, thienopyridinyl group, thienopyrazolyl group, 1,3-dihydrobenzimidazole group, dihydro-3H-benzoxazole group, dihydro-3H-benzothiazole group, and the like. Among them, naphthyl group, tetrahydronaphthyl group, indanyl group, indolyl group, and dihydrobenzodioxyl group are preferred examples, and indanyl group is one of particularly preferred examples.

Q binds to $A^2$ at an arbitrary position on the ring. Preferred examples of Q with indication of bonding position include phenyl group, 2- or 3-thienyl group, 2- or 3-furyl group, 2-, 3- or 4-pyridyl group, 2-, 4- or 5-oxazolyl group, 1- or 2-naphthyl group, 1-, 2-, 5- or 6-tetrahydronaphthyl group, indan-1-yl group, indan-2-yl group, indan-4-yl group, indan-5-yl group, 1-, 2-, 3-, 4-, 5-, 6-, or 7-indolyl group, 2-, 5- or 6-dihydrobenzodioxyl group, and the like. Among them, phenyl group, and indan-2-yl group are particularly preferred.

In Rb, $R^2$ and $R^3$ are defined to be substituents of Q, and independently represent hydrogen atom, a linear or branched saturated alkyl group having 1 to 4 carbon atoms, oxo group, thioxo group, fluorine atom, chlorine atom, bromine atom, trifluoromethyl group, —OR$^6$, —N(R$^6$)(R$^{6'}$), —NHCOR$^7$, —NHSO$_2$R$^8$, or -A$^6$-Qa, or bind to each other to represent methylenedioxy group.

Examples of the linear or branched saturated alkyl group having 1 to 4 carbon atoms include methyl group, ethyl group, propyl group, isopropyl group, butyl group, isobutyl group, t-butyl group, and the like, and methyl group is particularly preferred.

$R^6$ in —N(R$^6$)(R$^{6'}$) represents hydrogen atom or a lower alkyl group having 1 to 4 carbon atoms. $R^{6'}$ has the same meaning as R$^6$, or binds to R$^6$ to form a 3- to 6-membered ring together with the nitrogen atom to which they bind to form a saturated nitrogen-containing cycloalkyl group or morpholino group. Therefore, specific examples of —N(R$^6$)(R$^{6'}$) include amino group, N-methylamino group, N-ethylamino group, N-propylamino group, N-isopropylamino group, N,N-dimethylamino group, N,N-diethylamino group, piperidino group, pyrrolidino group, morpholino group, and the like. N,N-Dimethylamino group, piperidino group, morpholino group, and the like are preferred examples, and N,N-dimethylamino group is a particularly preferred example.

R$^5$ and R$^7$ are defined to independently represent hydrogen atom, a lower alkyl group having 1 to 4 carbon atoms, or a -A$^6$-Qa group. Examples of the lower alkyl group having 1 to 4 carbon atoms include methyl group, ethyl group, propyl group, isopropyl group, butyl group, isobutyl group, t-butyl group, and the like, and among them, methyl group is a preferred example.

A$^6$ in -A$^6$-Qa has the same meaning as that defined above. Qa is defined to be a partially unsaturated or completely unsaturated monocyclic or condensed bicyclic carbon ring or heterocyclic ring (qa), and the heterocyclic ring (qa) means a substituent containing 1 to 4 the same or different ring-constituting heteroatoms selected from the group consisting of nitrogen atom, oxygen atom, and sulfur atom. The monocyclic carbon ring or heterocyclic ring is a partially unsaturated or completely unsaturated ring having 5 to 7 atoms, and examples of residue thereof include, for example, phenyl group, thienyl group, furyl group, pyrrolyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, and the like. The condensed bicyclic carbon ring or heterocyclic ring is a partially unsaturated or completely unsaturated ring having 8 to 11 atoms, and examples of residue thereof include, for example, naphthyl group, indanyl group, indenyl group, quinolyl group, isoquinolyl group, indolyl group, benzofuryl group, benzothienyl group, benzimidazolyl group, benzoxazolyl group, benzothiazolyl group, indazolyl group, and the like.

Qa binds to A$^6$ at an arbitrary position on the ring. Further, Qa may be substituted with two or more of the same or different T$^1$. T$^1$ has the same meaning as defined above.

Specific examples of -A$^6$-Qa include phenyl group, methylphenyl group, chlorophenyl group, benzyl group, methylbenzyl group, chlorobenzyl group, dichlorobenzyl group, fluorobenzyl group, trifluoromethylbenzyl group, nitrobenzyl group, methoxyphenyl group, N-methylaminobenzyl group, N,N-dimethylaminobenzyl group, furyl group, thienyl group, pyrrolyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, indanyl group, indenyl group, quinolyl group, isoquinolyl group, indolyl group, benzofuryl group, benzothienyl group, benzimidazolyl group, benzoxazolyl group, benzothiazolyl group, indazolyl group, and the like.

R$^3$ each defined to be a lower alkyl group having 1 to 4 carbon atoms, and examples of the lower alkyl group having 1 to 4 carbon atoms include methyl group, ethyl group, propyl group, isopropyl group, butyl group, isobutyl group, t-butyl group, and the like.

Therefore, preferred examples of R$^2$ and R$^3$ include hydrogen atom, methyl group, fluorine atom, chlorine atom, trifluoromethyl group, methoxy group, dimethylamino group, acetylamino group, and methylsulfonylamino group, and hydrogen atom, methyl group, fluorine atom, chlorine atom, trifluoromethyl group, methoxy group, and dimethylamino group are particularly preferred. When Q represents phenyl group, A$^1$ represents a single bond, or unsubstituted methylene, and A$^2$ represents a single bond, at least one of R$^2$ and R$^3$ preferably represents a substituent other than hydrogen atom.

Particularly preferred examples of Rb include 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, and the like.

Symbol p in Rc is defined to be an integer of 2 to 4. Ethylene where p is 2, and trimethylene where p is 3 are preferred, and ethylene where p is 2 is particularly preferred. A$^4$ represents a single bond, or represents methylene or ethylene, and a single bond and methylene are particularly preferred. A$^5$ represents —C(O)—, —C(S)—, or —S(O)$_2$—, and all of them are preferred. Rd represents hydrogen atom, an alkyl group having 1 to 8 carbon atoms, or group Qa. Re represents an alkyl group having 1 to 8 carbon atoms, a -A$^6$-Qa group, a —(CH$_2$)$_r$R$^{14}$ group, a —OR$^{28}$ group, a —SR$^{28}$ group, or a —N(R$^{29}$)(R$^{30}$) group. The group Qa and -A$^6$-Qa have the same meanings as defined above.

The alkyl group having 1 to 8 carbon atoms is a linear or branched saturated alkyl group or a linear or branched partially unsaturated alkyl group, or an alkyl group which may contain a cycloalkyl group having 3 to 7 carbon atoms, and examples include, for example, methyl group, ethyl group, propyl group, isopropyl group, butyl group, isobutyl group, t-butyl group, pentyl group, isopentyl group, 2-methylbutyl group, 2,2-dimethylpropyl group, hexyl group, 4-methylpentyl group, 2,3-dimethylbutyl group, 2-ethylbutyl group, heptyl group, octyl group, cyclopropyl group, cyclobutyl group, cyclopentyl group, cyclohexyl group, cycloheptyl group, cyclopropylmethyl group, cyclobutylmethyl group, cyclopentylmethyl group, cyclohexylmethyl group, cycloheptylmethyl group, 2-cyclopentylethyl group, 2-cyclohexylethyl group, 2-methylcyclopentyl group, 3-methylcyclopentyl group, 3,4-dimethylcyclopentyl group, 4-methylcyclohexyl group, 4,4-dimethylcyclohexyl group, 4-ethylcyclohexyl group, 4-methylcyclohexylmethyl group, and the like.

Symbol i in —($CH_2$)$_i$$R^{14}$ represents an integer of 1 to 3, and $R^{14}$ represents hydroxyl group, an alkoxy group having 1 to 4 carbon atoms, carboxyl group, or an N,N-dialkylcarbamoyl group having 1 to 4 carbon atoms. Examples of the alkoxy group having 1 to 4 carbon atoms include methoxy group, ethoxy group, propyloxy group, isopropyloxy group, butoxy group, isobutyloxy group, t-butyloxy group, and the like. Examples of the N,N-dialkylcarbamoyl group having 1 to 4 carbon atoms include N,N-dimethylcarbamoyl group, N,N-diethylcarbamoyl group, and the like.

$R^{28}$ in —$OR^{28}$ or —$SR^{28}$ represents an alkyl group having 1 to 8 carbon atoms, or -$A^6$-Qa, and these have the same meanings as defined above.

$R^{29}$ in —N($R^{29}$)($R^{30}$) represents an alkyl group having 1 to 8 carbon atoms, an alkoxycarbonyl group having 1 to 4 carbon atoms, or -$A^6$-Qa. Among them, the alkyl group having 1 to 8 carbon atoms and -$A^6$-Qa have the same meanings as those defined above. Examples of the alkoxycarbonyl group having 1 to 4 carbon atoms include methyloxycarbonyl group, ethyloxycarbonyl group, propyloxycarbonyl group, isopropyloxycarbonyl group, butyloxycarbonyl group, isobutyloxycarbonyl group, t-butyloxycarbonyl group, and the like. $R^{30}$ represents hydrogen atom or a lower alkyl group having 1 to 4 carbon atoms, or binds to $R^{29}$ to form a 3- to 6-membered ring together with the nitrogen atom to which they bind to form a saturated nitrogen-containing cycloalkyl group or morpholino group. The lower alkyl group having 1 to 4 carbon atoms has the same meaning as defined above. Examples of the compound where "$R^{30}$ binds to $R^{29}$ to form a 3- to 6-membered ring together with the nitrogen atom to which they bind to form a saturated nitrogen-containing cycloalkyl group or morpholino group" include, for example, a compound wherein a cyclic aminoalkyl group containing nitrogen atom such as pyrrolidino group, piperazino group, and morpholino group is formed.

Preferred examples of Rd include hydrogen atom as well as methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorobenzyl group, 4-fluorobenzyl group, pyridin-2-yl group, pyridin-3-yl group, pyridin-4-yl group, and the like.

Particularly preferred examples of Rd include methyl group, ethyl group, propyl group, isopropyl group, butyl group, isobutyl group, cyclopropyl group, cyclopentyl group, cyclohexyl group, phenyl group, 4-methylphenyl group, 4-chlorophenyl group, 4-fluorophenyl group, benzyl group, 4-chlorophenylmethyl group, 4-fluorophenylmethyl group, and the like.

Preferred examples of substituted -$A^4$-Rd include methyl group, ethyl group, propyl group, isopropyl group, butyl group, isobutyl group, pentyl group, isoamyl group, cyclopropyl group, cyclopropylmethyl group, 2-(cyclopropyl)ethyl group, cyclopentyl group, cyclopentylmethyl group, 2-(cyclopentyl)ethyl group, cyclohexyl group, cyclohexylmethyl group, 2-(cyclohexyl)ethyl group, phenyl group, 4-methylphenyl group, 4-chlorophenyl group, 4-fluorophenyl group, benzyl group, 4-chlorophenylmethyl group, 4-fluorophenylmethyl group, 2-(4-chlorophenyl)ethyl group, 2-(4-fluorophenyl)ethyl group, pyridin-2-yl group, pyridin-3-yl group, pyridin-4-yl group, (pyridin-2-yl)methyl group, (pyridin-3-yl)methyl group, (pyridin-4-yl)methyl group, and the like.

Particularly preferred examples of substituted -$A^4$-Rd include methyl group, ethyl group, propyl group, isopropyl group, butyl group, isobutyl group, pentyl group, isoamyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, 2-(4-chlorophenyl)ethyl group, 2-(4-fluorophenyl)ethyl group, and the like.

Preferred examples of Re include methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, methylthioxo group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, ethyloxycarbonylamino group, and the like.

Particularly preferred examples of Re include isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, pyrrolidino group, piperidino group, morpholino group, and the like.

Preferred examples of -A⁵-Re include acetyl group, thioacetyl group, methanesulfonyl group, propionyl group, ethylthiocarbonyl group, butyryl group, propylthiocarbonyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, phenylmethylcarbonyl group, 4-methylphenylmethylcarbonyl group, 4-chlorophenylmethylcarbonyl group, 4-fluorophenylmethylcarbonyl group, (pyridin-2-yl)carbonyl group, (pyridin-2-yl)thiocarbonyl group, (pyridin-3-yl)carbonyl group, (pyridin-4-yl)carbonyl group, (furan-2-yl)carbonyl group, (thiophen-2-yl)carbonyl group, methyloxycarbonyl group, methylsulfanylcarbonyl group, methyloxythiocarbonyl group, methyloxycarbonylaminocarbonyl group, carbamoyl group, N-methylcarbamoyl group, N-methylthiocarbamoyl group, N,N-dimethylcarbamoyl group, N,N-dimethylthiocarbamoyl group, N,N-dimethylsulfamoyl group, ethyloxycarbonyl group, ethyloxycarbonylaminocarbonyl group, N-ethylcarbamoyl group, N-ethylthiocarbamoyl group, N,N-diethylcarbamoyl group, N,N-diethylthiocarbamoyl group, N,N-diethylsulfamoyl group, propyloxycarbonyl group, N-propylcarbamoyl group, N-propylthiocarbamoyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, phenylmethyloxycarbonyl group, 4-methylphenylmethyloxycarbonyl group, 4-chlorophenylmethyloxycarbonyl group, 4-fluorophenylmethyloxycarbonyl group, N-(pyridin-2-yl)carbamoyl group, N-(pyridin-2-yl)thiocarbamoyl group, N-(pyridin-3-yl)carbamoyl group, N-(pyridin-3-yl)thiocarbamoyl group, N-(pyridin-4-yl)carbamoyl group, N-(pyridin-4-yl)thiocarbamoyl group, N-(furan-2-yl)carbamoyl group, N-(thiophen-2-yl)carbamoyl group, (pyrrolidino-1-yl)carbonyl group, (piperidino-1-yl)carbonyl group, (morpholino-4-yl)carbonyl group, and the like.

Particularly preferred examples of -A⁵-Re include isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, (morpholino-4-yl)carbonyl group, and the like.

Specific examples of Rc include 2-(N-isobutyryl-N-methylamino)ethyl group, 2-(N-ethyl-N-isobutyrylamino)ethyl group, 2-(N-isobutyryl-N-propylamino)ethyl group, 2-(N-isobutyryl-N-isopropylamino)ethyl group, 2-(N-butyl-N-isobutyrylamino)ethyl group, 2-(N-isobutyl-N-isobutyrylamino)ethyl group, 2-(N-cyclopropyl-N-isobutyrylamino)ethyl group, 2-(N-cyclopentyl-N-isobutyrylamino)ethyl group, 2-(N-cyclopentylmethyl-N-isobutyrylamino)ethyl group, 2-(N-cyclohexyl-N-isobutyrylamino)ethyl group, 2-(N-cyclohexylmethyl-N-isobutyrylamino)ethyl group, 2-(N-isobutyryl-N-phenylamino)ethyl group, 2-[N-isobutyryl-N-(4-methylphenyl)amino]ethyl group, 2-[N-(4-chlorophenyl)-N-isobutyrylamino]ethyl group, 2-[N-(4-fluorophenyl)-N-isobutyrylamino]ethyl group, 2-(N-benzyl-N-isobutyrylamino)ethyl group, 2-[N-(4-chlorophenylmethyl)-N-isobutyrylamino]ethyl group, 2-[N-(4-fluorophenylmethyl)-N-isobutyrylamino]ethyl group, 2-[N-[2-(4-chlorophenyl)ethyl]-N-isobutyrylamino]ethyl group, 2-[N-[2-(4-fluorophenyl)ethyl]-N-isobutyrylamino]ethyl group, 2-(N-isobutylthiocarbonyl-N-methylamino)ethyl group, 2-(N-isobutylthiocarbonyl-N-isopropylamino)ethyl group, 2-(N-butyl-N-isobutylthiocarbonylamino)ethyl group, 2-(N-isobutyl-N-isobutylthiocarbonylamino)ethyl group, 2-(N-cyclopentyl-N-isobutylthiocarbonylamino)ethyl group, 2-(N-cyclopentylmethyl-N-isobutylthiocarbonylamino)ethyl group, 2-(N-isobutylthiocarbonyl-N-phenylamino)ethyl group, 2-(N-benzyl-N-isobutylthiocarbonylamino)ethyl group, 2-[N-(4-fluorophenylmethyl)-N-isobutylthiocarbonylamino]ethyl group, 2-(N-methyl-N-pivaloylamino)ethyl group, 2-(N-isopropyl-N-pivaloylamino)ethyl group, 2-(N-butyl-N-pivaloylamino)ethyl group, 2-(N-isobutyl-N-pivaloylamino)ethyl group, 2-(N-cyclohexyl-N-pivaloylamino)ethyl group, 2-(N- cyclohexylmethyl-N-pivaloylamino)ethyl group, 2-(N-phenyl-N-pivaloylamino)ethyl group, 2-(N-benzyl-N-pivaloylamino)ethyl group, 2-(N-cyclopentylcarbonyl-N-methylamino)ethyl group, 2-(N-butyl-N-cyclopentylcarbonylamino)ethyl group, 2-(N-cyclopentylcarbonyl-N-isobutylamino)ethyl group, 2-(N-cyclopentylcarbonyl-N-cyclopentylmethylamino)ethyl group, 2-(N-cyclopentylcarbonyl-N-phenylamino)ethyl group, 2-[N-cyclopentylcarbonyl-N-(4-fluorophenyl)amino]ethyl group, 2-(N-benzyl-N-cyclopentylcarbonylamino)ethyl group, 2-[N-cyclopentylcarbonyl-N-(4-fluorophenylmethyl)amino]ethyl group, 2-(N-methyl-N-phenylsulfonylamino)ethyl group, 2-(N-ethyl-N-phenylsulfonylamino)ethyl group, 2-(N-phenylsulfonyl-N-propylamino)ethyl group, 2-(N-isopropyl-N-phenylsulfonylamino)ethyl group, 2-(N-butyl-N-phenylsulfonylamino)ethyl group, 2-(N-isobutyl-N-phenylsulfonylamino)ethyl group, 2-(N-cyclopropyl-N-phenylsulfonylamino)ethyl group, 2-(N-cyclopentyl-N-phenylsulfonylamino)ethyl group, 2-(N-cyclopentylmethyl-N-phenylsulfonylamino)ethyl group, 2-(N-cyclohexyl-N-phenylsulfonylamino)ethyl group, 2-(N-cyclohexylmethyl-N-phenylsulfonylamino)ethyl group, 2-(N-phenyl-N-phenylsulfonylamino)ethyl group, 2-[N-(4-fluorophenyl)-N-phenylsulfonylamino]ethyl group, 2-(N-benzyl-N-phenylsulfonylamino)ethyl group, 2-[N—(N-butylcarbamoyl)-N-methylamino]ethyl group, 2-[N-butyl-N-(N-butylcarbamoyl)amino]ethyl group, 2-[N—(N-butylcarbamoyl)-N-isobutylamino]ethyl group, 2-[N—(N-butylcarbamoyl)-N-cyclopentylamino]ethyl group, 2-[N—(N-butylcarbamoyl)-N-cyclohexylmethylamino]ethyl group, 2-[N—(N-butylcarbamoyl)-N-phenylamino]ethyl group, 2-{N—(N-butylcarbamoyl)-N-(4-fluorophenyl)amino}ethyl group, 2-[N-benzyl-N-(N-butylcarbamoyl)amino]ethyl group, 2-{N—(N-butylcarbamoyl)-N-(4-fluorophenylmethyl)amino}ethyl group, 2-{N—(N-butylcarbamoyl)-N-[2-(4-fluorophenyl)ethyl]amino}ethyl group, 2-[N—(N-isopropylthiocarbamoyl)-N-methylamino]ethyl group, 2-[N-butyl-N-(N-isopropylthiocarbamoyl)amino]ethyl group, 2-[N-isobutyl-N-(N-isopropylthiocarbamoyl)amino]ethyl group, 2-[N-cyclopentyl-N-(N-isopropylthiocarbamoyl)amino]ethyl group, 2-[N-cyclohexylmethyl-N-(N-isopropylthiocarbamoyl)amino]ethyl group, 2-[N—(N-isopropylthiocarbamoyl)-N-phenylamino]ethyl group, 2-{N-(4-fluorophenyl)-N-(N-isopropylthiocarbamoyl)amino}ethyl group, 2-[N-benzyl-N-(N-isopropylthiocarbamoyl)amino]ethyl group, 2-(N-isobutyloxycarbonyl-N-methylamino)ethyl group, 2-(N-butyl-N-isobutyloxycarbonylamino)ethyl group, 2-(N-isobutyl-N-isobutyloxycarbonylamino)ethyl group, 2-(N-cyclopentyl-N-isobutyloxycarbonylamino)ethyl group, 2-(N-cyclohexylmethyl-N-isobutyloxycarbonylamino)ethyl group, 2-(N-isobutyloxycarbonyl-N-phenylamino)ethyl group, 2-[N-(4-fluorophenyl)-N-isobutyloxycarbonylamino]ethyl group, 2-(N-benzyl-N-isobutyloxycarbonylamino)ethyl group, 2-[N—(N-cyclopentylcarbamoyl)-N-methylamino]ethyl group, 2-[N-butyl-N-(N-cyclopentylcarbamoyl)amino]ethyl group, 2-[N—(N-cyclopentylcarbamoyl)-N-isobutylamino]ethyl group, 2-[N-cyclopentyl-N-(N-cyclopentylcarbamoyl)amino]ethyl group, 2-[N-cyclohexylmethyl-N-(N-cyclopentylcarbamoyl)amino]ethyl group, 2-[N—(N-cyclopentylcarbamoyl)-N-phenylamino]ethyl group, 2-[N-benzyl-N-(N-cyclopentylcarbamoyl)amino]ethyl group, 2-[N—(N-cyclohexylthiocarbamoyl)-N-methylamino]ethyl group, 2-[N-butyl-N-(N-cyclohexylthiocarbamoyl)amino]ethyl group, 2-[N—(N-cyclohexylthiocarbamoyl)-N-isobutylamino]ethyl group, 2-[N—(N-cyclohexylthiocarbamoyl)-N-cyclopentylamino]ethyl group, 2-[N-cyclohexylmethyl-N-(N-cyclohexylthiocarbamoyl)amino]ethyl group, 2-[N—(N-cyclohexylthiocarbamoyl)-N-phenylamino]ethyl group, 2-[N-benzyl-N-(N-cyclohexylthiocarbamoyl)amino]ethyl group, 2-(N-methyl-N-phenyloxycarbonylamino)ethyl group, 2-(N-butyl-N-phenyloxycarbonylamino)ethyl group, 2-(N-isobutyl-N-phenyloxycarbonylamino)ethyl group, 2-(N-cyclopentyl-N-phenyloxycarbonylamino)ethyl group, 2-(N-cyclohexylmethyl-N-phenyloxycarbonylamino)ethyl group, 2-(N-phenyl-N-phenyloxycarbonylamino)ethyl group, 2-(N-benzyl-N-phenyloxycarbonylamino)ethyl group, 2-[N-methyl-N-(N-phenylcarbamoyl)amino]ethyl group, 2-[N-butyl-N-(N-phenylcarbamoyl)amino]ethyl group, 2-[N-isobutyl-N-(N-phenylcarbamoyl)amino]ethyl group, 2-[N-cyclopentyl-N-(N-phenylcarbamoyl)amino]ethyl group, 2-[N-cyclohexylmethyl-N-(N-phenylcarbamoyl)amino]ethyl group, 2-[N-phenyl-N-(N-phenylcarbamoyl)amino]ethyl group, 2-[N-benzyl-N-(N-phenylcarbamoyl)amino]ethyl group, and the like.

When Rs in the formula (I) represents —N(Ry)(Rz), Rz is defined to have the same meaning as Rx, or Rz represents methyl group, ethyl group, or a -A$^5$-Re group. -A$^5$-Re has the same meaning as defined above.

Particularly preferred examples of Rz include butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy) ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, (morpholino-4-yl)carbonyl group, and the like.

Among the Rz, methyl group or ethyl group is particularly preferred when Ry is other than hydrogen atom.

Ry represents hydrogen atom, an alkyl group having 1 to 8 carbon atoms, or a -$A^6$-Qp group, or binds to Rz to form a saturated or unsaturated nitrogen-containing cyclic substituent having 3 to 7 atoms together with nitrogen atom to which they bind. The alkyl group having 1 to 8 carbon atoms is a linear or branched saturated alkyl group, a linear or branched partially unsaturated alkyl group, or an alkyl group which may contain a cyclic alkyl group having 3 to 7 carbon atoms. Examples include methyl group, ethyl group, propyl group, isopropyl group, butyl group, isobutyl group, t-butyl group, pentyl group, isopentyl group, 2-methylbutyl group, 2,2-dimethylpropyl group, hexyl group, 4-methylpentyl group, 2,3-dimethylbutyl group, 2-ethylbutyl group, heptyl group, octyl group, cyclopropyl group, cyclobutyl group, cyclopentyl group, cyclohexyl group, cycloheptyl group, cyclopropylmethyl group, cyclobutylmethyl group, cyclopentylmethyl group, cyclohexylmethyl group, cycloheptylmethyl group, 2-cyclopentylethyl group, 2-cyclohexylethyl group, 2-methylcyclopentyl group, 3-methylcyclopentyl group, 3,4-dimethylcyclopentyl group, 4-methylcyclohexyl group, 4,4-dimethylcyclohexyl group, 4-ethylcyclohexyl group, 4-methylcyclohexylmethyl group, and the like. -$A^6$-Qp has the same meaning as defined above.

Particularly preferred examples of Ry include hydrogen atom, methyl group, ethyl group, isobutyl group, and the like.

Ry also binds to Rz to represents a saturated or unsaturated nitrogen-containing cyclic substituent having 3 to 7 atoms formed together with the nitrogen atom to which they bind. Specific examples thereof include cyclic substituents containing nitrogen atom such as 1-pyrrolidino group, 1-piperidino group, 1-homopiperidino group, 1-piperazino group, 4-morpholino group, pyrrol-1-yl group, imidazol-1-yl group, and pyrazol-1-yl group, and all of these are preferred.

The nitrogen-containing cyclic substituent may be substituted with one or two lower alkyl groups having 1 to 4 carbon atoms wherein the two alkyl groups may be the same or different. Examples of the lower alkyl having 1 to 4 carbon atoms include methyl group, ethyl group, propyl group, isopropyl group, butyl group, isobutyl group, or t-butyl group.

Among the substituent —N(Ry)(Rz), particularly preferred examples include N,N-dimethylamino group, N-ethyl-N-methylamino group, N,N-diethylamino group, N-methyl-N-propylamino group, N-ethyl-N-propylamino group, N-isopropyl-N-methylamino group, N-ethyl-N-isopropylamino group, N-butylamino group, N-butyl-N-methylamino group, N-butyl-N-ethylamino group, N-isobutylamino group, N-isobutyl-N-methylamino group, N-ethyl-N-isobutylamino group, N-(2-ethylbutyl)amino group, N-(2-ethylbutyl)-N-methylamino group, N-cyclopentylamino group, N-cyclopentyl-N-methylamino group, N-cyclohexylamino group, N-cyclohexyl-N-methylamino group, N-cycloheptylamino group, N-(cyclopentylmethyl)amino group, N-(cyclopentylmethyl)-N-methylamino group, N-(cyclohexylmethyl)amino group, N-(cyclohexylmethyl)-N-methylamino group, N-(2-methylphenyl)amino group, N-(4-methylphenyl)amino group, N-(2-fluorophenyl)amino group, N-(3-fluorophenyl)amino group, N-(4-fluorophenyl)amino group, N-(2-chlorophenyl)amino group, N-(3-chlorophenyl)amino group, N-(4-chlorophenyl)amino group, N-(indan-2-yl) amino group, N-(1-phenylethyl)amino group, N-[1-(2-fluorophenyl)ethyl]amino group, N-[1-(3-fluorophenyl)ethyl] amino group, N-[1-(4-fluorophenyl)ethyl]amino group, N-[1-(2-chlorophenyl)ethyl]amino group, N-[1-(3-chlorophenyl)ethyl]amino group, N-[1-(4-chlorophenyl)ethyl] amino group, N-(2-methylphenylmethyl)amino group, N-methyl-N-(2-methylphenylmethyl)amino group, N-(3-methylphenylmethyl)amino group, N-methyl-N-(3-methylphenylmethyl)amino group, N-(4-methylphenylmethyl) amino group, N-methyl-N-(4-methylphenylmethyl)amino group, N-(2-fluorophenylmethyl)amino group, N-(2-fluorophenylmethyl)-N-methylamino group, N-(3-fluorophenylmethyl)amino group, N-(3-fluorophenylmethyl)-N-methylamino group, N-(4-fluorophenylmethyl)amino group, N-(4-fluorophenylmethyl)-N-methylamino group, N-(2-chlorophenylmethyl)amino group, N-(2-chlorophenylmethyl)-N-methylamino group, N-(3-chlorophenylmethyl)amino group, N-(3-chlorophenylmethyl)-N-methylamino group, N-(4-chlorophenylmethyl)amino group, N-(4-chlorophenylmethyl)-N-methylamino group, N-(2,3-difluorophenylmethyl)amino group, N-(2,3-difluorophenylmethyl)-N-methylamino group, N-(2,4-difluorophenylmethyl)amino group, N-(2,4-difluorophenylmethyl)-N-methylamino group, N-(2,5-difluorophenylmethyl)amino group, N-(2,5-difluorophenylmethyl)-N-methylamino group, N-(3,4-difluorophenylmethyl)amino group, N-(3,4-difluorophenylmethyl)-N-methylamino group, N-(3,5-difluorophenylmethyl)amino group, N-(3,5-difluorophenylmethyl)-N-methylamino group, N-(2,3-dichlorophenylmethyl)amino group, N-(2,3-dichlorophenylmethyl)-N-methylamino group, N-(2,4- dichlorophenylmethyl)amino group, N-(2,4-dichlorophenylmethyl)-N-methylamino group, N-(2,5-dichlorophenylmethyl)amino group, N-(2,5-dichlorophenylmethyl)-N-methylamino group, N-(2,6-dichlorophenylmethyl)amino group, N-(2,6-dichlorophenylmethyl)-N-methylamino group, N-(3,4-dichlorophenylmethyl)amino group, N-(3,4-dichlorophenylmethyl)-N-methylamino group, N-(3,5-dichlorophenylmethyl)amino group, N-(3,5-dichlorophenylmethyl)-N-methylamino group, N-[2-(trifluoromethyl)phenylmethyl]amino group, N-methyl-N-[2-(trifluoromethyl)phenylmethyl]amino group, N-[3-(trifluoromethyl)phenylmethyl]amino group, N-methyl-N-[3-(trifluoromethyl)phenylmethyl]amino group, N-[4-(trifluoromethyl)phenylmethyl]amino group, N-methyl-N-[4-(trifluoromethyl)phenylmethyl]amino group, 1-pyrrolidino group, 1-(4-methylpiperidino) group, 1-homopiperidino group, and 4-morpholino group.

A most preferred example of Rs in the aforementioned general formula (I) include Rs which meets the conditions of: Rs is -D-Rx wherein D is a single bond and Rx represents Rb, and $A^1$ and $A^2$ in Rb are single bonds. Specific examples include phenyl group, 2-methylphenyl group, 3-methylphenyl group, 4-methylphenyl group, 2,3-dimethylphenyl group, 3,5-dimethylphenyl group, 2-methoxyphenyl group, 3-methoxyphenyl group, 4-methoxyphenyl group, 2-fluorophenyl group, 3-fluorophenyl group, 4-fluorophenyl group, 2-chlorophenyl group, 3-chlorophenyl group, 4-chlorophenyl group, 2,3-difluorophenyl group, 2,4-difluorophenyl group, 2,5-difluorophenyl group, 3,4-difluorophenyl group, 2,3-dichlorophenyl group, 2,4-dichlorophenyl group, 2,5-dichlorophenyl group, 2,6-dichlorophenyl group, 3,4-dichlorophenyl group, 3,5-dichlorophenyl group, 2-trifluoromethylphenyl group, 3-trifluoromethylphenyl group, 4-trifluoromethylphenyl group, 4-(N,N-dimethylamino)phenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, furan-2-yl group, furan-3-yl group, thiophen-2-yl group, thiophen-3-yl group, pyridin-2-yl group, pyridin-3-yl group, pyridin-4-yl group, naphthalen-1-yl group, naphthalen-2-yl group, 1H-indol-5-yl group, 1-methyl-1H-indol-5-yl group, 1H-indazol-5-yl group, or 1-methyl-1H-indazol-5-yl group.

AR in the formula (I) is defined to be a residue of a partially unsaturated or completely unsaturated condensed bicyclic carbon ring or heterocyclic ring (ar). Further, AR may be substituted with one of Xa or two or more of the same or different Xa. The heterocyclic ring (ar) means a ring containing 1 to 4 the same or different ring-constituting heteroatoms selected from the group consisting of nitrogen atom, oxygen atom, and sulfur atom.

The "condensed bicyclic carbon ring or heterocyclic ring" means a partially unsaturated or completely unsaturated ring having 8 to 11 atoms. Preferred examples include a partially unsaturated or completely unsaturated ring consisting of 8 atoms formed by fusion of 5-membered heterocyclic rings containing 1 or 2 ring-constituting heteroatoms selected from the group consisting of nitrogen, oxygen, and sulfur atoms, a partially unsaturated or completely unsaturated ring consisting of 9 atoms formed by fusion of a 5-membered heterocyclic ring containing 1 or 2 ring-constituting heteroatoms selected from the group consisting of nitrogen, oxygen, and sulfur atoms and a 6-membered carbon ring or a 6-membered heterocyclic ring containing 1 or 2 ring-constituting heteroatoms selected from the group consisting of nitrogen, oxygen, and sulfur atoms, and a partially unsaturated or completely unsaturated substituent consisting of 10 atoms formed by fusion of a 6-membered carbon ring or a 6-membered heterocyclic ring containing 1 or 2 ring-constituting heteroatoms selected from the group consisting of nitrogen, oxygen, and sulfur atoms and a 6-membered carbon ring or 6-membered heterocyclic rings containing 1 or 2 ring-constituting heteroatoms selected from the group consisting of nitrogen, oxygen, and sulfur atom. As the carbon ring constituting AR not containing a heteroatom, among the rings constituting AR, naphthalene ring is particularly preferred. Further, as the heterocyclic ring (ar) containing a heteroatom, among the rings constituting AR, those containing 1 or 2 ring-constituting heteroatoms are preferred.

As for AR in the formula (I), specific examples of preferred ring constituting AR include naphthalene, benzofuran, benzo[b]thiophene, indole, benzothiazole, dihydro-3H-benzothiazole, quinoline, dihydro-1H-quinoline, benzo[d]isothiazole, 1H-indazole, benzo [c]isothiazole, 2H-indazole, imidazo[1,2-a]pyridine, 1H-pyrrolo[2,3-b]pyridine, isoquinoline, dihydro-2H-isoquinoline, cinnoline, quinazoline, quinoxaline, 1H-benzimidazole, benzoxazole, 1H-pyrrolo[3,2-b]pyridine, benzo[1,2,5]thiadiazole, 1H-benzotriazole, 1,3-dihydropyrrolo[2,3-b]pyridine, 1,3-dihydrobenzimidazole, dihydro-3H-benzoxazole, phthalazine, [1,8]naphthalidine, [1,5]naphthalidine, 1H-pyrrolo[3,2-c]pyridine, 1H-pyrrolo[2,3-c]pyridine, 1H-pyrazolo[4,3-b]pyridine, 1H-pyrazolo[4,3-c]pyridine, 1H-pyrazolo[3,4-c]pyridine, 1H-pyrazolo[3,4-b]pyridine, [1,2,4]triazolo[4,3-a]pyridine, thieno[3,2-c]pyridine, thieno[3,2-b]pyridine, 1H-thieno[3,2-c]pyrazole, benzo[d]isoxazole, benzo[c]isoxazole, indolizine, 1,3-dihydroindol, 1H-pyrazolo[3,4-d]thiazole, 2H-isoindol, [1,2,4]triazolo[1,5-a]pyrimidine, 1H-pyrazolo[3,4-b]pyrazine, 1H-imidazo[4,5-b]pyrazine, 7H-purine, 4H-chromene, and the like. Among them, naphthalene, benzofuran, benzo[b]thiophene, indole, benzothiazole, dihydro-3H-benzothiazole, quinoline, dihydro-1H-quinoline, benzo[d]isothiazole, 1H-indazole, benzo[c]isothiazole, 2H-indazole, imidazo[1,2-a]pyridine, 1H-pyrrolo[2,3-b]pyridine, isoquinoline and dihydro-2H-isoquinoline constitute a particularly preferred group, and cinnoline, quinazoline, quinoxaline, 1H-benzimidazole, benzoxazole, 1H-pyrrolo[3,2-b]pyridine, benzo[1,2,5]thiadiazole, 1H-benzotriazole, 1,3-dihydropyrrolo[2,3-b]pyridine, 1,3-dihydrobenzimidazole and dihydro-3H-benzoxazole also constitute a particularly preferred group. Further, naphthalene, benzofuran, benzo[b]thiophene, indole, benzothiazole, quinoline, 1H-indazole and isoquinoline are particularly preferred.

AR binds to any of the ring-constituting carbon atoms $C^2$, $C^8$, $C^4$, $C^5$, and $C^6$ in the aromatic ring (E) in the aforementioned formula (I) at an arbitrary carbon atom in AR. Preferred examples of the ring constituting AR include, as indicated with substitution position in the aromatic ring (E), naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7- yl group, dihydro-1H-quinolin-6-yl group, dihydro-1H-quinolin-5-yl group, benzo[c]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo [c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, 4H-chromen-5-yl group, and the like. Among them, naphthalen-2-yl group, naphthalen-1-yl group, benzofuran-5-yl group, benzofuran-4-yl group, benzo[b]thiophen-5-yl group, benzo[b]thiophen-4-yl group, indol-5-yl group, indol-4-yl group, benzothiazol-6-yl group, benzothiazol-7-yl group, quinolin-6-yl group, quinolin-3-yl group, dihydro-1H-quinolin-6-yl group, benzo[d]isothiazol-5-yl group, 1H-indazol-5-yl group, 1H-indazol-4-yl group, imidazo[1,2-a]pyridin-6-yl group, 1H-pyrrolo[2,3-b]pyridin-5-yl group, isoquinolin-6-yl group, dihydro-2H-isoquinolin-6-yl group, cinnolin-6-yl group, benzoxazol-5-yl group, and the like constitute a particularly preferred group, and naphthalen-2-yl group, benzofuran-5-yl group, benzo[b]thiophen-5-yl group, indol-5-yl group, benzothiazol-6-yl group, quinolin-6-yl group, quinolin-3-yl group, benzo[d]isothiazol-5-yl group, 1H-indazol-5-yl group, imidazo[1,2-a]pyridin-6-yl group, 1H-pyrrolo[2,3-b]pyridin-5-yl group, isoquinolin-6-yl group, cinnolin-6-yl group, benzoxazol-5-yl group and the like are particularly preferred.

Further, AR may be substituted with one of Xa or the same or different two or more of Xa. Examples of substitution position of Xa include a carbon atom of AR not bonding to the aromatic ring (E), and/or when nitrogen atom is present, that nitrogen atom.

The substituent Xa represents a linear or branched saturated alkyl group having 1 to 4 carbon atoms, a saturated cyclic alkyl group having 3 to 7 carbon atoms, oxo group, thioxo group, fluorine atom, chlorine atom, trifluoromethyl group, —$(CH_2)_rR^{14}$, —$OR^{10}$, —$N(R^{11})(R^{12})$, —$SO_2R^{13}$, or —$COR^{27}$. However, when nitrogen atom is present in AR, Xa which may substitute on the nitrogen atom represents a linear or branched saturated alkyl group having 1 to 4 carbon atoms, a saturated cyclic alkyl group having 3 to 7 carbon atoms, or —$(CH_2)_rR^{14}$.

Preferred examples of the substituent Xa are oxo group, thioxo group, fluorine atom, chlorine atom, and trifluoromethyl group.

Examples of the linear or branched saturated alkyl group having 1 to 4 carbon atoms as the substituent Xa include methyl group, ethyl group, propyl group, isopropyl group, butyl group, isobutyl group, t-butyl group, and the like, and among them, methyl group, ethyl group, and propyl group are particularly preferred.

Further, examples of the saturated cyclic alkyl group having 3 to 7 carbon atoms include cyclopropyl group, cyclobutyl group, cyclopentyl group, cyclohexyl group, cycloheptyl group, and the like.

—$(CH_2)_rR^{14}$ has the same meaning as defined above. Preferred examples are 2-hydroxyethyl group, carboxymethyl group, 2-carboxyethyl group, and N,N-dimethylcarbamoylmethyl group, and a particularly preferred example is 2-hydroxyethyl group.

$R^{10}$ in —$OR^{10}$ represents hydrogen atom, a lower alkyl group having 1 to 4 carbon atoms, or a —$(CH_2)_rR^{14}$ group, and among them, hydrogen atom is a particularly preferred example. Examples of the lower alkyl group having 1 to 4 carbon atoms include methyl group, ethyl group, propyl group, isopropyl group, butyl group, isobutyl group, t-butyl group, and the like. Among them, methyl group is particularly preferred. —$(CH_2)_rR^{14}$ has the same meaning as defined above. Therefore, preferred examples of —$OR^{10}$ are hydroxyl group, methoxy group, 2-hydroxyethyloxy group, carboxymethyloxy group, 2-carboxyethyloxy group, N,N-dimethylcarbamoylmethyloxy group, and the like, and hydroxyl group, methoxy group, and 2-hydroxyethyloxy group are particularly preferred.

$R^{11}$ in —$N(R^{11})(R^{12})$ represents hydrogen atom, or a lower alkyl group having 1 to 4 carbon atoms, and $R^1$ represents hydrogen atom, a lower alkyl group having 1 to 4 carbon atoms, a hydroxyalkyl group having 2 to 4 carbon atoms, —$COR^{15}$, or —$SO_2R^{16}$, or binds to $R^{11}$ to form a 3- to 6-membered ring together with the nitrogen atom to which they bind to form a saturated nitrogen-containing cycloalkyl group or morpholino group. $R^{15}$ in —$COR^{15}$ represents a lower alkyl group having 1 to 4 carbon atoms, a hydroxyalkyl group having 2 to 4 carbon atoms, amino group, a mono- or dialkylamino group having 1 to 4 carbon atoms, or -$A^6$-Qa.

$R^{16}$ in —$SO_2R^{16}$ represents a lower alkyl group having 1 to 4 carbon atoms, amino group, or a mono- or dialkylamino group having 1 to 4 carbon atoms. Specific examples of —$N(R^{11})(R^{12})$ include amino group, N-methylamino group, N-ethylamino group, N-propylamino group, N-isopropylamino group, N,N-dimethylamino group, N,N-diethylamino group, piperidino group, pyrrolidino group, morpholino group, 2-hydroxyethylamino group, formylamino group, acetylamino group, benzoyl group, furan-2-carboxyamino group, 2-hydroxyacetylamino group, 2-aminoacetylamino group, carbamoylamino group, N-methylcarbamoylamino group, N,N-dimethylcarbamoylamino group, methylsulfonylamino group, sulfamoylamino group, N-methylsulfamoylamino group, N,N-dimethylsulfamoylamino group, and the like. Among them, preferred examples are amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, and the like, and amino group, N-methylamino group, N,N-dimethylamino group, and 2-hydroxyethylamino group are particularly preferred.

$R^{13}$ is in —$SO_2R^{13}$ represents a lower alkyl group having 1 to 4 carbon atoms, amino group, or a mono- or dialkylamino group having 1 to 4 carbon atoms. Preferred examples of —$SO_2R^{13}$ include methanesulfonyl group, sulfamoyl group, N-methylsulfamoyl group, N,N-dimethylsulfamoyl group, and the like.

$R^{27}$ in —$COR^{27}$ represents hydrogen atom, hydroxyl group, an alkoxy group having 1 to 4 carbon atoms, a lower alkyl group having 1 to 4 carbon atoms, amino group, or a mono- or dialkylamino group having 1 to 4 carbon atoms. Specific examples of —$COR^{27}$ include formyl group, carboxyl group, methoxycarbonyl group, ethoxycarbonyl group, acetyl group, propionyl group, carbamoyl group, N-methylcarbamoyl group, N,N-dimethylcarbamoyl group, and the like. Carboxyl group, acetyl group, carbamoyl group, N,N-dimethylcarbamoyl group, and the like are preferred examples, and carboxyl group is particularly preferred.

Preferred examples of the group Xa include oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, N,N-dimethylcarbamoyl group, and the like. Particularly preferred examples of the group Xa include oxo group, methyl group, ethyl group, propyl group, 2-hydroxyethyl group, hydroxyl group, methoxy group, 2-hydroxyethyloxy group, amino group, N-methylamino group, N,N-dimethylamino group, 2-hydroxyethylamino group, carboxyl group, and the like. Preferred examples of the group Xa which may substitute on nitrogen atom include methyl group, ethyl group, propyl group, hydroxymethyl group, 2-hydroxyethyl group, carboxymethyl group, 2-carboxyethyl group, and N,N-dimethylcarbamoylmethyl group. Among them, particularly preferred examples are methyl group, ethyl group, propyl group, and 2-hydroxyethyl group.

Preferred examples of AR substituted with the group Xa or unsubstituted AR include naphthalen-1-yl group, naphthalen-2-yl group, 6-fluoronaphthalen-2-yl group, 6-chloronaphthalen-2-yl group, 6-(trifluoromethyl)naphthalen-2-yl group, 5-hydroxynaphthalen-1-yl group, 5-hydroxynaphthalen-2-yl group, 6-hydroxynaphthalen-1-yl group, 6-hydroxynaphthalen-2-yl group, 7-hydroxynaphthalen-1-yl group, 7-hydroxynaphthalen-2-yl group, 5-methoxynaphthalen-1-yl group, 5-methoxynaphthalen-2-yl group, 6-methoxynaphthalen-1-yl group, 6-methoxynaphthalen-2-yl group, 7-methoxynaphthalen-1-yl group, 7-methoxynaphthalen-2-yl group, 5-(2-hydroxyethyloxy)naphthalen-2-yl group, 6-(2-hydroxyethyloxy)naphthalen-2-yl group, 7-(2-hydroxyethyloxy)naphthalen-2-yl group, 5-(carboxymethyloxy)naphthalen-2-yl group, 6-(carboxymethyloxy)naphthalen-2-yl group, 7-(carboxymethyloxy)naphthalen-2-yl group, 5-(N,N-dimethylcarbamoylmethyloxy)naphthalen-2-yl group, 6-(N,N-dimethylcarbamoylmethyloxy)naphthalen-2-yl group, 7-(N,N-dimethylcarbamoylmethyloxy)naphthalen-2-yl group, 5-aminonaphthalen-1-yl group, 5-aminonaphthalen-2-yl group, 6-aminonaphthalen-1-yl group, 6-aminonaphthalen-2-yl group, 7-aminonaphthalen-1-yl group, 7-aminonaphthalen-2-yl group, 5-(N-methylamino)naphthalen-1-yl group, 5-(N-methylamino)naphthalen-2-yl group, 6-(N-methylamino)naphthalen-1-yl group, 6-(N-methylamino)naphthalen-2-yl group, 7-(N-methylamino)naphthalen-1-yl group, 7-(N-methylamino)naphthalen-2-yl group, 5-(N,N-dimethylamino)naphthalen-1-yl group, 5-(N,N-dimethylamino)naphthalen-2-yl group, 6-(N,N-dimethylamino)naphthalen-1-yl group, 6-(N,N-dimethylamino)naphthalen-2-yl group, 7-(N,N-dimethylamino)naphthalen-1-yl group, 7-(N,N-dimethylamino)naphthalen-2-yl group, 5-(2-hydroxyethylamino)naphthalen-2-yl group, 6-(2-hydroxyethylamino)naphthalen-2-yl group, 7-(2-hydroxyethylamino)naphthalen-2-yl group, 5-acetylaminonaphthalen-2-yl group, 6-acetylaminonaphthalen-2-yl group, 6-(2-aminoacetylamino)naphthalen-2-yl group, 6-(2-hydroxyacetylamino)naphthalen-2-yl group, 7-(2-hydroxyacetylamino)naphthalen-2-yl group, 6-[(furan-2-carbonyl)amino]naphthalen-2-yl group, 7-[(furan-2-carbonyl)amino]naphthalen-2-yl group, 6-[(benzene-2-carbonyl)amino]naphthalen-2-yl group, 7-[(benzene-2-carbonyl)amino]naphthalen-2-yl group, 6-carbamoylaminonaphthalen-2-yl group, 6-methylsulfonylaminonaphthalen-2-yl group, 6-sulfamoylaminonaphthalen-2-yl group, 6-(N,N-dimethylsulfamoylamino)naphthalen-2-yl group, 6-methanesulfonylnaphthalen-2-yl group, 6-sulfamoylnaphthalen-2-yl group, 6-(N-methylsulfamoyl)naphthalen-2-yl group, 6-(N,N-dimethylsulfamoyl)naphthalen-2-yl group, 6-carboxynaphthalen-2-yl group, benzo[b]furan-4-yl group, benzo[b]furan-5-yl group, 2-methylbenzo[b]furan-4-yl group, 2-methylbenzo[b]furan-5-yl group, 3-methylbenzo[b]furan-4-yl group, 3-methylbenzo[b]furan-5-yl group, 2,3-dimethylbenzo[b]furan-4-yl group, 2,3-dimethylbenzo[b]furan-5-yl group, 2-carboxybenzo[b]furan-4-yl group, 2-carboxybenzo[b]furan-5-yl group, 2-carboxy-3-methylbenzo[b]furan-4-yl group, 2-carboxy-3-methylbenzo[b]furan-5-yl group, 3-acetylbenzo[b]furan-4-yl group, 3-acetylbenzo[b]furan-5-yl group, 3-acetyl-2-methylbenzo[b]furan-4-yl group, 3-acetyl-2-methylbenzo[b]furan-5-yl group, 3-hydroxymethylbenzo[b]furan-4-yl group, 3-hydroxymethylbenzo[b]furan-5-yl group, 3-hydroxymethyl-2-methylbenzo[b]furan-4-yl group, 3-hydroxymethyl-2-methylbenzo[b]furan-5-yl group, benzo[b]thiophen-4-yl group, benzo[b]thiophen-5-yl group, 2-methylbenzo[b]thiophen-4- yl group, 2-methylbenzo[b]thiophen-5-yl group, 3-methylbenzo[b]thiophen-4-yl group, 3-methylbenzo[b]thiophen-5-yl group, 2,3-dimethylbenzo[b]thiophen-4-yl group, 2,3-dimethylbenzo[b]thiophen-5-yl group, 2-carboxybenzo[b]thiophen-4-yl group, 2-carboxybenzo[b]thiophen-5-yl group, 2-carboxy-3-methylbenzo[b]thiophen-4-yl group, 2-carboxy-3-methylbenzo[b]thiophen-5-yl group, 3-acetylbenzo[b])thiophen-4-yl group, 3-acetylbenzo[b]thiophen-5-yl group, 3-acetyl-2-methylbenzo[b]thiophen-4-yl group, 3-acetyl-2-methylbenzo[b]thiophen-5-yl group, 3-hydroxymethylbenzo[b]thiophen-4-yl group, 3-hydroxymethylbenzo[b]thiophen-5-yl group, 3-hydroxymethyl-2-methylbenzo[b]thiophen-4-yl group, 3-hydroxymethyl-2-methylbenzo[b]thiophen-5-yl group, 1H-indol-4-yl group, 1H-indol-5-yl group, 2-methyl-1H-indol-4-yl group, 2-methyl-1H-indol-5-yl group, 3-methyl-1H-indol-4-yl group, 3-methyl-1H-indol-5-yl group, 2,3-dimethyl-1H-indol-4-yl group, 2,3-dimethyl-1H-indol-5-yl group, 2-carboxy-1H-indol-4-yl group, 2-carboxy-1H-indol-5-yl group, 2-carboxy-3-methyl-1H-indol-4-yl group, 2-carboxy-3-methyl-1H-indol-5-yl group, 3-acetyl-1H-indol-4-yl group, 3-acetyl-1H-indol-5-yl group, 3-acetyl-2-methyl-1H-indol-4-yl group, 3-acetyl-2-methyl-1H-indol-5-yl group, 3-hydroxymethyl-1H-indol-4-yl group, 3-hydroxymethyl-1H-indol-5-yl group, 3-hydroxymethyl-2-methyl-1H-indol-4-yl group, 3-hydroxymethyl-2-methyl-1H-indol-5-yl group, 1-methyl-1H-indol-4-yl group, 1-methyl-1H-indol-5-yl group, 1,2-dimethyl-1H-indol-4-yl group, 1,2-dimethyl-1H-indol-5-yl group, 1,3-dimethyl-1H-indol-4-yl group, 1,3-dimethyl-1H-indol-5-yl group, 1,2,3-trimethyl-1H-indol-4-yl group, 1,2,3-trimethyl-1H-indol-5-yl group, 2-carboxy-1-methyl-1H-indol-4-yl group, 2-carboxy-1-methyl-1H-indol-5-yl group, 2-carboxy-1,3-dimethyl-1H-indol-4-yl group, 2-carboxy-1,3-dimethyl-1H-indol-5-yl group, 3-acetyl-1-methyl-1H-indol-4-yl group, 3-acetyl-1-methyl-1H-indol-5-yl group, 3-acetyl-1,2-dimethyl-1H-indol-4-yl group, 3-acetyl-1,2-dimethyl-1H-indol-5-yl group, 3-hydroxymethyl-1-methyl-1H-indol-4-yl group, 3-hydroxymethyl-1-methyl-1H-indol-5-yl group, 3-hydroxymethyl-1,2-dimethyl-1H-indol-4-yl group, 3-hydroxymethyl-1,2-dimethyl-1H-indol-5-yl group, 1-ethyl-1H-indol-4-yl group, 1-ethyl-1H-indol-5-yl group, 1-ethyl-2-methyl-1H-indol-4-yl group, 1-ethyl-2-methyl-1H-indol-5-yl group, 1-ethyl-3-methyl-1H-indol-4-yl group, 1-ethyl-3-methyl-1H-indol-5-yl group, 1-ethyl-2,3-dimethyl-1H-indol-4-yl group, 1-ethyl-2,3-dimethyl-1H-indol-5-yl group, 2-carboxy-1-ethyl-1H-indol-4-yl group, 2-carboxy-1-ethyl-1H-indol-5-yl group, 2-carboxy-1-ethyl-3-methyl-1H-indol-4-yl group, 2-carboxy-1-ethyl-3-methyl-1H-indol-5-yl group, 3-acetyl-1-ethyl-1H-indol-4-yl group, 3-acetyl-1-ethyl-1H-indol-5-yl group, 3-acetyl-1-ethyl-2-methyl-1H-indol-4-yl group, 3-acetyl-1-ethyl-2-methyl-1H-indol-5-yl group, 1-ethyl-3-hydroxymethyl-1H-indol-4-yl group, 1-ethyl-3-hydroxymethyl-1H-indol-5-yl group, 1-ethyl-3-hydroxymethyl-2-methyl-1H-indol-4-yl group, 1-ethyl-3-hydroxymethyl-2-methyl-1H-indol-5-yl group, 1-propyl-1H-indol-4-yl group, 1-propyl-1H-indol-5-yl group, 2-methyl-1-propyl-1H-indol-4-yl group, 2-methyl-1-propyl-1H-indol-5-yl group, 3-methyl-1-propyl-1H-indol-4-yl group, 3-methyl-1-propyl-1H-indol-5-yl group, 2,3-dimethyl-1-propyl-1H-indol-4-yl group, 2,3-dimethyl-1-propyl-1H-indol-5-yl group, 2-carboxy-1-propyl-1H-indol-4-yl group, 2-carboxy-1-propyl-1H-indol-5-yl group, 2-carboxy-3-methyl-1-propyl-1H-indol-4-yl group, 2-carboxy-3-methyl-1-propyl-1H-indol-5-yl group, 3-acetyl-1-propyl-1H-indol-4-yl group, 3-acetyl-1-propyl-1H-indol-5-yl group, 3-acetyl-2-methyl-1-propyl-1H-indol-4-yl group, 3-acetyl-2-methyl-1-propyl-1H-indol-5-yl group, 3-hydroxymethyl-1-propyl-1H-indol-4-yl group, 3-hydroxymethyl-1-propyl-1H-indol-5-yl group, 3-hydroxymethyl-2-methyl-1-propyl-1H-indol-4-yl group, 3-hydroxymethyl-2-methyl-1-propyl-1H-indol-5-yl group, 1-(2-hydroxyethyl)-1H-indol-4-yl group, 1-(2-hydroxyethyl)-1H-indol-5-yl group, 1-(2-hydroxyethyl)-2-methyl-1H-indol-4-yl group, 1-(2-hydroxyethyl)-2-methyl-1H-indol-5-yl group, 1-(2-hydroxyethyl)-3-methyl-1H-indol-4-yl group, 1-(2-hydroxyethyl)-3-methyl-1H-indol-5-yl group, 2,3-dimethyl-1-(2-hydroxyethyl)-1H-indol-4-yl group, 2,3-dimethyl-1-(2-hydroxyethyl)-1H-indol-5-yl group, 2-carboxy-1-(2-hydroxyethyl)-1H-indol-4-yl group, 2-carboxy-1-(2-hydroxyethyl)-1H-indol-5-yl group, 2-carboxy-1-(2-hydroxyethyl)-3-methyl-1H-indol-4-yl group, 2-carboxy-1-(2-hydroxyethyl)-3-methyl-1H-indol-5-yl group, 3-acetyl-1-(2-hydroxyethyl)-1H-indol-4-yl group, 3-acetyl-1-(2-hydroxyethyl)-1H-indol-5-yl group, 3-acetyl-1-(2-hydroxyethyl)-2-methyl-1H-indol-4-yl group, 3-acetyl-1-(2-hydroxyethyl)-2-methyl-1H-indol-5-yl group, 1-(2-hydroxyethyl)-3-hydroxymethyl-1H-indol-4-yl group, 1-(2-hydroxyethyl)-3-hydroxymethyl-1H-indol-5-yl group, 1-(2-hydroxyethyl)-3-hydroxymethyl-2-methyl-1H-indol-4-yl group, 1-(2-hydroxyethyl)-3-hydroxymethyl-2-methyl-1H-indol-5-yl group, 1-carboxymethyl-1H-indol-4-yl group, 1-carboxymethyl-1H-indol-5-yl group, 1-carboxymethyl-2-methyl-1H-indol-4-yl group, 1-carboxymethyl-2-methyl-1H-indol-5-yl group, 1-carboxymethyl-3-methyl-1H-indol-4-yl group, 1-carboxymethyl-3-methyl-1H-indol-5-yl group, 1-carboxymethyl-2,3-dimethyl-1H-indol-4-yl group, 1-carboxymethyl-2,3-dimethyl-1H-indol-5-yl group, 2-carboxy-1-carboxymethyl-1H-indol-4-yl group, 2-carboxy-1-carboxymethyl-1H-indol-5-yl group, 2-carboxy-1-carboxymethyl-3-methyl-1H-indol-4-yl group, 2-carboxy-1-carboxymethyl-3-methyl-1H-indol-5-yl group, 3-acetyl-1-carboxymethyl-1H-indol-4-yl group, 3-acetyl-1-carboxymethyl-1H-indol-5-yl group, 3-acetyl-1-carboxymethyl-2-methyl-1H-indol-4-yl group, 3-acetyl-1-carboxymethyl-2-methyl-1H-indol-5-yl group, 1-carboxymethyl-3-hydroxymethyl-1H-indol-4-yl group, 1-carboxymethyl-3-hydroxymethyl-1H-indol-5-yl group, 1-carboxymethyl-3-hydroxymethyl-2-methyl-1H-indol-4-yl group, 1-carboxymethyl-3-hydroxymethyl-2-methyl-1H-indol-5-yl group, benzothiazol-6-yl group, 2-methylbenzothiazol-6-yl group, 2-methoxybenzothiazol-6-yl group, 2-aminobenzothiazol-6-yl group, 2-(N-methylamino)benzothiazol-6-yl group, 2-(N,N-dimethylamino)benzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, 2-methylquinolin-3-yl group, quinolin-6-yl group, 2-methylquinolin-6-yl group, 2-oxo-1,2-dihydroquinolin-6-yl group, benzo[d]isothiazol-5-yl group, 3-methylbenzo[d]isothiazol-5-yl group, 1H-indazol-5-yl group, 3-methyl-1H-indazol-5-yl group, 1-methyl-1H-indazol-5-yl group, 1,3-dimethyl-1H-indazol-5-yl group, 1-ethyl-1H-indazol-5-yl group, 1-ethyl-3-methyl-1H-indazol-5-yl group, 1-propyl-1H-indazol-5-yl group, 3-methyl-1-propyl-1H-indazol-5-yl group, 1-(2-hydroxyethyl)-1H-indazol-5-yl group, 1-(2-hydroxyethyl)-3-methyl-1H-indazol-5-yl group, 1-(carboxymethyl)-1H-indazol-5-yl group, 1-(carboxymethyl)-3-methyl-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, benzo[c]isothiazol-5-yl group, 3-methylbenzo[c]isothiazol-5-yl group, 2-methyl-2H-indazol-5-yl group, 2,3-dimethyl-2H-indazol-5-yl group, 2-ethyl-2H-indazol-5-yl group, 2-ethyl-3-methyl-2H-indazol-5-yl group, 2-propyl-2H-indazol-5-yl group, 3-methyl-2-propyl-2H-indazol-5-yl group, 2-(2-hydroxyethyl)-2H-indazol-5-yl group, 2-(2-hydroxyethyl)-3-methyl-2H-indazol-5-yl group, 2-(carboxymethyl)-2H-indazol-5-yl group, 2-(carboxymethyl)-3-methyl-2H-indazol-5-yl group, imidazo[1,2-a]pyridin-6-yl group, 2-methyl-imidazo[1,2-a]pyridin-6-yl group, 3-methyl-imidazo[1,2-a]pyridin-6-yl group, 2,3-dimethyl-imidazo[1,2-a]pyridin-6-yl group, 1H-pyrrolo[2,3-b]pyridin-5-yl group, 2-methyl-1H-pyrrolo[2,3-b]pyridin-5-yl group, 3-methyl-1H-pyrrolo[2,3-b]pyridin-5-yl group, 1-methyl-1H-pyrrolo[2,3-b]pyridin-5-yl group, 1,2-dimethyl-1H-pyrrolo[2,3-b]pyridin-5-yl group, 1,3-dimethyl-1H-pyrrolo[2,3-b]pyridin-5-yl group, 2,3-dimethyl-1H-pyrrolo[2,3-b]pyridin-5-yl group, 1,2,3-trimethyl-1H-pyrrolo[2,3-b]pyridin-5-yl group, 1-ethyl-1H-pyrrolo[2,3-b]pyridin-5-yl group, 1-ethyl-2-methyl-1H-pyrrolo[2,3-b]pyridin-5-yl group, 1-ethyl-3-methyl-1H-pyrrolo[2,3-b]pyridin-5-yl group, 1-ethyl-2,3-dimethyl-1H-pyrrolo[2,3-b]pyridin-5-yl group, 1-propyl-1H-pyrrolo[2,3-b]pyridin-5-yl group, 2-methyl-1-propyl-1H-pyrrolo[2,3-b]pyridin-5-yl group, 3-methyl-1-propyl-1H-pyrrolo[2,3-b]pyridin-5-yl group, 2,3-dimethyl-1-propyl-1H-pyrrolo[2,3-b]pyridin-5-yl group, 1-(2-hydroxyethyl)-1H-pyrrolo[2,3-b]pyridin-5-yl group, 1-(2-hydroxyethyl)-2-methyl-1H-pyrrolo[2,3-b]pyridin-5-yl group, 1-(2-hydroxyethyl)-3-methyl-1H-pyrrolo[2,3-b]pyridin-5-yl group, 2,3-dimethyl-1-(2-hydroxyethyl)-1H-pyrrolo[2,3-b]pyridin-5-yl group, 1-(carboxymethyl)1H-pyrrolo[2,3-b]pyridin-5-yl group, 1-(carboxymethyl)-2-methyl-1H-pyrrolo[2,3-b]pyridin-5-yl group, 1-(carboxymethyl)-3-methyl-1H-pyrrolo[2,3-b]pyridin-5-yl group, 1-(carboxymethyl)-2,3-dimethyl-1H-pyrrolo[2,3-b]pyridin-5-yl group, isoquinolin-6-yl group, 1-methylisoquinolin-6-yl group, 1-oxo-1,2-dihydroisoquinolin-6-yl group, cinnolin-6-yl group, cinnolin-5-yl group, quinazolin-6-yl group, quinazolin-7-yl group, quinazolin-5-yl group, 2-methylquinazolin-6-yl group, quinoxalin-6-yl group, quinoxalin-5-yl group, 2-methylquinoxalin-6-yl group, 1H-benzimidazol-5-yl group, 1H-benzimidazol-4-yl group, 1-methyl-1H-benzimidazol-5-yl group, 2-methyl-1H-benzimidazol-5-yl group, 1,2-dimethyl-1H-benzimidazol-5-yl group, benzoxazol-5-yl group, benzoxazol-6-yl group, benzoxazol-4-yl group, benzoxazol-7-yl group, 2-methyl-benzoxazol-5-yl group, 1H-pyrrolo[3,2-b]pyridin-5-yl group, 1H-pyrrolo[3,2-b]pyridin-6-yl group, 1-methyl-1H-pyrrolo[3,2-b]pyridin-5-yl group, 1-ethyl-1H-pyrrolo[3,2-b]pyridin-5-yl group, 2-methyl-1H-pyrrolo[3,2-b]pyridin-5-yl group, 3-methyl-1H-pyrrolo[3,2-b]pyridin-5-yl group, 1,3-dimethyl-1H-pyrrolo[3,2-b]pyridin-5-yl group, benzo[1,2,5]thiadiazol-5-yl group, benzo[1,2,5]thiadiazol-4-yl group, 1H-benzotriazol-5-yl group, 1H-benzotriazol-4-yl group, 1-methyl-1H-benzotriazol-5-yl group, 1-ethyl-1H-benzotriazol-5-yl group, 1,3-dihydropyrrolo[2,3-b]pyridin-2-on-5-yl group, 1,3-dihydropyrrolo[2,3-b]pyridin-2-on-4-yl group, 1-methyl-1,3-dihydropyrrolo[2,3-b]pyridin-2-on-5-yl group, 1,3-dihydrobenzimidazol-2-on-5-yl group, 1,3-dihydrobenzimidazol-2-on-4-yl group, 1-methyl-1,3-dihydrobenzimidazol-2-on-5-yl group, 1,3-dihydrobenzimidazole-2-thion-5-yl group, 1,3-dihydrobenzimidazole-2-thion-4-yl group, 1-methyl-1,3-dihydrobenzimidazole-2-thion-5-yl group, 3H-benzoxazol-2-on-6-yl group, 3H-benzoxazol-2-on-7-yl group, 3H-benzoxazol-2-on-5-yl group, 3H-benzoxazol-2-on-4-yl group, 3-methyl-3H-benzoxazol-2-on-6-yl group, 3H-benzoxazole-2-thion-6-yl group, 3H-benzoxazole-2-thion-7-yl group, 3H-benzoxazole-2-thion-5-yl group, 3H-benzoxazole-2-thion-4-yl group, 3-methyl-3H-benzoxazole-2-thion-6-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1-methyl-1H-pyrrolo[3,2-c]pyridin-6-yl group, 1-ethyl-1H-pyrrolo[3,2-c]pyridin-6-yl group, 2-methyl-1H-pyrrolo[3,2-c]pyridin-6-yl group, 3-methyl-1H-pyrrolo[3,2-c]pyridin-6-yl group, 1,3-dimethyl-1H-pyrrolo[3,2-c]pyridin-6-yl group, 1H-pyrrolo[2,3-c]pyridin-5-yl group, 1H-pyrrolo[2,3-c]pyridin-4-yl group, 1-methyl-1H-pyrrolo[2,3-c]pyridin-5-yl group, 1-ethyl-1H-pyrrolo[2,3-c]pyridin-5-yl group, 2-methyl-1H-pyrrolo[2,3-c]pyridin-5-yl group, 3-methyl-1H-pyrrolo[2,3-c]pyridin-5-yl group, 1,3-dimethyl-1H-pyrrolo[2,3-c]pyridin-5-yl group, 1H-pyrazolo[4,3-b]pyridin-5-yl group, 1H-pyrazolo[4,3-b]pyridin-6-yl group, 1-methyl-1H-pyrazolo[4,3-b]pyridin-5-yl group, 1-ethyl-1H-pyrazolo[4,3-b]pyridin-5-yl group, 3-methyl-1H-pyrazolo[4,3-b]pyridin-5-yl group, 1,3-dimethyl-1H-pyrazolo[4,3-b]pyridin-5-yl group, 1H-pyrazolo[4,3-c]pyridin-6-yl group, 1H-pyrazolo[4,3-c]pyridin-4-yl group, 1-methyl-1H-pyrazolo[4,3-c]pyridin-6-yl group, 1-ethyl-1H-pyrazolo[4,3-c]pyridin-6-yl group, 3-methyl-1H-pyrazolo[4,3-c]pyridin-6-yl group, 1,3-dimethyl-1H-pyrazolo[4,3-c]pyridin-6-yl group, 1H-pyrazolo[3,4-c]pyridin-5-yl group, 1H-pyrazolo[3,4-c]pyridin-4-yl group, 1-methyl-1H-pyrazolo[3,4-c]pyridin-5-yl group, 1-ethyl-1H-pyrazolo[3,4-c]pyridin-5-yl group, 3-methyl-1H-pyrazolo[3,4-c]pyridin-5-yl group, 1,3-dimethyl-1H-pyrazolo[3,4-c]pyridin-5-yl group, 1H-pyrazolo[3,4-b]pyridin-5-yl group, 1H-pyrazolo[3,4-b]pyridin-4-yl group, 1-methyl-1H-pyrazolo[3,4-b]pyridin-5-yl group, 1-ethyl-1H-pyrazolo[3,4-b]pyridin-5-yl group, 3-methyl-1H-pyrazolo[3,4-b]pyridin-5-yl group, 1,3-dimethyl-1H-pyrazolo[3,4-b]pyridin-5-yl group, [1,2,4]triazolo[4,3-a]pyridin-6-yl group, [1,2,4]triazolo[4,3-a]pyridin-7-yl group, 3-methyl[1,2,4]triazolo[4,3-a]pyridin-6-yl group, thieno[3,2-c]pyridin-2-yl group, thieno[3,2-c]pyridin-3-yl group, thieno[3,2-c]pyridin-6-yl group, 2-methylthieno[3,2-c]pyridin-2-yl group, 3-methylthieno[3,2-c]pyridin-2-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 2-methylthieno[3,2-b]pyridin-2-yl group, 3-methylthieno[3,2-b]pyridin-2-yl group, 1H-thieno[3,2-c]pyrazol-5-yl group, 1H-thieno[3,2-c]pyrazol-4-yl group, 1-methyl-1H-thieno[3,2-c]pyrazol-5-yl group, 1-ethyl-1H-thieno[3,2-c]pyrazol-5-yl group, 3-methyl-1H-thieno[3,2-c]pyrazol-5-yl group, 1,3-dimethyl-1H-thieno[3,2-c]pyrazol-5-yl group, benzo[d]isoxazol-5-yl group, benzo[d]isoxazol-4-yl group, benzo[d]isoxazol-6-yl group, benzo[d]isoxazol-7-yl group, 3-methylbenzo[d]isoxazol-5-yl group, benzo[c]isoxazol-5-yl group, benzo[c]isoxazol-4-yl group, benzo[c]isoxazol-6-yl group, benzo[c]isoxazol-7-yl group, 3-methylbenzo[c]isoxazol-5-yl group, indolizin-7-yl group, indolizin-6-yl group, indolizine-8-yl group, 1,3-dihydroindol-2-on-5-yl group, 1,3-dihydroindol-2-on-4-yl group, 1,3-dihydroindol-2-on-6-yl group, 1-methyl-1,3-dihydro-indol-2-on-5-yl group, 1H-pyrazolo[3,4-d]thiazol-5-yl group, 2H-isoindol-5-yl group, 2H-isoindol-4-yl group, 2-methyl-2H-isoindol-5-yl group, 4H-chromen-6-yl group, 4H-chromen-5-yl group, chromen-4-on-7-yl group, chromen-4-on-6-yl group, and the like.

Particularly preferred examples include naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, benzoxazol-5-yl group, and the like.

Particularly preferred examples include naphthalen-2-yl group, 6-hydroxynaphthalen-2-yl group, 6-methoxynaphthalen-2-yl group, 6-aminonaphthalen-2-yl group, 6-(N,N-dimethylamino)naphthalen-2-yl group, benzo[b]furan-5-yl group, benzo[b]thiophen-5-yl group, 1H-indol-5-yl group, 1-methyl-1H-indol-5-yl group, 1-ethyl-1H-indol-5-yl group, benzothiazol-6-yl group, 2-aminobenzothiazol-6-yl group, 2-oxo-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, isoquinolin-6-yl group, 1-oxo-1,2-dihydroisoquinolin-6-yl group, cinnolin-6-yl group, benzoxazol-5-yl group, and the like.

In the formula (I), the group Y is defined to be hydrogen atom, a lower alkyl group having 1 to 4 carbon atoms, $-(CH_2)_mN(R^{18})(R^{19})$, or $-C(R^{20})_2OC(O)A^3R^{21}$, and among them, hydrogen atom is particularly preferred.

Examples of the lower alkyl group having 1 to 4 carbon atoms include methyl group, ethyl group, propyl group, isopropyl group, butyl group, isobutyl group, t-butyl group, and the like. Among them, methyl group, and ethyl group are particularly preferred.

Symbol m in $-(CH_2)_mN(R^{18})(R^{19})$ is defined to be an integer of 2 or 3. $R^{18}$ is the same as $R^{19}$, or binds to $R^{19}$ to represent a saturated nitrogen-containing cycloalkyl group forming a 3- to 6-membered ring together with nitrogen atom, or form morpholino group together with nitrogen atom, and $R^{19}$ is defined to be methyl group, ethyl group, or propyl group. Examples of $-(CH_2)_mN(R^{18})(R^{19})$ include 2-(N,N-dimethylamino)ethyl group, 2-(N,N-diethylamino)ethyl group, 2-(N,N-dipropylamino)ethyl group, 3-(N,N-dimethylamino)propyl group, 3-(N,N-diethylamino)propyl group, 2-(N,N-dipropylamino)propyl group, 2-pyrrolidin-1-ylethyl group, 2-piperidin-1-ylethyl group, 2-morpholin-4-ylethyl group, 3-pyrrolidin-1-ylpropyl group, 3-piperidin-1-ylpropyl group, 3-morpholin-4-ylpropyl group, and the like.

$R^{20}$ in $-C(R^{20})_2OC(O)A^8R^{21}$ is defined to be hydrogen atom, methyl group, ethyl group, or propyl group. $R^{21}$ is defined to be a lower alkyl group having 1 to 4 carbon atoms, a cyclic saturated alkyl group having 3 to 6 carbon atoms group, or phenyl group. Examples of the lower alkyl group having 1 to 4 carbon atoms include methyl group, ethyl group, propyl group, isopropyl group, butyl group, isobutyl group, t-butyl group, and the like, and examples of the cyclic saturated alkyl group having 3 to 6 carbon atoms group include cyclopropyl group, cyclobutyl group, cyclopentyl group, and cyclohexyl group. $A^3$ is defined to be a single bond, or oxygen atom. Examples of $-C(R^{20})_2OC(O)A^3R^{21}$ include acetoxymethyl group, propionyloxymethyl group, butyryloxymethyl group, (2-methylpropionyl)oxymethyl group, (2,2-dimethylpropionyl)oxymethyl group, cyclopropionyloxymethyl group, cyclopentanoyloxymethyl group, cyclohexanoyloxymethyl group, phenylcarboxymethyl group, 1-acetoxy-1-methylethyl group, 1-methyl-1-(2-methylpropionyloxy)ethyl group, 1-cyclopentanoyloxy-1-methylethyl group, 1-cyclohexanoyloxy-1-methylethyl group, methoxycarbonyloxymethyl group, ethoxycarbonyloxymethyl group, isopropyloxycarbonyloxymethyl group, t-butyloxycarbonyloxymethyl group, cyclopropyloxycarbonyloxymethyl group, cyclopentyloxycarbonyloxymethyl group, cyclohexyloxycarbonyloxymethyl group, phenyloxycarbonyloxymethyl group, 1-methoxycarbonyloxy-1-methylethyl group, 1-ethoxycarbonyloxy-1-methylethyl group, 1-isopropyloxycarbonyloxy-1-methylethyl group, 1-t-butyloxycarbonyloxy-1-methylethyl group, 1-cyclopropyloxycarbonyloxy-1-methylethyl group, 1-cyclopentyloxycarbonyloxy-1-methylethyl group, 1-cyclohexyloxycarbonyloxy-1-methylethyl group, 1-methyl-1-phenyloxycarbonyloxyethyl group, and the like.

In a preferred embodiment of the present invention, the compound represented by the formula (I) or a salt thereof satisfies all of the following requirements.

Link represents $-(CH_2)_n-$, symbol n represents an integer of 1 to 3.

AR binds to $C^2$, Rs binds to any of the atoms $C^3$, $C^4$ and $C^5$, and a ring-constituting carbon atom to which Rs does not bind among $C^3$, $C^4$, and $C^5$ may be replaced with V.

V represents nitrogen atom, or carbon atom substituted with Zx, and Zx represents a group as any one of fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, and N,N-dimethylsulfamoylamino group.

Rs represents -D-Rx, or $-N(Ry)(Rz)$. D represents oxygen atom, or sulfur atom. Rx represents butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or represents Rb or Rc. Q in Rb represents a group as any one of phenyl group, thienyl group, furyl group, pyridyl group, oxazolyl group, naphthyl group, tetrahydronaphthyl group, indanyl group, indolyl group, and dihydrobenzodioxyl group. $A^2$ represents a single bond, oxygen atom, sulfur atom, —N(methyl)-, or —N(ethyl)- (provided that when $A^2$ represents oxygen atom, sulfur atom, —N(methyl)-, or —N(ethyl)-, $A^1$ represents ethylene). $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q represents phenyl group, $A^1$ represents a single bond, or unsubstituted methylene, and $A^2$ represents a single bond, one of $R^2$ and $R^3$ represents a substituent other than hydrogen atom). Symbol p in Rc represents an integer of 2 or 3, and $A^4$ represents a single bond or methylene. $A^5$ represents —C(O)—, —C(S)—, or —S(O)$_2$—. Rd represents hydrogen atom, or a group as any one of methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, and pyridin-4-yl group. Re represents a group as any one of methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, and ethyloxycarbonylamino group.

Rz represents a group as any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl) ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy) ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, and (morpholino-4-yl)carbonyl group. Ry represents hydrogen atom, methyl group, ethyl group, or isobutyl group, or binds to Rz to form pyrrolidino group, piperidino group, piperazino group, morpholino group, pyrrol-1-yl group, imidazol-1-yl group, or pyrazol-1-yl group together with nitrogen atom.

AR represents naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (these groups may be substituted with one of Xa or two or more of the same or different Xa). The substituent Xa represents a group as any one of oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, and N,N-dimethylcarbamoyl group.

The group Y represents hydrogen atom, methyl group, or ethyl group.

In another preferred embodiment of the present invention, the compound represented by the formula (I) or a salt thereof satisfies all of the following requirements.

Link represents —$(CH_2)_n$—, symbol n represents an integer of 1 to 3.

AR binds to $C^3$, Rs binds to any of the atoms $C^4$, $C^5$, and $C^6$, and a ring-constituting carbon atom to which Rs does not bind among $C^4$, $C^5$, and $C^6$ may be replaced with V.

V represents nitrogen atom, or carbon atom substituted with Zx, and Zx represents a group as any one of fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, and N,N-dimethylsulfamoylamino group.

Rs represents -D-Rx, or —N(Ry)(Rz). D represents oxygen atom, or sulfur atom. Rx represents butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or represents Rb, or Rc. Q in Rb represents a group as any one of phenyl group, thienyl group, furyl group, pyridyl group, oxazolyl group, naphthyl group, tetrahydronaphthyl group, indanyl group, indolyl group, and dihydrobenzodioxyl group. $A^2$ represents a single bond, oxygen atom, sulfur atom, —N(methyl)-, or —N(ethyl)- (provided that when $A^2$ represents oxygen atom, sulfur atom, —N(methyl)-, or —N(ethyl)-, $A^1$ represents ethylene). $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q represents phenyl group, $A^1$ represents a single bond, or unsubstituted methylene, and $A^2$ represents a single bond, one of $R^2$ and $R^3$ represents a substituent other than hydrogen atom).

Symbol p in Rc represents an integer of 2 or 3, and $A^4$ represents a single bond or methylene. $A^5$ represents —C(O)—, —C(S)—, or —S(O)$_2$—. Rd represents hydrogen atom, or a group as any one of methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, and pyridin-4-yl group. Re represents a group as any one of methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, and ethyloxycarbonylamino group. Rz represents a group as any of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group; N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, and (morpholino-4-yl)carbonyl group. Ry represents hydrogen atom, methyl group, ethyl group, or isobutyl group, or binds to Rz to form pyrrolidino group, piperidino group, piperazino group, morpholino group, pyrrol-1-yl group, imidazol-1-yl group, or pyrazol-1-yl group together with the nitrogen atom to which they binds.

AR represents naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-e]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo [d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa). The substituent Xa represents a group as any one of oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, and N,N-dimethylcarbamoyl group.

The group Y represents hydrogen atom, methyl group, or ethyl group.

In a preferred embodiment of the present invention, a compound or a salt thereof satisfying all of the following requirements is excluded from the compound represented by the formula (I) or a salt thereof.

Link represents —(CH$_2$)$_n$—, symbol n represents an integer of 1 to 3.

$C^3$ represents carbon atom to which AR bonds, $C^4$ represents carbon atom to which Rs bonds, $C^5$ represents a ring-constituting carbon atom which may be substituted with Zx, and $C^2$ and $C^6$ represent unsubstituted ring-constituting carbon atom.

Zx represents fluorine atom, chlorine atom, nitro group, amino group, methyl group, or a $OR^9$ group, and $R^9$ represents hydrogen atom or a lower alkyl group having 1 to 4 carbon atoms.

Rs represents —O—Rx. Rx represents a linear or branched saturated alkyl group having 3 to 8 carbon atoms, or represents Ra or Rb, Q in Rb represents a residue of a partially unsaturated or completely unsaturated monocyclic or condensed bicyclic carbon ring or heterocyclic ring (q), and binds to $A^2$ at an arbitrary position on the ring. The heterocyclic ring (q) contains one or two of the same or different ring-constituting heteroatoms selected from the group consisting of nitrogen atom, oxygen atom, and sulfur atom.

AR represents a residue of naphthalene, benzofuran, benzo[b]thiophene, indole, benzothiazole, dihydro-3H-benzothiazole, quinoline, dihydro-1H-quinoline, benzo [d]isothiazole, 1H-indazole, benzo[c]isothiazole, 2H-indazole, imidazo[1,2-a]pyridine, 1H-pyrrolo[2,3-b]pyridine, isoquinoline, or dihydro-2H-isoquinoline (the aforementioned residue may be substituted with one of Xa or two or more of the same or different Xa).

In another preferred embodiment of the present invention, the compound represented by the formula (I) or a salt thereof satisfies all of the following requirements.

Link represents —(CH$_2$)$_n$—, symbol n represents an integer of 1 to 3.

$C^3$ represents carbon atom to which AR bonds, $C^4$ represents carbon atom to which Rs bonds, $C^5$ may be replaced with V, and $C^2$ and $C^6$ represent unsubstituted ring-constituting carbon atom.

V represents nitrogen atom, or carbon atom substituted with Zx, and Zx represents a group as any one of fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, and N,N-dimethylsulfamoylamino group.

Rs represents —O—Rx. Rx represents butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or represents Rb or Rc. Q in Rb represents a group as any one of phenyl group, thienyl group, furyl group, pyridyl group, oxazolyl group, naphthyl group, tetrahydronaphthyl group, indanyl group, indolyl group, or dihydrobenzodioxyl group. $A^2$ represents a single bond, oxygen atom, sulfur atom, —N(methyl)-, or —N(ethyl)- (provided that when $A^2$ represents oxygen atom, sulfur atom, —N(methyl)-, or —N(ethyl)-, $A^1$ represents ethylene). $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q represents phenyl group, $A^1$ represents a single bond, or unsubstituted methylene, and $A^2$ represents a single bond, one of $R^2$ and $R^3$ represents a substituent other than hydrogen atom). Symbol p in Rc represents an integer of 2 or 3, and $A^4$ represents a single bond or methylene. $A^5$ represents —C(O)—, —C(S)—, or —S(O)$_2$—. Rd represents hydrogen atom, or a group as any one of methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, and pyridin-4-yl group. Re represents a group as any one of methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, and ethyloxycarbonylamino group.

AR represents any one of cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, and 4H-chromen-5-yl group (these groups may be substituted with one of Xa or two or more of the same or different Xa). The substituent Xa represents a group as any one of oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, and N,N-dimethylcarbamoyl group.

The group Y represents hydrogen atom, methyl group, or ethyl group.

In another preferred embodiment of the present invention, the compound represented by the formula (I) or a salt thereof satisfies all of the following requirements.

Link represents —(CH$_2$)$_n$—, symbol n represents an integer of 1 to 3.

$C^3$ represents carbon atom to which AR bonds, $C^4$ represents carbon atom to which Rs bonds, $C^5$ may be replaced with V, and $C^2$ and $C^6$ represent unsubstituted ring-constituting carbon atom.

V represents nitrogen atom, or carbon atom substituted with Zx, and Zx represents a group as any one of, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, and N,N-dimethylsulfamoylamino group.

Rs represents —S-Rx. Rx represents butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or represents Rb or Rc. Q in Rb represents a group as any one of phenyl group, thienyl group, furyl group, pyridyl group, oxazolyl group, naphthyl group, tetrahydronaphthyl group, indanyl group, indolyl group, and dihydrobenzodioxyl group. $A^2$ represents a single bond, oxygen atom, sulfur atom, —N(methyl), or —N(ethyl)- (provided that when $A^2$ represents oxygen atom, sulfur atom, —N(methyl)-, or —N(ethyl)-, $A^1$ represents ethylene). $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q represents phenyl group, $A^1$ represents a single bond, or unsubstituted methylene, and $A^2$ represents a single bond, one of $R^2$ and $R^3$ represents a substituent other than hydrogen atom). Symbol p in Rc represents an integer of 2 or 3, and $A^4$ represents a single bond or methylene. $A^5$ represents —C(O)—, —C(S)—, or —S(O)$_2$—. Rd represents hydrogen atom, or a group as any one of methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, and pyridin-4-yl group. Re represents a group as any one of methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, and ethyloxycarbonylamino group.

AR represents naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[c]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (these groups may be substituted with one of Xa or two or more of the same or different Xa). The substituent Xa represents a group as any one of oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, and N,N-dimethylcarbamoyl group.

The group Y represents hydrogen atom, methyl group, or ethyl group.

In another preferred embodiment of the present invention, the compound represented by the formula (I) or a salt thereof satisfies all of the following requirements.

Link represents —$(CH_2)_n$—, symbol n represents an integer of 1 to 3.

$C^3$ represents carbon atom to which AR bonds, $C^4$ represents carbon atom to which Rs bonds, and $C^2$, $C^5$ and $C^6$ represent unsubstituted ring-constituting carbon atom.

Rs represents —N(Ry)(Rz). Rz represents a group as any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, and (morpholino-4-yl)carbonyl group. Ry represents hydrogen atom, methyl group, ethyl group, or isobutyl group, or binds to Rz to form pyrrolidino group, piperidino group, piperazino group, morpholino group, pyrrol-1-yl group, imidazol-1-yl group, or pyrazol-1-yl group together with the nitrogen atom to which they bind.

AR represents naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo [d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (these groups may be substituted with one of Xa or two or more of the same or different Xa). The substituent Xa represents a group as any one of oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, and N,N-dimethylcarbamoyl group.

The group Y represents hydrogen atom, methyl group, or ethyl group.

In another preferred embodiment of the present invention, the compound represented by the formula (I) or a salt thereof satisfies all of the following requirements.

Link represents —$(CH_2)_n$—, symbol n represents an integer of 1 to 3.

$C^3$ represents carbon atom to which AR bonds, $C^4$ represents carbon atom to which Rs bonds, $C^5$ may be replaced with V, and $C^2$ and $C^6$ represent unsubstituted ring-constituting carbon atom.

V represents nitrogen atom, or carbon atom substituted with Zx, and Zx represents a group as any one of chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, and N,N-dimethylsulfamoylamino group.

Rs represents -D-Rc, and D represents oxygen atom or sulfur atom. Symbol p in Rc represents an integer of 2 or 3, and $A^4$ represents a single bond or methylene. $A^5$ represents —C(O)—, —C(S)—, or —S(O)$_2$—. Rd represents hydrogen atom, or a group as any one of methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, and pyridin-4-yl group. Re represents a group as any one of methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, and ethyloxycarbonylamino group.

AR represents naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6- yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (these groups may be substituted with one of Xa or two or more of the same or different Xa). The substituent Xa represents a group as any one of oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, and N,N-dimethylcarbamoyl group.

The group Y represents hydrogen atom, methyl group, or ethyl group.

In another preferred embodiment of the present invention, the compound represented by the formula (I) or a salt thereof satisfies all of the following requirements.

Link is $-(CH_2)_n-$, n is an integer of 1 to 3, $C^3$ is carbon atom bound with AR, $C^4$ is carbon atom bound with Rs, $C^5$ may be replaced with V, $C^2$ and $C^6$ are unsubstituted ring-constituting carbon atoms, V is nitrogen atom or V is carbon atom substituted with Zx, Zx is any one of fluorine atom, methyl group, hydroxyl group, amino group, N-methylamino group, or N,N-dimethylamino group, Rs is -D-Rx, D is a single bond, Rx is butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or Rx is Rb or Rc (provided that Q in Rb is phenyl group, thienyl group, furyl group, pyridyl group, oxazolyl group, naphthyl group, tetrahydronaphthyl group, indanyl group, indolyl group, or dihydrobenzodioxyl group), $A^2$ is a single bond, oxygen atom, sulfur atom, —N(methyl)-, or —N(ethyl)- (provided that when $A^2$ represents oxygen atom, sulfur atom, —N(methyl)- or —N(ethyl)-, $A^1$ represents ethylene), $R^2$ and $R^3$ independently represent hydrogen atom, methyl group, fluorine atom, chlorine atom, trifluoromethyl group, methoxy group, dimethylamino group, acetylamino group, or methylsulfonylamino group, p in Rc is an integer of 2 or 3, $A^4$ is a single bond or methylene, $A^5$ is $-C(O)-$, $-C(S)-$, or $-S(O)_2-$, Rd is hydrogen atom, or methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, or pyridin-4-yl group, Re is methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, or ethyloxycarbonylamino group, AR is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d] isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa), Xa is oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, or N,N-dimethylcarbamoyl group, and Y is hydrogen atom, methyl group, or ethyl group.

In a particularly preferred embodiment of the present invention, the compound represented by the formula (I) or a salt thereof satisfies all of the following requirements.

Link represents —(CH$_2$)$_n$—, symbol n represents an integer of 2.

$C^2$ represents carbon atom to which AR bonds, $C^3$ represents carbon atom to which Rs bonds, $C^4$ may be replaced with V, and $C^5$ and $C^6$ represent unsubstituted ring-constituting carbon atom.

V represents nitrogen atom, or carbon atom substituted with Zx, and Zx represents a group as any one of fluorine atom, methyl group, hydroxyl group, amino group, N-methylamino group, and N,N-dimethylamino group.

Rs represents —O—Rx. Rx represents a group as any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

AR represents a group as any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group.

The group Y represents hydrogen atom, methyl group, or ethyl group.

In another particularly preferred embodiment of the present invention, the compound represented by the formula (I) or a salt thereof satisfies all of the following requirements.

Link represents —(CH$_2$)$_n$, symbol n represents an integer of 2.

$C^2$ represents carbon atom to which AR bonds, $C^4$ represents carbon atom to which Rs bonds, $C^5$ may be replaced with V, and $C^3$ and $C^6$ represent unsubstituted ring-constituting carbon atom.

V represents nitrogen atom, or carbon atom substituted with Zx, and Zx represents a group as any one of fluorine atom, methyl group, hydroxyl group, amino group, N-methylamino group, and N,N-dimethylamino group.

Rs represents —O—Rx. Rx represents a group as any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

AR represents a group as any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group.

The group Y represents hydrogen atom, methyl group, or ethyl group.

In another particularly preferred embodiment of the present invention, the compound represented by the formula (I) or a salt thereof satisfies all of the following requirements.

Link represents —(CH$_2$)$_n$—, symbol n represents an integer of 2.

$C^3$ represents carbon atom to which AR bonds, $C^5$ represents carbon atom to which Rs bonds, and $C^2$, $C^4$ and $C^6$ represent unsubstituted ring-constituting carbon atom.

Rs represents —O—Rx. Rx represents a group as any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

AR represents a group as any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group.

The group Y represents hydrogen atom, methyl group, or ethyl group.

In another particularly preferred embodiment of the present invention, the compound represented by the formula (I) or a salt thereof satisfies all of the following requirements.

Link represents —(CH$_2$)$_n$—, symbol n represents an integer of 2.

$C^3$ represents carbon atom to which AR bonds, $C^4$ represents carbon atom to which Rs bonds, $C^5$ represents nitrogen atom, and $C^2$ and $C^6$ represent unsubstituted ring-constituting carbon atom.

Rs represents —O—Rx. Rx represents a group as any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

AR represents a group as any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group.

The group Y represents hydrogen atom, methyl group, or ethyl group;

In another preferred embodiment of the present invention, the compound represented by the formula (I) or a salt thereof satisfies all of the following requirements.

Link represents —(CH$_2$)$_n$—, symbol n represents an integer of 2.

$C^3$ represents carbon atom to which AR bonds, $C^4$ represents carbon atom to which Rs bonds, $C^6$ represents carbon atom substituted with Zx, and $C^2$ and $C^5$ represent unsubstituted ring-constituting carbon atom.

Zx represents fluorine atom, methyl group, hydroxyl group, amino group, N-methylamino group, or N,N-dimethylamino group.

Rs represents —O—Rx. Rx represents a group as any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,6-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

AR represents a group as any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group.

The group Y represents hydrogen atom, methyl group, or ethyl group.

In another particularly preferred embodiment of the present invention, the compound represented by the formula (I) or a salt thereof satisfies all of the following requirements.

Link represents —$(CH_2)_n$—, symbol n represents an integer of 2.

$C^3$ represents carbon atom to which AR bonds, $C^4$ represents carbon atom to which Rs bonds, and $C^2$, $C^5$ and $C^6$ represent unsubstituted ring-constituting carbon atom.

Rs represents —N(Ry)(Rz). Rz represents a group as any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2- chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, and (morpholino-4-yl)carbonyl group. Ry represents hydrogen atom, methyl group, ethyl group, or isobutyl group, or binds to Rz to form pyrrolidino group, piperidino group, or morpholino group together with nitrogen atom to which they bonds.

AR represents a group as any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group.

The group Y represents hydrogen atom, methyl group, or ethyl group.

In another particularly preferred embodiment of the present invention, the compound represented by the formula (I) or a salt thereof satisfies all of the following requirements.

Link represents —(CH$_2$)$_n$—, symbol n represents an integer of 2.

C$^3$ represents carbon atom to which AR bonds, C$^4$ represents carbon atom to which Rs bonds, and C$^2$, C$^5$ and C$^6$ represent unsubstituted ring-constituting carbon atom.

Rs represents —N(Ry)(Rz). —N(Ry)(Rz) is any one of N,N-dimethylamino group, N-ethyl-N-methylamino group, N,N-diethylamino group, N-methyl-N-propylamino group, N-ethyl-N-propylamino group, N-isopropyl-N-methylamino group, N-ethyl-N-isopropylamino group, N-butylamino group, N-butyl-N-methylamino group, N-butyl-N-ethylamino group, N-isobutylamino group, N-isobutyl-N-methylamino group, N-ethyl-N-isobutylamino group, N-(2-ethylbutyl)amino group, N-(2-ethylbutyl)-N-methylamino group, N-cyclopentylamino group, N-cyclopentyl-N-methylamino group, N-cyclohexylamino group, N-cyclohexyl-N-methylamino group, N-cycloheptylamino group, N-(cyclopentylmethyl)amino group, N-(cyclopentylmethyl)-N-methylamino group, N-(cyclohexylmethyl)amino group, N-(cyclohexylmethyl)-N-methylamino group, N-(2-methylphenyl)amino group, N-(4-methylphenyl)amino group, N-(2-fluorophenyl)amino group, N-(3-fluorophenyl)amino group, N-(4-fluorophenyl)amino group, N-(2-chlorophenyl)amino group, N-(3-chlorophenyl)amino group, N-(4-chlorophenyl)amino group, N-(indan-2-yl)amino group, N-(1-phenylethyl)amino group, N-[1-(2-fluorophenyl)ethyl]amino group, N-[1-(3-fluorophenyl)ethyl]amino group, N-[1-(4-fluorophenyl)ethyl]amino group, N-[1-(2-chlorophenyl)ethyl]amino group, N-[1-(3-chlorophenyl)ethyl]amino group, N-[1-(4-chlorophenyl)ethyl]amino group, N-(2-methylphenylmethyl)amino group, N-methyl-N-(2-methylphenylmethyl)amino group, N-(3-methylphenylmethyl)amino group, N-methyl-N-(3-methylphenylmethyl)amino group, N-(4-methylphenylmethyl)amino group, N-methyl-N-(4-methylphenylmethyl)amino group, N-(2-fluorophenylmethyl)

amino group, N-(2-fluorophenylmethyl)-N-methylamino group, N-(3-fluorophenylmethyl)amino group, N-(3-fluorophenylmethyl)-N-methylamino group, N-(4-fluorophenylmethyl)amino group, N-(4-fluorophenylmethyl)-N-methylamino group, N-(2-chlorophenylmethyl)amino group, N-(2-chlorophenylmethyl)-N-methylamino group, N-(3-chlorophenylmethyl)amino group, N-(3-chlorophenylmethyl)-N-methylamino group, N-(4-chlorophenylmethyl)amino group, N-(4-chlorophenylmethyl)-N-methylamino group, N-(2,3-difluorophenylmethyl)amino group, N-(2,3-difluorophenylmethyl)-N-methylamino group, N-(2,4-difluorophenylmethyl)amino group, N-(2,4-difluorophenylmethyl)-N-methylamino group, N-(2,5-difluorophenylmethyl)amino group, N-(2,5-difluorophenylmethyl)-N-methylamino group, N-(3,4-difluorophenylmethyl)amino group, N-(3,4-difluorophenylmethyl)-N-methylamino group, N-(3,5-difluorophenylmethyl)amino group, N-(3,5-difluorophenylmethyl)-N-methylamino group, N-(2,3-dichlorophenylmethyl)amino group, N-(2,3-dichlorophenylmethyl)-N-methylamino group, N-(2,4-dichlorophenylmethyl)amino group, N-(2,4-dichlorophenylmethyl)-N-methylamino group, N-(2,5-dichlorophenylmethyl)amino group, N-(2,5-dichlorophenylmethyl)-N-methylamino group, N-(2,6-dichlorophenylmethyl)amino group, N-(2,6-dichlorophenylmethyl)-N-methylamino group, N-(3,4-dichlorophenylmethyl)amino group, N-(3,4-dichlorophenylmethyl)-N-methylamino group, N-(3,5-dichlorophenylmethyl)amino group, N-(3,5-dichlorophenylmethyl)-N-methylamino group, N-[2-(trifluoromethyl)phenylmethyl]amino group, N-methyl-N-[2-(trifluoromethyl)phenylmethyl]amino group, N-[3-(trifluoromethyl)phenylmethyl]amino group, N-methyl-N-[3-(trifluoromethyl)phenylmethyl]amino group, N-[4-(trifluoromethyl)phenylmethyl]amino group, N-methyl-N-[4-(trifluoromethyl)phenylmethyl]amino group, 1-pyrrolidino group, 1-(4-methylpiperidino) group, 1-homopiperidino group, or 4-morpholino group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino) naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

In another particularly preferred embodiment of the present invention, the compound represented by the formula (I) or a salt thereof satisfies all of the following requirements.

Link represents —$(CH_2)_n$—, symbol n represents an integer of 2.

$C^3$ represents carbon atom to which AR bonds, $C^4$ represents carbon atom to which Rs bonds, $C^5$ represents carbon atom substituted with Zx, and $C^2$ and $C^6$ represent unsubstituted ring-constituting carbon atom.

Zx represents N-methylamino group, N-ethylamino group, N-propylamino group, N-isopropylamino group, N,N-dimethylamino group, N,N-diethylamino group, formylamino group, acetylamino group, carbamoylamino group, mesylamino group, and N,N-dimethylsulfamoylamino group.

Rs represents —O—Rx. Rx represents a group as any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

AR represents a group as any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group.

The group Y represents hydrogen atom, methyl group, or ethyl group.

In another particularly preferred embodiment of the present invention, the compound represented by the formula (I) or a salt thereof satisfies all of the following requirements.

Link represents —$(CH_2)_n$—, symbol n represents an integer of 2.

$C^3$ represents carbon atom to which AR bonds, $C^4$ represents carbon atom to which Rs bonds, $C^5$ may be replaced with V, and $C^2$ and $C^6$ represent unsubstituted ring-constituting carbon atom.

V represents nitrogen atom, or carbon atom substituted with Zx, and Zx represents a group as any one of chlorine atom, bromine atom, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, and N,N-dimethylsulfamoylamino group.

Rs represents —O-Rc. p in Rc represents an integer of 2, and $A^4$ represents a single bond or methylene. $A^5$ represents —C(O)—, —C(S)—, or —S(O)$_2$—. Rd represents a group as any one of methyl group, ethyl group, propyl group, isopropyl group, butyl group, isobutyl group, cyclopropyl group, cyclopentyl group, cyclohexyl group, phenyl group, 4-methylphenyl group, 4-chlorophenyl group, 4-fluorophenyl group, benzyl group, 4-chlorophenylmethyl group, and 4-fluorophenylmethyl group. Re represents a group as any one of isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, pyrrolidino group, piperidino group, and morpholino group.

AR represents a group as any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-6-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol- 6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group.

The group Y represents hydrogen atom, methyl group, or ethyl group.

In another particularly preferred embodiment of the present invention, the compound represented by the formula (I) or a salt thereof satisfies all of the following requirements.

Link represents —$(CH_2)_n$—, symbol n represents an integer of 2.

$C^3$ represents carbon atom to which AR bonds, $C^4$ represents carbon atom to which Rs bonds, $C^5$ may be replaced with V, and $C^2$ and $C^6$ represent unsubstituted ring-constituting carbon atom.

V represents nitrogen atom, or carbon atom substituted with Zx, Zx is any one of fluorine atom, methyl group, hydroxyl group, amino group, N-methylamino group, or N,N-dimethylamino group, Rs represents -D-Rx and D represents a single bond. Rx is butyl group, isobutyl group, 2-ethylbutyl group, cyclopentyl group, cyclohexyl group, cycloheptyl group, cyclopentylmethyl group, cyclohexylmethyl group, phenyl group, 2-methylphenyl group, 3-methylphenyl group, 4-methylphenyl group, 2,3-dimethylphenyl group, 3,5-dimethylphenyl group, 2-methoxyphenyl group, 3-methoxyphenyl group, 4-methoxyphenyl group, 2-fluorophenyl group, 3-fluorophenyl group, 4-fluorophenyl group, 2-chlorophenyl group, 3-chlorophenyl group, 4-chlorophenyl group, 2,3-difluorophenyl group, 2,4-difluorophenyl group, 2,5-difluorophenyl group, 3,4-difluorophenyl group, 2,3-dichlorophenyl group, 2,4-dichlorophenyl group, 2,5-dichlorophenyl group, 2,6-dichlorophenyl group, 3,4-dichlorophenyl group, 3,5-dichlorophenyl group, 2-trifluoromethylphenyl group, 3-trifluoromethylphenyl group, 4-trifluoromethylphenyl group, 4-(N,N-dimethylamino)phenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, furan-2-yl group, furan-3-yl group, thiophen-2-yl group, thiophen-3-yl group, pyridin-2-yl group, pyridin-3-yl group, pyridin-4-yl group, naphthalen-1-yl group, naphthalen-2-yl group, 1H-indol-5-yl group, 1-methyl-1H-indol-5-yl group, 1H-indazol-5-yl group, 1-methyl-1H-indazol-5-yl group, biphenyl-2-yl group, biphenyl 3-yl group, biphenyl-4-yl group, 1-phenylethyl group, 1-(2-fluorophenyl)ethyl group, 1-(3-fluorophenyl)ethyl group, 1-(4-fluorophenyl) ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino)ethyl group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino) naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

In another particularly preferred embodiment of the present invention, the compound represented by the formula (I) or a salt thereof satisfies all of the following requirements.

Link represents —$(CH_2)_n$—, symbol n represents an integer of 2.

$C^3$ represents carbon atom to which AR bonds, $C^4$ represents carbon atom to which Rs bonds, $C^5$ may be replaced with V, and $C^2$ and $C^6$ represent unsubstituted ring-constituting carbon atom.

V represents nitrogen atom, or carbon atom substituted with Zx, Zx is any one of fluorine atom, methyl group, hydroxyl group, amino group, N-methylamino group, or N,N-dimethylamino group, Rs represents -D-Rx and D represents a single bond. Rx is phenyl group, 2-methylphenyl group, 3-methylphenyl group, 4-methylphenyl group, 2,3dimethylphenyl group, 3,5-dimethylphenyl group, 2-methoxyphenyl group, 3-methoxyphenyl group, 4-methoxyphenyl group, 2-fluorophenyl group, 3-fluorophenyl group, 4-fluorophenyl group, 2-chlorophenyl group, 3-chlorophenyl group, 4-chlorophenyl group, 2,3-difluorophenyl group, 2,4-difluorophenyl group, 2,5-difluorophenyl group, 3,4-difluorophenyl group, 2,3-dichlorophenyl group, 2,4-dichlorophenyl group, 2,5-dichlorophenyl group, 2,6-dichlorophenyl group, 3,4-dichlorophenyl group, 3,5-dichlorophenyl group, 2-trifluoromethylphenyl group, 3-trifluoromethylphenyl group, 4-trifluoromethylphenyl group, 4-(N,N-dimethylamino)phenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, furan-2-yl group, furan-3-yl group, thiophen-2-yl group, thiophen-3-yl group, pyridin-2-yl group, pyridin-3-yl group, pyridin-4-yl group, naphthalen-1-yl group, naphthalen-2-yl group, 1H-indol-5-yl group, 1-methyl-1H-indol-5-yl group, 1H-indazol-5-yl group, or 1-methyl-1H-indazol-5-yl group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

In another particularly preferred embodiment of the present invention, the compound represented by the formula (I) or a salt thereof satisfies all of the following requirements.

Link represents —$(CH_2)_n$—, symbol n represents an integer of 2.

$C^3$ represents carbon atom to which AR bonds, $C^4$ represents carbon atom to which Rs bonds, and $C^2$, $C^5$, and $C^6$ represent unsubstituted ring-constituting carbon atom.

Rs represents -D-Rx and D represents a single bond. Rx is phenyl group, 2-methylphenyl group, 3-methylphenyl group, 4-methylphenyl group, 2,3-dimethylphenyl group, 3,5-dimethylphenyl group, 2-methoxyphenyl group, 3-methoxyphenyl group, 4-methoxyphenyl group, 2-fluorophenyl group, 3-fluorophenyl group, 4-fluorophenyl group, 2-chlorophenyl group, 3-chlorophenyl group, 4-chlorophenyl group, 2,3-difluorophenyl group, 2,4-difluorophenyl group, 2,5-difluorophenyl group, 3,4-difluorophenyl group, 2,3-dichlorophenyl group, 2,4-dichlorophenyl group, 2,5-dichlorophenyl group, 2,6-dichlorophenyl group, 3,4-dichlorophenyl group, 3,5-dichlorophenyl group, 2-trifluoromethylphenyl group, 3-trifluoromethylphenyl group, 4-trifluoromethylphenyl group, 4-(N,N-dimethylamino)phenyl group, indan-2-yl group, furan-2-yl group, furan-3-yl group, thiophen-2-yl group, thiophen-3-yl group, pyridin-2-yl group, pyridin-3-yl group, pyridin-4-yl group, naphthalen-1-yl group, naphthalen-2-yl group, 1H-indol-5-yl group, 1-methyl-1H-indol-5-yl group, 1H-indazol-5-yl group, or 1-methyl-1H-indazol-5-yl group, AR is naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino) naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, or benzoxazol-5-yl group, and Y is hydrogen atom, methyl group, or ethyl group.

Compound (I) of the present invention may have one or more asymmetric carbons depending on types of substituents. For example, as for a compound wherein the group Rs contains one or more asymmetric carbons, two kinds of optical isomers exist when the number of asymmetric carbon is 1, and when the number of asymmetric carbons is 2, four kinds of optical isomers and two kinds of diastereomers exist. Pure stereoisomers including optical isomers and diastereoisomers, any mixtures thereof, racemates and the like of the stereoisomers fall within the scope of the present invention. Further, Compound (1) of the present invention may exist as geometrical isomers based on a cycloalkyl ring structure, and any geometrical isomers in pure forms, and any mixtures of the geometrical isomers also fall within the scope of the present invention. Mixtures such as racemates may sometimes be preferred from a viewpoint of easiness for manufacture.

As a salt of Compound (I) of the present invention, a pharmaceutically acceptable salt is preferred. It is meant that, when at least one of the conditions (1) to (3) is satisfied: (1) Y is hydrogen atom; (2) the group AR contains carboxyl group or phenolic hydroxyl group; (3) the group Zx is phenolic hydroxyl group, and the like, then the compound forms 1 to 3 alkali salts depending on the number of acidic groups. Examples the alkali salts include, for example, salts with inorganic bases such as sodium and ammonia and salts with organic bases such as triethylamine.

Alternatively, it is meant that, when at least one of the conditions (1) to (4) is satisfied: (1) the group Rs has properties as a base as in a compound wherein Rs contains a substituted or unsubstituted amino group and the like; (2) AR itself is a cyclic substituent having properties as a base; (3) the group Ar contains a substituted or unsubstituted amino group; (4) any carbon atom in the aromatic ring (E) is replaced with V, and V is nitrogen atom, V is carbon atom substituted with Zx, and Zx is a substituted or unsubstituted amino group and the like, then the compound forms 1 to 4 acidic salts depending on the number of basic groups. Examples of the acidic salts include, for example, salts with inorganic acids such as hydrochloric acid and sulfuric acid and salts with organic acids such as acetic acid and citric acid.

$C^{2'}$, $C^{3'}$, $C^{4'}$, $C^{5'}$, and $C^{6'}$ in the aromatic ring (E') in the aforementioned formula (II) each represent a ring-constituting carbon atom. Among them, any ring-constituting carbon atom to which Rs' and G do not bind may be replaced with V'. The substitution positions of Rs', G, and V' are similar to those described in the explanations of the substitution positions of Rs (corresponding to the position of Rs'), AR (corresponding to the position of the group G), and V (corresponding to the position of V') in the aforementioned formula (I).

V' represents nitrogen atom, or represents carbon atom substituted with Zx'. Zx' has the same meaning as that of Zx, provided that when Zx contains hydroxyl group (OH), the hydroxyl group may be protected with $Rp^1$, and when Zx contains amino group (NH), the amino group may be protected with $Rp^2$.

Rs' represents -D-Rx' or —N(Ry')(Rz'). -D-Rx' and —N(Ry')(Rz') have the same meanings as those of -D-Rx and —N(Ry)(Rz) mentioned above, respectively. Provided that when -D-Rx and —N(Ry)(Rz) contain hydroxyl group, the hydroxyl group may be protected with $Rp^1$, and when -D-Rx and —N(Ry)(Rz) contains amino group (NM), the amino group may be protected with $Rp^2$.

$Rp^1$ represents, for example, a silyl group substituted with 3 of identical or different linear or branched saturated alkyl groups having 1 to 4 carbon atoms or phenyl groups, tetrahydropyranyl group, tetrahydrofuryl group, allyl group, propargyl group, benzyl group which may be substituted with one $T^1$ or two or more identical or different $T^1$, —$CH_2$—U-$Rp^3$, —$C(O)Rp^3$, —$C(O)ORp^3$, or the like. U represents oxygen atom, or sulfur atom, and $Rp^3$ represents hydrogen atom, a linear or branched saturated alkyl group having 1 to 4 carbon atoms, trimethylsilylethyl group, chloromethyl group, trichloromethyl group, trifluoromethyl group, 9-fluorenylmethyl group, adamantyl group, allyl group, -$A^6$-Qp, or the like. $Rp^2$ represents, for example, benzyl group which may be substituted with one of $T^1$ or two or more of identical or different $T^1$, —$C(O)Rp^3$, —$C(O)ORp^3$, or the like. However, the protective groups of hydroxyl group and amino group are not limited to these, and they can be chosen by referring and examining methods for introduction of protective groups and deprotection described in usual publications in the chemical field, for example, Protective Groups In Organic Synthesis, THIRD EDITION, published by John Wiley & Sons or the references cited therein.

G represents chlorine atom, bromine atom, iodine atom, mesylate group, triflate group, or an arenesulfonate group of which aromatic moiety may be substituted with one of $T^1$ or two or more identical or different $T^1$. Examples of the arenesulfonate group include, for example, benzenesulfonate group, p-toluenesulfonate group, mesitylenesulfonate group, 2,4,6-triisopropylbenzenesulfonate group, 4-fluorobenzenesulfonate group, 2,5-dichlorobenzenesulfonate group, 3-(trifluoromethyl)benzenesulfonate group, pentafluorobenzenesulfonate group, 2-nitrobenzenesulfonate group, 2,4-dinitrobenzenesulfonate group, and the like. Preferred examples of G include chlorine atom, bromine atom, iodine atom, triflate group, and the like, and bromine atom and iodine atom are particularly preferred examples.

Y' represents a lower alkyl group having 1 to 4 carbon atoms. Examples of the lower alkyl group having 1 to 4 carbon atoms include methyl group, ethyl group, propyl group, isopropyl group, butyl group, isobutyl group, t-butyl group, and the like. Among these, methyl group, and ethyl group are particularly preferred examples.

In the aforementioned formula (II), n and D have the same meaning as defined above.

In a preferred embodiment, the compound represented by the formula (II) satisfies all of the following requirements.

Symbol n represents an integer of 1 to 3.

The group G binds to $C^{2'}$, Rs' binds to any of the atoms $C^{3'}$, $C^{4'}$ and $C^{5'}$, and a ring-constituting carbon atom to which Rs' does not bind among $C^{3'}$, $C^{4'}$, and $C^{5'}$ may be substituted with V'.

V' represents nitrogen atom, or carbon atom substituted with Zx', and Zx' represents any one of fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, and N,N-dimethylsulfamoylamino group, provided that when Zx' contains hydroxyl group, the hydroxyl group may be protected with $Rp^1$, and when the substituted Zx' contains amino group, the amino group may be protected with $Rp^2$.

Rs' represents -D-Rx' or —N(Ry')(Rz'). D represents oxygen atom or sulfur atom. Rx' represents butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or represents Rb or Rc. Q in Rb represents a group as any one of phenyl group, thienyl group, furyl group, pyridyl group, oxazolyl group, naphthyl group, tetrahydronaphthyl group, indanyl group, indolyl group, and dihydrobenzodioxyl group. $A^2$ represents a single bond, oxygen atom, sulfur atom, —N(methyl)-, or —N(ethyl)- (provided that when $A^2$ represents oxygen atom, sulfur atom, —N(methyl)-, or —N(ethyl)-, $A^1$ represents ethylene). $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q represents phenyl group, $A^1$ represents a single bond, or unsubstituted methylene, and $A^2$ represents a single bond, one of $R^2$ and $R^3$ represents a substituent other than hydrogen atom). Symbol p in Rc represents an integer of 2 or 3, and $A^4$ represents a single bond or methylene. $A^5$ represents —C(O)—, —C(S)—, or —S(O)$_2$—. Rd represents hydrogen atom, or a group as any one of methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, and pyridin-4-yl group. Re represents any one of methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, and ethyloxycarbonylamino group. Rz' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino) ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, and (morpholino-4-yl)carbonyl group. Ry' represents hydrogen atom, methyl group, ethyl group, or isobutyl group, or binds to Rz' to form pyrrolidino group, piperidino group, piperazino group, morpholino group, pyrrol-1-yl group, imidazol-1-yl group, or pyrazol-1-yl group together with the nitrogen atom to which they bonds. Provided that when -D-Rx' or —N(Ry')(Rz') contains hydroxyl group (OH), the hydroxyl group may be protected with $Rp^1$, and when -D-Rx' or —N(Ry')(Rz') contains amino group, the amino group may be protected with $Rp^2$.

The group G represents chlorine atom, bromine atom, iodine atom, or triflate group.

The group Y' represents methyl group, or ethyl group.

In another preferred embodiment, the compound represented by the formula (II) satisfies all of the following requirements.

Symbol n represents an integer of 1 to 3.

The group G binds to $C^{3'}$, Rs' binds to any of the atoms $C^{4'}$, $C^{5'}$, and $C^{6'}$, and a ring-constituting carbon atom to which Rs' does not bind among $C^{4'}$, $C^{5'}$ and $C^{6'}$ may be replaced with V'.

V' represents nitrogen atom, or carbon atom substituted with Zx', and Zx' represents any one of fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, and N,N-dimethylsulfamoylamino group, provided that when Zx' contains hydroxyl group, the hydroxyl group may be protected with $Rp^1$, and when the substituted Zx' contains amino group, the amino group may be protected with $Rp^2$.

Rs' represents -D-Rx', or —N(Ry')(Rz'). D represents oxygen atom or sulfur atom. Rx' represents butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or represents Rb or Rc. Q in Rb represents a group as any one of phenyl group, thienyl group, furyl group, pyridyl group, oxazolyl group, naphthyl group, tetrahydronaphthyl group, indanyl group, indolyl group, and dihydrobenzodioxyl group. $A^2$ represents a single bond, oxygen atom, sulfur atom, —N(methyl)-, or —N(ethyl)- (provided that when $A^2$ represents oxygen atom, sulfur atom, —N(methyl)-, or —N(ethyl)-, $A^1$ represents ethylene). $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q represents phenyl group, $A^1$ represents a single bond, or unsubstituted methylene, and $A^2$ represents a single bond, one of $R^2$ and $R^3$ represents a substituent other than hydrogen atom). Symbol p in Rc represents an integer of 2 or 3, and $A^4$ represents a single bond or methylene. $A^5$ represents —C(O)—, —C(S)—, or —S(O)$_2$—. Rd represents hydrogen atom, or a group as any one of methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, and pyridin-4-yl group. Re represents any one of methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, and ethyloxycarbonylamino group. Rz' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6- difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, and (morpholino-4-yl)carbonyl group. Ry' represents hydrogen atom, methyl group, ethyl group, or isobutyl group, or binds to Rz' to form pyrrolidino group, piperidino group, piperazino group, morpholino group, pyrrol-1-yl group, imidazol-1-yl group, or pyrazol-1-yl group together with nitrogen atom. Provided that when -D-Rx' or —N(Ry')(Rz') contains hydroxyl group, the hydroxyl group may be protected with $Rp^1$, and -D-Rx' or —N(Ry')(Rz') contains amino group, the amino group may be protected with $Rp^2$.

The group G represents chlorine atom, bromine atom, iodine atom, or triflate group.

The group Y' represents methyl group, or ethyl group.

In a particularly preferred embodiment, the compound represented by the formula (II) satisfies all of the following requirements.

Symbol n represents an integer of 2.

$C^{2'}$ represents carbon atom to which the group G bonds, $C^{3'}$ represents carbon atom to which Rs' binds, $C^{4'}$ may be replaced with V', and $C^{5'}$ and $C^{6'}$ represent an unsubstituted ring-constituting carbon atom.

V' represents nitrogen atom, or carbon atom substituted with Zx', and Zx' represents any one of fluorine atom, methyl group, hydroxyl group, amino group, N-methylamino group, and N,N-dimethylamino group, provided that when Zx' contains hydroxyl group, the hydroxyl group may be protected with $Rp^1$, and when the substituted Zx' contains amino group, the amino group may be protected with $Rp^2$.

Rs' represents —O—Rx'. Rx' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1 (4-fluorophenyl)ethyl group, 1-(2-chlorophenyl)ethyl group, 1-(3-chlorophenyl) ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

The group G represents bromine atom, or iodine atom.

The group Y' represents methyl group, or ethyl group.

In another particularly preferred embodiment, the compound represented by the formula (II) satisfies all of the following requirements.

Symbol n represents an integer of 2.

$C^{2\prime}$ represents carbon atom to which the group G bonds, $C^{4\prime}$ represents carbon atom to which Rs' binds, $C^{5\prime}$ may be replaced with V', and $C^{3\prime}$ and $C^{6\prime}$ represent an unsubstituted ring-constituting carbon atom.

V' represents nitrogen atom, or carbon atom substituted with Zx', and Zx' represents any one of fluorine atom, methyl group, hydroxyl group, amino group, N-methylamino group, and N,N-dimethylamino group, provided that when Zx' contains hydroxyl group, the hydroxyl group may be protected with $Rp^1$, and when the substituted Zx' contains amino group, the amino group may be protected with $Rp^2$.

Rs' represents —O—Rx'. Rx' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

The group G represents bromine atom, or iodine atom.

The group Y' represents methyl group, or ethyl group.

In another particularly preferred embodiment, the compound represented by the formula (II) satisfies all of the following requirements.

Symbol n represents an integer of 2.

$C^{3\prime}$ represents carbon atom to which the group G bonds, $C^{5\prime}$ represents carbon atom to which Rs' binds, and $C^{2\prime}$, $C^{4\prime}$ and $C^{6\prime}$ represent an unsubstituted ring-constituting carbon atom.

Rs' represents —O—Rx'. Rx' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

The group G represents bromine atom, or iodine atom.

The group Y' represents methyl group, or ethyl group.

In another particularly preferred embodiment, the compound represented by the formula (II) satisfies all of the following requirements.

Symbol n represents an integer of 2.

$C^{3\prime}$ represents carbon atom to which the group G bonds, $C^{4\prime}$ represents carbon atom to which Rs' binds, $C^{5\prime}$ represents nitrogen atom, and $C^{2\prime}$ and $C^{6\prime}$ represent an unsubstituted ring-constituting carbon atom.

Rs' represents —O—Rx'. Rx' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

The group G represents bromine atom, or iodine atom.

The group Y' represents methyl group, or ethyl group.

In another particularly preferred embodiment, the compound represented by the formula (II) satisfies all of the following requirements.

Symbol n represents an integer of 2.

$C^{3\prime}$ represents carbon atom to which the group G bonds, $C^{4\prime}$ represents carbon atom to which Rs' binds, $C^{6\prime}$ represents carbon atom substituted with Zx', and $C^{2\prime}$ and $C^{5\prime}$ represent an unsubstituted ring-constituting carbon atom.

Zx' represents any one of fluorine atom, methyl group, hydroxyl group, amino group, N-methylamino group, and N,N-dimethylamino group, provided that when Zx' contains hydroxyl group, the hydroxyl group may be protected with $Rp^1$, and when the substituted Zx' contains amino group, the amino group may be protected with $Rp^2$.

Rs' represents —O—Rx'. Rx' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

The group G represents bromine atom, or iodine atom.

The group Y' represents methyl group, or ethyl group.

In another particularly preferred embodiment, the compound represented by the formula (II) satisfies all of the following requirements.

Symbol n represents an integer of 2.

$C^{3\prime}$ represents carbon atom to which the group G bonds, $C^{4\prime}$ represents carbon atom to which Rs' binds, $C^{5\prime}$ represents carbon atom substituted with Zx', or unsubstituted carbon atom, and $C^{2\prime}$ and $C^{6\prime}$ represent an unsubstituted ring-constituting carbon atom.

Zx' represents any one of fluorine atom, methyl group, hydroxyl group, amino group, N-methylamino group, and N,N-dimethylamino group, provided that when Zx' contains hydroxyl group, the hydroxyl group may be protected with $Rp^1$, and when the substituted Zx' contains amino group, the amino group may be protected with $Rp^2$.

Rs' represents —S-Rx'. Rx' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

The group G represents bromine atom, or iodine atom.

The group Y' represents methyl group, or ethyl group.

In another particularly preferred embodiment, the compound represented by the formula (II) satisfies all of the following requirements.

Symbol n represents an integer of 2.

$C^{3'}$ represents carbon atom to which the group G bonds, $C^{4'}$ represents carbon atom to which Rs' binds, $C^{5'}$ represents carbon atom substituted with Zx', or unsubstituted ring-constituting carbon atom, and $C^{2'}$ and $C^{6'}$ represent an unsubstituted ring-constituting carbon atom.

Zx' represents any one of fluorine atom, methyl group, hydroxyl group, amino group, N-methylamino group, and N,N-dimethylamino group, provided that when Zx' contains hydroxyl group, the hydroxyl group may be protected with $Rp^1$, and when the substituted Zx' contains amino group, the amino group may be protected with $Rp^2$.

Rs' represents —N(Ry')(Rz'). Rz' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, and (morpholino-4-yl)carbonyl group. Ry' represents hydrogen atom, methyl group, ethyl group, or isobutyl group, or binds to Rz' to form pyrrolidino group, piperidino group, or morpholino group together with the nitrogen atom to which they bonds. Provided that when —N(Ry')(Rz') contains hydroxyl group, the hydroxyl group may be protected with $Rp^1$, and when Ry' or Rz' contains amino group, the amino group may be protected with $Rp^2$.

The group G represents bromine atom, or iodine atom.

The group Y' represents methyl group, or ethyl group.

In another particularly preferred embodiment, the compound represented by the formula (II) satisfies all of the following requirements.

Symbol n represents an integer of 2.

$C^{3'}$ represents carbon atom to which the group G bonds, $C^{4'}$ represents carbon atom to which Rs' binds, $C^{5'}$ represents carbon atom substituted with Zx', and $C^{2'}$ and $C^{6'}$ represent an unsubstituted ring-constituting carbon atom.

Zx' represents any one of N-methylamino group, N-ethylamino group, N-propylamino group, N-isopropylamino group, N,N-dimethylamino group, N,N-diethylamino group, formylamino group, acetylamino group, carbamoylamino group, mesylamino group, and N,N-dimethylsulfamoylamino group. Provided that when the substituted Zx' contains amino group (NH), the amino group may be protected with $Rp^2$.

Rs' represents —O—Rx'. Rx' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

The group G represents bromine atom, or iodine atom.

The group Y' represents methyl group, or ethyl group.

In another particularly preferred embodiment, the compound represented by the formula (II) satisfies all of the following requirements.

Symbol n represents an integer of 2.

$C^{3'}$ represents carbon atom to which the group G bonds, $C^4$ represents carbon atom to which Rs' binds, $C^{5'}$ represents carbon atom substituted with Zx', or unsubstituted carbon atom, and $C^{2'}$ and $C^{6'}$ represent an unsubstituted ring-constituting carbon atom.

Zx' represents any one of fluorine atom, methyl group, hydroxyl group, amino group, N-methylamino group, and N,N-dimethylamino group, provided that when Zx' contains hydroxyl group, the hydroxyl group may be protected with $Rp^1$, and when the substituted Zx' contains amino group, the amino group may be protected with $Rp^2$.

Rs' represents —O—Rx'. Rx' have the same meaning as that of Rc, provided that when Rc contains hydroxyl group (OH), the hydroxyl group may be protected with $Rp^1$. p in Rc represents an integer of 2, and $A^4$ represents a single bond or methylene. $A^5$ represents —C(O)—, —C(S)—, or —S(O)$_2$—. Rd represents a group as any one of methyl group, ethyl group, propyl group, isopropyl group, butyl group, isobutyl group, cyclopropyl group, cyclopentyl group, cyclohexyl group, phenyl group, 4-methylphenyl group, 4-chlorophenyl group, 4-fluorophenyl group, benzyl group, 4-chlorophenylmethyl group, and 4-fluorophenylmethyl group. Re represents a group as any one of isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, pyrrolidino group, piperidino group, and morpholino group.

The group G represents bromine atom, or iodine atom.

The group Y' represents methyl group, or ethyl group.

$C^{2'}$, $C^{3'}$, $C^{4'}$, $C^{5'}$, and $C^{6'}$ in the aromatic ring (E') in the aforementioned formula (III) each represent a ring-constituting carbon atom. Any ring-constituting carbon atom to which Rs' and AR' do not bond among them may be replaced with V'. The substitution positions of Rs', AR', and V' are similar to those described in the explanations of the substitution positions of Rs (corresponding to the position of Rs'), AR (corresponding to the position of the group AR'), and V (corresponding to the position of V') in the aforementioned formula (I).

AR' has the same meaning as that of AR mentioned above, provided that when AR contains hydroxyl group, the hydroxyl group may be protected with $Rp^1$. In this case, the hydroxyl group includes OH in carboxyl group (COOH). When the substituted AR contains amino group, the amino group represents a substituent, which may be protected with $Rp^2$. Examples of the amino group, which may be protected include NH present in a ring constituting AR, for example, as in indole ring, indazole ring, and the like.

Rs', V', n, and D in the aforementioned formula (III) have the same meanings as those defined above. $Rp^1$, and $Rp^2$ also have the same meanings as those defined above.

In a preferred embodiment, the compound represented by the formula (III) satisfies all of the following requirements.

AR' binds to $C^{2'}$, Rs' binds to any of the atoms $C^{3'}$, $C^{4'}$, and $C^{5'}$, and a ring-constituting carbon atom to which Rs' does not bind among $C^{3'}$, $C^{4'}$, and $C^{5'}$ may be replaced with V.

V' represents nitrogen atom, or carbon atom substituted with Zx', and Zx' represents any one of fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, and N,N-dimethylsulfamoylamino group, provided that when Zx' contains hydroxyl group, the hydroxyl group may be protected with $Rp^1$, and when the substituted Zx' contains amino group, the amino group may be protected with $Rp^2$.

Rs' represents -D-Rx' or —N(Ry')(Rz'). D represents oxygen atom or sulfur atom. Rx' represents butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or represents Rb or Rc. Q in Rb represents a group as any one of phenyl group, thienyl group, furyl group, pyridyl group, oxazolyl group, naphthyl group, tetrahydronaphthyl group, indanyl group, indolyl group, and dihydrobenzodioxyl group. $A^2$ represents a single bond, oxygen atom, sulfur atom, —N(methyl)-, or —N(ethyl)- (provided that when $A^2$ represents oxygen atom, sulfur atom, —N(methyl)-, or —N(ethyl)-, $A^1$ represents ethylene). $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q represents phenyl group, $A^1$ represents a single bond, or unsubstituted methylene, and $A^2$ represents a single bond, one of $R^2$ and $R^3$ represents a substituent other than hydrogen atom). Symbol p in Rc represents an integer of 2 or 3, and $A^4$ represents a single bond or methylene. $A^5$ represents —C(O)—, —C(S)—, or —S(O)$_2$—. Rd represents hydrogen atom, or a group as any one of methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, and pyridin-4-yl group. Re represents any one of methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, and ethyloxycarbonylamino group. Rz' represents butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl) ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl) ethyl group, 2-[2-(trifluoromethyl)phenyl]ethyl group, 2-[3-(trifluoromethyl)phenyl]ethyl group, 2-[4-(trifluoromethyl) phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino) ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, and (morpholino-4-yl)carbonyl group. Ry' represents hydrogen atom, methyl group, ethyl group, or isobutyl group, or binds to Rz to form pyrrolidino group, piperidino group, piperazino group, morpholino group, pyrrol-1-yl group, imidazol-1-yl group, or pyrazol-1-yl group together with the nitrogen atom to which they bond. However, -D-Rx' or —N(Ry')(Rz') contains hydroxyl group, the hydroxyl group may be protected with $Rp^1$, and when -D-Rx' or —N(Ry') (Rz') contains amino group, the amino group may be protected with $Rp^2$.

AR' represents any one of naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo [d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, and 4H-chromen-5-yl group (the aforementioned groups may be substituted with one of Xa or two or more of identical or different Xa). The substituent Xa represents a group as any one of oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N- dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, and N,N-dimethylcarbamoyl group. Provided that when AR' contains hydroxyl group, the hydroxyl group may be protected with $Rp^1$, and when substituted AR' contains amino group, the amino group may be protected with $Rp^2$.

In another preferred embodiment, the compound represented by the formula (III) satisfies all of the following requirements.

AR' binds to $C^{3'}$, Rs' binds to any of the ring-constituting carbon atoms $C^{4'}$, $C^{5'}$, and $C^{6'}$, and a ring-constituting carbon atom to which Rs' does not bind among $C^{4'}$, $C^{5'}$, and $C^{6'}$ may be replaced with V'.

V' represents nitrogen atom, or carbon atom substituted with Zx', and Zx' represents any one of fluorine atom, chlorine atom, bromine atom, nitro group, methyl group, hydroxyl group, methoxy group, amino group, N-methylamino group, N-ethylamino group, N-propylamino group, N-isopropylamino group, N,N-dimethylamino group, N,N-diethylamino group, formylamino group, acetylamino group, carbamoylamino group, mesylamino group, and N,N-dimethylsulfamoylamino group, provided that when Zx' contains hydroxyl group, the hydroxyl group may be protected with $Rp^1$, and when the substituted Zx' contains amino group, the amino group may be protected with $Rp^2$.

Rs' represents -D-Rx' or —N(Ry')(Rz'). D represents oxygen atom or sulfur atom. Rx' represents butyl group, isobutyl group, 2-ethylbutyl group, cyclopentyl group, cyclohexyl group, cycloheptyl group, cyclopentylmethyl group, cyclohexylmethyl group, 2-cyclopentylethyl group, or 2-cyclohexylethyl group, or represents Rb or Rc. Q in Rb represents a group as any one of phenyl group, thienyl group, furyl group, pyridyl group, oxazolyl group, naphthyl group, tetrahydronaphthyl group, indanyl group, indolyl group, and dihydrobenzodioxyl group. $A^2$ represents a single bond, oxygen atom, sulfur atom, —N(methyl)-, or —N(ethyl)- (provided that when $A^2$ represents oxygen atom, sulfur atom, —N(methyl)-, or —N(ethyl)-, $A^1$ represents ethylene). $R^2$ and $R^3$ independently represent hydrogen atom, methyl group, fluorine atom, chlorine atom, trifluoromethyl group, methoxy group, dimethylamino group, acetylamino group, or methylsulfonylamino group (provided that when Q represents phenyl group, $A^1$ represents a single bond, or unsubstituted methylene, and $A^2$ represents a single bond, one of $R^2$ and $R^3$ represents a substituent other than hydrogen atom). Symbol p in Rc represents an integer of 2 or 3, and $A^4$ represents a single bond or methylene. $A^5$ represents —C(O)—, —C(S)—, or —S(O)$_2$—. Rd represents hydrogen atom, or a group as any one of methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4-fluorophenylmethyl group, pyridin-2-yl group, pyridin-3-yl group, and pyridin-4-yl group. Re represents any one of methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, thiomethoxy group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, and ethyloxycarbonylamino group. Rz' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, and (morpholino-4-yl)carbonyl group. Ry' represents hydrogen atom, methyl group, ethyl group, or isobutyl group, or binds to Rz' to form pyrrolidino group, piperidino group, piperazino group, morpholino group, pyrrol-1-yl group, imidazol-1-yl group, or pyrazol-1-yl group together with nitrogen atom. Provided that when -D-Rx' or —N(Ry')(Rz') contains hydroxyl group, the hydroxyl group may be protected with $Rp^1$, and when -D-Rx' or —N(Ry')(Rz') contains amino group, the amino group may be protected with $Rp^2$.

AR' represents any one of naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-e]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, and 4H-chromen-5-yl group (the aforementioned groups may be substituted with one of Xa or two or more of identical or different Xa). The substituent Xa represents a group as any one of oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, and N,N-dimethylcarbamoyl group. Provided that when AR' contains hydroxyl group, the hydroxyl group may be protected with $Rp^1$, and when substituted AR' contains amino group, the amino group may be protected with $Rp^2$.

In a particularly preferred embodiment, the compound represented by the formula (III) satisfies all of the following requirements.

$C^{2\prime}$ represents carbon atom to which AR' binds, $C^{3\prime}$ represents carbon atom to which Rs' binds, $C^{4\prime}$ may be replaced with V', and $C^{5\prime}$ and $C^{6\prime}$ represent an unsubstituted ring-constituting carbon atom.

V' represents nitrogen atom, or carbon atom substituted with Zx', and Zx' represents any one of fluorine atom, methyl group, hydroxyl group, amino group, N-methylamino group, and N,N-dimethylamino group, provided that when Zx' contains hydroxyl group, the hydroxyl group may be protected with $Rp^1$, and when the substituted Zx' contains amino group, the amino group may be protected with $Rp^2$.

Rs' represents —O—Rx'. Rx' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

AR' represents any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group. Provided that when AR' contains hydroxyl group, the hydroxyl group may be protected with $Rp^1$, and when substituted AR' contains amino group, the amino group may be protected with $Rp^2$.

In another particularly preferred embodiment, the compound represented by the formula (III) satisfies all of the following requirements.

$C^{2\prime}$ represents carbon atom to which AR' binds, $C^{4\prime}$ represents carbon atom to which Rs' binds, $C^{3\prime}$ may be replaced with V', and $C^{3\prime}$ and $C^{6\prime}$ represent an unsubstituted ring-constituting carbon atom.

V' represents nitrogen atom, or carbon atom substituted with Zx', and Zx' represents any one of fluorine atom, methyl group, hydroxyl group, amino group, N-methylamino group, and N,N-dimethylamino group. Provided that when Zx' contains hydroxyl group, the hydroxyl group may be protected with $Rp^1$, and when the substituted Zx' contains amino group, the amino group may be protected with $Rp^2$.

Rs' represents —O—Rx'. Rx' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

AR' represents any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group. Provided that when AR' contains hydroxyl group, the hydroxyl group may be protected with $Rp^1$, and when substituted AR' contains amino group, the amino group may be protected with $Rp^2$.

In another particularly preferred embodiment, the compound represented by the formula (III) satisfies all of the following requirements.

$C^{3'}$ represents carbon atom to which AR' binds, $C^{5'}$ represents carbon atom to which Rs' binds, and $C^{2'}$, $C^{4'}$ and $C^{6'}$ represent an unsubstituted ring-constituting carbon atom.

Rs' represents —O—Rx'. Rx' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)

ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

AR' represents any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group. Provided that when AR' contains hydroxyl group, the hydroxyl group may be protected with $Rp^1$, and when substituted AR' contains amino group, the amino group may be protected with $Rp^2$.

In another particularly preferred embodiment, the compound represented by the formula (III) satisfies all of the following requirements.

$C^{3'}$ represents carbon atom to which AR' binds, $C^{4'}$ represents carbon atom to which Rs' binds, $C^{5'}$ represents nitrogen atom, and $C^{2'}$ and $C^{6'}$ represent an unsubstituted ring-constituting carbon atom.

Rs' represents —O—Rx'. Rx' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

AR' represents any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group. Provided that when AR' contains hydroxyl group, the hydroxyl group may be protected with $Rp^1$, and when substituted AR' contains amino group, the amino group may be protected with $Rp^2$.

In another particularly preferred embodiment, the compound represented by the formula (III) satisfies all of the following requirements.

$C^{3'}$ represents carbon atom to which AR' binds, $C^{4'}$ represents carbon atom to which Rs' binds, $C^{6'}$ represents carbon atom substituted with Zx', and $C^{2'}$ and $C^{5'}$ represent an unsubstituted ring-constituting carbon atom.

Zx' represents any one of fluorine atom, methyl group, hydroxyl group, amino group, N-methylamino group, and N,N-dimethylamino group, provided that when Zx' contains hydroxyl group, the hydroxyl group may be protected with $Rp^1$, and when the substituted Zx' contains amino group, the amino group may be protected with $Rp^2$.

Rs' represents —O—Rx'. Rx' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

AR' represents any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group. Provided that when AR' contains hydroxyl group, the hydroxyl group may be protected with $Rp^1$, and when substituted AR' contains amino group, the amino group may be protected with $Rp^2$.

In another particularly preferred embodiment, the compound represented by the formula (III) satisfies all of the following requirements.

$C^{3\prime}$ represents carbon atom to which AR' binds, $C^{4\prime}$ represents carbon atom to which Rs' binds, $C^{5\prime}$ represents carbon atom substituted with Zx', and $C^{2\prime}$ and $C^{6\prime}$ represent an unsubstituted ring-constituting carbon atom.

Zx' represents any one of N-methylamino group, N-ethylamino group, N-propylamino group, N-isopropylamino group, N,N-dimethylamino group, N,N-diethylamino group, formylamino group, acetylamino group, carbamoylamino group, mesylamino group, and N,N-dimethylsulfamoylamino group. Provided that when the substituted Zx' contains amino group (NH), the amino group may be protected with $Rp^2$.

Rs' represents —O—Rx'. Rx' represents any one of butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl) ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, and 2-(N-ethyl-N-phenylamino)ethyl group.

AR' represents any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-6-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group. Provided that when AR' contains hydroxyl group, the hydroxyl group may be protected with $Rp^1$, and when substituted AR' contains amino group, the amino group may be protected with $Rp^2$.

In another particularly preferred embodiment, the compound represented by the formula (III) satisfies all of the following requirements.

$C^{3\prime}$ represents carbon atom to which AR' binds, $C^{4\prime}$ represents carbon atom to which Rs' binds, $C^{5\prime}$ represents carbon atom substituted with Zx', or an unsubstituted ring-constituting carbon atom, and $C^{2\prime}$ and $C^{6\prime}$ represent an unsubstituted ring-constituting carbon atom.

Zx' represents any one of fluorine atom, methyl group, hydroxyl group, amino group, N-methylamino group, and N,N-dimethylamino group, provided that when Zx' contains hydroxyl group, the hydroxyl group may be protected with $Rp^1$, and when the substituted Zx' contains amino group, the amino group may be protected with $Rp^2$.

Rs' represents —O—Rx'. Rx' have the same meaning as that of Rc, provided that when Rc contains hydroxyl group, the hydroxyl group may be protected with $Rp^1$. p in Rc represents an integer of 2, and $A^4$ represents a single bond or methylene. $A^5$ represents —C(O)—, —C(S)—, or —S(O)$_2$—. Rd represents a group as any one of methyl group, ethyl group, propyl group, isopropyl group, butyl group, isobutyl group, cyclopropyl group, cyclopentyl group, cyclohexyl group, phenyl group, 4-methylphenyl group, 4-chlorophenyl group, 4-fluorophenyl group, benzyl group, 4-chlorophenylmethyl group, and 4-fluorophenylmethyl group. Re represents a group as any one of isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, pyrrolidino group, piperidino group, and morpholino group.

AR' represents any one of naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethylbenzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, and benzoxazol-5-yl group. Provided that when AR' contains hydroxyl group, the hydroxyl group may be protected with $Rp^1$, and when substituted AR' contains amino group, the amino group may be protected with $Rp^2$.

Compound (I) of the present invention can be produced by, for example, employing the reactions according to the following various methods.

[Preparation Method 1] (Step a-1)

As shown in the following scheme 1:

(Scheme 1)

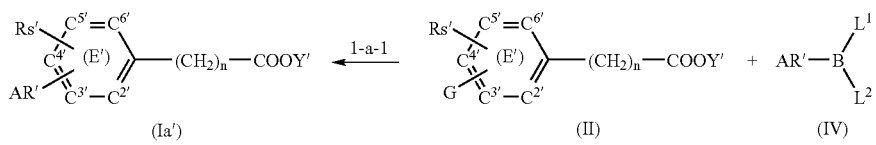

a compound of the present invention represented by the formula (Ia') wherein Y represents a lower alkyl group having 1 to 4 carbon atoms, and Rs, AR, and V on or in the aromatic ring (E) may be protected [hereinafter simply referred to as "Compound (Ia')"], which falls within the scope of Compound (I) of the present invention, can be prepared by reacting a compound represented by the formula (II) [simply referred to as "Compound (II)" hereinafter] with a boronic acid derivative represented by the formula (IV) [hereinafter simply referred to as "Compound (IV)"]. n, $C^{2'}$ to $C^{6'}$, Rs', AR', Y' and G in the formulas have the same meanings as defined above. In the formula of Compound (IV), $L^1$ and $L^2$ independently represent hydroxyl group, an alkoxyl group having 1 to 8 carbon atoms (e.g., methoxy group, ethoxy group, propoxy group, isopropoxy group, cyclohexyloxy group), or a substituted or unsubstituted phenyloxy group, or $L^1$ and $L^2$ bind to each other to represent a 5- or 6-membered cyclic ester of an arylboric acid (e.g., 9-borabicyclo[3,3,1]nonane, 1,3,2-dioxaborolane, 4,4,5,5-tetramethyl-1,3,2-dioxaborolane), which forms a ring containing boron atom [this ring may be saturated or unsaturated, may be a ring containing a heteroatom other than boron (e.g., oxygen atom), and may be further substituted].

Further, as shown in the following scheme 2:

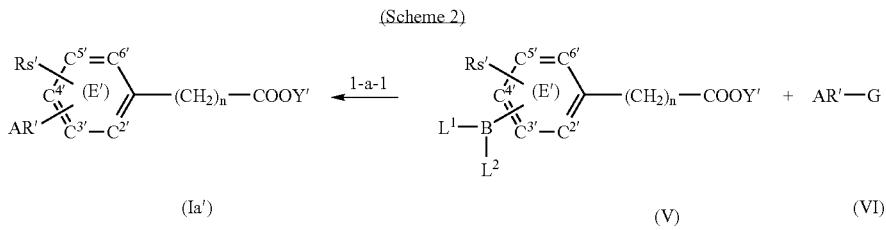

an example of the method for preparing Compound (Ia') includes a method of reacting a combination of a compound represented by the formula (V) [hereinafter simply referred to as "Compound (V)"] and a compound represented by the formula (VI) [hereinafter simply referred to as "Compound (VI)"].

Examples include a method of preparing Compound (Ia') by performing the Suzuki reaction described in, for example, Jikken Kagaku Koza, 4th Edition (edited by Chemical Society of Japan, published by Maruzen Co., Ltd.), vol. 25, p. 403 with a combination mentioned either in the scheme 1 or scheme 2 or the both. A specific example includes a reaction of Compound (II) [or Compound (V)] with Compound (IV) [or Compound (VI)] in a solvent in the presence of a commercially available palladium catalyst or a catalyst prepared from a palladium complex and a ligand, and a base.

As the palladium catalyst, a commercially available catalyst such as tetrakis(triphenylphosphine)palladium, tetrakis (methyldiphenylphosphine)palladium, dichlorobis(triphenylphosphine)palladium, dichlorobis(tri-o-tolylphosphine) palladium, dichlorobis(tricyclohexylphosphine)palladium, dichlorobis(triethylphosphine)palladium, palladium acetate, palladium chloride, bis(acetonitrile)palladium chloride, tris (dibenzylideneacetone)dipalladium and bis(diphenylphosphinoferrocene)palladium chloride may be purchased and added to the reaction system, per se, or a catalyst may be added which is separately prepared from palladium acetate, tris(dibenzylideneacetone)dipalladium or the like and arbitrary ligands and isolated. Further, a catalyst considered to actually participate in the reaction may also be prepared by mixing palladium acetate, tris(dibenzylideneacetone)dipalladium or the like and arbitrary ligands in the reaction system. The valence of palladium may be 0 or may be +2. Examples of the ligand include phosphine ligands such as trifurylphosphine, tri(o-tolyl)phosphine, tri(cyclohexyl)phosphine, tri(t-butyl)phosphine, dicyclohexylphenylphosphine, 1,1'-bis(di-t-butylphosphino)ferrocene, 2-dicyclohexylphosphino-2'-dimethylamino-1,1'-biphenyl and 2-(di-t-butylphosphino) biphenyl and phosphine mimic ligands such as imidazol-2-ylidenecarbenes. Chemical equivalents of the palladium catalyst may be one equivalent or a catalytic amount, and the amount may preferably be 0.01 to 20.0 mol %, and most preferably be 0.10 to 10.0 mol %.

Examples of the base include sodium carbonate, potassium carbonate, cesium carbonate, cesium fluoride, potassium fluoride, potassium phosphate, potassium acetate, triethylamine, potassium hydroxide, sodium hydroxide, sodium methoxide, lithium methoxide and the like. The reaction temperature is, for example, preferably 20° C. to 150° C., and particularly preferable examples include 20° C. to 120° C.

The reaction system may be either a two-phase system of water and an organic solvent, or a homogeneous system of a water-containing organic solvent or an organic solvent. As for the organic solvent, examples include uses of hydrocarbon-type solvents such as toluene, xylene and hexane, halogen-type solvents such as methylene chloride, sulfoxide-type solvents such as dimethyl sulfoxide, amide-type solvents such as dimethylformamide, ether-type solvents such as tetrahydrofuran, dioxane and diglyme, alcohol-type solvents such as methanol and ethanol, nitrile-type solvents such as acetonitrile, ketone-type solvents such as acetone and cyclohexanone, ester-type solvents such as ethyl acetate, heterocyclic-type solvents such as pyridine and the like. Two or more kinds of organic solvents may be mixed and used.

For the reaction conditions, Miyaura, N., Suzuki, A., Chemical Review, 1995, vol. 95, p. 2457; Snieckus, V., Chemical Review, 1990, vol. 90, p. 879 and the like and references cited therein can be referred to.

When hydroxyl group or amino group reactive under the aforementioned reaction conditions or inhibiting the reactions exists in the group AR', Rs' or V' in the aromatic ring (E'), this substituent is preferably protected.

When a protective group of hydroxyl group or amino group exist in the group AR', Rs' or V' in the aromatic ring (E') of the compound (Ia') prepared as described above, such a protective group can be eliminated during or after the preparation of Compound (Ia') to convert the compound into Compound (I) of the present invention. As for selection, introduction and deprotection of these protective groups of hydroxyl group and amino group, ordinary chemical publications, for example, Protective Groups In Organic Synthesis THIRD EDITION, John Wiley & Sons) and references cited therein can be referred to.

[Preparation Method 1] (Step a-2)

As Compound (IV), a compound commercially available as a reagent may be used, or as shown in the following scheme 3:

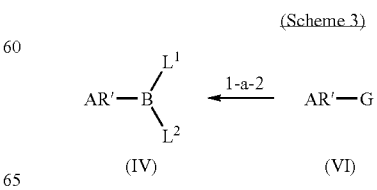

the compound can be produced from Compound (VI), which is commercially available or can be synthesized by a known method or a similar method thereto, according to the method described in the aforementioned reference (Chemical Review, vol. 95, p. 2457, 1995) or the method described in Satoh, Y. et al., SYNTHESIS, p. 1146, 1994 or according to the references cited therein.

For example, examples include a method of preparing Compound (VI) by converting Compound (VI) into a lithio-compound using an alkyl lithium such as n-butyl lithium and t-butyl lithium, then reacting the product with a trialkyl borate and treating the product with a mineral acid such as hydrochloric acid, sulfuric acid, and phosphoric acid; and a method of to preparing Compound (VI) by performing a cross-coupling reaction of Compound (VI) and an (alkoxyl)diboron in the presence of a palladium catalyst and a base.

An example of the preparation method of Compound (V) includes a method of subjecting Compound (II) to a reaction similar to that of the aforementioned Step a-2, as shown in the following scheme 4:

prepared by halogenating a compound represented by the formula (VII) [this compound is simply referred to as "Compound (VII)"], which is commercially available or can be prepared by a known method or a method similar thereto. In the formula of Compound (IIh), the group Hal represents a halogen atom, which may be any of chlorine atom, bromine atom and iodine atom. As for the halogenation, examples of chlorination include a preparation method described in ordinary publications in the filed of chemistry, for example, Shin Jikken Kagaku Koza (edited by Chemical Society of Japan, published by Maruzen Co., Ltd.), vol. 14, p. 354. Examples of the method include a method utilizing chlorine ($C^{12}$), a method utilizing sulfuryl chloride, and the like. Examples of bromination include a preparation method described in ordinary publications in the filed of chemistry, for example, Shin Jikken Kagaku Koza (edited by Chemical Society of Japan, published by Maruzen Co., Ltd.), vol. 14, p. 354. Examples of the method include a method utilizing bromine ($Br_2$), a method utilizing N-bromosuccinimide, and the like. Examples of iodination include a preparation method

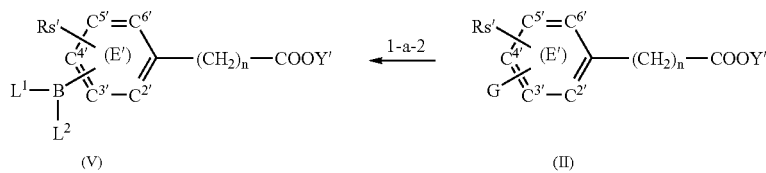

(Scheme 4)

[Preparation Method 1] (Step b)

As shown in the following scheme 5:

described in ordinary publications in the filed of chemistry, for example, Shin Jikken Kagaku Koza (edited by Chemical

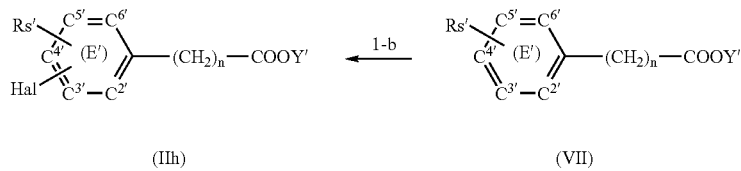

(Scheme 5)

a compound represented by the formula (IIh) (hereinafter simply referred to as "Compound (IIh)"), which correspond to the compounds (II) wherein G represents a halogen atom such as chlorine atom, bromine atom or iodine atom, can be Society of Japan, published by Maruzen Co., Ltd.), vol. 14, p. 423. Examples of the method include a method utilizing iodine (12), a method utilizing potassium triiodide, and the like.

[Preparation Method 1] (Step c)
As shown in the following scheme 6:

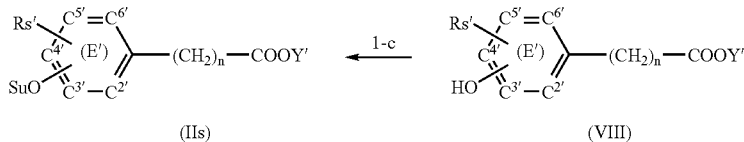

a compound represented by the formula (IIs) (this compound is hereinafter simply referred to as "Compound (IIs)"), which corresponds to Compound (II) wherein G represents mesylate group, triflate group, or an arenesulfonate group, can be prepared by converting a compound represented by the formula (VIII) (this compound is simply referred to as "Compound (VIII)"), which is commercially available or can be prepared by a known method or a method similar thereto, into a sulfonic acid ester. In the formula of Compound (IIs), the group Su represents methanesulfonyl group, trifluoromethanesulfonyl group, or arenesulfonyl group of which aromatic ring may be substituted with one of $T^1$ or two or more of identical or different $T^1$. Examples of the method for the conversion into sulfonic acid ester include a preparation method described in ordinary publications in the filed of chemistry, for example, Shin Jikken Kagaku Koza (edited by Chemical Society of Japan, published by Maruzen Co., Ltd.), vol. 14, p. 1793. Examples of the method include a method utilizing sulfonyl chloride, a method utilizing sulfonic anhydride, and the like.

[Preparation Method 2] (Step d)
As shown in the following scheme 7:

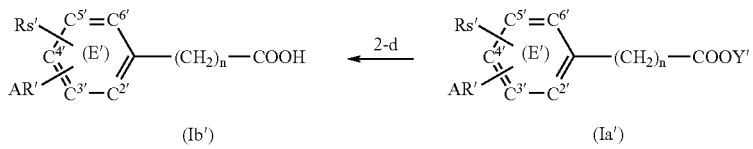

a compound represented by the formula (Ib') wherein Y represents hydrogen atom, and Rs, AR, and V on or in the aromatic ring (E) may be protected (this compound is hereinafter simply referred to as "Compound (Ib')"), which constitutes a part of the scope of Compound (I) of the present invention, can be prepared by hydrolyzing Compound (Ia') so as to convert the group OY' into hydroxyl group.

For the reaction of converting Compound (Ia') into Compound (Ib'), in general, the compound is preferably reacted in a base. Further, for the reaction of converting Compound (Ia') to Compound (Ib'), in general, the compound is preferably reacted in an inert medium that does not inhibit the reaction, preferably a polar solvent.

Examples of the base used in the above reaction include, for example, alkali metal bases such as sodium hydroxide, potassium hydroxide, sodium carbonate, potassium carbonate, sodium methoxide and potassium t-butoxide and organic bases such as triethylamine. As for amounts of the bases, generally 1 to 20 moles, preferably 1 to 10 moles, for alkali metal bases, or 1 to a large excess moles for organic bases based on Compound (Ia').

Examples of the polar solvent include water, methanol, ethanol, tetrahydrofuran, dioxane and the like, and these solvents may be used as a mixture as required. As the reaction temperature, an appropriate temperature of, for example, from room temperature to a refluxing temperature of solvent is chosen. The reaction time is, for example, generally 0.5 to 72 hours, preferably 1 to 48 hours, when an alkali metal base is used, or generally 5 hours to 14 days when an organic base is used. Since progress of the reaction can be monitored by thin layer chromatography (TLC), high performance liquid chromatography (HPLC) or the like, the reaction can generally be terminated appropriately so as to maximize the yield of Compound (Ib').

For collection of Compound (Ib') obtained as described above from the reaction solution as a free carboxylic acid, operations may preferably be carried out by, when the polar solvent is a water-soluble solvent, evaporating the solvent, neutralizing the residue with an inorganic acid such as aqueous hydrochloric acid, dissolving the residue in a water-insoluble solvent, then washing the solution with a weakly acidic aqueous solution, water or the like, and evaporating the solvent. When the polar solvent is a water-insoluble solvent, operations may preferably carried out by neutralizing the reaction solution with an inorganic acid, washing the solution with a weakly acidic aqueous solution, water or the like, and then evaporating the solvent.

Further, when Compound (Ib') forms a salt with the base used after the reaction to give a solid, the salt of Compound (Ib') can be obtained by isolation and purification of the solid in a conventional manner.

When a protective group of hydroxyl group or amino group exists in the group AR', Rs' or V' in the aromatic ring (E') of Compound (Ia') prepared as described above, Compound (Ia')

can be converted into Compound (I) of the present invention by removing the protective group during or after the preparation of Compound (Ia').

[Preparation Method 3] (Step e)
As shown by the following scheme 8:

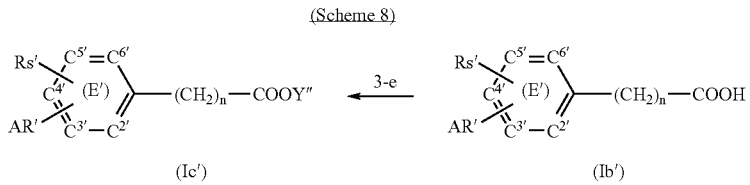

(Scheme 8)

a compound represented by the formula (Ic') [hereinafter simply referred to as "Compound (Ic')"] as Compound (I) of the present invention wherein the group Y represents Y''', and Rs, AR, and V in the aromatic ring (E) may be protected, can be produced by esterifying the carboxyl group (COOH) of Compound (Ib') in a conventional manner. In the formula of Compound (Ib'), Y' represents a lower alkyl group having 1 to 4 carbon atoms, a —$(CH_2)_m NR^{18}R^{19}$ group, or —$C(R^{26})_2OC(O)A^8R^{21}$.

Examples of the method for producing Compound (Ic') include a method of allowing Compound (Ib') to react with an inorganic halide without solvent or in an inert solvent to convert the compound into an acid halide and then allowing the acid halide per se or the same dissolved in an inert solvent to react with an excess amount of hydroxide of the targeted Y'''. Examples of the inorganic halide used in this method include thionyl chloride, phosphoryl chloride, phosphorus pentachloride, phosphorus trichloride and the like, and thionyl chloride is a preferred example. Examples of an amount used include generally an equimolar to a large excess amount, preferably 1.5 to 5 moles based on Compound (Ib'). Examples of the inert solvent used in this reaction include, for example, halogenated hydrocarbons such as dichloromethane, chloroform and 1,2-dichloroethane, ethers such as tetrahydrofuran and dioxane, and benzene compounds such as benzene, toluene, xylene and chlorobenzene. These solvents can be used, for example, each alone or as a mixed solvent. In order to promote the reaction, a catalytic amount of N,N-dimethylformamide may be added. As a reaction temperature, an appropriate temperature of from room temperature to a refluxing temperature of the solvent is generally chosen. Examples of the reaction time include generally 0.5 to 24 hours, preferably 1 to 6 hours.

Examples of the inert solvent used for the reaction with hydroxide of the targeted Y''' include, for example, halogenated hydrocarbons such as dichloromethane, chloroform and 1,2-dichloroethane, ethers such as tetrahydrofuran and dioxane, and benzene compounds such as benzene, toluene, and xylene. The reaction can also be performed with an excess amount of the hydroxide of the targeted Y''' without using a solvent. As the reaction temperature, an appropriate temperature of from −10° C. to room temperature is chosen. Examples of the reaction time include generally 0.5 to 24 hours, preferably 0.5 to 6 hours.

Other methods for producing Compound (Ic') include, for example, the "esterification using an alcohol" described in Shin Jikken Kagaku Koza (edited by the Chemical Society of Japan, published by Maruzen Co., Ltd.), vol. 14, p. 1002, "esterification using an O-alkylating agent", ibid, the same volume, p. 1002, "esterification using an alkyl halide", ibid, the same volume, p. 1008, "esterification reaction using a dehydrating agent", ibid, vol. 22, p. 45 and the like.

When hydroxyl group or amino group reactive under the aforementioned reaction conditions or inhibiting the reactions exists in AR', Rs' or V' in the aromatic ring (E'), this substituent is preferably protected.

When a protective group of hydroxyl group or amino group exist in AR', Rs' or V' in the aromatic ring (E') of the compound (Ic') prepared as described above, such a protecting group can be eliminated during or after the preparation of Compound (Ic') to convert the compound into Compound (I) of the present invention.

[Preparation Method 4]
As shown in the following scheme 9:

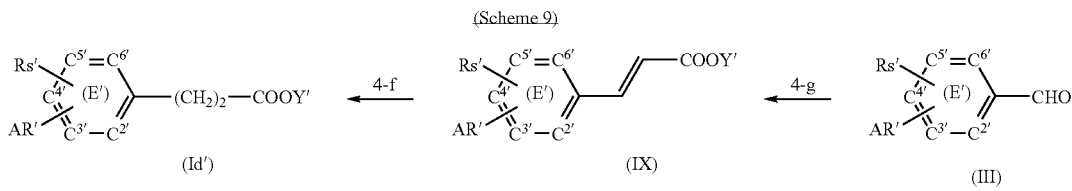

(Scheme 9)

a compound represented by the formula (Id') (hereinafter this compound is simply referred to as "Compound (Id')") as Compound (I) of the present invention wherein n in the methylene moiety is an integer of 2, and wherein Rs, AR, and V in the aromatic ring (E) may be protected, can also be prepared by the method shown below.

[Preparation Method 4] (Step f)

Compound (Id') can be prepared by reducing the double bond of a compound represented by the formula (IX) (hereinafter this compound is simply referred to as "Compound (IX)") using a reduction reaction described in ordinary publications in the filed of chemistry. Examples of the reaction include a method of converting the double bond of Compound (IX) into a single bond by hydrogenation using a hydrogen source such as hydrogen gas, ammonium formate, and hydrazine hydrate in a single solvent or a mixed solvent of alcoholic-type solvents such as methanol, ester-type solvents such as ethyl acetate in the presence of a catalyst such as palladium/carbon powder, platinum oxide ($PtO_2$), and activated nickel.

When hydroxyl group or amino group reactive under the aforementioned reaction conditions or inhibiting the reactions exists in AR', Rs' or V' in the aromatic ring (E'), this substituent is preferably protected.

When a protective group of hydroxyl group or amino group exist in AR', Rs' or V' in the aromatic ring (E') of the compound (Id') prepared as described above, such a protecting group can be eliminated during or after the preparation of Compound (Id') to convert the compound into Compound (I) of the present invention.

erably 2 to 8 hours. Since progress of the reaction can be monitored by thin layer chromatography (TLC), high performance liquid chromatography (HPLC) or the like, the reaction, can generally be terminated appropriately so as to maximize the yield of Compound (IX).

[Preparation Method 4] (Step a)

As shown in the following scheme 10:

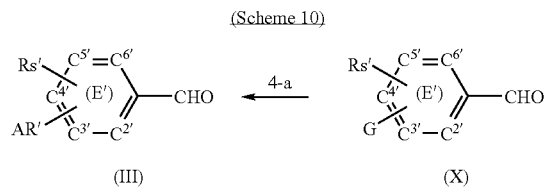

Compound (III) can be prepared by introducing the substituent AR' into a compound represented by the formula (X) [hereinafter this compound is simply referred to as "Compound (X)"] according to any of the methods described in the step a-1 of the preparation method 1 mentioned above.

[Preparation Method 5]

As shown in the following scheme 11:

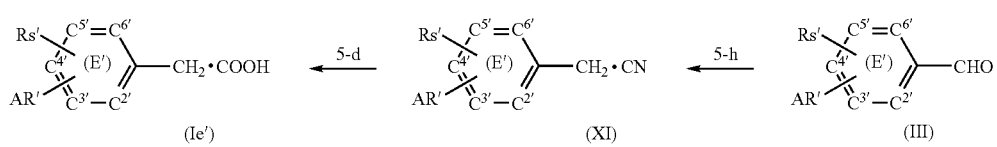

[Preparation Method 4] (Step g)

Compound (IX) can be prepared from a compound represented by the formula (III) [hereinafter this compound is simply referred to as "Compound (III)"]. Examples of the preparation method include a method utilizing the Horner-Emonds reaction described in Shin Jikken Kagaku Koza (edited by Chemical Society of Japan, published by Maruzen Co., Ltd.), vol. 14, p. 238. Specifically, the compound can be obtained by reacting Compound (III) with a commercially available dialkylphosphonoacetic acid ester in an inert solvent, for example, an alcohol-type solvent such as methanol and ethanol or ether-type solvent such as tetrahydrofuran and dimethoxyethane in the presence of a base such as sodium hydride and sodium alkoxide. As the reaction temperature, an appropriate temperature of from −10° C. to a refluxing temperature of a solvent is generally chosen, and preferred examples include a temperature of from 0° C. to room temperature. The reaction time is generally 1 to 16 hours, prefa compound represented by the formula (Ie') [hereinafter this compound is simply referred to as "Compound (Ie')"], as Compound (I) of the present invention wherein n in the methylene moiety is an integer of 1, Y represents hydrogen atom, and Rs, AR, and V in the aromatic ring (E) may be protected, can also be prepared by the method shown below.

[Preparation Method 7] (Step d)

Specifically, Compound (Ie') can be prepared by hydrolyzing nitrile group of a compound represented by the formula (XI) [hereinafter this compound is simply referred to as "Compound (XI)"] into carboxyl group according to a method similar to the method shown in the step d of the preparation method 2 mentioned above.

When a protective group of hydroxyl group or amino group exist in AR', Rs' or V' in the aromatic ring (E') of the compound (Ie') prepared as described above, such a protecting group can be eliminated during or after the preparation of Compound (Ie') to convert the compound into Compound (I) of the present invention.

[Preparation Method 5] (Step h)

Compound (XI) can be produced from Compound (III) mentioned above. For example, Compound (III) is reacted with a trimethylsilyl cyanide using a Lewis acid, particularly zinc iodide, as a catalyst in an inert solvent such as tetrahydrofuran as described in Jikken Kagaku Koza, 4th Edition (edited by Chemical Society of Japan, published by Maruzen Co., Ltd.), vol. 20, p. 445. Then, the reduction reaction using a hydrosilane described in Jikken Kagaku Koza, 4th Edition (edited by Chemical Society of Japan, published by Maruzen Co., Ltd.), vol. 26, p. 197 is performed. Examples of the method of the reduction reaction include a method of performing the reduction with a hydrosilane such as triethylsilane and a protonic acid such as trifluoroacetic acid or a Lewis acid such as boron trifluoride in a halogenated solvent such as dichloromethane.

The preparation method of Compound (I) is not limited to the methods described herein. For example, the compounds of the present invention can be produced by modifying or converting a substituent of a compound serving as a precursor of the compounds according to a method or a combination of methods described in ordinary publications in the field of chemistry.

Examples of the preparation method for Compound (I) of the present invention which contains an asymmetric carbon in the substituent Rs include a method of using a starting material in which a moiety corresponding to the asymmetric carbon in the substituent Rs is already optically active, which is commercially available (or can be prepared by a known method or a method similar thereto). A method is also available in which the compound of the present invention or a precursor thereof is separated as an optically active isomer in a conventional manner. Examples of such method include, for example, a method utilizing high performance liquid chromatography (HPLC) using a chiral column, a method comprising condensation with an optically active regent to form a diastereomer, successive separation and purification, followed by decomposition. When a precursor is separated to obtain an optical isomer, optically active Compound (I) of the present invention can then be prepared by performing the aforementioned preparation methods.

When Compound (I) of the present invention contains an acidic functional group such as carboxyl group or phenolic hydroxyl group, the compound can be converted into pharmaceutically acceptable salt (e.g., inorganic salts with sodium, ammonia and the like, or organic salts with triethylamine and the like) by a known means. For example, when an inorganic salt is to be obtained, it is preferable to dissolve Compound (I) of the present invention in water containing at least 1 equivalent of hydroxide, carbonate, bicarbonate or the like corresponding to a desired inorganic salt. For the reaction, an inactive water-miscible organic solvent such as methanol, ethanol, acetone, and dioxane may be mixed. For example, by using sodium hydroxide, sodium carbonate, or sodium hydrogencarbonate, a solution of sodium salt can be obtained.

When Compound (I) of the present invention contains a basic functional group such as amino group, or when Compound (I) of the present invention contains an aromatic ring which itself has properties of base (e.g., pyridine ring), the compound can be converted into a pharmaceutically acceptable salt (e.g., salt with inorganic acids such as hydrochloric acid and sulfuric acid, or salts with organic acids such as acetic acid and citric acid) by a known means. For example, when an inorganic salt is to be obtained, it is preferable to dissolve Compound (I) of the present invention in water containing at least 1 equivalent of a desired inorganic acid. For the reaction, an inactive water-miscible organic solvent such as methanol, ethanol, acetone, and dioxane may be mixed. For example, by using hydrochloric acid, a solution of hydrochloride can be obtained.

When a solid salt is desired, a solution may be evaporated, or a water-miscible organic solvent having polarity to some extent, such as butanol or ethyl methyl ketone, can be added to obtain a solid salt thereof. The various compounds disclosed by the present invention can be purified by known methods such as recrystallization, and variety of chromatography techniques (column chromatography, flash column chromatography, thin layer chromatography, high performance liquid chromatography).

Compound (I) of the present invention and pharmaceutically acceptable salts thereof have an action of suppressing the production of both of prostaglandins and leukotrienes. The action of suppressing the production of prostaglandins and/or leukotrienes includes, for example, an action of suppressing $PGE_2$ production, observed when cultured cells of MG-63 which is a human osteosarcoma cell line are stimulated with IL-1β and/or $PGD_2$ and $LTB_4$ production observed when cultured cells of RBL-2H3 which is a rat mastocytoma cell line are stimulated with IgE, by 10% or more, preferably 30% or more, most preferably 50% or more, compared with a positive control at a concentration of the compound not having cytotoxicity. As for a mode of action at a molecular level, it is considered that the compound of the present invention inhibits both of COX-1 and/or COX-2, which produce prostaglandins, and 5-LO, which produces leukotrienes. It is also considered that the compound of the present invention suppresses the production of arachidonic acid by inhibiting enzymatic activity of type 2A, 4, or 5 $PLA_2$ involved in prostaglandin and leukotrien production.

It is considered that, in these molecular action mechanisms, Compound (I) of the present invention inhibits the enzymatic activity of type 4 $PLA_2$. For the judgment, for example, the enzyme inhibitory action against type 4 $PLA_2$ can be examined, and known methods for measuring the enzymatic activity of type 4 $PLA_2$ are preferably utilized [Clark et al., Proceeding of National Academy of Science USA (Proc. Natl. Acad. Sci. USA), 1990, vol. 87, p. 7708; Gronich et al., Biochemical Journal (Biochem. J.), 1990, vol. 271, p. 37; Clark et al., Cell, 1991, vol. 65, p. 1043; Kramer et al., Journal of Biological Chemistry (J. Biol. Chem), 1991, vol. 266, p. 5268]. The type 4 PLA2 inhibitory action of the compounds of the present invention can be elucidated by employing these methods.

Compounds (I) of the present invention and pharmaceutically acceptable salts thereof inhibited mouse inflammatory edema, allergic edema, acetic acid writhing reaction, and rat adjuvant arthritis by oral administration at a dose of 0.1 to 500 mg/kg, and caused no death of the mice by oral administration at a dose of 500 mg/kg/day for 3 days. Therefore, they are safe compounds as drugs for mammals, preferably humans, pets or companion animals such as dogs and cats, and farm animals, and they are useful substances as active ingredients of medicaments. Preferred examples of the medicaments for mammals, preferably humans, pets or companion animals such as dogs and cats, and farm animals include agents for prophylactic and/or therapeutic treatment of various conditions, various diseases, and pathological conditions in which an acute or chronic inflammatory reaction resulted from production of prostaglandin and/or leukotriene is observed, specifically inflammatory diseases, allergic diseases, autoimmune diseases, and pain.

More specifically, the conditions or diseases include arthritis, chronic rheumatoid arthritis, malignant rheumatoid arthritis, juvenile rheumatoid arthritis, Felty's syndrome, adult Still's disease, osteoarthritis, synovitis, gout, slack of artificial joint implant, fervescence, common cold, algesia, burn, thermal injury, keloplasty, menstrual pain, dysmenorrhea, menstrual cramp, allergic reaction, allergic contact hypersensitivity, allergic rhinitis, pollinosis, allergic conjunctivitis, hypersensitivity pneumonitis, allergic bronchopulmonary mycosis, emphysema, acute respiratory distress syndrome, asthma, bronchitis, chronic obstructive pulmonary disease, chronic bronchitis, pulmonary emphysema, diffuse panbronchiolitis, respiratory obstruction, graft versus host syndrome, urticaria, ultraviolet radiation dermatitis, atopic dermatitis, cancer, myelogenous leukemia, sarcomata, brain tumor, cachexia, tissue ulcer, digestive ulcer, gastritis, acute and chronic pancreatitis, regional enteritis, ulcerative colitis, diverticulitis, recurrent gastroenteric disorder, gastroenteric bleeding, inflammatory bowel disease, Crohn's disease, intestinal tract type Behcet's disease, infectious enteritis, ischemic enteritis, radiation enteritis, drug-induced enteritis, irritable bowel syndrome, hepatic diseases (hepatopathies, liver failures) such as acute hepatitis, fulminant hepatitis, chronic hepatitis, hepatic cirrhosis, fatty liver, alcoholic liver injury, drug liver injury (drug-induced hepatitis), congestive hepatitis, autoimmune hepatitis, primary biliary cirrhosis and hepatic porphyria, coagulation, anemia, ankylosing spondilitis, restenosis, periodontosis, epidermolysis bullosa, atherosclerosis, aortic aneurysm, periarteritis nodosa, congestive cardiac failure, arrhythmia, myocardial infarction, cerebral infarction, attack, cerebral ischemia, head injury, spinal cord injury, myelopathic muscular atrophy, neuralgia, neurodegenerative disease, Alzheimer's disease, Lewy body disease, Shy-Drager syndrome, Reye's syndrome, progressive supranuclear palsy, progressive multifocal leukoencephalopathy, normal pressure hydrocephalus, subacute sclerosing panencephalitis, frontal lobe type dementia, acute anterior poliomyelitis (poliomyelitis), poliomyelitis neurosis, viral encephalitis, Creutzfeldt-Jakob disease, Kuru disease, bovine spongiform encephalopathy (mad cow disease), scrapie, epilepsy, cerebral amyloid angiopathy, autoimmune disease, Huntington's disease, Parkinson's disease, migraine, depression, mania, manic-depressive psychosis, hereditary cerebellar ataxia, peripheral neuropathy, glaucoma, pain, gingivitis, postoperative pain, amyotrophic lateral sclerosis, osteoporosis, multiple sclerosis, ocular angiogenesis, cornea damage, macular degeneration, conjunctivitis, abnormal wound healing, sprain or strain of muscle or joint, tendinitis, skin disease, psoriasis vulgaris, pustular psoriasis, erythroderma psoriaticum, arthritic psoriasis, myasthenia gravis, multiple myositis, myositis, bursitis, diabetes mellitus, tumor invasion, tumor growth, tumor metastasis, cornea scar, scleritis, immunodeficiency disease, pachydermia, eosinophilic fasciitis, sepsis, endotoxin shock, premature delivery, hypoprothrombinemia, hemophilia, thyroiditis, sarcoidosis, Behcet's syndrome, hypersensitivity, renal disease, rickettsial infectious disease, protozoal disease, reproduction disease, sepsis shock and the like. Other specific conditions and diseases include toothache, pain after tooth extraction, back or low back pain, periarthritis humeroscapularis, cervico-omo-brachial syndrome, tenosynovitis, acute upper respiratory inflammation, herpes zoster, fibrosis, pulmonary fibrosis, pneumoconiosis, chronic interstitial pneumonia, granulomatous interstitial pneumonia, fibrosing interstitial pneumonia, renal fibrosis, nephropyelitis, various types of secondary contracted kidney, glomerular nephritis, chronic nephritis, glomerulosclerosis, hepatic fibrosis, cardiac fibrosis after myocardial infarction, idiopathic cardiomyopathy, pancreatic sclerosis, pancreatic fibrosis, pancreatolithiasis, Takayasu's arteritis, chronic thyroiditis, dermatomyositis, multiple myositis, myelofibrosis, Banti disease, retroperitoneal fibrosis, various radiation injuries and the like. Further, the medicament comprising Compound (I) of the present invention as an active ingredient can be used for the aforementioned conditions or diseases of mammals, preferably humans, pets or companion animals such as dogs and cats or farm animals together with or in combination with one or more kinds of other prophylactic or therapeutic drugs.

Examples of the drugs that can be used together or in combination include, for example, the following drugs: immunomodulation-type antirheumatic drugs and antimetabolite used as therapeutic drugs for rheumatoid arthritis, specifically, gold preparations, bucillamine, lobenzarit, salazosulfapyridine, methotrexate, azathiopurin, mizoribine, leflunomide, tacrolimus, cyclosporin and the like and preparations containing the same; anti-cytokine antibody preparations directed to cytokines such as interleukin (IL) 1, IL-6, and tumor necrosis factor (TNF)-α or preparations of soluble receptors for those cytokines, which are biological preparations, specifically, infliximab, etanercept and the like and preparations containing the same; steroid preparations, specifically, dexamethasone, betamethasone, prednisolone, fluticasone, beclometasone and the like and preparations containing the same; bronchodilators used as therapeutic agents for chronic bronchial asthma, specifically, salmeterol and salbutamol, which are adrenalin β2 stimulants, ipratropium, which is an anticholinergic drug, and the like and preparations containing the same; therapeutic drugs for allergic diseases, for example, theophyline, which is a xanthine analogue drug, and the like, fexoquinadine, epinastatine, cetirizine, ketotifen, disodium cromoglycate, pemirolast and the like, which are antiallergic agents, fexoquinadine, cetirizine and the like, which are antihistaminic agents, and preparations containing the same; irinotecan, 5-fluorouracil and the like, which are antitumor agents, and preparations containing the same. Further, the medicament comprising Compound (I) of the present invention as an active ingredient is used, for example, together with or in combination with radiotherapy.

In order to use Compound (I) of the present invention or pharmaceutically acceptable salts thereof for the medicaments described above, an effective amount of Compound (I) of the present invention or a pharmaceutically acceptable salt thereof, per se, may be used, or the substance may be mixed with a pharmaceutically acceptable carrier to form a pharmaceutical composition. The carrier may be, for example, a suspending agent such as carboxymethylcellulose, or purified water, physiological saline or the like, if desired. Other known carriers can also be used. Examples include a method of dissolving Compound (I) of the present invention or a pharmaceutically acceptable salt thereof in purified water containing 0.5% carboxymethylcellulose and using the solution.

Examples of formulations for preparing the aforementioned pharmaceutical composition include tablet, powder, granule, syrup, suspension, capsule, and injection. For the manufacture of these formulations, various carriers suitable for these preparations are used. For example, examples of the carrier for oral preparations include excipients, binders, lubricants, fluid accelerators, and colorants.

When the compound of the present invention is formulated as a parenteral preparation such as an injection, water for injection, physiological saline, glucose aqueous solution, vegetable oil for injection, propylene glycol, polyethylene glycol and the like can generally be used as a diluent. Disinfectants, antiseptics, stabilizers, isotonic agents, soothing agents and the like may be further added, as required.

When the compound of the present invention is administered to a mammal, e.g., human, the compound can be administered in the form of a tablet, a powder, a granule, a suspension, a capsule or the like. The compound can also be parenterally administered in the form of a suppository, a gel, a lotion, an ointment, a cream, or a spray. A dose thereof varies depending on a disease to be applied, administration route, age, weight, degree of symptom of a patient and the like. Examples of the dose include generally an administration at a dose of 1 to 1,000 mg per day for an adult once to three times a day. Every day administration for a period of several days to two months is commonly applied. The daily dose and the administration period may be increased or decreased depending on symptoms of a patient.

Fibrosis, which is a disease characterized by fibrosing of tissues, is known as a severe disease which is often mortal. Fibrosing of tissues is caused by proliferation of interstitial cells, which represented by fibroblasts, and production of extracellular matrix such as collagen. Fibrosing is considered a repair mechanism against tissue affections in organs. Excessive fibrosing causes fibrosing diseases of organs, and further progression of fibrosing causes sclerotic diseases. Many of such sclerotic diseases are intractable, progressive and irreversible. Although fibrosing varies in various organs, etiological hypotheses of fibrosing have many similarities. That is, a certain inflammatory lesion precedes, and in its healing process, various kinds of cytokines and growth factors are produced mainly from immunocompetent cells and platelets as well as interstitial cells such as fibroblasts themselves involved in the healing, and activated to cause deposition of extracellular matrix (Takehara, Molecular Medicine, 2001, vol. 38, p. 854).

Among fibroses, pulmonary fibrosis is one of the representative diseases. Pulmonary fibrosis is a disease in which disruption of alveolar structure is caused by chronic inflammation and increase of collagenic fibers in alveolar walls, and which eventually leads to respiratory failure and death. For example, pulmonary fibrosis occurs following infectious pneumonia and the like. Examples of the infectious pneumonia include severe acute respiratory syndrome (SARS) and influenzal pneumonia. It has been reported that, in SARS, in particular, severe inflammation is caused in pulmonary stroma, and as a result, it highly likely to develop into pulmonary fibrosis (Antonino et al., Radiology, 2003). In addition, pulmonary fibrosis is also caused by various medicaments.

In recent years, with increase of medicaments used for diagnosis, prophylactic and therapeutic treatments of various kinds of diseases, drug-induced pulmonary fibrosis caused by such drugs is increasing. Drug-induced pulmonary fibrosis is a severe disease that eventually leads to death, and it causes serious problems in therapeutic treatments of various diseases. Therefore, prophylactic and therapeutic treatments of drug-induced pulmonary fibrosis constitute a particularly important subject of concern.

Against drug-induced pulmonary fibrosis, steroid therapy is currently used. However, effective rate of the steroid therapy is low and the effect is only partial and transient, and thus lesions often remain [Igaku no Ayumi, 2001, vol. 197, p. 313]. Further, side effect of steroid agents and acute aggravation due to decrease of doses or termination of their administrations are also often observed, which remains clinically far unsatisfactory level.

As a recent finding, it was reported that administration of pirfenidone was effective against pulmonary fibrosis in clinical tests in the United States (Raghu et al., American Journal of Respiratory and Critical Care Medicine, 1999, vol. 159, p. 1061) and Japan (Nagai et al., Internal Medicine, 2002, vol. 41, p. 1118). However, development of novel prophylactic and/or therapeutic agents highly effective for these diseases is desired at all events.

The medicament provided by the present invention is useful as a medicament containing a type 4 PLA2 inhibitor as an active ingredient for prophylactic and/or therapeutic treatment of fibrosis, preferably pulmonary fibrosis, further preferably drug-induced pulmonary fibrosis.

As described above, fibrosis, in particular, pulmonary fibrosis, is a severe disease and is an important object of prophylactic and/or therapeutic treatment. As for pulmonary fibrosis, more than 100 kinds of factors including toxic gases and various medicaments have been elucidated as the causes of early alveolopathy. As described above, with the increase of medicaments used for diagnosis, prophylactic and therapeutic treatments of various kinds of diseases, drug-induced pulmonary fibrosis caused by such drugs is increasing.

As for drug-induced pulmonary fibrosis, causality between expression of pathological conditions such as coughing, difficulty of breathing, or fervescence and the administration of medicaments is suspected, and it is considered that a diffuse interstitial shadow appears on a thoracic X-ray photograph simultaneously with or slightly after the administration of medicaments.

As medicaments reported to cause drug-induced pulmonary fibrosis, anticancer agents, anti-rheumatic agents, immunosuppressants, antibiotics, chemotherapeutants, anti-hypertensive agents, diuretics, anti-inflammatory/analgesic agents, biologics, Chinese medicines are known (Inooka et al., Therapeutics, 1995, vol. 29, p. 1295). Typical medicaments are shown in Table 1.

TABLE 1

| Classification | Examples of agent |
|---|---|
| 1) Anticancer agent immunosuppresant | Peplomycin, bleomycin, cychlophosphamide, nitrosourea, busulfan, methotrexate, azathioprine, mitomycin-C, tegafur, carmofur, tegafur/uracil preparation, cisplatin, doxorubicin, 6-mercaptopurine, daunomycin, vincristine, vinblastine, vindesine, procarbazine, neocarzinostatin, melphalan, thiotepa, nimustine, cytarabine, zinostatin stimalamer, chlorambucil, carmustine, lomustine, semustine, teniposide, etoposide, Taxol, taxotere, irinotecan, gefitinib, tamoxifen and the like. |
| 2) Antihypertensive agent diuretic | α-methyldopa, triclormethiazide, hydrochlorothiazide, enalapril, hexamethonium, mecamylamine, pentolinium, practolol, pindolol, propranolol, acebutolol, hydralazine |
| 3) Antibiotic, chemotherapeutant | Cephem antibiotics (cephaloridine, cephalothin, cephalexin, cefradine, cefazolin, cefaclor, cefmenoxime, cefmetazole, cefoperazone, cefotiam, cefroxadin, ceftizoxime, latamoxef and the like), tetracyclines (minocycline, oxycycline), antituberculous agents (isoniazid, paraaminosalicylic acid, rifampicin, streptomycin), penicillin antibiotics (ampicillin, piperacillin, vastcillin, pentcillin, amoxicillin), aminoglycoside antibiotics (streptomycin), macrolide antibiotics (midecamycin), phosphomycin, aminoglycosides (tobramycin, Micromycin), new quinolone drugs (enoxacin, ofloxacin, norfloxacin), antifungal agents (amphotericin) and the like |
| 4) Others | Inhalants (cromoglicic acid and the like), gold preparations (aurothiomalic acid and the like), psychotropic agents and nervines (aminotriptyline, diphenylhydantoin, carbamazepine, phenobarbital, valproate salt, imipramine, mephenesin, meprobamate), antiphlogistic and analgesics (naproxen, acetaminophen, acetylsalicylic acid, phenacetin, diclofenac, loxoprofen, fenbufen, nabumetone, aluminoprophen and the like), antiarrhythmic agents (amiodarone, procainamide, aprindine), antidiabetic agents (chlorpropamide), |

TABLE 1-continued

| Classification | Examples of agent |
| --- | --- |
| | antithyroid agents (thiouracil), proteolytic enzymes (serrapeptidase), antiparkinsonic agents (levodopa, bromocriptine), antirheumatic agents (bucillamine, auranofin, actarit), sho-saiko-to, chai-ling-tang, rikkunshi-to, interferon, warfarin, salazosulfapyridine, dichloroferamide, fominoben, D-penicillamine, propylthiouracil, corticosteroid, flavoxate, allopurinol, ethoxysclerol and the like |

In therapeutic treatment of rheumatoid arthritis, for example, agents that cause pulmonary fibrosis at high frequency such as methotrexate and sodium aurothiomalate are used as disease-modifying antirheumatic drugs. Further, disease-modifying antirheumatic drugs that may cause pulmonary fibrosis at a relatively low frequency, such as actarit, bucillamine, auranofin, salazosulfapyridine, and D-penicillamine are also used. Although these disease-modifying antirheumatic drugs are useful agent in the rheumatoid arthritis treatment system, pulmonary fibrosis caused as a side effect is a factor of restricting use of these drugs. In recent years, methotrexate, in particular, has come to be used as an antirheumatic agent, and onset of pulmonary fibrosis that is also histopathologically called interstitial pneumonia as the side effect of methotrexate becomes a problem in the rheumatoid arthritis treatment system.

Further, in cancer therapy, cychlophosphamide, Taxol, etoposide, cisplatin, vincristine, vinblastine, irinotecan, gefitinib, and bleomycin are useful as anticancer agents. However, because all of these anticancer agents cause pulmonary fibrosis that is also histopathologically called as interstitial pneumonia as a side effect at a high frequency, they have a problem in the therapeutic treatment system. Bleomycin, gefitinib, irinotecan, and cisplatin are used for therapeutic treatment of lung cancer. However, if patients with lung cancer develop pulmonary fibrosis, the condition is most likely for the patients to be fatal. Among these drugs, bleomycin suffers from a problem that it causes pulmonary fibrosis at a high frequency.

Preferred objects of application of the medicament of present invention are drug-induced pulmonary fibroses caused by these drugs.

In present invention, the type 4 $PLA_2$ inhibitor is not particularly limited so long as the inhibitor has type 4 $PLA_2$ inhibitory activity. For example, known type 4 $PLA_2$ inhibitors can be chosen. Examples of the known type 4 $PLA_2$ inhibitors include the following inhibitors: the compounds described in U.S. Pat. No. 5,462,954, preferably 2-phenyl-4-ethyl-5-[6-(2H-tetrazol-5-yl)-6-methylheptyloxy]phenol, 8-propyl-7-{3-[4-(4-fluorophenyl)-2-ethyl-5-hydroxyphenyloxy]propyloxy}-3,4-dihydro-2H-1-benzopyran-2-carboxylic acid, and 2-{3-[3-([5-ethyl-2-hydroxy(1,1'-biphenyl)-4-yl]oxy)propyloxy]-2-propylphenyloxy}propionic acid; the compounds described in WO99/43654, preferably 4-(1-benzhydryl-6-chloro-1H-indol-3-ylmethyl)-3-methoxybenzoic acid; the compounds described in WO98/33797, preferably N-{4-(biphenyl-2-ylmethyl-isobutylamino)-1-[2-(4-fluorobenzoyl)benzoyl]pyrrolidin-2-ylmethyl}-3-[4-(2,4-dioxothiazolidin-5-ylidenemethyl)phenyl]acrylamide and the like; the compounds described in WO01/30387, preferably N-{1-[2-(2,4-difluorobenzoyl)benzoyl]-4-tritylsulfanylpyrrolidin-2-ylmethyl}-4-(2,4-dioxothiazolidin-5-ylidenemethyl)benzoic acid amide and the like; the compounds described in WO99/15129, preferably 4-{4-[2-(2-[bis(4-chlorophenyl)methoxy]ethylsulfonyl)ethoxy]phenyl}-1,1,1-trifluoro-2-butanone and the like; the compounds described in WO98/05637, preferably 1-{2-[4-(carboxymethyl)phenoxy]ethyl}-3-dodecanoylindole-2-carboxylic acid and the like; the compounds described in Japanese Patent Unexamined Publication (Kokai) No. 2002-80368, preferably 4-methyl-2-oxo-5-(5,6,7,8-tetrahydronaphthalen-2-yl) oxazolidine-3-carboxylic acid (6-methoxytetrahydropyran-2-yl)amide, 4-methyl-2-oxo-5-(4-methylphenyl) thiazolidine-3-carboxylic acid (tetrahydropyran-2-yl)amide and the like; and the type 4 $PLA_2$ inhibitors selected from the compounds described in WO98/08818, the compounds described in WO99/43651, the compounds described in WO99/43672, the compounds described in WO03/048122, the compounds described in WO95/10508, the compounds described in WO97/05135, the compounds described in Japanese Patent Unexamined Publication No. 7-126166, the compounds described in Japanese Patent Unexamined Publication No. 7-224076, the compounds described in Japanese Patent Unexamined Publication No. 7-224076, the compounds described in Japanese Patent Unexamined Publication No. 2000-119292, the compounds described in Japanese Patent Unexamined Publication No. 2000-109432, the compounds described in Japanese Patent Unexamined Publication No. 7-223997, the compounds described in the U.S. Pat. No. 5,994,398, the compounds described in WO00/27824, the compounds described in Japanese Patent Unexamined Publication No. 2000-38380, the compounds described in WO00/71118, the compounds described in Japanese Patent No. 3107613, the compounds described in WO03/031414, the compounds described in U.S. Pat. No. 5,453,443, and the compounds described in WO02/038575. Examples further include the following known type 4 $PLA_2$ inhibitors described in references: arachidonyl trifluoromethyl ketone (Street et al., Biochemistry, 1993, vol. 32, p. 5935); methyl arachidonyl fluorophosphate (Kennedy et al., Mediators of Inflammation, 1994, vol. 3, p. 337); β-lactam derivatives (Burke et al., J. Enzyme Inhibition, 1998, vol. 13, p. 195); choline derivatives (Burke et al., J. Biol. Chem., 1999, vol. 274, p. 18864); 1,3-disubstituted propan-2-one derivatives, especially 4-[3-(4-decyloxyphenyloxy)-2-oxopropyloxy] benzoic acid (Connolly et al., J. Med. Chem., 2002, vol. 45, p. 1348); Surfactin (Kim et al., Biochem. Pharmacol., 1998, vol. 55, p. 975); 1,1,1-trifluorononadeca-10,13,16-trien-2-one and 1,1,1-trifluorononadeca-10,13-dien-2-one (Amandi-Burgermeister et al., Eur. J. Pharmacol., 1997, vol. 326, p. 237); and 2-oxoamide derivatives (Kokotos et al., J. Med. Chem., 2002, vol. 45, p. 2891).

In the present invention, preferred examples of type 4 $PLA_2$ inhibitor further include the compounds represented by the aforementioned formula (I) and pharmacologically acceptable salts thereof. Various combinations of the compounds represented by the formula (I) and pharmacologically acceptable salts thereof described in the specification can also be arbitrarily chosen.

When a medicament comprising a type 4 $PLA_2$ inhibitor as an active ingredient is used as a prophylactic and/or therapeutic agent for fibrosis, as for Compound (I) of the present invention, for example, Compound (I) of the present invention or a pharmaceutically acceptable salt thereof, per se, may be used in an effective amount, or the substance may be used after preparation of a pharmaceutical composition in the form of solid, liquid or gel by mixing the substance with a pharmaceutically acceptable carrier. As for the pharmaceutically acceptable carrier, known information and the information about carriers described in this specification can be referred to. As for known type 4 $PLA_2$ inhibitors, a known type 4 $PLA_2$ inhibitor or a pharmaceutically acceptable salt thereof, per se, may be used in an effective amount, or as mentioned above, the inhibitors may be used after preparation of a pharmaceutical composition by mixing the inhibitor with a pharmaceutically acceptable carrier.

It would be readily understood by those skilled in the art that progression-preventing agents, that is used for preventing progression of pathological conditions, occasionally fall within the scope of the agent for prophylactic and/or therapeutic treatment of the present invention.

Examples of the dosage form for preparation of the aforementioned pharmaceutical composition, tablet, powder, granule, syrup, suspension, capsule, inhalant, injection, and the like, and in order to prepare the compositions, various carriers are used depending on the type of the composition. Examples of the carrier for oral agents include, for example, excipients, binders, lubricants, flowability improvers, and colorants. When an inhalant is prepared (examples of administration method include a method of inhaling powder of the pharmaceutical composition or a solution obtained by dissolving or suspending the pharmaceutical composition in a solvent, per se, a method of inhaling mist of the composition prepared by using a sprayer called atomizer or nebulizer), the preparation the aforementioned pharmaceutical composition in the form of solid can be referred to for preparation of a powder for the inhalation, and a powder obtained is preferably further made into micropowder. When the composition is inhaled as a liquid, preferred examples of the preparation method include a method of dissolving a solid pharmaceutical composition, which is prepared by referring to the above explanation, in distilled water or a suitable solvent to obtain a solution of medicament upon use, and a method of preparing a liquid pharmaceutical composition prepared by referring the above explanation to obtain a solution of medicament. As for a size of the aforementioned powder or mist of a solution of a medicament to be inhaled, a particle size may be suitable for inhalation. For example, an upper limit is preferably 100 µm or less, further preferably 50 µm or less, most preferably 10 µm or less. A lower limit is not particularly limited, and a smaller particle size is more preferred. When an injection and the like are prepared, distilled water for injection, physiological saline, glucose solution, vegetable oil for injection, propylene glycol, polyethylene glycols and the like can generally be used as diluents. Further, antimicrobial agents, antiseptics, stabilizers, isotonic agents, soothing agents, and the like may be added, as required.

When the aforementioned prophylactic and/or therapeutic agent is administered, a suitable dosage form can be chosen and administered via a suitable route. For example, the agent can be orally administered in the form of a tablet, a powder, a granule, a syrup, a suspension, or a capsule. The agent can also be administered via transairway route in the form of an inhalant. Further, the agent can be administered subcutaneously, intradermally, intravascularly, intramuscularly or intraperitoneally in the form of injection including a drip infusion. Furthermore, the agent can be transmucosally administered in the form of a sublingual agent or a suppository, and can be transdermally administered in the form of a gel, a lotion, an ointment, a cream, or a spray.

A dose thereof varies depending on the dosage form, and the age, weight, degree of symptoms of a patient and the like. Examples of the dose include generally an administration at a dose of 1 to 1,000 mg per day for an adult once to three times a day. Every day administration for a period of several days to two months is commonly applied. The daily dose and the administration period may be increased or decreased depending on symptoms of a patient.

As for the application of the aforementioned prophylactic and/or therapeutic agent, the agent may be administered to patients with pulmonary fibrosis as explained above. In addition, the prophylactic and/or therapeutic agent of the present invention containing a type $PLA_2$ inhibitor as an active ingredient may preferably be administered after the administration of, most preferably immediately after the administration of an agent, which may possibly induces pulmonary fibrosis as an adverse reaction. Furthermore, as for the administration time, the prophylactic and/or therapeutic agent of the present invention may be administered simultaneously with an agent which may possibly induces pulmonary fibrosis as an adverse reaction, or the agent of the present invention may be administered beforehand.

EXAMPLES

The present invention will be further specifically explained with reference to examples. However, the scope of the present invention is not limited to the following examples. In the examples, for thin layer chromatography (TLC), Precoated Silica Gel 60 F254 (produced by Merck, product number: 5715-1M)) was used. After development with chloroform: methanol (1:0 to 1:1), acetonitrile:acetic acid:water (200:1:1 to 100:4:4) or ethyl acetate:hexane (1:0 to 0:1), spots were observed by UV irradiation (254 nm) or color development with ninhydrine or dinitrophenylhydrazine solution in hydrochloric acid. For drying organic solvent, anhydrous magnesium sulfate or anhydrous sodium sulfate was used. As for column chromatography, the indication of "Quad" means use of Quad 1 preparative chromatography system (produced by Biotage), and one or several columns selected from cartridge columns KP-Sil-12M, 40S and 40M produced by the same manufacturer were used depending on the amount of sample. For flash column chromatography, Silica gel 60N (spherical shape, neutral, 40 to 100 µm, produced by Kanto Chemicals) was used. Preparative thin layer chromatography (hereinafter abbreviated as "PTLC") was performed by using one or several plates of PLC Plate Silica Gel 60 F254 (20×20 cm, thickness: 2 mm, concentration zone: 4 cm, produced by Merck, product number: 13793-1M) were used depending on the amount of sample.

The indication of "LCMS" means that mass spectrum was measured by liquid chromatography-mass spectrometry (LC-MS). Platform-LC type mass spectrometry apparatus (produced by Micromass) was used as the mass spectrometer, and the measurement was performed by the electrospray ionization (ESI) method. As a liquid chromatography apparatus, an apparatus produced by GILSON was used. As a separation column, Mightysil RP-18 GP 50-4.6 (produced by Kanto Chemicals) was used. Elution was generally performed at a flow rate of 2 ml/minute, and Solution A=water [containing 0.1% (v/v) acetic acid] and Solution B=acetonitrile [containing 0.1% (v/v) acetic acid] were used as solvents.

In the tables mentioned below, data indicated by "LCMS" mean data of liquid chromatography-mass spectrometry spectra. In the columns of "Mass", data of mass spectrometry were shown (the indication "N.D" means that no molecular ion peak was detected). In the columns of "method", elution conditions of the liquid chromatography are described. In the columns of "RTime", retention times in the liquid chromatography are shown. For the indication of retention time in the liquid chromatography, the indication "A" for elution condition means that measurement was performed by elution with a linear gradient of 5 to 100% (v/v) Solution B from 0 minute to 5 minutes and then with 100% Solution B until 6 minutes.

Similarly, the indication "B" for elution condition means that measurement was performed by elution with 30% (v/v) Solution B from 0 minute to 0.5 minute, then with a linear gradient of 30 to 95% (v/v) Solution B from 0.5 minute to 4 minutes and then with 95% (v/v) Solution B until 6 minutes. For the compounds with the indication C in the columns of elution conditions, data of mass spectrometry measured by fast atomic bombardment mass spectrometry (FAB-MS) using JEOL-JMS-SX102 (produced by JEOL Co., Ltd.) were mentioned in the columns of "Mass". Further, for the compounds with the indication D in the elution conditions, an apparatus manufactured by Waters Ltd. was used as a liquid chromatography apparatus. As a column for separation, Develosil C$^{30}$-UG-5 (50×4.6 mm, Nomura Kagaku Co., Ltd.) was used. Measurement was performed under elution condition with a linear gradient of 5 to 98% (v/v) Solution B from 0 minute to 4 minutes and then with 100% Solution B until 6 minutes.

In the columns indicated as "Exp.", compound numbers are shown. When the tables include a column indicated as "position", substituting positions of substituents are indicated in the column. The abbreviations used in the tables have the following meanings.

n: normal, i: iso, s: secondary, t: tertiary, c: cyclo, D: di, Me: methyl, Et: ethyl, Pr: propyl, Bu: butyl, Pen: pentyl, Hex: hexyl, Hep: heptyl, Ph: phenyl, Bn: benzyl, Py: pyridyl, Indan: indanyl, Ac: acetyl, CHO: formyl, COOH: carboxyl, NO2: nitro, DMA: dimethylamino, NH2: amino, CF3: trifluoromethyl, F: fluoro, Cl: chloro, Br: bromo, OMe: methoxy, OH: hydroxy, TFA: trifluoroacetyl, SO2: sulfonyl, CO: carbonyl, Nap: naphthyl, Ind: 1H-indolyl, 1HIdz: 1H-indazolyl, 2HIdz: 2H-indazolyl, Bzt: benzothiazole, 2ABzt: 2-aminobenzothiazole, BF: benzofuranyl, BT: benzo[b]thienyl, Qu: Quinolyl, IQ: isoquinolyl The numbers given before the substituents indicate substituting positions. The numbers given with hyphens before abbreviations of aromatic rings indicate substituting positions of the aromatic rings. (S) indicates optically active substances with S-configuration, and (R) indicates optically active substances with R-configuration. Representative examples of the substituents shown in the tables with abbreviations are listed in Table 2 mentioned below.

TABLE 2

| Structure | abbreviation | Structure | abbreviation | Structure | abbreviation |
|---|---|---|---|---|---|
| (cyclopentylmethoxy) | cPenMeO | (cyclohexylmethoxy) | cHexMeO | (isobutoxy) | iBuO |
| (2-ethylbutoxy) | 2EtBuO | (2,3-dimethylbutoxy) | 2,3DMeBuO | (cyclopentyloxy) | cPenO |
| (cyclohexyloxy) | cHexO | (cycloheptyloxy) | cHepO | (benzyloxy) | BnO |
| (R)-1-phenylethoxy | (R)1PhEtO | (2-chlorobenzyloxy) | 2ClBnO | (4-fluorobenzyloxy) | 4FBnO |
| (2-indanyloxy) | 2-IndanO | 2-(4-fluorophenyl)ethoxy | 2(4FPh)EtO | 2-(4-dimethylaminophenyl)ethoxy | 2(4DMAPh)EtO |
| 2-(3-pyridyl)ethoxy | 2(3-Py)EtO | 2-(phenoxy)ethoxy | 2(PhO)EtO | 2-fluoro-4-methoxybenzyloxy | 2F,4(OMe)BnO |
| | | (2-naphthyl) | 2-Nap | (1-naphthyl) | 1-Nap |

TABLE 2-continued

| Structure | abbreviation | Structure | abbreviation | Structure | abbreviation |
|---|---|---|---|---|---|
| 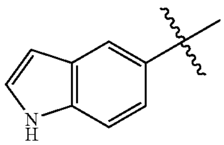 | 5-Ind | 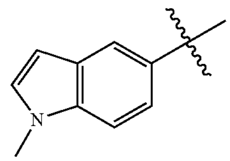 | 1Me-5-Ind | 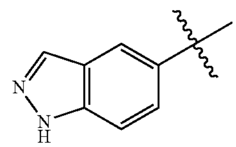 | 5-1HIdz |
| 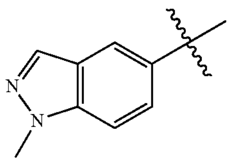 | 1Me-5-1HIdz | 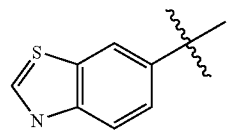 | 5-Bzt | 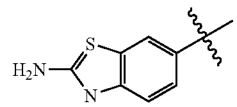 | 5-2ABzt |
| 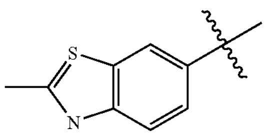 | 2Me-5-Bzt | 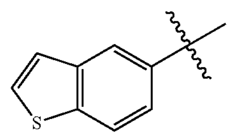 | 5-BT | 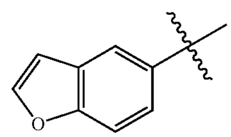 | 5-BF |
| 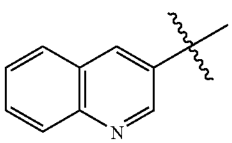 | 3-Qu | 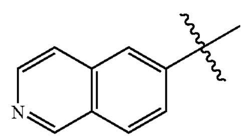 | 6-IQ | | |

The manufacturers of the regents used may sometimes be indicated with the following abbreviations.

TCI: Tokyo Kasei Kogyo Co., Ltd., Ald: Aldrich Co., KANTO: Kanto Kagaku, WAKO: Wako Pure Chemical Industries, Ltd., LANC: Lancaster Synthesis, MAYB: Maybridge, plc.

Example A-1

Synthesis of methyl 3-(4-hydroxyphenyl)propionate (Intermediate 1)

A solution obtained beforehand by adding thionyl chloride (18.3 ml, WAKO) dropwise to methanol (250 ml) and mixing the mixture under ice cooling was added dropwise with a solution of 3-(4-hydroxyphenyl)propionic acid (16.6 g, TCI) in methanol (50 ml) under ice cooling, stirred for 30 minutes, warmed to room temperature, and further stirred for 1.5 hours. The reaction mixture was concentrated under reduced pressure, and then extracted with diethyl ether (200 ml). The organic layer was washed successively with saturated aqueous sodium hydrogencarbonate, saturated aqueous ammonium chloride and saturated brine. The organic layer was dried, and then the solvent was evaporated under reduced pressure to obtain the title compound (Intermediate 1, 17.95 g).

Synthesis of methyl 3-(4-cyclopentylmethyloxyphenyl)propionate (Intermediate 2)

A solution of cyclopentane methanol (4.05 ml, Ald) in anhydrous tetrahydrofuran (abbreviated as "THF" hereinafter, 40 ml) was added with triethylamine (6.49 ml, WAKO), added dropwise with methanesulfonyl chloride (3.48 ml, WAKO) under ice cooling, and stirred for 30 minutes. The reaction mixture was added with water (50 ml), and extracted with diethyl ether (80 ml×2). The organic layer was washed with saturated brine and dried, and then the solvent was evaporated under reduced pressure. A solution obtained beforehand by adding 60% sodium hydride (1.15 g, KANTO) to a solution of Intermediate 1 (4.50 g) in N,N-dimethylformamide (abbreviated as "DMF" hereinafter, 35 ml) under ice cooling and stirring the solution for 15 minutes was added with a solution of the aforementioned residue in DMF (10 ml) under ice cooling. The reaction mixture was stirred for 15 minutes, then warmed to room temperature, stirred for 45 minutes, and further stirred at 60° C. for 15 hours. The reaction mixture was added with water (100 ml) and diethyl ether (200 ml) for extraction. The organic layer was successively washed with saturated aqueous sodium hydrogencarbonate, saturated aqueous ammonium chloride, and saturated brine and dried, and then the solvent was evaporated under reduced pressure. The residue was purified by flash column chromatography (hexane:isopropyl ether=9:1) to obtain the title compound (Intermediate 2, 5.58 g).

Synthesis of methyl 3-(3-bromo-4-cyclopentylmethyloxyphenyl)propionate (Compound No. A-1)

A solution of Intermediate 2 (1.31 g) in acetonitrile (50 ml) was added with N-bromosuccinimide (hereinafter abbreviated as "NBS", 979 mg, KANTO), stirred at room temperature for 2 hours, then warmed to 40° C., and stirred for 3 hours. The reaction mixture was concentrated under reduced pressure, then added with ethyl acetate (200 ml) and washed successively with saturated aqueous ammonium chloride, 5% aqueous sodium sulfite, saturated aqueous sodium hydrogencarbonate and saturated brine. The organic layer was dried, and then the solvent was evaporated under reduced pressure to obtain the title compound (Compound No. A-1, 1.69 g).

Example A-2

Synthesis of 3-(3-bromo-4-methoxyphenyl)propionic acid (Intermediate 3)

According to the procedure described in the synthesis method of Compound No. A-1 provided that the reaction was carried out under ice cooling for 30 minutes and at room temperature for 3 hours, 3-(4-methoxyphenyl)propionic acid (27.0 g, TCI) and NBS (29.4 g) were reacted and treated to obtain the title compound (Intermediate 3, 38.1 g).

Synthesis of 3-(3-bromo-4-hydroxyphenyl)propionic acid (Intermediate 4)

According to a procedure described in a literature (Carreno, M. C., J. Org. Chem., 1995, vol. 60, p. 5328), a 1 M solution of boron tribromide in methylene chloride (200 ml, Fluka) was added dropwise with a solution of Intermediate 4 (23.5 g) in methylene chloride (200 ml) at −78° C., warmed to room temperature after 30 minutes, and further stirred for 1.5 hours. The reaction mixture was poured into ice water (750 ml), and stirred at room temperature for 1 hour. The reaction mixture was added with diethyl ether (750 ml)) for extraction. The organic layer was added with 2 N aqueous sodium hydroxide (250 ml×2) for extraction, and then the aqueous layer was made acidic with 5 N aqueous hydrochloric acid under ice cooling, and extracted with diethyl ether (375 ml×2) again. The organic layer was washed with saturated brine and dried, and then the solvent was evaporated under reduced pressure. The organic layer was washed with saturated brine and dried, and then the solvent was evaporated under reduced pressure to obtain the title compound (Intermediate 4, 23.5 g).

Synthesis of methyl 3-(3-bromo-4-hydroxyphenyl)propionate (Intermediate 5)

According to the procedure described in the synthesis method of Intermediate 1 provided that the purification was performed by flash column chromatography (hexane:ethyl acetate=4:1), Intermediate 4 (21.15 g) and thionyl chloride (15.0 ml) were reacted and treated in methanol to obtain the title compound (Intermediate 5, 20.36 g).

Synthesis of methyl (3-bromo-4-cyclohexylmethyloxyphenyl)propionate (Compound No. A-2)

A solution of Intermediate 5 (1.29 g) in DMF (25 ml) was added with potassium carbonate (0.86 g) and bromomethylcyclohexane (1.05 ml, TCI), stirred under argon atmosphere at room temperature for 2 hours, then warmed to 60° C., and stirred for 17 hours. The reaction mixture was poured into ice water, and extracted with isopropyl ether (200 ml). The organic layer was successively washed with saturated aqueous sodium hydrogencarbonate, saturated aqueous ammonium chloride, and saturated brine and dried, and then the solvent was evaporated under reduced pressure. The residue was purified by flash column chromatography (hexane:isopropyl ether=9:1) to obtain the title compound (Compound No. A-2, 1.45 g).

Example A-5

Synthesis of methyl 3-(3-bromo-4-cyclopentyloxyphenyl)propionate (Compound No. A-5)

A solution of Intermediate 5 (4.50 g) in DMF (20 ml) was added with 60% sodium hydride (440 mg, KANTO) under ice cooling. The reaction mixture was stirred for 10 minutes, then added with bromocyclopentane (1.61 ml, TCI), warmed to room temperature, stirred for 1.5 hours, then warmed to 60° C., and further stirred for 16 hours. The reaction mixture was added with water (50 ml) and isopropyl ether (300 ml)) for extraction. The organic layer was successively washed with saturated aqueous sodium hydrogencarbonate, saturated aqueous ammonium chloride, and saturated brine and dried, and then the solvent was evaporated under reduced pressure. The residue was purified by flash column chromatography (hexane:isopropyl ether=7:1) to obtain the title compound (Compound No. A-5, 2.50 g).

Example A-6

Synthesis of methyl 3-(3-bromo-4-cyclohexyloxyphenyl)propionate (Compound No. A-6)

A solution of Intermediate 5 (2.06 g), triphenylphosphine (hereinafter abbreviated as "$Ph_3P$", 6.28 g, WAKO) and cyclohexanol (2.53 ml, WAKO) in anhydrous THF (60 ml) was added dropwise with a 40% solution of diisopropylazodicarboxylic acid ester in toluene (hereinafter abbreviated as "40% DIAD", 11.35 ml, WAKO) under ice cooling over 10 minutes. The reaction mixture was stirred for 10 minutes, then warmed to room temperature, and stirred for 18.5 hours. The reaction mixture was added with water (50 ml) and ethyl acetate (200 ml)) for extraction. The organic layer was successively washed with saturated aqueous sodium hydrogencarbonate, saturated aqueous ammonium chloride and saturated brine and dried, and then the solvent was evaporated under reduced pressure. The residue was purified by column chromatography (Quad, hexane:isopropyl ether=8:1) to obtain the title compound (Compound No. A-6, 2.35 g).

Example A-20

Synthesis of methyl 3-(3-bromo-5-chloro-4-hydroxyphenyl)propionate (Intermediate 6)

A solution of Intermediate 5 (516 mg) in chloroform (5 ml) was added with sulfuryl chloride (177 μl), and stirred at room temperature for 21 hours. The reaction mixture was poured into aqueous saturated sodium hydrogencarbonate (20 ml), and extracted with ethyl acetate. The organic layer was successively washed with saturated aqueous sodium hydrogencarbonate, saturated aqueous ammonium chloride, and saturated brine and dried, and then the solvent was evaporated under reduced pressure. The residue was purified by column chromatography (Quad, hexane:ethyl acetate=10:1) to obtain the title compound (Intermediate 6, 290 mg).

Synthesis of methyl 3-(3-bromo-5-chloro-4-cyclopentylmethyloxyphenyl)propionate (Compound No. A-20)

According to the procedure described in the synthesis method of Compound No. A-6 provided that the purification was performed by column chromatography (Quad, hexane:ethyl acetate=30:1), Intermediate 6 (278 mg), Ph$_3$P (747 mg), cyclopentane methanol (308 µl), and 40% DIAD (1.34 ml) were reacted and treated to obtain the title compound (Compound No. A-20, 337 mg).

Example A-21

Synthesis of ethyl 3-(3-fluoro-4-methyloxyphenyl)acrylate (Intermediate 7)

A solution of 3-fluoro-4-methoxybenzaldehyde (2.20 g, Ald) in 1,2-diethoxyethane (5 ml) was added with ethyl diethylphosphonoacetate (3.12 ml, TCI) and added with 60% sodium hydride (624 mg) under ice cooling. After being stirred for 10 minutes, the reaction mixture was warmed to room temperature, and stirred for 5 hours. The reaction mixture was added with ethyl acetate (90 ml), and washed successively with saturated aqueous sodium hydrogencarbonate, saturated aqueous ammonium chloride and saturated brine. The organic layer was dried, and then the solvent was evaporated under reduced pressure. The residue was purified by flash column chromatography (Quad, hexane:ethyl acetate=10:1) to obtain the title compound (Intermediate 7, 3.16 g).

Synthesis of ethyl 3-(3-fluoro-4-methoxyphenyl)propionate (Intermediate 8)

A solution of Intermediate 7 (3.01 g) in ethyl acetate (50 ml) and methanol (25 ml) was added with 10% palladium/carbon (300 mg, Merck), and stirred at room temperature for 2 hours under hydrogen atmosphere. The reaction mixture was filtered, and the solvent of the filtrate was evaporated under reduced pressure to obtain the title compound (Intermediate 8, 3.02 g).

Synthesis of 3-(3-fluoro-4-methoxyphenyl)propionic acid (Intermediate 9)

A solution of Intermediate 8 (2.97 g) in methanol (40.0 ml) was added with 2 N aqueous sodium hydroxide (15.0 ml) and stirred at 60° C. for 16 hours. The reaction mixture was concentrated under reduced pressure, then made acidic with aqueous 5% hydrochloric acid under ice cooling, and extracted with ethyl acetate (200 ml). The organic layer was washed with saturated brine and dried, and then the solvent was evaporated under reduced pressure to obtain the title compound (Intermediate 9, 2.40 g).

Synthesis of 3-(3-fluoro-4-hydroxyphenyl)propionic acid (Intermediate 10)

A pyridine/hydrochloric acid complex prepared by mixing pyridine (30 ml) and concentrated hydrochloric acid (30 ml) and heating the mixture at 190° C. for 1 hour was added with Intermediate 9 (2.40 g) and stirred at 190° C. for 1.5 hours. The reaction mixture was poured into 1 N hydrochloric acid (100 ml) cooled with ice, and extracted with ethyl acetate (200 ml). The organic layer was washed with saturated brine and dried, and then the solvent was evaporated under reduced pressure to obtain the title compound (Intermediate 10, 1.98 g).

Synthesis of methyl 3-(3-fluoro-4-hydroxyphenyl)propionate (Intermediate 11)

According to the procedure described in the synthesis method of Intermediate 1, Intermediate 10 (1.77 g) and thionyl chloride (1.65 ml) were reacted and treated in methanol to obtain the title compound (Intermediate 11, 1.85 g).

Synthesis of methyl 3-(3-bromo-5-fluoro-4-hydroxyphenyl)propionate (Intermediate 12)

According to the procedure described in the synthesis method of Compound No. A-1 with the modifications that the reaction was carried out for 2 hours under ice cooling, and the purification was performed by column chromatography (Quad, hexane:ethyl acetate=10:1), Intermediate 11 (1.84 g) and NBS (1.74 g) were reacted and treated to obtain the title compound (Intermediate 12, 1.74 g).

Synthesis of methyl 3-(3-bromo-4-cyclopentylmethyloxy-5-fluorophenyl)propionate (Compound No. A-21)

According to the procedure described in the synthesis method of Compound No. A-6 with the modifications that the reaction was carried out for 22 hours, and the purification was performed by column chromatography (Quad, hexane:ethyl acetate=50:1), Intermediate 11 (310 mg), tributylphosphine (hereinafter abbreviated as "$^n$Bu$_3$P", 405 µl, WAKO) instead of Ph$_3$P, cyclopentane methanol 176 µl), and N,N,N',N'-tetramethylazodicarboxamide (hereinafter abbreviated as "TMAD", 279 mg, TCI) instead of 40% DIAD were reacted and treated to obtain the title compound (Compound No. A-21, 386 mg).

Example A-24

Synthesis of 4-cyclopentyloxy-3-methylbenzaldehyde (Intermediate 13)

According to the procedure described in the synthesis method of Compound No. A-2 with the modifications that the reaction was carried out for 16 hours, and the purification was performed by column chromatography (Quad, hexane:ethyl acetate=9:1), 4-hydroxy-3-methylbenzaldehyde (283 mg, TCI), potassium carbonate (578 mg) and bromocyclopentane (430 µl) were reacted and treated to obtain the title compound (Intermediate 13, 350 mg).

Synthesis of ethyl 3-(4-cyclopentyl-3-methylphenyl)acrylate (Intermediate 14)

According to the procedure described in the synthesis method of Intermediate 7 with the modifications that the reaction was carried out for 2 hours, and the purification was performed by column chromatography (Quad, hexane:ethyl acetate=9:1), Intermediate 13 (342 mg), ethyl diethylphosphonoacetate (408 μl) and 60% sodium hydride (82 mg) were reacted and treated to obtain the title compound (Intermediate 14, 450 mg).

Synthesis of ethyl
3-(4-cyclopentyl-3-methylphenyl)propionate
(Intermediate 15)

According to the procedure described in the synthesis method of Intermediate 8, Intermediate 14 (446 mg) and 10% palladium/carbon (20 mg) were reacted and treated under hydrogen gas atmosphere to obtain the title compound (Intermediate 15, 439 mg).

Synthesis of ethyl 3-(3-bromo-4-cyclopentyl-5-methylphenyl)propionate (Compound No. A-24)

According to the procedure described in the synthesis method of Compound No. A-1, Intermediate 15 (437 mg) and NBS (320 mg) were reacted and treated to obtain the title compound (Compound No. A-24, 545 mg).

Example A-25

Synthesis of 3-bromo-4-(t-butyldimethylsilyloxy)-5-methoxybenzaldehyde (Intermediate 16)

A solution of 3-bromovanillin (1.16 g, TCI) in anhydrous DMF (20 ml) was added with imidazole (408 mg, TCI), added dropwise with a solution of 4-(N,N-dimethylamino)pyridine (25 mg) and t-butyldimethylsilyl chloride (904 mg, TCI) in DMF (15 ml) under ice cooling, stirred 30 minutes, then warmed to room temperature, and further stirred 3 hours. The reaction mixture was added with water (100 ml), and extracted with ethyl acetate (100 ml). The organic layer was washed with saturated brine and dried, and then the solvent was evaporated under reduced pressure. The residue was purified by flash column chromatography (hexane:ethyl acetate=9:1) to obtain the title compound (Intermediate 16, 1.75 g).

Synthesis of ethyl 3-[3-bromo-4-(t-butyldimethylsilyloxy)-5-methoxyphenyl]acrylate (Intermediate 17)

According to the procedure described in the synthesis method of Intermediate 7 with the modifications that the reaction was carried out for 1.5 hours, and the purification was performed by flash column chromatography (hexane:ethyl acetate=9:1), Intermediate 16 (910 mg), ethyl diethylphosphonoacetate (530 μl) and 60% sodium hydride (120 mg) were reacted and treated to obtain the title compound (Intermediate 17, 937 mg).

Synthesis of ethyl 3-[3-bromo-4-(t-butyldimethylsilyloxy)-5-methoxyphenyl]propionate (Intermediate 18)

According to the procedure described in the synthesis method of Intermediate 8, Intermediate 17 (945 mg) and 10% palladium/carbon (95 mg) were reacted and treated under hydrogen gas atmosphere to obtain the title compound (Intermediate 18, 760 mg).

Synthesis of ethyl
3-(3-bromo-4-hydroxy-5-methoxyphenyl)propionate
(Intermediate 19)

A solution of Intermediate 18 (750 mg) in THF (50 ml) was added with a 1 M solution of tetrabutylammonium fluoride in THF (5 ml, TCI), and stirred for 1.5 hours. The reaction mixture was added with saturated aqueous sodium hydrogencarbonate (30 ml), and extracted with ethyl acetate (50 ml). The organic layer was washed with saturated brine and dried, and then the solvent was evaporated under reduced pressure. The residue was purified by flash column chromatography (hexane:ethyl acetate=4:1) to obtain the title compound (Intermediate 19, 542 mg).

Synthesis of ethyl 3-(3-bromo-4-cyclopentyloxy-5-methoxyphenyl)propionate (Compound No. A-25)

According to the procedure described in the synthesis method of Compound No. A-6 with the modifications that the reaction was carried out for 16 hours, and the purification was performed by column chromatography (Quad, hexane:ethyl acetate=7:1), Intermediate 19 (400 mg), Ph$_3$P (1.31 g), cyclopentanol (450 μl), and TMAD (860 mg) were reacted and treated to obtain the title compound (Compound No. A-25, 376 mg).

Example A-26

Synthesis of methyl 3-(3-bromo-4-cyclopentylmethyloxy-5-nitrophenyl)propionate (Compound No. A-26)

A solution obtained beforehand by adding 70% nitric acid (3.9 ml) to acetic anhydride (30 ml) under ice cooling and stirring the mixture for 10 minutes was added with a solution of Compound No. A-1 (5.12 g) in acetonitrile (25 ml) at −15° C. over 15 minutes, and stirred further for 15 minutes. The reaction mixture was poured into 1 N aqueous sodium hydroxide (500 ml) containing ice, and extracted with diethyl ether (300 ml×2). The organic layer was successively washed with saturated aqueous sodium hydrogencarbonate, saturated aqueous ammonium chloride, and saturated brine and dried, and then the solvent was evaporated under reduced pressure. The residue was purified by column chromatography (Quad, hexane:ethyl acetate=10:1) to obtain the title compound (Compound No. A-26, 3.68 g).

Example A-31

Synthesis of methyl
3-(3-bromo-4-phenoxyphenyl)propionate
(Compound No. A-31)

A solution of Intermediate 5 (3.08 g) in anhydrous N-methylpyrrolidone (9.5 ml, WAKO) was successively added with cesium carbonate (3.58 g, WAKO), iodobenzene (1.4 ml, TCI), dipivaloylmethane (0.12 ml, TCI) and copper(I) chloride (275 mg, WAKO), and stirred 120° C. for 16 hours under argon gas atmosphere. The reaction mixture was added with t-butyl methyl ether (25 ml), and insoluble solids were removed by filtration. The filtrate was washed successively with 2 N aqueous hydrochloric acid and saturated brine and dried, and then the solvent was evaporated under reduced pressure. The residue was purified by flash column chromatography (hexane:ethyl acetate=1:10) to obtain the title compound (Compound No. A-31, 1.00 g).

Example B-96

Synthesis of methyl 3-(3-bromo-4-methoxyphenyl)propionate (Intermediate 20)

According to the procedure described in the synthesis method of Intermediate 1 provided that the purification was performed by flash column chromatography (hexane:ethyl acetate=6:1), Intermediate 3 (1.60 g) and thionyl chloride (1.44 ml) were reacted and treated in methanol to obtain the title compound (Intermediate 20, 1.63 g).

Synthesis of methyl 3-(3-bromo-4-methoxy-5-nitrophenyl)propionate (Intermediate 21)

A solution of Intermediate 20 (3.20 g) in acetic anhydride (25 ml) was added with potassium nitrate (1.30 g) under ice cooling and stirred for 10 minutes, and the solution was added dropwise with concentrated sulfuric acid (730 μl) over 10 minutes. The reaction mixture was stirred for 10 minutes for 10 minutes at the same temperature, then warmed to room temperature, and further stirred for 30 minutes. The reaction mixture was poured into 1 N aqueous sodium hydroxide (250 ml) containing ice, and extracted with isopropyl ether (200 ml×2). The organic layer was successively washed with saturated aqueous sodium hydrogencarbonate, saturated aqueous ammonium chloride, and saturated brine and dried, and then the solvent was evaporated under reduced pressure. The residue was purified by column chromatography (Quad, hexane:ethyl acetate=10:1) to obtain the title compound (Intermediate 21, 2.73 g).

Synthesis of 3-(3-bromo-4-methoxy-5-nitrophenyl)propionic acid (Intermediate 22)

According to the procedure described in the synthesis method of Intermediate 9 provided that the reaction was carried out for 1 hour, Intermediate 21 (12.73 g) and 2 N aqueous sodium hydroxide (40 ml) were reacted and treated to obtain the title compound (Intermediate 22, 11.53 g).

Synthesis of 3-(3-bromo-4-hydroxy-5-nitrophenyl)propionic acid (Intermediate 23)

According to the procedure described in the synthesis method of Intermediate 4 provided that the reaction was carried out for 2 hours, Intermediate 22 (11.53 g) and a 1 M solution of boron tribromide in methylene chloride (100 ml) were reacted and treated to obtain the title compound (Intermediate 23, 10.68 g).

Synthesis of methyl 3-(3-bromo-4-hydroxy-5-nitrophenyl)propionate (Intermediate 24)

According to the procedure described in the synthesis method of Intermediate 1 provided that the reaction was carried out for 17.5 hours, Intermediate 23 (10.68 g) and thionyl chloride (8.06 ml) were reacted and treated to obtain the title compound (Intermediate 24, 8.27 g).

Synthesis of methyl 3-[3-bromo-4-(indan-2-yloxy)-5-nitrophenyl]propionate (Compound No. B-96)

According to the procedure described in the synthesis method of Compound No. A-6 with the modifications that the reaction was carried out for 15 hours, and the purification was performed by column chromatography (Quad, hexane:ethyl acetate=19:1), Intermediate 24 (151 mg), Ph$_3$P (260 mg), 2-hydroxyindane (133 mg, TCI) and 40% DIAD (470 μl) were reacted and treated to obtain the title compound (Compound No. B-96, 192 mg).

Example B-99

Synthesis of methyl 3-(3-amino-5-bromo-4-cyclopentyloxyphenyl)propionate (Compound No. B-99)

A solution of Compound No. A-28 (416 mg) in a mixture of THF (5 ml) and methanol (5 ml) was added with Raney 2800 nickel (230 mg, Ald) and stirred at room temperature for 6 hours under hydrogen atmosphere. The reaction mixture was filtered, and the solvent of the filtrate was evaporated under reduced pressure. The residue was purified by column chromatography (Quad, hexane:ethyl acetate=5:2) to obtain the title compound (Compound No. B-99, 143 mg).

Example B-103

Synthesis of methyl 3-[4-benzyloxy-5-bromo-3-(2,2,2-trifluoroacetylamino)phenyl]propionate (Compound No. B-103)

A solution of Compound No. B-100 (58.7 mg) in methylene chloride (2 ml) was added with triethylamine (76 μl), added dropwise trifluoroacetic anhydride (91 μl, TCI) under ice cooling, stirred for 30 minutes, then warmed to room temperature, and further stirred for 2 hours. The reaction mixture was added with water (5 ml), and extracted with methylene chloride (20 ml). The organic layer was washed with saturated brine and dried, and then the solvent was evaporated under reduced pressure. The residue was purified by column chromatography (Quad, hexane:ethyl acetate=3:1) to obtain the title compound (Compound No. B-103, 59.1 mg).

Example B-105

Synthesis of methyl 3-[4-benzyloxy-5-bromo-3-(N-methylamino)phenyl]propionate (Compound No. B-105)

A solution of Compound No. B-100 (105 mg) in DMF (3 ml) was added with 60% sodium hydride (20 mg) under ice cooling, and stirred for 10 minutes. This reaction mixture was added dropwise with methyl iodide (32 μl), stirred for 10 minutes, then warmed to room temperature, and further stirred for 2 hours. The reaction mixture was poured into water, and added with ethyl acetate (30 ml) for extraction. The organic layer was successively washed with saturated aqueous sodium hydrogencarbonate, saturated aqueous ammonium chloride, and saturated brine and dried, and then the solvent was evaporated under reduced pressure. The residue was purified by column chromatography (Quad, hexane:ethyl acetate=6:1) to obtain the title compound (Compound No. B-105, 17 mg).

Example B-109

Synthesis of 3-[4-benzyloxy-5-bromo-3-(N,N-dimethylamino)phenyl]propionic acid (Compound No. B-109)

A solution of Compound No. B-100 (105 mg) in DMF (3 ml) was added with 60% sodium hydride (40 mg) under ice cooling, and stirred for 10 minutes. This reaction mixture was added dropwise with methyl iodide (300 µl), stirred for 10 minutes, then warmed to room temperature, and further stirred for 16 hours. The reaction mixture was poured into water, and added with ethyl acetate (30 ml) for extraction. The organic layer was successively washed with saturated aqueous sodium hydrogencarbonate, saturated aqueous ammonium chloride, and saturated brine and dried, and then the solvent was evaporated under reduced pressure. The residue was purified by column chromatography (Quad, hexane:ethyl acetate=6:1) to obtain the title compound (Compound No. B-109, 88 mg).

Examples B-113 and B-114

Syntheses of 3-(3-bromo-4-cyclopentyloxy-5-hydroxyphenyl)propionic acid (Compound No. B-113) and 3-(5-acetoxy-3-bromo-4-cyclopentyloxyphenyl)propionic acid (Compound No. B-114)

A solution of Compound No. B-99 (415 mg) in acetic acid (1.5 ml) was added with 20% sulfuric acid (1.0 ml). This reaction mixture was added dropwise with an aqueous solution (0.5 ml) of sodium nitrite (78 mg) over 10 minutes, while the temperature of the reaction mixture was maintained below 10° C., and further stirred for 5 minutes. This reaction mixture was added dropwise to a solution of sodium acetate (348 mg) in acetic acid (3.5 ml) heated and stirred at 100° C. beforehand over 5 minutes, and further stirred for 10 minutes with heating. The reaction solution was poured into ice water (50 ml), and extracted with isopropyl ether (100 ml×2). The organic layer was successively washed with saturated aqueous sodium hydrogencarbonate, saturated aqueous ammonium chloride and saturated brine and dried, and then the solvent was evaporated under reduced pressure. The residue was purified by column chromatography (Quad, hexane:ethyl acetate=10:1) to obtain the title compounds (Compound No. B-113, 47 mg and Compound No. B-114, 105 mg).

Example B-117

Synthesis of methyl 3-(3,5-dibromo-4-cyclopentylmethyloxyphenyl)propionate (Compound No. B-117)

A solution of Intermediate 1 (670 mg) in acetonitrile (30 ml) was added with NBS (990 mg), stirred at room temperature for 2 hours, then warmed to 40° C., and stirred for 18 hours. The reaction mixture was concentrated under reduced pressure, then added with ethyl acetate (100 ml), and washed successively with saturated aqueous ammonium chloride, 5% aqueous sodium sulfite, saturated aqueous sodium hydrogencarbonate and saturated brine. The organic layer was dried, and then the solvent was evaporated under reduced pressure. According to the procedure described in the synthesis method of Compound No. A-6 with the modifications that the reaction was carried out for 18 hours under ice cooling, and the purification was performed by column chromatography (Quad, hexane:ethyl acetate=10:1), the residue was reacted with $Ph_3P$ (1460 mg), cyclopentane methanol (560 mg) and 40% DIAD (2.6 ml) and treated to obtain the title compound (Compound No. B-117, 710 mg).

Examples A-1 to A-33

Typical examples of the compounds of the present invention that can be obtained by reacting and treating corresponding starting compounds using any of the methods described in the present specification including the examples described above are shown in Table-A-1. The compounds were prepared according to the preparation methods of the compound numbers (e.g., "A-1") or the intermediate numbers (e.g., "Int 2") shown in the columns of "Syn" in the tables. "Int" means an intermediate compound number. When the preparation required a plurality of steps, a plurality of compound numbers or intermediate compound numbers are mentioned in the columns of "Syn". For example, an indication of "Int 2, A-1" in a column of "Syn" means that "the compound is prepared from a compound prepared according to the procedure described in the synthesis method of Intermediate 2 according to the procedure described in the synthesis method of Compound No. A-1." When the compounds were synthesized according to the procedure described in the synthesis method of Compound No. A-6, TMAD or di-t-butyl azodicarboxylate (hereinafter abbreviated as "DBAB") was sometimes used instead of 40% DIAD.

TABLE A-1

| Exp. | Rx'O | Y' | Zx' | G | Syn | LCMS method | RTime | Mass |
|---|---|---|---|---|---|---|---|---|
| A-1 | cPenMeO | Me | H | Br | A-1 | C | | 341 (M$^+$ + 1) |
| A-2 | cHexMeO | Me | H | Br | A-2 | C | | 354 (M$^+$) |
| A-3 | iBuO | Me | H | Br | A-2 | A | 5.34 | N.D |
| A-4 | 2EtBuO | Me | H | Br | A-2 | | | |
| A-5 | cPenO | Me | H | Br | A-5 | C | | 326 (M$^+$) |
| A-6 | cHexO | Me | H | Br | A-6 | C | | 340 (M$^+$) |
| A-7 | cHepO | Me | H | Br | A-6 | | | |
| A-8 | BnO | Me | H | Br | A-2 | | | |
| A-9 | 1PhEtO | Me | H | Br | A-2 | | | |

TABLE A-1-continued

[Structure: Rx'—O—(phenyl with Zx' and G substituents)—CH2—C(=O)—O—Y']

| Exp. | Rx'O | Y' | Zx' | G | Syn | LCMS method | RTime | Mass |
|---|---|---|---|---|---|---|---|---|
| A-10 | 2FBnO | Me | H | Br | A-2 | | | |
| A-11 | 4FBnO | Me | H | Br | A-2 | | | |
| A-12 | 2ClBnO | Me | H | Br | A-2 | | | |
| A-13 | 4ClBnO | Me | H | Br | A-2 | A | 4.85 | N.D |
| A-14 | 4MeBnO | Me | H | Br | A-2 | | | |
| A-15 | 4CF3BnO | Me | H | Br | A-2 | | | |
| A-16 | 2(4DMAPh)EtO | Me | H | Br | A-6 | | | |
| A-17 | 2(PhO)EtO | Me | H | Br | A-6 | A | 5.04 | N.D |
| A-18 | 1(2FPh)EtO | Me | H | Br | A-6 | | | |
| A-19 | 1(4ClPh)EtO | Me | H | Br | A-6 | A | 4.82 | N.D |
| A-20 | cPenMeO | Me | Cl | Br | A-20 | C | | 375 (M$^+$ + 1) |
| A-21 | cPenMeO | Me | F | Br | A-21 | | | |
| A-22 | cPenO | Me | F | Br | A-21 | C | | 345 (M$^+$ + 1) |
| A-23 | cHexO | Me | F | Br | A-21 | | | |
| A-24 | cPenO | Et | Me | Br | A-24 | A | 5.82 | N.D |
| A-25 | cPenO | Et | OMe | Br | A-25 | | | |
| A-26 | cPenMeO | Me | NO2 | Br | A-26 | C | | 340 (M$^+$ + 1) |
| A-27 | cHexMeO | Me | NO2 | Br | A-26 | | | |
| A-28 | cPenO | Me | NO2 | Br | A-26 | C | | 372 (M$^+$ + 1) |
| A-29 | cHexO | Me | NO2 | Br | A-26 | | | |
| A-30 | 2-IndanO | Me | NO2 | Br | A-26 | A | 5.03 | N.D |
| A-31 | PhO | Me | H | Br | A-31 | A | 5.15 | N.D |
| A-32 | 4ClPhO | Me | H | Br | A-31 | A | 5.47 | N.D |
| A-33 | 4MeOPhO | Me | H | Br | A-31 | A | 5.02 | N.D |

Examples B-1 to B-119

Typical examples of the compounds of the present invention that can be obtained by reacting and treating corresponding starting compounds using any of the methods described in the present specification including the examples described above are shown in Table-B-1 to Table B-3.

TABLE B-1

[Structure: Rx'—O—(phenyl with Zx' and G substituents)—CH2—CH2—C(=O)—O—Y']

| Exp. | Rx'O | Y' | Zx' | G | Syn | LCMS method | RTime | Mass |
|---|---|---|---|---|---|---|---|---|
| B-1 | nPrO | Me | H | Br | A-2 | C | | 279 (M$^+$) |
| B-2 | iPrO | Me | H | Br | A-2 | | | |
| B-3 | sBuO | Me | H | Br | A-6 | | | |
| B-4 | iPenO | Me | H | Br | A-6 | | | |
| B-5 | 1,3DMeBuO | Me | H | Br | A-6 | | | |
| B-6 | 2MeBuO | Me | H | Br | A-6 | | | |
| B-7 | (3-methylbut-2-en-1-yl)O | Me | H | Br | A-6 | | | |

TABLE B-1-continued

| Exp. | Rx'O | Y' | Zx' | G | Syn | LCMS method | RTime | Mass |
|---|---|---|---|---|---|---|---|---|
| B-8 | (3,3-dimethylbutyl-O) | Me | H | Br | A-6 | | | |
| B-9 | 2,3DMeBuO | Me | H | Br | A-6 | | | |
| B-10 | cPenO | Me | H | Cl | A-6 | C | | 361 (M⁺ + 1) |
| B-11 | trans2Me,cPenO | Me | H | Br | A-6 | | | |
| B-12 | 3Me,cPenO | Me | H | Br | A-6 | | | |
| B-13 | trans2Me,cHexO | Me | H | Br | A-6 | | | |
| B-14 | cis2Me,cHexO | Me | H | Br | A-6 | | | |
| B-15 | 3Me,cHexO | Me | H | Br | A-6 | C | | 354 (M⁺ + 1) |
| B-16 | 4Me,cHexO | Me | H | Br | A-6 | | | |
| B-17 | 2,3DMe,cHexO | Me | H | Br | A-6 | | | |
| B-18 | 3,4DMe,cHexO | Me | H | Br | A-6 | C | | 368 (M⁺ + 1) |
| B-19 | 3,5DMe,cHexO | Me | H | Br | A-6 | | | |
| B-20 | (3,3,5-trimethylcyclohexyl-O) | Me | H | Br | A-6 | | | |
| B-21 | (menthyl-O) | Me | H | Br | A-6 | | | |
| B-22 | (norbornyl-CH2-O) | Me | H | Br | A-6 | | | |
| B-23 | 1PhPrO | Me | H | Br | A-6 | | | |
| B-24 | (S)1PhPrO | Me | H | Br | A-6 | | | |
| B-25 | BenzhydrylO | Me | H | Br | A-6 | | | |
| B-26 | (1-phenyl-2-methylpropyl-O) | Me | H | Br | A-6 | C | | 391 (M⁺ + 1) |
| B-27 | (1-(4-methoxy-3-fluorophenyl)ethyl-O) | Me | H | Br | A-6 | | | |
| B-28 | 2Ph,1MeEtO | Me | H | Br | A-6 | | | |
| B-29 | 2Ph,2MeEtO | Me | H | Br | A-6 | | | |
| B-30 | 2(2FPh),1MeEtO | Me | H | Br | A-6 | | | |
| B-31 | 2(3CF₃Ph),1MeEtO | Me | H | Br | A-6 | | | |
| B-32 | 3PhBuO | Me | H | Br | A-6 | | | |
| B-33 | 5OMe-2-IndanO | Me | H | Br | A-6 | | | |

TABLE B-1-continued

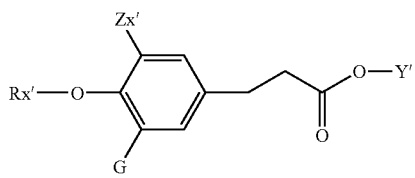

| Exp. | Rx'O | Y' | Zx' | G | Syn | LCMS method | RTime | Mass |
|---|---|---|---|---|---|---|---|---|
| B-34 | 5,6D(OMe)-2-IndanO | Me | H | Br | A-6 | | | |
| B-35 | 5F-2-IndaneO | Me | H | Br | A-6 | | | |
| B-36 | 1-IndaneO | Me | H | Br | A-6 | | | |
| B-37 | 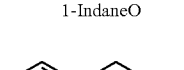 | Me | H | Br | A-6 | | | |

TABLE B-2

| Exp. | Rx'O | Y' | Zx' | G | Syn | LCMS method | RTime | Mass |
|---|---|---|---|---|---|---|---|---|
| B-38 | (phenoxy-CH-CH2-O) | Me | H | Br | A-6 | | | |
| B-39 | 3FBnO | Me | H | Br | A-6 | | | |
| B-40 | 2MeBnO | Me | H | Br | A-6 | C | | 363 (M⁺ + 1) |
| B-41 | 3MeBnO | Me | H | Br | A-6 | | | |
| B-42 | 3,5DMeBnO | Me | H | Br | A-6 | | | |
| B-43 | 4tBuBnO | Me | H | Br | A-6 | | | |
| B-44 | 2CF₃BnO | Me | H | Br | A-6 | | | |
| B-45 | 4CF₃BnO | Me | H | Br | A-6 | | | |
| B-46 | 3(CF₃O)BnO | Me | H | Br | A-6 | | | |
| B-47 | 4(CF₃O)BnO | Me | H | Br | A-6 | | | |
| B-48 | 4(nBuO)BnO | Me | H | Br | A-6 | | | |
| B-49 | (2-acetamido-BnO) | Me | H | Br | A-6 | C | | 406 (M⁺ + 1) |
| B-50 | 3,4DFBnO | Me | H | Br | A-6 | | | |
| B-51 | 2,4DFBnO | Me | H | Br | A-6 | | | |
| B-52 | 4Br,2FBnO | Me | H | Br | A-6 | | | |
| B-53 | 2,4DClBnO | Me | H | Br | A-6 | | | |
| B-54 | 3,4DClBnO | Me | H | Br | A-6 | | | |
| B-55 | 2,3DClBnO | Me | H | Br | A-6 | | | |
| B-56 | 2,6DClBnO | Me | H | Br | A-6 | | | |
| B-57 | 3,5DClBnO | Me | H | Br | A-6 | | | |
| B-58 | 2-NapMeO | Me | H | Br | A-6 | C | | 399 (M⁺ + 1) |
| B-59 | 1-NapMeO | Me | H | Br | A-6 | | | |
| B-60 | (2-thienyl-CH2-O) | Me | H | Br | A-6 | | | |
| B-61 | (2-furyl-CH2-O) | Me | H | Br | A-6 | | | |

TABLE B-2-continued

| | | | | | | | |
|---|---|---|---|---|---|---|---|
| B-62 | 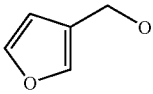 | Me | H | Br | A-6 | C | 339 (M⁺ + 1) |
| B-63 | 2PhBnO | Me | H | Br | A-6 | | |
| B-64 | 4PhBnO | Me | H | Br | A-6 | | |
| B-65 | 2PhEtO | Me | H | Br | A-6 | | |
| B-66 | 2(2MePh)EtO | Me | H | Br | A-6 | | |
| B-67 | 2(3MePh)EtO | Me | H | Br | A-6 | | |
| B-68 | 2(4MePh)EtO | Me | H | Br | A-6 | | |
| B-69 | 2(3FPh)EtO | Me | H | Br | A-6 | | |
| B-70 | 2(3ClPh)EtO | Me | H | Br | A-6 | | |
| B-71 | 2(2CF₃Ph)EtO | Me | H | Br | A-6 | | |
| B-72 | 2(4CF₃Ph)EtO | Me | H | Br | A-6 | | |
| B-73 | 2(2OMePh)EtO | Me | H | Br | A-6 | | |
| B-74 | 2(2-Nap)EtO | Me | H | Br | A-6 | C | 413 (M⁺ + 1) |
| B-75 | 2(3-Ind)EtO | Me | H | Br | A-6 | | |
| B-76 |  | Me | H | Br | A-6 | | |
| B-77 | 2(PhO)EtO | Me | H | Br | A-6 | | |
| B-78 | 2(2ClPhO)EtO | Me | H | Br | A-6 | | |
| B-79 | 2(4ClPhO)EtO | Me | H | Br | A-6 | | |

TABLE B-3

| | | | | | | | |
|---|---|---|---|---|---|---|---|
| B-80 | 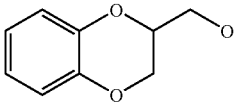 | Me | H | Br | A-6 | C | 407 (M⁺ + 1) |
| B-81 | 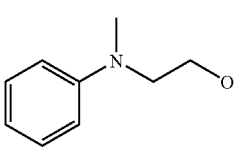 | Me | H | Br | A-6 | | |
| B-82 | 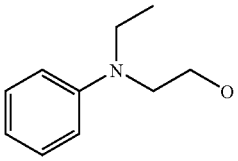 | Me | H | Br | A-6 | | |
| B-83 | 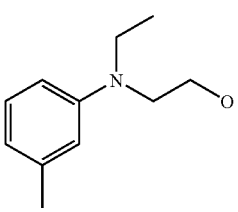 | Me | H | Br | A-6 | | |
| B-84 | 2(PhS)EtO | Me | H | Br | A-6 | C | 379 (M⁺ + 1) |
| B-85 | 2-BztO | Me | H | Br | A-6 | | |
| B-86 | (6OMe-2-Bzt)O | Me | H | Br | A-6 | | |
| B-87 | cPenO | Me | Cl | Br | A-20 | | |
| B-88 | 1(4FPh)EtO | Me | Cl | Br | A-20 | | |
| B-89 | 1PhEtO | Me | F | Br | A-21 | | |
| B-90 | 1(4FPh)EtO | Me | F | Br | A-21 | | |
| B-91 | 1PhEtO | Et | Me | Br | A-24 | | |
| B-92 | 1(4FPh)EtO | Et | Me | Br | A-24 | | |
| B-93 | 1PhEtO | Me | OMe | Br | A-25 | | |
| B-94 | 1(4FPh)EtO | Me | OMe | Br | A-25 | | |
| B-95 | BnO | Me | NO2 | Br | A-26 | | |

TABLE B-3-continued

| | | | | | | | | |
|---|---|---|---|---|---|---|---|---|
| B-96 | 2-IndanO | Me | NO2 | Br | A-26 | A | 4.44 | N.D |
| B-97 | 5OMe-2-IndanO | Me | NO2 | Br | A-26 | | | |
| B-98 | 4CF3BnO | Me | NO2 | Br | A-26 | | | |
| B-99 | cPenO | Me | NH2 | Br | B-99 | C | | 342 (M$^+$ + 1) |
| B-100 | BnO | Me | NH2 | Br | B-99 | | | |
| B-101 | 1PhEtO | Me | NH2 | Br | B-99 | | | |
| B-102 | 5OMe-2-IndanO | Me | NH2 | Br | B-99 | | | |
| B-103 | BnO | Me | NHTFA | Br | B-103 | | | |
| B-104 | cPenO | Me | NHTFA | Br | B-103 | C | | 438 (M$^+$ + 1) |
| B-105 | BnO | Me | NHMe | Br | B-105 | | | |
| B-106 | cPenO | Me | NHMe | Br | B-105 | C | | 356 (M$^+$ + 1) |
| B-107 | 1PhEtO | Me | NHMe | Br | B-105 | | | |
| B-108 | 1(4FPh)EtO | Me | NHMe | Br | B-105 | | | |
| B-109 | BnO | Me | NMe2 | Br | B-109 | | | |
| B-110 | cPenO | Me | NMe2 | Br | B-109 | C | | 370 (M$^+$ + 1) |
| B-111 | 1PhEtO | Me | NMe2 | Br | B-109 | | | |
| B-112 | 1(4FPh)EtO | Me | NMe2 | Br | B-109 | | | |
| B-113 | cPenO | Me | OH | Br | B-113 | C | | 343 (M$^+$ + 1) |
| B-114 | cPenO | Me | OCOMe | Br | B-114 | | | |
| B-115 | 1(4FPh)EtO | Me | OH | Br | B-113 | | | |
| B-116 | 1(4FPh)EtO | Me | OCOMe | Br | B-114 | | | |
| B-117 | cPenMeO | Me | Br | Br | B-117 | | | |
| B-118 | cPenO | Me | Br | Br | B-117 | A | 5.98 | N.D |
| B-119 | 1(4FPh)EtO | Me | Br | Br | B-117 | | | |

Example C-1

Synthesis of 3-bromo-4-cyclohexylmethyloxybenzaldehyde (Intermediate 25)

According to the procedure described in the synthesis method of Compound No. A-2 provided that the purification was performed by flash column chromatography (hexane: isopropyl ether=5:1), 3-bromo-4-hydroxybenzaldehyde (17.4 g), potassium carbonate (23.9 g) and bromomethylcyclohexane (36.2 ml) were reacted and treated to obtain the title compound (Intermediate 25, 18.7 g).

Synthesis of 4-cyclohexylmethyloxy-3-(naphthalen-2-yl)benzaldehyde (Compound No. C-1)

A solution of 2-naphthaleneboronic acid (535 mg) in methanol (5.0 ml), Intermediate 25 (1.16 g), and 2 M aqueous sodium carbonate (0.9 ml) were added with toluene (10.0 ml) and tetrakistriphenylphosphinepalladium(0) [hereinafter abbreviated as "(Ph$_3$P)$_4$Pd"] (116 mg, Nakarai Tecs), and stirred at 80° C. for 17 hours. The reaction mixture was added with ethyl acetate (100 ml), and washed successively with saturated aqueous sodium hydrogencarbonate, saturated aqueous ammonium chloride and saturated brine. The organic layer was dried, and then the solvent was evaporated under reduced pressure. The residue was purified by flash column chromatography (hexane:ethyl acetate=10:1) to obtain the title compound (Compound No. C-1, 345 mg).

Example D-10

Synthesis of 3-bromo-4-hydroxy-5-nitrobenzaldehyde (Intermediate 26)

A solution of 3-bromo-4-hydroxybenzaldehyde (6.30 g) in acetic acid (45 ml) was added dropwise with 70% nitric acid (5.85 ml) on a water bath, then added with sodium nitrite (62 mg), and further stirred for 2 hours. The reaction mixture was poured into ice water (300 ml), and precipitates were taken by filtration, and washed with water (50 ml×3). The precipitates were dried under reduced pressure for 24 hours to obtain the title compound (Intermediate 26, 5.88 g).

Synthesis of 3-bromo-4-cyclohexylmethyloxy-5-nitrobenzaldehyde (Intermediate 27)

According to the procedure described in the synthesis method of Compound No. A-2 provided that the purification was performed by flash column chromatography (hexane: ethyl acetate=7:1), Intermediate 26 (5.5 g), potassium carbonate (3.94 g) and bromomethylcyclohexane (3.94 ml) were reacted and treated to obtain the title compound (Intermediate 27, 5.2 g).

Synthesis of 4-cyclohexylmethyloxy-3-(naphthalen-2-yl)-5-nitrobenzaldehyde (Compound No. D-10)

According to the procedure described in the synthesis method of Compound No. C-1 with the modifications that the reaction was carried out for 15 hours at 80° C., and the purification was performed by column chromatography (Quad, hexane:ethyl acetate=7:1), Intermediate 27 (2.65 g), 2-naphthaleneboronic acid (3.01 g), 2 M aqueous sodium carbonate (7.5 ml) and (Ph$_3$P)$_4$Pd (960 mg) were reacted and treated to obtain the title compound (Compound No. D-10, 2.96 g).

Examples C-1 to C-8

Typical examples of the compounds of the present invention that can be obtained by reacting and treating corresponding starting compounds using any of the methods described in the present specification including the examples described above are shown in Table-C-1.

TABLE C-1

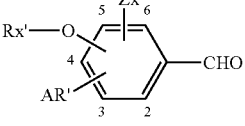

| Exp. | Rx'O | Position | Zx' | Position | AR' | Position | Syn | LCMS method | RTime | Mass |
|---|---|---|---|---|---|---|---|---|---|---|
| C-1 | cHexMeO | 4 | H | — | 2-Nap | 5 | C-1 | | | |
| C-2 | cHexMeO | 4 | H | — | 1-Nap | 5 | C-1 | | | |
| C-3 | cHexMeO | 4 | H | — | 2OMe-6-Nap | 5 | C-1 | C | | 374 (M⁺) |
| C-4 | cHexMeO | 4 | H | — | 5-Ind | 5 | C-1 | | | |
| C-5 | cPenMeO | 4 | H | — | 2-Nap | 5 | C-1 | | | |
| C-6 | cPenMeO | 4 | H | — | 5-Ind | 5 | C-1 | | | |
| C-7 | cPenO | 4 | H | — | 2-Nap | 5 | C-1 | C | | 316 (M⁺) |
| C-8 | cPenO | 4 | H | — | 5-Ind | 5 | C-1 | C | | 305 (M⁺) |

Examples D-1 to D-29

Typical examples of the compounds of the present invention that can be obtained by reacting and treating corresponding starting compounds using any of the methods described in the present specification including the examples described above are shown in Table-D-1.

TABLE D-1

| Exp. | Rx'O | Position | Zx' | Position | AR' | Position | Syn | LCMS method | RTime | Mass |
|---|---|---|---|---|---|---|---|---|---|---|
| D-1 | cHexMeO | 4 | H | — | 2-BT | 3 | C-1 | C | | 350 (M⁺) |
| D-2 | cHexMeO | 4 | H | — | 2-BF | 3 | C-1 | | | |
| D-3 | cHexMeO | 4 | H | — | 1Me-5-Ind | 3 | C-1 | C | | 316 (M⁺) |
| D-4 | cHexMeO | 4 | H | — | 5-1HIdz | 3 | C-1 | | | |
| D-5 | cHexMeO | 4 | H | — | 1Me-5-1HIdz | 3 | C-1 | | | |
| D-6 | 2(2FPh)EtO | 4 | H | — | 2-Nap | 3 | C-1 | | | |
| D-7 | 2(2FPh)EtO | 4 | H | — | 5-Ind | 3 | C-1 | | | |
| D-8 | 2-IndanO | 4 | H | — | 5-Ind | 3 | C-1 | | | |
| D-9 | 2-IndanO | 4 | H | — | 5-1HIdz | 3 | C-1 | | | |
| D-10 | cPenMeO | 4 | NO2 | 5 | 2-Nap | 3 | D-10 | C | | 330 (M⁺ + 1) |
| D-11 | cPenMeO | 4 | NO2 | 5 | 5-Ind | 3 | D-10 | | | |
| D-12 | cHexMeO | 4 | NO2 | 5 | 2-Nap | 3 | D-10 | | | |
| D-13 | cHexMeO | 4 | NO2 | 5 | 2-BF | 3 | D-10 | | | |
| D-14 | cPenO | 4 | NO2 | 5 | 2-Nap | 3 | D-10 | | | |
| D-15 | cPenO | 4 | NO2 | 5 | 5-Ind | 3 | D-10 | C | | 350 (M⁺) |
| D-16 | 2(2FPh)EtO | 4 | NO2 | 5 | 2-Nap | 3 | D-10 | | | |
| D-17 | 2(2FPh)EtO | 4 | NO2 | 5 | 5-Ind | 3 | D-10 | | | |
| D-18 | 2-IndanO | 4 | NO2 | 5 | 5-Ind | 3 | D-10 | | | |
| D-19 | 2-IndanO | 4 | NO2 | 5 | 1Me-5-1HIdz | 3 | D-10 | A | 3.85 | 414 (M⁺ + 1) |
| D-20 | cPenO | 2 | H | — | 2-Nap | 5 | C-1 | C | | 316 (M⁺) |
| D-21 | cPenO | 2 | H | — | 5-Ind | 5 | C-1 | C | | 305 (M⁺) |
| D-22 | cPenO | 3 | H | — | 2-Nap | 5 | C-1 | | | |
| D-23 | cPenO | 3 | H | — | 5-Ind | 5 | C-1 | | | |
| D-24 | cPenO | 5 | H | — | 2-Nap | 2 | C-1 | | | |
| D-25 | cPenO | 5 | H | — | 5-Ind | 2 | C-1 | | | |
| D-26 | cPenO | 4 | H | — | 2-Nap | 2 | C-1 | | | |
| D-27 | cPenO | 4 | H | — | 5-Ind | 2 | C-1 | | | |
| D-28 | cPenO | 3 | H | — | 2-Nap | 2 | C-1 | | | |
| D-29 | cPenO | 3 | H | — | 5-Ind | 2 | C-1 | | | |

Example E-1

Synthesis of 5-bromo-2-cyclopentylmethyloxypyridine (Intermediate 28)

A solution of potassium t-butoxide (550.6 mg, WAKO) in dehydrated THF (10 ml) was added with cyclopentane methanol (450 µl), and then added with a solution of 2,5-dibromopyridine (982.8 mg, TCI) in dehydrated THF (15 ml) under ice cooling. The reaction mixture was stirred for 30 minutes, then warmed to room temperature, and stirred for 11 hours. The reaction mixture was added with water (100 ml) and ethyl acetate (60 ml) for extraction. The organic layer was washed successively with saturated aqueous sodium hydrogencarbonate and saturated brine sequentially, and dried, and then the solvent was evaporated under reduced pressure. The residue was purified by column chromatography (Quad, hexane:ethyl acetate=15:1) to obtain the title compound (Intermediate 28, 896 mg).

Synthesis of 2-cyclopentylmethyloxypyridine-5-carbaldehyde (Intermediate 29)

A solution of Intermediate 28 (895 mg) in anhydrous THF (10 ml) was added dropwise with a 1.6 M solution of n-butyllithium in hexane (2.70 ml, Ald) over 5 minutes with cooling at −78° C. under argon gas atmosphere, and stirred for 20 minutes. This reaction mixture was added with dehydrated DMF (330 µl, WAKO) over 3 minutes, stirred for 30 minutes, then warmed to room temperature, and further stirred for 1 hour. The reaction mixture was added with water (10 ml), and extracted with ethyl acetate (30 ml×3). The organic layer was washed with saturated brine and dried, and then the solvent was evaporated under reduced pressure. The residue was purified by column chromatography (Quad, hexane:ethyl acetate=10:1) to obtain the title compound (Intermediate 29, 1.04 g).

Synthesis of ethyl 3-(2-cyclopentylmethyloxypyridin-5-yl)acrylate (Intermediate 30)

According to the procedure described in the synthesis method of Intermediate 7 with the modification that the reaction was carried out for 1 hour, Intermediate 29 (450 mg), ethyl diethylphosphonoacetate (530 µl) and 60% sodium hydride (120 mg) were reacted and treated to obtain the title compound (Intermediate 30, 394 mg).

Synthesis of ethyl 3 (2-cyclopentylmethyloxypyridine-5-yl)propionate (Intermediate 31)

According to the procedure described in the synthesis method of Intermediate 8 with the modifications that the reaction was carried out for 1 hour, and the purification was performed by column chromatography (Quad, hexane:ethyl acetate=15:1), Intermediate 30 (392 mg) and 10% palladium/carbon (30 mg) were reacted and treated to obtain the title compound (Intermediate 31, 246 mg).

Synthesis of ethyl 3-(3-bromo-2-cyclopentylmethyloxypyridin-5-yl)propionate (Compound No. E-1)

A solution of Intermediate 31 (5.20 g) in acetonitrile (50 ml) was warmed to 35° C., added dropwise with bromine (1.1 ml, WAKO), then added with NBS (3.72 g), and stirred at room temperature for 2 hours. The reaction mixture was concentrated under reduced pressure, then added with ethyl acetate (200 ml), and washed successively with saturated aqueous ammonium chloride, 5% aqueous sodium sulfite, saturated aqueous sodium hydrogencarbonate and saturated brine. The organic layer was dried, and then the solvent was evaporated under reduced pressure. The residue was purified by column chromatography (Quad, hexane:ethyl acetate=10:1) to obtain the title compound (Compound No. E-1, 6.51 g).

Example E-7

Synthesis of 2-benzyloxy-5-bromopyridine (Intermediate 32)

According to the procedure described in the synthesis method of Intermediate 28 provided that the reaction was carried out for 1 hour, potassium t-butoxide (3.13 g), benzyl alcohol (3.10 ml) and 2,5-dibromopyridine (4.79 g) were reacted and treated to obtain the title compound (Intermediate 32, 5.36 g).

Synthesis of 2-benzyloxypyridine-5-carbaldehyde (Intermediate 33)

According to the procedure described in the synthesis method of Intermediate 29, Intermediate 32 (5.10 g), a 1.6M solution of n-butyllithium in hexane (15.6 ml) and dehydrated DMF (1.9 ml) were reacted and treated to obtain the title compound (Intermediate 33, 2.75 g).

Synthesis of ethyl 3-(2-benzyloxypyridin-5-yl)acrylate (Intermediate 34)

According to the procedure described in the synthesis method of Intermediate 7, Intermediate 33 (2.74 g), ethyl diethylphosphonoacetate (3.12 ml) and 60% sodium hydride (635 mg) were reacted and treated to obtain the title compound (Intermediate 34, 2.12 g).

Synthesis of ethyl 3-(2-hydroxypyridin-5-yl)propionate (Intermediate 35)

According to the procedure described in the synthesis method of Intermediate 8 provided that the reaction was carried out for 2.5 hours, Intermediate 54 (2.12 g) and 10% palladium/carbon (120 mg) were reacted and treated to obtain the title compound (Intermediate 35, 1.26 g).

Synthesis of ethyl 3-(3-bromo-2-hydroxypyridin-5-yl)propionate (Intermediate 36)

According to the procedure described in the synthesis method of Compound No. E-1 with the modifications that the reaction was carried out for 2.5 hours, and the purification was performed by column chromatography (Quad, hexane:ethyl acetate=1:2), Intermediate 35 (1.23 g), bromine (340 µl) and NBS (1.19 g) were reacted and treated to obtain the title compound (Compound No. 36, 1.42 g).

Synthesis of ethyl 3-[5-bromo-6-[(S)-1-phenylethyloxy]pyridin-3-yl]propionate (Compound No. E-7)

According to the procedure described in the synthesis method of Compound No. A-6 with the modifications that the reaction was carried out for 11 hours, and the purification was performed by column chromatography (Quad, hexane:ethyl acetate=4:1), Intermediate 36 (137 mg), $Ph_3P$ (273 mg), (R)-1-phenylethanol (150 µl, TCI) and 40% DIAD (400 µl) were reacted and treated to obtain the title compound (Compound No. E-7, 167 mg).

Example E-13

Synthesis of ethyl 3-(5-bromo-6-(4-trifluoromethyl-benzyloxy)pyridin-3-yl)propionate (Compound No. E-13)

A solution of Intermediate 36 (71.5 mg) in chloroform (7 ml) was added with 4-trifluoromethylbenzyl bromide (109.2 mg, TCI) and silver carbonate (120 mg, WAKO), and stirred at room temperature for 11 hours under light shielding. The reaction mixture was filtered, and the solvent was evaporated under reduced pressure. The residue was purified by column chromatography (Quad, hexane:ethyl acetate=6:1) to obtain the title compound (Compound No. E-13, 114 mg).

Example E-1 to 16

Typical examples of the compounds of the present invention that can be obtained by reacting and treating corresponding starting compounds using any of the methods described in the present specification including the examples described above are shown in Table-E-1.

TABLE E-1

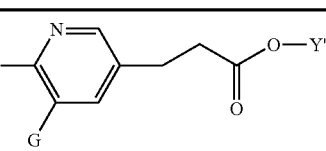

| | | | | | LCMS | |
|---|---|---|---|---|---|---|
| Exp. | Rx'O | Y' | G | Syn method | RTime | Mass |
| E-1 | cPenMeO | Et | Br | E-1 A | 5.98 | 356 (M⁺) |
| E-2 | cHexMeO | Et | Br | E-1 | | |
| E-3 | iBuO | Et | Br | E-1 A | 5.57 | N.D |
| E-4 | 2EtBuO | Et | Br | E-1 | | |
| E-5 | cPenO | Et | Br | E-1 A | 5.62 | 342 (M⁺) |
| E-6 | cHexO | Et | Br | E-1 | | |
| E-7 | (R)1PhEtO | Et | Br | E-7 A | 5.60 | N.D |
| E-8 | 2(4DMAPh)EtO | Et | Br | E-7 | | |
| E-9 | 2(2FPh)EtO | Et | Br | E-7 | | |
| E-10 | 2(3FPh)EtO | Et | Br | E-7 | | |
| E-11 | 2(4ClPh)EtO | Et | Br | E-7 | | |
| E-12 | 2(PhO)EtO | Et | Br | E-7 | | |
| E-13 | 4CF₃BnO | Et | Br | E-13 A | 5.78 | 432 (M⁺) |
| E-14 | 2MeBnO | Et | Br | E-13 | | |
| E-15 | 2ClBnO | Et | Br | E-13 | | |
| E-16 | 1(4FPh)EtO | Et | Br | E-7 | | |

Example F-1

Synthesis of 4-(3-bromo-4-methoxyphenyl)butyric acid (Intermediate 37)

According to the procedure described in the synthesis method of Compound No. A-1 provided that the reaction was carried out under ice cooling for 30 minutes and for 20 hours at room temperature, 4-(4-methoxyphenyl)butyric acid (11.64 g, Ald) and NBS (11.21 g) were reacted and treated to obtain the title compound (Intermediate 37, 16.30 g).

Synthesis of methyl 4-(3-bromo-4-hydroxyphenyl)butyrate (Intermediate 38)

According to the procedure described in the synthesis method of Intermediate 4, Intermediate 37 (12.51 g) and a 1 M solution of boron tribromide in methylene chloride (100 ml) were reacted and treated, and the obtained residue was reacted with thionyl chloride (8.4 ml) in methanol and treated according to the procedure described in the synthesis method of Intermediate 1 to obtain the title compound (Intermediate 38, 10.48 g).

Synthesis of methyl 4-(3-bromo-4-cyclopentylmethyloxyphenyl)butyrate (Compound No. F-1)

According to the procedure described in the synthesis method of Compound No. A-6 provided that the purification was performed by column chromatography (Quad, hexane: isopropyl alcohol=10:1), Intermediate 38 (2.72 g), Ph₃P (7.86 g), cyclopentane methanol (3.24 ml) and 40% DIAD (14.2 ml) were reacted and treated to obtain the title compound (Compound No. F-1, 3.33 g).

Examples F-1 to F-4

Typical examples of the compounds of the present invention that can be obtained by reacting and treating corresponding starting compounds using any of the methods described in the present specification including the examples described above are shown in Table-F-1.

TABLE F-1

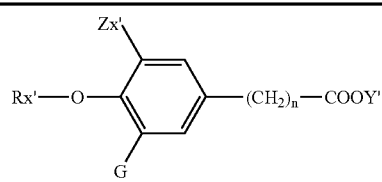

| | | | | | | | | LCMS | |
|---|---|---|---|---|---|---|---|---|---|
| Exp. | Rx'O | Y' | Zx' | G | n | Syn | method | RTime | Mass |
| F-1 | cPenMeO | Me | H | Br | 3 | F-1 | C | | 354 (M⁺) |
| F-2 | cPenO | Me | H | Br | 3 | F-1 | | | |
| F-3 | cHexO | Me | H | Br | 3 | F-1 | C | | 354 (M⁺) |
| F-4 | 1(4FPh)EtO | Me | H | Br | 3 | F-1 | | | |

Example G-1

Synthesis of methyl 3-[4-methoxy-3-(naphthalen-2-yl)phenyl]propionate (Intermediate 39)

According to the procedure described in the synthesis method of Compound No. C-1 with the modifications that the reaction was carried out for 2 hours, and the purification was performed by flash column chromatography (hexane:isopropyl ether=8:1), Intermediate 20 (460 mg), 2-naphthaleneboronic acid (886 mg), 2 M aqueous sodium carbonate (1.6 ml) and $(Ph_3P)_4Pd$ (298 mg) were reacted and treated to obtain the title compound (Intermediate 39, 580 mg).

Synthesis of 3-[4-methoxy-3-(naphthalen-2-yl)phenyl]propionic acid (Intermediate 40)

According to the procedure described in the synthesis method of Intermediate 9 provided that the reaction was carried out for 2 hours, Intermediate 39 (773 mg) and 2 N aqueous sodium hydroxide (2.3 ml) were reacted and treated to obtain the title compound (Intermediate 40, 674 mg).

Synthesis of methyl 3-[4-hydroxy-3-(naphthalen-2-yl)phenyl]propionate (Intermediate 41)

According to the procedure described in the synthesis method of Intermediate 10, pyridine (5 ml), concentrated hydrochloric acid (5 ml), and Intermediate 40 (551 mg) were reacted and treated to obtain crude powder substance. This substance was reacted with thionyl chloride (282 μl) in methanol and treated according to the procedure described in the synthesis method of Intermediate 1 to obtain the title compound (Intermediate 41, 531 mg).

Synthesis of methyl 3-[4-cyclopentyloxy-3-(naphthalen-2-yl)phenyl]propionate (Compound No. G-1)

According to the procedure described in the synthesis method of Compound No. A-6 with the modifications that the reaction was carried out for 15 hours, and the purification was performed by flash column chromatography (hexane:isopropyl ether=6:1), Intermediate 41 (100 mg), $Ph_3P$ (262 mg), cyclopentanol (91 μl, TCI) and 40% DIAD (473 μl) were reacted and treated to obtain the title compound (Compound No. G-1, 120 mg).

Example G-2

Synthesis of 3-[4-cyclopentyloxy-3-(naphthalen-2-yl)phenyl]propionic acid (Compound No. G-2)

According to the procedure described in the synthesis method of Intermediate 9 provided that the reaction was carried out for 4 hours, Compound No. G-1 (115 mg), and 2 N aqueous sodium hydroxide (0.75 ml) were reacted and treated to obtain the title compound (Compound No. G-2, 108 mg).

Example G-3

Synthesis of methyl 3-[4-cyclopentyloxy-3-(1H-indol-5-yl)phenyl]propionate (Compound No. G-3)

According to the procedure described in the synthesis method of Compound No. C-1 with the modifications that the reaction was carried out for 3 hours, and the purification was performed by flash column chromatography (hexane:ethyl acetate=4:1), Compound No. A-5 (833 mg), 5-indoleboronic acid (657 mg), 2 M aqueous sodium carbonate (2.4 ml) and $(Ph_3P)_4Pd$ (233 mg) were reacted and treated to obtain the title compound (Compound No. G-3, 900 mg).

Example G-4

Synthesis of 3-[4-cyclopentyloxy-3-(1H-indole-5-yl)phenyl]propionic acid (Compound No. G-4)

According to the procedure described in the synthesis method of Intermediate 9 provided that the reaction was carried out for 2 hours, Compound No. G-3 (144 mg) and 2 N aqueous sodium hydroxide (420 μl) were reacted and treated to obtain the title compound (Compound No. G-4, 127 mg).

Example G-9

Synthesis of methyl 3-[4-benzyloxy-5-(1-methyl-1H-indazol-5-yl)phenyl]propionate (Compound No. G-9)

According to the procedure described in the synthesis method of Compound No. C-1 with the modifications that the reaction was carried out at 80° C. for 6 hours, and the purification was performed by column chromatography (Quad, hexane:ethyl acetate=4:1), Compound No. A-8 (349 mg), 1-methyl-1H-indazole-5-boronic acid (283 mg), 2 M aqueous sodium carbonate (0.9 ml) and $(Ph_3P)_4Pd$ (94.3 mg) were reacted and treated to obtain the title compound (Compound No. G-9, 370 mg).

Example G-10

Synthesis of 3-[4-benzyloxy-5-(1-methyl-1H-indazol-5-yl)phenyl]propionic acid (Compound No. G-10)

According to the procedure described in the synthesis method of Intermediate 9 provided that the reaction was carried out for 4 hours, Compound No. G-9 (80 mg) and 2 N aqueous sodium hydroxide (0.20 ml) were reacted and treated to obtain the title compound (Compound No. G-10, 71 mg).

Synthesis of methyl 3-[4-hydroxy-5-(1-methyl-1H-indazol-5-yl)phenyl]propionate (Intermediate 42)

A solution of Compound No. G-9 (314 mg) in a mixture of ethyl acetate (3 ml) and methanol (3 ml) was added with 10% palladium/carbon (12 mg), and stirred at room temperature for 16 hours under hydrogen atmosphere. The reaction mixture was filtered, and the solvent of the filtrate was evaporated under reduced pressure to obtain the title compound (Intermediate 48, 288 mg).

Example G-23

Synthesis of methyl 3-(3-bromo-4-t-butyldimethylsilyloxyphenyl)propionate (Intermediate 43)

According to the procedure described in the synthesis method of Intermediate 16 provided that the reaction was carried out for 16 hours, Intermediate 5 (5.18 g), imidazole (2.04 g) and t-butyldimethylsilyl chloride (4.52 g) were reacted and treated to obtain the title compound (Intermediate 43, 8.42 g).

Synthesis of methyl 3-[4-(t-butyldimethylsilyloxy-3-(1H-indol-5-yl)phenyl)propionate (Intermediate 44)

According to the procedure described in the synthesis method of Compound No. C-1 with the modifications that reaction was performed for 12.5 hours, and the purification was performed by flash column chromatography (hexane:ethyl acetate=9:1), 5-indoleboronic acid (4.83 g), Intermediate 34 (7.46 g), 2 M aqueous sodium carbonate (18 ml) and $(Ph_3P)_4Pd$ (1.62 g) were reacted and treated to obtain the title compound (Intermediate 44, 5.04 g).

Synthesis of methyl 3-[4-hydroxy-3-(1H-indol-5-yl)phenyl]propionate (Intermediate 45)

According to the procedure described in the synthesis method of Intermediate 19 with the modifications that the reaction was carried out for 2 hours, and the purification was performed by column chromatography (Quad, hexane:ethyl acetate=3:1), Intermediate 35 (5.04 g), acetic acid (2.8 ml) and a 1 M solution of tetrabutylammonium fluoride in THF (49 ml, TCI) were reacted and treated to obtain the title compound (Intermediate 45, 3.13 g).

Synthesis of methyl 3-[3-(1H-indol-5-yl)-4-(4-methylphenylmethyloxy)phenyl]-propionate (Compound No. G-23)

According to the procedure described in the synthesis method of Compound No. A-2 with the modifications that the reaction was carried out for 15 hours, and the purification was performed by column chromatography (Quad, hexane:ethyl acetate=5:1), Intermediate 45 (80 mg), potassium carbonate (114 mg) and 4-methylbenzyl bromide (54 μl, TCI) were reacted and treated to obtain the title compound (Compound No. G-23, 104 mg).

Example G-24

Synthesis of 3-[3-(1H-indol-5-yl)-4-(4-methylphenylmethyloxy)phenyl]propionic acid (Compound No. G-24)

According to the procedure described in the synthesis method of Intermediate 9 provided that the reaction was carried out for 3 hours, Compound No. G-23 (99 mg) and 2 N aqueous sodium hydroxide (500 μl) were reacted and treated to obtain the title compound (Compound No. G-24, 84 mg).

Example G-106

Synthesis of N-[2-(t-butyldiphenylsilyloxy)ethyl]aniline (Intermediate 46)

A solution of 2-anilinoethanol (5.82 g, TCI) in anhydrous DMF (50 ml) was added with imidazole (3.23 g, TCI), added dropwise with a solution of t-butyldiphenylsilyl chloride (12.48 g, TCI) in DMF (50 ml) under ice cooling, stirred for 30 minutes, then warmed to room temperature, and further stirred for 3.5 hours. The reaction mixture was added with water (100 ml), and extracted with ethyl acetate (100 ml). The organic layer was washed successively with water and saturated brine, and dried, and then the solvent was evaporated under reduced pressure. The residue was purified by flash column chromatography (hexane:ethyl acetate=9:1) to obtain the title compound (Intermediate 46, 15.61 g).

Synthesis of N-benzyl-N-[2-(t-butyldiphenylsilyloxy)ethyl]aniline (Intermediate 47)

According to the procedure described in the synthesis method of Compound No. A-2 with the modifications that the reaction was carried out for 15 hours, and the purification was performed by column chromatography (Quad, hexane:ethyl acetate=5:1), Intermediate 46 (15.60 g), potassium carbonate (8.91 g) and benzyl bromide (6.05 ml, TCI) were reacted and treated to obtain the title compound (Intermediate 47, 19.23 g).

Synthesis of 2-(N-benzyl-N-phenylamino)ethanol (Intermediate 48)

According to the procedure described in the synthesis method of Intermediate 9 with the modifications that the reaction was carried out for 1 hour, and the purification was performed by flash column chromatography (hexane:ethyl acetate=5:1), Intermediate 47 (19.22 g) and a 1 M solution of tetrabutylammonium fluoride in THF (86 ml) were reacted and treated to obtain the title compound (Intermediate 48, 9.06 g).

Synthesis of methyl 3-{4-[2-(N-benzyl-N-phenylamino)ethyloxy]-3-(naphthalen-2-yl)phenyl}propionate (Compound No. G-106)

According to the procedure described in the synthesis method of Compound No. A-6 with the modifications that the reaction was carried out for 15 hours, and the purification was performed by column chromatography (Quad, hexane:ethyl acetate=7:1), Intermediate 41 (1.26 g), $Ph_3P$ (1.34 g), Intermediate 48 (1.01 g) and DBAB (1.18 g) instead of 40% DIAD were reacted and treated to obtain the title compound (Compound No. G-106, 1.39 g).

Example G-107

Synthesis of methyl 3-{3-(naphthalen-2-yl)-4-[2-(N-phenylamino)ethyloxy]phenyl}propionate (Compound No. G-107)

A solution of Compound No. G-106 (1.39 g) in a mixture of THF (10 ml) and methanol (20 ml) was added with concentrated hydrochloric acid (75 μl, WAKO) and 10% palladium/carbon (142 mg), and stirred at room temperature for 3 hours under hydrogen gas atmosphere. The reaction mixture was filtered, and the solvent of the filtrate was evaporated under reduced pressure to obtain the title compound (Compound No. G-107, 842 mg).

Example G-108

Synthesis of 3-{3-(naphthalen-2-yl)-4-[2-(phenylamino)ethyloxy]phenyl}propionic acid (Compound No. G-108)

According to the procedure described in the synthesis method of Intermediate 9 provided that the reaction was carried out for 2 hours, Compound No. G-107 (46 mg) and 2 N aqueous sodium hydroxide (0.25 ml) were reacted and treated to obtain the title compound (Compound No. G-108, 41 mg).

Examples G-1 to G-121

Typical examples of the compounds of the present invention that can be obtained by reacting and treating corresponding starting compounds using any of the methods described in the present specification including the examples described above are shown in Table-G-1 to Table-G-4.

TABLE G-1

| Exp. | RxO | Y | Zx | AR | Syn | LCMS method | RTime | Mass |
|---|---|---|---|---|---|---|---|---|
| G-1 | cPenMeO | Me | H | 2-Nap | G-1 | C | | 388 (M$^+$) |
| G-2 | cPenMeO | H | H | 2-Nap | G-2 | C | | 375 (M$^+$ + 1) |
| G-3 | cPenMeO | Me | H | 5-Ind | G-3 | | | |
| G-4 | cPenMeO | H | H | 5-Ind | G-4 | C | | 363 (M$^+$) |
| G-5 | cPenMeO | Me | H | 1Me-5-Ind | G-3 | | | |
| G-6 | cPenMeO | H | H | 1Me-5-Ind | G-4 | A | | 391 (M$^+$ + 1) |
| G-7 | cPenMeO | Me | H | 5-1HIdz | G-3 | | | |
| G-8 | cPenMeO | H | H | 5-1HIdz | G-4 | | | |
| G-9 | BnO | Me | H | 1Me-5-1HIdz | G-9 | | | |
| G-10 | BnO | H | H | 1Me-5-1HIdz | G-10 | | | |
| G-11 | cPenMeO | Me | H | 1Me-5-1HIdz | G-3 | | | |
| G-12 | cPenMeO | H | H | 1Me-5-1HIdz | G-4 | | | |
| G-13 | 2EtBuO | H | H | 2-Nap | G-1, G-2 | A | | 377 (M$^+$ + 1) |
| G-14 | 2EtBuO | H | H | 5-Ind | G-3, G-4 | | | |
| G-15 | 4Me,cHexO | H | H | 2-Nap | G-1, G-2 | | | |
| G-16 | 4Me,cHexO | H | H | 5-Ind | G-3, G-4 | D | 5.46 | 378 (M$^+$ + 1) |
| G-17 | (3,3,5-trimethylcyclohexyloxy) | H | H | 2-Nap | G-1, G-2 | | | |
| G-18 | (3,3,5-trimethylcyclohexyloxy) | H | H | 5-Ind | G-3, G-4 | | | |
| G-19 | cHepO | H | H | 5-Ind | G-3, G-4 | | | |
| G-20 | 3PhPrO | H | H | 2-Nap | G-1, G-2 | | | |
| G-21 | 4PhBuO | H | H | 5-Ind | G-3, G-4 | | | |
| G-22 | (2-methyl-1-phenylpropoxy) | H | H | 2-Nap | G-1, G-2 | D | 5.40 | 414 (M$^+$ + 1) |
| G-23 | 4MeBnO | Me | H | 5-Ind | G-23 | | | |
| G-24 | 4MeBnO | H | H | 5-Ind | G-24 | | | |
| G-25 | 2(4MePh)EtO | H | H | 2-Nap | G-1, G-2 | | | |
| G-26 | 2(4MePh)EtO | H | H | 5-Ind | G-1, G-2 | | | |
| G-27 | 4ClBnO | H | H | 2-Nap | G-23, G-24 | | | |

TABLE G-1-continued

| Exp. | RxO | Y | Zx | AR | Syn | LCMS method | RTime | Mass |
|---|---|---|---|---|---|---|---|---|
| G-28 | 4CF₃BnO | H | H | 5-Ind | G-23, G-24 | | | |
| G-29 | 3F,4(OMe)BnO | H | H | 2-Nap | G-1, G-2 | | | |
| G-30 | 3F,4(OMe)BnO | H | H | 5-Ind | G-1, G-2 | | | |
| G-31 | 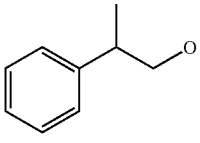 | H | H | 2-Nap | G-1, G-2 | | | |
| G-32 | 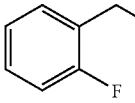 | H | H | 5-Ind | G-1, G-2 | | | |
| G-33 | 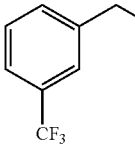 | H | H | 2-Nap | G-1, G-2 | | | |
| G-34 | 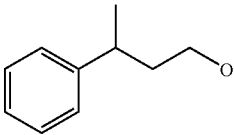 | H | H | 5-Ind | G-1, G-2 | | | |
| G-35 | 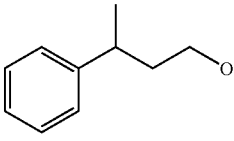 | H | H | 2-Nap | G-1, G-2 | | | |
| G-36 | 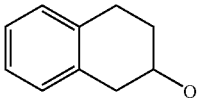 | H | H | 5-Ind | G-1, G-2 | | | |

TABLE G-2

| Exp. | RxO | Y | Zx | AR | Syn | method | RTime | Mass |
|---|---|---|---|---|---|---|---|---|
| G-37 | 1IndanO | H | H | 5-Ind | G-1, G-2 | D | 5.19 | 398 (M⁺ + 1) |
| G-38 | 2IndanO | H | H | 2-Nap | G-1, G-2 | | | |
| G-39 | 2IndanO | H | H | 5-Ind | G-1, G-2 | | | |
| G-40 | 5OMe-2-IndanO | H | H | 2-Nap | G-1, G-2 | C | | 439 (M⁺ + 1) |
| G-41 | 5,6D(OMe)-2-IndanO | H | H | 5-Ind | G-1, G-2 | C | | 458 (M⁺ + 1) |
| G-42 | 5F-2-IndanO | H | H | 2-Nap | G-1, G-2 | | | |
| G-43 | 5F-2-IndanO | H | H | 5-Ind | G-1, G-2 | C | | 416 (M⁺ + 1) |
| G-44 | 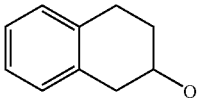 | H | H | 2-Nap | G-1, G-2 | | | |

TABLE G-2-continued

| ID | R | | | Ar | Method | Grade | RT | MS |
|---|---|---|---|---|---|---|---|---|
| G-45 | (2-tetrahydronaphthalenyloxy) | H | H | 5-Ind | G-1, G-2 | A | 5.46 | 412 (M$^+$ + 1) |
| G-46 | (1-tetrahydronaphthalenyloxy) | H | H | 2-Nap | G-1, G-2 | | | |
| G-47 | (1-tetrahydronaphthalenyloxy) | H | H | 5-1HInd | G-1, G-2 | | | |
| G-48 | 2(2MePh)EtO | H | H | 2-Nap | G-1, G-2 | | | |
| G-49 | 2(2MePh)EtO | H | H | 5-Ind | G-1, G-2 | | | |
| G-50 | 2(3FPh)EtO | H | H | 2-Nap | G-1, G-2 | | | |
| G-51 | 2(2ClPh)EtO | H | H | 2-Nap | G-1, G-2 | | | |
| G-52 | 2(3ClPh)EtO | H | H | 5-Ind | G-1, G-2 | | | |
| G-53 | 2(2CF$_3$Ph)EtO | H | H | 5-Ind | G-1, G-2 | | | |
| G-54 | 4(CF$_3$Ph)EtO | H | H | 2-Nap | G-1, G-2 | | | |
| G-55 | 2(2OMePh)EtO | H | H | 2-Nap | G-1, G-2 | C | | 427 (M$^+$ + 1) |
| G-56 | 2(4OMePh)EtO | H | H | 5-Ind | G-1, G-2 | | | |
| G-57 | 2(1-NapEt)O | H | H | 2-Nap | G-1, G-2 | | | |
| G-58 | 2(2-Nap)EtO | H | H | 2-Nap | G-1, G-2 | | | |
| G-59 | 2(2-Nap)EtO | H | H | 5-Ind | G-1, G-2 | C | | 435 (M$^+$) |
| G-60 | 2(4ClPh)EtO | H | H | 2-Nap | G-1, G-2 | | | |
| G-61 | (benzodioxan-2-yl)methoxy | H | H | 5-Ind | G-1, G-2 | D | 5.11 | 430 (M$^+$ + 1) |
| G-62 | (benzodioxan-2-yl)methoxy | H | H | 1Me-5-1HIdz | G-1, G-2 | | | |
| G-63 | 2(PhS)EtO | H | H | 2-Nap | G-1, G-2 | A | | 402 (M$^+$ + 1) |
| G-64 | 2(PhS)EtO | H | H | 5-Ind | G-1, G-2 | | | |
| G-65 | 3PhPrO | H | H | 5-Ind | G-1, G-2 | | | |
| G-66 | 2ClBnO | H | H | 2-Nap | G-1, G-2 | | | |
| G-67 | 2BrBnO | H | H | 5-Ind | G-1, G-2 | C | | 450 (M$^+$) |
| G-68 | 3,5DMeBnO | H | H | 5-Ind | G-1, G-2 | | | |
| G-69 | 4tBuBnO | H | H | 2-Nap | G-1, G-2 | | | |
| G-70 | 2CF$_3$BnO | H | H | | G-1, G-2 | | | |
| G-71 | 4CF$_3$BnO | H | H | | G-1, G-2 | | | |
| G-72 | 4nBuBnO | H | H | 5-Ind | G-1, G-2 | | | |
| G-73 | 3,5DClBnO | H | H | 2-Nap | G-1, G-2 | | | |
| G-74 | 2,3DClBnO | H | H | 5-Ind | G-1, G-2 | | | |
| G-75 | 2PhBnO | H | H | 2-Nap | G-1, G-2 | | | |
| G-76 | 4PhBnO | H | H | 5-Ind | G-1, G-2 | A | | 448 (M$^+$ + 1) |

TABLE G-3

| | | | | | | | |
|---|---|---|---|---|---|---|---|
| G-77 | ![1-methylimidazol-5-yl-methoxy] | H | H | 2-Nap | G-1, G-2 | | |
| G-78 | ![1-benzylimidazol-5-yl-methoxy] | H | H | 5-Ind | G-1, G-2 | | |
| G-79 | ![1,5-dimethylpyrazol-3-yl-methoxy] | H | H | 2-Nap | G-1, G-2 | | |
| G-80 | ![1,5-dimethylpyrazol-3-yl-methoxy] | H | H | 5-Ind | G-1, G-2 | | |
| G-81 | ![2-(pyrrol-1-yl)ethoxy] | H | H | 2-Nap | G-1, G-2 | C | 386 (M$^+$ + 1) |
| G-82 | ![2-(pyrrol-1-yl)ethoxy] | H | H | 5-Ind | G-1, G-2 | | |
| G-83 | ![3,5-dimethylpyrazol-1-yl-methoxy] | H | H | 2-Nap | G-1, G-2 | | |
| G-84 | ![3,5-dimethylpyrazol-1-yl-methoxy] | H | H | 5-Ind | G-1, G-2 | | |
| G-85 | ![5-methylisoxazol-3-yl-methoxy] | H | H | 2-Nap | G-1, G-2 | | |
| G-86 | ![5-methylisoxazol-3-yl-methoxy] | H | H | 5-Ind | G-1, G-2 | | |
| G-87 | ![3-methyl-5-phenylisoxazol-4-yl-methoxy] | H | H | 2-Nap | G-1, G-2 | | |

TABLE G-3-continued

| | | | | | | | |
|---|---|---|---|---|---|---|---|
| G-88 | (3-methyl-5-phenylisoxazol-4-yl)methoxy | H | H | 5-Ind | G-1, G-2 | | |
| G-89 | (5-phenyloxazol-4-yl)methoxy | H | H | 2-Nap | G-1, G-2 | | |
| G-90 | (5-phenyloxazol-4-yl)methoxy | H | H | 5-Ind | G-1, G-2 | | |
| G-91 | (6-methylpyridin-2-yl)methoxy | H | H | 2-Nap | G-1, G-2 | | |
| G-92 | (2-methylpyridin-3-yl)methoxy | H | H | 5-Ind | G-1, G-2 | | |
| G-93 | (6-(trifluoromethyl)pyridin-3-yl)methoxy | H | H | 2-Nap | G-1, G-2 | | |
| G-94 | pyridin-4-ylmethoxy | H | H | 2-Nap | G-1, G-2 | C | 384 (M$^+$ + 1) |
| G-95 | pyridin-4-ylmethoxy | H | H | 5-Ind | G-1, G-2 | | |
| G-96 | 2-(pyridin-4-yl)ethoxy | H | H | 2-Nap | G-1, G-2 | | |
| G-97 | 2-(pyridin-4-yl)ethoxy | H | H | 5-Ind | G-1, G-2 | | |

TABLE G-4

| ID | Structure/Group | | | | | | |
|---|---|---|---|---|---|---|---|
| G-98 | 2-(pyridin-2-yl)ethoxy | H | H | 2-Nap | G-1, G-2 | | |
| G-99 | 2-(pyridin-3-yl)ethoxy | H | H | 5-Ind | G-1, G-2 | | |
| G-100 | (quinolin-2-yl)methoxy | H | H | 2-Nap | G-1, G-2 | | |
| G-101 | (quinolin-2-yl)methoxy | H | H | 5-Ind | G-1, G-2 | C | 423 ($M^+ + 1$) |
| G-102 | 2-(4-methylthiazol-5-yl)ethoxy | H | H | 2-Nap | G-1, G-2 | | |
| G-103 | 2-(4-methylthiazol-5-yl)ethoxy | H | H | 5-Ind | G-1, G-2 | | |
| G-104 | 2-(2,4-dimethylthiazol-5-yl)ethoxy | H | H | 2-Nap | G-1, G-2 | | |
| G-105 | 2-(2,4-dimethylthiazol-5-yl)ethoxy | H | H | 5-Ind | G-1, G-2 | | |
| G-106 | 2(Ph,BnN)EtO | Me | H | 2-Nap | G-106 | | |
| G-107 | 2(PhNH)EtO | Me | H | 2-Nap | G-107 | | |
| G-108 | 2(PhNH)EtO | H | H | 2-Nap | G-108 | C | 412 ($M^+ + 1$) |
| G-109 | 2(PhNH)EtO | Me | H | 5-Ind | G-107 | | |
| G-110 | 2(PhNH)EtO | H | H | 5-Ind | G-108 | | |
| G-111 | 2(PhNH)EtO | Me | H | 1Me-5-Ind | G-107 | | |
| G-112 | 2(PhNH)EtO | H | H | 1Me-5-Ind | G-108 | C | 415 ($M^+ + 1$) |
| G-113 | 2(PhNH)EtO | Me | H | 5-1HIdz | G-107 | | |
| G-114 | 2(PhNH)EtO | H | H | 5-1HIdz | G-108 | | |
| G-115 | 2(PhNH)EtO | Me | H | 1Me-5-1HIdz | G-107 | A | 4.76 | 430 ($M^+ + 1$) |
| G-116 | 2(PhNH)EtO | H | H | 1Me-5-1HIdz | G-108 | C | 416 ($M^+ + 1$) |
| G-117 | iBuO | H | H | 1Me-5-Ind | G-1, G-2 | C | 352 ($M^+ + 1$) |
| G-118 | iBuO | H | H | 1Me-5-1HIdz | G-1, G-2 | C | 353 ($M^+ + 1$) |
| G-119 | PhO | H | H | 1Me-5-1HIdz | G-3, G-4 | A | 4.10 | 373 ($M^+ + 1$) |
| G-120 | 4ClPhO | H | H | 1Me-5-1HIdz | G-3, G-4 | A | 4.46 | 407 ($M^+ + 1$) |
| G-121 | 4MeOPhO | H | H | 1Me-5-1HIdz | G-3, G-4 | A | 4.12 | 403 ($M^+ + 1$) |

Examples H-1 to H-32

Typical examples of the compounds of the present invention that can be obtained by reacting and treating corresponding starting compounds using any of the methods described in the present specification are shown in Table-H-1 and Table-H-2.

TABLE H-1

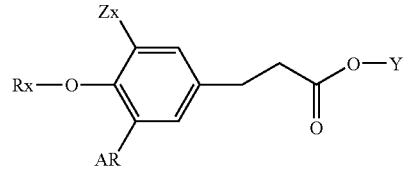

| Exp. | RxO | Y | Zx | AR | Syn | LCMS method | RTime | Mass |
|---|---|---|---|---|---|---|---|---|
| H-1 | 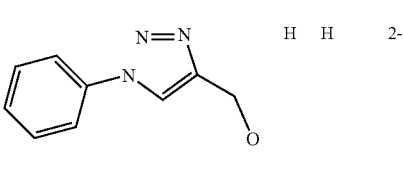 | Me | H | 2-Nap | G-1 | | | |
| H-2 | 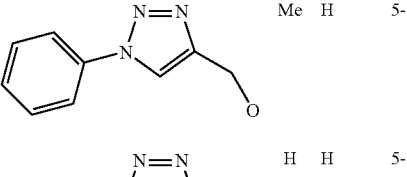 | H | H | 2-Nap | G-2 | | | |
| H-3 | 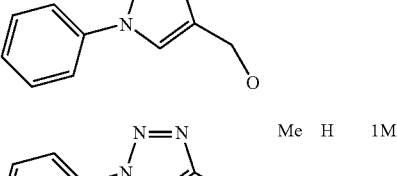 | Me | H | 5-Ind | G-1 | C | | 375 (M$^+$ + 1) |
| H-4 | 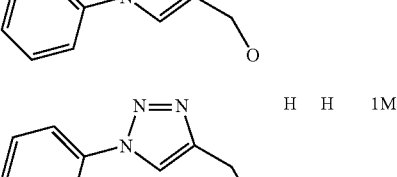 | H | H | 5-Ind | G-2 | | | |
| H-5 | 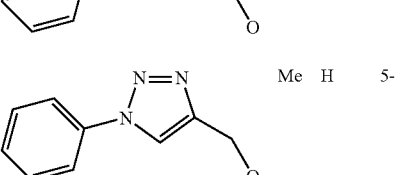 | Me | H | 1Me-5-Ind | G-1 | | | |
| H-6 | 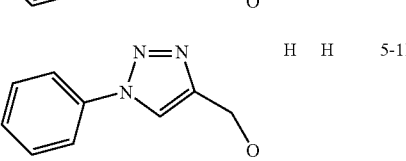 | H | H | 1Me-5-Ind | G-2 | | | |
| H-7 | 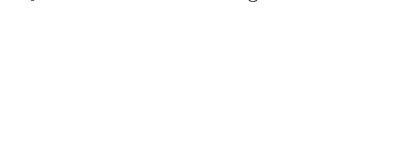 | Me | H | 5-1HIdz | G-1 | | | |
| H-8 | | H | H | 5-1HIdz | G-2 | | | |

TABLE H-1-continued
| Exp. | RxO | Y | Zx | AR | Syn | LCMS method | RTime | Mass |
|---|---|---|---|---|---|---|---|---|
| H-9 |  | Me | H | 1Me-5-1HIdz | G-1 | | | |
| H-10 |  | H | H | 1Me-5-1HIdz | G-2 | C | | 454 (M⁺ + 1) |
| H-11 |  | H | H | 2-Nap | G-1, G-2 | | | |
| H-12 | 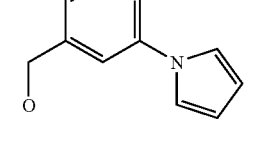 | H | H | 1Me-5-Ind | G-1, G-2 | C | | 452 (M⁺ + 1) |
| H-13 | 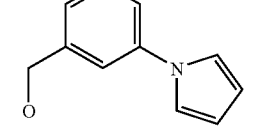 | H | H | 2-Nap | G-1, G-2 | | | |
| H-14 |  | H | H | 1Me-5-Ind | G-1, G-2 | | | |
| H-15 | 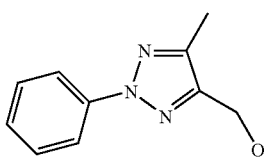 | H | H | 2-Nap | G-1, G-2 | C | | 464 (M⁺ + 1) |
| H-16 |  | H | H | 1Me-5-Ind | G-1, G-2 | | | |
| H-17 |  | H | H | 2-Nap | G-1, G-2 | C | | 450 (M⁺ + 1) |

TABLE H-1-continued

| Exp. | RxO | Y | Zx | AR | Syn | LCMS method | RTime | Mass |
|---|---|---|---|---|---|---|---|---|
| H-18 | (5-phenylisoxazol-3-yl)methoxy | H | H | 1Me-5-Ind | G-1, G-2 | | | |

TABLE H-2

| Exp. | RxO | Y | Zx | AR | Syn | LCMS method | RTime | Mass |
|---|---|---|---|---|---|---|---|---|
| H-19 | (5-(thiophen-2-yl)-1,2,4-oxadiazol-3-yl)methoxy | H | H | 2-Nap | G-1, G-2 | | | |
| H-20 | (5-(thiophen-2-yl)-1,2,4-oxadiazol-3-yl)methoxy | H | H | 1Me-5-Ind | G-1, G-2 | | | |
| H-21 | (2-morpholinophenyl)methoxy | H | H | 2-Nap | G-1, G-2 | | | |
| H-22 | (2-morpholinophenyl)methoxy | H | H | 1Me-5-Ind | G-1, G-2 | C | | 471 (M⁺ + 1) |
| H-23 | (2-morpholinopyridin-3-yl)methoxy | H | H | 2-Nap | G-1, G-2 | | | |
| H-24 | (2-morpholinopyridin-3-yl)methoxy | H | H | 1Me-5-Ind | G-1, G-2 | | | |
| H-25 | 2-(6-phenoxypyridin-3-yl)ethoxy | H | H | 2-Nap | G-1, G-2 | | | |

TABLE H-2-continued
| | | | | | | | | |
|---|---|---|---|---|---|---|---|---|
| H-26 |  | H | H | 1Me-5-Ind | G-1, G-2 | | | |
| H-27 |  | H | H | 2-Nap | G-1, G-2 | | | |
| H-28 |  | H | H | 1Me-5-Ind | G-1, G-2 | C | 460 (M$^+$ + 1) | |
| H-29 |  | H | H | 2-Nap | G-1, G-2 | | | |
| H-30 |  | H | H | 1Me-5-Ind | G-1, G-2 | | | |
| H-31 |  | H | H | 2-Nap | G-1, G-2 | C | 452 (M$^+$ + 1) | |
| H-32 |  | H | H | 1Me-5-Ind | G-1, G-2 | | | |

Example J-1

Synthesis of methyl 3-[4-cyclopentylmethyloxy-3-fluoro-5-(1H-indol-5-yl)phenyl]propionate (Compound No. J-1)

According to the procedure described in the synthesis method of Compound No. C-1 with the modifications that the reaction was carried out for 13 hours, and the purification was performed by column chromatography (Quad, hexane:ethyl acetate=10:1), Compound No. A-21 (154 mg), 5-indoleboronic acid (100 mg), 2 M aqueous sodium carbonate (1.5 ml) and $(Ph_3P)_4Pd$ (50 mg) were reacted and treated to obtain the title compound (Compound No. J-1, 125 mg).

Example J-2

Synthesis of 3-[4-cyclopentylmethyloxy-3-fluoro-5-(1H-indol-5-yl)phenyl]propionic acid (Compound No. J-2)

According to the procedure described in the synthesis method of Intermediate 9 provided that the reaction was carried out for 2 hours, Compound No. J-1 (124 mg) and 2 N aqueous sodium hydroxide (630 µl) were reacted and treated to obtain the title compound (Compound No. J-2, 97 mg).

Example J-3

Synthesis of methyl 3-[3-chloro-4-cyclopentylmethyloxy-5-(1H-indol-5-yl)phenyl]propionate (Compound No. J-3)

According to the procedure described in the synthesis method of Compound No. C-1 with the modifications that the reaction was carried out for 13 hours, and the purification was performed by column chromatography (Quad, hexane:ethyl acetate=10:1), Compound No. A-20 (151 mg), 5-indoleboronic acid (97 mg), 2 M aqueous sodium carbonate (1.5 ml) and $(Ph_3P)_4Pd$ (46 mg) were reacted and treated to obtain the title compound (Compound No. J-3, 160 mg).

Example J-4

Synthesis of 3-[3-chloro-4-cyclopentylmethyloxy-5-(1H-indol-5-yl)phenyl]propionic acid (Compound No. J-4)

According to the procedure described in the synthesis method of Intermediate 9 provided that the reaction was carried out for 2 hours, Compound No. J-3 (135 mg) and 2 N aqueous sodium hydroxide (660 µl) were reacted and treated to obtain the title compound (Compound No. J-4, 97 mg).

Examples J-1 to J-92

Typical examples of the compounds of the present invention that can be obtained by reacting and treating corresponding starting compounds using any of the methods described in the present specification including the examples described above are shown in Table-J-1 to Table-J-3

TABLE J-1

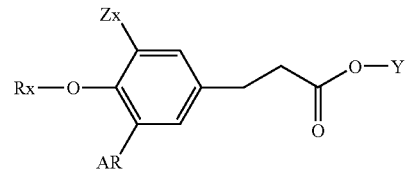

| Exp. | RxO | Y | Zx | AR | Syn | LCMS method | RTime | Mass |
|---|---|---|---|---|---|---|---|---|
| J-1 | cPenMeO | Me | F | 5-Ind | J-1 | A | | 396 ($M^+$ + 1) |
| J-2 | cPenMeO | H | F | 5-Ind | J-2 | | | |
| J-3 | cPenMeO | Me | Cl | 5-Ind | J-3 | | | |
| J-4 | cPenMeO | H | Cl | 5-Ind | J-4 | C | | 398 ($M^+$ + 1) |
| J-5 | cPenMeO | Me | F | 2-Nap | J-1 | | | |
| J-6 | cPenMeO | H | F | 2-Nap | J-2 | | | |
| J-7 | cPenMeO | Me | F | 1Me-5-Ind | J-1 | | | |
| J-8 | cPenMeO | H | F | 1Me-5-Ind | J-2 | | | |
| J-9 | cPenMeO | Me | F | 5-1HIdz | J-1 | | | |
| J-10 | cPenMeO | H | F | 5-1HIdz | J-2 | | | |
| J-11 | cPenMeO | Me | F | 1Me-5-1HIdz | J-1 | | | |
| J-12 | cPenMeO | H | F | 1Me-5-1HIdz | J-2 | C | | 397 ($M^+$ + 1) |
| J-13 | 2EtBuO | H | F | 2-Nap | G-1, G-2 | | | |
| J-14 | 2EtBuO | H | F | 5-Ind | G-1, G-2 | | | |
| J-15 | 4Me,cHexO | H | F | 2-Nap | G-1, G-2 | | | |
| J-16 | 4Me,cHexO | H | F | 1Me-5-Ind | G-1, G-2 | | | |

TABLE J-1-continued

| Exp. | RxO | Y | Zx | AR | Syn | LCMS method | RTime | Mass |
|---|---|---|---|---|---|---|---|---|
| J-17 | 3,3,5-trimethylcyclohexyloxy | H | F | 2-Nap | G-1, G-2 | | | |
| J-18 | 3,3,5-trimethylcyclohexyloxy | H | F | 1Me-5-Ind | G-1, G-2 | C | | 452 (M⁺ + 1) |
| J-19 | cHepO | H | F | 2-Nap | G-1, G-2 | | | |
| J-20 | 3PhPrO | H | F | 1Me-5-Ind | G-1, G-2 | | | |
| J-21 | 4PhBuO | H | F | 2-Nap | G-1, G-2 | | | |
| J-22 | 1-phenyl-2-methylpropyloxy | H | F | 1Me-5-Ind | G-1, G-2 | | | |
| J-23 | 1(4MePh)EtO | H | F | 2-Nap | G-1, G-2 | | | |
| J-24 | 4ClBnO | H | F | 1Me-5-Ind | G-1, G-2 | | | |
| J-25 | 4CF3BnO | H | F | 2-Nap | G-1, G-2 | | | |
| J-26 | 3F,4(OMe)BnO | H | F | 1Me-5-Ind | G-1, G-2 | | | |
| J-27 | 1-methyl-2-phenylethoxy | H | F | 2-Nap | G-1, G-2 | C | | 429 (M⁺ + 1) |
| J-28 | 2-phenylpropoxy | H | F | 1Me-5-Ind | G-1, G-2 | | | |
| J-29 | 1-(2-fluorophenyl)propan-2-yloxy | H | F | 1Me-5-Ind | G-1, G-2 | | | |
| J-30 | 1-(3-trifluoromethylphenyl)propan-2-yloxy | H | F | 2-Nap | G-1, G-2 | | | |

TABLE J-1-continued

| Exp. | RxO | Y | Zx | AR | Syn | LCMS method | RTime | Mass |
|---|---|---|---|---|---|---|---|---|
| J-31 |  | H | F | 2-Nap | G-1, G-2 | | | |

TABLE J-2

| J-32 | 1-IndanO | H | F | 2-Nap | G-1, G-2 | | | |
|---|---|---|---|---|---|---|---|---|
| J-33 | 2-IndaneO | H | F | 1Me-5-Ind | G-1, G-2 | | | |
| J-34 | 2-IndaneO | H | F | 2-Nap | G-1, G-2 | | | |
| J-35 | 5OMe-2-IndanO | H | F | 1Me-5-Ind | G-1, G-2 | | | |
| J-36 | 5,6D(OMe)-2-IndanO | H | F | 2-Nap | G-1, G-2 | | | |
| J-37 | 5F-2-IndanO | H | F | 2-Nap | G-1, G-2 | | | |
| J-38 | 5F-2-IndanO | H | F | 1Me-5-Ind | G-1, G-2 | | | |
| J-39 | 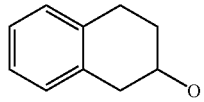 | H | F | 2-Nap | G-1, G-2 | C | | 441 (M$^+$ + 1) |
| J-40 | 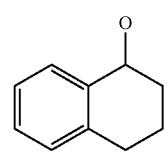 | H | F | 1Me-5-Ind | G-1, G-2 | | | |
| J-41 | 2(3MePh)EtO | H | F | 2-Nap | G-1, G-2 | | | |
| J-42 | 2(4MePh)EtO | H | F | 1Me-5-Ind | G-1, G-2 | | | |
| J-43 | 2(2ClPh)EtO | H | F | 1Me-5-Ind | G-1, G-2 | | | |
| J-44 | 2(3ClPh)EtO | H | F | 2-Nap | G-1, G-2 | | | |
| J-45 | 2(2CF$_3$Ph)EtO | H | F | 2-Nap | G-1, G-2 | | | |
| J-46 | 2(2OMePh)EtO | H | F | 1Me-5-Ind | G-1, G-2 | | | |
| J-47 | 2(4OMePh)EtO | H | F | 2-Nap | G-1, G-2 | | | |
| J-48 | 2(2-Nap)EtO | H | F | 1Me-5-Ind | G-1, G-2 | | | |
| J-49 | 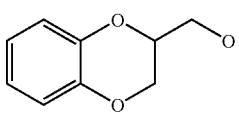 | H | F | 2-Nap | G-1, G-2 | C | | 458 (M$^+$ + 1) |
| J-50 | 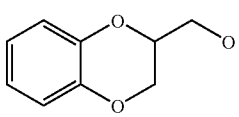 | H | F | 1Me-5-1HIdz | G-1, G-2 | | | |
| J-51 | 2(PhS)EtO | H | F | 1Me-5-Ind | G-1, G-2 | | | |
| J-52 | 3PhPrO | H | F | 2-Nap | G-1, G-2 | | | |
| J-53 | 2ClBnO | H | F | 1Me-5-Ind | G-1, G-2 | | | |
| J-54 | 2BrBnO | H | F | 2-Nap | G-1, G-2 | | | |
| J-55 | 3,5DMeBnO | H | F | 2-Nap | G-1, G-2 | | | |
| J-56 | 4tBuBnO | H | F | 1Me-5-Ind | G-1, G-2 | C | | 460 (M$^+$ + 1) |
| J-57 | 2CF$_3$BnO | H | F | 1Me-5-Ind | G-1, G-2 | | | |
| J-58 | 4CF$_3$BnO | H | F | 2-Nap | G-1, G-2 | | | |
| J-59 | 4nBuOBnO | H | F | 2-Nap | G-1, G-2 | | | |
| J-60 | 3,5DClBnO | H | F | 1Me-5-Ind | G-1, G-2 | | | |
| J-61 | 2,3DClBnO | H | F | 2-Nap | G-1, G-2 | | | |

TABLE J-2-continued
| | | | | | | | |
|---|---|---|---|---|---|---|---|
| J-62 | 2-NapMeO | H | F | 2-Nap | G-1, G-2 | C | 451 (M⁺ + 1) |
| J-63 | 1-NapMeO | H | F | 1Me-5-Ind | G-1, G-2 | | |
| J-64 | 2PhBnO | H | F | 1Me-5-Ind | G-1, G-2 | | |
| J-65 | 4PhBnO | H | F | 1Me-5-Ind | G-1, G-2 | | |
| J-66 | 5OMe-2-IndanO | H | F | 2-Nap | G-1, G-2 | | |
| J-67 | 5OMe-2-IndanO | H | F | 1Me-5-Ind | G-1, G-2 | | |
| J-68 | 5,6D(OMe)-2-IndanO | H | F | 2-Nap | G-1, G-2 | | |
| J-69 | 5,6D(OMe)-2-IndanO | H | F | 1Me-5-Ind | G-1, G-2 | | |
| J-70 | 5F-2-IndanO | H | F | 2-Nap | G-1, G-2 | | |
| J-71 | 5F-2-IndanO | H | F | 1Me-5-Ind | G-1, G-2 | | |
TABLE J-3
| | | | | | | | |
|---|---|---|---|---|---|---|---|
| J-72 | 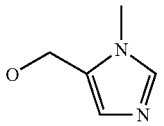 | H | F | 1Me-5-Ind | G-1, G-2 | | |
| J-73 | 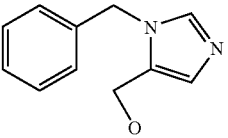 | H | F | 2-Nap | G-1, G-2 | C | 481 (M⁺ + 1) |
| J-74 | 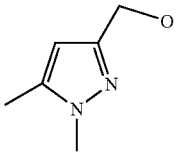 | H | F | 1Me-5-Ind | G-1, G-2 | | |
| J-75 | 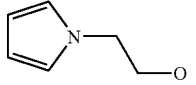 | H | F | 2-Nap | G-1, G-2 | | |
| J-76 | 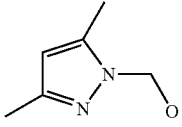 | H | F | 1Me-5-Ind | G-1, G-2 | | |
| J-77 | 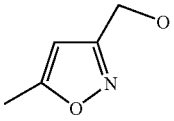 | H | F | 1Me-5-1HIdz | G-1, G-2 | C | 410 (M⁺ + 1) |
| J-78 | 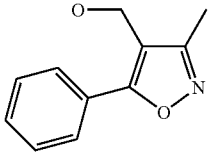 | H | F | 1Me-5-Ind | G-1, G-2 | | |
| J-79 | 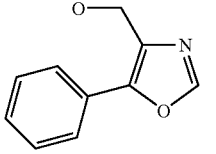 | H | F | 2-Nap | G-1, G-2 | | |
| J-80 | 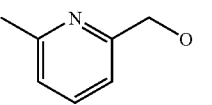 | H | F | 1Me-5-Ind | G-1, G-2 | | |

TABLE J-3-continued
| | | | | | | | |
|---|---|---|---|---|---|---|---|
| J-81 | 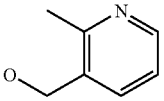 | H | F | 2-Nap | G-1, G-2 | | |
| J-82 | 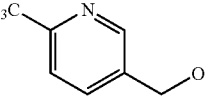 | H | F | 1Me-5-Ind | G-1, G-2 | | |
| J-83 | 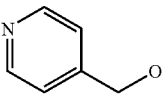 | H | F | 1Me-5-Ind | G-1, G-2 | | |
| J-84 | 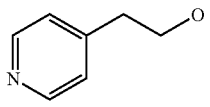 | H | F | 1Me-5-Ind | G-1, G-2 | | |
| J-85 | 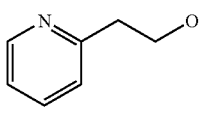 | H | F | 1Me-5-Ind | G-1, G-2 | C | 419 (M$^+$ + 1) |
| J-86 | 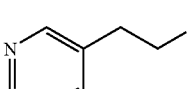 | H | F | 1Me-5-Ind | G-1, G-2 | | |
| J-87 | 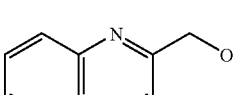 | H | F | 2-Nap | G-1, G-2 | | |
| J-88 | 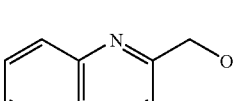 | H | F | 1Me-5-Ind | G-1, G-2 | | |
| J-89 | 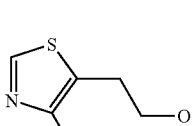 | H | F | 2-Nap | G-1, G-2 | C | 436 (M$^+$ + 1) |
| J-90 | 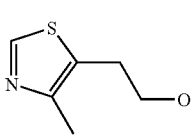 | H | F | 1Me-5-Ind | G-1, G-2 | | |
| J-91 |  | H | F | 2-Nap | G-1, G-2 | | |
| J-92 | 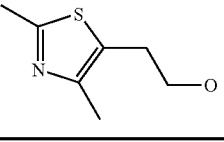 | H | F | 1Me-5-Ind | G-1, G-2 | | |

Example K-11

Synthesis of methyl 3-[3-bromo-4-cyclopentylmethyloxy-5-(naphthalen-2-yl)phenyl]propionate (Compound No. K-11)

According to the procedure described in the synthesis method of Compound No. C-1 with the modifications that the reaction was carried out for 15 hours, and the purification was performed by column chromatography (Quad, hexane:ethyl acetate=9:1), Compound No. B-117 (306 mg), 2-naphthaleneboronic acid (163 mg), 2 M aqueous sodium carbonate (689 μl) and $(Ph_3P)_4Pd$ (74.2 mg) were reacted and treated to obtain the title compound (Compound No. K-11, 261 mg).

Synthesis of 3-[3-bromo-4-cyclopentylmethyloxy-5-(1H-indol-5-yl)phenyl]propionic acid (Compound No. K-12)

According to the procedure described in the synthesis method of Intermediate 9 provided that the reaction was carried out for 2 hours, Compound No. K-11 (131 mg) and 2 N aqueous sodium hydroxide (400 μl) were reacted and treated to obtain the title compound (Compound No. K-12, 109 mg).

Example K-13

Synthesis of methyl 3-[3-bromo-4-cyclopentylmethyloxy-5-(1H-indol-5-yl)phenyl]propionate (Compound No. K-13)

According to the procedure described in the synthesis method of Compound No. C-1 with the modifications that the reaction was carried out for 13 hours, and the purification was performed by column chromatography (Quad, hexane:ethyl acetate=5:1), Compound No. B-117 (102 mg), 5-indoleboronic acid (97 mg), 2 M aqueous sodium carbonate (1.5 ml) and $(Ph_3P)_4Pd$ (46 mg) were reacted and treated to obtain the title compound (Compound No. K-13, 85 mg).

Example K-14

Synthesis of 3-[3-bromo-4-cyclopentylmethyloxy-5-(1H-indol-5-yl)phenyl]propionic acid (Compound No. K-14)

According to the procedure described in the synthesis method of Intermediate 9 provided that the reaction was carried out for 2 hours, Compound No. K-13 (85 mg) and 2 N aqueous sodium hydroxide (200 μl) were reacted and treated to obtain the title compound (Compound No. K-14, 79 mg).

Example K-17

Synthesis of methyl 3-[3-bromo-4-cyclopentyloxy-5-(1-methyl-1H-indazol-5-yl)phenyl]propionate (Compound No. K-17)

According to the procedure described in the synthesis method of Compound No. C-1 with the modifications that the reaction was carried out for 14 hours at 80° C., and the purification was performed by column chromatography (Quad, hexane:ethyl acetate=4:1), Compound No. B-118 (306 mg), 1-methyl-1H-indazole-5-boronic acid (175 mg), 2 M aqueous sodium carbonate (0.68 ml) and $(Ph_3P)_4Pd$ (70.1 mg) were reacted and treated to obtain the title compound (Compound No. K-17, 148 mg).

Examples K-1 to K-40

Typical examples of the compounds of the present invention that can be obtained by reacting and treating corresponding starting compounds using any of the methods described in the present specification including the examples described above are shown in Table-K-1 and Table-K-2.

TABLE K-1

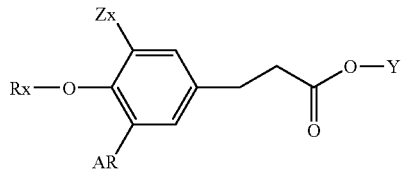

| | | | | | | LCMS | | |
|---|---|---|---|---|---|---|---|---|
| Exp. | RxO | Y | Zx | AR | Syn | method | RTime | Mass |
| K-1 | ![structure] | Me | F | 2-Nap | G-1 | | | |
| K-2 | ![structure] | H | F | 2-Nap | G-2 | | | |

TABLE K-1-continued

| Exp. | RxO | Y | Zx | AR | Syn | LCMS method | RTime | Mass | |
|---|---|---|---|---|---|---|---|---|---|
| K-3 | 1-phenyl-1,2,3-triazol-4-ylmethoxy | Me | F | 5-Ind | G-1 | | | | |
| K-4 | 1-phenyl-1,2,3-triazol-4-ylmethoxy | H | F | 5-Ind | G-2 | C | | 457 | (M$^+$ + 1) |
| K-5 | 1-phenyl-1,2,3-triazol-4-ylmethoxy | Me | F | 1Me-5-Ind | G-1 | | | | |
| K-6 | 1-phenyl-1,2,3-triazol-4-ylmethoxy | H | F | 1Me-5-Ind | G-2 | C | | 471 | (M$^+$ + 1) |
| K-7 | 1-phenyl-1,2,3-triazol-4-ylmethoxy | Me | F | 5-1HIdz | G-1 | | | | |
| K-8 | 1-phenyl-1,2,3-triazol-4-ylmethoxy | H | F | 5-1HIdz | G-2 | | | | |
| K-9 | 1-phenyl-1,2,3-triazol-4-ylmethoxy | Me | F | 1Me-5-1HIdz | G-1 | | | | |
| K-10 | 1-phenyl-1,2,3-triazol-4-ylmethoxy | H | F | 1Me-5-1HIdz | G-2 | | | | |
| K-11 | cPenMeO | Me | Br | 2-Nap | K-11 | | | | |
| K-12 | cPenMeO | H | Br | 2-Nap | K-12 | | | | |
| K-13 | cPenMeO | Me | Br | 2-Nap | K-13 | | | | |
| K-14 | cPenMeO | H | Br | 5-Ind | Int50, K-13 | C | | 456 | (M$^+$) |
| K-15 | cPenO | H | Br | 2-Nap | K-11, K-12 | | | | |
| K-16 | cPenO | H | Br | 1Me-5-Ind | K-11, K-12 | | | | |
| K-17 | cPenO | Me | Br | 1Me-5-1HIdz | K-11, K-12 | | | | |
| K-18 | cPenO | H | Br | 1Me-5-1HIdz | K-11, K-12 | A | 4.78 | 443 | (M$^+$) |

TABLE K-1-continued
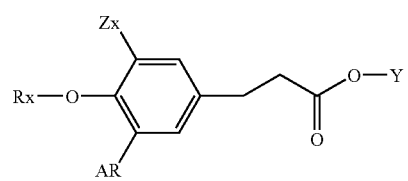
| Exp. | RxO | Y | Zx | AR | Syn | LCMS method | RTime | Mass |
|---|---|---|---|---|---|---|---|---|
| K-19 |  | H | F | 2-Nap | G-1, G-2 | | | |
| K-20 |  | H | F | 1Me-5-Ind | G-1, G-2 | | | |
| K-21 |  | H | F | 2-Nap | G-1, G-2 | | | |
| K-22 | 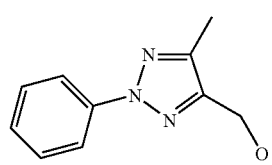 | H | F | 1Me-5-Ind | G-1, G-2 | | | |
| K-23 | 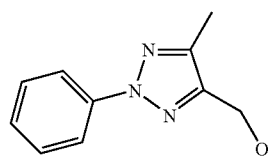 | H | F | 2-Nap | G-1, G-2 | | | |
| K-24 | 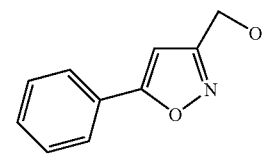 | H | F | 1Me-5-Ind | G-1, G-2 | C | 485 | (M$^+$ + 1) |
| K-25 | 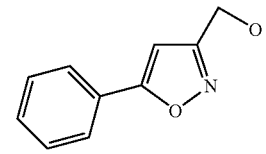 | H | F | 2-Nap | G-1, G-2 | | | |
| K-26 | | H | F | 1Me-5-Ind | G-1, G-2 | | | |

TABLE K-2
| | | | | | | | |
|---|---|---|---|---|---|---|---|
| K-27 | 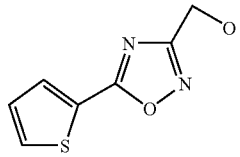 | H | F | 2-Nap | G-1, G-2 | | |
| K-28 | 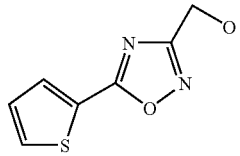 | H | F | 1Me-5-Ind | G-1, G-2 | | |
| K-29 | 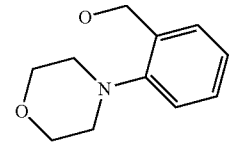 | H | F | 2-Nap | G-1, G-2 | | |
| K-30 | 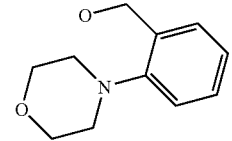 | H | F | 1Me-4-Ind | G-1, G-2 | | |
| K-31 | 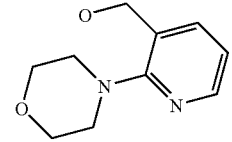 | H | F | 2-Nap | G-1, G-2 | C | 486 ($M^+ + 1$) |
| K-32 | 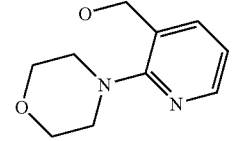 | H | F | 1Me-5-Ind | G-1, G-2 | | |
| K-33 | 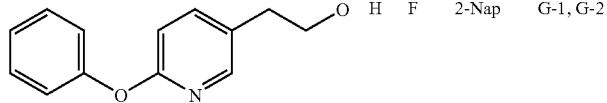 | H | F | 2-Nap | G-1, G-2 | | |
| K-34 | 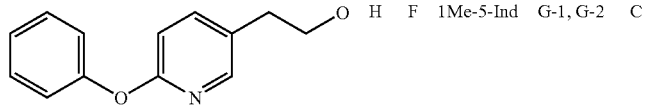 | H | F | 1Me-5-Ind | G-1, G-2 | C | 511 ($M^+ + 1$) |

TABLE K-2-continued
| K-35 | 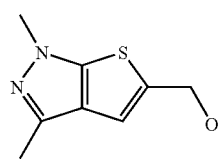 | H | F | 2-Nap | G-1, G-2 |
| K-36 | 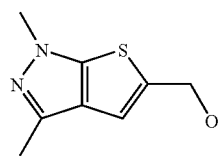 | H | F | 1Me-5-Ind | G-1, G-2 |
| K-37 | 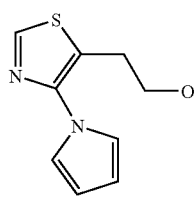 | H | F | 2-Nap | G-1, G-2 |
| K-38 | 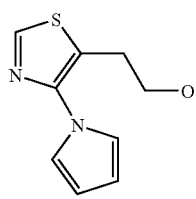 | H | F | 1Me-5-Ind | G-1, G-2 |
| K-39 | 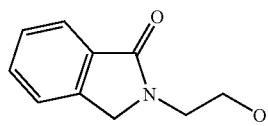 | H | F | 2-Nap | G-1, G-2 |
| K-40 | 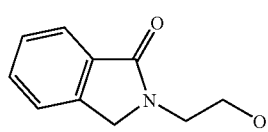 | H | F | 1Me-5-Ind | G-1, G-2 |

Example L-1

Synthesis of 3-[4-cyclopentyloxy-3-methyl-5-(naphthalen-2-yl)phenyl]propionic acid (Compound No. L-1)

According to the procedure described in the synthesis method of Compound No. C-1 with the modifications that the reaction was carried out at 80° C. for 6 hours, and the purification was performed by column chromatography (Quad, hexane:ethyl acetate=20:1), Compound A-24 (63 mg), 2-naphthaleneboronic acid (67 mg), 2 M aqueous sodium carbonate (130 μl) and $(Ph_3P)_4Pd$ (18 mg) were reacted and treated. The obtained substance was reacted with 2 N aqueous sodium hydroxide (200 μl) and treated according to the procedure described in the synthesis method of Intermediate 9 to obtain the title compound (Compound No. L-1, 25 mg).

Example L-2

Synthesis of methyl 3-[4-cyclopentyloxy-3-methyl-5-(1-methyl-1H-indazol-5-yl)phenyl]propionate (Compound No. L-2)

According to the procedure described in the synthesis method of Compound No. C-1 with the modifications that the reaction was carried out at 80° C. for 12 hours, and the purification was performed by column chromatography (Quad, hexane:ethyl acetate=4:1), Compound No. K-17 (115 mg), methylboronic acid (66 mg, Ald), 2 M aqueous sodium carbonate (0.40 ml) and $(Ph_3P)_4Pd$ (39.4 mg) were reacted and treated to obtain the title compound (Intermediate 52, 84 mg).

Example L-3

Synthesis of 3-[4-cyclopentyloxy-3-methyl-5-(1-methyl-1H-indazol-5-yl)phenyl]propionic acid (Compound No. L-3)

According to the procedure described in the synthesis method of Intermediate 9 provided that the reaction was carried out for 1.5 hours, Compound No. L-2 (82 mg) and 2 N aqueous sodium hydroxide (0.26 ml) were reacted and treated to obtain the title compound (Compound No. L-3, 62 mg).

Examples L-1 to L-95

Typical examples of the compounds of the present invention that can be obtained by reacting and treating corresponding starting compounds using any of the methods described in the present specification including the examples described above are shown in Table-L-1 to Table-L-3.

TABLE L-1

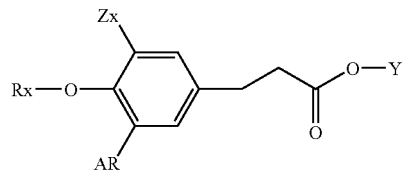

|      |          |    |    |              |        | LCMS   |       |               |
|------|----------|----|----|--------------|--------|--------|-------|---------------|
| Exp. | RxO      | Y  | Zx | AR           | Syn    | method | RTime | Mass          |
| L-1  | cPenO    | H  | Me | 2-Nap        | L-1    | A      | 5.65  | 375 ($M^+$ + 1) |
| L-2  | cPenO    | Me | Me | 1Me-5-1HIdz  | L-2    |        |       |               |
| L-3  | cPenO    | H  | Me | 1Me-5-1HIdz  | L-3    | A      | 4.50  | 379 ($M^+$ + 1) |
| L-4  | 2EtBuO   | Me | Me | 2-Nap        | L-2    |        |       |               |
| L-5  | 2EtBuO   | H  | Me | 2-Nap        | L-3    | C      |       | 391 ($M^+$ + 1) |
| L-6  | 2EtBuO   | H  | Me | 6-OMe-2-Nap  | L-2, L-3 |      |       |               |
| L-7  | 2EtBuO   | Me | Me | 5-Ind        | L-2    |        |       |               |
| L-8  | 2EtBuO   | H  | Me | 5-Ind        | L-3    |        |       |               |
| L-9  | 2EtBuO   | Me | Me | 1Me-5-Ind    | L-2    |        |       |               |
| L-10 | 2EtBuO   | H  | Me | 1Me-5-Ind    | L-3    |        |       |               |
| L-11 | 2EtBuO   | Me | Me | 5-1HIdz      | L-2    |        |       |               |
| L-12 | 2EtBuO   | H  | Me | 5-1HIdz      | L-3    |        |       |               |
| L-13 | 2EtBuO   | Me | Me | 1Me-5-1HIdz  | L-2    |        |       |               |
| L-14 | 2EtBuO   | H  | Me | 1Me-5-1HIdz  | L-3    | C      |       | 395 ($M^+$ + 1) |
| L-15 | 2EtBuO   | Me | Me | 5-Bzt        | L-2    |        |       |               |
| L-16 | 2EtBuO   | H  | Me | 5-Bzt        | L-3    |        |       |               |
| L-17 | 2EtBuO   | Me | Me | 5-2ABzt      | L-2    |        |       |               |
| L-18 | 2EtBuO   | H  | Me | 5-2ABzt      | L-3    |        |       |               |
| L-19 | 2EtBuO   | Me | Me | 2Me-5-Bzt    | L-2    |        |       |               |
| L-20 | 2EtBuO   | H  | Me | 2Me-5-Bzt    | L-3    |        |       |               |
| L-21 | 4Me,cHexO | H | Me | 1Me-5-Ind    | G-1, G-2 |      |       |               |
| L-22 | 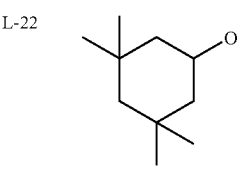 | H | Me | 2-Nap | G-1, G-2 | | | |

TABLE L-1-continued

| Exp. | RxO | Y | Zx | AR | Syn | LCMS method | RTime | Mass |
|---|---|---|---|---|---|---|---|---|
| L-23 | cHepO | H | Me | 2-Nap | G-1, G-2 | | | |
| L-24 | cHepO | H | Me | 1Me-5-Ind | G-1, G-2 | C | | 406 (M$^+$ + 1) |
| L-25 | 3PhPrO | H | Me | 2-Nap | G-1, G-2 | | | |
| L-26 | 4PhBuO | H | Me | 1Me-5-Ind | G-1, G-2 | | | |
| L-27 | (PhCH(iPr)O) | H | Me | 2-Nap | G-1, G-2 | | | |
| L-28 | 1(4MePh)EtO | H | Me | 1Me-5-Ind | G-1, G-2 | C | | 428 (M$^+$ + 1) |
| L-29 | 4ClBnO | H | Me | 2-Nap | G-1, G-2 | | | |
| L-30 | 4CF$_3$BnO | H | Me | 1Me-5-Ind | G-1, G-2 | | | |
| L-31 | 3F,4(OMe)BnO | H | Me | 2-Nap | G-1, G-2 | | | |
| L-32 | (PhCH$_2$CH(Me)O) | H | Me | 1Me-5-Ind | G-1, G-2 | | | |
| L-33 | (PhCH(Me)CH$_2$O) | H | Me | 2-Nap | G-1, G-2 | | | |
| L-34 | (2-F-PhCH$_2$CH(Me)O) | H | Me | 2-Nap | G-1, G-2 | | | |
| L-35 | (3-CF$_3$-PhCH$_2$CH(Me)O) | H | Me | 1Me-5-Ind | G-1, G-2 | | | |

TABLE L-2

| L-36 | (PhCH(Me)CH$_2$CH$_2$O) | H | Me | 1Me-5-Ind | G-1, G-2 |
| L-37 | (PhCH(Me)CH$_2$CH$_2$O) | H | Me | 1Me-5-Ind | G-1, G-2 |

TABLE L-2-continued

| | | | | | | | |
|---|---|---|---|---|---|---|---|
| L-38 | 1-IndanO | H | Me | 2-Nap | G-1, G-2 | | |
| L-39 | 2-IndanO | H | Me | 2-Nap | G-1, G-2 | C | 423 (M$^+$ + 1) |
| L-40 | 2-IndanO | H | Me | 1Me-5-Ind | G-1, G-2 | | |
| L-41 | 5OMe-2-IndanO | H | Me | 1Me-5-Ind | G-1, G-2 | | |
| L-42 | 5,6D(OMe)-2-IndanO | H | Me | 2-Nap | G-1, G-2 | | |
| L-43 | 5F-2-IndaneO | H | Me | 2-Nap | G-1, G-2 | | |
| L-44 | 5F-2-IndaneO | H | Me | 1Me-5-Ind | G-1, G-2 | | |
| L-45 | *[2-tetralinyloxy structure]* | H | Me | 1Me-5-Ind | G-1, G-2 | | |
| L-46 | *[1-tetralinyloxy structure]* | H | Me | 2-Nap | G-1, G-2 | | |
| L-47 | 2(3MePh)EtO | H | Me | 2-Nap | G-1, G-2 | | |
| L-48 | 2(3FPh)EtO | H | Me | 1Me-5-Ind | G-1, G-2 | C | 432 (M$^+$ + 1) |
| L-49 | 2(2ClPh)EtO | H | Me | 1Me-5-Ind | G-1, G-2 | | |
| L-50 | 2(4CF$_3$Ph)EtO | H | Me | 1Me-5-Ind | G-1, G-2 | | |
| L-51 | 2(2OMePh)EtO | H | Me | 2-Nap | G-1, G-2 | C | 441 (M$^+$ + 1) |
| L-52 | 2(4OMePh)EtO | H | Me | 1Me-5-Ind | G-1, G-2 | | |
| L-53 | 2(2-Nap)EtO | H | Me | 2-Nap | G-1, G-2 | | |
| L-54 | 2(2-Nap)EtO | H | Me | 1Me-5-Ind | G-1, G-2 | | |
| L-55 | *[benzodioxane-CH2O structure]* | H | Me | 1Me-5-Ind | G-1, G-2 | | |
| L-56 | *[benzodioxane-CH2O structure]* | H | Me | 1Me-5-1HIdz | G-1, G-2 | C | 459 (M$^+$ + 1) |
| L-57 | 2(PhS)EtO | H | Me | 2-Nap | G-1, G-2 | | |
| L-58 | 3PhPrO | H | Me | 1Me-5-Ind | G-1, G-2 | | |
| L-59 | 2ClBnO | H | Me | 2-Nap | G-1, G-2 | | |
| L-60 | 2BrBnO | H | Me | 1Me-5-Ind | G-1, G-2 | | |
| L-61 | 3,5DMeBnO | H | Me | 2-Nap | G-1, G-2 | | |
| L-62 | 4tBuBnO | H | Me | 2-Nap | G-1, G-2 | | |
| L-63 | 2CF$_3$BnO | H | Me | 2-Nap | G-1, G-2 | | |
| L-64 | 4tBuBnO | H | Me | 1Me-5-Ind | G-1, G-2 | | |
| L-65 | 4nBuBnO | H | Me | 2-Nap | G-1, G-2 | C | 453 (M$^+$ + 1) |
| L-66 | 3,5DClBnO | H | Me | 2-Nap | G-1, G-2 | | |
| L-67 | 2,3DClBnO | H | Me | 1Me-5-Ind | G-1, G-2 | | |
| L-68 | 2-NapMeO | H | Me | 1Me-5-Ind | G-1, G-2 | | |
| L-69 | 1-NapMeO | H | Me | 2-Nap | G-1, G-2 | | |
| L-70 | 2PhBnO | H | Me | 1Me-5-Ind | G-1, G-2 | | |
| L-71 | 4PhBnO | H | Me | 2-Nap | G-1, G-2 | C | 476 (M$^+$ + 1) |
| L-72 | 5OMe-2-IndanO | H | Me | 1Me-5-Ind | G-1, G-2 | | |
| L-73 | 5F-2-IndaneO | H | Me | 2-Nap | G-1, G-2 | | |

TABLE L-3

| | | | | | | | |
|---|---|---|---|---|---|---|---|
| L-74 | *[1-methylimidazole-CH2O structure]* | H | Me | 2-Nap | G-1, G-2 | C | 401 (M$^+$ + 1) |
| L-75 | *[1-benzylimidazole-CH2O structure]* | H | Me | 1Me-5-Ind | G-1, G-2 | | |

TABLE L-3-continued

| | | | | | | | |
|---|---|---|---|---|---|---|---|
| L-76 | [3,5-dimethyl-1H-pyrazol-... CH2O-] | H | Me | 2-Nap | G-1, G-2 | | |
| L-77 | [1-(2-ethoxy)pyrrole] | H | Me | 1Me-5-Ind | G-1, G-2 | | |
| L-78 | [3,5-dimethylpyrazol-1-yl-CH2O] | H | Me | 2-Nap | G-1, G-2 | | |
| L-79 | [5-methylisoxazol-3-yl-CH2O] | H | Me | 1Me-5-Ind | G-1, G-2 | | |
| L-80 | [5-phenyloxazol-4-yl-CH2O] | H | Me | 2-Nap | G-1, G-2 | | |
| L-81 | [5-phenyloxazol-4-yl-CH2O] | H | Me | 1Me-5-Ind | G-1, G-2 | | |
| L-82 | [6-methylpyridin-2-yl-CH2O] | H | Me | 2-Nap | G-1, G-2 | C | 412 (M$^+$ + 1) |
| L-83 | [2-methylpyridin-3-yl-CH2O] | H | Me | 1Me-5-Ind | G-1, G-2 | | |
| L-84 | [6-trifluoromethylpyridazin-3-yl-CH2O] | H | Me | 2-Nap | G-1, G-2 | | |
| L-85 | [pyridin-4-yl-CH2O] | H | Me | 1Me-5-Ind | G-1, G-2 | | |
| L-86 | [pyridin-4-yl-CH2CH2O] | H | Me | 2-Nap | G-1, G-2 | | |
| L-87 | [pyridin-2-yl-CH2CH2O] | H | Me | 1Me-5-Ind | G-1, G-2 | | |

TABLE L-3-continued
| L-88 | 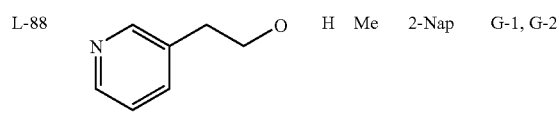 | H | Me | 2-Nap | G-1, G-2 | | |
| L-89 | 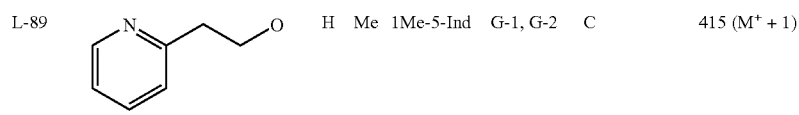 | H | Me | 1Me-5-Ind | G-1, G-2 | C | 415 (M$^+$ + 1) |
| L-90 | 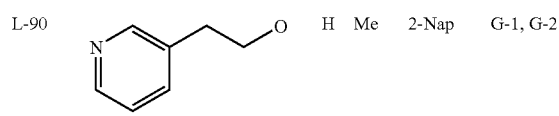 | H | Me | 2-Nap | G-1, G-2 | | |
| L-91 | 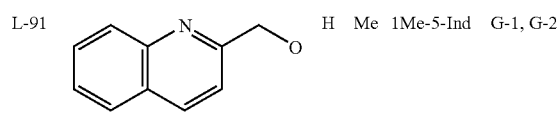 | H | Me | 1Me-5-Ind | G-1, G-2 | | |
| L-92 | 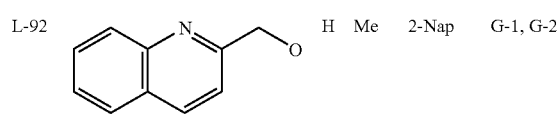 | H | Me | 2-Nap | G-1, G-2 | | |
| L-93 | 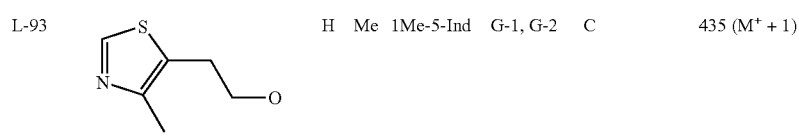 | H | Me | 1Me-5-Ind | G-1, G-2 | C | 435 (M$^+$ + 1) |
| L-94 | 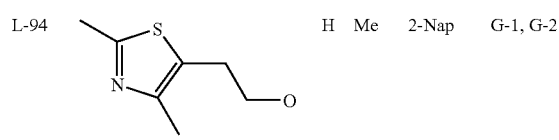 | H | Me | 2-Nap | G-1, G-2 | | |
| L-95 | 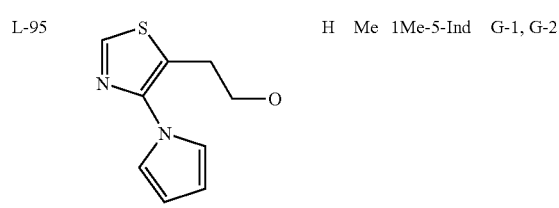 | H | Me | 1Me-5-Ind | G-1, G-2 | | |

Examples M-1 to M-32

Typical examples of the compounds of the present invention that can be obtained by reacting and treating corresponding starting compounds using any of the methods described in the present specification are shown in Table-M-1 and Table-M-2.

TABLE M-1

| Exp. | RxO | Y | Zx | AR | Syn | LCMS method | RTime | Mass |
|---|---|---|---|---|---|---|---|---|
| M-1 | (phenyl-N-triazolyl-CH$_2$O-) | Me | Me | 2-Nap | G-1 | C | | 478 (M$^+$ + 1) |
| M-2 | (phenyl-N-triazolyl-CH$_2$O-) | H | Me | 2-Nap | G-2 | C | | 464 (M$^+$ + 1) |
| M-3 | (phenyl-N-triazolyl-CH$_2$O-) | Me | Me | 5-Ind | G-1 | | | |
| M-4 | (phenyl-N-triazolyl-CH$_2$O-) | H | Me | 5-Ind | G-2 | | | |
| M-5 | (phenyl-N-triazolyl-CH$_2$O-) | Me | Me | 1Me-5-Ind | G-1 | | | |
| M-6 | (phenyl-N-triazolyl-CH$_2$O-) | H | Me | 1Me-5-Ind | G-2 | C | | 467 (M$^+$ + 1) |
| M-7 | (phenyl-N-triazolyl-CH$_2$O-) | Me | Me | 5-1HIdz | G-1 | | | |
| M-8 | (phenyl-N-triazolyl-CH$_2$O-) | H | Me | 5-1HIdz | G-2 | | | |

TABLE M-1-continued

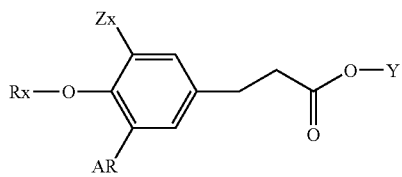

| Exp. | RxO | Y | Zx | AR | Syn | LCMS method | RTime | Mass |
|---|---|---|---|---|---|---|---|---|
| M-9 | [N-phenyl-triazolyl-CH2O-] | Me | Me | 1Me-5-1HIdz | G-1 | | | |
| M-10 | [N-phenyl-triazolyl-CH2O-] | H | Me | 1Me-5-1HIdz | G-2 | | | |
| M-11 | [4-(imidazol-1-yl)benzyl-O-] | H | Me | 2-Nap | G-1, G-2 | C | | 463 ($M^+ + 1$) |
| M-12 | [4-(imidazol-1-yl)benzyl-O-] | H | Me | 1Me-5-Ind | G-1, G-2 | | | |
| M-13 | [3-(pyrrol-1-yl)benzyl-O-] | H | Me | 2-Nap | G-1, G-2 | | | |
| M-14 | [3-(pyrrol-1-yl)benzyl-O-] | H | Me | 1Me-5-Ind | G-1, G-2 | C | | 465 ($M^+ + 1$) |
| M-15 | [2-phenyl-4-methyl-triazolyl-CH2O-] | H | Me | 2-Nap | G-1, G-2 | | | |
| M-16 | [2-phenyl-4-methyl-triazolyl-CH2O-] | H | Me | 1Me-5-Ind | G-1, G-2 | | | |
| M-17 | [5-phenyl-isoxazol-3-yl-CH2O-] | H | Me | 2-Nap | G-1, G-2 | C | | 464 ($M^+ + 1$) |

TABLE M-1-continued

[Structure: Rx—O—phenyl ring with Zx (ortho), AR (ortho), and -CH2CH2-C(=O)-O-Y substituent]

| Exp. | RxO | Y | Zx | AR | Syn | LCMS method | RTime | Mass |
|---|---|---|---|---|---|---|---|---|
| M-18 | [5-phenyl-isoxazol-3-yl-methoxy] | H | Me | 1Me-5-Ind | G-1, G-2 | | | |
| M-19 | [5-(thiophen-2-yl)-1,2,4-oxadiazol-3-yl-methoxy] | H | Me | 2-Nap | G-1, G-2 | | | |
| M-20 | [5-(thiophen-2-yl)-1,2,4-oxadiazol-3-yl-methoxy] | H | Me | 1Me-5-Ind | G-1, G-2 | | | |
| M-21 | [2-(morpholin-4-yl)benzyloxy] | H | Me | 2-Nap | G-1, G-2 | | | |

TABLE M-2

| | | | | | | | | |
|---|---|---|---|---|---|---|---|---|
| M-22 | [2-(morpholin-4-yl)benzyloxy] | H | Me | 1Me-5-Ind | G-1, G-2 | | | |
| M-23 | [2-(morpholin-4-yl)pyridin-3-yl-methoxy] | H | Me | 2-Nap | G-1, G-2 | | | |
| M-24 | [2-(morpholin-4-yl)pyridin-3-yl-methoxy] | H | Me | 1Me-5-Ind | G-1, G-2 | C | | 486 (M$^+$ + 1) |
| M-25 | [6-phenoxy-pyridin-3-yl-ethoxy] | H | Me | 2-Nap | G-1, G-2 | | | |

TABLE M-2-continued
| | | | | | | | |
|---|---|---|---|---|---|---|---|
| M-26 | 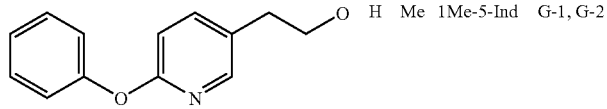 | H | Me | 1Me-5-Ind | G-1, G-2 | | |
| M-27 | 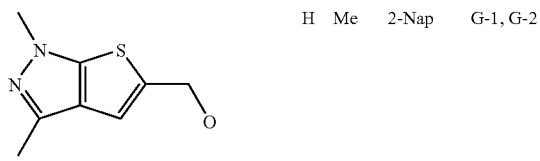 | H | Me | 2-Nap | G-1, G-2 | | |
| M-28 | 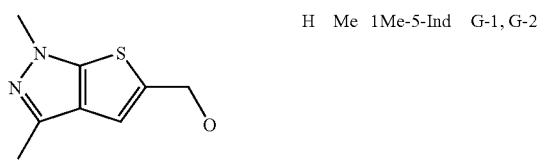 | H | Me | 1Me-5-Ind | G-1, G-2 | | |
| M-29 | 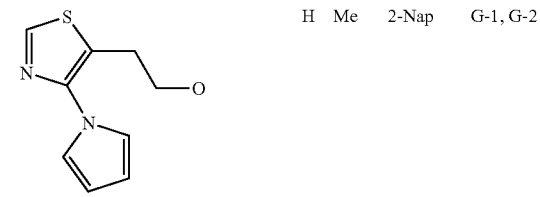 | H | Me | 2-Nap | G-1, G-2 | | |
| M-30 | 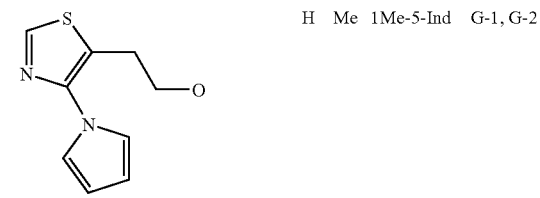 | H | Me | 1Me-5-Ind | G-1, G-2 | C | 472 (M$^+$ + 1) |
| M-31 | 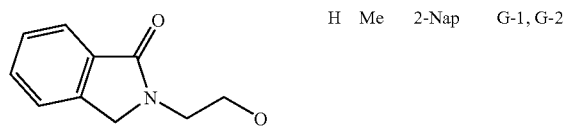 | H | Me | 2-Nap | G-1, G-2 | | |
| M-32 | 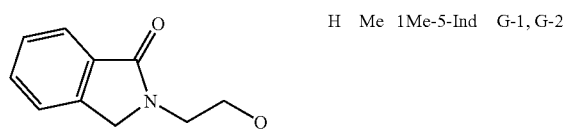 | H | Me | 1Me-5-Ind | G-1, G-2 | | |

Example N-1

Synthesis of methyl 3-{4-[2-(N-acetyl-N-phenylamino)ethyloxy]-3-(naphthalen-2-yl)phenyl}propionate (Compound No. N-1)

A solution of Compound No. G-107 (32 mg) in methylene chloride (1 ml) was added with pyridine (24 µl, TCI) and acetyl chloride (21 µl, TCI), and stirred for 17 hours. The reaction mixture was added with water (3 ml), and extracted with methylene chloride (10 ml). The organic layer was washed with saturated brine and dried, and then the solvent was evaporated under reduced pressure. The residue was purified by column chromatography (Quad, hexane:ethyl acetate=2:1) to obtain the title compound (Compound No. N-1, 28.1 mg).

Example N-2

Synthesis of 3-{4-[2-(N-acetyl-N-phenylamino)ethyloxy]-3-(naphthalen-2-yl)phenyl}propionic acid (Compound No. N-2)

According to the procedure described in the synthesis method of Intermediate 9 provided that the reaction was carried out for 3 hours, Compound No. N-1 (28 mg) and 2 N aqueous sodium hydroxide (0.25 ml) were reacted and treated to obtain the title compound (Compound No. N-2, 22 mg).

Example N-29

Synthesis of methyl 3-{4-[2-(N-methoxycarbonyl-N-phenylamino)ethyloxy]-3-(naphthalen-2-yl)phenyl}propionate (Compound No. N-29)

According to the procedure described in the synthesis method of Compound No. N-1, Compound No. G-107 (32 mg), pyridine (23 µl) and methyl chloroformate (23 µl, TCI) were reacted and treated to obtain the title compound (Compound No. N-29, 17.3 mg).

Example N-30

Synthesis of 3-{4-[2-(N-methoxycarbonyl-N-phenylamino)ethyloxy]-3-(naphthalen-2-yl)phenyl}propionic acid (Compound No. N-30)

According to the procedure described in the synthesis method of Intermediate 9 provided that the reaction was carried out for 3 hours, Compound No. N-29 (17 mg) and 2 N aqueous sodium hydroxide (0.25 ml) were reacted and treated to obtain the title compound (Compound No. N-30, 10.1 mg).

Example N-48

Synthesis of methyl 3-{4-[2-(N-methylsulfonyl-N-phenylamino)ethyloxy]-3-(naphthalen-2-yl)phenyl}propionate (Compound No. N-48)

According to the procedure described in the synthesis method of Compound No. N-1, Compound No. G-107 (32 mg), pyridine (24 µl) and methanesulfonyl chloride (23 µl) were reacted and treated to obtain the title compound (Compound No. N-48, 32.3 mg).

Example N-49

Synthesis of 3-{4-[2-(N-methylsulfonyl-N-phenylamino)ethyloxy]-3-(naphthalen-2-yl)phenyl}propionic acid (Compound No. N-49)

According to the procedure described in the synthesis method of Intermediate 9 provided that the reaction was carried out for 3 hours, Compound No. N-48 (32 mg) and 2 N aqueous sodium hydroxide (0.25 ml) were reacted and treated to obtain the title compound (Compound No. N-49, 17 mg).

Example N-55

Synthesis of methyl 3-{4-[2-(3-ethyl-1-phenylureido)ethyloxy]-3-(naphthalen-2-yl)phenyl}propionate (Compound No. N-55)

According to the procedure described in the synthesis method of Compound No. N-1 provided that the reaction was carried out for 41 hours, Compound No. G-107 (32 mg), pyridine (24 µl) and ethyl isocyanate (24 µl, Nakarai Tecs) were reacted and treated to obtain the title compound (Compound No. N-55, 31.2 mg).

Example N-56

Synthesis of 3-{4-[2-(3-ethyl-1-phenylureido)ethyloxy]-3-(naphthalen-2-yl)phenyl}propionic acid (Compound No. N-56)

According to the procedure described in the synthesis method of Intermediate 9 provided that the reaction was carried out for 3 hours, Compound No. N-55 (31 mg) and 2 N aqueous sodium hydroxide (0.25 ml) were reacted and treated to obtain the title compound (Compound No. N-56, 15 mg).

Example N-64

Synthesis of methyl 3-{4-[2-(3-ethyl-1-phenylthioureido)ethyloxy]-3-(naphthalen-2-yl)phenyl}propionate (Compound No. N-64)

According to the procedure described in the synthesis method of Compound No. N-1 provided that the reaction was carried out for 41 hours, Compound No. G-107 (32 mg), pyridine (24 µl) and ethyl isothiocyanate (21 µl, Nakarai Tecs) were reacted and treated to obtain the title compound (Compound No. N-64, 27.4 mg).

Example N-65

Synthesis of 3-{4-[2-(3-ethyl-1-phenylthioureido)ethyloxy]-3-(naphthalen-2-yl)phenyl}propionic acid (Compound No. N-65)

According to the procedure described in the synthesis method of Intermediate 9 provided that the reaction was carried out for 3 hours, Compound No. N-64 (27 mg) and 2 N aqueous sodium hydroxide (0.25 ml) were reacted and treated to obtain the title compound (Compound No. N-65, 8.9 mg).

Examples N-1 to N-74

Typical examples of the compounds of the present invention that can be obtained by reacting and treating corresponding starting compounds using any of the methods described in the present specification including the examples described above are shown in Table-N-1 and Table-N-2.

TABLE N-1

| Exp. | A⁵Re | Y | Zx | AR | Syn | LCMS method | RTime | Mass |
|---|---|---|---|---|---|---|---|---|
| N-1 | COMe | Me | H | 2-Nap | N-1 | | | |
| N-2 | COMe | H | H | 2-Nap | N-2 | | | |
| N-3 | COMe | Me | H | 5-Ind | N-1 | | | |
| N-4 | COMe | H | H | 5-Ind | N-2 | C | | 457 (M⁺ + 1) |
| N-5 | COMe | Me | H | 1Me-5-Ind | N-1 | | | |
| N-6 | COMe | H | H | 1Me-5-Ind | N-2 | | | |
| N-7 | COMe | Me | H | 5-1HIdz | N-1 | | | |
| N-8 | COMe | H | H | 5-1HIdz | N-2 | | | |
| N-9 | COMe | Me | H | 1Me-5-1HIdz | N-1 | | | |
| N-10 | COMe | H | H | 1Me-5-1HIdz | N-2 | | | |
| N-11 | COPh | H | H | 2-Nap | N-1, N-2 | C | | 516 (M⁺ + 1) |
| N-12 | COPh | H | H | 1Me-5-Ind | N-1, N-2 | | | |
| N-13 | COtBu | H | H | 2-Nap | N-1, N-2 | | | |
| N-14 | COtBu | H | H | 1Me-5-Ind | N-1, N-2 | | | |
| N-15 | COiPr | H | H | 2-Nap | N-1, N-2 | C | | 496 (M⁺ + 1) |
| N-16 | COiPr | H | H | 1Me-5-Ind | N-1, N-2 | | | |
| N-17 | COCH(Et)nBu | H | H | 2-Nap | N-1, N-2 | | | |
| N-18 | COCH(Et)nBu | H | H | 1Me-5-Ind | N-1, N-2 | | | |
| N-19 | COCH₂OMe | H | H | 2-Nap | N-1, N-2 | | | |
| N-20 | COCH₂OMe | H | H | 1Me-5-Ind | N-1, N-2 | | | |
| N-21 | COCH=CHMe | H | H | 2-Nap | N-1, N-2 | | | |
| N-22 | COCH=CHMe | H | H | 1Me-5-Ind | N-1, N-2 | C | | 483 (M⁺ + 1) |
| N-23 | COiBu | H | H | 2-Nap | N-1, N-2 | | | |
| N-24 | COiBu | H | H | 1Me-5-Ind | N-1, N-2 | | | |
| N-25 | COcPr | H | H | 2-Nap | N-1, N-2 | | | |
| N-26 | COcPr | H | H | 1Me-5-Ind | N-1, N-2 | C | | 483 (M⁺ + 1) |
| N-27 | CO(CH₂)₂cPen | H | H | 2-Nap | N-1, N-2 | | | |
| N-28 | CO(CH₂)₂cPen | H | H | 1Me-5-Ind | N-1, N-2 | | | |
| N-29 | COOMe | Me | H | 2-Nap | N-29 | | | |
| N-30 | COOMe | H | H | 2-Nap | N-30 | | | |
| N-31 | COOMe | H | H | 1Me-5-Ind | N-29, N-30 | | | |
| N-32 | COOPh | H | H | 2-Nap | N-29, N-30 | C | | 516 (M⁺ + 1) |
| N-33 | COOPh | H | H | 1Me-5-Ind | N-29, N-30 | | | |
| N-34 | CONMe₂ | H | H | 2-Nap | N-29, N-30 | C | | 483 (M⁺ + 1) |
| N-35 | CONMe₂ | H | H | 1Me-5-Ind | N-29, N-30 | | | |
| N-36 | COOiBu | H | H | 2-Nap | N-29, N-30 | | | |
| N-37 | COOiBu | H | H | 1Me-5-Ind | N-29, N-30 | | | |
| N-38 | C(O)SMe | H | H | 2-Nap | N-29, N-30 | | | |
| N-39 | C(O)SMe | H | H | 1Me-5-Ind | N-29, N-30 | | | |
| N-40 | (2-methyl-2-morpholinocarbonyl group) | H | H | 2-Nap | N-29, N-30 | | | |
| N-41 | (2-methyl-2-morpholinocarbonyl group) | H | H | 1Me-5-Ind | N-29, N-30 | C | | 528 (M⁺ + 1) |

TABLE N-2

| | | | | | | | |
|---|---|---|---|---|---|---|---|
| N-42 | [pyrrolidine-C(O)- with gem-dimethyl linker] | H | H | 2-Nap | Int53, N-29 | | |
| N-43 | [pyrrolidine-C(O)- with gem-dimethyl linker] | H | H | 1Me-5-Ind | Int53, N-29 | | |
| N-44 | COO(CH$_2$)$_2$OMe | H | H | 2-Nap | Int53, N-29 | | |
| N-45 | COO(CH$_2$)$_2$OMe | H | H | 1Me-5-Ind | Int53, N-29 | | |
| N-46 | [piperidine-C(O)- with gem-dimethyl linker] | H | H | 2-Nap | Int53, N-29 | | |
| N-47 | [piperidine-C(O)- with gem-dimethyl linker] | H | H | 1Me-5-Ind | Int53, N-29 | | |
| N-48 | SO$_2$Me | Me | H | 2-Nap | N-48 | | |
| N-49 | SO$_2$Me | H | H | 2-Nap | N-49 | | |
| N-50 | SO$_2$Me | H | H | 1Me-5-Ind | N-48, N-49 | C | 493 (M$^+$ + 1) |
| N-51 | SO$_2$Ph | H | H | 2-Nap | N-48, N-49 | | |
| N-52 | SO$_2$Ph | H | H | 1Me-5-Ind | N-48, N-49 | | |
| N-53 | SO$_2$NMe$_2$ | H | H | 2-Nap | N-48, N-49 | C | 519 (M$^+$ + 1) |
| N-54 | SO$_2$NMe$_2$ | H | H | 1Me-5-Ind | N-48, N-49 | | |
| N-55 | CONHEt | Me | H | 2-Nap | N-55 | | |
| N-56 | CONHEt | H | H | 2-Nap | N-56 | C | 483 (M$^+$ + 1) |
| N-57 | CONHEt | H | H | 1Me-5-Ind | N-55, N-56 | | |
| N-58 | CONHPh | H | H | 2-Nap | N-55, N-56 | | |
| N-59 | CONHPh | H | H | 1Me-5-Ind | N-55, N-56 | | |
| N-60 | CONHcHex | H | H | 2-Nap | N-55, N-56 | | |
| N-61 | CONHcHex | H | H | 1Me-5-Ind | N-55, N-56 | C | 540 (M$^+$ + 1) |
| N-62 | CONHBn | H | H | 2-Nap | N-55, N-56 | | |
| N-63 | CONHBn | H | H | 1Me-5-Ind | N-55, N-56 | | |
| N-64 | CSNHMe | Me | H | 2-Nap | N-64 | | |
| N-65 | CSNHMe | H | H | 2-Nap | H-65 | | |
| N-66 | CSNHMe | H | H | 1Me-5-Ind | N-64, N-65 | | |
| N-67 | CSNHPh | H | H | 2-Nap | N-64, N-65 | | |
| N-68 | CSNHPh | H | H | 1Me-5-Ind | N-64, N-65 | | |
| N-69 | CSNH(3-Py) | H | H | 2-Nap | N-64, N-65 | C | 548 (M$^+$ + 1) |
| N-70 | CSNH(3-Py) | H | H | 1Me-5-Ind | N-64, N-65 | | |
| N-71 | CSNHiPr | H | H | 2-Nap | N-64, N-65 | | |
| N-72 | CSNHiPr | H | H | 1Me-5-Ind | N-64, N-65 | C | 516 (M$^+$ + 1) |
| N-73 | CSNHBn | H | H | 2-Nap | N-64, N-65 | | |
| N-74 | CSNHBn | H | H | 1Me-5-Ind | N-64, N-65 | | |

Example P-1

Synthesis of ethyl 3-[2-cyclopentylmethyloxy-3-(naphthalen-2-yl)pyridin-5-yl]propionate (Compound No. P-1)

According to the procedure described in the synthesis method of Compound No. C-1 with the modifications that the reaction was carried out for 14 hours, and the purification was performed by column chromatography (Quad, hexane:ethyl acetate=5:1), 2-naphthaleneboronic acid (119 mg), Compound No. E-1 (83 mg), 2 M aqueous sodium carbonate (0.3 ml) and (Ph$_3$P)$_4$Pd (38.1 mg) were reacted and treated to obtain the title compound (Compound No. P-1, 76 mg).

Example P-2

Synthesis of 3-[2-cyclopentylmethyloxy-3-(naphthalen-2-yl)pyridin-5-yl]propionic acid (Compound No. P-2)

According to the procedure described in the synthesis method of Intermediate 9 provided that the reaction was carried out for 2 hours, Compound No. P-1 (47.8 mg) and 2 N aqueous sodium hydroxide (0.2 ml) were reacted and treated to obtain the title compound (Compound No. P-2, 20 mg).

Example P-36

Synthesis of ethyl 3-{3-(naphthalen-2-yl)-2-[(R)-1-phenylethyloxy]pyridin-5-yl}propionate (Compound No. P-36)

According to the procedure described in the synthesis method of Compound No. C-1 with the modifications that the reaction was carried out for 2 hours, and the purification was performed by column chromatography (Quad, hexane:ethyl acetate=6:1), 2-naphthaleneboronic acid (44 mg), Compound No. E-7 (73.3 mg), 2 M aqueous sodium carbonate (120 μl) and (Ph$_3$P)$_4$Pd (21.3 mg) were reacted and treated to obtain the title compound (Compound No. P-36, 44 mg).

Example P-37

Synthesis of 3-{3-(naphthalen-2-yl)-2-[(R)-1-phenylethyloxy]pyridin-5-yl}propionic acid (Compound No. P-37)

According to the procedure described in the synthesis method of Intermediate 9, Compound No. P-36 (41.2 mg) and 2 N aqueous sodium hydroxide (0.1 ml) were reacted and treated to obtain the title compound (Compound No. P-37, 38 mg).

Example P-42

Synthesis of ethyl 3-{3-(naphthalen-2-yl)-2-[4-(trifluoromethyl)phenylmethyloxy]pyridin-5-yl}propionate (Compound No. P-42)

According to the procedure described in the synthesis method of Compound No. C-1 with the modifications that the reaction was carried out for 2 hours, and the purification was performed by column chromatography (Quad, hexane:ethyl acetate=6:1), 2-naphthaleneboronic acid (37.4 mg), Compound No. E-13 (42.4 mg), 2 M aqueous sodium carbonate (90 μl) and (Ph$_3$P)$_4$Pd (21.4 mg) were reacted and treated to obtain the title compound (Compound No. P-42, 30.4 mg).

Example P-43

Synthesis of 3-{3-(naphthalen-2-yl)-2-[4-(trifluoromethyl)phenylmethyloxy]pyridin-5-yl}propionic acid (Compound No. P-43)

According to the procedure described in the synthesis method of Intermediate 9, Compound No. P-42 (29.5 mg) and 2 N aqueous sodium hydroxide (0.15 ml) were reacted and treated to obtain the title compound (Compound No. P-43, 24.1 mg).

Examples P-1 to P-50

Typical examples of the compounds of the present invention that can be obtained by reacting and treating corresponding starting compounds using any of the methods described in the present specification including the examples described above are shown in Table-P-1 and Table-P-2.

TABLE P-1

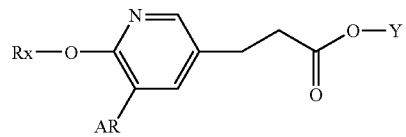

| Exp. | RxO | Y | AR | Syn | LCMS method | RTime | Mass |
|---|---|---|---|---|---|---|---|
| P-1 | cPenMeO | Et | 2-Nap | P-1 | | | |
| P-2 | cPenMeO | H | 2-Nap | P-2 | A | 5.60 | 376 (M$^+$ + 1) |
| P-3 | cPenMeO | Et | 5-Ind | P-1 | A | 5.37 | 393 (M$^+$ + 1) |
| P-4 | cPenMeO | H | 5-Ind | P-2 | | | |
| P-5 | cPenMeO | Et | 1Me-5-Ind | P-1 | | | |
| P-6 | cPenMeO | H | 1Me-5-Ind | P-2 | A | 4.90 | 379 (M$^+$ + 1) |
| P-7 | cPenMeO | Et | 1Me-5-Ind | P-1 | | | |
| P-8 | cPenMeO | H | 5-1HIdz | P-2 | | | |
| P-9 | cPenMeO | Et | 5-1HIdz | P-1 | | | |
| P-10 | cPenMeO | H | 1Me-5-1HIdz | P-2 | | | |

TABLE P-1-continued

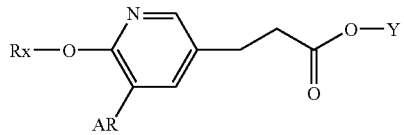

| Exp. | RxO | Y | AR | Syn | LCMS method | RTime | Mass |
|---|---|---|---|---|---|---|---|
| P-11 | cPenMeO | Et | 5-Bzt | P-1 | | | |
| P-12 | cPenMeO | H | 5-Bzt | P-2 | | | |
| P-13 | cPenMeO | Et | 5-2ABzt | P-1 | | | |
| P-14 | cPenMeO | H | 5-2ABzt | P-2 | | | |
| P-15 | cPenMeO | H | 6-IQ | P-1, P-2 | C | | 377 ($M^+ + 1$) |
| P-16 | cPenO | H | 2-Nap | P-1, P-2 | | | |
| P-17 | cPenO | H | 5-Ind | P-1, P-2 | C | | 351 ($M^+ + 1$) |
| P-18 | cPenO | H | 1Me-5-Ind | P-1, P-2 | | | |
| P-19 | cPenO | H | 5-1HIdz | P-1, P-2 | | | |
| P-20 | cPenO | H | 1Me-5-1HIdz | P-1, P-2 | | | |
| P-21 | cPenO | H | 5-Bzt | P-1, P-2 | | | |
| P-22 | cPenO | H | 5-2ABzt | P-1, P-2 | | | |
| P-23 | cHexO | H | 2-Nap | P-1, P-2 | A | 5.51 | 376 ($M^+ + 1$) |
| P-24 | cHexO | H | 5-Ind | P-1, P-2 | | | |
| P-25 | cHexO | H | 1Me-5-Ind | P-1, P-2 | | | |
| P-26 | cHexO | H | 1Me-5-1HIdz | P-1, P-2 | | | |
| P-27 | 2EtBuO | H | 2-Nap | P-1, P-2 | A | 5.68 | 378 ($M^+ + 1$) |
| P-28 | 2EtBuO | H | 5-Ind | P-1, P-2 | | | |
| P-29 | 2EtBuO | H | 1Me-5-Ind | P-1, P-2 | | | |
| P-30 | iBuO | H | 2-Nap | P-1, P-2 | A | 5.13 | 350 ($M^+ + 1$) |
| P-31 | iBuO | H | 5-Ind | P-1, P-2 | | | |
| P-32 | iBuO | H | 1Me-5-Ind | P-1, P-2 | | | |
| P-33 | iBuO | H | 1Me-5-1HIdz | P-1, P-2 | | | |
| P-34 | BnO | H | 2-Nap | P-1, P-2 | | | |
| P-35 | BnO | H | 1Me-5-Ind | P-1, P-2 | | | |
| P-36 | (R)1PhEtO | Et | 2-Nap | P-36 | | | |
| P-37 | (R)1PhEtO | H | 2-Nap | P-37 | | | |
| P-38 | (S)1PhEtO | H | 2-Nap | P-36, P37 | A | 5.31 | 398 ($M^+ + 1$) |
| P-39 | (S)1PhEtO | H | 1Me-5-Ind | P-36, P37 | A | 4.75 | 401 ($M^+ + 1$) |
| P-40 | 2MeBnO | H | 2-Nap | P-1, P-2 | | | |
| P-41 | 2MeBnO | H | 1Me-5-Ind | P-1, P-2 | | | |

TABLE P-2

| Exp. | RxO | Y | AR | Syn | LCMS method | RTime | Mass |
|---|---|---|---|---|---|---|---|
| P-42 | 4CF3BnO | Et | 2-Nap | P-42 | | | |
| P-43 | 4CF3BnO | H | 2-Nap | P-43 | A | 5.52 | 452 ($M^+ + 1$) |
| P-44 | 4CF3BnO | H | 1Me-5-Ind | P-1, P-2 | | | |
| P-45 | 3PhBuO | H | 1Me-5-Ind | P-1, P-2 | | | |
| P-46 | 2(2-Nap)EtO | H | 2-Nap | P-1, P-2 | | | |
| P-47 | 2(2-Nap)EtO | H | 1Me-5-Ind | P-1, P-2 | | | |
| P-48 | 2(2FPh)EtO | H | 2-Nap | P-1, P-2 | | | |
| P-49 | 2(2FPh)EtO | H | 5-Ind | P-1, P-2 | A | 4.18 | 405 ($M^+ + 1$) |
| P-50 | 2(2FPh)EtO | H | 1Me-5-Ind | P-1, P-2 | | | |

Example Q-1

Synthesis of methyl 3-[4-methoxy-3-(naphthalen-2-yl)-5-nitrophenyl]propionate (Intermediate 49)

According to the procedure described in the synthesis method of Compound No. C-1 with the modifications that the reaction was carried out at 80° C. for 15 hours, and the purification was performed by column chromatography (Quad, hexane:ethyl acetate=10:1), Intermediate 21 (2.65 g), 2-naphthaleneboronic acid (2.87 g), 2 M aqueous sodium carbonate (7.5 ml) and (Ph$_3$P)$_4$Pd (960 mg) were reacted and treated to obtain the title compound (Intermediate 49, 2.47 g).

Synthesis of 3-[4-methoxy-3-(naphthalen-2-yl)-5-nitrophenyl]propionic acid (Intermediate 50)

According to the procedure described in the synthesis method of Intermediate 9 provided that the reaction was carried out for 40 minutes, Intermediate 49 (2.45 g) and 2 N aqueous sodium hydroxide (6.7 ml) were reacted and treated to obtain the title compound (Intermediate 60, 1.96 g).

Synthesis of methyl 3-[4-hydroxy-3-(naphthalen-2-yl)-5-nitrophenyl]propionate (Intermediate 51)

According to the procedure described in the synthesis method of Intermediate 10 provided that the reaction was carried out for 3 hours, pyridine (10 ml), concentrated hydrochloric acid (10 ml), and Intermediate 50 (1.00 g) were reacted and treated to obtain crude powder substance. This substance was reacted with thionyl chloride (282 µl) in methanol and treated according to the procedure described in the synthesis method of Intermediate 1 to obtain the title compound (Intermediate 51, 306 mg).

Synthesis of methyl 3-[4-cyclopentyloxy-3-(naphthalen-2-yl)-5-nitrophenyl]propionate (Compound No. Q-1)

According to the procedure described in the synthesis method of Compound No. A-6 with the modifications that the reaction was carried out for 15.5 hours, and the purification was performed by column chromatography (Quad, hexane: ethyl acetate=19:1), Intermediate 51 (84 mg), Ph₃P (125 mg), cyclopentanol (50 µl) and 40% DIAD (224 µl) were reacted and treated to obtain the title compound (Compound No. Q-1, 90 mg).

Example Q-2

Synthesis of methyl 3-[3-amino-4-cyclopentyloxy-5-(naphthalen-2-yl)phenyl]propionate (Compound No. Q-2)

A solution of Compound No. Q-1 (59.1 mg) in methanol (5 ml) was added with platinum oxide (5 mg, Ald), and stirred at room temperature for 30 minutes under hydrogen atmosphere. The reaction mixture was filtered, and the solvent of the filtrate was evaporated under reduced pressure. The residue was purified by column chromatography (Quad, hexane: ethyl acetate=4:1) to obtain the title compound (Compound No. Q-2, 49 mg).

Example Q-3

Synthesis of 3-[3-amino-4-cyclopentyloxy-5-(naphthalen-2-yl)phenyl]propionic acid (Compound No. Q-3)

According to the procedure described in the synthesis method of Intermediate 9 provided that the reaction was carried out for 2 hours, Compound No. Q-2 (40 mg) and 2 N aqueous sodium hydroxide (150 µl) were reacted and treated to obtain the title compound (Compound No. Q-3, 38 mg).

Example Q-4

Synthesis of methyl 3-[4-cyclopentyloxy-3-(1H-indol-5-yl)-5-nitrophenyl]propionate (Compound No. Q-4)

According to the procedure described in the synthesis method of Compound No. C-1 with the modifications that the reaction was carried out at 80° C. for 16 hours, and the purification was performed by column chromatography (Quad, hexane:ethyl acetate=4:1), Compound No. A-28 (187 mg), 5-indoleboronic acid (143 mg), 2 M aqueous sodium carbonate (400 µl) and (Ph₃P)₄Pd (51 mg) were reacted and treated to obtain the title compound (Compound No. Q-4, 192 mg).

Example Q-5

Synthesis of methyl 3-[3-amino-4-cyclopentyloxy-5-(1H-indol-5-yl)phenyl]propionate (Compound No. Q-5)

According to the procedure described in the synthesis method of Compound No. Q-2 with the modification that the purification was performed by column chromatography (Quad, hexane:ethyl acetate=2:1), Compound No. Q-4 (59.1 mg) and platinum oxide (5 mg) were reacted and treated to obtain the title compound (Compound No. Q-5, 49.3 mg).

Example Q-6

Synthesis of 3-[3-amino-4-cyclopentyloxy-5-(1H-indol-5-yl)phenyl]propionic acid (Compound No. Q-6)

According to the procedure described in the synthesis method of Intermediate 9, Compound No. Q-5 (44 mg) and 2 N aqueous sodium hydroxide (150 µl) were reacted and treated to obtain the title compound (Compound No. Q-6, 41 mg).

Example Q-8

Synthesis of methyl 3-[4-cyclopentyloxy-3-(1-methyl-1H-indazol-5-yl)-5-nitrophenyl]propionate (Compound No. Q-8)

According to the procedure described in the synthesis method of Compound No. C-1 with the modifications that the reaction was carried out at 80° C. for 16 hours, and the purification was performed by column chromatography (Quad, hexane:ethyl acetate=3:1), Compound No. A-28 (182 mg), 1-methyl-5-indazoleboronic acid (152 mg), 2 M aqueous sodium carbonate (400 µl) and (Ph₃P)₄Pd (58.9 mg) were reacted and treated to obtain the title compound (Compound No. Q-8, 181 mg).

Example Q-9

Synthesis of methyl 3-[3-amino-4-cyclopentyloxy-5-(1-methyl-1H-indazol-5-yl)phenyl]propionic acid (Compound No. Q-9)

A solution of Compound No. Q-8 (578 mg) in a mixture of ethyl acetate (2 ml) and methanol (5 ml) was added with Raney 2800 nickel (230 mg) and stirred at room temperature for 6 hours under hydrogen atmosphere. The reaction mixture was filtered, and the solvent of the filtrate was evaporated under reduced pressure. The residue was purified by column chromatography (Quad, hexane:ethyl acetate=2:1) to obtain the title compound (Compound No. Q-9, 484 mg).

Example Q-10

Synthesis of 3-[3-amino-4-cyclopentyloxy-5-(1H-indazol-5-yl)phenyl]propionic acid (Compound No. Q-10)

According to the procedure described in the synthesis method of Intermediate 9, Compound No. Q-9 (56 mg) and 2 N aqueous sodium hydroxide (200 µl) were reacted and treated to obtain the title compound (Compound No. Q-10, 50 mg).

Example Q-47

Synthesis of methyl 3-[4-benzyloxy-3-(naphthalen-2-yl)-5-nitrophenyl]propionate (Compound No. Q-47)

According to the procedure described in the synthesis method of Compound No. C-1 with the modifications that the reaction was carried out at 80° C. for 12 hours, and the purification was performed by column chromatography (Quad, hexane:ethyl acetate=8:1), Compound No. B-95 (6.00 g), 2-naphthaleneboronic acid (4.11 g), 2 M aqueous sodium carbonate (13.5 ml) and (Ph₃P)₄Pd (1.36 g) were reacted and treated to obtain the title compound (Compound No. Q-47, 5.81 g).

Example Q-48

Synthesis of methyl 3-[3-amino-4-benzyloxy-5-(naphthalen-2-yl)phenyl]propionate (Compound No. Q-48)

According to the procedure described in the synthesis method of Compound No. Q-9 with the modifications that the reaction was carried out for 20 hours, and the purification was performed by column chromatography (Quad, hexane:ethyl acetate=2:1), Compound No. Q-47 (5.04 g) and Raney 2800 nickel (2.50 g) were reacted and treated to obtain the title compound (Compound No. Q-48, 4.21 g).

Example Q-1 to Q-52

Typical examples of the compounds of the present invention that can be obtained by reacting and treating corresponding starting compounds using any of the methods described in the present specification including the examples described above are shown in Table-Q-1.

TABLE Q-1

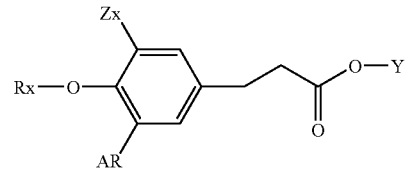

| Exp. | RxO | Y | Zx | AR | Syn | LCMS method | RTime | Mass |
|---|---|---|---|---|---|---|---|---|
| Q-1 | cPenO | Me | NO2 | 2-Nap | Q-1 | | | |
| Q-2 | cPenO | Me | NH2 | 2-Nap | Q-2 | | | |
| Q-3 | cPenO | H | NH2 | 2-Nap | Q-3 | A | 4.78 | 376 (M⁺ + 1) |
| Q-4 | cPenO | Me | NO2 | 5-Ind | Q-4 | | | |
| Q-5 | cPenO | Me | NH2 | 5-Ind | Q-5 | | | |
| Q-6 | cPenO | H | NH2 | 5-Ind | Q-6 | A | 3.75 | 365 (M⁺ + 1) |
| Q-7 | cPenO | H | NH2 | 1Me-5-Ind | Q-4, Q-5, Q-6 | A | 4.19 | 379 (M⁺ + 1) |
| Q-8 | cPenO | Me | NO2 | 1Me-5-1HIdz | Q-8 | | | |
| Q-9 | cPenO | Me | NH2 | 1Me-5-1HIdz | Q-9 | | | |
| Q-10 | cPenO | H | NH2 | 1Me-5-1HIdz | Q-10 | | | |
| Q-11 | cPenO | H | NH2 | 5-1HIdz | Q-8, Q-9, Q-10 | | | |
| Q-12 | cPenO | H | NH2 | 5-Bzt | Q-8, Q-9, Q-10 | | | |
| Q-13 | cPenO | H | NH2 | 5-2ABzt | Q-8, Q-9, Q-10 | | | |
| Q-14 | cPenO | H | NH2 | 2Me-5-Bzt | Q-8, Q-9, Q-10 | | | |
| Q-15 | cHexO | H | NH2 | 2-Nap | Q-1, Q-2, Q-3 | A | 5.66 | 404 (M⁺ + 1) |
| Q-16 | cHexO | H | NH2 | 1Me-5-Ind | Q-4, Q-5, Q-6 | | | |
| Q-17 | cHexO | H | NH2 | 1Me-5-1HIdz | Q-8, Q-9, Q-10 | | | |
| Q-18 | 2EtBuO | H | NH2 | 2-Nap | Q-1, Q-2, Q-3 | | | |
| Q-19 | 2EtBuO | H | NH2 | 5-Ind | Q-4, Q-5, Q-6 | A | 4.26 | 381 (M⁺ + 1) |
| Q-20 | 2EtBuO | H | NH2 | 1Me-5-Ind | Q-4, Q-5, Q-6 | | | |
| Q-21 | 2EtBuO | H | NH2 | 5-1HIdz | Q-8, Q-9, Q-10 | | | |
| Q-22 | 2EtBuO | H | NH2 | 1Me-5-1HIdz | Q-8, Q-9, Q-10 | | | |
| Q-23 | 2EtBuO | H | NH2 | 5-Bzt | Q-8, Q-9, Q-10 | | | |
| Q-24 | 2EtBuO | H | NH2 | 5-2ABzt | Q-8, Q-9, Q-10 | | | |
| Q-25 | 2EtBuO | H | NH2 | 2Me-5-Bzt | Q-8, Q-9, Q-10 | | | |
| Q-26 | iBuO | H | NH2 | 2-Nap | Q-1, Q-2, Q-3 | A | 4.82 | 364 (M⁺ + 1) |
| Q-29 | iBuO | H | NH2 | 1Me-5-Ind | Q-4, Q-5, Q-6 | | | |
| Q-28 | iBuO | H | NH2 | 1Me-5-1HIdz | Q-8, Q-9, Q-10 | A | 3.66 | 368 (M⁺ + 1) |
| Q-29 | (S)1PhEtO | H | NH2 | 2-Nap | Q-1, Q-2, Q-3 | A | 4.87 | 412 (M⁺ + 1) |
| Q-30 | (S)1PhEtO | H | NH2 | 1Me-5-Ind | Q-4, Q-5, Q-6 | A | 4.31 | 415 (M⁺ + 1) |
| Q-31 | (S)1PhEtO | H | NH2 | 1Me-5-1HIdz | Q-8, Q-9, Q-10 | A | 3.76 | 416 (M⁺ + 1) |
| Q-32 | 4CF₃BnO | H | NH2 | 2-Nap | Q-1, Q-2, Q-3 | A | 5.26 | 466 (M⁺ + 1) |
| Q-33 | 4CF₃BnO | H | NH2 | 1Me-5-Ind | Q-4, Q-5, Q-6 | A | 4.20 | 455 (M⁺ + 1) |
| Q-34 | 4CF₃BnO | H | NH2 | 1Me-5-1HIdz | Q-8, Q-9, Q-10 | | | |
| Q-35 | 2-IndanO | H | NH2 | 2-Nap | Q-1, Q-2, Q-3 | A | 5.10 | 424 (M⁺ + 1) |
| Q-36 | 2-IndanO | H | NH2 | 1Me-5-Ind | Q-4, Q-5, Q-6 | A | 4.63 | 427 (M⁺ + 1) |
| Q-37 | 2-IndanO | H | NH2 | 1Me-5-1HIdz | Q-8, Q-9, Q-10 | A | 4.14 | 428 (M⁺ + 1) |
| Q-38 | 5OMe-2-IndanO | H | NH2 | 2-Nap | Q-1, Q-2, Q-3 | | | |
| Q-39 | 5,6(OMe)-2-IndaO | H | NH2 | 1Me-5-Ind | Q-4, Q-5, Q-6 | | | |
| Q-40 | 5F-2-IndanO | H | NH2 | 1Me-5-1HIdz | Q-8, Q-9, Q-10 | | | |
| Q-41 | 2(4FPh)EtO | H | NH2 | 2-Nap | Q-1, Q-2, Q-3 | | | |
| Q-42 | 2(4FPh)EtO | H | NH2 | 1Me-5-Ind | Q-4, Q-5, Q-6 | | | |
| Q-43 | 2(4FPh)EtO | H | NH2 | 1Me-5-1HIdz | Q-8, Q-9, Q-10 | A | 4.48 | 448 (M⁺ + 1) |
| Q-44 | 2(4DMAPh)EtO | H | NH2 | 2-Nap | Q-1, Q-2, Q-3 | A | 4.28 | 455 (M⁺ + 1) |
| Q-45 | 2(4DMAPh)EtO | H | NH2 | 1Me-5-Ind | Q-4, Q-5, Q-6 | | | |
| Q-48 | 2(4DMAPh)EtO | H | NH2 | 1Me-5-1HIdz | Q-8, Q-9, Q-10 | A | 3.12 | 459 (M⁺ + 1) |
| Q-47 | BnO | Me | NO2 | 2-Nap | Q-47 | | | |
| Q-48 | BnO | Me | NH2 | 2-Nap | Q-48 | | | |
| Q-49 | BnO | H | NH2 | 2-Nap | Q-3 | | | |

TABLE Q-1-continued

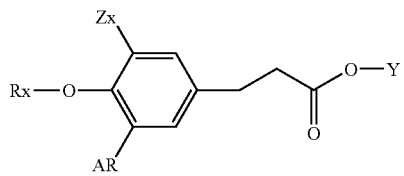

| Exp. | RxO | Y | Zx | AR | Syn | LCMS method | RTime | Mass |
|---|---|---|---|---|---|---|---|---|
| Q-50 | BnO | Me | NO2 | 1Me-5-1HIdz | Q-47 | | | |
| Q-51 | BnO | Me | NH2 | 1Me-5-1HIdz | Q-48 | | | |
| Q-52 | BnO | H | NH2 | 1Me-5-1HIdz | Q-10 | | | |

Example S-1

Synthesis of methyl 3-{4-benzyloxy-3-(naphthalen-2-yl)-5-[N-(2,2,2-trifluoroacetyl)amino]phenyl}propionate (Intermediate 52)

According to the procedure described in the synthesis method of Compound No. B-103 with the modifications that the reaction was carried out for 1.5 hours, and the purification was performed by column chromatography (Quad, hexane:ethyl acetate=4:1), Compound No. Q-48 (4.18 g), triethylamine (4.65 ml) and trifluoroacetic anhydride (7.40 ml) were reacted and treated to obtain the title compound (Intermediate 52, 4.72 g).

Synthesis of methyl 3-{4-hydroxy-3-(naphthalen-2-yl)-5-[N-(2,2,2-trifluoroacetyl)amino]phenyl}propionate (Intermediate 53)

A solution of Intermediate 52 (3.20 g) in a mixture of ethyl acetate (50 ml) and methanol (25 ml) was added with 10% palladium/carbon (98 mg), and stirred at room temperature for 2 hours under hydrogen atmosphere. The reaction mixture was filtered, and the solvent of the filtrate was evaporated under reduced pressure to obtain the title compound (Intermediate 53, 2.39 g).

Synthesis of methyl 3-{4-cyclopentyloxy-3-(naphthalen-2-yl)-5-[N-(2,2,2-trifluoroacetyl)amino]phenyl}propionate (Intermediate 54)

According to the procedure described in the synthesis method of Compound No. A-6 with the modifications that the reaction was carried out for 15.5 hours, and the purification was performed by column chromatography (Quad, hexane:ethyl acetate=19:1), Intermediate 53 (84 mg), $Ph_3P$ (125 mg), cyclopentanol (50 µl) and 40% DIAD (224 µl) were reacted and treated to obtain the title compound (Intermediate 54, 90 mg).

Synthesis of methyl 3-{4-cyclopentyloxy-3-[N-methyl-N-(2,2,2-trifluoroacetyl)amino]-5-(naphthalen-2-yl)phenyl}propionate (Intermediate 55)

A solution of Intermediate 54 (208 mg) in DMF (5 ml) was added with 60% sodium hydride (21 mg) under ice cooling, and stirred for 20 minutes. This reaction mixture was added dropwise with methyl iodide (150 µl), stirred for 10 minutes, then warmed to room temperature, and further stirred for 1 hour. The reaction mixture was poured into ice water, and ethyl acetate (100 ml) was added for extraction. The organic layer was successively washed with saturated aqueous sodium hydrogencarbonate, saturated aqueous ammonium chloride, and saturated brine and dried, and then the solvent was evaporated under reduced pressure. The residue was purified by column chromatography (Quad, hexane:ethyl acetate 5:1) to obtain the title compound (Intermediate 55, 200 mg).

Synthesis of 3-[4-cyclopentyloxy-3-(N-methylamino)-5-(naphthalen-2-yl)phenyl]propionic acid (Compound No. S-1)

According to the procedure described in the synthesis method of Intermediate 9 provided that the reaction was carried out for 6 hours, Intermediate 55 (198 mg) and 2 N aqueous sodium hydroxide (800 µl) were reacted and treated to obtain the title compound (Compound No. S-1, 38 mg).

Example S-3

Synthesis of methyl 3-[3-acetylamino-4-cyclopentyloxy-5-(naphthalen-2-yl)phenyl]propionate (Compound No. S-3)

A solution of Compound No. Q-2 (81 mg) in methylene chloride (2 ml) was added with N-methylmorpholine (33 µl, WAKO), and added with acetyl chloride (22 µl) under ice cooling. The reaction mixture was stirred for 10 minutes, then warmed to room temperature, and further stirred for 18 hours. The reaction mixture was poured into aqueous sodium hydrogencarbonate (100 ml), and added with ethyl acetate (150 ml) for extraction. The organic layer was successively washed with saturated aqueous sodium hydrogencarbonate, saturated aqueous ammonium chloride, and saturated brine and dried, and then the solvent was evaporated under reduced pressure. The residue was purified by column chromatography (Quad, hexane:ethyl acetate=6:1) to obtain the title compound (Compound No. S-3, 85 mg).

Example S-4

Synthesis of 3-[3-acetylamino-4-cyclopentylmethyloxy-5-(naphthalen-2-yl)phenyl]propionic acid (Compound No. S-4)

According to the procedure described in the synthesis method of Intermediate 9 provided that the reaction was carried out for 15 hours, Compound No. S-3 (80 mg) and 2 N aqueous sodium hydroxide (400 µl) were reacted and treated to obtain the title compound (Compound No. S-4, 75 mg).

Example S-5

Synthesis of 3-[4-cyclopentyloxy-3-formylamino-5-(naphthalen-2-yl)phenyl]propionic acid (Compound No. S-5)

A solution of Compound No. Q-2 (90 mg) in DMF (5 ml) was added with a mixture of formic acid (200 µl) and acetic anhydride (100 µl) under ice cooling. The reaction mixture was stirred 10 minutes, then warmed to room temperature, and further stirred for 18 hours. The reaction mixture was poured into aqueous sodium hydrogencarbonate (100 ml), and added with ethyl acetate (150 ml) for extraction. The organic layer was successively washed with saturated aqueous sodium hydrogencarbonate, saturated aqueous ammonium chloride, and saturated brine and dried, and then the solvent was evaporated under reduced pressure. The residue was purified by column chromatography (Quad, hexane:ethyl acetate=5:1). The obtained substance was reacted and treated with 2N aqueous sodium hydroxide (400 µl) according to the procedure described in the synthesis method of Intermediate 9 to obtain the title compound (Compound No. S-5, 65 mg).

Example S-6

Synthesis of methyl 3-[3-(2-acetoxyacetylamino)-4-cyclopentyloxy-5-(naphthalen-2-yl)phenyl]propionate (Compound No. S-6)

According to the procedure described in the synthesis method of Intermediate 70, Compound No. Q-2 (88 mg), N-methylmorpholine (36 µl) and acetoxyacetyl chloride (35 µl, Ald) were reacted and treated to obtain the title compound (Compound No. S-6, 75 mg).

Example S-7

Synthesis of 3-[4-cyclopentyloxy-3-(2-hydroxyacetylamino)-5-(naphthalen-2-yl)phenyl]propionic acid (Compound No. S-7)

According to the procedure described in the synthesis method of Intermediate 9 provided that the reaction was carried out for 15.5 hours, Compound No. S-6 (102 mg) and 2 N aqueous sodium hydroxide (500 µl) were reacted and treated to obtain the title compound (Compound No. S-7, 80 mg).

Example S-8

Synthesis of 3-[3-carbamoylamino-4-cyclopentyloxy-5-(naphthalen-2-yl)phenyl]propionic acid (Compound No. S-8)

A solution of Compound No. Q-2 (100 mg) in a mixture of acetic acid (2 ml) and purified water (0.4 ml) was added with potassium cyanate (45 mg, Wako Pure Chemical Industries), and stirred at room temperature for 1 hour. The reaction mixture was poured into water (50 ml) containing ice, and extracted with isopropyl ether (150 ml×2). The organic layer was successively washed with saturated aqueous sodium hydrogencarbonate, saturated aqueous ammonium chloride, and saturated brine and dried, and then the solvent was evaporated under reduced pressure. The obtained substance was reacted with 2 N aqueous sodium hydroxide (300 µl) and treated according to the procedure described in the synthesis method of Intermediate 9 to obtain the title compound (Compound No. S-8, 70 mg).

Example S-9

Synthesis of methyl 3-[4-cyclopentyloxy-3-methylsulfonylamino-5-(naphthalen-2-yl)phenyl]propionate (Compound No. S-9)

A solution of Compound No. Q-2 (81 mg) in methylene chloride (2 ml) was added with pyridine (300 µl), and then added with methanesulfonyl chloride (40 µl) under ice cooling. The reaction mixture was stirred for 10 minutes, then warmed to room temperature, and further stirred for 2 hours. The reaction mixture was poured into 1 N hydrochloric acid, and added with ethyl acetate (150 ml) for extraction. The organic layer was washed successively with saturated aqueous sodium hydrogencarbonate, and saturated brine, and dried, and then the solvent of the organic layer was evaporated under reduced pressure. The residue was purified by column chromatography (Quad, hexane:ethyl acetate=13:2) to obtain the title compound (Compound No. S-9, 96 mg).

Synthesis of 3-[4-cyclopentyloxy-3-methylsulfonylamino-5-(naphthalen-2-yl)phenyl]propionic acid (Compound No. S-10)

According to the procedure described in the synthesis method of Intermediate 9 provided that the reaction was carried out at room temperature for 17.5 hours and at 60° C. for 3 hours, Compound No. S-9 (81 mg) and 2 N aqueous sodium hydroxide (400 µl) were reacted and treated to obtain the title compound (Compound No. S-10, 80 mg).

Example S-11

Synthesis of 3-[4-cyclopentyloxy-3-(N,N-dimethylsulfamoylamino)-5-(naphthalen-2-yl)phenyl]propionic acid (Compound No. S-11)

A solution of Compound No. Q-2 (163 mg) in pyridine (5 ml) was successively added with 4-dimethylaminopyridine (104 mg, TCI) and dimethylsulfamoyl chloride (520 µl, TCI), and stirred for 5 days. The reaction mixture was added with water (30 ml) and ethyl acetate (90 ml) for extraction. The organic layer was washed with saturated brine and dried, and then the solvent was evaporated under reduced pressure. The residue was purified by column chromatography (Quad, hexane:ethyl acetate=6:1). The obtained substance was reacted with 2 N aqueous sodium hydroxide (300 µl) and treated according to the procedure described in the synthesis method of Intermediate 9 to obtain the title compound (Compound No. S-11, 105 mg).

Example S-12

Synthesis of 3-[4-cyclopentyloxy-3-(N,N-dimethylamino)-5-(naphthalen-2-yl)phenyl]propionic acid (Compound No. S-12)

A solution of Compound No. Q-2 (60 mg) in DMF (3 ml) was added with 60% sodium hydride (26 mg) under ice cooling, and stirred for 10 minutes. The reaction mixture was added with methyl iodide (100 µl), stirred for 10 minutes, then warmed to 60° C., and further stirred for 2 hours. The reaction mixture was poured into water (20 ml), and ethyl acetate (50 ml) was added for extraction. The organic layer was successively washed with saturated aqueous sodium hydrogencarbonate, saturated aqueous ammonium chloride, and saturated brine and dried, and then the solvent was evaporated under reduced pressure. The residue was purified by column chromatography (Quad, hexane:ethyl acetate=8:1). The obtained substance was reacted with 2 N aqueous sodium hydroxide (150 μl) and treated according to the procedure described in the synthesis method of Intermediate 9 to obtain the title compound (Compound No. S-12, 46 mg).

Synthesis of methyl 3-{4-benzyloxy-3-(1-methyl-1H-indazol-5-yl)-5-[N-(2,2,2-trifluoroacetyl)amino]phenyl}propionate (Intermediate 56)

According to the procedure described in the synthesis method of Compound No. B-103 with the modifications that the reaction was carried out for 1.5 hours, and the purification was performed by column chromatography (Quad, hexane: ethyl acetate=3:1), Compound No. Q-51 (2.09 g), triethylamine (3.70 ml) and trifluoroacetic anhydride (2.35 ml) were reacted and treated to obtain the title compound (Intermediate 56, 2.36 g).

Synthesis of methyl 3-{4-hydroxy-3-(1-methyl-1H-indazol-5-yl)-5-[N-(2,2,2-trifluoroacetyl)amino]phenyl}propionate (Intermediate 57)

A solution of Intermediate 56 (1.62 g) in a mixture of ethyl acetate (10 ml) and methanol (3 ml) was added with 10% palladium/carbon (29 mg), and stirred at room temperature for 17 hours under hydrogen atmosphere. The reaction mixture was filtered, and the solvent of the filtrate was evaporated under reduced pressure to obtain the title compound (Intermediate 57, 1.19 g).

Examples S-1 to S-73

Typical examples of the compounds of the present invention that can be obtained by reacting and treating corresponding starting compounds using any of the methods described in the present specification including the examples described above are shown in Table-S-1 and Table-S-2.

TABLE S-1

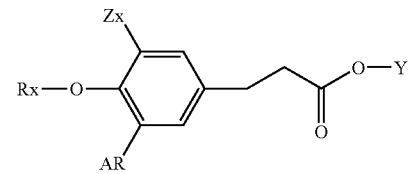

| Exp. | RxO | Y | Zx | AR | Syn | LCMS method | RTime | Mass |
|---|---|---|---|---|---|---|---|---|
| S-1 | cPenO | H | NHMe | 2-Nap | S-1 | | | |
| S-2 | cPenO | H | NHEt | 2-Nap | S-1 | | | |
| S-3 | cPenO | Me | NHAc | 2-Nap | S-3 | | | |
| S-4 | cPenO | H | NHAc | 2-Nap | S-4 | C | | 421($M^+$ + 1) |
| S-5 | cPenO | H | NHCHO | 2-Nap | S-5 | C | | 407($M^+$ + 1) |
| S-6 | cPenO | H | NHCOCH$_2$OAc | 2-Nap | S-6 | | | |
| S-7 | cPenO | H | NHCOCH$_2$OH | 2-Nap | S-7 | C | | 437($M^+$ + 1) |
| S-8 | cPenO | H | NHCONH$_2$ | 2-Nap | S-8 | C | | 422($M^+$ + 1) |
| S-9 | cPenO | Me | NHSO$_2$Me | 2-Nap | S-9 | | | |
| S-10 | cPenO | H | NHSO$_2$Me | 2-Nap | S-10 | C | | 456($M^+$) |
| S-11 | cPenO | H | NHSO$_2$NMe$_2$ | 2-Nap | S-11 | C | | 483($M^+$ + 1) |
| S-12 | cPenO | H | NMe$_2$ | 2-Nap | S-12 | | | |
| S-13 | cPenO | H | NHMe | 1Me-5-Ind | S-1 | | | |
| S-14 | cPenO | H | NMe$_2$ | 1Me-S-Ind | S-12 | C | | 407($M^+$ + 1) |
| S-15 | cPenO | H | NHMe | 1Me-5-1HIdz | S-1 | C | | 394($M^+$ + 1) |
| S-16 | cPenO | H | NMe$_2$ | 1Me-5-1HIdz | S-12 | | | |
| S-17 | cPenO | H | NHMe | 5-Bzt | S-1 | | | |
| S-18 | cPenO | H | NMe$_2$ | 5-Bzt | S-12 | | | |
| S-19 | cPenO | H | NHMe | 5-2ABzt | S-1 | | | |
| S-20 | cPenO | H | NMe$_2$ | 5-2ABzt | S-12 | | | |
| S-21 | cPenO | H | NHMe | 2Me-5-Bzt | S-1 | | | |
| S-22 | cPenO | H | NMe$_2$ | 2Me-5-Bzt | S-12 | | | |
| S-23 | cPenMeO | H | NHMe | 1Me-5-Ind | S-1 | | | |
| S-24 | cPenMeO | H | NMe$_2$ | 1Me-5-Ind | S-12 | | | |
| S-25 | cPenMeO | H | NHMe | 1Me-5-1HIdz | S-1 | | | |
| S-26 | cPenMeO | H | NMe$_2$ | 1Me-5-1HIdz | S-12 | | | |
| S-27 | cHexO | H | NHMe | 2-Nap | S-1 | | | |
| S-28 | cHexO | H | NMe$_2$ | 2-Nap | S-12 | | | |
| S-29 | cHexO | H | NHMe | 1Me-5-Ind | S-1 | C | | 421($M^+$ + 1) |
| S-30 | cHexO | H | NMe$_2$ | 1Me-5-Ind | S-12 | | | |
| S-31 | cHexO | H | NHMe | 1Me-5-1HIdz | S-1 | | | |
| S-32 | cHexO | H | NMe$_2$ | 1Me-5-1HIdz | S-12 | | | |
| S-33 | 2EtBuO | H | NHMe | 2-Nap | S-1 | C | | 406($M^+$ + 1) |
| S-34 | 2EtBuO | H | NHMe | 6-OMe-2-Nap | S-1 | | | |
| S-35 | 2EtBuO | H | NHMe | 1Me-5-Ind | S-1 | | | |
| S-36 | 2EtBuO | H | NHMe | 5-Bzt | S-1 | | | |
| S-37 | 2EtBuO | H | NHMe | 1Me-5-1HIdz | S-1 | | | |

TABLE S-1-continued

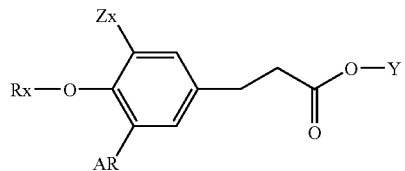

| Exp. | RxO | Y | Zx | AR | Syn | LCMS method | RTime | Mass |
|---|---|---|---|---|---|---|---|---|
| S-38 | iBuO | H | NHMe | 2-Nap | S-1 | | | |
| S-39 | iBuO | H | NMe$_2$ | 2-Nap | S-12 | C | | 392(M$^+$ + 1) |
| S-40 | iBuO | H | NHMe | 1Me-5-Ind | S-1 | C | | 381(M$^+$ + 1) |
| S-41 | iBuO | H | NMe$_2$ | 1Me-5-Ind | S-12 | | | |
| S-42 | iBuO | H | NHMe | 1Me-5-1HIdz | S-1 | | | |
| S-43 | iBuO | H | NMe$_2$ | 1Me-5-1HIdz | S-12 | | | |
| S-44 | 1PhEtO | H | NHMe | 2-Nap | S-1 | C | | 426(M$^+$ + 1) |
| S-45 | 1PhEtO | H | NMe$_2$ | 2-Nap | S-12 | | | |

TABLE S-2

| S-46 | 1PhEtO | H | NHMe | 1Me-5-Ind | S-1 | | | |
|---|---|---|---|---|---|---|---|---|
| S-47 | 1PhEtO | H | NMe$_2$ | 1Me-5-Ind | S-12 | C | | 443(M$^+$ + 1) |
| S-48 | 1PhEtO | H | NHMe | 1Me-5-1HIdz | S-1 | C | | 429(M$^+$ + 1) |
| S-49 | 1PhEtO | H | NMe$_2$ | 1Me-5-1HIdz | S-12 | | | |
| S-50 | 4CF$_3$BnO | H | NHMe | 2-Nap | S-1 | | | |
| S-51 | 4CF$_3$BnO | H | NMe$_2$ | 2-Nap | S-12 | | | |
| S-52 | 4CF$_3$BnO | H | NHMe | 1Me-5-Ind | S-1 | | | |
| S-53 | 4CF$_3$BnO | H | NMe$_2$ | 1Me-5-Ind | S-12 | C | | 497(M$^+$ + 1) |
| S-54 | 4CF$_3$BnO | H | NHMe | 1Me-5-1HIdz | S-1 | | | |
| S-55 | 4CF$_3$BnO | H | NMe$_2$ | 1Me-5-1HIdz | S-12 | | | |
| S-56 | 2-IndanO | H | NHMe | 2-Nap | S-1 | | | |
| S-57 | 2-IndanO | H | NMe$_2$ | 2-Nap | S-12 | | | |
| S-58 | 2-IndanO | H | NHMe | 1Me-5-Ind | S-1 | C | | 441(M$^+$ + 1) |
| S-59 | 2-IndanO | H | NMe$_2$ | 1Me-5-Ind | S-12 | | | |
| S-60 | 2-IndanO | H | NHMe | 1Me-5-1HIdz | S-1 | A | 4.16 | 442(M$^+$ + 1) |
| S-61 | 2-IndanO | H | NMe$_2$ | 1Me-5-1HIdz | S-1 | A | 4.18 | 456(M$^+$ + 1) |
| S-62 | 2(4FPh)EtO | H | NHMe | 2-Nap | S-1 | | | |
| S-63 | 2(4FPh)EtO | H | NMe$_2$ | 2-Nap | S-12 | C | | 458(M$^+$ + 1) |
| S-64 | 2(4FPh)EtO | H | NHMe | 1Me-5-Ind | S-1 | C | | 447(M$^+$ + 1) |
| S-65 | 2(4FPh)EtO | H | NMe$_2$ | 1Me-5-Ind | S-12 | | | |
| S-66 | 2(4FPh)EtO | H | NHMe | 1Me-5-1HIdz | S-1 | | | |
| S-67 | 2(4FPh)EtO | H | NMe$_2$ | 1Me-5-1HIdz | S-12 | | | |
| S-68 | 2(4DMAPh)EtO | H | NHMe | 2-Nap | S-1 | C | | 469(M$^+$ + 1) |
| S-69 | 2(4DMAPh)EtO | H | NMe$_2$ | 2-Nap | S-12 | | | |
| S-70 | 2(4DMAPh)EtO | H | NHMe | 1Me-5-Ind | S-1 | | | |
| S-71 | 2(4DMAPh)EtO | H | NMe$_2$ | 1Me-5-Ind | S-12 | C | | 486(M$^+$ + 1) |
| S-72 | 2(4DMAPh)EtO | H | NHMe | 1Me-5-1HIdz | S-1 | C | | 473(M$^+$ + 1) |
| S-73 | 2(4DMAPh)EtO | H | NMe$_2$ | 1Me-5-1HIdz | S-12 | | | |

Example T-1

Synthesis of 3-[4-cyclopentylmethyloxy-3-hydroxy-5-(naphthalen-2-yl)phenyl]propionic acid (Compound No. T-1)

A solution of Compound No. Q-2 (403 mg) in acetic acid (1.5 ml) was added with 20% sulfuric acid (1.0 ml). This reaction mixture was added dropwise with an aqueous solution (0.5 ml) of sodium nitrite (76 mg) over 10 minutes while keeping the temperature of the reaction mixture below 10° C., and further stirred for 5 minutes. This reaction solution was added to a solution of sodium acetate (328 mg) in acetic acid (3.5 ml) heated and stirred at 100° C. beforehand, and further stirred for 10 minutes with heating. The reaction solution was poured into ice water (50 ml), and extracted with isopropyl ether (100 ml×2). The organic layer was washed successively with saturated aqueous sodium hydrogencarbonate, saturated aqueous ammonium chloride and saturated brine and dried, and then the solvent was evaporated under reduced pressure. The residue was purified by column chromatography (Quad, hexane:ethyl acetate=10:1). The obtained substance was reacted with 2 N aqueous sodium hydroxide (500 μl) and treated according to the procedure described in the synthesis method of Intermediate 9 to obtain the title compound (Compound No. T-1, 78 mg).

Example T-2

Synthesis of ethyl 3-[3-acetoxy-4-cyclopentyloxy-5-(naphthalen-2-yl)phenyl]propionate (Intermediate 58)

According to the procedure described in the synthesis method of Compound No. C-1 with the modifications that the reaction was carried out for 13 hours, and the purification was performed by column chromatography (Quad, hexane:ethyl acetate=9:1), Compound No. B-114 (160 mg), 2-naphthaleneboronic acid (382 mg, Ald), 2 M aqueous sodium carbonate (0.7 ml) and (Ph₃P)₄Pd (105 mg) were reacted and treated to obtain the title compound (Intermediate 58, 152 mg).

Synthesis of 3-[4-cyclopentyloxy-3-hydroxy-5-(naphthalen-2-yl)phenyl]propionic acid (Compound No. T-2)

According to the procedure described in the synthesis method of Intermediate 9 provided that the reaction was carried out for 2 hours, Intermediate 58 (146 mg) and 2 N aqueous sodium hydroxide (0.35 ml) were reacted and treated to obtain the title compound (Compound No. T-2, 135 mg).

Example T-31

Synthesis of ethyl 3-[4-cyclopentyloxy-3-methoxy-5-(naphthalen-2-yl)phenyl]propionate (Compound No. T-31)

According to the procedure described in the synthesis method of Compound No. C-1 with the modifications that the reaction was carried out for 14 hours, and the purification was performed by column chromatography (Quad, hexane:ethyl acetate=9:1), Compound No. A-25 (210 mg), 2-naphthaleneboronic acid (184 mg), 2 M aqueous sodium carbonate (0.5 ml) and (Ph₃P)₄Pd (65.3 mg) were reacted and treated to obtain the title compound (Compound No. T-31, 181 mg).

Example T-32

Synthesis of 3-[4-cyclopentyloxy-3-methoxy-5-(naphthalen-2-yl)phenyl]propionic acid (Compound No. T-32)

According to the procedure described in the synthesis method of Intermediate 9 provided that the reaction was carried out for 2 hours, Compound No. T-31 (166 mg) and 2 N aqueous sodium hydroxide (0.45 ml) were reacted and treated to obtain the title compound (Compound No. T-32, 135 mg).

Example T-33

Synthesis of 4-(t-butyldimethylsilyloxy)-3-(1H-indol-5-yl)-5-methoxybenzaldehyde (Intermediate 59)

According to the procedure described in the synthesis method of Compound No. C-1 with the modifications that the reaction was carried out for 12.5 hours, and the purification was performed by flash column chromatography (hexane:ethyl acetate=7:1), 5-indoleboronic acid (1.29 g), Intermediate 16 (1.75 g), 2 M aqueous sodium carbonate (4.8 ml) and (Ph₃P)₄Pd (400 mg) were reacted and treated to obtain the title compound (Intermediate 59, 910 mg).

Synthesis of ethyl 3-[4-(t-butyldimethylsilyloxy)-3-(1H-indol-5-yl)-5-methoxyphenyl]acrylate (Intermediate 60)

According to the procedure described in the synthesis method of Intermediate 7 with the modifications that the reaction was carried out for 1.5 hours, and the purification was performed by flash column chromatography (hexane:ethyl acetate=3:1), Intermediate 59 (910 mg), ethyl diethylphosphonoacetate (500 µl) and 60% sodium hydride (100 mg) were reacted and treated to obtain the title compound (Intermediate 60, 945 mg).

Synthesis of ethyl 3-[4-(t-butyldimethylsilyloxy)-3-(1H-indol-5-yl)-5-methoxyphenyl]propionate (Intermediate 61)

According to the procedure described in the synthesis method of Intermediate 8, Intermediate 60 (945 mg) and 10% palladium/carbon (95 mg) were reacted and treated under hydrogen gas atmosphere to obtain the title compound (Intermediate 61, 940 mg).

Synthesis of ethyl 3-[4-hydroxy-3-(1H-indol-5-yl)-5-methoxyphenyl]propionate (Intermediate 62)

According to the procedure described in the synthesis method of Intermediate 19 with the modifications that the reaction was carried out for 1.5 hours, and the purification was performed by flash column chromatography (hexane:ethyl acetate=2:1), Intermediate 61 (750 mg) and a 1 M solution of tetrabutylammonium fluoride in THF (5.0 ml) were reacted and treated to obtain the title compound (Intermediate 62, 555 mg).

Synthesis of ethyl 3-[4-cyclopentyloxy-3-(1H-indol-5-yl)-5-methoxyphenyl]propionate (Compound No. T-33)

According to the procedure described in the synthesis method of Compound No. A-6 with the modifications that the reaction was carried out for 16 hours, and the purification was performed by column chromatography (Quad, hexane:ethyl acetate=7:1), Intermediate 62 (340 mg), Ph₃P (1.31 g), cyclopentanol (450 µl) and TMAD (860 mg) were reacted and treated to obtain the title compound (Compound No. T-33, 376 mg).

Example T-34

Synthesis of 3-[4-cyclopentyloxy-3-(1H-indol-5-yl)-5-methoxyphenyl]propionic acid (Compound No. T-34)

According to the procedure described in the synthesis method of Intermediate 9 provided that the reaction was carried out for 2 hours, Compound No. T-33 (99 mg) and 2 N aqueous sodium hydroxide (500 µl) were reacted and treated to obtain the title compound (Compound No. T-34, 76 mg).

Examples T-1 to T-61

Typical examples of the compounds of the present invention that can be obtained by reacting and treating corresponding starting compounds using any of the methods described in the present specification including the examples described above are shown in Table-T-1 and Table T-2.

TABLE T-1

| Exp. | RxO | Y | Zx | AR | Syn | LCMS method | RTime | Mass |
|---|---|---|---|---|---|---|---|---|
| T-1 | cPenMeO | H | OH | 2-Nap | T-1 | A | 5.03 | 382 (M⁺ + 1) |
| T-2 | cPenO | H | OH | 2-Nap | T-2 | | | |
| T-3 | cPenO | H | OH | 5-Ind | Int73, T-2 | C | | 366 (M⁺ + 1) |
| T-4 | cPenO | H | OH | 1Me-5-Ind | Int73, T-2 | | | |
| T-5 | cPenO | H | OH | 5-1HIdz | Int73, T-2 | | | |
| T-6 | cPenO | H | OH | 1Me-5-Idz | Int73, T-2 | C | | 381 (M⁺ + 1) |
| T-7 | cHexO | H | OH | 2-Nap | T-1 | | | |
| T-8 | cHexO | H | OH | 1Me-5-Ind | T-1 | | | |
| T-9 | cHexO | H | OH | 1Me-5-Idz | T-1 | | | |
| T-10 | 2EtBuO | H | OH | 2-Nap | T-1 | C | | 393 (M⁺ + 1) |
| T-11 | 2EtBuO | H | OH | 1Me-5-Ind | T-1 | | | |
| T-12 | 2EtBuO | H | OH | 1Me-5-Idz | T-1 | | | |
| T-13 | iBuO | H | OH | 2-Nap | T-1 | | | |
| T-14 | iBuO | H | OH | 1Me-5-Ind | T-1 | | | |
| T-15 | iBuO | H | OH | 1Me-5-Idz | T-1 | | | |
| T-16 | 1PhEtO | H | OH | 2-Nap | T-1 | | | |
| T-17 | 1PhEtO | H | OH | 1Me-5-Ind | T-1 | C | | 416 (M⁺ + 1) |
| T-18 | 1PhEtO | H | OH | 1Me-5-Idz | T-1 | | | |
| T-19 | 4CF₃BnO | H | OH | 2-Nap | T-1 | | | |
| T-20 | 4CF₃BnO | H | OH | 1Me-5-Ind | T-1 | | | |
| T-21 | 4CF₃BnO | H | OH | 1Me-5-Idz | T-1 | | | |
| T-22 | 2-IndanO | H | OH | 2-Nap | T-1 | | | |
| T-23 | 2-IndanO | H | OH | 1Me-5-Ind | T-1 | | | |
| T-24 | 2-IndanO | H | OH | 1Me-5-Idz | T-1 | A | 3.91 | 429 (M⁺ + 1) |
| T-25 | 2(4FPh)EtO | H | OH | 2-Nap | T-1 | | | |
| T-26 | 2(4FPh)EtO | H | OH | 1Me-5-Ind | T-1 | | | |
| T-27 | 2(4FPh)EtO | H | OH | 1Me-5-Idz | T-1 | | | |
| T-28 | 2(4DMAPh)EtO | H | OH | 2-Nap | T-1 | | | |
| T-29 | 2(4DMAPh)EtO | H | OH | 1Me-5-Ind | T-1 | C | | 459 (M⁺ + 1) |
| T-30 | 2(4DMAPh)EtO | H | OH | 1Me-5-Idz | T-1 | | | |
| T-31 | cPenO | Et | OMe | 2-Nap | T-31 | | | |
| T-32 | cPenO | H | OMe | 2-Nap | T-32 | | | |
| T-33 | cPenO | Et | OMe | 5-Ind | T-33 | | | |
| T-34 | cPenO | H | OMe | 5-Ind | T-34 | | | |
| T-35 | cPenO | H | OMe | 1Me-5-Ind | T-33, T-34 | A | 4.72 | 394 (M⁺ + 1) |
| T-36 | cPenO | H | OMe | 5-1HIdz | T-31, T-32 | | | |
| T-37 | cPenO | H | OMe | 1Me-5-Idz | T-31, T-32 | | | |
| T-38 | cHexO | H | OMe | 2-Nap | T-31, T-32 | C | | 405 (M⁺ + 1) |
| T-39 | cHexO | H | OMe | 1Me-5-Ind | T-33, T-34 | | | |
| T-40 | cHexO | H | OMe | 1Me-5-Idz | T-31, T-32 | | | |
| T-41 | 2EtBuO | H | OMe | 2-Nap | T-31, T-32 | | | |
| T-42 | 2EtBuO | H | OMe | 1Me-5-Ind | T-33, T-34 | | | |
| T-43 | 2EtBuO | H | OMe | 1Me-5-Idz | T-31, T-32 | | | |

TABLE T-2

| T-44 | iBuO | H | OMe | 2-Nap | T-31, T-32 | | | |
|---|---|---|---|---|---|---|---|---|
| T-45 | iBuO | H | OMe | 1Me-5-Ind | T-33, T-34 | | | |
| T-46 | iBuO | H | OMe | 1Me-5-1HIdz | T-31, T-32 | C | | 382 (M⁺ + 1) |
| T-47 | 1PhEtO | H | OMe | 2-Nap | T-31, T-32 | | | |
| T-48 | 1PhEtO | H | OMe | 1Me-5-Ind | T-33, T-34 | | | |
| T-49 | 1PhEtO | H | OMe | 1Me-5-1HIdz | T-31, T-32 | C | | 431 (M⁺ + 1) |
| T-50 | 4CF₃BnO | H | OMe | 2-Nap | T-31, T-32 | | | |
| T-51 | 4CF₃BnO | H | OMe | 1Me-5-Ind | T-33, T-34 | | | |
| T-52 | 4CF₃BnO | H | OMe | 1Me-5-1HIdz | T-31, T-32 | | | |
| T-53 | 2-IndanO | H | OMe | 2-Nap | T-31, T-32 | | | |
| T-54 | 2-IndanO | H | OMe | 1Me-5-Ind | T-33, T-34 | | | |
| T-55 | 2-IndanO | H | OMe | 1Me-5-1HIdz | T-31, T-32 | C | | 443 (M⁺ + 1) |
| T-56 | 2(4FPh)EtO | H | OMe | 2-Nap | T-31, T-32 | | | |
| T-57 | 2(4FPh)EtO | H | OMe | 1Me-5-Ind | T-33, T-34 | C | | 448 (M⁺ + 1) |
| T-58 | 2(4FPh)EtO | H | OMe | 1Me-5-1HIdz | T-31, T-32 | | | |

TABLE T-2-continued

| T-59 | 2(4DMAPh)EtO | H | OMe | 2-Nap | T-31, T-32 | C | 470(M+ + 1) |
| T-60 | 2(4DMAPh)EtO | H | OMe | 1Me-5-Ind | T-33, T-34 | | |
| T-61 | 2(4DMAPh)EtO | H | OMe | 1Me-5-1HIdz | T-31, T-32 | | |

Example U-1

Synthesis of 4-cyclohexylmethyloxy-3-(naphthalen-2-yl)phenylacetonitrile (Intermediate 63)

A solution of Compound No. C-1 (172 mg) in dehydrated THF (5 ml) was added successively with trimethylsilylnitrile (133 µl, TCI) under ice cooling and zinc iodide (16 mg, WAKO) under argon gas atmosphere, stirred for 15 minutes, then warmed to room temperature, and further stirred for 27 hours. The reaction mixture was added with ethyl acetate (90 ml), and washed successively with saturated aqueous sodium hydrogencarbonate, saturated aqueous ammonium chloride and saturated brine. The organic layer was dried, and then the solvent was evaporated under reduced pressure. A solution of the residue in anhydrous methylene chloride (5 ml) was added with triethylsilane (240 µl, TCI) under ice cooling and boron trifluoride diethyl ether complex (366 µl, TCI) under argon gas atmosphere, warmed to room temperature, and stirred for 3.5 hours. The reaction mixture was poured into ice water (50 ml), and extracted with ethyl acetate (90 ml). The organic layer was successively washed with saturated aqueous sodium hydrogencarbonate, saturated aqueous ammonium chloride, and saturated brine and dried, and then the solvent was evaporated under reduced pressure. The residue was purified by column chromatography (Quad, hexane:ethyl acetate=10:1) to obtain the title compound (Intermediate 63, 116 mg).

Synthesis of 4-cyclohexylmethyloxy-3-(naphthalen-2-yl)phenylacetic acid (Compound No. U-1)

According to the procedure described in the synthesis method of Intermediate 9 with the modifications that the reaction was carried out for 24 hours under reflux by heating, and the purification was performed by column chromatography (Quad, hexane:ethyl acetate=2:1), Intermediate 63 (110 mg) and 5 N aqueous sodium hydroxide (900 µl) were reacted and treated to obtain the title compound (Compound No. U-1, 62 mg).

Example U-10

Synthesis of methyl 4-[4-cyclopentylmethyloxy-3-(naphthalen-2-yl)phenyl]butyrate (Compound No. U-10)

According to the procedure described in the synthesis method of Compound No. C-1 with the modifications that the reaction was carried out for 18 hours, and the purification was performed by column chromatography (Quad, hexane:isopropyl ether=8:1), Compound No. F-1 (355 mg), 2-naphthaleneboronic acid (344 mg), 2 M aqueous sodium carbonate (2.1 ml) and $(Ph_3P)_4Pd$ (115 mg) were reacted and treated to obtain the title compound (Compound No. U-10, 392 mg).

Example U-11

Synthesis of 4-[4-cyclopentylmethyloxy-3-(naphthalen-2-yl)phenyl]butyric acid (Compound No. U-11)

According to the procedure described in the synthesis method of Intermediate 9 provided that the reaction was carried out for 3.5 hours, Compound No. U-10 (380 mg) and 2 N aqueous sodium hydroxide (1.0 ml) were reacted and treated to obtain the title compound (Compound No. U-11, 342 mg).

Examples U-1 to U-18

Typical examples of the compounds of the present invention that can be obtained by reacting and treating corresponding starting compounds using any of the methods described in the present specification including the examples described above are shown in Table-U-1.

TABLE U-1

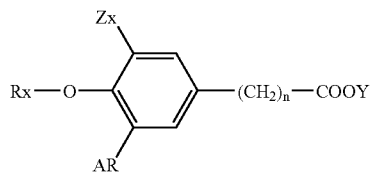

| | | | | | | | LCMS | |
| Exp. | RxO | Y | Zx | n | AR | Syn | method | RTime | Mass |
|---|---|---|---|---|---|---|---|---|---|
| U-1 | cHexMeO | H | H | 1 | 2-Nap | U-1 | C | | 374 (M+) |
| U-2 | cHexMeO | H | H | 1 | 1Me-5-Ind | Int63, U-1 | | | |
| U-3 | cHexMeO | H | H | 1 | 1Me-5-Idz | Int63, U-1 | | | |
| U-4 | cPenMeO | H | H | 1 | 2-Nap | Int63, U-1 | C | | 360 (M+) |
| U-5 | cPenMeO | H | H | 1 | 1Me-5-Ind | Int63, U-1 | | | |
| U-6 | cPenO | H | H | 1 | 2-Nap | Int63, U-1 | | | |
| U-7 | cPenO | H | H | 1 | 1Me-5-Ind | Int63, U-1 | C | | 349 (M+) |
| U-8 | 2(4FPh)EtO | H | H | 1 | 2-Nap | Int63, U-1 | | | |
| U-9 | 2(4FPh)EtO | H | H | 1 | 1Me-5-Ind | Int63, U-1 | | | |
| U-10 | cPenMeO | Me | H | 3 | 2-Nap | U-10 | C | | 374 (M+) |

TABLE U-1-continued

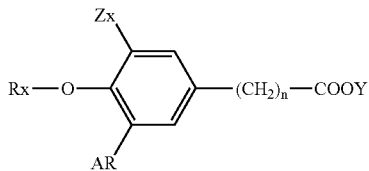

| Exp. | RxO | Y | Zx | n | AR | Syn | LCMS method | RTime | Mass |
|---|---|---|---|---|---|---|---|---|---|
| U-11 | cPenMeO | H | H | 3 | 2-Nap | U-11 | C | | 374 (M⁺) |
| U-12 | cPenMeO | H | H | 3 | 1Me-5-Ind | U-10, U-11 | | | |
| U-13 | cPenO | H | H | 3 | 2-Nap | U-10, U-11 | | | |
| U-14 | cPenO | H | H | 3 | 1Me-5-Ind | U-10, U-11 | C | | 377 (M⁺) |
| U-15 | cHexO | H | H | 3 | 2-Nap | U-10, U-11 | | | |
| U-16 | cHexO | H | H | 3 | 1Me-5-Ind | U-10, U-11 | | | |
| U-17 | 2(4FPh)EtO | H | H | 3 | 2-Nap | U-10, U-11 | | | |
| U-18 | 2(4FPh)EtO | H | H | 3 | 1Me-5-Ind | U-10, U-11 | | | |

Example V-1

Synthesis of ethyl 3-[4-cyclohexylmethyloxy-3-(naphthalen-1-yl)phenyl]acrylate (Intermediate 64)

According to the procedure described in the synthesis method of Intermediate 7 provided that the reaction was carried out for 1 hour, Compound No. C-2 (361 mg), ethyl diethylphosphonoacetate (240 µl), 60% sodium hydride (69 mg) were reacted and treated to obtain the title compound (Intermediate 64, 377 mg).

Synthesis of ethyl 3-[4-cyclohexylmethyloxy-3-(naphthalen-1-yl)phenyl]propionate (Compound No. V-1)

According to the procedure described in the synthesis method of Intermediate 8 with the modifications that the reaction was carried out for 1.5 hours, and the purification was performed by flash column chromatography (hexane:ethyl acetate=10:1), Intermediate 64 (361 mg) and 10% palladium/carbon (49 mg) were reacted under hydrogen atmosphere and treated to obtain the title compound (Compound No. V-1, 344 mg).

Example V-2

Synthesis of 3-[4-cyclohexylmethyloxy-3-(naphthalen-1-yl)phenyl]propionic acid (Compound No. V-2)

According to the procedure described in the synthesis method of Intermediate 9 provided that the reaction was carried out for 1.5 hours, Compound No. V-1 (332 mg) and 2 N aqueous sodium hydroxide (900 µl) were reacted and treated to obtain the title compound (Compound No. V-2, 295 mg).

Example V-3

Synthesis of methyl 3-[4-cyclopentylmethyloxy-3-(6-hydroxynaphthalen-2-yl)phenyl]propionate (Compound No. V-3)

A solution of 2-bromo-6-hydroxynaphthalene (243 mg, TCI) in anhydrous THF (10 ml) was cooled to −78° C., added dropwise with a 1.6 M solution of n-butyllithium in hexane (1.18 ml) over 20 minutes under argon gas atmosphere, and stirred for 30 minutes. The reaction mixture was added dropwise with (ⁱPrO)₃B (1.73 ml) over 10 minutes, stirred for 30 minutes, then warmed to room temperature, and further stirred for 2 hours. The reaction mixture was added with 0.5 M aqueous sulfuric acid (2 ml), and extracted with diethyl ether (40 ml×3). The organic layer was washed with saturated brine and dried, and then the solvent was evaporated under reduced pressure to obtain crude 6-hydroxy-2-naphthaleneboronic acid (378 mg). A solution of this substance in ethanol (1 ml), Compound No. A-1 (230 mg), and 2 M aqueous sodium carbonate (2.4 ml) were added with toluene (3 ml) and (Ph₃P)₄Pd (115 mg) and stirred at 100° C. for 13 hours. The reaction mixture was added with ethyl acetate (100 ml), and washed successively with saturated aqueous sodium hydrogencarbonate, saturated aqueous ammonium chloride and saturated brine. The organic layer was dried, and then the solvent was evaporated under reduced pressure. The residue was purified by flash column chromatography (hexane:ethyl acetate=6:1) to obtain the title compound (Compound No. V-3, 270 mg).

Example V-4

Synthesis of 3-[4-cyclopentylmethyloxy-3-(6-hydroxynaphthalen-2-yl)phenyl]propionic acid (Compound No. V-4)

According to the procedure described in the synthesis method of Intermediate 9 provided that the reaction was carried out for 14 hours, Compound No. V-3 (149 mg) and 2 N aqueous sodium hydroxide (370 µl) were reacted and treated to obtain the title compound (Compound No. V-4, 117 mg).

Example V-5

Synthesis of methyl 3-[4-cyclopentylmethyloxy-3-(5-hydroxynaphthalen-2-yl)phenyl]propionate (Compound No. V-5)

2-Amino-5-hydroxynaphthalene (4.80 g, TCI) was dissolved in 6 N hydrochloric acid (300 ml), added dropwise with an aqueous solution (22.5 ml) of sodium nitrite (2.25 g)

over 30 minutes under ice cooling, and stirred for 30 minutes. The reaction mixture was added dropwise with an aqueous solution (75 ml) of potassium iodide (9.90 g, WAKO), stirred for 30 minutes, then warmed to room temperature, and further stirred for 3.5 hours. The reaction mixture was neutralized with aqueous ammonia, and then filtered through a Celite layer. The filtrate was added with ethyl acetate (90 ml×2) for extraction. The organic layer was washed successively with saturated aqueous sodium hydrogencarbonate, saturated aqueous ammonium chloride and saturated brine, and dried, and then the solvent was evaporated under reduced pressure. The residue was purified by column chromatography (Quad, hexane:ethyl acetate=10:1) to obtain 1-hydroxy-6-iodonaphthalene (1.48 g). A solution of this substance (539 mg) in anhydrous THF (10 ml) was added with 60% sodium hydride (171 mg) under ice cooling, and stirred for 1 hour. The reaction mixture was cooled to −78° C. under argon gas atmosphere, added dropwise with a 1.6 M solution of n-butyllithium in hexane (3.75 ml) over 10 minutes, and stirred for 30 minutes. The reaction mixture was added dropwise with ($^i$PrO)$_3$B (1.16 ml) over 10 minutes, stirred for 30 minutes, then warmed to room temperature, and further stirred for 3 hours. The reaction mixture was added with water (3 ml) and 0.5 M aqueous sulfuric acid (7 ml), and extracted with diethyl ether (100 ml×3). The organic layer was washed with saturated brine and dried, and then the solvent was evaporated under reduced pressure to obtain crude 7-hydroxy-2-naphthaleneboronic acid. A solution of this substance in ethanol (1 ml), Compound No. A-1 (350 mg), 2 M aqueous sodium carbonate (2.4 ml) and (Ph$_3$P)$_4$Pd (116 mg) were reacted and treated according to the procedure described in the synthesis method of Compound No. V-3 with the modifications that the reaction was carried out for 14 hours, and the purification was performed by column chromatography (Quad, hexane:ethyl acetate=6:1) to obtain the title compound (Compound No. V-5, 388 mg).

Example V-6

Synthesis of 3-[4-cyclopentylmethyloxy-3-(5-hydroxynaphthalen-2-yl)phenyl]propionic acid (Compound No. V-6)

According to the procedure described in the synthesis method of Intermediate 9 provided that the reaction was carried out for 12 hours, Compound No. V-5 (355 mg) and 2 N aqueous sodium hydroxide (1.75 ml) were reacted and treated to obtain the title compound (Compound No. V-6, 158 mg).

Example V-7

Synthesis of methyl 3-[4-cyclopentylmethyloxy-3-(7-hydroxynaphthalen-2-yl)phenyl]propionate (Compound No. V-7)

According to the procedure described in the synthesis method of Compound No. V-5 with the modifications that the reaction was carried out for 4 hours, and the purification was performed by flash column chromatography (hexane:ethyl acetate=6:1), crude 7-hydroxy-2-naphthaleneboronic acid prepared from 2-bromo-7-hydroxynaphthalene (559 mg, MAYB), a 1.6M solution of n-butyllithium in hexane (3.91 ml) and ($^i$PrO)$_3$B (1.16 ml), Compound No. A-1 (386 mg), 2 M aqueous sodium carbonate (4.0 ml) and (Ph$_3$P)$_4$Pd (195 mg) were reacted and treated to obtain the title compound (Compound No. V-7, 460 mg).

Example V-8

Synthesis of 3-[4-cyclopentylmethyloxy-3-(7-hydroxynaphthalen-2-yl)phenyl]propionic acid (Compound No. V-8)

According to the procedure described in the synthesis method of Intermediate 9 provided that the reaction was carried out for 27 hours, Compound No. V-7 (176 mg) and 2 N aqueous sodium hydroxide (436 µl) were reacted and treated to obtain the title compound (Compound No. V-8, 109 mg).

Example V-11

Synthesis of methyl 3-{4-cyclohexylmethyloxy-3-[6-(N,N-dimethylcarbamoylmethyloxy)naphthalen-2-yl]phenyl}propionate (Compound No. V-11)

A solution of Compound No. V-3 (185 mg) in DMF (5 ml) was added with potassium carbonate (274 mg), and 2-chloro-N,N-dimethylacetamide (411 µl, KANTO), and stirred at 50° C. for 18 hours. The reaction mixture was added with ethyl acetate (90 ml), and washed with saturated brine. The organic layer was dried, and then the solvent was evaporated under reduced pressure. The residue was purified by PTLC (chloroform:methanol=10:1) to obtain the title compound (Compound No. V-11, 213 mg).

Example V-12

Synthesis of 3-{4-cyclohexylmethyloxy-3-[6-(N,N-dimethylcarbamoylmethyloxy)naphthalen-2-yl]phenyl}propionic acid (Compound No. v-10)

According to the procedure described in the synthesis method of Intermediate 9 with the modifications that the reaction was carried out at room temperature for 18 hours and at 60° C. for 8 hours, and the purification was performed by PTLC (chloroform:methanol=10:1), Compound No. V-11 (213 mg) and 2 N aqueous sodium hydroxide (420 µl) were reacted and treated to obtain the title compound (Compound No. V-12, 115 mg).

Example V-13

Synthesis of methyl 3-[3-(6-aminonaphthalen-2-yl)-4-cyclopentylmethyloxyphenyl]propionate (Compound No. V-13)

According to a known method described in a publication (Anderson, L. C. et al., J. Am. Chem. Soc, 1943, vol. 65, p. 241), a solution of 2-amino-6-bromonaphthalene (223 mg) obtainable from commercially available 2-bromo-6-hydroxynaphthalene (TCI) in anhydrous THF (10 ml) was added with 30% potassium hydride (191 mg, Ald) under ice cooling, and stirred for 1 hour. The reaction mixture was cooled to −78° C. under argon gas atmosphere, added dropwise with a 1.7 M solution of t-butyllithium in pentane (1.88 ml) over 10 minutes, and stirred for 30 minutes. This reaction mixture was added dropwise with ($^i$PrO)$_3$B (0.92 ml) over 10 minutes, stirred for 30 minutes, then warmed to room temperature, and further stirred for 3 hours. The reaction mixture was added with water (3 ml) and 0.5 M aqueous sulfuric acid (4 ml), and extracted with diethyl ether (100 ml×3). The organic layer was washed with saturated brine and dried, and then the solvent was evaporated under reduced pressure to obtain crude 6-amino-2-naphthaleneboronic acid (402 mg). A solution of this substance in ethanol (0.5 ml), Compound No. A-1 (119 mg), 2 M aqueous sodium carbonate (1.5 ml) and $(Ph_3P)_4Pd$ (61 mg) were reacted and treated according to the procedure described in the synthesis method of Compound No. V-3 with the modifications that the reaction was carried out for 13 hours, and the purification was performed by flash column chromatography (hexane:ethyl acetate 4:1) to obtain the title compound (Compound No. V-13, 129 mg).

Example V-14

Synthesis of 3-[3-(6-aminonaphthalen-2-yl)-4-cyclopentylmethyloxyphenyl]propionic acid (Compound No. V-14)

According to the procedure described in the synthesis method of Intermediate 9 provided that the reaction was carried out for 14 hours, Compound No. V-13 (120 mg) and 2 N aqueous sodium hydroxide (1.75 ml) were reacted and treated to obtain the title compound (Compound No. V-14, 89 mg).

Example V-16

Synthesis of methyl 3-[3-({6-[2-(acetyloxy)acetylamino)naphthalen-2-yl}-4-cyclopentylmethyloxyphenyl]propionate (Intermediate 65)

A solution of Compound No. V-13 (151 mg) in dichloromethane (4 ml) was added with N-methylmorpholine (50 µl), and then added with acetyloxyacetyl chloride (48.3 µl) under ice cooling. The reaction mixture was stirred for 10 minutes, then warmed to room temperature, and further stirred for 4 hours. The reaction mixture was poured into aqueous sodium hydrogencarbonate (100 ml), and ethyl acetate (150 ml) was added for extraction. The organic layer was successively washed with saturated aqueous sodium hydrogencarbonate, saturated aqueous ammonium chloride, and saturated brine and dried, and then the solvent was evaporated under reduced pressure. The residue was purified by PTLC (hexane:ethyl acetate=1:1) to obtain the title compound (Intermediate 88, 136 mg).

Synthesis of 3-(4-cyclopentylmethyloxy-3-{6-[2-(hydroxyacetyl)amino]naphthalen-2-yl}phenyl) propionic acid (Compound No. V-16)

According to the procedure described in the synthesis method of Intermediate 9 provided that the reaction was carried out at room temperature for 5 hours and at 60° C. for 1 hour, Intermediate 65 (135 mg) and 2 N aqueous sodium hydroxide (1.12 ml) were reacted and treated to obtain the title compound (Compound No. V-16, 102 mg).

Example V-18

Synthesis of methyl 3-[4-cyclopentylmethyloxy-3-(6-methylsulfonylaminonaphthalen-2-yl)phenyl] propionate (Compound No. V-18)

A solution of Compound No. V-13 (149.1 mg) in 1,2-dichloroethane (5 ml) was added successively with pyridine (500 µl) and methanesulfonyl chloride (62 µl) under ice cooling, stirred for 1.5 hours, then warmed to room temperature, and stirred for 12 hours. The reaction mixture was added with water (30 ml) and ethyl acetate (90 ml) for extraction. The organic layer was successively washed with saturated aqueous sodium hydrogencarbonate, saturated aqueous ammonium chloride, and saturated brine and dried, and then the solvent was evaporated under reduced pressure. The residue was purified by PTLC (hexane:ethyl acetate=2:1) to obtain the title compound (Compound No. V-18, 126 mg).

Example V-19

Synthesis of 3-[4-cyclopentylmethyloxy-3-(6-methylsulfonylaminonaphthalen-2-yl)phenyl]propionic acid (Compound No. V-19)

According to the procedure described in the synthesis method of Intermediate 9 provided that the reaction was carried out at room temperature for 3 hours and at 60° C. for 1 hour, Compound No. V-18 (129 mg) and 2 N aqueous sodium hydroxide (535 µl) were reacted and treated to obtain the title compound (Compound No. V-19, 98 mg).

Example V-20

Synthesis of methyl 3-{4-cyclopentylmethyloxy-3-[6-(N,N-dimethylsulfamoylamino)naphthalen-2-yl] phenyl}propionate (Compound No. V-20)

A solution of Compound No. V-13 (165 mg) in pyridine (5 ml) was added successively with 4-dimethylaminopyridine (104 mg, TCI) and dimethylsulfamoyl chloride (520 µl, TCI), stirred for 5 days, and then further stirred at 50° C. for 4 hours. The reaction mixture was added with water (30 ml) and ethyl acetate (90 ml)) for extraction. The organic layer was washed with saturated brine and dried, and then the solvent was evaporated under reduced pressure. The residue was purified by column chromatography (Quad, hexane:ethyl acetate=6:1) to obtain the title compound (Compound No. V-20, 125 mg).

Example V-21

Synthesis of 3-{4-cyclopentylmethyloxy-3-[6-(N,N-dimethylsulfamoylamino)naphthalen-2-yl] phenyl}propionic acid (Compound No. V-21)

According to the procedure described in the synthesis method of Intermediate 9 provided that the reaction was carried out for 1.5 hours, Compound No. V-20 (118 mg) and 2 N aqueous sodium hydroxide (460 µl) were reacted and treated to obtain the title compound (Compound No. V-21, 87 mg).

Example V-22

Synthesis of 2-bromo-6-sulfamoylaminonaphthalene (Intermediate 66)

A solution of chlorosulfonyl isocyanate (870 µl, WAKO) in benzene (10 ml) was added dropwise with formic acid (377 µl, WAKO) under ice cooling, warmed to room temperature, stirred and for 19.5 hours, then warmed to 40° C., and further stirred for 4 hours. The reaction mixture was added dropwise with a solution of 2-amino-6-bromonaphthalene (443 mg) in benzene (5 ml) under ice cooling, warmed to room temperature, and stirred 21.5 hours. The reaction mixture was filtered to obtain solid, and the solid was added with ethyl acetate, mixed and filtered again. The solvent of the filtrate was evaporated under reduced pressure. The residue was purified by Synthesis of methyl 3-[4-cyclopentylmethyloxy-3-(6-sulfamoylaminonaphthalen-2-yl)phenyl]propionate (Compound No. V-22)

According to a procedure described in literature (Miyaura, N. et al., Tetrahedron. Lett., 1997, p. 3447), Compound No. A-1 (209 mg), bis(pinacolate)diboron (177 mg, Ald), [1,1'-bis(diphenylphosphono)ferrocene]palladium(II) dichloride (hereinafter abbreviated as "PdCl$_2$(dppf)", 28 mg, TCI) and potassium acetate (182.3 mg, Ald) were added to DMF (6 ml), and heated to 80° C. with stirring under argon gas atmosphere for 5 hours. The reaction mixture was cooled to room temperature, then added with Intermediate 91 (130 mg), PdCl$_2$(dppf) (30 mg) and 2 M aqueous sodium carbonate (0.9 ml), and heated to 80° C. for 21 hours with stirring under argon gas atmosphere. The reaction mixture was added with ethyl acetate (100 ml), washed with saturated brine and dried, and then the solvent was evaporated under reduced pressure. The residue was purified by column chromatography (Quad, hexane:ethyl acetate=3:1) to obtain the title compound (Compound No. V-22, 46 mg).

Example V-23

Synthesis of 3-[4-cyclopentylmethyloxy-3-(6-sulfamoylaminonaphthalen-2-yl)phenyl]propionic acid (Compound No. V-23)

According to the procedure described in the synthesis method of Intermediate 9 provided that the reaction was carried out for 24 hours, Compound No. V-22 (41 mg) and 2 N aqueous sodium hydroxide (340 µl) were reacted and treated to obtain the title compound (Compound No. V-23, 22 mg).

Example V-27

Synthesis of methyl 3-[4-cyclopentyloxy-3-(1H-indol-5-yl)phenyl]propionate (Compound No. V-27)

According to the procedure described in the synthesis method of Compound No. C-1 with the modifications that the reaction was carried out at 80° C. for 5 hours, and the purification was performed by flash column chromatography (hexane:ethyl acetate=5:1), Compound No. A-5 (367 mg), 5-indoleboronic acid (310 mg, Frontier), 2 M aqueous sodium carbonate (0.9 ml) and (Ph$_3$P)$_4$Pd (132 mg) were reacted and treated to obtain the title compound (Compound No. V-27, 340 mg).

Example V-28

Synthesis of 3-[4-cyclopentyloxy-3-(1H-indol-5-yl)phenyl]propionic acid (Compound No. V-28)

According to the procedure described in the synthesis method of Intermediate 9 provided that the reaction was carried out for 2 hours, Compound No. V-27 (330 mg) and 2 N aqueous sodium hydroxide (1.40 ml) were reacted and treated to obtain the title compound (Compound No. V-28, 310 mg).

Example V-29

Synthesis of methyl 3-[4-cyclopentyloxy-3-(1-methyl-1H-indol-5-yl)phenyl]propionate (Compound No. V-29)

A solution of Compound No. V-27 (123 mg) in DMF (5 ml) was added with 60% sodium hydride (19 mg) under ice cooling, and stirred for 10 minutes. The reaction mixture was added dropwise with methyl iodide (100 µl), stirred for 10 minutes, then warmed to room temperature, and further stirred for 1 hour. The reaction mixture was poured into ice water, and ethyl acetate (100 ml) was added for extraction. The organic layer was successively washed with saturated aqueous sodium hydrogencarbonate, saturated aqueous ammonium chloride, and saturated brine and dried, and then the solvent was evaporated under reduced pressure. The residue was purified by flash column chromatography (hexane:ethyl acetate=8:1) to obtain the title compound (Compound No. V-29, 126 mg).

Example V-30

Synthesis of 3-[4-cyclopentyloxy-3-(1-methyl-1H-indol-5-yl)phenyl]propionic acid (Compound No. V-30)

According to the procedure described in the synthesis method of Intermediate 9 provided that the reaction was carried out for 1 hour, Compound No. V-29 (123 mg) and 2 N aqueous sodium hydroxide (330 µl) were reacted and treated to obtain the title compound (Compound No. V-30, 110 mg).

Example V-31

Synthesis of methyl 3-[4-cyclopentylmethyloxy-3-(1H-indol-4-yl)phenyl]propionate (Compound No. V-31)

According to the procedure described in the synthesis method of Compound No. C-1 with the modifications that the reaction was carried out for 21 hours, and the purification was performed by column chromatography (Quad, hexane:ethyl acetate=6:1), Compound No. A-1 (200 mg), 4-indoleboronic acid (170 mg) obtainable from 4-bromoindole (TCI) according to a known method described in a publication (Doll, M. et al., J. Org. Chem., 1999, vol. 64, p. 1372), 2 M aqueous sodium carbonate (550 µl) and (Ph$_3$P)$_4$Pd (60 mg) were reacted and treated to obtain the title compound (Compound No. V-31, 214 mg).

Example V-32

Synthesis of 3-[4-cyclopentylmethyloxy-3-(1H-indol-4-yl)phenyl]propionic acid (Compound No. V-32)

According to the procedure-described in the synthesis method of Intermediate 9 provided that the reaction was carried out for 1 hour, Compound No. V-31 (210 mg) and 2 N aqueous sodium hydroxide (0.60 ml) were reacted and treated to obtain the title compound (Compound No. V-32, 173 mg).

Example V-33

Synthesis of 4-bromo-1-methyl-1H-indole (Intermediate 67)

According to the procedure described in the synthesis method of Compound No. V-29 with the modifications that the reaction was carried out for 30 minutes, and the purification was performed by column chromatography (Quad, hexane:ethyl acetate=10:1), 4-bromoindole (5 g), 60% sodium hydride (1.14 g) and methyl iodide (3.18 ml, TCI) were reacted and treated to obtain the title compound (Intermediate 67, 4.95 g).

Synthesis of 1-methyl-1H-indole-4-boronic acid (Intermediate 68)

A solution of Intermediate 67 (4.90 g) in anhydrous THF (30 ml) was cooled to −78° C. under argon gas atmosphere, then added dropwise with a 1.62 M solution of t-butyllithium in pentane (28.8 ml) over 30 minutes, and stirred for 30 minutes. This reaction mixture was added dropwise with ($^i$PrO)$_3$B (10.77 ml) over 10 minutes, stirred for 1 hour, then warmed to room temperature, and further stirred for 2.5 hours. The reaction mixture was poured into 1.2 N aqueous phosphoric acid (250 ml) containing ice, and extracted with diethyl ether (200 ml×3). The organic layer was extracted with 0.4 N aqueous sodium hydroxide (150 ml×3), and the aqueous layer was made acidic with 5 N hydrochloric acid under ice cooling, and extracted with diethyl ether (200 ml×3) again. The organic layer was washed with saturated brine and dried, and then the solvent was evaporated under reduced pressure. The residue was washed with hexane to obtain the title compound (Intermediate 68, 3.17 g).

Synthesis of methyl 3-[4-cyclopentylmethyloxy-3-(1-methyl-1H-indol-4-yl)phenyl]propionate (Compound No. V-33)

According to the procedure described in the synthesis method of Compound No. C-1 with the modifications that the reaction was carried out for 18 hours, and the purification was performed by column chromatography (Quad, hexane:ethyl acetate=9:1), Compound No. A-1 (200 mg), Intermediate 68 (185 mg), 2 M aqueous sodium carbonate (550 µl) and (Ph$_3$P)$_4$Pd (60 mg) were reacted and treated to obtain the title compound (Compound No. V-33, 208 mg).

Example V-34

Synthesis of 3-[4-cyclopentylmethyloxy-3-(1-methyl-1H-indol-4-yl)phenyl]propionic acid (Compound No. V-34)

According to the procedure described in the synthesis method of Intermediate 9 provided that the reaction was carried out for 3 hours, Compound No. V-33 (200 mg) and 2 N aqueous sodium hydroxide (0.60 ml) were reacted and treated to obtain the title compound (Compound No. V-34, 182 mg).

Example V-43

Synthesis of 3-{4-cyclopentylmethyloxy-3-[1-(2-hydroxyethyl)-1H-indol-5-yl]phenyl}propionic acid (Compound No. V-43)

According to the procedure described in the synthesis method of Compound No. V-29 with the modifications that the reaction was carried out for 1.5 hours, and the purification was performed by column chromatography (Quad, hexane:ethyl acetate=8:1), Compound No. V-27 (144 mg), 60% sodium hydride (38 mg) and ethyl bromoacetate (160 µl, TCI) were reacted and treated to obtain an oily substance. This substance was reacted with 2 N aqueous sodium hydroxide (300 µl) and treated according to the procedure described in the synthesis method of Intermediate 9 provided that the reaction was carried out for 1 hour to obtain the title compound (Compound No. V-43, 36 mg).

Example V-44

Synthesis of methyl 3-[4-cyclopentylmethyloxy-3-(3-formyl-1H-indol-5-yl)phenyl]propionate (Compound No. V-44)

A solution of Compound No. V-27 (75 mg) in DMF (6 ml) was added dropwise with phosphoryl chloride (30 µl, TCI) under ice cooling, stirring for 1 hour, then warmed to 35° C., and further stirred for 1 hour. The reaction mixture was added with 1 N aqueous sodium hydroxide (3 ml) containing ice, and extracted with ethyl acetate (90 ml). The organic layer was washed with saturated brine and dried, and then the solvent was evaporated under reduced pressure. The residue was purified by flash column chromatography (hexane:ethyl acetate=5:1) to obtain the title compound (Compound No. V-44, 86 mg).

Example V-45

Synthesis of 3-[4-cyclopentylmethyloxy-3-(3-formyl-1H-indol-5-yl)phenyl]propionic acid (Compound No. V-45)

According to the procedure described in the synthesis method of Intermediate 9 provided that the reaction was carried out for 3 hours, Compound No. V-44 (86 mg) and 2 N aqueous sodium hydroxide (110 µl) were reacted and treated to obtain the title compound (Compound No. V-45, 60 mg).

Example V-47

Synthesis of methyl 3-[3-(3-acetyl-1H-indol-5-yl)-4-cyclopentylmethyloxyphenyl]propionate (Compound No. V-47)

A solution of Compound No. V-27 (98 mg) in methylene chloride (2 ml) was added with aluminum chloride (81 mg, Ald) and acetyl chloride (60 µl), and stirred for 4 hours. The reaction mixture was added with 1 N hydrochloric acid (2 ml), and extracted with methylene chloride (60 ml). The organic layer was washed with saturated brine and dried, and then the solvent was evaporated under reduced pressure. The residue was purified by flash column chromatography (hexane:ethyl acetate=4:1) to obtain the title compound (Compound No. V-47, 47 mg).

Example V-48

Synthesis of 3-[3-(3-acetyl-1H-indol-5-yl)-4-cyclopentylmethyloxyphenyl]propionic acid (Compound No. V-48)

According to the procedure described in the synthesis method of Intermediate 9 provided that the reaction was carried out for 4 hours, Compound No. V-47 (45 mg) and 2 N aqueous sodium hydroxide (110 μl) were reacted and treated to obtain the title compound (Compound No. V-48, 44 mg).

Example V-50

Synthesis of methyl 3-[4-cyclopentylmethyloxy-3-(3-methyl-1H-indol-5-yl)phenyl]propionate (Compound No. V-50)

According to the procedure described in the synthesis method of Intermediate 95 with the modifications that the reaction was carried out for 13 hours, and the purification was performed by flash column chromatography (hexane:ethyl acetate=4:1), 5-bromo-3-methylindole (1.63 g) obtainable from 5-bromoindole (TCI) by a known method described in a publication (Wayland, E. N., J. Org. Chem, 1967, vol. 32, p. 828) was reacted with 30% potassium hydride (1.08 g), a 1.7 M solution of t-butyllithium in pentane (9.7 ml) and ($^i$PrO)$_3$B (3.75 ml) and treated to obtain crude 3-methyl-5-indoleboronic acid. This compound was reacted with Compound No. A-1 (803 mg), 2 M aqueous sodium carbonate (2 ml) and (Ph$_3$P)$_4$Pd (241 mg) and treated to obtain the title compound (Compound No. V-50, 552 mg).

Example V-51

Synthesis of 3-[4-cyclopentylmethyloxy-3-(3-methyl-1H-indol-5-yl)phenyl]propionic acid (Compound No. V-51)

According to the procedure described in the synthesis method of Intermediate 9 provided that the reaction was carried out for 2 hours, Compound No. V-50 (130 mg) and 2 N aqueous sodium hydroxide (370 μl) were reacted and treated to obtain the title compound (Compound No. V-51, 127 mg).

Example V-54

Synthesis of 4-bromo-1H-indazole (Intermediate 69)

According to a known method described in a publication (Schumann, P. et al., Bioorg. Med. Chem. Lett., 2001, vol. 11, p. 1153), the title compound (Intermediate 69, 1.68 g) was obtained from commercially available 3-bromotoluidine (4.51 g, Ald).

Synthesis of methyl 3-[4-cyclopentyloxy-3-(1H-indazol-4-yl)phenyl]propionate (Compound No. V-54)

According to the procedure described in the synthesis method of Compound No. V-22 provided that the purification was performed by flash column chromatography (hexane: ethyl acetate=2:1), Compound No. A-5 (328 mg), bis(pinacolate)diboron (281 mg), PdCl$_2$(dppf) (61 mg) and potassium acetate (303 mg) were reacted at 80° C. for 4 hours, and then this reaction mixture was added with Intermediate 105 (161 mg), PdCl$_2$(dppf) (64 mg) and 2 M aqueous sodium carbonate (1.5 ml), reacted at 80° C. for 9 hours and treated to obtain the title compound (Compound No. V-54, 111 mg).

Example V-55

Synthesis of 3-[4-cyclopentyloxy-3-(1H-indazol-4-yl)phenyl]propionic acid (Compound No. V-55)

According to the procedure described in the synthesis method of Intermediate 9 provided that the reaction was carried out for 2 hours, Compound No. V-54 (108 mg) and 2 N aqueous sodium hydroxide (400 μl) were reacted and treated to obtain the title compound (Compound No. V-55, 99 mg).

Example V-57

Synthesis of 4-(4,4,5,5-tetramethyl-1,3,2-dioxaborolan-2-yl)-2-methylnitrobenzene (Intermediate 70)

According to the procedure described in the synthesis method of Compound No. V-22, 5-bromo-2-nitrotoluene (4.30 g) synthesized by nitrating 3-bromotoluene (WAKO) by a known method, bis(pinacolate)diboron (5.59 g), PdCl$_2$(dppf) (440 mg) and potassium acetate (6.09 g) were heated with stirring at 80° C. for 3 hours under argon gas atmosphere. The reaction mixture was added with ethyl acetate (300 ml), and washed successively with saturated aqueous sodium hydrogencarbonate, saturated aqueous ammonium chloride and saturated brine. The organic layer was dried, and then the solvent was evaporated under reduced pressure. The residue was purified by flash column chromatography (hexane:ethyl acetate=8:1) to obtain the title compound (Intermediate 70, 4.21 g).

Synthesis of 4-(4,4,5,5-tetramethyl-1,3,2-dioxaborolan-2-yl)-2-methylaniline (Intermediate 71)

According to the procedure described in the synthesis method of Compound No. Q-2 with the modification that the reaction was carried out for 30 minutes, Intermediate 70 (4.20 g) and platinum oxide (50 mg) were added, then reacted and treated under hydrogen atmosphere to obtain the title compound (Intermediate 71, 2.81 g).

Synthesis of methyl 3-(4'-amino-6-cyclopentyloxy-3'-methylbiphenyl-3-yl)propionate (Intermediate 72)

According to the procedure described in the synthesis method of Compound No. C-1 with the modifications that the reaction was carried out for 15.5 hours, and the purification was performed by column chromatography (Quad, hexane: ethyl acetate=6:1), Compound No. A-5 (701 mg), Intermediate 71 (604 mg), 2 M aqueous sodium carbonate (1.8 ml), and (Ph$_3$P)$_4$Pd (182 mg) were reacted and treated to obtain the title compound (Intermediate 72, 762 mg).

Synthesis of methyl 3-[4-cyclopentyloxy-3-(1H-indazol-5-yl)phenyl]propionate (Compound No. V-57)

A solution of Intermediate 72 (760 mg) in acetic acid (4 ml) was added with an aqueous solution (0.7 ml) of sodium nitrite (156 mg) under ice cooling, and stirred for 30 minutes. This reaction mixture was added with urea (350 mg), warmed to room temperature, stirred for 30 minutes, then added with toluene (8 ml) and water (4 ml), and further stirred for 60 hours. The reaction mixture was extracted with toluene (50 ml×2). The organic layer was washed successively with saturated aqueous sodium hydrogencarbonate, and saturated brine and dried, and then the solvent was evaporated under reduced pressure. The residue was purified by column chromatography (Quad, hexane:ethyl acetate=6:1) to obtain the title compound (Compound No. V-57, 411 mg).

Example V-58

Synthesis of 3-[4-cyclopentyloxy-3-(1H-indazol-5-yl)phenyl]propionic acid (Compound No. V-58)

According to the procedure described in the synthesis method of Intermediate 9 provided that the reaction was carried out for 2.5 hours, Compound No. V-57 (86 mg) and 2 N aqueous sodium hydroxide (250 μl) were reacted and treated to obtain the title compound (Compound No. V-58, 82 mg).

Example V-66

Synthesis of 5-bromo-3-methyl-1H-indazole (Intermediate 73)

According to the procedure described in the synthesis method of Compound No. V-57 provided that the reaction was carried out for 121 hours, 4-bromo-2-ethylaniline (5.01 g, LANC) and sodium nitrite (1.918 g) were reacted and treated to obtain the title compound (Intermediate 73, 3.30 g).

Synthesis of methyl 3-[4-cyclopentyloxy-3-(3-methyl-1H-indazol-5-yl)phenyl]propionate (Compound No. V-66)

According to the procedure described in the synthesis method of Compound No. V-22 provided that the purification was performed by column chromatography (Quad, hexane:ethyl acetate=5:2), Compound No. A-5 (434 mg), bis(pinacolate)diboron (367 mg), $PdCl_2(dppf)$ (101 mg), and potassium acetate (339 mg) were reacted at 80° C. for 4 hours, and then this reaction mixture was added with Intermediate 108 (273 mg), $PdCl_2(dppf)$ (104 mg) and 2 M aqueous sodium carbonate (1.1 ml), reacted at 80° C. for 18 hours and treated to obtain the title compound (Compound No. V-66, 98 mg).

Example V-67

Synthesis of 3-[4-cyclopentyloxy-3-(3-methyl-1H-indazol-5-yl)phenyl]propionic acid (Compound No. V-67)

According to the procedure described in the synthesis method of Intermediate 9 provided that the reaction was carried out for 2 hours, Compound No. V-66 (97 mg) and 2 N aqueous sodium hydroxide (400 μl) were reacted and treated to obtain the title compound (Compound No. V-67, 54 mg).

Example V-68

Synthesis of methyl 3-[4-cyclopentyloxy-3-(1,3-dimethyl-1H-indazol-5-yl)phenyl]propionate (Compound No. V-68)

According to the procedure described in the synthesis method of Compound No. V-29 with the modifications that the reaction was carried out for 16 hours, and the purification was performed by column chromatography (Quad, hexane:ethyl acetate=3:1), Compound No. V-66 (112 mg), 60% sodium hydride (24 mg) and methyl iodide (95 μl) were reacted and treated to obtain the title compound (Intermediate 110, 45 mg).

Example V-69

Synthesis of 3-[4-cyclopentyloxy-3-(1,3-dimethyl-1H-indazol-5-yl)phenyl]propionic acid (Compound No. V-69)

According to the procedure described in the synthesis method of Intermediate 9 provided that the reaction was carried out for 3 hours, Compound No. V-68 (45 mg) and 2 N aqueous sodium hydroxide (120 μl) were reacted and treated to obtain the title compound (Compound No. V-69, 42 mg).

Example V-73

Synthesis of methyl 3-[3-(benzo[b]thiophen-5-yl)-4-cyclopentylmethyloxyphenyl]propionate (Compound No. V-73)

According to the procedure described in the synthesis method of Compound No. V-22 provided that the purification was performed by column chromatography (Quad, hexane:ethyl acetate=10:1), Compound No. A-1 (371 mg), bis(pinacolate)diboron (294 mg), $PdCl_2(dppf)$ (67 mg) and potassium acetate (308 mg) were reacted at 80° C. for 10 hours, and then this reaction mixture was added with 5-bromobenzo[b]thiophene (301.4 mg) obtainable from 4-bromothiophenol (TCI) by a known method described in a publication (Seed, A. J., J. Mater. Chem., 2000, vol. 10, p. 2069), $PdCl_2(dppf)$ (65 mg) and 2 M aqueous sodium carbonate (0.9 ml), reacted at 80° C. for 16 hours and treated to obtain the title compound (Compound No. V-73, 97 mg).

Example V-74

Synthesis of 3-[3-(benzo[b]thiophen-5-yl)-4-cyclopentylmethyloxyphenyl]propionic acid (Compound No. V-74)

According to the procedure described in the synthesis method of Intermediate 9 provided that the reaction was carried out for 3 hours, Compound No. V-73 (95 mg) and 2 N aqueous sodium hydroxide (250 μl) were reacted and treated to obtain the title compound (Compound No. V-74, 93 mg).

Example V-77

Synthesis of (3-bromophenyl)thiourea (Intermediate 74)

A solution of 3-bromoaniline (10.89 ml, TCI) in 20% aqueous hydrochloric acid (18.2 ml) was added with ammonium thiocyanate (8.02 g, WAKO) and sodium hydrogensulfite (701 mg, WAKO), and stirred at 100° C. for 22 hours. The reaction mixture was added with chloroform (20 ml) for extraction, and the organic layer was dried. Then, the solvent was evaporated under reduced pressure. The residue was purified by column chromatography (Quad, hexane:ethyl acetate=2:1) to obtain the title compound (Intermediate 74, 4.45 g).

Synthesis of 2-amino-5-bromobenzothiazole (Intermediate 75)

A solution of Intermediate 74 (1.29 g) in chloroform (12 ml) was added dropwise with a solution of bromine (272 µl, WAKO) in chloroform (1.5 ml), refluxed by heating for 2.5 hours, and stirred at room temperature for 16 hours. The reaction mixture was concentrated under reduced pressure, neutralized with 5% aqueous ammonia, and then added with water (50 ml) and methylene chloride (150 ml) for extraction. The organic layer was dried, and then the solvent was evaporated under reduced pressure. The residue was purified by column chromatography (Quad, hexane:ethyl acetate=2:1) to obtain the title compound (Intermediate 75, 609 mg).

Synthesis of methyl 3-[3-(2-aminobenzothiazol-5-yl)-4-cyclopentylmethyloxyphenyl]propionate (Compound No. V-77)

A solution of Intermediate 75 (459.1 mg) in anhydrous THF (30 ml) was added with N,N,N',N'-tetramethylethylenediamine (1.51 ml, WAKO), cooled to −78° C. under argon gas atmosphere, then added dropwise with a 1.62 M solution of t-butyllithium in pentane (7.06 ml), and stirred for 30 minutes. The reaction mixture was added dropwise with ($^i$PrO)$_3$B (2.77 ml), stirred for 30 minutes, then warmed to room temperature, and further stirred for 1.5 hours. The reaction mixture was added with 0.5 M aqueous sulfuric acid (7.5 ml) and extracted with diethyl ether (50 ml×3). The organic layer was washed with saturated brine and dried, and then the solvent was evaporated under reduced pressure to obtain crude 2-amino-5-benzothiazoleboronic acid. This compound was reacted with Compound No. A-1 (344 mg), 2 M aqueous sodium carbonate (4.5 ml) and (Ph$_3$P)$_4$Pd (179 mg) and treated according to the procedure described in the synthesis method of Compound No. V-3 with the modifications that the reaction was carried out for 12 hours, and the purification was performed by flash column chromatography (hexane:ethyl acetate=2:1) to obtain the title compound (Compound No. V-77, 76 mg).

Example V-78

Synthesis of 3-[3-(2-aminobenzothiazol-5-yl)-4-cyclopentylmethyloxyphenyl]propionic acid (Compound No. V-78)

According to the procedure described in the synthesis method of Intermediate 9 provided that the reaction was carried out for 2.5 hours, Compound No. V-77 (77 mg) and 2 N aqueous sodium hydroxide (380 µl) were reacted and treated to obtain the title compound (Compound No. V-78, 69 mg).

Example V-79

Synthesis of ethyl 3-[3-(benzothiazol-5-yl)-4-cyclopentylmethyloxyphenyl]propionate (Compound No. V-79)

A solution of Compound No. V-77 (215 mg) in acetonitrile (10 ml) was added with 30% aqueous hypophosphorous acid (3 ml, WAKO), cooled to 0° C., added dropwise with an aqueous solution (1 ml) of sodium nitrite (187 mg), stirred for 30 minutes, then warmed to room temperature, and further stirred for 20 hours. The reaction mixture was poured into water (50 ml), neutralized by addition of 2 N aqueous sodium hydroxide, and added with ethyl acetate (90 ml×3) for extraction. The organic layer was washed with saturated brine and dried, and then the solvent was evaporated under reduced pressure. The residue was purified by column chromatography (Quad, hexane:ethyl acetate=10:1) to obtain the title compound (Compound No. V-79, 78 mg).

Example V-80

Synthesis of 3-[3-(benzothiazol-5-yl)-4-cyclopentylmethyloxyphenyl]propionic acid (Compound No. V-80)

According to the procedure described in the synthesis method of Intermediate 9 provided that the reaction was carried out for 2 hours, Compound No. V-79 (75 mg) and 2 N aqueous sodium hydroxide (500 µl) were reacted and treated to obtain the title compound (Compound No. V-80, 66 mg).

Example V-81

Synthesis of methyl 3-[4-cyclopentylmethyloxy-3-(2-methylbenzothiazol-5-yl)phenyl]propionate (Compound No. V-81)

According to the procedure described in the synthesis method of Compound No. V-13 with the modifications that the reaction was carried out for 13 hours, and the purification was performed by flash column chromatography (hexane:ethyl acetate=5:1), crude 2-methyl-5-benzothiazoleboronic acid prepared from 5-bromo-2-methylbenzothiazole (684 mg, TCI), a 1.7 M solution of t-butyllithium in pentane (7.06 ml) and ($^i$PrO)$_3$B (3.46 ml), Compound No. A-1 (515 mg), 2 M aqueous sodium carbonate (6.5 ml) and (Ph$_3$P)$_4$Pd (258 mg) were reacted and treated to obtain the title compound (Compound No. V-81, 240 mg).

Example V-82

Synthesis of 3-[4-cyclopentylmethyloxy-3-(2-methylbenzothiazol-5-yl)phenyl]propionic acid (Compound No. V-82)

According to the procedure described in the synthesis method of Intermediate 9 provided that the reaction was carried out for 4 hours, Compound No. V-81 (227 mg) and 2 N aqueous sodium hydroxide (1.11 ml) were reacted and treated to obtain the title compound (Compound No. V-82, 132 mg).

Example V-83

Synthesis of ethyl 3-{4-cyclopentylmethyloxy-3-[2-(N,N-dimethylamino)benzothiazol-6-yl]phenyl}propionate (Compound No. V-83)

According to the procedure described in the synthesis method of Compound No. V-29 with the modifications that the reaction was carried out for 4 hours, and the purification was performed by column chromatography (Quad, hexane:ethyl acetate=7:1), Compound No. V-77 (155 mg), 60% sodium hydride (16 mg) and methyl iodide (68.5 µl) were reacted and treated to obtain the title compound (Compound No. V-83, 48 mg).

Example V-84

Synthesis of 3-{4-cyclopentylmethyloxy-3-[2-(N,N-dimethylamino)benzothiazol-6-yl]phenyl}propionic acid (Compound No. V-84)

According to the procedure described in the synthesis method of Intermediate 9 provided that the reaction was carried out for 3 hours, Compound No. V-83 (47 mg) and 2 N aqueous sodium hydroxide (200 µl) were reacted and treated to obtain the title compound (Compound No. V-84, 35 mg).

Example V-88

Synthesis of ethyl 3-[3-(2-bromobenzothiazol-6-yl)-4-cyclohexylmethyloxyphenyl]propionate (Intermediate 76)

A solution obtained beforehand by adding t-butyl nitrite (178 µl, TCI) and copper(I) bromide (241 mg, WAKO) to acetonitrile (10 ml) and mixing them was added dropwise with a solution of Compound No. V-83 (381 mg) in acetonitrile (5 ml) and stirred at room temperature for 1.5 hours. The solvent of the reaction mixture was concentrated under reduced pressure, and the residue was purified by column chromatography (Quad, hexane:ethyl acetate=10:1) to obtain the title compound (Intermediate 76, 341 mg).

Synthesis of 3-[4-cyclopentylmethyloxy-3-(2-methoxybenzothiazol-6-yl)phenyl]propionic acid (Compound No. V-88)

According to the procedure described in the synthesis method of Intermediate 9 provided that the reaction was carried out for 18 hours, Intermediate 76 (169 mg) and 2 N aqueous sodium hydroxide (500 µl) were reacted and treated to obtain the title compound (Compound No. V-88, 114 mg).

Example V-89

Synthesis of 3-[4-cyclopentylmethyloxy-3-(2-oxo-2,3-dihydrobenzothiazol-6-yl)phenyl]propionic acid (Compound No. V-64)

A solution of Intermediate 76 (202 mg) in ethanol (8 ml) was added with 5 N aqueous hydrochloric acid (1.5 ml), and stirred at 80° C. for 18.5 hours. The reaction mixture was concentrated under reduced pressure, and added with water (20 ml) and ethyl acetate (80 ml) for extraction. The organic layer was washed with saturated brine and dried, and then the solvent was evaporated under reduced pressure. The residue was added with 2 N aqueous sodium hydroxide (1.0 ml), reacted and treated according to the procedure described in the synthesis method of Intermediate 9 provided that the reaction was carried out for 2 hours to obtain the title compound (Compound No. V-89, 250 mg).

Example V-91

Synthesis of 3-[4-cyclopentylmethyloxy-3-(2-thioxo-2,3-dihydrobenzothiazol-6-yl)phenyl]propionic acid (Compound No. V-91)

A solution obtained beforehand by adding thiourea (52 mg, WAKO) to 1 M sulfuric acid (5 ml) and mixing them was added with a solution of Intermediate 76 (101 mg) in acetonitrile (5 ml), and stirred at 90° C. for 20 hours. The reaction mixture was poured into water (20 ml), neutralized by addition of 1 N aqueous sodium hydroxide under ice cooling, and then extracted with ethyl acetate (80 ml×3). The organic layer was washed with saturated brine and dried, and then the solvent was evaporated under reduced pressure. The residue was purified by column chromatography (Quad, methylene chloride:ethanol=30:1) to obtain the title compound (Compound No. V-91, 46 mg).

Synthesis examples for compounds used for preparation of the compounds mentioned in the examples are shown below.

Syntheses of 4-bromo-1-methyl-1H-indazole (Intermediate 77) and 4-bromo-2-methyl-2H-indazole (Intermediate 78)

According to the procedure described in the synthesis method of Compound No. V-29 with the modifications that the reaction was carried out for 8 hours, and the purification was performed by column chromatography (Quad, hexane:ethyl acetate=5:1), Intermediate 69 (600 mg), 60% sodium hydride (191 mg), and methyl iodide (379 µl) were reacted and treated to obtain the title compounds (Intermediate 119, 432 mg and Intermediate 120, 164 mg).

Synthesis of 5-bromo-1H-indazole (Intermediate 79)

The title compound (Intermediate 121, 0.91 g) was obtained from commercially available 4-bromotoluidine (3.33 g, Ald) by a method known from the aforementioned literature (Bioorg. Med. Chem. Lett., 2001, vol. 11, p. 1153).

Syntheses of 5-bromo-1-methyl-1H-indazole (Intermediate 80) and 5-bromo-2-methyl-2H-indazole (Intermediate 81)

According to the procedure described in the synthesis method of Compound No. V-29 with the modifications that the reaction was carried out for 4.5 hours, and the purification was performed by column chromatography (Quad, hexane:ethyl acetate=5:1), Intermediate 79 (300 mg), 60% sodium hydride (80 mg), and methyl iodide (161 µl) were reacted and treated to obtain the title compounds (Intermediate 80, 201 mg and Intermediate 81, 87 mg).

Synthesis of 1-methyl-1H-indazole-5-boronic acid (Intermediate 82)

According to the procedure described in the synthesis method of Compound No. V-3, Intermediate 80 (1.69 g), a 1.6 M solution of n-butyllithium in hexane (7.50 ml) and ($^i$PrO)$_3$B (3.23 ml) were reacted and treated to obtain the title compound (Intermediate 82, 1.39 g).

Syntheses of 5-bromo-1-ethyl-1H-indazole (Intermediate 83) and 5-bromo-2-ethyl-2H-indazole (Intermediate 84)

According to the procedure described in the synthesis method of Compound No. V-29 with the modifications that the reaction was carried out for 2 hours, and the purification was performed by column chromatography (Quad, hexane: ethyl acetate=5:1), Intermediate 79 (420 mg), 60% sodium hydride (111 mg), and ethyl iodide (375 µl) were reacted and treated to obtain the title compounds (Intermediate 83, 250 mg and Intermediate 84, 127 mg).

Synthesis of 6-bromo-1H-indazole (Intermediate 85)

The title compound was obtained from commercially available 5-bromotoluidine (3.33 g, Ald) by the method known from the aforementioned literature (Bioorg. Med. Chem. Lett., 2001, vol. 11, p. 1153) to obtain the title compound (Intermediate 85, 0.42 g).

Syntheses of 6-bromo-1-methyl-1H-indazole (Intermediate 86) and 6-bromo-2-methyl-2H-indazole (Intermediate 87)

According to the procedure described in the synthesis method of Compound No. V-29 with the modifications that the reaction was carried out for 2.5 hours, and the purification was performed by column chromatography (Quad, hexane: ethyl acetate=5:1), Intermediate 85 (277 mg), 60% sodium hydride (86 mg), and methyl iodide (175 µl) were reacted and treated to obtain the title compounds (Intermediate 86, 196 mg and Intermediate 87, 89 mg).

Synthesis of 5-bromo-2-t-butylthiobenzaldehyde (Intermediate 88)

A solution of 5-bromo-2-fluorobenzaldehyde (4.06 g, Avocado) in 2-propanol (20 ml) was added with 2-methyl-2-propanethiol (2.26 ml, Ald) and potassium carbonate (3.04 g), and heated with stirring for 18 hours. The reaction mixture was cooled to room temperature, then poured into water (50 ml), and extracted with chloroform (75 ml×3). The organic layer was washed twice with saturated brine and dried, and then the solvent was evaporated under reduced pressure. The residue was purified by flash column chromatography (hexane:ethyl acetate=20:1) to obtain the title compound (Intermediate 88, 754 mg).

Synthesis of 5-bromobenzo[d]isothiazole (Intermediate 89)

A solution obtained beforehand by mixing 2 N aqueous sodium hydroxide (2.19 ml) in an aqueous solution (5 ml) of hydroxylamine hydrochloride (308 mg, WAKO) was added dropwise to a solution of Intermediate 88 (401 mg) in ethanol (5 ml) at room temperature over 15 minutes. The reaction mixture was refluxed by heating for further 2 hours, then cooled to room temperature, poured into water (30 ml), and extracted with ethyl acetate (100 ml×3). The organic layer was washed successively with aqueous saturated ammonium chloride aqueous, saturated aqueous sodium hydrogencarbonate, and saturated brine and dried, and then the solvent was evaporated under reduced pressure. The residue was added with polyphosphoric acid (21.4 g), and heated with stirring at 100° C. for 2 hours. The reaction mixture was poured into ice water (100 ml), neutralized with 5 N aqueous sodium hydroxide under ice cooling, and then extracted with ethyl acetate (100 ml×3). The organic layer was washed twice with saturated brine and dried, and then the solvent was evaporated under reduced pressure. The residue was purified by flash column chromatography (hexane:ethyl acetate=20:1) to obtain the title compound (Intermediate 89, 143 mg).

Synthesis of 5-bromobenzo[c]isothiazole (Intermediate 90)

A solution of methanesulfonamide (5.34 g, TCI) in dehydrated benzene (9 ml) was added with thionyl chloride (6.0 ml) under ice cooling, and refluxed by heating for 24 hours. The reaction mixture was concentrated under reduced pressure, and a solution of the residue in dehydrated benzene (4 ml) was added dropwise to a solution of 4-bromotoluidine (1.49 g) in dehydrated benzene (40 ml) under ice cooling. This mixture was added dropwise with a solution of pyridine (0.97 ml) in dehydrated benzene (4 ml) under ice cooling, and refluxed by heating for 80 hours under argon gas atmosphere. The reaction mixture was cooled to room temperature, poured into water (100 ml), and extracted with chloroform (100 ml×3). The organic layer was dried, and then the solvent was evaporated under reduced pressure. The residue was purified by flash column chromatography (hexane:ethyl acetate=10:1) to obtain the title compound (Intermediate 90, 618 mg).

Synthesis of 6-bromoimidazo[1,2-a]pyridine (Intermediate 91)

The title compound (Intermediate 91, 3.36 g) was obtained from commercially available bromoacetaldehyde-diethylacetal (4.7 ml, WAKO) and 2-amino-5-bromopyridine (4.32 g, Ald) by a known method described in a publication (Yamanaka, M. et al., Chem. Pharm. Bull., 1991, vol. 39, p. 1556).

Synthesis of 5-bromo-1H-pyrrolo[2,3-b]pyridine (Intermediate 92)

The title compound (Intermediate 92, 182 mg) was obtained from commercially available 1H-pyrrolo[2,3-b]pyridine (1.3 g, TCI) by a known method described in a publication (Mazeas, D. et al, Heterocycles, 1999, vol. 50, p. 1065).

Synthesis of 5-bromo-1-methyl-1H-pyrrolo[2,3-b]pyridine (Intermediate 93)

According to the procedure described in the synthesis method of Compound No. V-29 with the modifications that the reaction was carried out for 2 hours, and the purification was performed by column chromatography (Quad, hexane: ethyl acetate=15:1), Intermediate 92 (98 mg), 60% sodium hydride (33 mg), and methyl iodide (53 µl) were reacted and treated to obtain the title compound (Intermediate 93, 88 mg).

Synthesis of 6-bromoisoquinoline (Intermediate 94)

The title compound (Intermediate 94, 1.46 g) was obtained from commercially available 4-bromobenzaldehyde (15.0 g, WAKO) by a known method described in a publication (Nerenz, H. et al., J. Chem. Soc. Perkin Trans. 2, 1998, p. 437).

Synthesis of 6-bromo-2H-isoquinolin-1-one (Intermediate 95)

A solution of Intermediate 94 (1.04 g) in methylene chloride (3 ml) was added with a solution of 3-chloroperbenzoic acid (2.16 g) in methylene chloride (3 ml), and stirred for 20 hours. The reaction mixture was added with methylene chloride (200 ml), and washed successively with saturated aqueous sodium hydrogencarbonate, saturated aqueous ammonium chloride and saturated brine. The organic layer was dried, and then the solvent was evaporated under reduced pressure. A solution of the residue in acetic anhydride (10 ml) was refluxed by heating for 5 hours. The reaction mixture was concentrated under reduced pressure, and then the residue was added with 2.5 N aqueous sodium hydroxide (20 ml), and stirred at 100° C. for 1 hour. The reaction mixture was cooled to room temperature, and neutralized with 5 N aqueous hydrochloric acid under ice cooling to obtain the precipitated title compound (Intermediate 95, 623 mg).

Examples V-1 to V-115

Typical examples of the compounds of the present invention that can be obtained by reacting and treating corresponding starting compounds using any of the methods described in the present specification including the examples described above are shown in Table-V-1 to Table-V-3.

TABLE V-1

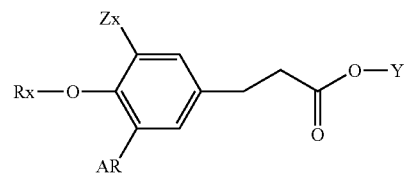

| Exp. | RxO | Y | Zx | AR | Syn | LCMS method | RTime | Mass |
|---|---|---|---|---|---|---|---|---|
| V-1 | cHexMeO | Et | H | 1-Nap | V-1 | | | |
| V-2 | cHexMeO | H | H | 1-Nap | V-2 | C | | 375 ($M^+ + 1$) |
| V-3 | cPenMeO | Me | H | 6OH-2-Nap | V-3 | | | |
| V-4 | cPenMeO | H | H | 6OH-2-Nap | V-4 | | | |
| V-5 | cPenMeO | Me | H | 5OH-2-Nap | V-5 | | | |
| V-6 | cPenMeO | H | H | 5OH-2-Nap | V-6 | | | |
| V-7 | cPenMeO | Me | H | 7OH-2-Nap | V-7 | | | |
| V-8 | cPenMeO | H | H | 7OH-2-Nap | V-8 | | | |
| V-9 | cPenMeO | Me | H | 6OMe-2-Nap | V-1 | | | |
| V-10 | cPenMeO | H | H | 6OMe-2-Nap | V-2 | C | | 418 ($M^+$) |
| V-11 | cPenMeO | Me | H | 6($OCH_2CONMe_2$)-2-Nap | V-11 | | | |
| V-12 | cPenMeO | H | H | 6($OCH_2CONMe_2$)-2-Nap | V-12 | | | |
| V-13 | cPenMeO | Me | H | 6$NH_2$-2-Nap | V-13 | | | |
| V-14 | cPenMeO | H | H | 6$NH_2$-2-Nap | V-14 | | | |
| V-15 | cPenMeO | H | H | 6($NMe_2$)-2-Nap | V-13, V-14 | C | | 418 ($M^+ + 1$) |
| V-16 | cPenMeO | H | H | 6($NHCOCH_2OH$)-2-Nap | V-16 | | | |
| V-17 | cPenMeO | H | H | 6(NHCO-2-Furan)-2-Nap | V-16 | C | | 484 ($M^+ + 1$) |
| V-18 | cPenMeO | Me | H | 6($NHSO_2Me$)-2-Nap | V-18 | | | |
| V-19 | cPenMeO | H | H | 6($NHSO_2Me$)-2-Nap | V-19 | | | |
| V-20 | cPenMeO | Me | H | 6($NHSO_2NMe_2$)-2-Nap | V-20 | | | |
| V-21 | cPenMeO | H | H | 6($NHSO_2NMe_2$)-2-Nap | V-21 | | | |
| V-22 | cPenMeO | Me | H | 6($NHSO_2NH_2$)-2-Nap | V-22 | | | |
| V-23 | cPenMeO | H | H | 6($NHSO_2NH_2$)-2-Nap | V-23 | | | |
| V-24 | cPenMeO | H | H | 6($SO_2Me$)-2-Nap | V-22, V-23 | C | | 452 ($M^+$) |
| V-25 | cPenMeO | H | H | 6($SO_2NH_2$)-2-Nap | V-22, V-23 | C | | 453 ($M^+$) |
| V-26 | cPenMeO | H | H | 6($SO_2NHMe$)-2-Nap | V-22, V-23 | C | | 468 ($M^+ + 1$) |
| V-27 | cPenO | Me | H | 5-Ind | V-27 | | | |
| V-28 | cPenO | H | H | 5-Ind | V-28 | | | |
| V-29 | cPenO | Me | H | 1Me-5-Ind | V-29 | | | |
| V-30 | cPenO | H | H | 1Me-5-Ind | V-30 | | | |
| V-31 | cPenMeO | Me | H | 4-Ind | V-31 | | | |
| V-32 | cPenMeO | H | H | 4-Ind | V-32 | | | |
| V-33 | cPenMeO | Me | H | 1Me-4-Ind | V-33 | | | |
| V-34 | cPenMeO | H | H | 1Me-4-Ind | V-34 | | | |
| V-35 | cPenMeO | H | H | 6-Ind | V-31, V-32 | C | | 377 ($M^+$) |
| V-36 | cPenMeO | H | H | 1-Me-6-Ind | V-33, V-34 | | | |
| V-37 | cPenMeO | H | H | 2-Ind | V-31, V-32 | A | 5.35 | 364 ($M^+ + 1$) |
| V-38 | cPenMeO | H | H | 1Me-2-Ind | V-29, V-30 | | | |
| V-39 | cPenMeO | H | H | 3-Ind | V-31, V-32 | | | |
| V-40 | cPenMeO | H | H | 1Me-3-Ind | V-29, V-30 | A | 4.75 | 363 ($M^+ + 1$) |
| V-41 | cPenMeO | H | H | 1iPr-5-Ind | V-29, V-30 | C | | 405 ($M^+$) |
| V-42 | cPenMeO | H | H | 1cPen-5-Ind | V-29, V-30 | C | | 431 ($M^+$) |
| V-43 | cPenMeO | H | H | 1-(2OHEt)-5-Ind | V-43 | | | |

TABLE V-2

| V-44 | cPenMeO | Me | H | 3CHO-5-Ind | V-44 | | | |
|---|---|---|---|---|---|---|---|---|
| V-45 | cPenMeO | H | H | 3CHO-5-Ind | V-45 | | | |
| V-46 | cPenMeO | H | H | 3CHO, 1Me-5-Ind | V-29, V-30 | C | | 406 ($M^+ + 1$) |

TABLE V-2-continued

| | | | | | | | |
|---|---|---|---|---|---|---|---|
| V-47 | cPenMeO | Me | H | 3Ac-5-Ind | V-47 | | |
| V-48 | cPenMeO | H | H | 3Ac-5-Ind | V-48 | | |
| V-49 | cPenMeO | H | H | 3Ac, 1Me-5-Ind | V-29, V-30 | C | 420 (M$^+$ + 1) |
| V-50 | cPenMeO | Me | H | 3Me-5-Ind | V-50 | | |
| V-51 | cPenMeO | H | H | 3Me-5-Ind | V-51 | | |
| V-52 | cPenMeO | H | H | 1,3DMe-5Ind | V-29, V-30 | C | 391 (M$^+$) |
| V-53 | cPenMeO | H | H | 1,2,3triMe-5Ind | V-22, V-29, V-30 | C | 405 (M$^+$) |
| V-54 | cPenO | Me | H | 4-1HIdz | V-54 | | |
| V-55 | cPenO | H | H | 4-1HIdz | V-55 | | |
| V-56 | cPenO | H | H | 1Me-4-1HIdz | V-29, V-30 | | |
| V-57 | cPenO | Me | H | 5-1HIdz | V-57 | | |
| V-58 | cPenO | H | H | 5-1HIdz | V-58 | | |
| V-59 | cPenO | H | H | 1Me-5-1HIdz | V-29, V-30 | | |
| V-60 | cPenO | H | H | 1Et-5-1HIdz | V-29, V-30 | | |
| V-61 | cPenO | H | H | 1Pr-5-1HIdz | V-29, V-30 | | |
| V-62 | cPenO | H | H | 2Me-5-2HIdz | V-29, V-30 | | |
| V-63 | cPenMeO | H | H | 6-1HIdz | V-57, V-58 | | |
| V-64 | cPenMeO | H | H | 1Me-6-1HIdz | V-29, V-30 | | |
| V-65 | cPenMeO | H | H | 1Et-5-1HIdz | V-29, V-30 | | |
| V-66 | cPenO | Me | H | 3Me-5-1HIdz | V-66 | | |
| V-67 | cPenO | H | H | 3Me-5-1HIdz | V-67 | | |
| V-68 | cPenO | Me | H | 1,3DMe-5-1HIdz | V-68 | | |
| V-68 | cPenO | H | H | 1,3DMe-5-1HIdz | V-69 | | |
| V-69 | cPenO | H | H | 3(CHO)-5-1HIdz | V-22, V-23 | | |
| V-70 | cPenO | H | H | 3(CHO), 1Me-5-1HIdz | V-22, V-23 | A | 4.38 | 365 (M$^+$ + 1) |
| V-71 | cPenO | H | H | 3OH-5-1HIdz | V-22, V-23 | | |
| V-72 | cPenO | H | H | 3OH, 1Me-5-1HIdz | V-22, V-23 | A | 3.71 | 381 (M$^+$ + 1) |
| V-73 | cPenMeO | Me | H | 5-BT | V-73 | | |
| V-74 | cPenMeO | H | H | 5-BT | V-74 | | |
| V-75 | cPenMeO | H | H | 5-BF | V-22, V-23 | C | 378 (M$^+$) |
| V-76 | cPenMeO | H | H | 2,3DMe-5-BF | V-22, V-23 | C | 406 (M$^+$) |
| V-77 | cPenMeO | Me | H | 5-2ABzt | V-77 | | |
| V-78 | cPenMeO | H | H | 5-2ABzt | V-78 | | |
| V-79 | cPenMeO | Et | H | 5-Bzt | V-79 | | |
| V-80 | cPenMeO | H | H | 5-Bzt | V-80 | | |
| V-81 | cPenMeO | Me | H | 2Me-5-Bzt | V-81 | | |
| V-82 | cPenMeO | H | H | 2Me-5-Bzt | V-82 | | |
| V-83 | cPenMeO | Et | H | 2,2DMe-5-2ABzt | V-83 | | |
| V-84 | cPenMeO | H | H | 2,2DMe-5-2ABzt | V-84 | | |
| V-85 | cPenMeO | H | H | 6-2ABzt | V-77, V-78 | C | 397 (M$^+$ + 1) |
| V-86 | cPenMeO | H | H | 6-Bzt | V-79, V-80 | C | 453 (M$^+$ + 1) |
| V-87 | cPenMeO | H | H | 2Me-6-Bzt | V-81, V-82 | C | 410 (M$^+$ + 1) |
| V-88 | cPenMeO | H | H | 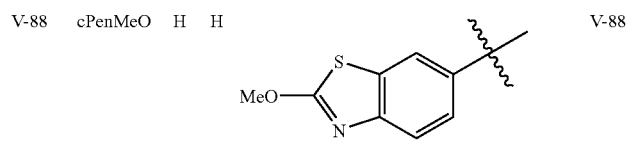 | V-88 | | |
| V-89 | cPenMeO | H | H | 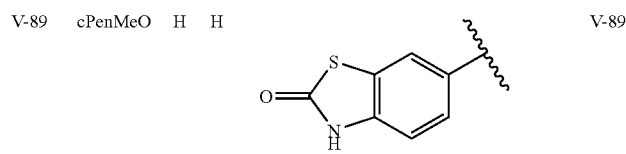 | V-89 | | |

TABLE V-3

| | | | | | | | |
|---|---|---|---|---|---|---|---|
| V-90 | cPenMeO | H | H | 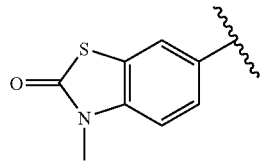 | V-29, V-30 | C | 412 (M$^+$ + 1) |
| V-91 | cPenMeO | H | H | 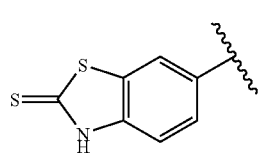 | V-91 | C | 414 (M$^+$ + 1) |

TABLE V-3-continued
| V-92 | cPenMeO | H | H | 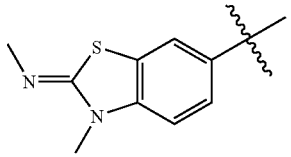 | V-29, V-30 | C | | 425 (M⁺ + 1) |
| --- | --- | --- | --- | --- | --- | --- | --- | --- |
| V-93 | cPenO | H | H | 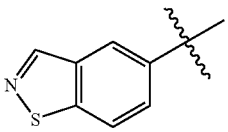 | V-22, V-23 | B | 3.87 | 368 (M⁺ + 1) |
| V-94 | cPenO | H | H | 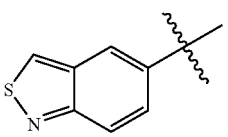 | V-22, V-23 | B | 3.58 | 368 (M⁺ + 1) |
| V-95 | cPenO | H | H | 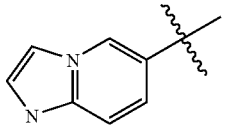 | V-22, V-23 | A | 2.57 | 315 (M⁺ + 1) |
| V-96 | cPenO | H | H | 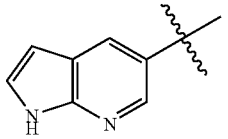 | V-22, V-23 | A | 3.84 | 351 (M⁺ + 1) |
| V-97 | cPenO | H | H | 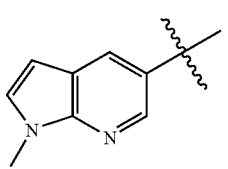 | V-29, V-30 | A | 4.28 | 365 (M⁺ + 1) |
| V-98 | cPenMeO | H | H | 3-Qu | V-22, V-23 | C | | 376 (M⁺ + 1) |
| V-99 | cPenMeO | H | H | 6-Qu | V-22, V-23 | C | | 376 (M⁺ + 1) |
| V-100 | cPenO | H | H | 6-IQ | V-22, V-23 | A | 2.15 | 452 (M⁺ + 1) |
| V-101 | cPenO | H | H | 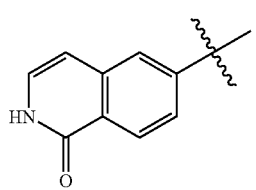 | V-22, V-23 | A | 3.74 | 378 (M⁺ + 1) |

TABLE V-3-continued

| | | | | | | | | |
|---|---|---|---|---|---|---|---|---|
| V-102 | cPenMeO | H | H | 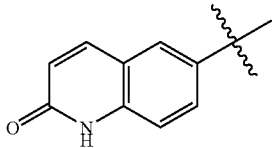 | V-22, V-23 | C | | 378 (M$^+$ + 1) |
| V-103 | cHexMeO | Et | H | 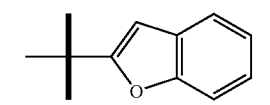 | V-33 | C | | 406 (M$^+$) |
| V-104 | cHexMeO | H | H | 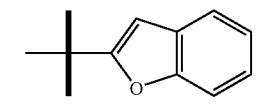 | V-34 | C | | 378 (M$^+$ + 1) |
| V-105 | cHexMeO | Et | H | 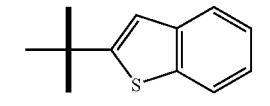 | V-33 | C | | 422 (M$^+$) |
| V-106 | cHexMeO | H | H | 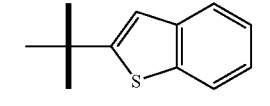 | V-34 | C | | 394 (M$^+$) |
| V-107 | cHexMeO | H | H | 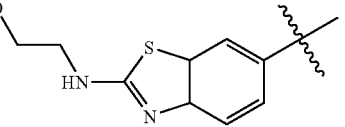 | V-22, V-23 | C | | 455 (M$^+$ + 1) |
| V-108 | cHexMeO | H | H | 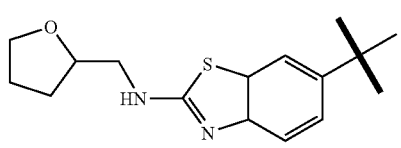 | V-22, V-23 | C | | 495 (M$^+$ + 1) |
| V-109 | cHexMeO | H | H | 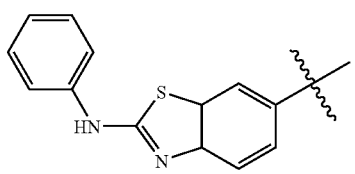 | V-22, V-23 | C | | 487 (M$^+$ + 1) |
| V-110 | cPenO | H | H | 3(COOH), 1Me-7-1HIdz | V-22, V-23 | A | 3.99 | 409 (M$^+$ + 1) |
| V-111 | cPenO | H | H | 3(COOH), 1Me-5-1HIdz | V-22, V-23 | A | 3.75 | 409 (M$^+$ + 1) |
| V-112 | cPenO | H | H | 3(COOH), 2Me-5-2HIdz | V-22, V-23 | A | 3.96 | 409 (M$^+$ + 1) |
| V-113 | cPenO | H | H | 3(COOH), 2Me-7-2HIdz | V-22, V-23 | A | 3.80 | 409 (M$^+$ + 1) |
| V-114 | cPenO | H | H | 3(COOH)-7-1HIdz | V-22, V-23 | A | 3.66 | 395 (M$^+$ + 1) |
| V-115 | cPenO | H | H | 3(COOH)-5-1HIdz | V-22, V-23 | A | 3.49 | 395 (M$^+$ + 1) |

Examples W-1 to W-25

Synthesis of 6-bromocinnoline (Intermediate 96)

The title compound (Intermediate 96, 134 mg) was obtained from commercially available 4-bromo-2-iodoanjiine (711 mg, Ald) by a method known from literature (Kimball, D. et al., Organic Letter, 2000, p. 3825).

Synthesis of 7-bromoquinazoline (Intermediate 97)

The title compound (Intermediate 97, 921 mg) was obtained from commercially available quinazoline (2.11 g, WAKO) by a known method described in a publication (Dalby, B. et al., Synthesis, 2002, p. 83).

Typical examples of the compounds of the present invention that can be obtained by reacting and treating corresponding starting compounds using any of the methods described in the present specification are shown in Table-W-1 and Table-W-2.

TABLE W-1

| Exp. | RxO | Y | Zx | AR | Syn | LCMS method | RTime | Mass |
|---|---|---|---|---|---|---|---|---|
| W-1 | cPenMeO | H | H | benzotriazole-5-yl | V-22, V-23 | C | | 366 ($M^+ + 1$) |
| W-2 | cPenMeO | H | H | benzothiadiazole-5-yl | V-22, V-23 | C | | 383 ($M^+ + 1$) |
| W-3 | cPenMeO | H | H | benzimidazole-5-yl | V-22, V-23 | C | | 365 ($M^+ + 1$) |
| W-4 | cPenMeO | H | H | 2-methylbenzimidazole-5-yl | V-22, V-23 | C | | 380 ($M^+ + 1$) |
| W-5 | cPenMeO | H | H | benzoxazole-5-yl | V-22, V-23 | C | | 366 ($M^+ + 1$) |
| W-6 | cPenMeO | H | H | 2-methylbenzoxazole-5-yl | V-22, V-23 | C | | 380 ($M^+ + 1$) |
| W-7 | cPenMeO | H | H | 2-aminobenzoxazole-5-yl | V-22, V-23 | C | | 381 ($M^+ + 1$) |

TABLE W-1-continued

| Exp. | RxO | Y | Zx | AR | Syn | LCMS method | RTime | Mass |
|---|---|---|---|---|---|---|---|---|
| W-8 | cPenMeO | H | H | benzoxazole-2-thione-5-yl | V-22, V-23 | C | | 398 (M$^+$ + 1) |
| W-9 | cPenMeO | H | H | benzoxazol-2(3H)-one-5-yl | V-22, V-23 | C | | 382 (M$^+$ + 1) |
| W-10 | cPenMeO | H | H | benzoxazol-6-yl | V-22, V-23 | C | | 366 (M$^+$ + 1) |
| W-11 | cPenMeO | H | H | quinoxalin-6-yl | V-22, V-23 | C | | 377 (M$^+$ + 1) |
| W-12 | cPenO | H | H | cinnolin-6-yl | V-22, V-23 | A | 3.97 | 363 (M$^+$ + 1) |
| W-13 | cPenO | H | H | quinazolin-7-yl | V-22, V-23 | A | 4.06 | 363 (M$^+$ + 1) |
| W-14 | cPenMeO | H | H | 2-amino-1H-benzimidazol-5-yl | V-22, V-23 | C | | 380 (M$^+$ + 1) |
| W-15 | cPenO | H | H | 1,3-benzodioxol-5-yl | V-22, V-23 | C | | 355 (M$^+$ + 1) |
| W-16 | cPenMeO | H | H | 2-thioxo-2,3-dihydro-1H-benzimidazol-5-yl | V-22, V-23 | C | | 397 (M$^+$ + 1) |

TABLE W-1-continued
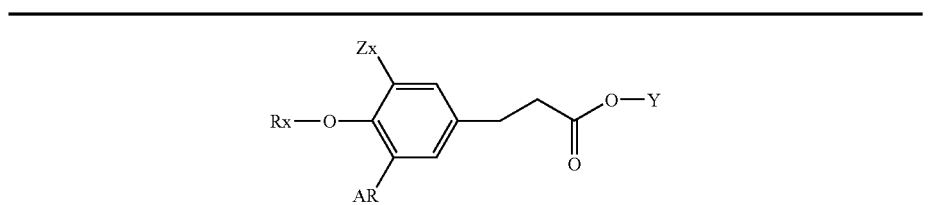
| Exp. | RxO | Y | Zx | AR | Syn | LCMS method | RTime | Mass |
|---|---|---|---|---|---|---|---|---|
| W-17 | cPenMeO | H | H | (1,3-dihydro-2-oxo-benzimidazol-5-yl) | V-22, V-23 | C | | 381 (M$^+$ + 1) |
| W-18 | cPenMeO | H | H | (2-methyl-benzoxazol-6-yl) | V-22, V-23 | C | | 380 (M$^+$ + 1) |
TABLE W-2
| W-19 | cPenMeO | H | H | (2-amino-benzoxazol-6-yl) | V-22, V-23 | C | | 381 (M$^+$ + 1) |
| W-20 | cPenMeO | H | H | (2-thioxo-2,3-dihydro-benzoxazol-6-yl) | V-22, V-23 | C | | 398 (M$^+$ + 1) |
| W-21 | cPenMeO | H | H | (2-oxo-2,3-dihydro-benzoxazol-6-yl) | V-22, V-23 | C | | 382 (M$^+$ + 1) |
| W-22 | cPenO | H | H | (1H-pyrrolo[3,2-b]pyridin-5-yl) | V-22, V-23 | C | | 351 (M$^+$ + 1) |

TABLE W-2-continued

| | | | | | | | |
|---|---|---|---|---|---|---|---|
| W-23 | cPenO | H | H | (imidazo-pyrazine) | V-22, V-23 | C | 353 (M⁺ + 1) |
| W-24 | cPenO | H | H | (triazolo-pyrimidine) | V-22, V-23 | C | 353 (M⁺ + 1) |
| W-25 | cPenO | H | H | (oxo-dihydropyrrolopyridine) | V-22, V-23 | C | 367 (M⁺ + 1) |

Example X-1

Synthesis of ethyl 3-[2-cyclopentyloxy-5-(naphthalen-2-yl)phenyl]acrylate (Intermediate 98)

According to the procedure described in the synthesis method of Intermediate 7 provided that the reaction was carried out for 1 hour, Compound No. D-20 (396 mg), ethyl diethylphosphonoacetate (288 µl), and 60% sodium hydride (59 mg) were reacted and treated to obtain the title compound (Intermediate 98, 428 mg).

Synthesis of ethyl 3-[2-cyclohexylmethyloxy-5-(naphthalen-1-yl)phenyl]propionate (Compound No. X-1)

According to the procedure described in the synthesis method of Intermediate B-99 with the modifications that the reaction was carried out at 50° C. for 5 hours, and the purification was performed by column chromatography (Quad, hexane:ethyl acetate=10:1), Intermediate 98 (361 mg) and Raney 2800 nickel (380 mg) were reacted and treated to obtain the title compound (Compound No. X-1, 397 mg).

Example X-2

Synthesis of 3-[2-cyclohexylmethyloxy-5-(naphthalen-1-yl)phenyl]propionic acid (Compound No. X-2)

According to the procedure described in the synthesis method of Intermediate 9 provided that the reaction was carried out for 2.5 hours, Compound No. X-1 (390 mg) and 2 N aqueous sodium hydroxide (1.1 ml) were reacted and treated to obtain the title compound (Compound No. X-2, 338 mg).

Examples X-1 to X-4

Typical examples of the compounds of the present invention that can be obtained by reacting and treating corresponding starting compounds using any of the methods described in the present specification including the examples described above are shown in Table-X-1.

TABLE X-1

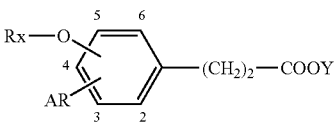

| Exp. | RxO | Y | RxO positio | Ar | Syn | AR position | LCMS method | RTime | Mass |
|---|---|---|---|---|---|---|---|---|---|
| X-1 | cPenO | Et | 2 | 2-Nap | X-1 | 5 | | | |
| X-2 | cPenO | H | 2 | 2-Nap | X-2 | 5 | C | | 347 (M⁺ + 1) |
| X-3 | cPenO | H | 2 | 1Me-5-Ind | X-1, X-2 | 5 | C | | 350 (M⁺ + 1) |
| X-4 | cPenO | H | 2 | 1Me-5-1HIdz | X-1, X-2 | 5 | C | | 351 (M⁺ + 1) |

Reference Examples

Intermediates Aa-1 to Aa-47

Synthesis of methyl 3-[3-(naphthalen-2-yl)-4-trifluoromethanesulfonylphenyl]-propionate (Intermediate Aa-1)

A solution of Intermediate 41 (4.34 g) in dehydrated pyridine (120 ml) was added with trifluoromethanesulfonic anhydride (2.6 ml, ALD) under ice cooling, then warmed to room temperature, and stirred for 4 hours. The reaction mixture was concentrated under reduced pressure, and then extracted with ethyl acetate (800 ml). The organic layer was washed successively with 1 N hydrochloric acid, saturated aqueous ammonium chloride and saturated brine, and dried, and then the solvent was evaporated under reduced pressure. The residue was purified by flash column chromatography (hexane:ethyl acetate=6:1) to obtain the title compound (Intermediate Aa-1, 4.98 g).

Typical examples of the reaction intermediates including those mentioned above, that can be obtained by reacting and treating corresponding starting compounds according to the synthesis method of Intermediate Aa-1, are shown in Table-Aa-1.

In the column indicated as "Mass" in the table, data of mass spectra measured by fast atom bombardment mass spectrometry (FAB-MS) are shown.

TABLE Aa-1

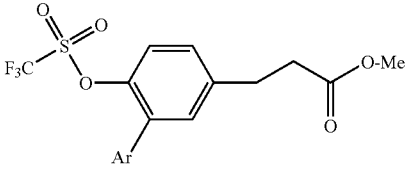

| Exp. | AR | Mass |
|---|---|---|
| Aa-1 | 2-Nap | 439($M^+$ + 1) |
| Aa-2 | 5-Ind | 428($M^+$ + 1) |
| Aa-3 | 1Me-5-Ind | 442($M^+$ + 1) |
| Aa-4 | 5-1HIdz | 429($M^+$ + 1) |
| Aa-5 | 1Me-5-1HIdz | 443($M^+$ + 1) |
| Aa-6 | 5-BF | 432($M^+$ + 1) |
| Aa-7 | 3-Qu | 440($M^+$ + 1) |
| Aa-8 | 1-Nap | 439($M^+$ + 1) |
| Aa-9 | 6(MeO)-2-Nap | 469($M^+$ + 1) |
| Aa-10 | 6($NMe_2$)-2-Nap | 482($M^+$ + 1) |
| Aa-11 | 4-Ind | 428($M^+$ + 1) |
| Aa-12 | 1Me-4-Ind | 442($M^+$ + 1) |
| Aa-13 | 6-Ind | 428($M^+$ + 1) |
| Aa-14 | 1Me-6-Ind | 442($M^+$ + 1) |
| Aa-15 | 2-Ind | 428($M^+$ + 1) |
| Aa-16 | 1Me-2-Ind | 442($M^+$ + 1) |
| Aa-17 | 3-Ind | 428($M^+$ + 1) |
| Aa-18 | 1Me-3-Ind | 442($M^+$ + 1) |
| Aa-19 | 1iPr-5-Ind | 470($M^+$ + 1) |
| Aa-20 | 1cPen-5-Ind | 496($M^+$ + 1) |
| Aa-21 | 3Me-5-Ind | 442($M^+$ + 1) |
| Aa-22 | 1,3DMe-5Ind | 456($M^+$ + 1) |
| Aa-23 | 1,2,3triMe-5Ind | 470($M^+$ + 1) |
| Aa-24 | 4-1HIdz | 429($M^+$ + 1) |
| Aa-25 | 1Me-4-1HIdz | 443($M^+$ + 1) |
| Aa-26 | 5-1HIdz | 429($M^+$ + 1) |
| Aa-27 | 1Me-5-1HIdz | 443($M^+$ + 1) |
| Aa-28 | 1Et-5-1HIdz | 457($M^+$ + 1) |
| Aa-29 | 1Pr-5-1HIdz | 471($M^+$ + 1) |
| Aa-30 | 2Me-5-2HIdz | 443($M^+$ + 1) |
| Aa-31 | 6-1HIdz | 429($M^+$ + 1) |
| Aa-32 | 1Me-6-1HIdz | 443($M^+$ + 1) |
| Aa-33 | 3Me-5-1HIdz | 443($M^+$ + 1) |

TABLE Aa-1-continued

| Exp. | AR | Mass |
|---|---|---|
| Aa-34 | 1,3DMe-5-1HIdz | 457($M^+$ + 1) |
| Aa-35 | 5-BT | 445($M^+$ + 1) |
| Aa-36 | 2,3DMe-5-BF | 457($M^+$ + 1) |
| Aa-37 | 5-2ABzt | 461($M^+$ + 1) |
| Aa-38 | 5-Bzt | 456($M^+$ + 1) |
| Aa-39 | 2Me-5-Bzt | 460($M^+$ + 1) |
| Aa-40 | 2,2DMe-5-2ABzt | 489($M^+$ + 1) |
| Aa-41 | 6-2ABzt | 461($M^+$ + 1) |
| Aa-42 | 6-Bzt | 456($M^+$ + 1) |
| Aa-43 | 2Me-6-Bzt | 460($M^+$ + 1) |
| Aa-44 | 6-Qu | 440($M^+$ + 1) |
| Aa-45 | 6-IQ | 440($M^+$ + 1) |
| Aa-46 | 2-BF | 429($M^+$ + 1) |
| Aa-47 | 2-BT | 445($M^+$ + 1) |

Example Ca-1

Synthesis of methyl 3-[4-(phenyl)-3-(naphthalen-2-yl)phenyl]propionate (Compound No. Ca-1)

Compound No. Aa-1 (138.4 mg, corresponding to the substance mentioned in the column of SM1 in Table-Ca-1 mentioned later), phenylboronic acid (71.3 mg, corresponding to the substance mentioned in the column of SM 2 mentioned in Table-Ca-1 mentioned later), cesium carbonate (254.9 mg), $PdCl_2$(dppf) (25.6 mg) were added with toluene (600 μl), methanol (1.2 ml), and water (1.2 ml), and stirred at 80° C. for 17 hours under nitrogen atmosphere. The reaction mixture was added with ethyl acetate (30 ml), washed successively with water and saturated brine. The organic layer was dried, and then the solvent was evaporated under reduced pressure. The residue was purified by flash column chromatography (hexane:ethyl acetate=8:1) to obtain the title compound (Compound No. Ca-1, 140.6 mg).

Example Ca-2

Synthesis of 3-[4-phenyl-3-(naphthalen-2-yl)phenyl] propionic acid (Compound No. Ca-2)

A solution of Compound Ca-1 (137.7 mg) in methanol (4.0 ml) was added with 2 N aqueous sodium hydroxide (720 μl), and stirred at 60° C. for 16 hours. The reaction mixture was concentrated under reduced pressure, then made acidic with 5% aqueous hydrochloric acid under ice cooling, and extracted with ethyl acetate (50 ml). The organic layer was washed with saturated brine, and dried, and then the solvent was evaporated under reduced pressure to obtain the title compound (Compound No. Ca-2, 108 mg).

Examples Ca-1 to Ca-270 and Examples Cb-1 to Cb-95

Typical examples of the compounds of the present invention including those mentioned in the examples described above, that can be obtained by reacting and treating corresponding starting compounds according to the methods described in Examples Ca-1 and Ca-2, are shown in Table-Ca-1 to Table-Ca-5, Table-Cb-1 and Table-Cb-2.

The substances mentioned in the columns of "SM1" in the tables correspond to reaction intermediates, and those mentioned in the columns of "SM2" in the tables correspond to the boronic acid reagent used in Example Ca-1. The boronic acid reagents shown with the symbols of "BRA (number)" mentioned in the columns of "SM2" are those mentioned in Table-Ba-1 and Table-Ba-2. The regents for which cells of the columns of "Manufacturer" in the tables are blank are synthesized according to a method described in ordinary chemical literatures.

TABLE Ba-1

| Reagen | Name of reagent | Manufacturer |
|---|---|---|
| BRA1 | Naphthalene-2-boronic acid | TCI |
| BRA2 | (1H-Indol-5-yl) boronic acid | Frontier |
| BRA3 | (1-Methyl-1H-indol-5-yl) boronic acid | Frontier |
| BRA4 | (1-Ethyl-1H-indol-5-yl) boronic acid | |
| BRA5 | (1H-Indazol-5-yl) boronic acid | |
| BRA6 | (1-Methyl-1H-indazol-5-yl) boronic acid | |
| BRA7 | (1-Ethyl-1H-indazol-5-yl) boronic acid | |
| BRA8 | (2-Methyl-2H-indazol-5-yl) boronic acid | |
| BRA9 | Benzothiazole-6-yl-4,4,5,5-tetramethyl-1,3,2-dioxaborolan | |
| BRA10 | Quinoline-3-boronic acid | Frontier |
| BRA11 | Quinoline-6-yl-4,4,5,5-tetramethyl-1,3,2-dioxaborolan | Ald |
| BRA12 | Isoquinoline-6-yl-4,4,5,5-tetramethyl-1,3,2-dioxaborolan | |
| BRA13 | Methyl boronic acid | Ald |
| BRA14 | Phenyl boronic acid | Ald |
| BRA15 | 4-Hydroxyphenyl boronic acid | Ald |
| BRA16 | Naphthalene-1-boronic acid | Ald |
| BRA17 | 3.5-Bis(trifluoromethyl) phenyl boronic acid | TCI |
| BRA18 | Benzo[b]furan-2-boronic acid | Ald |
| BRA19 | 4-Methoxypheny boronic acid | Ald |
| BRA20 | 2-Methylpropyl boronic acid | Ald |
| BRA21 | 4-(Dimethylamino) phenyl boronic acid | Ald |
| BRA22 | 4-Fluorophenyl boronic acid | TCI |
| BRA23 | Cyclopropyl boronic acid | |
| BRA24 | 6-Ethoxynaphthalene-2-boronic acid | Ald |
| BRA25 | Benzo[b]thiophene-2-boronic acid | LANC |
| BRA26 | Pyridine-4-boronic acid | ALD |
| BRA27 | Dibenzofuran-2-boronic acid | Ald |
| BRA28 | Cyclopentyl boronic acid | LANC |
| BRA29 | 4-Methylphenyl boronic acid | Ald |
| BRA30 | 4-Chlorophenyl boronic acid | Ald |
| BRA31 | 1-n-Butyl boronic acid | Ald |
| BRA32 | 2-Fluorophenyl boronic acid | Ald |
| BRA33 | 3-Fluorophenyl boronic acid | Ald |
| BRA34 | 4-Fluorophenyl boronic acid | Ald |
| BRA35 | 2-Furyl boronic acid | Ald |

TABLE Ba-1-continued

| BRA36 | 2-Thienyl boronic acid | Ald |
|---|---|---|
| BRA37 | 3-Methoxyphenyl boronic acid | Ald |
| BRA38 | 2-Methoxyphenyl boronic acid | |
| BRA39 | 2-(Trifluoromethyl) phenyl boronic acid | |
| BRA40 | 3-(Trifluoromethyl) phenyl boronic acid | |
| BRA41 | 4-(Trifluoromethyl) phenyl boronic acid | |
| BRA42 | Indan-2-yl-4,4,5,5-tetramethyl-1,3,2-dioxaborolane | |
| BRA43 | 4-Methylindan-2-yl-4,4,5,5-tetramethyl-1,3,2-dioxaborolane | |
| BRA44 | 5-Methylindan-2-yl-4,4.5,5-tetra methyl-1,3,2-dioxaborolane | |

TABLE Ba-2

| Reagent | Name of reagent | Manufacture |
|---|---|---|
| BRA45 | 4,7-Dimethylindan-2-yl-4,4,5,5-tetramethyl-1,3,2-dioxaborolane | |
| BRA46 | 5,6-Dimethylindan-2-yl-4,4,5,5-tetramethyl-1,3,2-dioxaborolane | |
| BRA47 | 5-Fluoroindan-2-yl-4,4,5,5-tetramethyl-1,3,2-dioxaborolane | |
| BRA48 | 4-Fluoroindan-2-yl-4,4,5,5-tetramethyl-1,3,2-dioxaborolane | |
| BRA49 | 4,7-Difluoroindan-2-yl-4,4,5,5-tetramethyl-1,3,2-dioxaborolane | |
| BRA50 | 5,6-Difluoroindan-2-yl-4,4,5,5-tetramethyl-1,3,2-dioxaborolane | |
| BRA51 | 4-Chloroindan-2-yl-4,4,5,5-tetramethyl-1,3,2-dioxaborolane | |
| BRA52 | 5-Chloroindan-2-yl-4,4,5,5-tetramethyl-1,3,2-dioxaborolane | |
| BRA53 | 4,7-Dichloroindan-2-yl-4,4,5,5-tetramethyl-1,3,2-dioxaborolane | |
| BRA54 | 5,6-Dichloroindan-2-yl-4,4,5,5-tetramethyl-1,3,2-dioxaborolane | |
| BRA55 | 4-Methoxyindan-2-yl-4,4,5,5-tetramethyl-1,3,2-dioxaborolane | |
| BRA56 | 5-Methoxyindan-2-yl-4,4,5,5-tetramethyl-1,3,2-dioxaborolane | |
| BRA57 | 5,6-Dimethoxyindan-2-yl-4,4,5,5-tetramethyl-1,3,2- | |
| BRA58 | Cyclohexyl boronic acid | Ald |
| BRA59 | 2-Methylphenyl boronic acid | Ald |
| BRA60 | 3-Methylphenyl boronic acid | Ald |
| BRA61 | 2-Chlorophenyl boronic acid | Ald |
| BRA62 | 3-Chlorophenyl boronic acid | Ald |
| BRA63 | 2,3-Bis(trifluoromethyl) phenyl boronic acid | |
| BRA64 | 2,4-Bis(trifluoromethyl) phenyl boronic acid | |
| BRA65 | 2,5-Bis(trifluoromethyl) phenyl boronic acid | |
| BRA66 | 3,4-Bis(trifluoromethyl) phenyl boronic acid | |
| BRA67 | 3-Furyl boronic acid | Ald |
| BRA68 | 3-Thienyl boronic acid | Ald |
| BRA69 | Pyridine-2-yl-4,4,5,5-tetramethyl-1,3,2-dioxaborolane | |
| BRA70 | Pyridine-3-boronic acid | Ald |
| BRA71 | 2,3-Dimethylphenyl boronic acid | Ald |
| BRA72 | 2,5-Dimethylphenyl boronic acid | Ald |
| BRA73 | 3,5-Dimethylphenyl boronic acid | Ald |
| BRA74 | 2,3-DiChlorophenyl boronic acid | Ald |

TABLE Ba-2-continued

| Reagent | Name of reagent | Manufacture |
|---|---|---|
| BRA75 | 2,4-DiChlorophenyl boronic acid | Ald |
| BRA76 | 2,5-DiChlorophenyl boronic acid | Ald |
| BRA77 | 2,6-DiChlorophenyl boronic acid | Acros |
| BRA78 | 3,4-DiChlorophenyl boronic acid | Ald |
| BRA79 | 3,5-DiChlorophenyl boronic acid | Ald |
| BRA80 | 2,3-Difluorophenyl boronic acid | Ald |
| BRA81 | 2,4-Difluorophenyl boronic acid | Ald |
| BRA82 | 2,5-Difluorophenyl boronic acid | Ald |
| BRA83 | 2,6-Difluorophenyl boronic acid | Ald |
| BRA84 | 3,4-Difluorophenyl boronic acid | Ald |
| BRA85 | 3,5-Difluorophenyl boronic acid | Ald |
| BRA86 | 2-(Dimethylamino) phenyl boronic acid | Digital |
| BRA87 | 3-(Dimethylamino) phenyl boronic acid | Digital |
| BRA88 | 4-Phenoxy phenyl boronic acid | Ald |

TABLE Ca 1

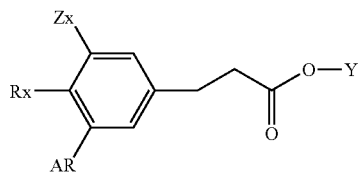

| | | | | | | | LCMS | | |
|---|---|---|---|---|---|---|---|---|---|
| Exp. | Rx | Y | Zx | AR | SM1 | SM2 | method | RTime | Mass |
| Ca-1 | Ph | Me | H | 2-Nap | Aa-1 | BRA14 | D | | N.D |
| Ca-2 | Ph | H | H | 2-Nap | Ca-1 | — | C | | 353 (M⁺ + 1) |
| Ca-3 | Ph | Me | H | 5-Ind | Aa-2 | BRA14 | C | | 356 (M⁺ + 1) |
| Ca-4 | Ph | H | H | 5-Ind | Ca-3 | — | C | | 342 (M⁺ + 1) |
| Ca-5 | Ph | Me | H | 1Me-5-Ind | Aa-3 | BRA14 | C | | 370 (M⁺ + 1) |
| Ca-6 | Ph | H | H | 1Me-5-Ind | Ca-5 | — | C | | 356 (M⁺ + 1) |
| Ca-7 | Ph | H | H | 5-1HIdz | Aa-4 | BRA14 | C | | 343 (M⁺ + 1) |
| Ca-8 | Ph | Me | H | 1Me-5-1HIdz | Aa-5 | BRA14 | C | | 371 (M⁺ + 1) |
| Ca-9 | Ph | H | H | 1Me-5-1HIdz | Ca-8 | — | C | | 357 (M⁺ + 1) |
| Ca-10 | Ph | H | H | 5-BF | Aa-6 | BRA14 | C | | 342 (M⁺ + 1) |
| Ca-11 | Ph | H | H | 3-Qu | Aa-7 | BRA14 | C | | 354 (M⁺ + 1) |
| Ca-12 | Ph | H | H | 1-Nap | Aa-8 | BRA14 | C | | 353 (M⁺ + 1) |
| Ca-13 | Ph | H | H | 6(OMe)-2-Nap | Aa-9 | BRA14 | C | | 383 (M⁺ + 1) |
| Ca-14 | Ph | H | H | 6(NMe₂)-2-Nap | Aa-10 | BRA14 | C | | 396 (M⁺ + 1) |
| Ca-15 | Ph | H | H | 4-Ind | Aa-11 | BRA14 | C | | 342 (M⁺ + 1) |
| Ca-16 | Ph | H | H | 1Me-4-Ind | Aa-12 | BRA14 | C | | 356 (M⁺ + 1) |
| Ca-17 | Ph | H | H | 6-Ind | Aa-13 | BRA14 | C | | 342 (M⁺ + 1) |
| Ca-18 | Ph | H | H | 1Me-6-Ind | Aa-14 | BRA14 | C | | 356 (M⁺ + 1) |
| Ca-19 | Ph | H | H | 2-Ind | Aa-15 | BRA14 | C | | 342 (M⁺ + 1) |
| Ca-20 | Ph | H | H | 1Me-2-Ind | Aa-16 | BRAl4 | C | | 356 (M⁺ + 1) |
| Ca-21 | Ph | H | H | 3-Ind | Aa-17 | BRA14 | C | | 342 (M⁺ + 1) |
| Ca-22 | Ph | H | H | 1Me-3-Ind | Aa-18 | BRA14 | C | | 356 (M⁺ + 1) |
| Ca-23 | Ph | H | H | 1iPr-5-Ind | Aa-19 | BRA14 | C | | 384 (M⁺ + 1) |
| Ca-24 | Ph | H | H | 1cPen-5-Ind | Aa-20 | BRA14 | C | | 410 (M⁺ + 1) |
| Ca-25 | Ph | H | H | 3Me-5-Ind | Aa-21 | BRA14 | C | | 356 (M⁺ + 1) |
| Ca-26 | Ph | H | H | 1,3DMe-5Ind | Aa-22 | BRA14 | C | | 370 (M⁺ + 1) |
| Ca-27 | Ph | H | H | 1,2,3triMe-5Ind | Aa-23 | BRA14 | C | | 384 (M⁺ + 1) |
| Ca-28 | Ph | H | H | 4-1HIdz | Aa-24 | BRA14 | C | | 343 (M⁺ + 1) |
| Ca-29 | Ph | H | H | 1Me-4-1HIdz | Aa-25 | BRA14 | C | | 357 (M⁺ + 1) |
| Ca-30 | Ph | H | H | 5-1HIdz | Aa-26 | BRA14 | C | | 343 (M⁺ + 1) |
| Ca-31 | Ph | H | H | 1Me-5-1HIdz | Aa-27 | BRA14 | C | | 357 (M⁺ + 1) |
| Ca-32 | Ph | H | H | 1Et-5-1HIdz | Aa-28 | BRA14 | C | | 371 (M⁺ + 1) |
| Ca-33 | Ph | H | H | 1Pr-5-1HIdz | Aa-29 | BRA14 | C | | 385 (M⁺ + 1) |
| Ca-34 | Ph | H | H | 2Me-5-2HIdz | Aa-30 | BRA14 | C | | 357 (M⁺ + 1) |
| Ca-35 | Ph | H | H | 6-1HIdz | Aa-31 | BRA14 | C | | 343 (M⁺ + 1) |
| Ca-36 | Ph | H | H | 1Me-6-1HIdz | Aa-32 | BRA14 | C | | 357 (M⁺ + 1) |
| Ca-37 | Ph | H | H | 3Me-5-1HIdz | Aa-33 | BRA14 | C | | 357 (M⁺ + 1) |
| Ca-38 | Ph | H | H | 1,3DMe-5-1HIdz | Aa-34 | BRA14 | C | | 371 (M⁺ + 1) |
| Ca-39 | Ph | H | H | 5-BT | Aa-35 | BRA14 | C | | 359 (M⁺ + 1) |
| Ca-40 | Ph | H | H | 2,3DMe-5-BF | Aa-36 | BRA14 | C | | 387 (M⁺ + 1) |
| Ca-41 | Ph | H | H | 5-2ABzt | Aa-37 | BRA14 | C | | 375 (M⁺ + 1) |
| Ca-42 | Ph | H | H | 5-Bzt | Aa-38 | BRA14 | C | | 360 (M⁺ + 1) |
| Ca-43 | Ph | H | H | 2Me-5-Bzt | Aa-39 | BRA14 | C | | 374 (M⁺ + 1) |

TABLE Ca 1-continued

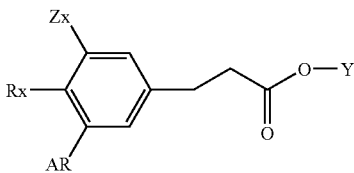

| Exp. | Rx | Y | Zx | AR | SM1 | SM2 | LCMS method | RTime | Mass |
|---|---|---|---|---|---|---|---|---|---|
| Ca-44 | Ph | H | H | 2,2DMe-5-2ABzt | Aa-40 | BRA14 | C | | 403 (M$^+$ + 1) |
| Ca-45 | Ph | H | H | 6-2ABzt | Aa-41 | BRA14 | C | | 375 (M$^+$ + 1) |
| Ca-46 | Ph | H | H | 6-Bzt | Aa-42 | BRA14 | C | | 360 (M$^+$ + 1) |
| Ca-47 | Ph | H | H | 2Me-6-Bzt | Aa-43 | BRA14 | C | | 374 (M$^+$ + 1) |
| Ca-48 | Ph | H | H | 6-Qu | Aa-44 | BRA14 | C | | 354 (M$^+$ + 1) |
| Ca-49 | Ph | H | H | 6-IQ | Aa-45 | BRA14 | C | | 354 (M$^+$ + 1) |
| Ca-50 | Ph | H | H | 2-BF | Aa-46 | BRA14 | C | | 342 (M$^+$ + 1) |

TABLE Ca-2

| Exp. | Rx | Y | Zx | AR | SM1 | SM2 | LCMS method | RTime | Mass |
|---|---|---|---|---|---|---|---|---|---|
| Ca-51 | Ph | H | H | 2-BT | Aa-47 | BRA14 | C | | 359 (M$^+$ + 1) |
| Ca-52 | 4MeOPh | H | H | 2-Nap | Aa-1 | BRA19 | C | | 383 (M$^+$ + 1) |
| Ca-53 | 4MeOPh | H | H | 1-Me-5-Ind | Aa-3 | BRA19 | C | | 386 (M$^+$ + 1) |
| Ca-54 | 4MeOPh | H | H | 5-1HIdz | Aa-4 | BRA19 | C | | 373 (M$^+$ + 1) |
| Ca-55 | 4MeOPh | H | H | 1Me-5-1HIdz | Aa-5 | BRA19 | C | | 387 (M$^+$ + 1) |
| Ca-56 | 4MeOPh | H | H | 3-Qu | Aa-7 | BRA19 | C | | 384 (M$^+$ + 1) |
| Ca-57 | 4MeOPh | H | H | 1Et-5-1HIdz | Aa-28 | BRA19 | C | | 401 (M$^+$ + 1) |
| Ca-58 | 3MeOPh | H | H | 5-Ind | Aa-2 | BRA37 | C | | 372 (M$^+$ + 1) |
| Ca-59 | 3MeOPh | H | H | 1Me-5-Ind | Aa-3 | BRA37 | C | | 386 (M$^+$ + 1) |
| Ca-60 | 3MeOPh | H | H | 5-1HIdz | Aa-4 | BRA37 | C | | 373 (M$^+$ + 1) |
| Ca-61 | 3MeOPh | H | H | 1Me-5-1HIdz | Aa-5 | BRA37 | C | | 387 (M$^+$ + 1) |
| Ca-62 | 3MeOPh | H | H | 3-Qu | Aa-7 | BRA37 | C | | 384 (M$^+$ + 1) |
| Ca-63 | 3MeOPh | H | H | 1Et-5-1HIdz | Aa-28 | BRA37 | C | | 401 (M$^+$ + 1) |
| Ca-64 | 2MeOPh | H | H | 2-Nap | Aa-1 | BRA38 | C | | 383 (M$^+$ + 1) |
| Ca-65 | 2MeOPh | H | H | 5-Ind | Aa-2 | BRA38 | C | | 372 (M$^+$ + 1) |
| Ca-66 | 2MeOPh | H | H | 1Me-5-Ind | Aa-3 | BRA38 | C | | 386 (M$^+$ + 1) |
| Ca-67 | 2MeOPh | H | H | 5-1HIdz | Aa-4 | BRA38 | C | | 373 (M$^+$ + 1) |
| Ca-68 | 2MeOPh | H | H | 1Me-5-1HIdz | Aa-5 | BRA38 | C | | 387 (M$^+$ + 1) |
| Ca-69 | 2MeOPh | H | H | 5-Bzt | Aa-38 | BRA38 | C | | 390 (M$^+$ + 1) |
| Ca-70 | 2MeOPh | H | H | 3-Qu | Aa-7 | BRA38 | C | | 384 (M$^+$ + 1) |
| Ca-71 | 2MeOPh | H | H | 1Et-5-1HIdz | Aa-28 | BRA38 | C | | 401 (M$^+$ + 1) |
| Ca-72 | 2MePh | H | H | 2-Nap | Aa-1 | BRA59 | C | | 367 (M$^+$ + 1) |
| Ca-73 | 2MePh | H | H | 5-Ind | Aa-2 | BRA59 | C | | 356 (M$^+$ + 1) |
| Ca-74 | 2MePh | H | H | 1Me-5-Ind | Aa-3 | BRA59 | C | | 370 (M$^+$ + 1) |
| Ca-75 | 2MePh | H | H | 5-1HIdz | Aa-4 | BRA59 | C | | 357 (M$^+$ + 1) |
| Ca-76 | 2MePh | H | H | 1Me-5-1HIdz | Aa-5 | BRA59 | C | | 371 (M$^+$ + 1) |
| Ca-77 | 2MePh | H | H | 5-Bzt | Aa-38 | BRA59 | C | | 374 (M$^+$ + 1) |
| Ca-78 | 3MePh | H | H | 2-Nap | Aa-1 | BRA60 | C | | 367 (M$^+$ + 1) |
| Ca-79 | 3MePh | H | H | 5-Ind | Aa-2 | BRA60 | C | | 356 (M$^+$ + 1) |
| Ca-80 | 3MePh | H | H | 5-1HIdz | Aa-4 | BRA60 | C | | 357 (M$^+$ + 1) |
| Ca-81 | 3MePh | H | H | 1Me-5-1HIdz | Aa-5 | BRA60 | C | | 371 (M$^+$ + 1) |
| Ca-82 | 3MePh | H | H | 5-Bzt | Aa-38 | BRA60 | C | | 374 (M$^+$ + 1) |
| Ca-83 | 3MePh | H | H | 1Et-5-1HIdz | Aa-28 | BRA60 | C | | 385 (M$^+$ + 1) |
| Ca-84 | 4MePh | H | H | 2-Nap | Aa-1 | BRA29 | C | | 367 (M$^+$ + 1) |
| Ca-85 | 4MePh | H | H | 5-Ind | Aa-2 | BRA29 | C | | 356 (M$^+$ + 1) |
| Ca-86 | 4MePh | H | H | 1Me-5-Ind | Aa-3 | BRA29 | C | | 370 (M$^+$ + 1) |
| Ca-87 | 4MePh | H | H | 5-1HIdz | Aa-4 | BRA29 | C | | 357 (M$^+$ + 1) |
| Ca-88 | 4MePh | H | H | 1Me-5-1HIdz | Aa-5 | BRA29 | C | | 371 (M$^+$ + 1) |
| Ca-89 | 4MePh | H | H | 5-Bzt | Aa-38 | BRA29 | C | | 374 (M$^+$ + 1) |
| Ca-90 | 4MePh | H | H | 3-Qu | Aa-7 | BRA29 | C | | 368 (M$^+$ + 1) |
| Ca-91 | 4MePh | H | H | 1Et-5-1HIdz | Aa-28 | BRA29 | C | | 385 (M$^+$ + 1) |
| Ca-92 | 2,3DMePh | H | H | 5-Ind | Aa-2 | BRA71 | C | | 370 (M$^+$ + 1) |
| Ca-93 | 2,3DMePh | H | H | 1Me-5-Ind | Aa-3 | BRA71 | C | | 384 (M$^+$ + 1) |
| Ca-94 | 2,3DMePh | H | H | 5-1HIdz | Aa-4 | BRA71 | C | | 371 (M$^+$ + 1) |
| Ca-95 | 2,3DMePh | H | H | 1Me-5-1HIdz | Aa-5 | BRA71 | C | | 385 (M$^+$ + 1) |
| Ca-96 | 2,3DMePh | H | H | 1Et-5-1HIdz | Aa-28 | BRA71 | C | | 399 (M$^+$ + 1) |
| Ca-97 | 2,5DMePh | H | H | 2-Nap | Aa-1 | BRA72 | C | | 381 (M$^+$ + 1) |
| Ca-98 | 2,5DMePh | H | H | 1Me-5-Ind | Aa-3 | BRA72 | C | | 384 (M$^+$ + 1) |
| Ca-99 | 2,5DMePh | H | H | 5-1HIdz | Aa-4 | BRA72 | C | | 371 (M$^+$ + 1) |

TABLE Ca-2-continued

| | | | | | | | LCMS | | |
|---|---|---|---|---|---|---|---|---|---|
| Exp. | Rx | Y | Zx | AR | SM1 | SM2 | method | RTime | Mass |
| Ca-100 | 2,5DMePh | H | H | 1Me-5-1HIdz | Aa-5 | BRA72 | C | | 385 (M$^+$ + 1) |
| Ca-101 | 2,5DMePh | H | H | 1Et-5-1HIdz | Aa-28 | BRA72 | C | | 399 (M$^+$ + 1) |
| Ca-102 | 3,5DMePh | H | H | 2-Nap | Aa-1 | BRA73 | C | | 381 (M$^+$ + 1) |
| Ca-103 | 3,5DMePh | H | H | 1Me-5-Ind | Aa-3 | BRA73 | C | | 384 (M$^+$ + 1) |
| Ca-104 | 3,5DMePh | H | H | 1Me-5-1HIdz | Aa-5 | BRA73 | C | | 385 (M$^+$ + 1) |
| Ca-105 | 2CF$_3$Ph | H | H | 2-Nap | Aa-1 | BRA39 | C | | 421 (M$^+$ + 1) |

TABLE Ca-3

| | | | | | | | LCMS | | |
|---|---|---|---|---|---|---|---|---|---|
| Exp. | Rx | Y | Zx | AR | SM1 | SM2 | method | RTime | Mass |
| Ca-106 | 2CF$_3$Ph | H | H | 5-Ind | Aa-2 | BRA39 | C | | 410 (M$^+$ + 1) |
| Ca-107 | 2CF$_3$Ph | H | H | 1Me-5-1HIdz | Aa-5 | BRA39 | C | | 425 (M$^+$ + 1) |
| Ca-108 | 2CF$_3$Ph | H | H | 5-Bzt | Aa-38 | BRA39 | C | | 428 (M$^+$ + 1) |
| Ca-109 | 2CF$_3$Ph | H | H | 3-Qu | Aa-7 | BRA39 | C | | 422 (M$^+$ + 1) |
| Ca-110 | 2CF$_3$Ph | H | H | 1Et-5-1HIdz | Aa-28 | BRA39 | C | | 439 (M$^+$ + 1) |
| Ca-111 | 3CF$_3$Ph | H | H | 2-Nap | Aa-1 | BRA40 | C | | 421 (M$^+$ + 1) |
| Ca-112 | 3CF$_3$Ph | H | H | 5-Ind | Aa-2 | BRA40 | C | | 410 (M$^+$ + 1) |
| Ca-113 | 3CF$_3$Ph | H | H | 1Me-5-Ind | Aa-3 | BRA40 | C | | 424 (M$^+$ + 1) |
| Ca-114 | 3CF$_3$Ph | H | H | 1Me-5-1HIdz | Aa-5 | BRA40 | C | | 425 (M$^+$ + 1) |
| Ca-115 | 3CF$_3$Ph | H | H | 5-Bzt | Aa-38 | BRA40 | C | | 428 (M$^+$ + 1) |
| Ca-116 | 3CF$_3$Ph | H | H | 3-Qu | Aa-7 | BRA40 | C | | 422 (M$^+$ + 1) |
| Ca-117 | 4CF$_3$Ph | H | H | 5-Ind | Aa-2 | BRA41 | C | | 410 (M$^+$ + 1) |
| Ca-118 | 4CF$_3$Ph | H | H | 5-1HIdz | Aa-4 | BRA41 | C | | 411 (M$^+$ + 1) |
| Ca-119 | 4CF$_3$Ph | H | H | 1Me-5-1HIdz | Aa-5 | BRA41 | C | | 425 (M$^+$ + 1) |
| Ca-120 | 4CF$_3$Ph | H | H | 5-Bzt | Aa-38 | BRA41 | C | | 428 (M$^+$ + 1) |
| Ca-121 | 4CF$_3$Ph | H | H | 3-Qu | Aa-7 | BRA41 | C | | 422 (M$^+$ + 1) |
| Ca-122 | 4CF$_3$Ph | H | H | 1Et-5-1HIdz | Aa-28 | BRA41 | C | | 439 (M$^+$ + 1) |
| Ca-123 | 2ClPh | H | H | 5-Ind | Aa-2 | BRA61 | C | | 376 (M$^+$ + 1) |
| Ca-124 | 2ClPh | H | H | 5-1HIdz | Aa-4 | BRA61 | C | | 377 (M$^+$ + 1) |
| Ca-125 | 2ClPh | H | H | 1Me-5-1HIdz | Aa-5 | BRA61 | C | | 391 (M$^+$ + 1) |
| Ca-126 | 2ClPh | H | H | 3-Qu | Aa-7 | BRA61 | C | | 388 (M$^+$ + 1) |
| Ca-127 | 3ClPh | H | H | 2-Nap | Aa-1 | BRA62 | C | | 387 (M$^+$ + 1) |
| Ca-128 | 3ClPh | H | H | 1Me-5-Ind | Aa-3 | BRA62 | C | | 390 (M$^+$ + 1) |
| Ca-129 | 3ClPh | H | H | 5-1HIdz | Aa-4 | BRA62 | C | | 377 (M$^+$ + 1) |
| Ca-130 | 3ClPh | H | H | 1Me-5-1HIdz | Aa-5 | BRA62 | C | | 391 (M$^+$ + 1) |
| Ca-131 | 3ClPh | H | H | 5-Bzt | Aa-38 | BRA62 | C | | 394 (M$^+$ + 1) |
| Ca-132 | 4ClPh | H | H | 5-Ind | Aa-2 | BRA30 | C | | 376 (M$^+$ + 1) |
| Ca-133 | 4ClPh | H | H | 1Me-5-Ind | Aa-3 | BRA30 | C | | 390 (M$^+$ + 1) |
| Ca-134 | 4ClPh | H | H | 1Me-5-1HIdz | Aa-5 | BRA30 | C | | 391 (M$^+$ + 1) |
| Ca-135 | 4ClPh | H | H | 5-Bzt | Aa-38 | BRA30 | C | | 394 (M$^+$ + 1) |
| Ca-136 | 2,3DClPh | H | H | 5-Ind | Aa-2 | BRA74 | C | | 411 (M$^+$ + 1) |
| Ca-137 | 2,3DClPh | H | H | 1Me-5-Ind | Aa-3 | BRA74 | C | | 425 (M$^+$ + 1) |
| Ca-138 | 2,3DClPh | H | H | 1Me-5-1HIdz | Aa-5 | BRA74 | C | | 426 (M$^+$ + 1) |
| Ca-139 | 2,4DClPh | H | H | 5-Ind | Aa-2 | BRA75 | C | | 411 (M$^+$ + 1) |
| Ca-140 | 2,4DClPh | H | H | 1Me-5-1HIdz | Aa-5 | BRA75 | C | | 426 (M$^+$ + 1) |
| Ca-141 | 2,4DClPh | H | H | 5-Bzt | Aa-38 | BRA75 | C | | 429 (M$^+$ + 1) |
| Ca-142 | 2,5DClPh | H | H | 1Me-5-Ind | Aa-3 | BRA76 | C | | 425 (M$^+$ + 1) |
| Ca-143 | 2,5DClPh | H | H | 1Me-5-1HIdz | Aa-5 | BRA76 | C | | 426 (M$^+$ + 1) |
| Ca-144 | 2,6DClPh | H | H | 1Me-5-1HIdz | Aa-5 | BRA77 | C | | 426 (M$^+$ + 1) |
| Ca-145 | 3,4DClPh | H | H | 2-Nap | Aa-1 | BRA78 | C | | 421 (M$^+$ + 1) |
| Ca-146 | 3,4DClPh | H | H | 5-Ind | Aa-2 | BRA78 | C | | 411 (M$^+$ + 1) |
| Ca-147 | 3,4DClPh | H | H | 1Me-5-Ind | Aa-3 | BRA78 | C | | 425 (M$^+$ + 1) |
| Ca-148 | 3,4DClPh | H | H | 1Me-5-1HIdz | Aa-5 | BRA78 | C | | 426 (M$^+$ + 1) |
| Ca-149 | 3,5DClPh | H | H | 2-Nap | Aa-1 | BRA79 | C | | 421 (M$^+$ + 1) |
| Ca-150 | 3,5DClPh | H | H | 1Me-5-Ind | Aa-3 | BRA79 | C | | 425 (M$^+$ + 1) |
| Ca-151 | 3,5DClPh | H | H | 1Me-5-1HIdz | Aa-5 | BRA79 | C | | 426 (M$^+$ + 1) |
| Ca-152 | 2FPh | H | H | 2-Nap | Aa-1 | BRA32 | C | | 371 (M$^+$ + 1) |
| Ca-153 | 2FPh | H | H | 1Me-5-Ind | Aa-3 | BRA32 | C | | 374 (M$^+$ + 1) |
| Ca-154 | 2FPh | H | H | 5-1HIdz | Aa-4 | BRA32 | C | | 361 (M$^+$ + 1) |
| Ca-155 | 2FPh | H | H | 1-Me-5-1HIdz | Aa-5 | BRA32 | C | | 375 (M$^+$ + 1) |
| Ca-156 | 2FPh | H | H | 5-Bzt | Aa-38 | BRA32 | C | | 378 (M$^+$ + 1) |
| Ca-157 | 2FPh | H | H | 3-Qu | Aa-7 | BRA32 | C | | 372 (M$^+$ + 1) |
| Ca-158 | 3FPh | H | H | 5-Ind | Aa-2 | BRA33 | C | | 360 (M$^+$ + 1) |
| Ca-159 | 3FPh | H | H | 5-1HIdz | Aa-4 | BRA33 | C | | 361 (M$^+$ + 1) |
| Ca-160 | 3FPh | H | H | 1Me-5-1HIdz | Aa-5 | BRA33 | C | | 375 (M$^+$ + 1) |

TABLE Ca-4

| Exp. | Rx | Y | Zx | AR | SM1 | SM2 | LCMS method | RTime | Mass |
|---|---|---|---|---|---|---|---|---|---|
| Ca-161 | 3FPh | H | H | 3-Qu | Aa-7 | BRA33 | C | | 372 (M$^+$ + 1) |
| Ca-162 | 4FPh | H | H | 2-Nap | Aa-1 | BRA34 | C | | 371 (M$^+$ + 1) |
| Ca-163 | 4FPh | H | H | 5-Ind | Aa-2 | BRA34 | C | | 360 (M$^+$ + 1) |
| Ca-164 | 4FPh | H | H | 5-1HIdz | Aa-4 | BRA34 | C | | 361 (M$^+$ + 1) |
| Ca-165 | 4FPh | H | H | 1Me-5-1HIdz | Aa-5 | BRA34 | C | | 375 (M$^+$ + 1) |
| Ca-166 | 4FPh | H | H | 3-Qu | Aa-7 | BRA34 | C | | 372 (M$^+$ + 1) |
| Ca-167 | 2,3DFPh | H | H | 2-Nap | Aa-1 | BRA80 | C | | 389 (M$^+$ + 1) |
| Ca-168 | 2,3DFPh | H | H | 5-Ind | Aa-2 | BRA80 | C | | 378 (M$^+$ + 1) |
| Ca-169 | 2,3DFPh | H | H | 1Me-5-1HIdz | Aa-5 | BRA80 | C | | 393 (M$^+$ + 1) |
| Ca-170 | 2,4DFPh | H | H | 2-Nap | Aa-1 | BRA81 | C | | 389 (M$^+$ + 1) |
| Ca-171 | 2,4DFPh | H | H | 5-Ind | Aa-2 | BRA81 | C | | 378 (M$^+$ + 1) |
| Ca-172 | 2,4DFPh | H | H | 1Me-5-Ind | Aa-3 | BRA81 | C | | 392 (M$^+$ + 1) |
| Ca-173 | 2,4DFPh | H | H | 1Me-5-1HIdz | Aa-5 | BRA81 | C | | 393 (M$^+$ + 1) |
| Ca-174 | 2,5DFPh | H | H | 2-Nap | Aa-1 | BRA82 | C | | 389 (M$^+$ + 1) |
| Ca-175 | 2,5DFPh | H | H | 1Me-5-Ind | Aa-3 | BRA82 | C | | 392 (M$^+$ + 1) |
| Ca-176 | 2,5DFPh | H | H | 1Me-5-1HIdz | Aa-5 | BRA82 | C | | 393 (M$^+$ + 1) |
| Ca-177 | 2,6DFPh | H | H | 2-Nap | Aa-1 | BRA83 | C | | 389 (M$^+$ + 1) |
| Ca-178 | 2,6DFPh | H | H | 1Me-5-Ind | Aa-3 | BRA83 | C | | 392 (M$^+$ + 1) |
| Ca-179 | 2,6DFPh | H | H | 5-1HIdz | Aa-4 | BRA83 | C | | 379 (M$^+$ + 1) |
| Ca-180 | 2,6DFPh | H | H | 1-Me-5-1HIdz | Aa-5 | BRA83 | C | | 393 (M$^+$ + 1) |
| Ca-181 | 3,4DFPh | H | H | 2-Nap | Aa-1 | BRA84 | C | | 389 (M$^+$ + 1) |
| Ca-182 | 3,4DFPh | H | H | 5-Ind | Aa-2 | BRA84 | C | | 378 (M$^+$ + 1) |
| Ca-183 | 3,4DFPh | H | H | 1Me-5-1HIdz | Aa-5 | BRA84 | C | | 393 (M$^+$ + 1) |
| Ca-184 | 3,5DFPh | H | H | 2-Nap | Aa-1 | BRA85 | C | | 389 (M$^+$ + 1) |
| Ca-185 | 3,5DFPh | H | H | 1Me-5-Ind | Aa-3 | BRA85 | C | | 392 (M$^+$ + 1) |
| Ca-186 | 3,5DFPh | H | H | 5-1HIdz | Aa-4 | BRA85 | C | | 379 (M$^+$ + 1) |
| Ca-187 | 3,5DFPh | H | H | 1Me-5-1HIdz | Aa-5 | BRA85 | C | | 393 (M$^+$ + 1) |
| Ca-188 | 2,3(CF$_3$)$_2$Ph | H | H | 2-Nap | Aa-1 | BRA63 | C | | 489 (M$^+$ + 1) |
| Ca-189 | 2,3(CF$_3$)$_2$Ph | H | H | 1Me-5-Ind | Aa-3 | BRA63 | C | | 492 (M$^+$ + 1) |
| Ca-190 | 2,3(CF$_3$)$_2$Ph | H | H | 1Me-5-1HIdz | Aa-5 | BRA63 | C | | 493 (M$^+$ + 1) |
| Ca-191 | 2,4(CF$_3$)$_2$Ph | H | H | 2-Nap | Aa-1 | BRA64 | C | | 489 (M$^+$ + 1) |
| Ca-192 | 2,4(CF$_3$)$_2$Ph | H | H | 1Me-5-1HIdz | Aa-5 | BRA64 | C | | 493 (M$^+$ + 1) |
| Ca-193 | 2,5(CF$_3$)$_2$Ph | H | H | 2-Nap | Aa-1 | BRA65 | C | | 489 (M$^+$ + 1) |
| Ca-194 | 2,5(CF$_3$)$_2$Ph | H | H | 5-Ind | Aa-2 | BRA65 | C | | 478 (M$^+$ + 1) |
| Ca-195 | 2,5(CF$_3$)$_2$Ph | H | H | 1Me-5-1HIdz | Aa-5 | BRA65 | C | | 493 (M$^+$ + 1) |
| Ca-196 | 2,5(CF$_3$)$_2$Ph | H | H | 3-Qu | Aa-7 | BRA65 | C | | 490 (M$^+$ + 1) |
| Ca-197 | 3,4(CF$_3$)$_2$Ph | H | H | 2-Nap | Aa-1 | BRA66 | C | | 489 (M$^+$ + 1) |
| Ca-198 | 3,4(CF$_3$)$_2$Ph | H | H | 1Me-5-Ind | Aa-3 | BRA66 | C | | 492 (M$^+$ + 1) |
| Ca-199 | 3,4(CF$_3$)$_2$Ph | H | H | 5-1HIdz | Aa-4 | BRA66 | C | | 479 (M$^+$ + 1) |
| Ca-200 | 3,4(CF$_3$)$_2$Ph | H | H | 1Me-5-1HIdz | Aa-5 | BRA66 | C | | 493 (M$^+$ + 1) |
| Ca-201 | 3,5(CF$_3$)$_2$Ph | H | H | 5-Ind | Aa-2 | BRA17 | C | | 478 (M$^+$ + 1) |
| Ca-202 | 3,5(CF$_3$)$_2$Ph | H | H | 5-1HIdz | Aa-4 | BRA17 | C | | 479 (M$^+$ + 1) |
| Ca-203 | 3,5(CF$_3$)$_2$Ph | H | H | 1Me-5-1HIdz | Aa-5 | BRA17 | C | | 493 (M$^+$ + 1) |
| Ca-204 | 2-Furyl | H | H | 2-Nap | Aa-1 | BRA35 | C | | 343 (M$^+$ + 1) |
| Ca-205 | 2-Furyl | H | H | 5-Ind | Aa-2 | BRA35 | C | | 332 (M$^+$ + 1) |
| Ca-206 | 2-Furyl | H | H | 1Me-5-1HIdz | Aa-5 | BRA35 | C | | 347 (M$^+$ + 1) |
| Ca-207 | 2-Furyl | H | H | 3-Qu | Aa-7 | BRA35 | C | | 344 (M$^+$ + 1) |
| Ca-208 | 3-Furyl | H | H | 1Me-5-Ind | Aa-3 | BRA67 | C | | 346 (M$^+$ + 1) |
| Ca-209 | 3-Furyl | H | H | 5-1HIdz | Aa-4 | BRA67 | C | | 333 (M$^+$ + 1) |
| Ca-210 | 3-Furyl | H | H | 1Me-5-1HIdz | Aa-5 | BRA67 | C | | 347 (M$^+$ + 1) |
| Ca-211 | 2-Thienyl | H | H | 2-Nap | Aa-1 | BRA36 | C | | 359 (M$^+$ + 1) |
| Ca-212 | 2-Thienyl | H | H | 1Me-5-Ind | Aa-3 | BRA36 | C | | 362 (M$^+$ + 1) |
| Ca-213 | 2-Thienyl | H | H | 1Me-5-1HIdz | Aa-5 | BRA36 | C | | 363 (M$^+$ + 1) |
| Ca-214 | 2-Thienyl | H | H | 1Et-5-1HIdz | Aa-28 | BRA36 | C | | 377 (M$^+$ + 1) |
| Ca-215 | 3-Thienyl | H | H | 5-Ind | Aa-2 | BRA68 | C | | 348 (M$^+$ + 1) |

TABLE Ca-5

| Exp. | Rx | Y | Zx | AR | SM1 | SM2 | LCMS method | RTime | Mass |
|---|---|---|---|---|---|---|---|---|---|
| Ca-216 | 3-Thienyl | H | H | 1Me-5-Ind | Aa-3 | BRA68 | C | | 362 (M$^+$ + 1) |
| Ca-217 | 3-Thienyl | H | H | 5-1HIdz | Aa-4 | BRA68 | C | | 349 (M$^+$ + 1) |
| Ca-218 | 3-Thienyl | H | H | 1Me-5-1HIdz | Aa-5 | BRA68 | C | | 363 (M$^+$ + 1) |
| Ca-219 | 3-Thienyl | H | H | 5-Bzt | Aa-38 | BRA68 | C | | 366 (M$^+$ + 1) |
| Ca-220 | 3-Thienyl | H | H | 3-Qu | Aa-7 | BRA68 | C | | 360 (M$^+$ + 1) |
| Ca-221 | 3-Thienyl | H | H | 1Et-5-1HIdz | Aa-28 | BRA68 | C | | 377 (M$^+$ + 1) |
| Ca-222 | 2-Py | H | H | 5-Ind | Aa-2 | BRA69 | C | | 343 (M$^+$ + 1) |
| Ca-223 | 2-Py | H | H | 1Me-5-1HIdz | Aa-5 | BRA69 | C | | 358 (M$^+$ + 1) |
| Ca-224 | 2-Py | H | H | 5-Bzt | Aa-38 | BRA69 | C | | 361 (M$^+$ + 1) |
| Ca-225 | 3-Py | H | H | 2-Nap | Aa-1 | BRA70 | C | | 354 (M$^+$ + 1) |

TABLE Ca-5-continued

| Exp. | Rx | Y | Zx | AR | SM1 | SM2 | LCMS method | RTime | Mass |
|---|---|---|---|---|---|---|---|---|---|
| Ca-226 | 3-Py | H | H | 5-Ind | Aa-2 | BRA70 | C | | 343 (M$^+$ + 1) |
| Ca-227 | 3-Py | H | H | 1Me-5-Ind | Aa-3 | BRA70 | C | | 357 (M$^+$ + 1) |
| Ca-228 | 3-Py | H | H | 1Me-5-1HIdz | Aa-5 | BRA70 | C | | 358 (M$^+$ + 1) |
| Ca-229 | 3-Py | H | H | 1Et-5-1HIdz | Aa-28 | BRA70 | C | | 372 (M$^+$ + 1) |
| Ca-230 | 4-Py | H | H | 2-Nap | Aa-1 | BRA26 | C | | 354 (M$^+$ + 1) |
| Ca-231 | 4-Py | H | H | 5-Ind | Aa-2 | BRA26 | C | | 343 (M$^+$ + 1) |
| Ca-232 | 4-Py | H | H | 1Me-5-Ind | Aa-3 | BRA26 | C | | 357 (M$^+$ + 1) |
| Ca-233 | 4-Py | H | H | 5-1HIdz | Aa-4 | BRA26 | C | | 344 (M$^+$ + 1) |
| Ca-234 | 4-Py | H | H | 1Me-5-1HIdz | Aa-5 | BRA26 | C | | 358 (M$^+$ + 1) |
| Ca-235 | 4-Py | H | H | 5-Bzt | Aa-38 | BRA26 | C | | 361 (M$^+$ + 1) |
| Ca-236 | 4-Py | H | H | 3-Qu | Aa-7 | BRA26 | C | | 355 (M$^+$ + 1) |
| Ca-237 | 4-Py | H | H | 1Et-5-1HIdz | Aa-28 | BRA26 | C | | 372 (M$^+$ + 1) |
| Ca-238 | 2DMAPh | H | H | 2-Nap | Aa-1 | BRA86 | C | | 396 (M$^+$ + 1) |
| Ca-239 | 2DMAPh | H | H | 5-Ind | Aa-2 | BRA86 | C | | 385 (M$^+$ + 1) |
| Ca-240 | 2DMAPh | H | H | 1Me-5-1HIdz | Aa-5 | BRA86 | C | | 400 (M$^+$ + 1) |
| Ca-241 | 2DMAPh | H | H | 5-Bzt | Aa-38 | BRA86 | C | | 403 (M$^+$ + 1) |
| Ca-242 | 2DMAPh | H | H | 1Et-5-1HIdz | Aa-28 | BRA86 | C | | 414 (M$^+$ + 1) |
| Ca-243 | 3DMAPh | H | H | 1Me-5-Ind | Aa-3 | BRA87 | C | | 399 (M$^+$ + 1) |
| Ca-244 | 3DMAPh | H | H | 5-1HIdz | Aa-4 | BRA87 | C | | 386 (M$^+$ + 1) |
| Ca-245 | 3DMAPh | H | H | 1Me-5-1HIdz | Aa-5 | BRA87 | C | | 400 (M$^+$ + 1) |
| Ca-246 | 3DMAPh | H | H | 5-Bzt | Aa-38 | BRA87 | C | | 403 (M$^+$ + 1) |
| Ca-247 | 3DMAPh | H | H | 3-Qu | Aa-7 | BRA87 | C | | 397 (M$^+$ + 1) |
| Ca-248 | 4DMAPh | H | H | 2-Nap | Aa-1 | BRA21 | C | | 396 (M$^+$ + 1) |
| Ca-249 | 4DMAPh | H | H | 1Me-5-Ind | Aa-3 | BRA21 | C | | 399 (M$^+$ + 1) |
| Ca-250 | 4DMAPh | H | H | 1Me-5-1HIdz | Aa-5 | BRA21 | C | | 400 (M$^+$ + 1) |
| Ca-251 | 4DMAPh | H | H | 3-Qu | Aa-7 | BRA21 | C | | 397 (M$^+$ + 1) |
| Ca-252 | 4DMAPh | H | H | 1Et-5-1HIdz | Aa-28 | BRA21 | C | | 414 (M$^+$ + 1) |
| Ca-253 | 1-Nap | H | H | 2-Nap | Aa-1 | BRA16 | C | | 403 (M$^+$ + 1) |
| Ca-254 | 1-Nap | H | H | 5-Ind | Aa-2 | BRA16 | C | | 392 (M$^+$ + 1) |
| Ca-255 | 1-Nap | H | H | 1Me-5-1HIdz | Aa-5 | BRA16 | C | | 407 (M$^+$ + 1) |
| Ca-256 | 1-Nap | H | H | 5-Bzt | Aa-38 | BRA16 | C | | 410 (M$^+$ + 1) |
| Ca-257 | 2-Nap | H | H | 2-Nap | Aa-1 | BRA1 | C | | 403 (M$^+$ + 1) |
| Ca-258 | 2-Nap | H | H | 1Me-5-Ind | Aa-3 | BRA1 | C | | 406 (M$^+$ + 1) |
| Ca-259 | 2-Nap | H | H | 5-1HIdz | Aa-4 | BRA1 | C | | 393 (M$^+$ + 1) |
| Ca-260 | 2-Nap | H | H | 1Me-5-1HIdz | Aa-5 | BRA1 | C | | 407 (M$^+$ + 1) |
| Ca-261 | 2-Nap | H | H | 5-Bzt | Aa-38 | BRA1 | C | | 410 (M$^+$ + 1) |
| Ca-262 | 5-Ind | H | H | 2-Nap | Aa-1 | BRA2 | C | | 392 (M$^+$ + 1) |
| Ca-263 | 5-Ind | H | H | 5-Ind | Aa-2 | BRA2 | C | | 381 (M$^+$ + 1) |
| Ca-264 | 5-Ind | H | H | 1Me-5-1HIdz | Aa-5 | BRA2 | C | | 396 (M$^+$ + 1) |
| Ca-265 | 5-Ind | H | H | 3-Qu | Aa-7 | BRA2 | C | | 393 (M$^+$ + 1) |
| Ca-266 | 5-Ind | H | H | 1Et-5-1HIdz | Aa-28 | BRA2 | C | | 410 (M$^+$ + 1) |
| Ca-267 | 1Me-5-1HIdz | H | H | 2-Nap | Aa-1 | BRA6 | C | | 407 (M$^+$ + 1) |
| Ca-268 | 1Me-5-1HIdz | H | H | 1Me-5-Ind | Aa-3 | BRA6 | C | | 410 (M$^+$ + 1) |
| Ca-269 | 1Me-5-1HIdz | H | H | 1Me-5-1HIdz | Aa-5 | BRA6 | C | | 411 (M$^+$ + 1) |
| Ca-270 | 1Me-5-1HIdz | H | H | 5-Bzt | Aa-38 | BRA6 | C | | 414 (M$^+$ + 1) |

TABLE Cb-1

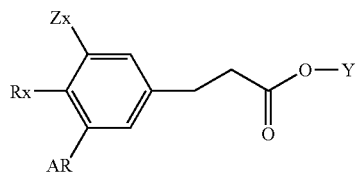

| Exp. | Rx | Y | Zx | AR | SM1 | SM2 | LCMS method | RTime | Mass |
|---|---|---|---|---|---|---|---|---|---|
| Cb-1 | cPen | H | H | 2-Nap | Aa-1 | BRA28 | C | | 345 (M$^+$ + 1) |
| Cb-2 | cPen | H | H | 5-Ind | Aa-2 | BRA28 | C | | 334 (M$^+$ + 1) |
| Cb-3 | cPen | H | H | 1Me-5-Ind | Aa-3 | BRA28 | C | | 348 (M$^+$ + 1) |
| Cb-4 | cPen | H | H | 5-1HIdz | Aa-4 | BRA28 | C | | 335 (M$^+$ + 1) |
| Cb-5 | cPen | H | H | 1Me-5-1HIdz | Aa-5 | BRA28 | C | | 349 (M$^+$ + 1) |
| Cb-6 | cPen | H | H | 5-Bzt | Aa-38 | BRA28 | C | | 352 (M$^+$ + 1) |
| Cb-7 | cPen | H | H | 3-Qu | Aa-7 | BRA28 | C | | 346 (M$^+$ + 1) |
| Cb-8 | cPen | H | H | 1Et-5-1HIdz | Aa-28 | BRA28 | C | | 363 (M$^+$ + 1) |
| Cb-9 | nBu | H | H | 2-Nap | Aa-1 | BRA31 | C | | 333 (M$^+$ + 1) |
| Cb-10 | nBu | H | H | 5-Ind | Aa-2 | BRA31 | C | | 322 (M$^+$ + 1) |
| Cb-11 | nBu | H | H | 1Me-5-1HIdz | Aa-5 | BRA31 | C | | 337 (M$^+$ + 1) |

TABLE Cb-1-continued

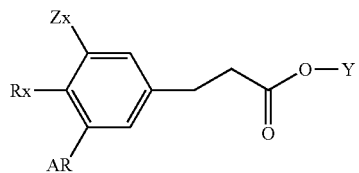

| Exp. | Rx | Y | Zx | AR | SM1 | SM2 | LCMS method | RTime | Mass |
|---|---|---|---|---|---|---|---|---|---|
| Cb-12 | iBu | H | H | 2-Nap | Aa-1 | BRA20 | C | | 333 (M+ + 1) |
| Cb-13 | iBu | H | H | 1Me-5-Ind | Aa-3 | BRA20 | C | | 336 (M+ + 1) |
| Cb-14 | iBu | H | H | 1Me-5-1HIdz | Aa-5 | BRA20 | C | | 337 (M+ + 1) |
| Cb-15 | iBu | H | H | 5-Bzt | Aa-38 | BRA20 | C | | 340 (M+ + 1) |
| Cb-16 | iBu | H | H | 1Et-5-1HIdz | Aa-28 | BRA20 | C | | 351 (M+ + 1) |
| Cb-17 | 2-Indan | H | H | 2-Nap | Aa-1 | BRA42 | C | | 393 (M+ + 1) |
| Cb-18 | 2-Indan | H | H | 5-Ind | Aa-2 | BRA42 | C | | 382 (M+ + 1) |
| Cb-19 | 2-Indan | H | H | 1Me-5-Ind | Aa-3 | BRA42 | C | | 396 (M+ + 1) |
| Cb-20 | 2-Indan | H | H | 5-1HIdz | Aa-4 | BRA42 | C | | 382 (M+ + 1) |
| Cb-21 | 2-Indan | H | H | 1Me-5-1HIdz | Aa-5 | BRA42 | C | | 397 (M+ + 1) |
| Cb-22 | 2-Indan | H | H | 5-Bzt | Aa-38 | BRA42 | C | | 400 (M+ + 1) |
| Cb-23 | 2-Indan | H | H | 3-Qu | Aa-7 | BRA42 | C | | 394 (M+ + 1) |
| Cb-24 | 2-Indan | H | H | 1Et-5-1HIdz | Aa-28 | BRA42 | C | | 411 (M+ + 1) |
| Cb-25 | 4Me-2-Indan | H | H | 5-Ind | Aa-2 | BRA43 | C | | 396 (M+ + 1) |
| Cb-26 | 4Me-2-Indan | H | H | 5-1HIdz | Aa-4 | BRA43 | C | | 397 (M+ + 1) |
| Cb-27 | 4Me-2-Indan | H | H | 1Me-5-1HIdz | Aa-5 | BRA43 | C | | 411 (M+ + 1) |
| Cb-28 | 4Me-2-Indan | H | H | 3-Qu | Aa-7 | BRA43 | C | | 408 (M+ + 1) |
| Cb-29 | 5Me-2-Indan | H | H | 2-Nap | Aa-1 | BRA44 | C | | 407 (M+ + 1) |
| Cb-30 | 5Me-2-Indan | H | H | 5-Ind | Aa-2 | BRA44 | C | | 396 (M+ + 1) |
| Cb-31 | 5Me-2-Indan | H | H | 5-1HIdz | Aa-4 | BRA44 | C | | 397 (M+ + 1) |
| Cb-32 | 5Me-2-Indan | H | H | 1Me-5-1HIdz | Aa-5 | BRA44 | C | | 411 (M+ + 1) |
| Cb-33 | 5Me-2-Indan | H | H | 5-Bzt | Aa-38 | BRA44 | C | | 414 (M+ + 1) |
| Cb-34 | 5Me-2-Indan | H | H | 1Et-5-1HIdz | Aa-28 | BRA44 | C | | 425 (M+ + 1) |
| Cb-35 | 4,7DMe-2-Indan | H | H | 5-Ind | Aa-2 | BRA45 | C | | 410 (M+ + 1) |
| Cb-36 | 4,7DMe-2-Indan | H | H | 5-1HIdz | Aa-4 | BRA45 | C | | 411 (M+ + 1) |
| Cb-37 | 4,7DMe-2-Indan | H | H | 1Me-5-1HIdz | Aa-5 | BRA45 | C | | 425 (M+ + 1) |
| Cb-38 | 5,6DMe-2-Indan | H | H | 2-Nap | Aa-1 | BRA46 | C | | 421 (M+ + 1) |
| Cb-39 | 5,6DMe-2-Indan | H | H | 1Me-5-1HIdz | Aa-5 | BRA46 | C | | 425 (M+ + 1) |
| Cb-40 | 5F-2-Indan | H | H | 2-Nap | Aa-1 | BRA47 | C | | 411 (M+ + 1) |
| Cb-41 | 5F-2-Indan | H | H | 5-Ind | Aa-2 | BRA47 | C | | 400 (M+ + 1) |
| Cb-42 | 5F-2-Indan | H | H | 5-1HIdz | Aa-4 | BRA47 | C | | 401 (M+ + 1) |
| Cb-43 | 5F-2-Indan | H | H | 1Me-5-1HIdz | Aa-5 | BRA47 | C | | 415 (M+ + 1) |
| Cb-44 | 5F-2-Indan | H | H | 5-Bzt | Aa-38 | BRA47 | C | | 418 (M+ + 1) |
| Cb-45 | 5F-2-Indan | H | H | 3-Qu | Aa-7 | BRA47 | C | | 412 (M+ + 1) |
| Cb-46 | 5F-2-Indan | H | H | 1Et-5-1HIdz | Aa-28 | BRA47 | C | | 429 (M+ + 1) |
| Cb-47 | 4F-2-Indan | H | H | 2-Nap | Aa-1 | BRA48 | C | | 411 (M+ + 1) |
| Cb-48 | 4F-2-Indan | H | H | 1Me-5-Ind | Aa-3 | BRA48 | C | | 414 (M+ + 1) |
| Cb-49 | 4F-2-Indan | H | H | 1Me-5-1HIdz | Aa-5 | BRA48 | C | | 415 (M+ + 1) |
| Cb-50 | 4,7DF-2-Indan | H | H | 2-Nap | Aa-1 | BRA49 | C | | 429 (M+ + 1) |

TABLE Cb-2

| Exp. | Rx | Y | Zx | AR | SM1 | SM2 | LGMS method | RTime | Mass |
|---|---|---|---|---|---|---|---|---|---|
| Cb-51 | 4,7DF-2-Indan | H | H | 1Me-5-Ind | Aa-3 | BRA49 | C | | 432 (M+ +1) |
| Cb-52 | 4,7DF-2-Indan | H | H | 1Me-5-1HIdz | Aa-5 | BRA49 | C | | 433 (M+ + 1) |
| Cb-53 | 5,6DF-2-Indan | H | H | 2-Nap | Aa-1 | BRA50 | C | | 429 (M+ + 1) |
| Cb-54 | 5,6DF-2-Indan | H | H | 5-Ind | Aa-2 | BRA50 | C | | 418 (M+ + 1) |
| Cb-55 | 5,6DF-2-Indan | H | H | 1Me-5-Ind | Aa-3 | BRA50 | C | | 432 (M+ + 1) |
| Cb-56 | 5,6DF-2-Indan | H | H | 5-1HIdz | Aa-4 | BRA50 | C | | 419 (M+ + 1) |
| Cb-57 | 5,6DF-2-Indan | H | H | 1Me-5-1HIdz | Aa-5 | BRA50 | C | | 433 (M+ + 1) |
| Cb-58 | 5,6DF-2-Indan | H | H | 5-Bzt | Aa-38 | BRA50 | C | | 436 (M+ + 1) |
| Cb-59 | 5,6DF-2-Indan | H | H | 3-Qu | Aa-7 | BRA50 | C | | 430 (M+ + 1) |
| Cb-60 | 5,6DF-2-Indan | H | H | 1Et-5-1HIdz | Aa-28 | BRA50 | C | | 447 (M+ + 1) |
| Cb-61 | 4Cl-2-Indan | H | H | 5-Ind | Aa-2 | BRA51 | C | | 416 (M+ + 1) |
| Cb-62 | 4Cl-2-Indan | H | H | 1Me-5-1HIdz | Aa-5 | BRA51 | C | | 431 (M+ + 1) |
| Cb-63 | 4Cl-2-Indan | H | H | 5-Bzt | Aa-38 | BRA51 | C | | 434 (M+ + 1) |
| Cb-64 | 5Cl-2-Indan | H | H | 2-Nap | Aa-1 | BRA52 | C | | 427 (M+ + 1) |
| Cb-65 | 5Cl-2-Indan | H | H | 5-Ind | Aa-2 | BRA52 | C | | 416 (M+ + 1) |
| Cb-66 | 5Cl-2-Indan | H | H | 1Me-5-1HIdz | Aa-5 | BRA52 | C | | 431 (M+ + 1) |
| Cb-67 | 5Cl-2-Indan | H | H | 3-Qu | Aa-7 | BRA52 | C | | 428 (M+ + 1) |

TABLE Cb-2-continued

| Exp. | Rx | Y | Zx | AR | SM1 | SM2 | LGMS method | RTime | Mass |
|---|---|---|---|---|---|---|---|---|---|
| Cb-68 | 5Cl-2-Indan | H | H | 1Et-5-1HIdz | Aa-28 | BRA52 | C | | 445 ($M^+$ + 1) |
| Cb-69 | 4,7DCl-2-Indan | H | H | 2-Nap | Aa-1 | BRA53 | C | | 462 ($M^+$ + 1) |
| Cb-70 | 4,7DCl-2-Indan | H | H | 5-Ind | Aa-2 | BRA53 | C | | 451 ($M^+$ + 1) |
| Cb-71 | 4,7DCl-2-Indan | H | H | 1Me-5-1HIdz | Aa-5 | BRA53 | C | | 466 ($M^+$ + 1) |
| Cb-72 | 5,6DCl-2-Indan | H | H | 2-Nap | Aa-1 | BRA54 | C | | 462 ($M^+$ + 1) |
| Cb-73 | 5,6DCl-2-Indan | H | H | 1Me-5-Ind | Aa-3 | BRA54 | C | | 465 ($M^+$ + 1) |
| Cb-74 | 5,6DCl-2-Indan | H | H | 1Me-5-1HIdz | Aa-5 | BRA54 | C | | 466 ($M^+$ + 1) |
| Cb-75 | 5,6DCl-2-Indan | H | H | 5-Bzt | Aa-38 | BRA54 | C | | 469 ($M^+$ + 1) |
| Cb-76 | 5,6DCl-2-Indan | H | H | 3-Qu | Aa-7 | BRA54 | C | | 463 ($M^+$ + 1) |
| Cb-77 | 5,6DCl-2-Indan | H | H | 1Et-5-1HIdz | Aa-28 | BRA54 | C | | 480 ($M^+$ + 1) |
| Cb-78 | 4MeO-2-Indan | H | H | 5-Ind | Aa-2 | BRA55 | C | | 412 ($M^+$ + 1) |
| Cb-79 | 4MeO-2-Indan | H | H | 5-1HIdz | Aa-4 | BRA55 | C | | 413 ($M^+$ + 1) |
| Cb-80 | 4MeO-2-Indan | H | H | 1Me-5-1HIdz | Aa-5 | BRA55 | C | | 427 ($M^+$ + 1) |
| Cb-81 | 5MeO-2-Indan | H | H | 2-Nap | Aa-1 | BRA56 | C | | 423 ($M^+$ + 1) |
| Cb-82 | 5MeO-2-Indan | H | H | 5-Ind | Aa-2 | BRA56 | C | | 412 ($M^+$ + 1) |
| Cb-83 | 5MeO-2-Indan | H | H | 1Me-5-1HIdz | Aa-5 | BRA56 | C | | 427 ($M^+$ + 1) |
| Cb-84 | 5MeO-2-Indan | H | H | 5-Bzt | Aa-38 | BRA56 | C | | 430 ($M^+$ + 1) |
| Cb-90 | 5,6DMeO-2-Indan | H | H | 2-Nap | Aa-1 | BRA57 | C | | 453 ($M^+$ + 1) |
| Cb-91 | 5,6DMeO-2-Indan | H | H | 1Me-5-Ind | Aa-3 | BRA57 | C | | 456 ($M^+$ + 1) |
| Cb-92 | 5,6DMeO-2-Indan | H | H | 1Me-5-1HIdz | Aa-5 | BRA57 | C | | 457 ($M^+$ + 1) |
| Cb-93 | 5,6DMeO-2-Indan | H | H | 5-Bzt | Aa-38 | BRA57 | C | | 460 ($M^+$ + 1) |
| Cb-94 | 5,6DMeO-2-Indan | H | H | 3-Qu | Aa-7 | BRA57 | C | | 454 ($M^+$ + 1) |
| Cb-95 | 5,6-DMeO-2-Indan | H | H | 1Et-5-1HIdz | Aa-28 | BRA57 | C | | 471 ($M^+$ + 1) |
| Cb-85 | cHex | H | H | 2-Nap | Aa-1 | BRA58 | C | | 359 ($M^+$ + 1) |
| Cb-86 | cHex | H | H | 5-Ind | Aa-2 | BRA58 | C | | 348 ($M^+$ + 1) |
| Cb-87 | cHex | H | H | 1Me-5-Ind | Aa-3 | BRA58 | C | | 362 ($M^+$ + 1) |
| Cb-88 | cHex | H | H | 5-1HIdz | Aa-4 | BRA58 | C | | 349 ($M^+$ + 1) |
| Cb-89 | cHex | H | H | 1Me-5-1HIdz | Aa-5 | BRA58 | C | | 363 ($M^+$ + 1) |

Reference Examples

Intermediate Ab-1 to Ab-47

Synthesis of methyl 3-[4-(4,4,5,5-tetramethyl-1,3,2-dioxaborolan-2-yl)-3-(naphthalen-2-yl)phenyl]propionate (Intermediate Ab-1)

Compound No. Aa-1 (253.2 mg), bispinacolate diboron (202.6 mg, A1d), PdCl$_2$(dppf) (43.4 mg) and potassium acetate (289 mg) were added to DMF (5.7 ml), and stirred with heating at 80° C. for 20 hours under argon gas atmosphere. The reaction mixture was added with ethyl acetate (200 ml), washed with saturated brine, and dried, and then the solvent was evaporated under reduced pressure. The residue was purified by column chromatography (Quad, hexane:ethyl acetate=4:1) to obtain the title compound (Intermediate Ab-1, 194.6 mg).

Typical examples of the compounds of the present invention including those mentioned above that can be obtained by reacting and treating corresponding starting compounds according to the synthesis method of Intermediate Ab-1 are shown in Table-Ab-1.

In the column indicated as "Mass" in the table, data of mass spectra measured by fast atom bombardment mass spectrometry (FAB-MS) are shown.

TABLE Ab-1

| Exp. | AR | Mass |
|---|---|---|
| Ab-1 | 2-Nap | 417($M^+$ + 1) |
| Ab-2 | 5-Ind | 406($M^+$ + 1) |
| Ab-3 | 1Me-5-Ind | 420($M^+$ + 1) |
| Ab-4 | 5-1HIdz | 407($M^+$ + 1) |
| Ab-5 | 1Me-5-1HIdz | 421($M^+$ + 1) |
| Ab-6 | 5-BF | 410($M^+$ + 1) |
| Ab-7 | 3-Qu | 418($M^+$ + 1) |
| Ab-8 | 1-Nap | 417($M^+$ + 1) |
| Ab-9 | 6MeO-2-Nap | 447($M^+$ + 1) |
| Ab-10 | 6(NMe$_2$N)-2-Nap | 460($M^+$ + 1) |
| Ab-11 | 4-Ind | 406($M^+$ + 1) |
| Ab-12 | 1Me-4-Ind | 420($M^+$ + 1) |
| Ab-13 | 6-Ind | 406($M^+$ + 1) |
| Ab-14 | 1Me-6-Ind | 420($M^+$ + 1) |
| Ab-15 | 2-Ind | 406($M^+$ + 1) |
| Ab-16 | 1Me-2-Ind | 420($M^+$ + 1) |
| Ab-17 | 3-Ind | 406($M^+$ + 1) |
| Ab-18 | 1Me-3-Ind | 420($M^+$ + 1) |
| Ab-19 | 1iPr-5-Ind | 448($M^+$ + 1) |
| Ab-20 | 1cPen-5-Ind | 474($M^+$ + 1) |
| Ab-21 | 3Me-5-Ind | 420($M^+$ + 1) |
| Ab-22 | 1,3DMe-5Ind | 434($M^+$ + 1) |
| Ab-23 | 1,2,3triMe-5Ind | 448($M^+$ + 1) |
| Ab-24 | 4-1HIdz | 407($M^+$ + 1) |
| Ab-25 | 1Me-4-1HIdz | 421($M^+$ + 1) |
| Ab-26 | 5-1HIdz | 407($M^+$ + 1) |
| Ab-27 | 1Me-5-1HIdz | 421($M^+$ + 1) |
| Ab-28 | 1Et-5-1HIdz | 435($M^+$ + 1) |
| Ab-29 | 1Pr-5-1HIdz | 449($M^+$ + 1) |
| Ab-30 | 2Me-5-2HIdz | 421($M^+$ + 1) |

TABLE Ab-1-continued

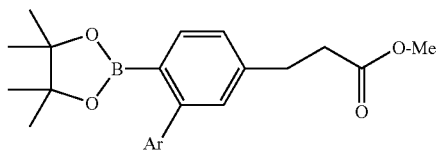

| Exp. | AR | Mass |
|---|---|---|
| Ab-31 | 6-1HIdz | 407($M^+ + 1$) |
| Ab-32 | 1Me-6-1HIdz | 421($M^+ + 1$) |
| Ab-33 | 3Me-5-1HIdz | 421($M^+ + 1$) |
| Ab-34 | 1,3DMe-5-1HIdz | 435($M^+ + 1$) |
| Ab-35 | 5-BT | 423($M^+ + 1$) |
| Ab-36 | 2,3DMe-5-BF | 435($M^+ + 1$) |
| Ab-37 | 5-2ABzt | 439($M^+ + 1$) |
| Ab-38 | 5-Bzt | 434($M^+ + 1$) |
| Ab-39 | 2Me-5-Bzt | 438($M^+ + 1$) |
| Ab-40 | 2,2DMe-5-2ABzt | 467($M^+ + 1$) |
| Ab-41 | 6-2ABzt | 439($M^+ + 1$) |
| Ab-42 | 6-Bzt | 434($M^+ + 1$) |
| Ab-43 | 2Me-6-Bzt | 438($M^+ + 1$) |
| Ab-44 | 6-Qu | 418($M^+ + 1$) |
| Ab-45 | 6-IQ | 418($M^+ + 1$) |
| Ab-46 | 2-BF | 407($M^+ + 1$) |
| Ab-47 | 2-BT | 423($M^+ + 1$) |

Example Da-1

Synthesis of methyl 3-[4-(phenylmethyl)-3-(naphthalen-2-yl)phenyl]propionate (Compound No. Da-1)

According to a procedure described in literature (S. Chowdhury et al., Tetrahedron. Lett., 1999, p. 7599), $(Ph_3P)_4$Pd (14.8 mg) and a solution of benzyl bromide (corresponding to the substance mentioned in the column of SM2 in Table-Da-1 mentioned later) in dimethoxyethane (1.3 ml) were stirred with heating at 50° C. for 10 minutes under argon atmosphere, then added with Compound Ab-1 (52.4 mg, corresponding to the substance mentioned in the column of SM1 in Table-Da-1 mentioned later), and 2 N sodium carbonate (160 μl), and refluxed by heating for 58 hours. The reaction mixture was added with ethyl acetate (60 ml), washed successively with saturated aqueous sodium hydrogencarbonate and saturated brine, dried, and then concentrated under reduced pressure. The residue was purified by flash column chromatography (hexane:ethyl acetate=8:1) to obtain the title compound (Compound No. Da-1, 33.2 mg).

Example Da-2

Synthesis of 3-[4-(phenylmethyl)-3-(naphthalen-2-yl)phenyl]propionic acid (Compound No. Da-2)

According to the procedure described in the synthesis method of Compound Ca-2 provided that the reaction was performed for 3 hours, Compound No. Da-1 (28.2 mg) and 2 N aqueous sodium hydroxide (38 μl) were reacted and treated to obtain the title compound (Compound No. Da-2, 23.7 mg).

Examples Da-1 to Da-70

Typical examples of the compounds of the present invention including those mentioned in the examples described above, that can be obtained by reacting and treating corresponding starting compounds according to the methods described in Examples Da-1 and Da-2, are shown in Table-Da-1 and Table-Da-2.

The substances mentioned in the columns of "SM1" in the tables correspond to reaction intermediates, and those mentioned in the columns of "SM2" in the tables correspond to the acid halide mentioned in Example Da-1. The halide reagents mentioned in the columns of "SM2" with the symbols of "HAL (number))" are those mentioned in Table-Ha. The regents for which cells of the columns of "Manufacturer" are blank in the tables are synthesized according to a method described in ordinary chemical literature.

TABLE Ha

| Reagent | Name of reagent | Manufacturer |
|---|---|---|
| HAL-1 | Benzyl bromide | Ald |
| HAL-2 | 4-Methoxybenzyl bromide | Ald |
| HAL-3 | 3-Methoxybenzyl bromide | Ald |
| HAL-4 | 2-Methoxybenzyl bromide | Ald |
| HAL-5 | 4-Methylbenzyl bromide | Ald |
| HAL-6 | 3-Methylbenzyl bromide | Ald |
| HAL-7 | 2-Methylbenzyl bromide | Ald |
| HAL-8 | 4-Trifluoromethylbenzyl bromide | Ald |
| HAL-9 | 3-Trifluoromethylbenzyl bromide | Ald |
| HAL-10 | 2-Trifluoromethylbenzyl bromide | Ald |
| HAL-11 | 4-Chlorobenzyl bromide | Ald |
| HAL-12 | 3-Chlorobenzyl bromide | Ald |
| HAL-13 | 2-Chlorobenzyl bromide | Ald |
| HAL-14 | 4-Fluorobenzyl bromide | Ald |
| HAL-15 | 3-Fluorobenzyl bromide | Ald |
| HAL-16 | 2-Fluorobenzyl bromide | Ald |
| HAL-17 | 1-Bromo-2-phenyl ethane | Ald |
| HAL-18 | 1-Bromo-2-(4-chloro phenyl) ethane | Ald |
| HAL-19 | 1-Bromo-2-(3-chloro phenyl) ethane | |
| HAL-20 | 1-Bromo-2-(2-chloro phenyl) ethane | |
| HAL-21 | 1-Bromo-2-(4-dimethyl aminophenyl) ethane | |
| HAL-22 | Benzoyl chloride | TCI |
| HAL-23 | Acetyl chloride | WAKO |
| HAL-24 | i-Butyryl chloride | Ald |
| HAL-25 | Cyclohexylcarbonyl chloride | Ald |
| HAL-26 | 4-Methoxybenzoyl chloride | TCI |
| HAL-27 | 4-Methylbenzoyl chloride | Ald |
| HAL-28 | 4-Chlorobenzoyl chloride | TCI |
| HAL-29 | Phenylacetyl chloride | WAKO |
| HAL-30 | 2-Phenylpropionyl chloride | TCI |

TABLE Da-1

[Structure: benzene ring with Rx-CH2- substituent, Zx substituent, AR substituent, and -CH2CH2-C(=O)-O-Y group]

| Exp. | Rx | Y | Zx | AR | SM1 | SM2 | LCMS method | RTime | Mass |
|---|---|---|---|---|---|---|---|---|---|
| Da-1 | Ph | Me | H | 2-Nap | Ab-1 | HAL-1 | D | | N.D |
| Da-2 | Ph | H | H | 2-Nap | Da-1 | — | C | | 367 (M$^+$ + 1) |
| Da-3 | Ph | Me | H | 5-Ind | Ab-2 | HAL-1 | | | |
| Da-4 | Ph | H | H | 5-Ind | Da-3 | — | | | |
| Da-5 | Ph | Me | H | 1Me-5-Ind | Ab-3 | Ha-1 | C | | 384 (M$^+$ + 1) |
| Da-6 | Ph | H | H | 1Me-5-Ind | Da-5 | — | C | | 369 (M$^+$ + 1) |
| Da-7 | Ph | Me | H | 5-1HIdz | Ab-4 | Ha-1 | | | |
| Da-8 | Ph | H | H | 5-1HIdz | Da-7 | — | | | |
| Da-9 | Ph. | Me | H | 1Me-5-1HIdz | Ab-5 | HAL-1 | C | | 385 (M$^+$ + 1) |
| Da-10 | Ph | H | H | 1Me-5-1HIdz | Da-9 | — | C | | 370 (M$^+$ + 1) |
| Da-11 | 4MeOPh | H | H | 2-Nap | Ab-1 | HAL-2 | | | |
| Da-12 | 4MeOPh | H | H | 5-Ind | Ab-2 | HAL-2 | | | |
| Da-13 | 4MeOPh | H | H | 1Me-5-1HIdz | Ab-5 | HAL-2 | | | |
| Da-14 | 3MeOPh | H | H | 2-Nap | Ab-1 | HAL-3 | C | | 397 (M$^+$ + 1) |
| Da-15 | 3MeOPh | H | H | 5-Ind | Ab-2 | HAL-3 | | | |
| Da-16 | 3MeOPh | H | H | 1Me-5-1HIdz | Ab-5 | HAL-3 | | | |
| Da-17 | 2MeOPh | H | H | 2-Nap | Ab-1 | HAL-4 | | | |
| Da-18 | 2MeOPh | H | H | 5-Ind | Ab-2 | HAL-4 | | | |
| Da-19 | 2MeOPh | H | H | 1Me-5-1HIdz | Ab-5 | HAL-4 | | | |
| Da-20 | 4MePh | H | H | 2-Nap | Ab-1 | HAL-5 | C | | 381 (M$^+$ + 1) |
| Da-21 | 4MePh | H | H | 5-Ind | Ab-2 | HAL-5 | | | |
| Da-22 | 4MePh | H | H | 1Me-5-1HIdz | Ab-5 | HAL-5 | | | |
| Da-23 | 3MePh | H | H | 2-Nap | Ab-1 | HAL-6 | | | |
| Da-24 | 3MePh | H | H | 5-Ind | Ab-2 | HAL-6 | | | |
| Da-25 | 3MePh | H | H | 1Me-5-1HIdz | Ab-5 | HAL-6 | | | |
| Da-26 | 2MePh | H | H | 2-Nap | Ab-1 | HAl-7 | C | | 381 (M$^+$ + 1) |
| Da-27 | 2MePh | H | H | 5-Ind | Ab-2 | HAl-7 | C | | 370 (M$^+$ + 1) |
| Da-28 | 2MePh | H | H | 1Me-5-1HIdz | Ab-5 | HAl-7 | | | |
| Da-29 | 4CF$_3$Ph | H | H | 2-Nap | Ab-1 | HAL-8 | | | |
| Da-30 | 4CF$_3$Ph | H | H | 5-Ind | Ab-2 | HAL-8 | | | |
| Da-31 | 4CF$_3$Ph | H | H | 1Me-5-1HIdz | Ab-5 | HAL-8 | | | |
| Da-32 | 3CF$_3$Ph | H | H | 2-Nap | Ab-1 | HAL-9 | | | |
| Da-33 | 3CF$_3$Ph | H | H | 5-Ind | Ab-2 | HAL-9 | | | |
| Da-34 | 3CF$_3$Ph | H | H | 1Me-5-1HIdz | Ab-5 | HAL-9 | | | |
| Da-35 | 2CF$_3$Ph | H | H | 2-Nap | Ab-1 | HAL-10 | | | |
| Da-36 | 2CF$_3$Ph | H | H | 5-Ind | Ab-2 | HAL-10 | | | |
| Da-37 | 2CF$_3$Ph | H | H | 1Me-5-1HIdz | Ab-5 | HAL-10 | | | |
| Da-38 | 4ClPh | H | H | 2-Nap | Ab-1 | HAL-11 | C | | 401 (M$^+$ + 1) |
| Da-39 | 4ClPh | H | H | 5-Ind | Ab-2 | HAL-11 | C | | 390 (M$^+$ + 1) |
| Da-40 | 4ClPh | H | H | 1Me-5-1HIdz | Ab-5 | HAL-11 | | | |
| Da-41 | 3ClPh | H | H | 2-Nap | Ab-1 | HAL-12 | | | |
| Da-42 | 3ClPh | H | H | 5-Ind | Ab-2 | HAL-12 | | | |
| Da-43 | 3ClPh | H | H | 1Me-5-1HIdz | Ab-5 | HAL-12 | | | |
| Da-44 | 2ClPh | H | H | 2-Nap | Ab-1 | HAL-13 | | | |
| Da-45 | 2ClPh | H | H | 5-Ind | Ab-2 | HAL-13 | | | |
| Da-46 | 2ClPh | H | H | 1Me-5-1HIdz | Ab-5 | HAL-13 | | | |
| Da-47 | 4FPh | H | H | 2-Nap | Ab-1 | HAL-14 | C | | 385 (M$^+$ + 1) |
| Da-48 | 4FPh | H | H | 5-Ind | Ab-2 | HAL-14 | | | |
| Da-49 | 4FPh | H | H | 1Me-5-1HIdz | Ab-5 | HAL-14 | C | | 389 (M$^+$ + 1) |
| Da-50 | 3FPh | H | H | 2-Nap | Ab-1 | HAL-15 | | | |

TABLE Da-2

| Exp. | Rx | Y | Zx | AR | SM1 | SM2 | LCMS method | RTime | Mass |
|---|---|---|---|---|---|---|---|---|---|
| Da-51 | 3FPh | H | H | 5-Ind | Ab-2 | HAL-15 | | | |
| Da-52 | 3FPh | H | H | 1Me-5-1HIdz | Ab-5 | HAL-15 | | | |
| Da-53 | 2FPh | H | H | 2-Nap | Ab-1 | HAL-16 | | | |
| Da-54 | 2FPh | H | H | 5-Ind | Ab-2 | HAL-16 | | | |
| Da-55 | 2FPh | H | H | 1Me-5-1HIdz | Ab-5 | HAL-16 | | | |
| Da-56 | Bn | H | H | 2-Nap | Ab-1 | HAL-17 | C | | 381 (M$^+$ + 1) |

TABLE Da-2-continued

| Exp. | Rx | Y | Zx | AR | SM1 | SM2 | LCMS method | RTime | Mass |
|---|---|---|---|---|---|---|---|---|---|
| Da-57 | Bn | H | H | 5-Ind | Ab-2 | HAL-17 | | | |
| Da-58 | Bn | H | H | 1Me-5-1HIdz | Ab-5 | HAL-17 | C | | 419 (M$^+$ + 1) |
| Da-59 | 4ClBn | H | H | 2-Nap | Ab-1 | HAL-18 | | | |
| Da-60 | 4ClBn | H | H | 5-Ind | Ab-2 | HAL-18 | | | |
| Da-61 | 4ClBn | H | H | 1Me-5-1HIdz | Ab-5 | HAL-18 | C | | 385 (M$^+$ + 1) |
| Da-62 | 3ClBn | H | H | 2-Nap | Ab-1 | HAL-19 | C | | 415 (M$^+$ + 1) |
| Da-63 | 3ClBn | H | H | 5-Ind | Ab-2 | HAL-19 | | | |
| Da-64 | 3ClBn | H | H | 1Me-5-1HIdz | Ab-5 | HAL-19 | | | |
| Da-65 | 2ClBn | H | H | 2-Nap | Ab-1 | HAL-20 | | | |
| Da-66 | 2ClBn | H | H | 5-Ind | Ab-2 | HAL-20 | | | |
| Da-67 | 2ClBn | H | H | 1Me-5-1HIdz | Ab-5 | HAL-20 | | | |
| Da-68 | 4DMABn | H | H | 2-Nap | Ab-1 | HAL-21 | C | | 424 (M$^+$ + 1) |
| Da-69 | 4DMABn | H | H | 5-Ind | Ab-2 | HAL-21 | C | | 413 (M$^+$ + 1) |
| Da-70 | 4DMABn | H | H | 1Me-5-1HIdz | Ab-5 | HAL-21 | | | |

Example Ea-1

Synthesis of methyl 3-[4-(phenylcarbonyl)-3-(naphthalen-2-yl)phenyl]propionate (Compound No. Ea-1)

According to a procedure described in literature (Y. Urawa et al, Tetrahedron. Lett., 2003, p. 271), Compound Ab-1 (112.1 mg, corresponding to the substance mentioned in the column of SM1 in Table-Ea-1 mentioned later), dichlorobis(triphenylphosphine)palladium (18.9 mg, KANTO), and a solution of potassium phosphate (147.1 mg) in toluene (2.6 ml) were added with benzoyl chloride (47 μg, corresponding to the substance mentioned in the column of SM2 in Table-Ea-1), and stirred with heating at 110° C. for 48 hours under nitrogen atmosphere. The reaction mixture was washed successively with saturated aqueous sodium hydrogencarbonate, water and saturated brine, dried, and then concentrated under reduced pressure. The residue was purified by flash column chromatography (hexane:ethyl acetate=7:1) to obtain the title compound (Compound No. Ea-1, 88.3 mg).

Example Ea-2

Synthesis of 3-[4-phenylcarbonyl-3-(naphthalen-2-yl)phenyl]propionic acid (Compound No. Ea-2)

According to the procedure described in the synthesis method of Compound Ca-2 with the modification that the reaction was carried out for 3 hour, Compound No. Ea-1 (82.6 mg) and 2 N aqueous sodium hydroxide (105 ml) were reacted and treated to obtain the title compound (Compound No. Ea-2, 70.7 mg).

Examples Ea-1 to Ea-34

Typical examples of the compounds of the present invention including those mentioned in the examples described above, that can be obtained by reacting and treating corresponding starting compounds according to the methods described in Examples Ea-1 and Ea-2, are shown in Table-Ea-1.

The substances mentioned in the column of "SM1" in the table correspond to reaction intermediates, and those mentioned in the column of "SM2" in the table correspond to acid chlorides mentioned in Table Ea-1. The acid chlorides mentioned with the symbols of "HAL (number)" in the column of "SM2" are those mentioned in Table-Ha.

TABLE Ea-1

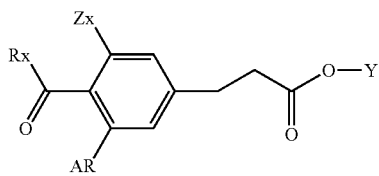

| Exp. | Rx | Y | Zx | AR | SM1 | SM2 | LCMS method | RTime | Mass |
|---|---|---|---|---|---|---|---|---|---|
| Ea-1 | Ph | Me | H | 2-Nap | Ab-1 | HAL-22 | C | | 395(M$^+$ + 1) |
| Ea-2 | Ph | H | H | 2-Nap | Ea-1 | — | C | | 381(M$^+$ + 1) |
| Ea-3 | Ph | Me | H | 5-Ind | Ab-2 | HAL-22 | | | |
| Ea-4 | Ph | H | H | 5-Ind | Ea-3 | — | | | |
| Ea-5 | Ph | Me | H | 1Me-5-Ind | Ab-3 | HAL-22 | C | | 398(M$^+$ + 1) |
| Ea-6 | Ph | H | H | 1Me-5-Ind | Ea-5 | — | C | | 384(M$^+$ + 1) |
| Ea-7 | Ph | Me | H | 5-1HIdz | Ab-4 | HAL-22 | | | |
| Ea-8 | Ph | H | H | 5-1HIdz | Ea-7 | — | | | |
| Ea-9 | Ph | Me | H | 1Me-5-1HIdz | Ab-5 | HAL-22 | C | | 399(M$^+$ + 1) |

TABLE Ea-1-continued

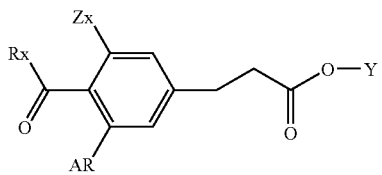

| Exp. | Rx | Y | Zx | AR | SM1 | SM2 | LCMS method | RTime | Mass |
|---|---|---|---|---|---|---|---|---|---|
| Ea-10 | Ph | H | H | 1Me-5-1HIdz | Ea-9 | — | C | | 385($M^+$ + 1) |
| Ea-11 | Me | H | H | 2-Nap | Ab-1 | HAL-23 | C | | 319($M^+$ + 1) |
| Ea-12 | Me | H | H | 5-Ind | Ab-2 | HAL-23 | C | | 308($M^+$ + 1) |
| Ea-13 | Me | H | H | 1Me-5-1HIdz | Ab-5 | HAL-23 | | | |
| Ea-14 | iBu | H | H | 2-Nap | Ab-1 | HAL-24 | C | | 361($M^+$ + 1) |
| Ea-15 | iBu | H | H | 5-Ind | Ab-2 | HAL-24 | | | |
| Ea-16 | iBu | H | H | 1Me-5-1HIdz | Ab-5 | HAL-24 | C | | 365($M^+$ + 1) |
| Ea-17 | cHex | H | H | 2-Nap | Ab-1 | HAL-25 | C | | 386($M^+$ + 1) |
| Ea-18 | cHex | H | H | 5-Ind | Ab-2 | HAL-25 | | | |
| Ea-19 | cHex | H | H | 1Me-S-1HIdz | Ab-5 | HAL-25 | | | |
| Ea-20 | 4MeOPh | H | H | 2-Nap | Ab-1 | HAL-26 | C | | 411($M^+$ + 1) |
| Ea-21 | 4MeOPh | H | H | 5-Ind | Ab-2 | HAL-26 | C | | 400($M^+$ + 1) |
| Ea-22 | 4MeOPh | H | H | 1Me-5-1HIdz | Ab-5 | HAL-26 | | | |
| Ea-23 | 4MePh | H | H | 2-Nap | Ab-1 | HAL-27 | | | |
| Ea-24 | 4MePh | H | H | 5-Ind | Ab-2 | HAL-27 | | | |
| Ea-25 | 4MePh | H | H | 1Me-5-1HIdz | Ab-5 | HAL-27 | | | |
| Ea-26 | 4ClPh | H | H | 2-Nap | Ab-1 | HAL-28 | C | | 415($M^+$ + 1) |
| Ea-27 | 4ClPh | H | H | 5-Ind | Ab-2 | HAL-28 | | | |
| Ea-28 | 4ClPh | H | H | 1Me-5-1HIdz | Ab-5 | HAL-28 | | | |
| Ea-29 | Bn | H | H | 2-Nap | Ab-1 | HAL-29 | C | | 395($M^+$ + 1) |
| Ea-30 | Bn | H | H | 5-Ind | Ab-2 | HAL-29 | | | |
| Ea-31 | Sn | H | H | 1Me-5-1HIdz | Ab-5 | HAL-29 | C | | 399($M^+$ + 1) |
| Ea-32 | 1PhEt | H | H | 2-Nap | Ab-1 | HAL-30 | C | | 409($M^+$ + 1) |
| Ea-33 | 1PhEt | H | H | 5-Ind | Ab-2 | HAL-30 | C | | 398($M^+$ + 1) |
| Ea-34 | 1PhEt | H | H | 1Me-5-1HIdz | Ab-5 | HAL-30 | | | |

Reference Examples

Intermediate Ac-1 and Ac-2

Synthesis of t-butyldimethylsilyl 3-[3-bromo-4-(t-butyldimethylsilyloxy)phenyl]acrylate (Intermediate Ac-1)

According to the procedure described in the synthesis method of Intermediate 43, 3-[3-bromo-4-hydroxylphenyl]acrylic acid (12.01 g) obtainable from 4-hydroxybenzaldehyde (TCI) by a method known from literature (Y. Nagao et al., Tetrahedron Lett., 1980, p. 4931) was reacted with imidazole (16.01 g) and t-butyldimethylsilyl chloride (7.43 g) and treated to obtain the title compound (Intermediate Ac-1, 17.43 g).

Synthesis of 3-[3-bromo-4-(t-butyldimethylsilyloxy)phenyl]acrylic acid (Intermediate Ac-2)

A solution of Compound Ac-1 (17.43 g) in methanol (100 ml) was added with 1 N hydrochloric acid (5 ml), and stirred at room temperature for 3 hours. The reaction solution was extracted with ethyl acetate (500 ml), and washed with saturated brine. The organic layer was dried, and then the solvent was evaporated under reduced pressure. The residue was purified by flash column chromatography (hexane:ethyl acetate=6:1) to obtain the title compound (Compound No. Ac-2, 14.60 g).

Example Ga-1

Synthesis of methyl 3-[3-(1H-indol-5-yl)-4-(3-pyridinemethyloxy)phenyl]acrylate (Compound No. Ga-1)

(Step 1)

A solution of Compound Ac-2 (3.06 g), diisopropyl carbodiimide (henceforth abbreviated as "DIC", 1.33 ml) and dimethylaminopyridine (86.8 mg) in DMF (100 ml) was added with SynPhase-PS-D-series Lantern, Hydroxymethylphenoxy Linker (henceforth abbreviated as "PSL", 0.035 mmol per lantern, 81 lanterns, Mimotopes), and left standing at room temperature for 16 hours. After the reaction mixture was removed, PSL was washed successively with DMF (100 ml), methanol (100 ml), dichloromethane (100 ml), and THF (100 ml) three times for each, and dried under reduced pressure.

PSL (81 lanterns mentioned above) was added to a solution of tetrabutylammonium fluoride (8.5 ml, Ald, 1 N THF solution) in THF (80 ml), and left standing at room temperature for 23 hours. After the reaction mixture was removed, PSL was successively washed with DMF (100 ml) three times, alternately with DMF:water:acetic acid (75:25:1, 100 ml) and methanol:water:acetic acid (75:25:1, 100 ml) twice for each, alternately with DMF:water (4:1, 100 ml) and methanol:water (4:1, 100 ml) twice for each, and with THF (100 ml), chloroform (100 ml), DMF (100 ml), and chloroform (100 ml) twice for each, and then dried under reduced pressure to obtain PLS-1 (81 lanterns).

(Step 2)

PSL-1 (3 lanterns out of those mentioned above) was added to a mixed solution of 3-pyridinemethanol (147.6 μl, corresponding to the substance mentioned in the column of SM1 in Table-Ga-1 mentioned later), DBAB (242.1 mg, Sigma) and Ph$_3$P (275.6 mg, KANTO) in dehydrated THF (3.24 ml), and left standing at room temperature for 15 hours. After the reaction mixture was removed, PSL was successively washed with THF (3.5 ml) and DMF (3.5 ml) four times for each, alternately with methanol (3.5 ml) and DMF (3.5 ml) twice for each, alternately with DMF (3.5 ml) and dichloromethane (3.5 ml) twice for each, with dichloromethane (3.5 ml) twice, and dried under reduced pressure to obtain PSL-2 (3 vials).

(Step 3)

PSL-2 (1 lantern out of those mentioned above) was added to a mixed solution of 1H-indole-5-boronic acid (11.3 mg, corresponding to the substance mentioned in the column of SM2 in Table-Ga-1 mentioned later), (Ph$_3$P)$_4$Pd (8.1 mg), and 2 N aqueous cesium carbonate (176 μl) in DMF (800 μl), and heated at 80° C. for 18 hours under argon atmosphere. After the reaction mixture was removed, PSL was successively washed with DMF (1.0 ml) four times, with methanol (1.0 ml) twice, alternately with DMF (1.0 ml) and methanol (1.0 ml) twice for each, alternately with DMF (1.0 ml) and dichloromethane (1.0 ml) twice for each, and with dichloromethane (1.0 ml) twice, and dried under reduced pressure. This PSL was added to a solution of sodium methoxide (175 μl, WAKO, 1 N solution in methanol) in THF:methanol (2:1, 1.5 ml), and left standing at room temperature for 19 hours. After the reaction, PSL was removed, and the reaction solution was added with water (500 μl), and stirred with heating at 60° C. for 3 hours. The reaction solution was concentrated under reduced pressure, then added with water (200 μl) and chloroform (1 ml), and passed through a diatomaceous earth column, and the obtained filtrate was concentrated under reduced pressure to obtain the title compound (Compound No. Ga-1, 10.6 mg).

Examples Ga-1 to Ga-55

Typical examples of the compounds of the present invention including those mentioned in the examples described above, that can be obtained by reacting and treating corresponding starting compounds according to the method described in Example Ga-1, are shown in Table-Ga-1 and Table-Ga-2.

The substances mentioned in the columns of "SM1" in the tables correspond to the alcohol reagent mentioned in Example Ga-1, and those mentioned in the columns of "SM2" in the tables correspond to the boronic acid reagent mentioned in Table Ga-1. The alcohol reagents mentioned in the columns of "SM1" with the symbols of "ALC (number))" are those mentioned in Table-I. The boronic acid reagents mentioned with the symbols of "BRA (number))" in the columns of "SM2" are those mentioned in Table-Ba-1 and Table-Ba-2.

TABLE I

| Reagent | Name of reagent | Manufacture |
|---|---|---|
| ALC-1 | Cyclopentanol | KANTO |
| ALC-2 | Cyclohexanol | Ald |
| ALC-3 | Benzyl Alcohol | Ald |
| ALC-4 | 2-Methyl-1-propyl alcohol | TCI |
| ALC-5 | 4-Fluorophenetyl alcohol | Ald |
| ALC-6 | 1-Phenylethanol | WAKO |
| ALC-7 | 2-(N-Methylanilino) ethanol | TCI |
| ALC-8 | 2-Hydroxy indane | TCI |
| ALC-9 | 2-Hydroxymethyl-1,4-benzodioxane | TCI |
| ALC-10 | 2-(4-Dimethyl) phenyl ethanol | Ald |
| ALC-11 | 3-Pyridine methanol | TCI |
| ALC-12 | m-Chlorobenzyl alcohol | TCI |
| ALC-13 | 4-n-Butoxybenzyl alcohol | TCI |
| ALC-14 | 2-Hydroxyacetophenone | TCI |
| ALC-15 | 2-Phenoxy ethanol | TCI |
| ALC-16 | 2-Phenylthio ethanol | TCI |
| ALC-17 | 5-(2-Hydroxyethyl)-4-methylthiazol | TCI |
| ALC-18 | 1-Butanol | TCI |
| ALC-19 | 2-Hydroxyethyl acetate | TCI |
| ALC-20 | N-(2-Hydroxyethyl) morpholine | TCI |
| ALC-21 | 2-(2-Dimethylaminoethoxy) | TCI |
| ALC-22 | Methyl glycolate | TCI |
| ALC-23 | 1-Phenyl ethanol | TCI |
| ALC-24 | 2-Chlorobenzyl alcohol | TCI |
| ALC-25 | 3-Chlorobenzyl alcohol | TCI |
| ALC-26 | 4-Chlorobenzyl alcohol | TCI |
| ALC-27 | 2-Methoxybenzyl alcohol | TCI |
| ALC-28 | 3-Methoxybenzyl alcohol | TCI |
| ALC-29 | 4-Methoxybenzyl alcohol | TCI |

TABLE GA-1

| Exp. | RxO | Y | Zx | AR | SM1 | SM2 | LCMS method | RTime | Mass |
|---|---|---|---|---|---|---|---|---|---|
| Ga-1 | 3PyMeO | H | H | 5-Ind | ALC-11 | BRA2 | A | 3.27 | 371 (M$^+$ + 1) |
| Ga-2 | 2(PhS)EtO | H | H | 5-Ind | ALC-16 | BRA2 | | | |
| Ga-3 | ![4-methylthiazol-5-yl-ethoxy structure] | H | H | 5-Ind | ALC-17 | BRA2 | A | 3.07 | 405 (M$^+$ + 1) |
| Ga-4 | nBuO | H | H | 5-Ind | ALC-18 | BRA2 | | | |

TABLE GA-1-continued

| Exp. | RxO | Y | Zx | AR | SM1 | SM2 | LCMS method | RTime | Mass |
|---|---|---|---|---|---|---|---|---|---|
| Ga-5 | (CH3)2N-CH2CH2-O-CH2CH2-O- | H | H | 5-Ind | ALC-21 | BRA2 | | | |
| Ga-6 | cPenO | H | H | 5-Ind | ALC-1 | BRA2 | | | |
| Ga-7 | cHexO | H | H | 5-Ind | ALC-2 | BRA2 | | | |
| Ga-8 | PhMeO | H | H | 5-Ind | ALC-3 | BRA2 | A | 3.79 | 356 (M$^+$ + 1) |
| Ga-9 | cPenO | H | H | 2-BF | ALC-1 | BRA18 | | | |
| Ga-10 | cHexO | H | H | 2-BF | ALC-2 | BRA18 | | | |
| Ga-11 | 2-IndanO | H | H | 2-BF | ALC-8 | BRA18 | A | 3.85 | 397 (M$^+$ + 1) |
| Ga-12 | 3PyMeO | H | H | 2-BF | ALC-11 | BRA18 | | | |
| Ga-13 | 2(PhS)EtO | H | H | 2-BF | ALC-16 | BRA18 | A | 3.61 | 417 (M$^+$ + 1) |
| Ga-14 | 4-methylthiazol-5-yl-CH2CH2-O- | H | H | 2-BF | ALC-17 | BRA18 | | | |
| Ga-15 | nBuO | H | H | 2-BF | ALC-18 | BRA18 | | | |
| Ga-16 | (CH3)2N-CH2CH2-O-CH2CH2-O- | H | H | 2-BF | ALC-21 | BRA18 | | | |
| Ga-17 | cPenO | H | H | 1Me-5-1HIdz | ALC-1 | BRA6 | | | |
| Ga-18 | cHexO | H | H | 1Me-5-1HIdz | ALC-2 | BRA6 | A | 3.74 | 377 (M$^+$ + 1) |
| Ga-19 | 2-IndenO | H | H | 1Me-5-1HIdz | ALC-8 | BRA6 | | | |
| Ga-20 | 3PyMeO | H | H | 1Me-5-1HIdz | ALC-11 | BRA6 | | | |
| Ga-21 | 2(PhS)EtO | H | H | 1Me-5-1HIdz | ALC-16 | BRA6 | | | |
| Ga-22 | 4-methylthiazol-5-yl-CH2CH2-O- | H | H | 1Me-5-1HIdz | ALC-17 | BRA6 | | | |
| Ga-23 | nBuO | H | H | 1Me-5-1HIdz | ALC-18 | BRA6 | | | |
| Ga-24 | (CH3)2N-CH2CH2-O-CH2CH2-O- | H | H | 1Me-5-1HIdz | ALC-21 | BRA6 | | | |
| Ga-25 | 3PyMeO | H | H | 1-Nap | ALC-11 | BRA16 | | | |
| Ga-26 | 2(PhS)EtO | H | H | 1-Nap | ALC-16 | BRA16 | C | | 427 (M$^+$ + 1) |
| Ga-27 | 4-methylthiazol-5-yl-CH2CH2-O- | H | H | 1-Nap | ALC-17 | BRA16 | | | |
| Ga-28 | nBuO | H | H | 1Nap | ALC-18 | BRA16 | | | |
| Ga-29 | (CH3)2N-CH2CH2-O-CH2CH2-O- | H | H | 1-Nap | ALC-21 | BRA16 | | | |
| Ga-30 | 1PhEtO | H | H | 5-Ind | ALC-6 | BRA2 | | | |

TABLE Ga-2

| Exp. | RxO | Y | Zx | AR | SM1 | SM2 | method | RTime | Mass |
|---|---|---|---|---|---|---|---|---|---|
| Ga-31 | 1PhEtO | H | H | 2-BF | ALC-6 | BRA18 | | | |
| Ga-32 | 1PhEtO | H | H | 1Me-5-1HIdz | ALC-6 | BRA6 | A | 3.55 | 399 (M⁺ + 1) |
| Ga-33 | 1PhEtO | H | H | 1-Nap | ALC-6 | BRA16 | | | |
| Ga-34 | 1PhEtO | H | H | 2-Nap | ALC-6 | BRA1 | | | |
| Ga-35 | 1PhEtO | H | H | 2-Nap | ALC-6 | BRA1 | C | | 395 (M⁺ + 1) |
| Ga-36 | 1PhEtO | H | H | 5-Ind | ALC-6 | BRA2 | | | |
| Ga-37 | 2ClPhMeO | H | H | 2-Nap | ALC-24 | BRA1 | | | |
| Ga-38 | 2ClPhMeO | H | H | 5-Ind | ALC-24 | BRA2 | | | |
| Ga-39 | 3ClPhMeO | H | H | 2-Nap | ALC-25 | BRA1 | C | | 415 (M⁺ + 1) |
| Ga-40 | 3ClPhMeO | H | H | 5-Ind | ALC-25 | BRA2 | | | |
| Ga-41 | 4ClPhMeO | H | H | 2-Nap | ALC-26 | BRA1 | | | |
| Ga-42 | 4ClPhMeO | H | H | 5-Ind | ALC-26 | BRA2 | C | | 404 (M⁺ + 1) |
| Ga-43 | 2MeOPhMeO | H | H | 2-Nap | ALC-27 | BRA1 | | | |
| Ga-44 | 2MeOPhMeO | H | H | 5-Ind | ALC-27 | BRA2 | | | |
| Ga-45 | 3MeOPhMeO | H | H | 2-Nap | ALC-28 | BRA1 | | | |
| Ga-46 | 3MeOPhMeO | H | H | 5-Ind | ALC-28 | BRA2 | | | |
| Ga-47 | 4MeOPhMeO | H | H | 2-Nap | ALC-29 | BRA1 | | | |
| Ga-48 | 4MeOPhMeO | H | H | 5-Ind | ALC-29 | BRA2 | | | |
| Ga-49 | nBuO | H | H | 3-Qu | ALC-18 | BRA10 | C | | 348 (M⁺ + 1) |
| Ga-50 | nBuO | H | H | 3-Thienyl | ALC-18 | BRA36 | | | |
| Ga-51 | nBuO | H | H | 4-Py | ALC-18 | BRA26 | | | |
| Ga-52 | nBuO | H | H | cPen | ALC-18 | BRA28 | | | |
| Ga-53 | nBuO | H | H | 2FPh | ALC-18 | BRA32 | C | | 315 (M⁺ + 1) |
| Ga-54 | nBuO | H | H | 3FPh | ALC-18 | BRA33 | | | |
| Ga-55 | nBuO | H | H | 4FPh | ALC-18 | BRA34 | | | |

Reference Examples

Intermediate s-1 to s-52

Synthesis of methyl 3-[4-(4-methylphenylthio)-3-nitrophenyl]acrylate (Intermediate s-1) (Synthesis method SF)

A solution of 3-[4-(4-methylphenylthio)-3-nitrophenyl] acrylic acid (631 mg, MAYB) in a mixture of methanol (12.6 ml), ethyl acetate (6.3 ml) and THF (6.3 ml) was added dropwise to methanol (12.6 ml) beforehand under ice cooling, and then the mixture was added with a solution of thionyl chloride (735 µl, KANTO) in methanol (50 ml) under ice cooling, stirred for 30 minutes, then warmed to room temperature, and further stirred for 15.5 hours. The reaction mixture was poured into aqueous sodium hydrogencarbonate (50 ml) for neutralization, and extracted with ethyl acetate (50 ml), and the organic layer was washed with saturated brine. The organic layer was dried, and then the solvent was evaporated under reduced pressure to obtain the title compound (Intermediate s-1, 659 mg).

Synthesis of methyl 3-[4-(4-methylphenylthio)-3-nitrophenyl]propionate (Intermediate s-2) (Synthesis method SD1)

A solution of Intermediate s-1 (494 mg) in ethyl acetate (75 ml) was added with 10% palladium hydroxide/carbon (150 mg, NE CHEMCAT), and stirred at room temperature for 14 hours under hydrogen atmosphere. The reaction mixture was filtered, and the solvent of the filtrate was evaporated under reduced pressure. The residue was dissolved in methanol (75 ml) again, added with 5 N hydrochloric acid (600 µl) and 10% palladium hydroxide/carbon (151 mg), and stirred at room temperature for 22 hours under hydrogen atmosphere. The reaction mixture was filtered, and the solvent of the filtrate was evaporated under reduced pressure to obtain the title compound (Intermediate s-2, 419 mg).

Synthesis of methyl 3-[3-bromo-4-(4-methylphenylthio)phenyl]propionate (Intermediate s-3) (Synthesis method SE1)

A solution of hydrobromic acid (690 µl) in methanol (3.2 ml) was added with a solution of Intermediate s-2 (362 mg) in methanol (3.2 ml) under ice cooling. This mixture was added dropwise with an aqueous solution (320 µl) of sodium nitrite (84 mg, WAKO).

An aqueous solution (3.2 ml) of copper(II) bromide (270 mg, WAKO) was heated to 40° C., added dropwise with the previously obtained solution over 20 minutes, and stirred at the same temperature for 1.5 hours.

The reaction mixture was extracted with ethyl acetate (40 ml). The organic layer was washed successively with water and saturated brine, and dried, and then the solvent was evaporated under reduced pressure. The residue was purified by flash column chromatography (hexane:ethyl acetate=9:1) to obtain the title compound (Intermediate s-3, 167 mg).

Synthesis of methyl 3-(3-bromo-4-fluorophenyl)acrylate (Intermediate s-4) (Synthesis method SF)

According to the procedure described in the synthesis method of Intermediate n-1 (Synthesis method SF) provided that the reaction was performed for 1 hour, 3-bromo-4-fluorocinnamic acid (3.30 g, LANC) and thionyl chloride (1.5 ml, WAKO) were reacted and treated to obtain the title compound (Intermediate n-25, 3.47 g).

Synthesis of methyl 3-[3-bromo-4-(4-methoxyphenylthio)phenyl]acrylate (Intermediate s-5) (Synthesis method SC)

A solution of Intermediate s-4 (259.1 mg) in DMSO (4 ml) was added with potassium carbonate (156.9 mg) and p-methoxythiophenol (148 µl, TCI), and stirred at 70° C. for 16 hours. The reaction mixture was extracted with ethyl acetate (30 ml), and then the organic layer was washed successively with water and saturated brine, and dried. Then, the solvent was evaporated under reduced pressure. The residue was purified by column chromatography (Quad, hexane:ethyl acetate=8:1) to obtain the title compound (Intermediate s-5, 283.3 mg).

Synthesis of methyl 3-[3-bromo-4-(4-methoxyphenylthio)phenyl)propionate (Intermediate s-6) (Synthesis method SD2)

According to a procedure described in literature [D. J. Hart et al., Journal of Organic Chemistry (J. Org. Chem.), 1987, vol. 52, p. 4665], a solution of Intermediate s-5 (579.1 mg) in dimethoxyethane (40 ml) was added with p-toluenesulfonhydrazide (1.99 g, TCI), and refluxed by heating at 110° C. Then, the reaction mixture was added dropwise with an aqueous solution (40 ml) of sodium acetate (1.54 g, WAKO) over 1 hour, and further stirred for 3 hours. The reaction mixture was extracted with dichloromethane (150 ml), and the organic layer was washed with water, and dried. Then, the solvent was evaporated under reduced pressure. The residue was purified by column chromatography (Quad, hexane:ethyl acetate=7:1) to obtain the title compound (Intermediate s-6, 583.5 mg).

Synthesis of 3-bromo-4-(cyclopentylthio)benzaldehyde (Intermediate s-23) (Synthesis method SC)

A solution of 3-bromo-4-fluorobenzaldehyde (517.4 mg) in DMSO (8 ml) was added with potassium carbonate (514.9 mg) and cyclopentanethiol (250 µl, TCI), and stirred at 90° C. for 17 hours. The reaction mixture was extracted with ethyl acetate (50 ml), and the organic layer was washed successively with water and saturated brine, and dried. Then, the solvent was evaporated under reduced pressure. The residue was purified by column chromatography (Quad, hexane:ethyl acetate=8:1) to obtain the title compound (Intermediate S-23, 644.7 mg).

Synthesis of ethyl 3-[3-bromo-4-(cyclopentylthio)phenyl]acrylate (Intermediate s-24) (Synthesis method SE2)

A solution of Intermediate s-23 (243.7 mg) in 1,2-dimethoxyethane (8 ml) was added with ethyl diethylphosphonoacetate (300 µl, TCI), and added with 60% sodium hydride (49.8 mg) under ice cooling. The reaction mixture was stirred for 10 minutes, then warmed to room temperature, and stirred for 1 hour. The reaction mixture was added with water (5 ml) for quenching, added with dichloromethane (30 ml) for extraction, and washed with saturated brine. The organic layer was dried, and then the solvent was evaporated under reduced pressure. The residue was purified by column chromatography (Quad, hexane:ethyl acetate=4:1) to obtain the title compound (Intermediate s-24, 286.2 mg).

Typical examples of the intermediates including those mentioned above that can be obtained by reacting and treating corresponding starting compounds using any of the methods described in the present specification are shown in Table-Int. S-1 and Table-Int. S-2. In the tables, intermediate numbers are mentioned in the columns indicated as "Exp". In the tables, used methods among those described above are mentioned in the columns of "Syn" with symbols, the starting compounds 1 are mentioned in the columns of "SM1", and the starting compounds 2 are mentioned in the columns of "SM2". Further, the compounds indicated as "Single" in the columns of "Single or Double" in Table-Int.S-1 are compounds in which two of the carbon atoms binding the benzene ring and carbonyl group in the compounds are bound with a single bond, and those indicated as "Double" in the same are compounds in which two of the carbon atoms binding the benzene ring and carbonyl group in the compounds are bound with a double bond.

TABLE Int.S-1

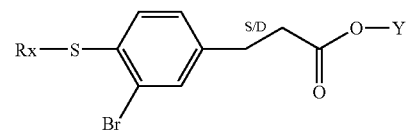

| Exp. | Syn. | SM1 | SM2 | Rx-S | Y | Single or Double | LCMS method | RTime | Mass |
|---|---|---|---|---|---|---|---|---|---|
| Int.s-5 | SC | Int.s-4 | 4MeOPhSH | 4MeOPhS | Me | Double | D | 5.87 | 378(M+ + 1) |
| Int.s-6 | SD2 | Int.s-5 | | 4MeOPhS | Me | Single | C | | 380(M+ + 1) |
| Int.s-7 | SC | Int.s-4 | 2MeOPhSH | 2MeOPhS | Me | Double | C | | 378(M+ + 1) |
| Int.s-8 | SD2 | Int.s-7 | | 2MeOPhS | Me | Single | C | | 380(M+ + 1) |
| Int.s-9 | SC | Int.s-4 | 3MeOPhSH | 3MeOPhS | Me | Double | C | | 378(M+ + 1) |
| Int.s-10 | SD2 | Int.s-9 | | 3MeOPhS | Me | Single | C | | 380(M+ + 1) |
| Int.s-11 | SC | Int.s-4 | 2MePhSH | 2MePhS | Me | Double | C | | 368(M+ + 1) |
| Int.s-12 | SD2 | Int.s-11 | | 2MePhS | Me | Single | D | 5.70 | N.D |
| Int.s-13 | SC | Int.s-4 | 3MePhSH | 3MePhS | Me | Double | C | | 368(M+ + 1) |
| Int.s-14 | SD2 | Int.s-13 | | 3MePhS | Me | Single | C | | 366(M+ + 1) |
| Int.s-15 | SC | Int.s-4 | 4MePhSH | 4MePhS | Me | Double | C | | 368(M+ + 1) |
| Int.s-16 | SD2 | Int.s-15 | | 4MePhS | Me | Single | C | | 366(M+ + 1) |
| Int.s-17 | SC | Int.s-4 | 2FPhSH | 2FPhS | Me | Double | C | | 368(M+ + 1) |
| Int.s-18 | SD2 | Int.s-17 | | 2FPhS | Me | Single | C | | 370(M+ + 1) |
| Int.s-19 | SC | Int.s-4 | 3FPhSH | 3FPhS | Me | Double | C | | 368(M+ + 1) |
| Int.s-20 | SD2 | Int.s-19 | | 3FPhS | Me | Single | C | | 370(M+ + 1) |
| Int.s-21 | SD | Int.s-4 | 4FPhSH | 4FPhS | Me | Double | C | | 368(M+ + 1) |
| Int.s-22 | SD2 | Int.s-21 | | 4FPhS | Me | Single | C | | 370(M+ + 1) |
| Int.s-24 | SE2 | Int.s-23 | | cPenS | Me | Double | D | 6.35 | 340(M+ + 1) |
| Int.s-25 | SD2 | Int.s-24 | | cPenS | Me | Single | C | | 342(M+ + 1) |

TABLE Int.S-1-continued

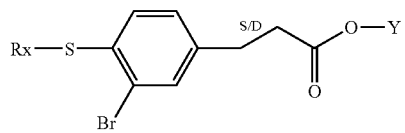

| Exp. | Syn. | SM1 | SM2 | Rx-S | Y | Single or Double | LCMS method | RTime | Mass |
|---|---|---|---|---|---|---|---|---|---|
| Int.s-27 | SE2 | Int.s-26 | | cHexS | Et | Double | C | | 354(M$^+$ + 1) |
| Int.s-28 | SD2 | Int.s-21 | | cHexS | Et | Single | C | | 356(M$^+$ + 1) |
| Int.s-30 | SE2 | Int.s-29 | | nPrS | Et | Double | C | | 328(M$^+$ + 1) |
| Int.s-31 | SD2 | Int.s-30 | | nPrS | Et | Single | C | | 330(M$^+$ + 1) |
| Int.s-33 | SE2 | Int.s-32 | | iPrS | Et | Double | C | | 328(M$^+$ + 1) |
| Int.s-34 | SD2 | Int.s-33 | | iPrS | Et | Single | C | | 330(M$^+$ + 1) |
| Int.s-36 | SE2 | Int.s-35 | | nBuS | Et | Double | C | | 328(M$^+$ + 1) |
| Int.s-37 | SD2 | Int.s-36 | | nBuS | Et | Single | C | | 330(M$^+$ + 1) |
| Int.s-39 | SE2 | Int.s-38 | | iBuS | Me | Double | D | 5.86 | 330(M$^+$ + 1) |
| Int.s-40 | SD2 | Int.s-39 | | iBuS | Me | Single | D | 6.23 | 330(M$^+$ + 1) |
| Int.s-42 | SE2 | Int.s-41 | | 2PhEtS | Me | Double | D | 6.18 | 376(M$^+$) |
| Int.s-43 | SD2 | Int.s-42 | | 2PhEtS | Me | Single | D | 6.21 | 378(M$^+$) |
| Int.s-45 | SE2 | Int.s-44 | | 4MeOBnS | Et | Double | C | | 393(M$^+$ + 1) |
| Int.s-46 | SD2 | Int.s-45 | | 4MeOBnS | Et | Single | C | | 395(M$^+$ + 1) |
| Int.s-48 | SE2 | Int.s-47 | | 4FBnS | Et | Double | C | | 381(M$^+$ + 1) |
| Int.s-49 | SD2 | Int.s-48 | | 4FBnS | Et | Single | C | | 383(M$^+$ + 1) |
| Int.s-51 | SE2 | Int.s-50 | | 2MeBnS | Et | Double | C | | 377(M$^+$ + 1) |
| Int.s-52 | SD2 | Int.s-51 | | 2MeBnS | Et | Single | C | | 379(M$^+$ + 1) |

TABLE Int.S-2

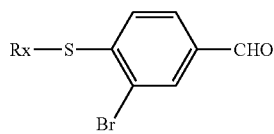

| Exp. | Syn. | SM1 | SM2 | Rx-S | LCMS method | RTime | Mass |
|---|---|---|---|---|---|---|---|
| Int.s-23 | SC | | cPenSH | cPenS | C | | 286 (M$^+$ + 1) |
| Int.s-26 | SC | | cHexSH | cHexS | C | | 300 (M$^+$ + 1) |
| Int.s-29 | SC | | nPrSH | nPrS | C | | 260 (M$^+$ + 1) |
| Int.s-32 | SC | | iPrSH | iPrS | C | | 260 (M$^+$ + 1) |
| Int.s-35 | SC | | nBuSH | nBuS | C | | 274 (M$^+$ + 1) |
| Int.s-38 | SC | | iBuSH | iBuS | C | | 274 (M$^+$ + 1) |
| Int.s-41 | SC | | 2PhEtSH | 2PhEtS | C | | 322 (M$^+$ + 1) |
| Int.s-44 | SC | | 4MeOBnSH | 4MeOBnS | C | | 322 (M$^+$ + 1) |
| Int.s-47 | SC | | 4FBnSH | 4FBnS | C | | 326 (M$^+$ + 1) |
| Int.s-50 | SC | | 2MeBnSH | 2MeBnS | C | | 322 (M$^+$ + 1) |

Example S-a-1

Synthesis of methyl 3-[3-(naphthalen-2-yl)-4-(4-methylphenylthio)phenyl]propionate (Compound No. N-a-1) (Synthesis method SB)

A solution of Intermediate s-3 (146 mg) in toluene (2 ml) was added with 2-naphthaleneboronic acid (132.3 mg, TCI), 2 M aqueous sodium carbonate (600 μl), methanol (500 μl), and tetrakistriphenylphosphine palladium(0) (henceforth abbreviated as "$(Ph_3P)_4Pd$", 38 mg, Nacalai Tesque), and stirred at 80° C. for 14.5 hours. The reaction mixture was added with ethyl acetate (40 ml), and washed successively with saturated aqueous sodium hydrogencarbonate, saturated aqueous ammonium chloride and saturated brine. The organic layer was dried, and then the solvent was evaporated under reduced pressure. The residue was purified by flash column chromatography (hexane:ethyl acetate=4:1) to obtain the title compound (Compound No. S-a-1, 78 mg).

Example S-a-2

Synthesis of 3-[3-(naphthalen-2-yl)-4-(4-methylphenylthio)phenyl]propionic acid (Compound No. S-a-2) (Synthesis method SA)

A solution of the compound of Example S-a-1 (51 mg) in methanol (5.0 ml) was added with 2 N aqueous sodium hydroxide (130 μl), and stirred at 60° C. for 2 hours. The reaction mixture was concentrated under reduced pressure, then made acidic with 5% aqueous hydrochloric acid under ice cooling, and then extracted with ethyl acetate (30 ml). The organic layer was washed with saturated brine, and dried, and then the solvent was evaporated under reduced pressure to obtain the title compound (Compound No. S-a-2, 47 mg).

Example S-c-1

Synthesis of methyl 3-[4-(4-methoxyphenylthio)-3-(naphthalen-2-yl)phenyl]propionate (Compound No. S-c-1) (Synthesis method SD2)

According to the procedure described in the synthesis method of Intermediate s-6 (Synthesis method), the compound of Example S-b-1 (3.01 g), p-toluenesulfonhydrazide (430.1 mg), and sodium acetate (380.4 mg) were reacted and treated to obtain the title compound (Compound-No. S-c-1, 95.1 mg).

Examples S-a-1 to S-a-24, S-b-1 to S-b-138 and S-c-1 to S-c-138

Typical examples of the compounds of the present invention that can be obtained by reacting and treating corresponding starting compounds using any of the methods described in the present specification including the examples described above are shown in Table-S-A-1, Table-S-B-1 to Table-S-B-3 and Table-S-C-1 to Table-S-C-3. In the tables, the compound numbers are mentioned in the columns indicated as "Exp.". In the tables, used methods among the aforementioned synthesis methods are shown in the columns of "Syn" with symbols, the starting compounds 1 are mentioned in the columns of "SM1", and the starting compounds 2 are mentioned in the columns of "SM2". The boronic acid reagents shown with the symbols of "BRA (number)" in the columns of "SM2" are those mentioned in Table-Ba-1 and Table-Ba-2.

TABLE S-A-1

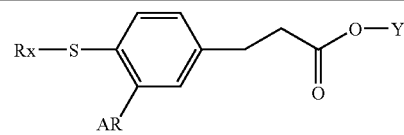

| Exp. | Syn. | SM1 | SM2 | Rx | Y | AR | LCMS method | RTime | Mass |
|---|---|---|---|---|---|---|---|---|---|
| S-a-1 | SB | Int.s-3 | BRA1 | 4MePh | Me | 2-Nap | C | | 413 ($M^+ + 1$) |
| S-a-2 | SA | S-a-1 | | 4MePh | H | 2-Nap | C | | 399 ($M^+ + 1$) |
| S-a-3 | SB | Int.s-3 | BRA2 | 4MePh | Me | 5-Ind | C | | 402 ($M^+ + 1$) |
| S-a-4 | SA | S-a-3 | | 4MePh | H | 5-Ind | C | | 388 ($M^+ + 1$) |
| S-a-5 | SB | Int.s-3 | BRA3 | 4MePh | Me | 1Me-5-Ind | C | | 416 ($M^+ + 1$) |
| S-a-6 | SA | S-a-5 | | 4MePh | H | 1Me-5-Ind | C | | 402 ($M^+ + 1$) |
| S-a-7 | SB | Int.s-3 | BRA4 | 4MePh | Me | 1Et-5-Ind | C | | 430 ($M^+ + 1$) |
| S-a-8 | SA | S-a-7 | | 4MePh | H | 1Et-5-Ind | C | | 416 ($M^+ + 1$) |
| S-a-9 | SB | Int.s-3 | BRA5 | 4MePh | Me | 5-1HIdz | C | | 403 ($M^+ + 1$) |
| S-a-10 | SA | S-a-9 | | 4MePh | H | 5-1HIdz | C | | 389 ($M^+ + 1$) |
| S-a-11 | SB | Int.s-3 | BRA6 | 4MePh | Me | 1Me-5-1HIdz | C | | 417 ($M^+ + 1$) |
| S-a-12 | SA | S-a-11 | | 4MePh | H | 1Me-5-1HIdz | C | | 403 ($M^+ + 1$) |
| S-a-13 | SB | Int.s-3 | BRA7 | 4MePh | Me | 1Et-5-1HIdz | C | | 431 ($M^+ + 1$) |
| S-a-14 | SA | S-a-13 | | 4MePh | H | 1Et-5-1HIdz | C | | 417 ($M^+ + 1$) |
| S-a-15 | SB | Int.s-3 | BRA8 | 4MePh | Me | 2Me-5-2HIdz | C | | 417 ($M^+ + 1$) |
| S-a-16 | SA | S-a-15 | | 4MePh | H | 2Me-5-2HIdz | C | | 403 ($M^+ + 1$) |
| S-a-17 | SB | Int.s-3 | BRA9 | 4MePh | Me | 5-Bzt | C | | 420 ($M^+ + 1$) |
| S-a-18 | SA | S-a-17 | | 4MePh | H | 5-Bzt | C | | 406 ($M^+ + 1$) |
| S-a-19 | SB | Int.s-3 | BRA10 | 4MePh | Me | 3-Qu | C | | 414 ($M^+ + 1$) |
| S-a-20 | SA | S-a-19 | | 4MePh | H | 3-Qu | C | | 400 ($M^+ + 1$) |
| S-a-21 | SB | Int.s-3 | BRA11 | 4MePh | Me | 6-Qu | C | | 414 ($M^+ + 1$) |
| S-a-22 | SA | S-a-21 | | 4MePh | H | 6-Qu | C | | 400 ($M^+ + 1$) |
| S-a-23 | SB | Int.s-3 | BRA12 | 4MePh | Me | 6-IQ | C | | 414 ($M^+ + 1$) |
| S-a-24 | SA | N-a-23 | | 4MePh | H | 6-IQ | C | | 400 ($M^+ + 1$) |

TABLE S-B-1

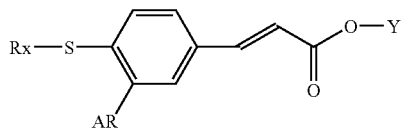

| Exp. | Syn | SM1 | SM2 | Rx | Y | AR | LCMS method | RTime | Mass |
|---|---|---|---|---|---|---|---|---|---|
| S-b-1 | SB | Int.s-5 | BRA1 | 4MeOPh | Me | 2-Nap | C | | 427 (M⁺ + 1) |
| S-b-2 | SA | S-b-1 | | 4MeOPh | H | 2-Nap | C | | 413 (M⁺ + 1) |
| S-b-3 | SB | Int.s-5 | BRA2 | 4MeOPh | Me | 5-Ind | C | | 416 (M⁺ + 1) |
| S-b-4 | SA | S-b-3 | | 4MeOPh | H | 5-Ind | C | | 402 (M⁺ + 1) |
| S-b-5 | SB | Int.s-5 | BRA3 | 4MeOPh | Me | 1Me-5-Ind | C | | 430 (M⁺ + 1) |
| S-b-6 | SA | S-b-5 | | 4MeOPh | H | 1Me-5-Ind | C | | 416 (M⁺ + 1) |
| S-b-7 | SB | Int.s-5 | BRA4 | 4MeOPh | Me | 1Et-5-Ind | C | | 444 (M⁺ + 1) |
| S-b-8 | SA | S-b-7 | | 4MeOPh | H | 1Et-5-Ind | C | | 430 (M⁺ + 1) |
| S-b-9 | SB | Int.s-5 | BRA5 | 4MeOPh | Me | 5-1HIdz | C | | 417 (M⁺ + 1) |
| S-b-10 | SA | S-b-9 | | 4MeOPh | H | 5-1HIdz | C | | 403 (M⁺ + 1) |
| S-b-11 | SB | Int.s-5 | BRA6 | 4MeOPh | Me | 1Me-5-1HIdz | C | | 431 (M⁺ + 1) |
| S-b-12 | SA | S-b-11 | | 4MeOPh | H | 1Me-5-1HIdz | C | | 417 (M⁺ + 1) |
| S-b-13 | SB | Int.s-5 | BRA7 | 4MeOPh | Me | 1Et-5-1HIdz | C | | 445 (M⁺ + 1) |
| S-b-14 | SA | S-b-13 | | 4MeOPh | H | 1Et-5-1HIdz | C | | 431 (M⁺ + 1) |
| S-b-15 | SB | Int.s-5 | BRA8 | 4MeOPh | Me | 2Me-5-2HIdz | C | | 431 (M⁺ + 1) |
| S-b-16 | SA | S-b-15 | | 4MeOPh | H | 2Me-5-2HIdz | C | | 417 (M⁺ + 1) |
| S-b-17 | SB | Int.s-5 | BRA9 | 4MeOPh | Me | 5-Bzt | C | | 434 (M⁺ + 1) |
| S-b-18 | SA | S-b-17 | | 4MeOPh | H | 5-Bzt | C | | 420 (M⁺ + 1) |
| S-b-19 | SB | Int.s-5 | BRA10 | 4MeOPh | Me | 3-Qu | C | | 428 (M⁺ + 1) |
| S-b-20 | SA | S-b-19 | | 4MeOPh | H | 3-Qu | C | | 414 (M⁺ + 1) |
| S-b-21 | SB | Int.s-5 | BRA11 | 4MeOPh | Me | 6-Qu | C | | 428 (M⁺ + 1) |
| S-b-22 | SA | S-b-21 | | 4MeOPh | H | 6-Qu | C | | 414 (M⁺ + 1) |
| S-b-23 | SB | Int.s-5 | BRA12 | 4MeOPh | Me | 6-IQ | C | | 428 (M⁺ + 1) |
| S-b-24 | SA | S-b-23 | | 4MeOPh | H | 6-IQ | C | | 414 (M⁺ + 1) |
| S-b-25 | SB | Int.s-7 | BRA1 | 2MeOPh | Me | 2-Nap | C | | 427 (M⁺ + 1) |
| S-b-26 | SA | S-b-25 | | 2MeOPh | H | 2-Nap | C | | 413 (M⁺ + 1) |
| S-b-27 | SB | Int.s-7 | BRA2 | 2MeOPh | Me | 5-Ind | C | | 416 (M⁺ + 1) |
| S-b-28 | SA | S-b-27 | | 2MeOPh | H | 5-Ind | C | | 402 (M⁺ + 1) |
| S-b-29 | SB | Int.s-7 | BRA5 | 2MeOPh | Me | 5-1HIdz | C | | 417 (M⁺ + 1) |
| S-b-30 | SA | S-b-29 | | 2MeOPh | H | 5-1HIdz | C | | 403 (M⁺ + 1) |
| S-b-31 | SB | Int.s-7 | BRA10 | 2MeOPh | Me | 3-Qu | C | | 428 (M⁺ + 1) |
| S-b-32 | SA | S-b-31 | | 2MeOPh | H | 3-Qu | C | | 414 (M⁺ + 1) |
| S-b-33 | SB | Int.s-9 | BRA1 | 3MeOPh | Me | 2-Nap | C | | 427 (M⁺ + 1) |
| S-b-34 | SA | S-b-33 | | 3MeOPh | H | 2-Nap | C | | 413 (M⁺ + 1) |
| S-b-35 | SB | Int.s-9 | BRA3 | 3MeOPh | Me | 1Me-5-Ind | C | | 430 (M⁺ + 1) |
| S-b-36 | SA | S-b-35 | | 3MeOPh | H | 1Me-5-Ind | C | | 416 (M⁺ + 1) |
| S-b-37 | SB | Int.s-9 | BRA6 | 3MeOPh | Me | 1Me-5-1HIdz | C | | 431 (M⁺ + 1) |
| S-b-38 | SA | S-b-37 | | 3MeOPh | H | 1Me-5-1HIdz | C | | 417 (M⁺ + 1) |
| S-b-39 | SB | Int.s-9 | BRA11 | 3MeOPh | Me | 6-Qu | C | | 428 (M⁺ + 1) |
| S-b-40 | SA | S-b-39 | | 3MeOPh | H | 6-Qu | C | | 414 (M⁺ + 1) |
| S-b-41 | SB | Int.s-11 | BRA2 | 2MePh | Me | 5-Ind | C | | 400 (M⁺ + 1) |
| S-b-42 | SA | S-b-41 | | 2MePh | H | 5-Ind | C | | 386 (M⁺ + 1) |
| S-b-43 | SB | Int.s-11 | BRA3 | 2MePh | Me | 1Me-5-Ind | C | | 414 (M⁺ + 1) |
| S-b-44 | SA | S-b-43 | | 2MePh | H | 1Me-5-Ind | C | | 400 (M⁺ + 1) |
| S-b-45 | SB | Int.s-11 | BRA5 | 2MePh | Me | 5-1HIdz | C | | 401 (M⁺ + 1) |
| S-b-46 | SA | S-b-45 | | 2MePh | H | 5-1HIdz | C | | 387 (M⁺ + 1) |

TABLE S-B-2

| Exp. | Syn | SM1 | SM2 | Rx | Y | AR | LCMS method | RTime | Mass |
|---|---|---|---|---|---|---|---|---|---|
| S-b-47 | SB | Int.s-13 | BRA3 | 3MePh | Me | 1Me-5-Ind | C | | 414 (M⁺ + 1) |
| S-b-48 | SA | N-b-47 | | 3MePh | H | 1Me-5-Ind | C | | 400 (M⁺ + 1) |
| S-b-49 | SB | Int.s-13 | BRA6 | 3MePh | Me | 1Me-5-1HIdz | C | | 415 (M⁺ + 1) |
| S-b-50 | SA | N-b-49 | | 3MePh | H | 1Me-5-1HIdz | C | | 401 (M⁺ + 1) |
| S-b-51 | SB | Int.s-13 | BRA9 | 3MePh | Me | 5-Bzt | C | | 418 (M⁺ + 1) |
| S-b-52 | SA | N-b-51 | | 3MePh | H | 5-Bzt | C | | 404 (M⁺ + 1) |
| S-b-53 | SB | Int.s-15 | BRA1 | 4MePh | Me | 2-Nap | C | | 411 (M⁺ + 1) |
| S-b-54 | SA | N-b-53 | | 4MePh | H | 2-Nap | C | | 397 (M⁺ + 1) |
| S-b-55 | SB | Int.s-15 | BRA2 | 4MePh | Me | 5-Ind | C | | 400 (M⁺ + 1) |
| S-b-56 | SA | N-b-55 | | 4MePh | H | 5-Ind | C | | 386 (M⁺ + 1) |
| S-b-57 | SB | Int.s-15 | BRA3 | 4MePh | Me | 1Me-5-Ind | C | | 418 (M⁺ + 1) |
| S-b-58 | SA | N-b-57 | | 4MePh | H | 1Me-5-Ind | C | | 404 (M⁺ + 1) |

TABLE S-B-2-continued

| Exp. | Syn | SM1 | SM2 | Rx | Y | AR | LCMS method | RTime | Mass |
|---|---|---|---|---|---|---|---|---|---|
| S-b-59 | SB | Int.s-17 | BRA5 | 2FPh | Me | 5-1HIdz | C | | 404 (M⁺ + 1) |
| S-b-60 | SA | N-b-59 | | 2FPh | H | 5-1HIdz | C | | 390 (M⁺ + 1) |
| S-b-61 | SB | Int.s-17 | BRA6 | 2FPh | Me | 1Me-5-Ind | C | | 418 (M⁺ + 1) |
| S-b-62 | SA | N-b-61 | | 2FPh | H | 1Me-5-Ind | C | | 404 (M⁺ + 1) |
| S-b-63 | SB | Int.s-17 | BRA11 | 2FPh | Me | 6-Qu | C | | 415 (M⁺ + 1) |
| S-b-64 | SA | N-b-63 | | 2FPh | H | 6-Qu | C | | 401 (M⁺ + 1) |
| S-b-65 | SB | Int.s-19 | BRA1 | 3FPh | Me | 2-Nap | C | | 415 (M⁺ + 1) |
| S-b-66 | SA | N-b-65 | | 3FPh | H | 2-Nap | C | | 401 (M⁺ + 1) |
| S-b-67 | SB | Int.s-19 | BRA2 | 3FPh | Me | 5-Ind | C | | 403 (M⁺ + 1) |
| S-b-68 | SA | N-b-67 | | 3FPh | H | 5-Ind | C | | 389 (M⁺ + 1) |
| S-b-69 | SB | Int.s-19 | BRA6 | 3FPh | Me | 1Me-5-1HIdz | C | | 418 (M⁺ + 1) |
| S-b-70 | SA | N-b-69 | | 3FPh | H | 1Me-5-1HIdz | C | | 404 (M⁺ + 1) |
| S-b-71 | SB | Int.s-21 | BRA3 | 4FPh | Me | 1Me-5-Ind | C | | 418 (M⁺ + 1) |
| S-b-72 | SA | N-b-71 | | 4FPh | H | 1Me-5-Ind | C | | 404 (M⁺ + 1) |
| S-b-73 | SB | Int.s-21 | BRA5 | 4FPh | Me | 5-1HIdz | C | | 404 (M⁺ + 1) |
| S-b-74 | SA | N-b-73 | | 4FPh | H | 5-1HIdz | C | | 390 (M⁺ + 1) |
| S-b-75 | SB | Int.s-21 | BRA10 | 4FPh | Me | 3-Qu | C | | 415 (M⁺ + 1) |
| S-b-76 | SA | N-b-75 | | 4FPh | H | 3-Qu | C | | 401 (M⁺ + 1) |
| S-b-77 | SB | Int.s-24 | BRA1 | cPen | Me | 2-Nap | C | | 389 (M⁺ + 1) |
| S-b-78 | SA | N-b-77 | | cPen | H | 2-Nap | C | | 375 (M⁺ + 1) |
| S-b-79 | SB | Int.s-24 | BRA2 | cPen | Me | 5-Ind | C | | 378 (M⁺ + 1) |
| S-b-80 | SA | N-b-79 | | cPen | H | 5-Ind | C | | 364 (M⁺ + 1) |
| S-b-81 | SB | Int.s-24 | BRA6 | cPen | Me | 1Me-5-1HIdz | C | | 407 (M⁺ + 1) |
| S-b-82 | SA | N-b-81 | | cPen | H | 1Me-5-1HIdz | C | | 393 (M⁺ + 1) |
| S-b-83 | SB | Int.s-27 | BRA3 | cHex | Et | 1Me-5-Ind | C | | 406 (M⁺ + 1) |
| S-b-84 | SA | N-b-83 | | cHex | H | 1Me-5-Ind | C | | 392 (M⁺ + 1) |
| S-b-85 | SB | Int.s-27 | BRA5 | cHex | Et | 5-1HIdz | C | | 393 (M⁺ + 1) |
| S-b-86 | SA | N-b-85 | | cHex | H | 5-1HIdz | C | | 379 (M⁺ + 1) |
| S-b-87 | SB | Int.s-27 | BRA12 | cHex | Et | 6-Qu | C | | 363 (M⁺ + 1) |
| S-b-88 | SA | N-b-87 | | cHex | H | 6-Qu | C | | 349 (M⁺ + 1) |
| S-b-89 | SB | Int.s-30 | BRA1 | nPr | Et | 2-Nap | C | | 362 (M⁺ + 1) |
| S-b-90 | SA | N-b-89 | | nPr | H | 2-Nap | C | | 348 (M⁺ + 1) |
| S-b-91 | SB | Int.s-30 | BRA2 | nPr | Et | 5-Ind | C | | 351 (M⁺ + 1) |
| S-b-92 | SA | N-b-91 | | nPr | H | 5-Ind | C | | 337 (M⁺ + 1) |

TABLE S-B-3

| Exp. | Syn | SM1 | SM2 | Rx | Y | AR | LCMS method | RTime | Mass |
|---|---|---|---|---|---|---|---|---|---|
| S-b-93 | SB | Int.s-30 | BRA6 | nPr | Et | 1Me-5-1HIdz | C | | 366 (M⁺ + 1) |
| S-b-94 | SA | N-b-93 | | nPr | H | 1Me-5-1HIdz | C | | 352 (M⁺ + 1) |
| S-b-95 | SB | Int.s-33 | BRA1 | iPr | Et | 2-Nap | C | | 362 (M⁺ + 1) |
| S-b-96 | SA | N-b-95 | | iPr | H | 2-Nap | C | | 348 (M⁺ + 1) |
| S-b-97 | SB | Int.s-33 | BRA3 | iPr | Et | 1Me-5-Ind | C | | 365 (M⁺ + 1) |
| S-b-98 | SA | N-b-97 | | iPr | H | 1Me-5-Ind | C | | 351 (M⁺ + 1) |
| S-b-99 | SB | Int.s-33 | BRA5 | iPr | Et | 5-1HIdz | C | | 352 (M⁺ + 1) |
| S-b-100 | SA | N-b-99 | | iPr | H | 5-1HIdz | C | | 338 (M⁺ + 1) |
| S-b-101 | SB | Int.s-36 | BRA2 | nBu | Et | 5-Ind | C | | 366 (M⁺ + 1) |
| S-b-102 | SA | N-b-101 | | nBu | H | 5-Ind | C | | 352 (M⁺ + 1) |
| S-b-103 | SB | Int.s-36 | BRA5 | nBu | Et | 5-1HIdz | C | | 366 (M⁺ + 1) |
| S-b-104 | SA | N-b-103 | | nBu | H | 5-1HIdz | C | | 352 (M⁺ + 1) |
| S-b-105 | SB | Int.s-36 | BRA11 | nBu | Et | 6-Qu | C | | 378 (M⁺ + 1) |
| S-b-106 | SA | N-b-105 | | nBu | H | 6-Qu | C | | 364 (M⁺ + 1) |
| S-b-107 | SB | Int.s-39 | BRA1 | iBu | Me | 2-Nap | C | | 377 (M⁺ + 1) |
| S-b-108 | SA | N-b-107 | | iBu | H | 2-Nap | C | | 363 (M⁺ + 1) |
| S-b-109 | SB | Int.s-39 | BRA3 | iBu | Me | 1Me-5-Ind | C | | 380 (M⁺ + 1) |
| S-b-110 | SA | N-b-109 | | iBu | H | 1Me-5-Ind | C | | 366 (M⁺ + 1) |
| S-b-111 | SB | Int.s-39 | BRA5 | iBu | Me | 5-1HIdz | C | | 366 (M⁺ + 1) |
| S-b-112 | SA | N-b-111 | | iBu | H | 5-1HIdz | C | | 352 (M⁺ + 1) |
| S-b-113 | SB | Int.s-39 | BRA6 | iBu | Me | 1Me-5-1HIdz | C | | 381 (M⁺ + 1) |
| S-b-114 | SA | N-b-113 | | iBu | H | 1Me-5-1HIdz | C | | 367 (M⁺ + 1) |
| S-b-115 | SB | Int.s-42 | BRA1 | PhEt | Me | 2-Nap | C | | 425 (M⁺ + 1) |
| S-b-116 | SA | N-b-115 | | PhEt | H | 2-Nap | C | | 411 (M⁺ + 1) |
| S-b-117 | SB | Int.s-42 | BRA2 | PhEt | Me | 5-Ind | C | | 414 (M⁺ + 1) |
| S-b-118 | SA | N-b-117 | | PhEt | H | 5-Ind | C | | 400 (M⁺ + 1) |
| S-b-119 | SB | Int.s-42 | BRA3 | PhEt | Me | 1Me-5-Ind | C | | 428 (M⁺ + 1) |
| S-b-120 | SA | N-b-119 | | PhEt | H | 1Me-5-Ind | C | | 414 (M⁺ + 1) |
| S-b-121 | SB | Int.s-45 | BRA1 | 4MeOBn | Et | 2-Nap | C | | 441 (M⁺ + 1) |
| S-b-122 | SA | N-b-121 | | 4MeOBn | H | 2-Nap | C | | 427 (M⁺ + 1) |
| S-b-123 | SB | Int.s-45 | BRA5 | 4MeOBn | Et | 5-1HIdz | C | | 431 (M⁺ + 1) |

TABLE S-B-3-continued

| Exp. | Syn | SM1 | SM2 | Rx | Y | AR | LCMS method | RTime | Mass |
|---|---|---|---|---|---|---|---|---|---|
| S-b-124 | SA | N-b-123 | | 4MeOBn | H | 5-1HIdz | C | | 417 (M⁺ + 1) |
| S-b-125 | SB | Int.s-45 | BRA6 | 4MeOBn | Et | 1Me-5-1HIdz | C | | 431 (M⁺ + 1) |
| S-b-126 | SA | N-b-125 | | 4MeOBn | H | 1Me-5-1HIdz | C | | 417 (M⁺ + 1) |
| S-b-127 | SB | Int.s-48 | BRA1 | 4FBn | Et | 2-Nap | C | | 429 (M⁺ + 1) |
| S-b-128 | SA | N-b-127 | | 4FBn | H | 2-Nap | C | | 415 (M⁺ + 1) |
| S-b-129 | SB | Int.s-48 | BRA2 | 4FBn | Et | 5-Ind | C | | 418 (M⁺ + 1) |
| S-b-130 | SA | N-b-129 | | 4FBn | H | 5-Ind | C | | 404 (M⁺ + 1) |
| S-b-131 | SB | Int.s-48 | BRA6 | 4FBn | Et | 1Me-5-1HIdz | C | | 418 (M⁺ + 1) |
| S-b-132 | SA | N-b-131 | | 4FBn | H | 1Me-5-1HIdz | C | | 404 (M⁺ + 1) |
| S-b-133 | SB | Int.s-51 | BRA3 | 2MeBn | Et | 1Me-5-Ind | C | | 428 (M⁺ + 1) |
| S-b-134 | SA | N-b-133 | | 2MeBn | H | 1Me-5-Ind | C | | 414 (M⁺ + 1) |
| S-b-135 | SB | Int.s-51 | BRA5 | 2MeBn | Et | 5-1HIdz | C | | 415 (M⁺ + 1) |
| S-b-136 | SA | N-b-135 | | 2MeBn | H | 5-1HIdz | C | | 401 (M⁺ + 1) |
| S-b-137 | SB | Int.s-51 | BRA10 | 2MeBn | Et | 3-Qu | C | | 426 (M⁺ + 1) |
| S-b-138 | SA | N-b-137 | | 2MeBn | H | 3-Qu | C | | 412 (M⁺ + 1) |

TABLE S-C-1

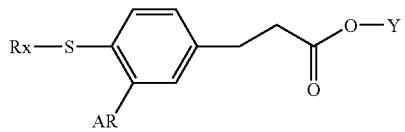

| Exp. | Syn | SM1 | SM2 | Rx | Y | AR | LCMS method | RTime | Mass |
|---|---|---|---|---|---|---|---|---|---|
| S-c-1 | SB | Int.s-6 | BRA1 | 4MeOPh | Me | 2-Nap | C | | 429 (M⁺ + 1) |
| S-c-2 | SA | S-c-1 | | 4MeOPh | H | 2-Nap | C | | 415 (M⁺ + 1) |
| S-c-3 | SB | Int.s-6 | BRA2 | 4MeOPh | Me | 5-Ind | C | | 418 (M⁺ + 1) |
| S-c-4 | SA | S-c-3 | | 4MeOPh | H | 5-Ind | C | | 404 (M⁺ + 1) |
| S-c-5 | SB | Int.s-6 | BRA3 | 4MeOPh | Me | 1Me-5-Ind | C | | 432 (M⁺ + 1) |
| S-c-6 | SA | S-c-5 | | 4MeOPh | H | 1Me-5-Ind | C | | 418 (M⁺ + 1) |
| S-c-7 | SB | Int.s-6 | BRA4 | 4MeOPh | Me | 1Et-5-Ind | C | | 446 (M⁺ + 1) |
| S-c-8 | SA | S-c-7 | | 4MeOPh | H | 1Et-5-Ind | C | | 432 (M⁺ + 1) |
| S-c-9 | SB | Int.s-6 | BRA5 | 4MeOPh | Me | 5-1HIdz | C | | 419 (M⁺ + 1) |
| S-c-10 | SA | S-c-9 | | 4MeOPh | H | 5-1HIdz | C | | 405 (M⁺ + 1) |
| S-c-11 | SB | Int.s-6 | BRA6 | 4MeOPh | Me | 1Me-5-1HIdz | C | | 433 (M⁺ + 1) |
| S-c-12 | SA | S-c-11 | | 4MeOPh | H | 1Me-5-1HIdz | C | | 419 (M⁺ + 1) |
| S-c-13 | SB | Int.s-6 | BRA7 | 4MeOPh | Me | 1Et-5-1HIdz | C | | 447 (M⁺ + 1) |
| S-c-14 | SA | S-c-13 | | 4MeOPh | H | 1Et-5-1HIdz | C | | 433 (M⁺ + 1) |
| S-c-15 | SB | Int.s-6 | BRA8 | 4MeOPh | Me | 2Me-5-2HIdz | C | | 433 (M⁺ + 1) |
| S-c-16 | SA | S-c-15 | | 4MeOPh | H | 2Me-5-2HIdz | C | | 419 (M⁺ + 1) |
| S-c-17 | SB | Int.s-6 | BRA9 | 4MeOPh | Me | 5-Bzt | C | | 436 (M⁺ + 1) |
| S-c-18 | SA | S-c-17 | | 4MeOPh | H | 5-Bzt | C | | 422 (M⁺ + 1) |
| S-c-19 | SB | Int.s-6 | BRA10 | 4MeOPh | Me | 3-Qu | C | | 430 (M⁺ + 1) |
| S-c-20 | SA | S-c-19 | | 4MeOPh | H | 3-Qu | C | | 416 (M⁺ + 1) |
| S-c-21 | SB | Int.s-6 | BRA11 | 4MeOPh | Me | 6-Qu | C | | 430 (M⁺ + 1) |
| S-c-22 | SA | S-c-21 | | 4MeOPh | H | 6-Qu | C | | 416 (M⁺ + 1) |
| S-c-23 | SB | Int.s-6 | BRA12 | 4MeOPh | Me | 6-IQ | C | | 430 (M⁺ + 1) |
| S-c-24 | SA | S-c-23 | | 4MeOPh | H | 6-IQ | C | | 416 (M⁺ + 1) |
| S-c-25 | SB | Int.s-8 | BRA1 | 2MeOPh | Me | 2-Nap | C | | 429 (M⁺ + 1) |
| S-c-26 | SA | S-c-25 | | 2MeOPh | H | 2-Nap | C | | 415 (M⁺ + 1) |
| S-c-27 | SB | Int.s-8 | BRA3 | 2MeOPh | Me | 1Me-5-Ind | C | | 431 (M⁺ + 1) |
| S-c-28 | SA | S-c-27 | | 2MeOPh | H | 1Me-5-Ind | C | | 418 (M⁺ + 1) |
| S-c-29 | SB | Int.s-8 | BRA5 | 2MeOPh | Me | 5-1HIdz | C | | 419 (M⁺ + 1) |
| S-c-30 | SA | S-c-29 | | 2MeOPh | H | 5-1HIdz | C | | 405 (M⁺ + 1) |
| S-c-31 | SB | Int.s-8 | BRA10 | 2MeOPh | Me | 3-Qu | C | | 430 (M⁺ + 1) |
| S-c-32 | SA | S-c-31 | | 2MeOPh | H | 3-Qu | C | | 416 (M⁺ + 1) |
| S-c-33 | SB | Int.s-10 | BRA1 | 3MeOPh | Me | 2-Nap | C | | 429 (M⁺ + 1) |
| S-c-34 | SA | S-c-33 | | 3MeOPh | H | 2-Nap | C | | 415 (M⁺ + 1) |
| S-c-35 | SB | Int.s-10 | BRA2 | 3MeOPh | Me | 5-Ind | C | | 418 (M⁺ + 1) |
| S-c-36 | SA | S-c-35 | | 3MeOPh | H | 5-Ind | C | | 403 (M⁺ + 1) |
| S-c-37 | SB | Int.s-10 | BRA6 | 3MeOPh | Me | 1Me-5-1HIdz | C | | 433 (M⁺ + 1) |
| S-c-38 | SA | S-c-37 | | 3MeOPh | H | 1Me-5-1HIdz | C | | 419 (M⁺ + 1) |
| S-c-39 | SB | Int.s-10 | BRA11 | 3MeOPh | Me | 6-Qu | C | | 430 (M⁺ + 1) |
| S-c-40 | SA | S-c-39 | | 3MeOPh | H | 6-Qu | C | | 416 (M⁺ + 1) |
| S-c-41 | SB | Int.s-12 | BRA3 | 2MePh | Me | 1-Me-5-Ind | C | | 402 (M⁺ + 1) |
| S-c-42 | SA | S-c-41 | | 2MePh | H | 1-Me-5-Ind | C | | 388 (M⁺ + 1) |
| S-c-43 | SB | Int.s-12 | BRA5 | 2MePh | Me | 5-1HIdz | C | | 416 (M⁺ + 1) |

TABLE S-C-1-continued

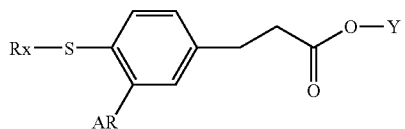

| Exp. | Syn | SM1 | SM2 | Rx | Y | AR | LCMS method | RTime | Mass |
|---|---|---|---|---|---|---|---|---|---|
| S-c-44 | SA | S-c-43 | | 2MePh | H | 5-1HIdz | C | | 402 (M$^+$ + 1) |
| S-c-45 | SB | Int.s-12 | BRA6 | 2MePh | Me | 1-Me-5-1HIdz | C | | 417 (M$^+$ + 1) |
| S-c-46 | SA | S-c-45 | | 2MePh | H | 1-Me-5-1HIdz | C | | 403 (M$^+$ + 1) |

TABLE S-C-2

| Exp. | Syn | SM1 | SM2 | Rx | Y | AR | LCMS method | RTime | Mass |
|---|---|---|---|---|---|---|---|---|---|
| S-c-47 | SB | Int.s-14 | BRA3 | 3MePh | Me | 1-Me-5-Ind | C | | 416 (M$^+$ + 1) |
| S-c-48 | SA | N-c-47 | | 3MePh | H | 1-Me-5-Ind | C | | 402 (M$^+$ + 1) |
| S-c-49 | SB | Int.s-14 | BRA6 | 3MePh | Me | 1-Me-5-1HIdz | C | | 417 (M$^+$ + 1) |
| S-c-50 | SA | N-c-49 | | 3MePh | H | 1-Me-5-1HIdz | C | | 403 (M$^+$ + 1) |
| S-c-51 | SB | Int.s-14 | BRA9 | 3MePh | Me | 5-Bzt | C | | 420 (M$^+$ + 1) |
| S-c-52 | SA | N-c-51 | | 3MePh | H | 5-Bzt | C | | 406 (M$^+$ + 1) |
| S-c-53 | SB | Int.s-16 | BRA1 | 4MePh | Me | 2-Nap | C | | 413 (M$^+$ + 1) |
| S-c-54 | SA | N-c-53 | | 4MePh | H | 2-Nap | C | | 399 (M$^+$ + 1) |
| S-c-55 | SB | Int.s-16 | BRA2 | 4MePh | Me | 5-Ind | C | | 402 (M$^+$ + 1) |
| S-c-56 | SA | N-c-55 | | 4MePh | H | 5-Ind | C | | 388 (M$^+$ + 1) |
| S-c-57 | SB | Int.s-16 | BRA3 | 4MePh | Me | 1Me-5-Ind | C | | 420 (M$^+$ + 1) |
| S-c-58 | SA | N-c-57 | | 4MePh | H | 1Me-5-Ind | C | | 406 (M$^+$ + 1) |
| S-c-59 | SB | Int.s-18 | BRA5 | 2FPh | Me | 5-1HIdz | C | | 406 (M$^+$ + 1) |
| S-c-60 | SA | N-c-59 | | 2FPh | H | 5-1HIdz | C | | 392 (M$^+$ + 1) |
| S-c-61 | SB | Int.s-18 | BRA6 | 2FPh | Me | 1Me-5-1HInd | C | | 420 (M$^+$ + 1) |
| S-c-62 | SA | N-c-61 | | 2FPh | H | 1Me-5-1HInd | C | | 406 (M$^+$ + 1) |
| S-c-63 | SB | Int.s-18 | BRA11 | 2FPh | Me | 6-Qu | C | | 418 (M$^+$ + 1) |
| S-c-64 | SA | N-c-63 | | 2FPh | H | 6-Qu | C | | 404 (M$^+$ + 1) |
| S-c-65 | SB | Int.s-20 | BRA1 | 3FPh | Me | 2-Nap | C | | 417 (M$^+$ + 1) |
| S-c-66 | SA | N-c-65 | | 3FPh | H | 2-Nap | C | | 403 (M$^+$ + 1) |
| S-c-67 | SB | Int.s-20 | BRA2 | 3FPh | Me | 5-Ind | C | | 405 (M$^+$ + 1) |
| S-c-68 | SA | N-c-67 | | 3FPh | H | 5-Ind | C | | 391 (M$^+$ + 1) |
| S-c-69 | SB | Int.s-20 | BRA6 | 3FPh | Me | 1Me-5-1HIdz | C | | 421 (M$^+$ + 1) |
| S-c-70 | SA | N-c-69 | | 3FPh | H | 1Me-5-1HIdz | C | | 407 (M$^+$ + 1) |
| S-c-71 | SB | Int.s-22 | BRA3 | 4FPh | Me | 1Me-5-Ind | C | | 420 (M$^+$ + 1) |
| S-c-72 | SA | N-c-71 | | 4FPh | H | 1Me-5-Ind | C | | 406 (M$^+$ + 1) |
| S-c-73 | SB | Int.s-22 | BRA5 | 4FPh | Me | 5-1HIdz | C | | 406 (M$^+$ + 1) |
| S-c-74 | SA | N-c-73 | | 4FPh | H | 5-1HIdz | C | | 392 (M$^+$ + 1) |
| S-c-75 | SB | Int.s-22 | BRA10 | 4FPh | Me | 3-Qu | C | | 418 (M$^+$ + 1) |
| S-c-76 | SA | N-c-75 | | 4FPh | H | 3-Qu | C | | 404 (M$^+$ + 1) |
| S-c-77 | SB | Int.s-25 | BRA1 | cPen | Et | 2-Nap | C | | 391 (M$^+$ + 1) |
| S-c-78 | SA | N-c-77 | | cPen | H | 2-Nap | C | | 377 (M$^+$ + 1) |
| S-c-79 | SB | Int.s-25 | BRA2 | cPen | Et | 5-Ind | C | | 380 (M$^+$ + 1) |
| S-c-80 | SA | N-c-79 | | cPen | H | 5-Ind | C | | 366 (M$^+$ + 1) |
| S-c-81 | SB | Int.s-25 | BRA6 | cPen | Et | 1Me-5-1HIdz | C | | 409 (M$^+$ + 1) |
| S-c-82 | SA | N-c-81 | | cPen | H | 1Me-5-1HIdz | C | | 395 (M$^+$ + 1) |
| S-c-83 | SB | Int.s-28 | BRA3 | cHex | Et | 1Me-5-Ind | C | | 408 (M$^+$ + 1) |
| S-c-84 | SA | N-c-83 | | cHex | H | 1Me-5-Ind | C | | 394 (M$^+$ + 1) |
| S-c-85 | SB | Int.s-28 | BRA5 | cHex | Et | 5-1HIdz | C | | 395 (M$^+$ + 1) |
| S-c-86 | SA | N-c-85 | | cHex | H | 5-1HIdz | C | | 381 (M$^+$ + 1) |
| S-c-87 | SB | Int.s-28 | BRA12 | cHex | Et | 6-Qu | C | | 365 (M$^+$ + 1) |
| S-c-88 | SA | N-c-87 | | cHex | H | 6-Qu | C | | 351 (M$^+$ + 1) |
| S-c-89 | SB | Int.s-31 | BRA1 | nPr | Et | 2-Nap | C | | 365 (M$^+$ + 1) |
| S-c-90 | SA | N-c-89 | | nPr | H | 2-Nap | C | | 351 (M$^+$ + 1) |
| S-c-91 | SB | Int.s-31 | BRA2 | nPr | Et | 5-Ind | C | | 353 (M$^+$ + 1) |
| S-c-92 | SA | N-c-91 | | nPr | H | 5-Ind | C | | 339 (M$^+$ + 1) |

TABLE S-C-3

| Exp. | Syn | SM1 | SM2 | Rx | Y | AR | LCMS method | RTime | Mass |
|---|---|---|---|---|---|---|---|---|---|
| S-c-93 | SB | Int.s-31 | BRA6 | nPr | Et | 1Me-5-1HIdz | C | | 368 (M⁺ + 1) |
| S-c-94 | SA | N-c-93 | | nPr | H | 1Me-5-1HIdz | C | | 354 (M⁺ + 1) |
| S-c-95 | SB | Int.s-34 | BRA3 | iPr | Et | 1Me-5-Ind | C | | 368 (M⁺ + 1) |
| S-c-96 | SA | N-c-95 | | iPr | H | 1Me-5-Ind | C | | 354 (M⁺ + 1) |
| S-c-97 | SB | Int.s-34 | BRA5 | iPr | Et | 5-1HIdz | C | | 354 (M⁺ + 1) |
| S-c-98 | SA | N-c-97 | | iPr | H | 5-1HIdz | C | | 340 (M⁺ + 1) |
| S-c-99 | SB | Int.s-34 | BRA12 | iPr | Et | 6-IQ | C | | 380 (M⁺ + 1) |
| S-c-100 | SA | N-c-99 | | iPr | H | 6-IQ | C | | 366 (M⁺ + 1) |
| S-c-101 | SB | Int.s-37 | BRA1 | nBu | Et | 2-Nap | C | | 379 (M⁺ + 1) |
| S-c-102 | SA | N-c-101 | | nBu | H | 2-Nap | C | | 365 (M⁺ + 1) |
| S-c-103 | SB | Int.s-37 | BRA2 | nBu | Et | 5-Ind | C | | 368 (M⁺ + 1) |
| S-c-104 | SA | N-c-103 | | nBu | H | 5-Ind | C | | 354 (M⁺ + 1) |
| S-c-105 | SB | Int.s-37 | BRA6 | nBu | Et | 1Me-5-1HIdz | C | | 383 (M⁺ + 1) |
| S-c-106 | SA | N-c-105 | | nBu | H | 1Me-5-1HIdz | C | | 369 (M⁺ + 1) |
| S-c-107 | SB | Int.s-40 | BRA1 | iBu | Et | 2-Nap | C | | 379 (M⁺ + 1) |
| S-c-108 | SA | N-c-107 | | iBu | H | 2-Nap | C | | 365 (M⁺ + 1) |
| S-c-109 | SB | Int.s-40 | BRA3 | iBu | Et | 1Me-5-Ind | C | | 382 (M⁺ + 1) |
| S-c-110 | SA | N-c-109 | | iBu | H | 1Me-5-Ind | C | | 368 (M⁺ + 1) |
| S-c-111 | SB | Int.s-40 | BRA5 | iBu | Et | 5-1HIdz | C | | 369 (M⁺ + 1) |
| S-c-112 | SA | N-c-111 | | iBu | H | 5-1HIdz | C | | 355 (M⁺ + 1) |
| S-c-113 | SB | Int.s-40 | BRA6 | iBu | Et | 1Me-5-1HIdz | C | | 383 (M⁺ + 1) |
| S-c-114 | SA | N-c-113 | | iBu | H | 1Me-5-1HIdz | C | | 369 (M⁺ + 1) |
| S-c-115 | SB | Int.s-43 | BRA1 | PhEt | Et | 2-Nap | C | | 427 (M⁺ + 1) |
| S-c-116 | SA | N-c-115 | | PhEt | H | 2-Nap | C | | 413 (M⁺ + 1) |
| S-c-117 | SB | Int.s-43 | BRA2 | PhEt | Et | 5-Ind | C | | 416 (M⁺ + 1) |
| S-c-118 | SA | N-c-117 | | PhEt | H | 5-Ind | C | | 402 (M⁺ + 1) |
| S-c-119 | SB | Int.s-43 | BRA6 | PhEt | Et | 1Me-5-1HIdz | C | | 431 (M⁺ + 1) |
| S-c-120 | SA | N-c-119 | | PhEt | H | 1Me-5-1HIdz | C | | 417 (M⁺ + 1) |
| S-c-121 | SB | Int.s-46 | BRA1 | 4MeOBn | Et | 2-Nap | C | | 443 (M⁺ + 1) |
| S-c-122 | SA | N-c-121 | | 4MeOBn | H | 2-Nap | C | | 429 (M⁺ + 1) |
| S-c-123 | SB | Int.s-46 | BRA3 | 4MeOBn | Et | 1Me-5-Ind | C | | 446 (M⁺ + 1) |
| S-c-124 | SA | N-c-123 | | 4MeOBn | H | 1Me-5-Ind | C | | 432 (M⁺ + 1) |
| S-c-125 | SB | Int.s-46 | BRA5 | 4MeOBn | Et | 5-1HIdz | C | | 419 (M⁺ + 1) |
| S-c-126 | SA | N-c-125 | | 4MeOBn | H | 5-1HIdz | C | | 405 (M⁺ + 1) |
| S-c-127 | SB | Int.s-49 | BRA1 | 4FBn | Et | 2-Nap | C | | 431 (M⁺ + 1) |
| S-c-128 | SA | N-c-127 | | 4FBn | H | 2-Nap | C | | 417 (M⁺ + 1) |
| S-c-129 | SB | Int.s-49 | BRA2 | 4FBn | Et | 5-Ind | C | | 420 (M⁺ + 1) |
| S-c-130 | SA | N-c-129 | | 4FBn | H | 5-Ind | C | | 406 (M⁺ + 1) |
| S-c-131 | SB | Int.s-49 | BRA5 | 4FBn | Et | 5-1HIdz | C | | 406 (M⁺ + 1) |
| S-c-132 | SA | N-c-131 | | 4FBn | H | 5-1HIdz | C | | 392 (M⁺ + 1) |
| S-c-133 | SB | Int.s-52 | BRA3 | 2MeBn | Et | 1Me-5-Ind | C | | 430 (M⁺ + 1) |
| S-c-134 | SA | N-c-133 | | 2MeBn | H | 1Me-5-Ind | C | | 416 (M⁺ + 1) |
| S-c-135 | SB | Int.s-52 | BRA6 | 2MeBn | Et | 1Me-5-1HIdz | C | | 431 (M⁺ + 1) |
| S-c-136 | SA | N-c-135 | | 2MeBn | H | 1Me-5-1HIdz | C | | 417 (M⁺ + 1) |
| S-c-137 | SB | Int.s-52 | BRA11 | 2MeBn | Et | 6-Qu | C | | 428 (M⁺ + 1) |
| S-c-138 | SA | N-c-137 | | 2MeBn | H | 6-Qu | C | | 414 (M⁺ + 1) |

Example S-d-1
Synthesis of ethyl 3-{4-[(4-methoxyphenyl)methyl-sulfinyl]-3-(naphthalen-2-yl)phenyl}propionate (Compound No. S-d-1) (Synthesis method SG)

A solution of the compound of Example S-c-121 (130.9 mg) in dichloromethane (4 ml) was added with 3-chloroperoxybenzoic acid (60.0 mg, TCI), and stirred at room temperature for 1.5 hours. The reaction mixture was added with water (10 ml), extracted with dichloromethane (20 ml), and then washed with saturated brine. The organic layer was dried, and then the solvent was evaporated under reduced pressure. The residue was purified by column chromatography (Quad, chloroform:methanol=30:1) to obtain the title compound (Compound No. S-d-1, 108.7 mg).

Example S-d-7
Synthesis of ethyl 3-{4-[(4-methoxyphenyl)methyl-sulfonyl]-3-(naphthalen-2-yl)phenyl}propionate (Compound No. S-d-7) (Synthesis method SG)

A solution of the compound of Example S-c-121 (53.1 mg) in dichloromethane (3 ml) was added with 3-chloroperoxy benzoic acid (74.5 mg, TCI), and stirred at room temperature for 5 hours. The reaction mixture was added with water (10 ml), extracted with dichloromethane (20 ml), and then washed with saturated brine. The organic layer was dried, and then the solvent was evaporated under reduced pressure. The residue was purified by column chromatography (Quad, hexane:ethyl acetate=4:1) to obtain the title compound (Compound No. S-d-7, 48.1 mg).

Examples S-d-1 to S-d-36

Typical examples of the compounds of the present invention that can be obtained by reacting and treating corresponding starting compounds using any of the methods described in the present specification including the examples described above are shown in Table-S-D-1. In the tables, the compound numbers are mentioned in the columns indicated as "Exp.". In the tables, used methods among the aforementioned synthesis methods are shown in the columns of "Syn" with symbols, and the starting compounds 1 are mentioned in the columns of "SM1".

TABLE S-D-1

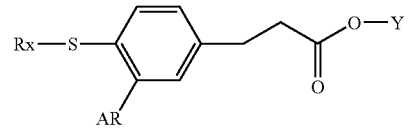

| Exp. | Syn | SM1 | RS(O)n | Y | AR | LCMS method | RTime | Mass |
|---|---|---|---|---|---|---|---|---|
| S-d-1 | SG | S-c-121 | 4MeOBnSO | Et | 2-Nap | C | | 473 ($M^+ + 1$) |
| S-d-2 | SA | S-d-1 | 4MeOBnSO | H | 2-Nap | C | | 445 ($M^+ + 1$) |
| S-d-3 | SG | S-c-123 | 4MeOBnSO | Et | 1Me-5-Ind | C | | 476 ($M^+ + 1$) |
| S-d-4 | SA | S-d-3 | 4MeOBnSO | H | 1Me-5-Ind | C | | 448 ($M^+ + 1$) |
| S-d-5 | SG | S-c-125 | 4MeOBnSO | Et | 5-1HIdz | C | | 463 ($M^+ + 1$) |
| S-d-6 | SA | S-d-5 | 4MeOBnSO | H | 5-1HIdz | C | | 435 ($M^+ + 1$) |
| S-d-7 | SG | S-c-121 | 4MeOnSO2 | Et | 2-Nap | C | | 489 ($M^+ + 1$) |
| S-d-8 | SA | S-d-7 | 4MeOBnSO2 | H | 2-Nap | C | | 461 ($M^+ + 1$) |
| S-d-9 | SG | S-c-123 | 4MeOBNSO2 | Et | 1Me-5-Ind | C | | 492 ($M^+ + 1$) |
| S-d-10 | SA | S-d-9 | 4MeOBnSO2 | H | 1Me-5-Ind | C | | 464 ($M^+ + 1$) |
| S-d-11 | SG | S-c-125 | 4MeOBnSO2 | Et | 5-1HIdz | C | | 479 ($M^+ + 1$) |
| S-d-12 | SA | S-d-11 | 4MeOBnSO2 | H | 5-1HIdz | C | | 451 ($M^+ + 1$) |
| S-d-13 | SG | S-c-77 | cPenSO | Et | 2-Nap | C | | 421 ($M^+ + 1$) |
| S-d-14 | SA | S-d-13 | cPenSO | H | 2-Nap | C | | 393 ($M^+ + 1$) |
| S-d-15 | SG | S-c-79 | cPenSO | Et | 5-Ind | C | | 410 ($M^+ + 1$) |
| S-d-16 | SA | S-d-15 | cPenSO | H | 5-Ind | C | | 381 ($M^+ + 1$) |
| S-d-17 | SG | S-c-81 | cPenSO | Et | 1Me-5-1HIdz | C | | 425 ($M^+ + 1$) |
| S-d-18 | SA | S-d-17 | cPenSO | H | 1Me-5-1HIdz | C | | 397 ($M^+ + 1$) |
| S-d-19 | SG | S-c-77 | cPenSO2 | Et | 2-Nap | C | | 437 ($M^+ + 1$) |
| S-d-20 | SA | S-d-19 | cPenSO2 | H | 2-Nap | C | | 409 ($M^+ + 1$) |
| S-d-21 | SG | S-c-79 | cPenSO2 | Et | 5-Ind | C | | 426 ($M^+ + 1$) |
| S-d-22 | SA | S-d-21 | cPenSO2 | H | 5-Ind | C | | 397 ($M^+ + 1$) |
| S-d-23 | SG | S-c-81 | cPenSO2 | Et | 1Me-5-1HIdz | C | | 441 ($M^+ + 1$) |
| S-d-24 | SA | S-d-23 | cPenSO2 | H | 1Me-5-1HIdz | C | | 413 ($M^+ + 1$) |
| S-d-25 | SG | S-c-101 | nBuSO | Et | 2-Nap | C | | 409 ($M^+ + 1$) |
| S-d-26 | SA | S-d-25 | nBuSO | H | 2-Nap | C | | 377 ($M^+ + 1$) |
| S-d-27 | SG | S-c-103 | nBuSO | Et | 5-Ind | C | | 398 ($M^+ + 1$) |
| S-d-28 | SA | S-d-27 | nBuSO | H | 5-Ind | C | | 365 ($M^+ + 1$) |
| S-d-29 | SG | S-c-105 | nBuSO | Et | 1Me-5-1HIdz | C | | 413 ($M^+ + 1$) |
| S-d-30 | SA | S-d-29 | nBuSO | H | 1Me-5-1HIdz | C | | 381 ($M^+ + 1$) |
| S-d-31 | SG | S-c-101 | nBuSO2 | Et | 2-Nap | C | | 425 ($M^+ + 1$) |
| S-d-32 | SA | S-d-31 | nBuSO2 | H | 2-Nap | C | | 397 ($M^+ + 1$) |
| S-d-33 | SG | S-c-103 | nBuSO2 | Et | 5-Ind | C | | 410 ($M^+ + 1$) |
| S-d-34 | SA | S-d-33 | nBuSO2 | H | 5-Ind | C | | 385 ($M^+ + 1$) |
| S-d-35 | SG | S-c-105 | nBuSO2 | Et | 1Me-5-1HIdz | C | | 425 ($M^+ + 1$) |
| S-d-36 | SA | S-d-35 | nBuSO2 | H | 1Me-5-1HIdz | C | | 401 ($M^+ + 1$) |

Reference Examples

Intermediates An-1 to An-5

Synthesis of ethyl 3-[2-hydroxy-3-(naphthalen-2-yl)pyridin-5-yl]propionate (Intermediate Ah-1)

A solution of the compound of Example P-42 (452 mg) in a mixture of ethyl acetate (5 ml) and methanol (2.5 ml) was added with 10% palladium/carbon (50 mg), and stirred at room temperature for 2 hours under hydrogen atmosphere. The reaction mixture was filtered, and the solvent of the filtrate was evaporated under reduced pressure to obtain the title compound (Intermediate Ah-1, 321 mg). Mass (FAB): 322 ($M^+$+1).

Synthesis of ethyl 3-[3-(naphthalen-2-yl)-2-(trifluoromethanesulfonyl)pyridin-5-yl]propionate (Intermediate An-1)

According to the procedure described in the synthesis method of Intermediate Aa-1, Intermediate Ah-1 (310 mg) and trifluoromethanesulfonic anhydride (170 µl) were reacted and treated to obtain the title compound (Intermediate An-1, 355 mg). Mass (FAB): 454 ($M^+$+1).

Typical examples of the reaction intermediates that can be obtained by reacting and treating corresponding starting compounds according to the method described above are shown below.

Intermediate An-2: ethyl 3-[3-(1H-indol-5-yl)-2-(trifluoromethanesulfonyl)pyridin-5-yl]propionate Intermediate An-3: ethyl 3-[3-(1-methyl-1H-indol-5-yl)-2-(trifluoromethanesulfonyl)pyridin-5-yl]propionate Intermediate An-4: ethyl 3-[3-(1H-indazol-5-yl)-2-(trifluoromethanesulfonyl)pyridin-5-yl]propionate Intermediate An-5: ethyl 3-[3-(1-methyl-1H-indazol-5-yl)-2-(trifluoromethanesulfonyl)pyridin-5-yl]propionate

Examples Cn-1 to Cn-45

Typical examples of the compounds of the present invention that can be obtained by reacting and treating corresponding starting compounds according to the methods described in Examples Ca-1 and Ca-2 are shown in Table-Cn-1.

In the table, the substances mentioned in the column of "SM1" correspond to reaction intermediates, and the substances mentioned in the column of "SM2" correspond to the boronic acid reagent used in Example Ca-1. The boronic acid reagents indicated with the symbols of "BRA (number)" in the columns of "SM2" are those mentioned in Table-Ba-1 and Table-Ba-2.

TABLE Cn-1

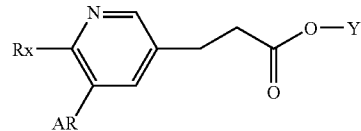

| Exp. | Rx | Y | AR | SM1 | SM2 | LCMS method | RTime | Mass |
|---|---|---|---|---|---|---|---|---|
| Cn-1 | Ph | Et | 2-Nap | An-1 | BRA14 | D | | 382 ($M^+$ + 1) |
| Cn-2 | Ph | H | 2-Nap | Cn-1 | — | C | | 354 ($M^+$ + 1) |
| Cn-3 | Ph | Et | 5-Ind | An-2 | BRA14 | C | | 371 ($M^+$ + 1) |
| Cn-4 | Ph | H | 5-Ind | Cn-3 | — | C | | 343 ($M^+$ + 1) |
| Cn-5 | Ph | Et | 1Me-5-Ind | An-3 | BRA14 | C | | 385 ($M^+$ + 1) |
| Cn-6 | Ph | H | 1Me-5-Ind | Cn-5 | — | C | | 357 ($M^+$ + 1) |
| Cn-7 | Ph | Et | 5-1HIdz | An-4 | BRA14 | C | | 372 ($M^+$ + 1) |
| Cn-8 | Ph | H | 5-1HIdz | Cn-7 | — | C | | 344 ($M^+$ + 1) |
| Cn-9 | Ph | Et | 1Me-5-1HIdz | An-5 | BRA14 | C | | 386 ($M^+$ + 1) |
| Cn-10 | Ph | H | 1Me-5-1HIdz | Cn-9 | — | C | | 358 ($M^+$ + 1) |
| Cn-11 | 4MeOPh | H | 2-Nap | An-1 | BRA19 | C | | 384 ($M^+$ + 1) |
| Cn-12 | 4MeOPh | H | 5-Ind | An-2 | BRA19 | C | | 373 ($M^+$ + 1) |
| Cn-13 | 4MeOPh | H | 5-1HIdz | An-4 | BRA19 | C | | 374 ($M^+$ + 1) |
| Cn-14 | 4MeOPh | H | 1Me-5-1HIdz | An-5 | BRA19 | C | | 388 ($M^+$ + 1) |
| Cn-15 | 3MeOPh | H | 2-Nap | An-1 | BRA37 | C | | 384 ($M^+$ + 1) |
| Cn-16 | 2MeOPh | H | 2-Nap | An-1 | BRA38 | C | | 384 ($M^+$ + 1) |
| Cn-17 | 2MeOPh | H | 1Me-5-Ind | An-3 | BRA38 | C | | 387 ($M^+$ + 1) |
| Cn-18 | 2MeOPh | H | 1Me-5-1HIdz | An-5 | BRA38 | C | | 388 ($M^+$ + 1) |
| Cn-19 | 2MePh | H | 2-Nap | An-1 | BRA59 | C | | 368 ($M^+$ + 1) |
| Cn-20 | 2MePh | H | 1Me-5-Ind | An-3 | BRA59 | C | | 371 ($M^+$ + 1) |
| Cn-21 | 2MePh | H | 1Me-5-1HIdz | An-5 | BRA59 | C | | 372 ($M^+$ + 1) |
| Cn-22 | 3MePh | H | 2-Nap | An-1 | BRA60 | C | | 368 ($M^+$ + 1) |
| Cn-23 | 3MePh | H | 5-1HIdz | An-4 | BRA60 | C | | 358 ($M^+$ + 1) |
| Cn-24 | 4MePh | H | 2-Nap | An-1 | BRA29 | C | | 368 ($M^+$ + 1) |
| Cn-25 | 4MePh | H | 5-Ind | An-2 | BRA29 | C | | 357 ($M^+$ + 1) |
| Cn-26 | 4MePh | H | 1Me-5-Ind | An-3 | BRA29 | C | | 371 ($M^+$ + 1) |
| Cn-27 | 4MePh | H | 5-1HIdz | An-4 | BRA29 | C | | 358 ($M^+$ + 1) |
| Cn-28 | 4MePh | H | 1Me-5-1HIdz | An-5 | BRA29 | C | | 372 ($M^+$ + 1) |
| Cn-29 | 4CF$_3$Ph | H | 5-Ind | An-2 | BRA41 | C | | 411 ($M^+$ + 1) |
| Cn-30 | 4CF$_3$Ph | H | 5-1HIdz | An-4 | BRA41 | C | | 412 ($M^+$ + 1) |
| Cn-31 | 4CF$_3$Ph | H | 1Me-5-1HIdz | An-5 | BRA41 | C | | 426 ($M^+$ + 1) |
| Cn-32 | 4ClPh | H | 5-Ind | An-2 | BRA30 | C | | 377 ($M^+$ + 1) |
| Cn-33 | 4ClPh | H | 1Me-5-Ind | An-3 | BRA30 | C | | 391 ($M^+$ + 1) |
| Cn-34 | 4ClPh | H | 1Me-5-1HIdz | An-5 | BRA30 | C | | 392 ($M^+$ + 1) |
| Cn-35 | 2FPh | H | 2-Nap | An-1 | BRA32 | C | | 372 ($M^+$ + 1) |

TABLE Cn-1-continued

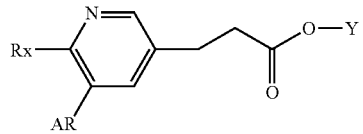

| Exp. | Rx | Y | AR | SM1 | SM2 | method | RTime | Mass |
|---|---|---|---|---|---|---|---|---|
| Cn-36 | 2FPh | H | 1Me-5-Ind | An-3 | BRA32 | C | | 375 ($M^+$ + 1) |
| Cn-37 | 2FPh | H | 5-1HIdz | An-4 | BRA32 | C | | 362 ($M^+$ + 1) |
| Cn-38 | 2FPh | H | 1Me-5-1HIdz | An-5 | BRA32 | C | | 376 ($M^+$ + 1) |
| Cn-39 | 3FPh | H | 5-Ind | An-2 | BRA33 | C | | 361 ($M^+$ + 1) |
| Cn-40 | 3FPh | H | 5-1HIdz | An-4 | BRA33 | C | | 362 ($M^+$ + 1) |
| Cn-41 | 3FPh | H | 1Me-5-1HIdz | An-5 | BRA33 | C | | 376 ($M^+$ + 1) |
| Cn-42 | 4FPh | H | 2-Nap | An-1 | BRA34 | C | | 372 ($M^+$ + 1) |
| Cn-43 | 4FPh | H | 5-Ind | An-2 | BRA34 | C | | 361 ($M^+$ + 1) |
| Cn-44 | 4FPh | H | 5-1HIdz | An-4 | BRA34 | C | | 362 ($M^+$ + 1) |
| Cn-45 | 4FPh | H | 1Me-5-1HIdz | An-5 | BRA34 | C | | 376 ($M^+$ + 1) |

Reference Examples

Intermediates Int. n-1 to Int. n-115

Synthesis of methyl 3-(4-aminophenyl)propionate (Intermediate Int. n-1) (Synthesis method NL)

A solution obtained beforehand by adding thionyl chloride (6.7 ml, WAKO) dropwise to methanol (50 ml) under ice cooling and mixing them was added dropwise with a solution of 4-aminohydrocinnamic acid (9.97 g, TCI) in methanol (50 ml) under ice cooling, stirred for 30 minutes, then warmed to room temperature, and further stirred for 16.5 hours. The reaction mixture was concentrated under reduced pressure, and then extracted with ethyl acetate (200 ml), and the organic layer was washed successively with saturated aqueous sodium hydrogencarbonate, saturated aqueous ammonium chloride and saturated brine. The organic layer was dried, and then the solvent was evaporated under reduced pressure to obtain the title compound (Intermediate Int. n-1, 13.13 g).

Synthesis of methyl 3-(4-amino-3-bromophenyl) propionate (Intermediate Int. n-2) (Synthesis method NK)

A solution of Intermediate Int. n-1 (9.93 g) in acetic acid (55 ml) was added with potassium bromide (6.60 g, WAKO) and sodium tungstenate(IV) dihydrate (18.23 g, WAKO), stirred for 5 minutes, then added dropwise with aqueous hydrogen peroxide (3.5 ml, WAKO) at 0° C. over 5 minutes, warmed to room temperature, and then stirred for 1 hour. The reaction mixture was poured into 5% aqueous ammonia containing ice, thereby adjusted to pH of about 6, and then added with dichloromethane (200 ml) for extraction. The organic layer was washed successively with saturated aqueous ammonium chloride, saturated aqueous sodium hydrogencarbonate and saturated brine, and then dried, and the solvent was evaporated under reduced pressure. The residue was purified by column chromatography (Quad, hexane:ethyl acetate=3:1) to obtain the title compound (Intermediate Int. n-2, 3.07 g).

Synthesis of methyl 3-(4-benzylamino-3-bromophenyl)propionate (Intermediate Int. n-3) (Synthesis method NC1)

A solution of Intermediate Int. n-2 (10.97 g) in methanol (30 ml) was added with benzaldehyde (5.25 ml, TCI) and anhydrous sodium sulfate (6.49 g, WAKO), and stirred at 60° C. for 13 hours. The reaction mixture was added with sodium cyanotrihydoridoborate (2.73 g, WAKO), and further stirred for 5 hours. The reaction mixture was concentrated under reduced pressure, and then extracted with dichloromethane (150 ml), and the organic layer was washed with saturated brine, and dried. Then, the solvent was evaporated under reduced pressure. The residue was purified by column chromatography (Quad, hexane:ethyl acetate=4:1) to obtain the title compound (Intermediate Int. n-3, 13.45 g).

Synthesis of methyl 3-[3-bromo-(4-fluorobenzylamino)phenyl]propionate (Intermediate Int. n-4) (Synthesis method NC2)

A solution of Intermediate Int. n-2 (5.80 g) in dichloromethane (100 ml) was added with p-fluorobenzaldehyde (2.83 ml, TCI), sodium triacetoxyborohydride (7.14 g, Ald) and acetic acid (1.4 ml), and stirred at room temperature for 19 hours. The reaction mixture was extracted with dichloromethane (300 ml), and the organic layer was washed with saturated brine, and dried, and then the solvent was evaporated under reduced pressure. The residue was purified by column chromatography (Quad, hexane:ethyl acetate=4:1) to obtain the title compound (Intermediate Int. n-4, 7.51 g).

Synthesis of methyl 3-[4-amino-3-(naphthalen-2-yl) phenyl]propionate (Intermediate Int. n-7) (Synthesis method ND1)

A solution of the compound of Example N-a-1 (3.01 g) in a mixture of methanol (40 ml) and THF (20 ml) was added with 10% palladium/carbon (410.3 mg, Merck) and one drop of concentrated hydrochloric acid, and stirred at room temperature for 5 hours under hydrogen atmosphere. The reaction mixture was filtered, and the solvent of the filtrate was evaporated under reduced pressure. The residue was added with ethyl acetate (200 ml), and washed successively with saturated aqueous sodium hydrogencarbonate and saturated

Synthesis of methyl 3-[3-nitro-4-(piperazin-1-yl) phenyl]acrylate (Intermediate Int. n-19) (Synthesis method NJ)

A solution of methoxycarbonylmethyl(triphenyl)phosphonium bromide (1.1 g, TCI) in THF (12.5 ml) was added with sodium hydride (115 mg, WAKO) under ice cooling, warmed to room temperature, then added dropwise with a solution of 3-nitro-4-(piperazin-1-yl)benzaldehyde (550.6 mg, MAYB) in THF (12.5 ml), and stirred at the same temperature for 16.5 hours. The reaction mixture was poured into brine (40 ml), and extracted with ethyl acetate (100 ml). The organic layer was washed successively with saturated aqueous sodium hydrogencarbonate and saturated brine, and dried, and then the solvent was evaporated under reduced pressure. The residue was purified by flash column chromatography (hexane:ethyl acetate=5:1) to obtain the title compound (Intermediate Int. n-19, 511 mg).

Synthesis of methyl 3-[3-amino-4-(piperazin-1-yl) phenyl]propionate (Intermediate Int. n-20) (Synthesis method ND1)

According to the procedure described in the synthesis method of Intermediate Int. n-7 (Synthesis method ND1) provided that the reaction was carried out in ethyl acetate for 13 hours, Intermediate Int. n-19 (505 mg) and 10% palladium/carbon (50 mg) were reacted and treated to obtain the title compound (Intermediate Int. n-20, 658.9 mg).

Synthesis of methyl 3-[3-bromo-4-(piperazin-1-yl) phenyl]propionate (Intermediate Int. n-21) (Synthesis method NI)

A solution of hydrobromic acid (570 µl) in methanol (2.3 ml) was added dropwise with a solution of Intermediate Int. n-20 (235 mg) in methanol (2.3 ml) over 10 minutes under ice cooling. This reaction mixture was added with an aqueous solution (250 µl) of sodium nitrite (69 mg, WAKO). The reaction mixture was added dropwise with an aqueous solution (2.3 ml) of copper(II) bromide (222 mg, WAKO) heated to 50° C. over 15 minutes, stirred for 4 hours at the same temperature, and then further stirred at room temperature for 12.5 hours. The reaction mixture was poured into aqueous sodium hydrogencarbonate (20 ml), and extracted with ethyl acetate (40 ml). The organic layer was washed with saturated brine, and dried, and then the solvent was evaporated under reduced pressure. The residue was purified by flash column chromatography (hexane:ethyl acetate=4:1) to obtain the title compound (Intermediate Int. n-21, 89 mg).

Synthesis of methyl 4-fluoro-3-bromocinnamate (Intermediate Int. n-25) (Synthesis method NL)

According to the procedure described in the synthesis method of Intermediate Int. n-1 (Synthesis method NL) provided that the reaction was carried out for 1 hour, 3-bromo-4-fluorocinnamic acid (3.30 g, LANC) and thionyl chloride (1.5 ml) were reacted and treated to obtain the title compound (Intermediate Int. n-25, 3.47 g)

Synthesis of methyl 3-[3-bromo-4-(piperidin-1-yl) phenyl]cinnamate (Intermediate Int. n-26) (Synthesis method NG)

A solution of Intermediate Int. n-25 (136.4 mg) in DMSO (5 ml) was added with potassium carbonate (109.8 mg) and piperidine (84.8 µl, TCI), and stirred at 90° C. for 15 hours. The reaction mixture was extracted with ethyl acetate (50 ml), and then the organic layer was washed successively with saturated aqueous sodium hydrogencarbonate, saturated aqueous ammonium chloride and saturated brine, and dried. Then, the solvent was evaporated under reduced pressure. The residue was purified by column chromatography (Quad, hexane:isopropyl ether=6:1) to obtain the title compound (Intermediate Int. n-26, 120.4 mg).

Synthesis of methyl 3-[3-bromo-4-(piperidin-1-yl) phenyl]propionate (Intermediate Int. n-27) (Synthesis method ND2)

According to a procedure described in literature [D. J. Hart et al., Journal of Organic Chemistry (J. Org. Chem.), 1987, vol. 52, p. 4665], absolution of Intermediate Int. n-26 (690.6 mg) in dimethoxyethane (100 ml) was added with p-toluenesulfonhydrazide (2.97 g, TCI), and refluxed by heating at 110° C. Then, the reaction mixture was added dropwise with an aqueous solution (100 ml) of sodium acetate (2.85 g, WAKO) over 2 hours, and further stirred for 1 hour. The reaction mixture was extracted with dichloromethane (450 ml), and the organic layer was washed with water, and dried, and then the solvent was evaporated under reduced pressure. The residue was purified by column chromatography (Quad, hexane:ethyl acetate=6:1) to obtain the title compound (Intermediate Int. n-27, 648.2 mg).

Synthesis of 3-bromo-(4-imidazol-1-yl)benzaldehyde (Intermediate Int. n-32) (Synthesis method NG)

According to the procedure described in the synthesis method of Intermediate Int. n-26 (Synthesis method NG) provided that the reaction was performed for 20 hours, and the column chromatography was performed with chloroform:methanol=100:1, 3-bromo-4-fluorobenzaldehyde (1.246 g, TCI), potassium carbonate (825.1 mg) and imidazole (444 mg, TCI) were reacted and treated to obtain the title compound (Intermediate Int. n-32, 986.1 mg).

Synthesis of ethyl 3-[3-bromo-(4-imidazol-1-yl)phenyl]acrylate (Intermediate Int. n-33) (Synthesis method NJ)

A solution of Intermediate Int. n-32 (986.1 mg) and ethyl diethylphosphonoacetate (705 µl) in 1,2-dimethoxyethane (8 ml) was added with 60% sodium hydride (180.2 mg) under ice cooling, stirred for 10 minutes, then warmed to room temperature, and stirred for 1 hour. The reaction mixture was added with dichloromethane (60 ml) for extraction, and the organic layer was washed with saturated brine, and dried. Then, the solvent was evaporated under reduced pressure. The residue was purified by column chromatography (Quad, dichloromethane:methanol=100:1) to obtain the title compound (Intermediate Int. n-33, 1.00 g).

Synthesis of methyl 3-(4-cyclopentylaminophenyl)propionate (Intermediate Int. n-38) (Synthesis method NC1)

According to the procedure described in the synthesis method of Intermediate Int. n-3 provided that the reaction was (The page begins with:)
brine, and then dried, and the solvent was evaporated under reduced pressure to obtain the title compound (Intermediate Int. n-7, 2.58 g).

carried out for 6 hours, Intermediate Int. n-1 (1.03 g), cyclopentanone (450 μl, TCI), sodium triacetoxyborohydride (1.56 g) and acetic acid (350 μl) were reacted and treated to obtain the title compound (Intermediate Int. n-37, 1.21 g).

Synthesis of methyl 3-(4-cyclopentylamino-3,5-dibromophenyl)propionate (Intermediate Int. n-39) (Synthesis method NK)

A solution of Intermediate Int. n-37 (1.21 g) in acetonitrile was warmed to 35° C., then added with N-bromosuccinimide (2.44 g, TCI), and stirred for 1 hour. The reaction mixture was concentrated under reduced pressure, then added with ethyl acetate (150 ml), washed successively with aqueous sodium thiosulfate, saturated aqueous sodium hydrogencarbonate, saturated aqueous ammonium chloride and saturated brine, and dried, and then the solvent was evaporated under reduced pressure. The residue was purified by column chromatography (Quad, hexane:ethyl acetate=6:1) to obtain the title compound (Intermediate Int. n-38, 1.41 g).

Synthesis of 2-bromopyridine-5-carbaldehyde (Intermediate Int. n-44) (Synthesis method NM According to a procedure described in literature (Xin Wang et al., Tetrahedron. Lett., 2000, vol. 41, p. 4335], a solution of 2,5-dibromopyridine (3.17 g) in anhydrous diethyl ether (140 ml) was added dropwise with a 1.6 M solution of n-butyl lithium in hexane (11 ml) with cooling at −78° C. under argon gas atmosphere over 5 minutes, and stirred for 20 minutes. This reaction mixture was added dropwise with dehydrated DMF (1 ml) over 3 minutes, stirred for 30 minutes, then warmed to room temperature, and further stirred for 1 hour. The reaction mixture was added with water (20 ml), and extracted with ethyl acetate (30 ml×2). The organic layer was washed with saturated brine, and dried, and then the solvent was evaporated under reduced pressure. The residue was purified by column chromatography (Quad, hexane:ethyl acetate=6:1) to obtain the title compound (Intermediate Int. n-44, 1.46 g).

Synthesis of ethyl 3-(2-bromopyridin-5-yl)acrylate (Intermediate Int. n-45) (Synthesis method NJ)

According to the procedure described in the synthesis method of Intermediate n-7 provided that the reaction was carried out for 15 minutes, Intermediate Int. n-44 (1.45 g), ethyl diethylphosphonoacetate (2.1 ml) and 60% sodium hydride (355 mg) were reacted and treated to obtain the title compound (Intermediate Int. n-45, 1.87 g).

Synthesis of ethyl 3-[2-(piperidin-1-yl)pyridin-5-yl] acrylate (Intermediate Int. n-46) (Synthesis method NG)

Intermediate Int. n-45 (565.7 mg) was added with potassium carbonate (286.4 mg) and piperidine (3 ml), and stirred at 90° C. for 21 hours. The reaction mixture was added with ethyl acetate (50 ml), washed successively with saturated aqueous sodium hydrogencarbonate, saturated aqueous ammonium chloride and saturated brine, and dried, and then the solvent was evaporated under reduced pressure. The residue was purified by column chromatography (Quad, hexane: ethyl acetate=4:1) to obtain the title compound (Intermediate Int. n-46, 165.9 mg).

Synthesis of ethyl 3-[2-(piperidin-1-yl)pyridin-5-yl] propionate (Intermediate Int. n-47) (Synthesis method ND1)

According to the procedure described in the synthesis method of Intermediate Int. n-7 with the modifications that the reaction was carried out for 1 hour, and the purification was performed by column chromatography (Quad, hexane: ethyl acetate=6:1), Intermediate Int. n-46 (392 mg) and 10% palladium/carbon (30 mg) were reacted and treated to obtain the title compound (Intermediate Int. n-47; 246 mg).

Synthesis of ethyl 3-[3-bromo-2-(piperidin-1-yl) pyridin-3-yl]propionate (Intermediate Int. n-48) (Synthesis method NK2)

A solution of Intermediate Int. n-47 (242 mg) in acetonitrile was added with bromine (84 μl), and stirred at 40° C. for 1 hour. The reaction mixture was concentrated under reduced pressure, then added with ethyl acetate (50 ml), washed successively with aqueous sodium thiosulfate, saturated aqueous sodium hydrogencarbonate, saturated aqueous ammonium chloride and saturated brine, and dried, and then the solvent was evaporated under reduced pressure. The residue was purified by column chromatography (Quad, hexane:ethyl acetate=6:1) to obtain the title compound (Intermediate Int. n-48, 224 mg).

Synthesis of 2-benzylaminopyridine-5-carbaldehyde (Intermediate Int. n-59) (Synthesis method NG)

Intermediate Int. n-44 (102.0 mg) was added with benzylamine (1 ml, TCI), and stirred at 120° C. for 39 hours. The reaction mixture was added with ethyl acetate (50 ml), washed successively with saturated aqueous sodium hydrogencarbonate, saturated aqueous ammonium chloride and saturated brine, and dried, and then the solvent was evaporated under reduced pressure. The residue was purified by column chromatography (Quad, hexane:ethyl acetate=4:1) to obtain the title compound (Intermediate Int. n-59, 58.3 mg).

Synthesis of 2-benzylamino-3-bromopyridine-5-carbaldehyde (Intermediate Int. n-60) (Synthesis method NK)

A solution of Intermediate Int. n-59 (56.8 mg) in acetonitrile was added with N-bromosuccinimide (134 mg), and stirred at room temperature for 14 hours. The reaction mixture was concentrated under reduced pressure, then added with ethyl acetate (50 ml), washed successively with aqueous sodium thiosulfate, saturated aqueous sodium hydrogencarbonate, saturated aqueous ammonium chloride and saturated brine, and dried, and then the solvent was evaporated under reduced pressure. The residue was purified by column chromatography (Quad, hexane:ethyl acetate=4:1) to obtain the title compound (Intermediate Int. n-60, 50 mg).

Synthesis of ethyl 3-(2-benzylamino-3-bromopyridin-5-yl)acrylate (Intermediate Int. n-61) (Synthesis method NJ)

According to the procedure described in the synthesis method of Intermediate Int. n-7 provided that the reaction was carried out for 30 minutes, Intermediate Int. n-60 (49.1 g), ethyl diethylphosphonoacetate (92 μl) and 60% sodium hydride (30 mg) were reacted and treated to obtain the title compound (Intermediate Int. n-61, 28 mg).

Synthesis of ethyl 3 (2-benzylamino-3-bromopyridin-5-yl)propionate (Intermediate Int. n-62) (Synthesis method ND2)

According to the procedure described in the synthesis method of Intermediate Int. n-27 provided that the reaction was carried out for 4 hours, Intermediate Int. n-60 (49.1 mg), p-toluenesulfonhydrazide (320.6 mg) and sodium acetate (412.4 mg) were reacted and treated to obtain the title compound (Intermediate Int. n-62, 38.9 mg).

Synthesis of methyl 3-(4-amino-3-bromo-5-nitrophenyl)propionate (Intermediate Int. n-76) (Synthesis method NM)

A solution obtained by adding potassium nitrate (1.10 g) to a solution of Intermediate Int. n-2 (2.57 g) in acetic anhydride (20 ml) under ice cooling and stirring them for 10 minutes was added dropwise with concentrated sulfuric acid (700 μl) over 10 minutes. The reaction mixture was stirred for 10 minutes at the same temperature, then warmed to room temperature, and further stirred for 30 minutes. The reaction mixture was poured into 1 N aqueous sodium hydroxide (250 ml) containing ice, and extracted with isopropyl ether (200 ml×2). The organic layer was washed successively with saturated aqueous sodium hydrogencarbonate and saturated brine, and dried, and then the solvent was evaporated under reduced pressure. The residue was purified by column chromatography (Quad, hexane:ethyl acetate=3:1) to obtain the title compound (Intermediate Int. n-76, 0.72 g).

Typical examples of the intermediates for synthesizing the compounds of the present invention that can be obtained by reacting and treating corresponding starting compounds using any of the methods described in the present specification are shown in Table-Int. N-1 to Table-Int. N-8. In the tables, the intermediate numbers "Int. n-(number)" are mentioned in the columns indicated as "Exp.". In the tables, used methods among the aforementioned synthesis methods are shown in the columns of "Syn" with symbols, the starting compounds 1 are mentioned in the columns of "SM1", and the starting compounds 2 are mentioned in the columns of "SM2". Further, the compounds indicated as "Single" in the columns of "Single or Double" in the tables are compound in which two of the carbon atoms binding the benzene ring and carbonyl group in the compounds are bound with a single bond, and those indicated as "Double" in the same are compounds in which two of the carbon atoms binding the benzene ring and carbonyl group in the compounds are bound with a double bond. The aldehydes and ketones used for the synthesis of the compounds are mentioned in Table-Carb, and amines used for the same are mentioned in Table-AMN.

TABLE Carb

| Reagent | Aldehyde or Ketone | Manufacture |
|---|---|---|
| CHO1 | HCHO | WAKO |
| CHO2 | $CH_3CHO$ | Aldich |
| CHO3 | $CH_3CH_2CHO$ | TCI |
| CHO4 | nPrCHO | TCI |
| CHO5 | Acetone | WAKO |
| CHO6 | nBuCHO | TCI |
| CHO7 | iPrCHO | TCI |
| CHO8 | BnCHO | TCI |
| CHO9 | 4FBnCHO | TCI |
| CHO10 | 2FBnCHO | TCI |
| CHO11 | 3FBnCHO | TCI |
| CHO12 | 2ClBnCHO | TCI |
| CHO13 | 2BrBnCHO | TCI |

TABLE Carb-continued

| Reagent | Aldehyde or Ketone | Manufacture |
|---|---|---|
| CHO14 | 2,3DFBnCHO | TCI |
| CHO15 | 3,4DFBnCHO | TCI |
| CHO16 | 4PhBnCHO | TCI |
| CHO17 | $2CF_3BnCHO$ | TCI |
| CHO18 | 2,3DClBnCHO | TCI |
| CHO19 | 2-ThiofeneCHO(2-TFCHO) | TCI |
| CHO20 | 3-ThiofeneCHO(3-TFCHO) | TCI |
| CHO21 | 2-FuranCHO(2-FRCHO) | TCI |
| CHO22 | Cyclopentanone | TCI |
| CHO23 | Cyclohexanone | TCI |
| CHO24 | 2(Me)cHexanone | TCI |
| CHO25 | 2-Indanone | Aldlich |

TABLE AMN

| Reagent | Amine | Manufacture |
|---|---|---|
| AMN1 | pyrrolidine (NH) | TCI |
| AMN2 | morpholine | TCI |
| AMN3 | piperidine | TCI |
| AMN4 | 4-methylpiperidine | TCI |
| AMN5 | azepane | TCI |
| AMN6 | imidazole | TCI |
| AMN7 | pyrrole | TCI |
| AMN8 | EtMeNH | Aldrich |
| AMN9 | $Et_2NH$ | Aldrich |
| AMN10 | nPrMeNH | Aldrich |
| AMN11 | iPrMeNH | Aldrich |
| AMN12 | nBuMeNH | Aldrich |
| AMN13 | nBuEtNH | Aldrich |
| AMN14 | iBuMeNH | Aldrich |
| AMN15 | $4MeBnNH_2$ | Aldrich |
| AMN16 | $3MeBnNH_2$ | Aldrich |
| AMN17 | $2MeBnNH_2$ | Aldrich |
| AMN18 | $4FBnNH_2$ | Aldrich |
| AMN19 | $3FBnNH_2$ | Aldrich |
| AMN20 | $2FBnNH_2$ | Aldrich |
| AMN21 | $3MeOBnNH_2$ | Aldrich |
| AMN22 | $4MeOBnNH_2$ | Aldrich |
| AMN23 | $2MeOBnNH_2$ | Aldrich |
| AMN24 | $4CF_3BnNH_2$ | Aldrich |
| AMN25 | $2EtOBnNH_2$ | Aldrich |
| AMN26 | $3iPrOBnNH_2$ | Sigma-Aldrich |
| AMN27 | $3,5DFBnNH_2$ | Aldrich |

TABLE Int.N-1

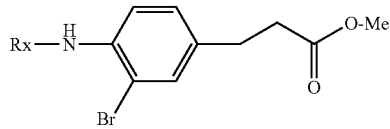

| Exp. | Syn | SM1 | SM2 | Rz | LCMS method | RTime | Mass |
|---|---|---|---|---|---|---|---|
| Int.n-5 | NC2 | Int.n-2 | CHO10 | 2FBn | C | | 366 (M$^+$) |
| Int.n-6 | NC1 | Int.n-2 | CHO11 | 3FBn | C | | 366 (M$^+$) |
| Int.n-12 | NC2 | Int.n-2 | CHO2 | Et | C | | 386 (M$^+$) |
| Int.n-13 | NC2 | Int.n-2 | CHO3 | nPr | D | 5.02 | 300 (M$^+$) |
| Int.n-14 | NC2 | Int.n-2 | CHO5 | iPr | D | 5.38 | 341 (M$^+$) |
| Int.n-15 | NC2 | Int.n-2 | CHO7 | iBu | D | 5.50 | 400 (M$^+$) |
| Int.n-16 | NC2 | Int.n-2 | CHO22 | cPen | C | | 326 (M$^+$) |
| Int.n-17 | NC2 | Int.n-2 | CHO23 | cHex | C | | 340 (M$^+$) |
| Int.n-18 | NC2 | Int.n-2 | CHO24 | 2(Me)cHex | C | | 354 (M$^+$) |

TABLE Int.N-2

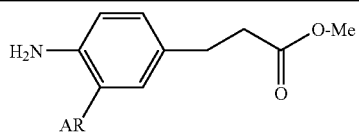

| Exp. | Syn | SM1 | AR | LCMS method | RTime | Mass |
|---|---|---|---|---|---|---|
| Int.n-8 | ND1 | N-a-3 | 5-Ind | C | | 295 (M$^+$ + 1) |
| Int.n-9 | ND1 | N-a-5 | 1Me-5-Ind | C | | 309 (M$^+$ + 1) |
| Int.n10 | ND1 | N-a-7 | 5-1HIdz | C | | 296 (M$^+$ + 1) |
| Int.n-11 | ND1 | N-a-9 | 1Me-5-1HIdz | C | | 310 (M$^+$ + 1) |

TABLE Int.N-3

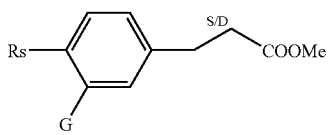

| Exp. | Syn. | Rs | G | Single or Double | LCMS method | RTime | Mass |
|---|---|---|---|---|---|---|---|
| Int.n-22 | NJ | morpholino | NO2 | Double | A | 3.91 | 293 (M$^+$ + 1) |
| Int.n-23 | ND1 | morpholino | NH2 | Single | A | 2.97 | 265 (M$^+$ + 1) |
| Int.n-24 | NI | morpholino | Br | Single | A | 4.31 | 328 (M$^+$ + 1) |

TABLE Int.N-4
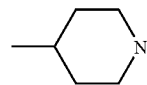
| Exp. | Syn | SM1 | RzRyN | Single or Double | LCMS method | RTime | Mass |
|---|---|---|---|---|---|---|---|
| Int.n-28 | NC2 | Int.n-25 | 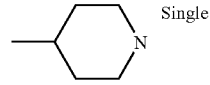 | Double | A | 6.54 | 338 (M$^+$) |
| Int.n-29 | NC1 | Int.n-28 | 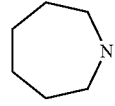 | Single | A | 6.01 | 342 (M$^+$ + 1) |
| Int.n-30 | NC2 | Int.n-25 | 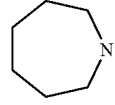 | Double | A | 6.29 | 340 (M$^+$ + 1) |
| Int.n-31 | NC1 | Int.n-30 |  | Single | A | 6.12 | 342 (M$^+$ + 1) |
| Int.n-33 | NC2 | Int.n-32 |  | Double | C |  | 307 (M$^+$) |
| Int.n-35 | NC2 | Int.n-32 |  | Double | C |  | 306 (M$^+$) |
| Int.n-36 | NC2 | Int.n-25 | 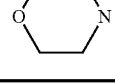 | Double | A | 5.60 | 310 (M$^+$) |
| Int.n-37 | NC2 | Int.n-32 |  | Double | C |  | 326 (M$^+$) |

TABLE Int.N-5

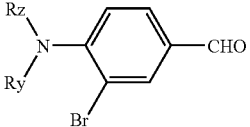

| Exp. | Syn | SM1 | RzRyN | LCMS method | RTime | Mass |
|---|---|---|---|---|---|---|
| Int.n-32 | NC2 | Int.n-25 | (imidazole) | C | | 351 (M⁺) |
| Int.n-34 | NC2 | Int.n-25 | (pyrrole) | C | | 250 (M⁺) |

TABLE Int.N-6

| Exp. | Syn | SM1 | SM2 | Rz | Z' | H or Br | LCMS method | RTime | Mass |
|---|---|---|---|---|---|---|---|---|---|
| Int.n-40 | NC1 | Int.n-1 | CHO3 | nPr | H | H | C | | 222 (M⁺ + 1) |
| Int.n-41 | NK | Int.n-40 | | nPr | Br | Br | C | | 380 (M⁺ + 1) |
| Int.n-42 | NC1 | Int.n-1 | CHO5 | iPr | H | H | C | | 222 (M⁺ + 1) |
| Int.n-43 | NK | Int.n-42 | | iPr | Br | Br | C | | 380 (M⁺ + 1) |

TABLE Int.N-7

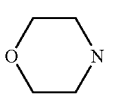

| Exp. | Syn | RzRyN | LCMS method | RTime | Mass |
|---|---|---|---|---|---|
| Int.n-48 | NG | cHex | C | | 327 (M⁺) |
| Int.n-49 | NG | cPen | C | | 313 (M⁺) |
| Int.n-50 | NG | 4(Me)cHex | C | | 341 (M⁺) |
| Int.n-51 | NG | (morpholine) | C | | 343 (M⁺) |
| Int.n-52 | NG | cHep | C | | 355 (M⁺) |

| Exp. | Syn | Rz | Ry | LCMS method | RTime | Mass |
|---|---|---|---|---|---|---|
| Int.n-53 | NG | Et | Me | C | | 301 (M⁺) |

TABLE Int.N-7-continued

| Exp. | Syn | Rz | Ry | method | RTime | Mass |
|---|---|---|---|---|---|---|
| Int.n-54 | NG | Et | Et | C | | 315 (M⁺) |
| Int.n-55 | NG | nPr | Me | C | | 315 (M⁺) |
| Int.n-56 | NG | iPr | Me | C | | 315 (M⁺) |
| Int.n-57 | NG | nBu | Me | C | | 329 (M⁺) |
| Int.n-58 | NG | iBu | Me | C | | 329 (M⁺) |
| Int.n-63 | NG | 4MeBn | H | C | | 363 (M⁺) |
| Int.n-64 | NG | 3MeBn | H | C | | 363 (M⁺) |
| Int.n-65 | NG | 2MeBn | H | C | | 363 (M⁺) |
| Int.n-66 | NG | 4FBn | H | C | | 368 (M⁺ + 1) |
| Int.n-67 | NG | 3FBn | H | C | | 368 (M⁺ + 1) |
| Int.n-68 | NG | 2FBn | H | C | | 368 (M⁺ + 1) |
| Int.n-69 | NG | 4MeOPh | H | C | | 365 (M⁺) |
| Int.n-70 | NG | 3MeOPh | H | C | | 365 (M⁺) |
| Int.n-71 | NG | 2MeOPh | H | C | | 365 (M⁺) |
| Int.n-72 | NG | 4CF3Ph | H | C | | 403 (M⁺) |
| Int.n-73 | NG | 2EtOPh | H | C | | 380 (M⁺ + 1) |
| Int.n-74 | NG | 3iPrOPh | H | C | | 393 (M⁺) |
| Int.n-75 | NG | 3,5DFPh | H | C | | 372 (M⁺ + 1) |

TABLE Int.N-8

| Exp. | Syn | SM1 | SM2 | Rz | Ry | LCMS method | RTime | Mass |
|---|---|---|---|---|---|---|---|---|
| Int.n-77 | NC2 | Int.n-76 | CHO22 | cPen | H | C | | 371 (M$^+$) |
| Int.n-78 | NC2 | Int.n-76 | CHO3 | nPr | H | C | | 345 (M$^+$) |
| Int.n-79 | NC2 | Int.n-76 | CHO5 | iPr | H | C | | 345 (M$^+$) |
| Int.n-80 | NC2 | Int.n-76 | CHO25 | 2-Indane | H | C | | 419 (M$^+$) |
| Int.n-81 | NC2 | Int.n-76 | CHO23 | cHex | H | C | | 385 (M$^+$) |
| Int.n-82 | NC2 | Int.n-76 | CHO24 | 2(Me)cHex | H | C | | 399 (M$^+$) |
| Int.n-83 | NC1 | Int.n-77 | CHO1 | cPen | Me | C | | 385 (M$^+$) |
| Int.n-84 | NC1 | Int.n-78 | CHO1 | nPr | Me | C | | 359 (M$^+$) |
| Int.n-85 | NC1 | Int.n-79 | CHO1 | iPr | Me | C | | 359 (M$^+$) |
| Int.n-86 | NC1 | Int.n-80 | CHO1 | 2-Indane | Me | C | | 433 (M$^+$) |
| Int.n-87 | NC1 | Int.n-81 | CHO1 | cHex | Me | C | | 399 (M$^+$) |
| Int.n-88 | NC1 | Int.n-82 | CHO1 | 2(Me)cHex | Me | C | | 413 (M$^+$) |
| Int.n-89 | NC1 | Int.n-76 | CHO8 | Bn | H | C | | 393 (M$^+$) |
| Int.n-90 | NC1 | Int.n-76 | CHO9 | 4FBn | H | C | | 411 (M$^+$) |
| Int.n-91 | NC2 | Int.n-76 | CHO10 | 2FBn | H | C | | 411 (M$^+$) |
| Int.n-92 | NC2 | Int.n-76 | CHO11 | 3FBn | H | C | | 411 (M$^+$) |
| Int.n-93 | NC2 | Int.n-76 | CHO14 | 2,3DFBn | H | C | | 429 (M$^+$) |
| Int.n-94 | NC2 | Int.n-76 | CHO15 | 3,4DFBn | H | C | | 429 (M$^+$) |
| Int.n-95 | NC2 | Int.n-76 | CHO16 | 4PhBn | H | C | | 469 (M$^+$) |
| Int.n-96 | NC2 | Int.n-76 | CHO17 | 2CF3Bn | H | C | | 461 (M$^+$) |
| Int.n-97 | NC2 | Int.n-76 | CHO19 | 2-TF | H | C | | 399 (M$^+$) |
| Int.n-98 | NC2 | Int.n-76 | CHO20 | 3-TF | H | C | | 399 (M$^+$) |
| Int.n-99 | NC2 | Int.n-76 | CHO21 | 2-FR | H | C | | 383 (M$^+$) |
| Int.n-100 | NC1 | Int.n-89 | CHO1 | Bn | Me | C | | 407 (M$^+$) |
| Int.n-101 | NC1 | Int.n-90 | CHO1 | 4FBn | Me | C | | 428 (M$^+$) |
| Int.n-102 | NC1 | Int.n-91 | CHO1 | 2FBn | Me | C | | 425 (M$^+$) |
| Int.n-103 | NC1 | Int.n-92 | CHO1 | 3FBn | Me | C | | 425 (M$^+$) |
| Int.n-104 | NC1 | Int.n-93 | CHO1 | 2,3DFBn | Me | C | | 443 (M$^+$) |
| Int.n-105 | NC1 | Int.n-94 | CHO1 | 3,4DFBn | Me | C | | 443 (M$^+$) |
| Int.n-106 | NC1 | Int.n-95 | CHO1 | 4PhBn | Me | C | | 483 (M$^+$) |
| Int.n-107 | NC1 | Int.n-96 | CHO1 | 2CF3Bn | Me | C | | 475 (M$^+$) |
| Int.n-108 | NC1 | Int.n-97 | CHO1 | 2-TF | Me | C | | 413 (M$^+$) |
| Int.n-109 | NC1 | Int.n-98 | CHO1 | 3-TF | Me | C | | 413 (M$^+$) |
| Int.n-110 | NC1 | Int.n-99 | CHO1 | 2-FR | Me | C | | 397 (M$^+$) |

| Exp | Syn | SM1 | SM2 | RzRyN | LCMS method | RTime | Mass |
|---|---|---|---|---|---|---|---|
| Int.n-111 | NM | Int.n-21 | |  | C | | 357 (M$^+$) |
| Int.n-112 | NM | Int.n-24 | |  | C | | 373 (M$^+$) |
| Int.n-113 | NM | Int.n-27 | |  | C | | 371 (M$^+$) |
| Int.n-114 | NM | Int.n-29 | |  | C | | 385 (M$^+$) |
| Int.n-115 | NM | Int.n-31 | |  | C | | 385 (M$^+$) |

Example N-a-1

Synthesis of methyl 3-[4-benzylamino-3-(naphthalen-2-yl)phenyl]propionate (Compound No. N-a-1) (Synthesis method NB1)

A solution of Intermediate n-3 (8.18 g) in toluene (60 ml) was added with 2-naphthaleneboronic acid (5.04 g, TCI), 2 M aqueous sodium carbonate (21.6 ml), methanol (24 ml) and tetrakistriphenylphosphine palladium(0) (henceforth abbreviated as "$(Ph_3P)_4Pd$", 1.94 g, Nacalai Tesque), and stirred at 90° C. for 15 hours. The reaction mixture was added with ethyl acetate (300 ml), and washed successively with saturated aqueous sodium hydrogencarbonate, saturated aqueous ammonium chloride, and saturated brine. The organic layer was dried, and then the solvent was evaporated under reduced pressure. The residue was purified by flash column chromatography (hexane:ethyl acetate=3:1) to obtain the title compound (Compound No. N-a-1, 5.70 g).

Example N-a-2

Synthesis of 3-[4-benzylamino-3-(naphthalen-2-yl)phenyl]propionic acid (Compound No. N-a-2) (Synthesis method NA)

A solution of the compound of Example N-a-1 (51 mg) in methanol (5.0 ml) was added with 2 N aqueous sodium hydroxide (130 μl), and stirred at 60° C. for 2 hours. The reaction mixture was concentrated under reduced pressure, then neutralized with 5% aqueous hydrochloric acid under ice cooling, and then extracted with ethyl acetate (30 ml). The organic layer was washed with saturated brine, and dried, and then the solvent was evaporated under reduced pressure to obtain the title compound (Compound No. N-a-2, 47 mg).

Example N-a-25

Synthesis of methyl 3-[4-(N-benzyl-N-methylamino)-3-(naphthalen-2-yl)phenyl]propionate (Compound No. N-a-25) (Synthesis method NC1)

According to the procedure described in the synthesis method of Intermediate n-3 provided that the reaction was carried out for 5 hours, the compound of Example N-a-1 (234.2 mg), 30% aqueous solution of formaldehyde (208.8 μl, WAKO) and sodium cyanotrihydoridoborate (140.9 mg) were reacted and treated to obtain the title compound (Compound No. N-a-25, 176.3 mg).

Example N-A-137

Synthesis of methyl 3-{3-(1-methyl-1H-indol-5-yl)-4-[N-(1-phenylethyl)amino]phenyl}propionate (Compound No. N-a-137) (Synthesis method NE1)

According to a procedure described in literature [Shin-Shyong Tseng et al., Journal of Organic Chemistry (J. Org. Chem.), 1979, vol. 44, p. 4113], a solution of Intermediate n-9 (630.7 mg) in methylene chloride (10 ml) was added with triethylamine (405 μl, Kokusan Chemical), cooled to −78° C., then added dropwise with trifluoromethanesulfonyl chloride (426 μl, TCI), and stirred for 1.5 hours. The reaction mixture was poured into ice water (10 ml), and added with dichloromethane (30 ml) for extraction. The organic layer was washed with saturated brine, and dried, and then the solvent was evaporated under reduced pressure to obtain a crude product. A solution of the obtained crude product in DMF (15 ml) was added with potassium carbonate (394.2 mg) and (1-bromoethyl)benzene (386.4 μl, TCI), and stirred at room temperature for 13 hours. The reaction mixture was extracted with ethyl acetate (100 ml), and the organic layer was washed successively with saturated aqueous sodium hydrogencarbonate, saturated aqueous ammonium chloride and saturated brine, and dried. Then, the solvent was evaporated under reduced pressure. The residue was purified by column chromatography (Quad, hexane:ethyl acetate=4:1) to obtain the title compound (Compound No. N-a-137, 310.3 mg).

Example N-a-141

Synthesis of methyl 3-[3-(1-methyl-1H-indol-5-yl)-4-{N-[2-(4-fluorophenyl)ethyl]amino}phenyl]propionate (Compound No. N-a-141) (Synthesis method NE2)

A solution of Intermediate n-9 (210.1 mg) in methylene chloride (10 ml) was added with triethylamine (135 μl, Kokusan Chemical), cooled to −78° C., then added dropwise with trifluoromethanesulfonyl chloride (143 μl, TCI), and stirred for 1.5 hours. The reaction mixture was poured into ice water (10 ml), and added with dichloromethane (15 ml) for extraction. The organic layer was washed with saturated brine, and dried, and then the solvent was evaporated under reduced pressure to obtain a crude product. A solution of the obtained crude product in anhydrous DMF (15 ml) was added with triphenylphosphine (485.9 g, WAKO), di-t-butyl azodicarboxylate (299.8 mg, Ald) and 4-fluorophenylethyl alcohol (357 μl, TCI), and stirred at room temperature for 12 hours. The reaction mixture was added with water (10 ml) and ethyl acetate (10 ml) for extraction, and the organic layer was washed successively with saturated aqueous sodium hydrogencarbonate, saturated aqueous ammonium chloride, and saturated brine, and dried. Then, the solvent was evaporated under reduced pressure. The residue was purified by column chromatography (Quad, hexane:ethyl acetate=4:1) to obtain the title compound (Compound No. N-a-141, 63.5 mg).

Example N-a-143

Synthesis of methyl 3-[4-(N-acetyl-N-benzylamino)-3-(1-methyl-1H-indol-5-yl)phenyl]propionate (Compound No. N-a-143) (Synthesis method NF)

A solution of Compound No. N-a-5 (32 mg) in methylene chloride (3 ml) was added with pyridine (49.6 μl, TCI) and acetyl chloride (50 μl, TCI), and stirred for 13 hours. The reaction mixture was added with water (1 ml), and the solvent was evaporated. The residue was purified by column chromatography (Quad, hexane:ethyl acetate=4:1) to obtain the title compound (Compound No. N-a-143, 20.3 mg).

Example N-a-153

Synthesis of methyl 3-[4-benzoylamino-3-(1-methyl-1H-indol-5-yl)phenyl]propionate (Compound No. N-a-153) (Synthesis method NF)

According to the procedure described in the synthesis method of the compound of Example N-a-143 provided that the reaction was carried out for 16 hours, Intermediate Int. n-9 (26.5 mg), pyridine (23.8 μl) and benzoyl chloride (30 μl, WAKO) were reacted and treated to obtain the title compound (Compound No. N-a-153, 18.4 mg).

Examples N-a-1 to N-a-166

Typical examples of the compounds of the present invention that can be obtained by reacting and treating corresponding starting compounds using any of the methods described in the present specification including the examples described above are shown in Table-N-A-1 to Table-N-A-4. In the tables, the compound numbers are mentioned in the columns indicated as "Exp.". In the tables, used methods among the aforementioned synthesis methods are shown in the columns of "Syn" with symbols, the starting compounds 1 are mentioned in the columns of "SM1", and the starting compounds 2 are mentioned in the columns of "SM2".

TABLE N-A-1

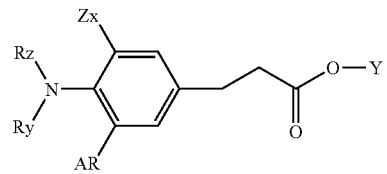

| Exp. | Syn | SM1 | SM2 | Rz | Ry | Y | Zx | AR | LCMS method | RTime | Mass |
|---|---|---|---|---|---|---|---|---|---|---|---|
| N-a-1 | NB1 | Int.n-3 | BRN1 | Bn | H | Me | H | 2-Nap | C | | 396 ($M^+$ + 1) |
| N-a-2 | NA | N-a-1 | | Bn | H | H | H | 2-Nap | C | | 382 ($M^+$ + 1) |
| N-a-3 | NB1 | Int.n-3 | BRN2 | Bn | H | Me | H | 5-1Ind | C | | 385 ($M^+$ + 1) |
| N-a-4 | NA | N-a-3 | | Bn | H | H | H | 5-1Ind | C | | 371 ($M^+$ + 1) |
| N-a-5 | NB1 | Int.n-3 | BRN3 | Bn | H | Me | H | 1Me-5-1Ind | C | | 399 ($M^+$ + 1) |
| N-a-6 | NA | N-a-5 | | Bn | H | H | H | 1Me-5-1Ind | C | | 385 ($M^+$ + 1) |
| N-a-7 | NB1 | Int.n-3 | BRN4 | Bn | H | Me | H | 1Et-5-1Ind | C | | 413 ($M^+$ + 1) |
| N-a-8 | NA | N-a-7 | | Bn | H | H | H | 1Et-5-1Ind | C | | 399 ($M^+$ + 1) |
| N-a-9 | NB1 | Int.n-3 | BRN5 | Bn | H | Me | H | 5-1HIdz | C | | 386 ($M^+$ + 1) |
| N-a-10 | NA | N-a-9 | | Bn | H | H | H | 5-1HIdz | C | | 372 ($M^+$ + 1) |
| N-a-11 | NB1 | Int.n-3 | BRN6 | Bn | H | Me | H | 1Me-5-1HIdz | C | | 400 ($M^+$ + 1) |
| N-a-12 | NA | N-a-11 | | Bn | H | H | H | 1Me-5-1HIdz | C | | 386 ($M^+$ + 1) |
| N-a-13 | NB1 | Int.n-3 | BRN7 | Bn | H | Me | H | 1Et-5-1HIdz | C | | 414 ($M^+$ + 1) |
| N-a-14 | NA | N-a-13 | | Bn | H | H | H | 1Et-5-1HIdz | C | | 400 ($M^+$ + 1) |
| N-a-15 | NB1 | Int.n-3 | BRN8 | Bn | H | Me | H | 2Me-5-2HIdz | C | | 400 ($M^+$ + 1) |
| N-a-16 | NA | N-a-15 | | Bn | H | H | H | 2Me-5-2HIdz | C | | 386 ($M^+$ + 1) |
| N-a-17 | NB1 | Int.n-3 | BRN9 | Bn | H | Me | H | 5-Bzt | C | | 403 ($M^+$ + 1) |
| N-a-18 | NA | N-a-17 | | Bn | H | H | H | 5-Bzt | C | | 389 ($M^+$ + 1) |
| N-a-19 | NB1 | Int.n-3 | BRN10 | Bn | H | Me | H | 3-Qu | C | | 397 ($M^+$ + 1) |
| N-a-20 | NA | N-a-19 | | Bn | H | H | H | 3-Qu | C | | 383 ($M^+$ + 1) |
| N-a-21 | NB1 | Int.n-3 | BRN11 | Bn | H | Me | H | 6-Qu | C | | 397 ($M^+$ + 1) |
| N-a-22 | NA | N-a-21 | | Bn | H | H | H | 6-Qu | C | | 383 ($M^+$ + 1) |
| N-a-23 | NB1 | Int.n-3 | BRN12 | Bn | H | Me | H | 6-IQ | C | | 397 ($M^+$ + 1) |
| N-a-24 | NA | N-a-23 | | Bn | H | H | H | 6-IQ | C | | 383 ($M^+$ + 1) |
| N-a-25 | NC1 | N-a-1 | CHO1 | Bn | Me | Me | H | 2-Nap | C | | 410 ($M^+$ + 1) |
| N-a-26 | NA | N-a-25 | | Bn | Me | H | H | 2-Nap | C | | 396 ($M^+$ + 1) |
| N-a-27 | NC1 | N-a-1 | CHO2 | Bn | Et | Me | H | 2-Nap | C | | 424 ($M^+$ + 1) |
| N-a-28 | NA | N-a-27 | | Bn | Et | H | H | 2-Nap | C | | 410 ($M^+$ + 1) |
| N-a-29 | NC1 | N-a-3 | CHO1 | Bn | Me | Me | H | 5-1Ind | C | | 399 ($M^+$ + 1) |
| N-a-30 | NA | N-a-29 | | Bn | Me | H | H | 5-1Ind | C | | 384 ($M^+$ + 1) |
| N-a-31 | NC1 | N-a-5 | CHO1 | Bn | Me | Me | H | 1Me-5-Ind | C | | 413 ($M^+$ + 1) |
| N-a-32 | NA | N-a-31 | | Bn | Me | H | H | 1Me-5-Ind | C | | 399 ($M^+$ + 1) |
| N-a-33 | NB1 | Int.n-4 | BRA1 | 4FBn | H | Me | H | 2-Nap | C | | 414 ($M^+$ + 1) |
| N-a-34 | NA | N-a-33 | | 4FBn | H | H | H | 2-Nap | C | | 400 ($M^+$ + 1) |
| N-a-35 | NB1 | Int.n-4 | BRA2 | 4FBn | H | Me | H | 5-1Ind | D | 5.20 | 403 ($M^+$ + 1) |
| N-a-36 | NA | N-a-35 | | 4FBn | H | H | H | 5-1Ind | D | 4.73 | 389 ($M^+$ + 1) |
| N-a-37 | NB1 | Int.n-4 | BRA3 | 4FBn | H | Me | H | 1Me-5-Ind | D | 5.51 | 417 ($M^+$ + 1) |
| N-a-38 | NA | N-a-37 | | 4FBn | H | H | H | 1Me-5-Ind | D | 4.78 | 403 ($M^+$ + 1) |
| N-a-39 | NB1 | Int.n-4 | BRA5 | 4FBn | H | Me | H | 5-1HIdz | D | 4.60 | 404 ($M^+$ + 1) |
| N-a-40 | NA | N-a-39 | | 4FBn | H | H | H | 5-1HIdz | C | | 390 ($M^+$ + 1) |
| N-a-41 | NB1 | Int.n-4 | BRA6 | 4FBn | H | Me | H | 1Me-5-1HIdz | A | 4.85 | 418 ($M^+$ + 1) |
| N-a-42 | NA | N-a-41 | | 4FBn | H | H | H | 1Me-5-1HIdz | A | 4.14 | 404 ($M^+$ + 1) |
| N-a-43 | NB1 | Int.n-4 | BRA10 | 4FBn | H | Me | H | 3-Qu | D | 4.72 | 415 ($M^+$ + 1) |
| N-a-44 | NA | N-a-43 | | 4FBn | H | H | H | 3-Qu | C | | 401 ($M^+$ + 1) |

TABLE N-A-2

| Exp. | Syn | SM1 | SM2 | Rz | Ry | Y | Zx | AR | LCMS method | RTime | Mass |
|---|---|---|---|---|---|---|---|---|---|---|---|
| N-a-45 | NC2 | N-a-35 | CHO1 | 4FBn | Me | Me | H | 5-Ind | D | 4.17 | 417 (M⁺ + 1) |
| N-a-46 | NA | N-a-45 | | 4FBn | Me | H | H | 5-Ind | D | 3.38 | 403 (M⁺ + 1) |
| N-a-47 | NC2 | N-a-37 | CHO1 | 4FBn | Me | Me | H | 1Me-5-Ind | C | | 431 (M⁺ + 1) |
| N-a-48 | NA | N-a-47 | | 4FBn | Me | H | H | 1Me-5-Ind | C | | 418 (M⁺ + 1) |
| N-a-49 | NC2 | N-a-41 | CHO1 | 4FBn | Me | Me | H | 1Me-5-1HIdz | C | | 432 (M⁺ + 1) |
| N-a-50 | NA | N-a-49 | | 4FBn | Me | H | H | 1Me-5-1HIdz | C | | 418 (M⁺ + 1) |
| N-a-51 | NC2 | N-a-37 | CHO2 | 4FBn | Et | Me | H | 1Me-5-Ind | C | | 445 (M⁺ + 1) |
| N-a-52 | NA | N-a-51 | | 4FBn | Et | H | H | 1Me-5-Ind | C | | 431 (M⁺ + 1) |
| N-a-53 | NC2 | N-a-39 | CHO2 | 4FBn | Et | Me | H | 5-1Idz | C | | 433 (M⁺ + 1) |
| N-a-54 | NA | N-a-53 | | 4FBn | Et | H | H | 5-1Idz | C | | 419 (M⁺ + 1) |
| N-a-55 | NB1 | Int.n-5 | | 2FBn | H | Me | H | 2-Nap | C | | 414 (M⁺ + 1) |
| N-a-56 | NA | N-a-55 | | 2FBn | H | H | H | 2-Nap | C | | 400 (M⁺ + 1) |
| N-a-57 | NB1 | Int.n-5 | | 2FBn | H | Me | H | 1Me-5-Ind | C | | 417 (M⁺ + 1) |
| N-a-58 | NA | N-a-57 | | 2FBn | H | H | H | 1Me-5-Ind | C | | 403 (M⁺ + 1) |
| N-a-59 | NB1 | Int.n-5 | | 2FBn | H | Me | H | 1Me-5-1HIdz | C | | 418 (M⁺ + 1) |
| N-a-60 | NA | N-a-59 | | 2FBn | H | H | H | 1Me-5-1HIdz | C | | 404 (M⁺ + 1) |
| N-a-61 | NC2 | N-a-59 | CHO1 | 2FBn | Me | Me | H | 1Me-5-1HIdz | C | | 432 (M⁺ + 1) |
| N-a-62 | NA | N-a-61 | | 2FBn | Me | H | H | 1Me-5-1HIdz | C | | 418 (M⁺ + 1) |
| N-a-63 | NB1 | Int.n-6 | | 3FBn | H | Me | H | 2-Nap | C | | 414 (M⁺ + 1) |
| N-a-64 | NA | N-a-63 | | 3FBn | H | H | H | 2-Nap | C | | 400 (M⁺ + 1) |
| N-a-65 | NB1 | Int.n-6 | | 3FBn | H | Me | H | 5-1Ind | C | | 403 (M⁺ + 1) |
| N-a-66 | NA | N-a-65 | | 3FBn | H | H | H | 5-1Ind | C | | 389 (M⁺ + 1) |
| N-a-67 | NB1 | Int.n-6 | | 3FBn | H | Me | H | 1Me-5-Ind | C | | 417 (M⁺ + 1) |
| N-a-68 | NA | N-a-67 | | 3FBn | H | H | H | 1Me-5-Ind | C | | 403 (M⁺ + 1) |
| N-a-69 | NC2 | N-a-67 | CHO1 | 3FBn | Me | Me | H | 1Me-5-Ind | C | | 431 (M⁺ + 1) |
| N-a-70 | NA | N-a-69 | | 3FBn | Me | H | H | 1Me-5-Ind | C | | 417 (M⁺ + 1) |
| N-a-71 | NC1 | Int.n-7 | CHO12 | 2ClBn | H | Me | H | 2-Nap | C | | 430 (M⁺ + 1) |
| N-a-72 | NA | N-a-71 | | 2ClBn | H | H | H | 2-Nap | C | | 416 (M⁺ + 1) |
| N-a-73 | NC1 | Int.n-7 | CHO13 | 2BrBn | H | Me | H | 2-Nap | C | | 475 (M⁺ + 1) |
| N-a-74 | NA | N-a-73 | | 2BrBn | H | H | H | 2-Nap | C | | 461 (M⁺ + 1) |
| N-a-75 | NC1 | Int.n-7 | CHO14 | 2,3DFBn | H | Me | H | 2-Nap | C | | 432 (M⁺ + 1) |
| N-a-76 | NA | N-a-75 | | 2,3DFBn | H | H | H | 2-Nap | C | | 418 (M⁺ + 1) |
| N-a-77 | NC1 | Int.n-7 | CHO21 | 2-FR | H | Me | H | 2-Nap | C | | 386 (M⁺ + 1) |
| N-a-78 | NA | N-a-77 | | 2-FR | H | H | H | 2-Nap | C | | 372 (M⁺ + 1) |
| N-a-79 | NC1 | Int.n-7 | CHO20 | 3-TF | H | Me | H | 2-Nap | C | | 402 (M⁺ + 1) |
| N-a-80 | NA | N-a-79 | | 3-TF | H | H | H | 2-Nap | C | | 388 (M⁺ + 1) |
| N-a-81 | NC1 | Int.n-7 | CHO17 | 2CF3Bn | H | Me | H | 2-Nap | C | | 464 (M⁺ + 1) |
| N-a-82 | NA | N-a-80 | | 2CF3Bn | H | H | H | 2-Nap | C | | 450 (M⁺ + 1) |
| N-a-83 | NC1 | Int.n-8 | CHO12 | 2ClBn | H | Me | H | 5-1Ind | C | | 302 (M⁺ + 1) |
| N-a-84 | NA | N-a-80 | | 2ClBn | H | H | H | 5-1Ind | C | | 288 (M⁺ + 1) |
| N-a-85 | NC2 | N-a-80 | CHO1 | 2ClBn | Me | Me | H | 5-1Ind | C | | 316 (M⁺ + 1) |
| N-a-86 | NA | N-a-85 | | 2ClBn | Me | H | H | 5-1Ind | C | | 302 (M⁺ + 1) |
| N-a-87 | NC1 | Int.n-8 | CHO14 | 2,3DFBn | H | Me | H | 5-1Ind | C | | 304 (M⁺ + 1) |
| N-a-88 | NA | N-a-87 | | 2,3DFBn | H | H | H | 5-1Ind | C | | 290 (M⁺ + 1) |
| N-a-89 | NC1 | Int.n-8 | CHO16 | 4PhBn | H | Me | H | 5-1Ind | C | | 344 (M⁺ + 1) |
| N-a-90 | NA | N-a-89 | | 4PhBn | H | H | H | 5-1Ind | C | | 330 (M⁺ + 1) |

TABLE N-A-3

| Exp. | Syn | SM1 | SM2 | Rz | Ry | Y | Zx | AR | LCMS method | RTime | Mass |
|---|---|---|---|---|---|---|---|---|---|---|---|
| N-a-91 | NC1 | Int.n-8 | CHO19 | 2-TF | H | Me | H | 5-Ind | C | | 391 (M⁺ + 1) |
| N-a-92 | NA | N-a-91 | | 2-TF | H | H | H | 5-Ind | C | | 377 (M⁺ + 1) |
| N-a-93 | NC1 | Int.n-8 | CHO17 | 2CF3Bn | H | Me | H | 5-Ind | C | | 453 (M⁺ + 1) |
| N-a-94 | NA | N-a-93 | | 2CF3Bn | H | H | H | 5-Ind | C | | 439 (M⁺ + 1) |
| N-a-95 | NC1 | Int.n-8 | CHO18 | 2,3DClBn | H | Me | H | 5-Ind | C | | 454 (M⁺ + 1) |
| N-a-96 | NA | N-a-71 | | 2,3DClBn | H | H | H | 5-Ind | C | | 440 (M⁺ + 1) |
| N-a-97 | NC1 | Int.n-9 | CHO13 | 2BrBn | H | Me | H | 1Me-5-Ind | C | | 478 (M⁺ + 1) |
| N-a-98 | NA | N-a-97 | | 2BrBn | H | H | H | 1Me-5-Ind | C | | 464 (M⁺ + 1) |
| N-a-99 | NC1 | Int.n-9 | CHO15 | 3,4DFBn | H | Me | H | 1Me-5-Ind | C | | 435 (M⁺ + 1) |
| N-a-100 | NA | N-a-99 | | 3,4DFBn | H | H | H | 1Me-5-Ind | C | | 421 (M⁺ + 1) |
| N-a-101 | NC1 | Int.n-9 | CHO16 | 4PhBn | H | Me | H | 1Me-5-Ind | C | | 475 (M⁺ + 1) |
| N-a-102 | NA | N-a-101 | | 4PhBn | H | H | H | 1Me-5-Ind | C | | 461 (M⁺ + 1) |
| N-a-103 | NC1 | Int.n-9 | CHO21 | 2-FR | H | Me | H | 1Me-5-Ind | C | | 389 (M⁺ + 1) |
| N-a-104 | NA | N-a-103 | | 2-FR | H | H | H | 1Me-5-Ind | C | | 375 (M⁺ + 1) |
| N-a-105 | NC1 | Int.n-9 | CHO20 | 3-TF | H | Me | H | 1Me-5-Ind | C | | 405 (M⁺ + 1) |
| N-a-106 | NA | N-a-105 | | 3-TF | H | H | H | 1Me-5-Ind | C | | 391 (M⁺ + 1) |
| N-a-107 | NC1 | Int.n-9 | CHO18 | 2,3DClBn | H | Me | H | 1Me-5-Ind | C | | 468 (M⁺ + 1) |
| N-a-108 | NA | N-a-107 | | 2,3DClBn | H | H | H | 1Me-5-Ind | C | | 454 (M⁺ + 1) |
| N-a-109 | NC1 | Int.n-10 | CHO13 | 2BrBn | H | Me | H | 5-1HIdz | C | | 465 (M⁺ + 1) |

TABLE N-A-3-continued

| Exp. | Syn | SM1 | SM2 | Rz | Ry | Y | Zx | AR | LCMS method | RTime | Mass |
|---|---|---|---|---|---|---|---|---|---|---|---|
| N-a-110 | NA | N-a-109 | | 2BrBn | H | H | H | 5-1HIdz | C | | 451 (M⁺ + 1) |
| N-a-111 | NC1 | Int.n-10 | CHO15 | 3,4DFBn | H | Me | H | 5-1HIdz | C | | 422 (M⁺ + 1) |
| N-a-112 | NA | N-a-111 | | 3,4DFBn | H | H | H | 5-1HIdz | C | | 408 (M⁺ + 1) |
| N-a-113 | NC2 | N-a-111 | CHO1 | 3,4DFBn | Me | Me | H | 5-1HIdz | C | | 436 (M⁺ + 1) |
| N-a-114 | NA | N-a-113 | | 3,4DFBn | Me | H | H | 5-1HIdz | C | | 422 (M⁺ + 1) |
| N-a-115 | NC1 | Int.n-10 | CHO21 | 2-FR | H | Me | H | 5-1HIdz | C | | 376 (M⁺ + 1) |
| N-a-116 | NA | N-a-115 | | 2-FR | H | H | H | 5-1HIdz | C | | 362 (M⁺ + 1) |
| N-a-117 | NC1 | Int.n-10 | CHO20 | 3-TF | H | Me | H | 5-1HIdz | C | | 392 (M⁺ + 1) |
| N-a-118 | NA | N-a-116 | | 3-TF | H | H | H | 5-1HIdz | C | | 378 (M⁺ + 1) |
| N-a-119 | NC1 | Int.n-10 | CHO17 | 2CF3Bn | H | Me | H | 5-1HIdz | C | | 454 (M⁺ + 1) |
| N-a-120 | NA | N-a-120 | | 2CF3Bn | H | H | H | 5-1HIdz | C | | 440 (M⁺ + 1) |
| N-a-121 | NC1 | Int.n-10 | CHO18 | 2,3DClBn | H | Me | H | 1Me-5-1HIdz | C | | 469 (M⁺ + 1) |
| N-a-122 | NA | N-a-122 | | 2,3DClBn | H | H | H | 1Me-5-1HIdz | C | | 455 (M⁺ + 1) |
| N-a-123 | NC1 | Int.n-11 | CHO12 | 2ClBn | H | Me | H | 1Me-5-1HIdz | C | | 434 (M⁺ + 1) |
| N-a-124 | NA | N-a-123 | | 2ClBn | H | H | H | 1Me-5-1HIdz | C | | 420 (M⁺ + 1) |
| N-a-125 | NC2 | N-a-123 | CHO1 | 2ClBn | Me | Me | H | 1Me-5-1HIdz | C | | 448 (M⁺ + 1) |
| N-a-126 | NA | N-a-125 | | 2ClBn | Me | H | H | 1Me-5-1HIdz | C | | 434 (M⁺ + 1) |
| N-a-127 | NC1 | Int.n-11 | CHO14 | 2,3DFBn | H | Me | H | 1Me-5-1HIdz | C | | 436 (M⁺ + 1) |
| N-a-128 | NA | N-a-127 | | 2,3DFBn | H | H | H | 1Me-5-1HIdz | C | | 422 (M⁺ + 1) |
| N-a-129 | NC1 | Int.n-11 | CHO15 | 3,4DFBn | H | Me | H | 1Me-5-1HIdz | C | | 436 (M⁺ + 1) |
| N-a-130 | NA | N-a-129 | | 3,4DFBn | H | H | H | 1Me-5-1HIdz | C | | 422 (M⁺ + 1) |
| N-a-131 | NC1 | Int.n-11 | CHO16 | 4PhBn | H | Me | H | 1Me-5-1HIdz | C | | 476 (M⁺ + 1) |
| N-a-132 | NA | N-a-131 | | 4PhBn | H | H | H | 1Me-5-1HIdz | C | | 462 (M⁺ + 1) |
| N-a-133 | NC1 | Int.n-11 | CHO19 | 2-TF | H | Me | H | 1Me-5-1HIdz | C | | 406 (M⁺ + 1) |
| N-a-134 | NA | N-a-133 | | 2-TF | H | H | H | 1Me-5-1HIdz | C | | 392 (M⁺ + 1) |
| N-a-135 | NC1 | Int.n-11 | CHO17 | 2CF3Bn | H | Me | H | 1Me-5-1HIdz | C | | 468 (M⁺ + 1) |
| N-a-136 | NA | N-a-135 | | 2CF3Bn | H | H | H | 1Me-5-1HIdz | C | | 454 (M⁺ + 1) |

TABLE N-A-4

| Exp. | Syn | SM1 | SM2 | Rz | Ry | Y | Zx | AR | LCMS method | R-Time | Mass |
|---|---|---|---|---|---|---|---|---|---|---|---|
| N-a-137 | NE1 | Int.n-9 | 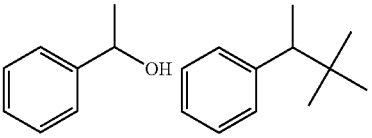 | 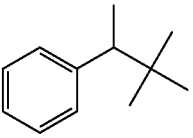 | H | Me | H | 1Me-5-Ind | C | | 413 (M⁺ + 1) |
| N-a-138 | NA | N-a-137 | | 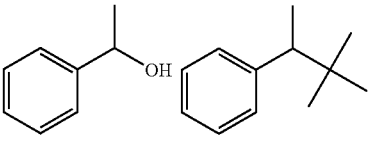 | H | H | H | 1Me-5-Ind | C | | 399 (M⁺ + 1) |
| N-a-139 | NE1 | Int.n-11 | 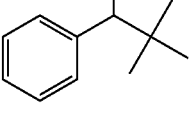 | | H | Me | H | 1Me-5-1HIdz | D | 5.06 | 414 (M⁺ + 1) |
| N-a-140 | NA | N-a-139 | | | H | H | H | 1Me-5-1HIdz | D | 4.30 | 400 (M⁺ + 1) |
| N-a-141 | NE2 | Int.n-11 | 2(4FPh)EtOH | 2(4FPh)Et | H | Me | H | 1Me-5-1HIdz | D | 5.08 | 432 (M⁺ + 1) |
| N-a-142 | NA | N-a-141 | | 2(4FPh)Et | H | H | H | 1Me-5-1HIdz | D | 4.25 | 418 (M⁺ + 1) |
| N-a-143 | NF | N-a-5 | AcCl | Bn | Ac | Me | H | 1Me-5-1HIdz | C | | 444 (M⁺ + 1) |
| N-a-144 | NA | N-a-143 | | Bn | Ac | H | H | 1Me-5-1HIdz | C | | 430 (M⁺ + 1) |
| N-a-145 | NF | N-a-5 | PhCOCl | Bn | PhC(O) | Me | H | 1Me-5-Ind | C | | 504 (M⁺ + 1) |
| N-a-146 | NA | N-a-145 | | Bn | PhC(O) | H | H | 1Me-5-Ind | C | | 490 (M⁺ + 1) |
| N-a-147 | NF | N-a-5 | MeOCH2COCl | Bn | MeOCH₂C(O) | Me | H | 1Me-5-Ind | C | | 472 (M⁺ + 1) |
| N-a-148 | NA | N-a-147 | | Bn | MeOCH₂C(O) | H | H | 1Me-5-Ind | C | | 458 (M⁺ + 1) |

TABLE N-A-4-continued

| Exp. | Syn | SM1 | SM2 | Rz | Ry | Y | Zx | AR | LCMS method | R-Time | Mass |
|---|---|---|---|---|---|---|---|---|---|---|---|
| N-a-149 | NF | N-a-5 | MeOCOCl | Bn | MeOC(O) | Me | H | 1Me-5-Ind | C | | 458 (M$^+$ + 1) |
| N-a-150 | NA | N-a-149 | | Bn | MeOC(O) | H | H | 1Me-5-Ind | C | | 444 (M$^+$ + 1) |
| N-a-151 | NF | N-a-5 | PhOCOCl | Bn | PhOC(O) | Me | H | 1Me-5-Ind | C | | 520 (M$^+$ + 1) |
| N-a-152 | NA | N-a-151 | | Bn | PhOC(O) | H | H | 1Me-5-Ind | C | | 506 (M$^+$ + 1) |
| N-a-153 | NF | N-a-5 | NMe2COCl | Bn | Me$_2$NC(O) | Me | H | 1Me-5-Ind | C | | 471 (M$^+$ + 1) |
| N-a-154 | NA | N-a-153 | | Bn | Me$_2$NC(O) | H | H | 1Me-5-Ind | C | | 457 (M$^+$ + 1) |
| N-a-155 | NF | N-a-11 | AcCl | Bn | Ac | Me | H | 1Me-5-Ind | C | | 442 (M$^+$ + 1) |
| N-a-156 | NA | N-a-155 | | Bn | Ac | H | H | 1Me-5-Ind | C | | 428 (M$^+$ + 1) |
| N-a-157 | NF | N-a-5 | AcCl | 4FBn | Ac | Me | H | 1Me-5-Ind | C | | 461 (M$^+$ + 1) |
| N-a-158 | NA | N-a-157 | | 4FBn | Ac | H | H | 1Me-5-Ind | C | | 447 (M$^+$ + 1) |
| N-a-159 | NF | N-a-5 | MeOCH2COCl | 4FBn | MeOCH$_2$C(O) | Me | H | 1Me-5-Ind | C | | 491 (M$^+$ + 1) |
| N-a-160 | NA | N-a-159 | | 4FBn | MeOCH$_2$C(O) | H | H | 1Me-5-Ind | C | | 477 (M$^+$ + 1) |
| N-a-161 | NF | N-a-5 | MeOCOCl | 4FBn | MeOC(O) | Me | H | 1Me-5-Ind | C | | 477 (M$^+$ + 1) |
| N-a-162 | NA | N-a-161 | | 4FBn | MeOC(O) | H | H | 1Me-5-Ind | C | | 463 (M$^+$ + 1) |
| N-a-163 | NF | N-a-11 | AcCl | 4FBn | Ac | Me | H | 1Me-5-1HIdz | C | | 462 (M$^+$ + 1) |
| N-a-164 | NA | N-a-163 | | 4FBn | Ac | H | H | 1Me-5-1HIdz | C | | 448 (M$^+$ + 1) |
| N-a-165 | NF | N-a-11 | MeOCOCl | 4FBn | MeOC(O) | Me | H | 1Me-5-1HIdz | C | | 478 (M$^+$ + 1) |
| N-a-166 | NA | N-a-165 | | 4FBn | MeOC(O) | H | H | 1Me-5-1HIdz | C | | 464 (M$^+$ + 1) |

Example N-b-1

Synthesis of methyl 3-[4-(N-methylamino)-3-(naphthalen-2-yl)phenyl]propionate (Compound No. N-b-1) (Synthesis method ND1)

According to the procedure described in the synthesis method of Intermediate Int. n-7 (Synthesis method ND1) provided that the reaction was carried out for 2 hours, the compound of Example N-a-25 (100.3 mg) and 10% palladium/carbon (10.2 mg) were reacted and treated to obtain the title compound (Compound No. N-b-1, 89.7 mg).

Example N-b-35

Synthesis of methyl 3-[4-(N-ethylamino)-3-(naphthalen-2-yl)phenyl]propionate (Compound No. N-b-35) (Synthesis method NB1)

According to the procedure described in the synthesis method of the compound of Example N-a-1 (Synthesis method NB1) provided that the reaction was carried out for 17 hours, Intermediate n-12 (99.87 mg), 2-naphthaleneboronic acid (87.3 mg), 2 M aqueous sodium carbonate (350 µl) and (Ph$_3$P)$_4$Pd (59.6 mg) were reacted and treated to obtain the title compound (Compound No. N-b-35, 103.5 mg).

Example N-b-79

Synthesis of methyl 3-[4-(N-n-butylamino)-3-(naphthalen-2-yl)phenyl]propionate (Compound No. N-b-79) (Synthesis method NC2)

According to the procedure described in the synthesis method of Intermediate n-3 provided that the reaction was carried out for 13 hours, Intermediate n-7 (164.7 mg) and n-butylaldehyde (38.5/1, KANTO), sodium triacetoxyborohydride (138.6 mg) and acetic acid (75 µl) were reacted and treated to obtain the title compound (Compound No. N-b-79, 161.3 mg).

Example N-b-183

Synthesis of methyl 3-[4-(N-acetyl-N-methylamino)-3-(naphthalen-2-yl)phenyl]propionate (Compound No. N-b-183) (Synthesis method NF)

According to the procedure described in the synthesis method of the compound of Example N-a-143 provided that the reaction was carried out for 18 hours, the compound of Example N-b-1 (22.7 mg), pyridine (23.8 µl) and acetyl chloride (40 µl) were reacted and treated to obtain the title compound (Compound No. N-b-183, 16.3 mg).

Example N-b-197

Synthesis of 3-[4-(N-benzoyl-N-methylamino)-3-(naphthalen-2-yl)phenyl]propionic acid (Compound No. N-b-197) (Synthesis method NF)

According to the procedure described in the synthesis method of the compound of Example N-a-143 provided that the reaction was carried out for 14 hours, the compound of Example N-b-1 (21.8 mg), pyridine (23.8 µl) and benzoyl chloride (345 µl) were reacted and treated. A solution of the obtained residue in methanol (3 ml) was added with 2 N aqueous sodium hydroxide (100 µl), and stirred at 60° C. for 2 hours. The reaction mixture was concentrated under reduced pressure, then made acidic with 5% aqueous hydrochloric acid under ice cooling, and extracted with dichloromethane (5 ml). The organic layer was washed successively with saturated brine, and dried, and then the solvent was evaporated under reduced pressure to obtain the title compound (Compound No. N-b-197, 13.5 mg).

Examples N-b-1 to N-b-212

Typical examples of the compounds of the present invention that can be obtained by reacting and treating corresponding starting compounds using any of the methods described in the present specification including the examples described above are shown in Table-N-B-1 to Table-N-B-5. In the tables, the compound numbers are mentioned in the columns indicated as "Exp.". In the tables, used methods among the aforementioned synthesis methods are shown in the columns of "Syn" with symbols, the starting compounds 1 are mentioned in the columns of "SM1", and the starting compounds 2 are mentioned in the columns of "SM2".

TABLE N-B-1

[Chemical structure: benzene ring with Rz-N(Ry)- group, Zx substituent, AR substituent, and -CH2CH2-C(=O)-O-Y side chain]

| Exp. | Syn | SM1 | SM2 | Rz | Ry | Y | Zx | AR | LCMS method | RTime | Mass |
|---|---|---|---|---|---|---|---|---|---|---|---|
| N-b-1 | ND1 | N-a-25 | | Me | H | Me | H | 2-Nap | C | | 320 (M⁺ + 1) |
| N-b-2 | NA | N-b-1 | | Me | H | H | H | 2-Nap | C | | 306 (M⁺ + 1) |
| N-b-3 | ND1 | N-aa-29 | | Me | H | Me | H | 5-Ind | C | | 309 (M⁺ + 1) |
| N-b-4 | NA | N-b-3 | | Me | H | H | H | 5-Ind | C | | 295 (M⁺ + 1) |
| N-b-5 | ND1 | N-a-31 | | Me | H | Me | H | 1Me-5-Ind | C | | 323 (M⁺ + 1) |
| N-b-6 | NA | N-b-5 | | Me | H | H | H | 1Me-5-Ind | C | | 309 (M⁺ + 1) |
| N-b-7 | ND1 | N-a-69 | | Me | H | Me | H | 5-1HIdz | C | | 310 (M⁺ + 1) |
| N-b-8 | NA | N-b-7 | | Me | H | H | H | 5-1HIdz | C | | 296 (M⁺ + 1) |
| N-b-9 | ND1 | N-a-49 | | Me | H | Me | H | 1Me-5-1HIdz | C | | 324 (M⁺ + 1) |
| N-b-10 | NA | N-b-9 | | Me | H | H | H | 1Me-5-1HIdz | C | | 310 (M⁺ + 1) |
| N-b-11 | NC2 | N-b-1 | CHO1 | Me | Me | Me | H | 2-Nap | C | | 334 (M⁺ + 1) |
| N-b-12 | NA | N-b-11 | | me | Me | H | H | 2-Nap | C | | 320 (M⁺ + 1) |
| N-b-13 | NC2 | N-b-1 | CHO2 | Me | Et | Me | H | 2-Nap | C | | 348 (M⁺ + 1) |
| N-b-14 | NA | N-b-13 | | Me | Et | H | H | 2-Nap | C | | 334 (M⁺ + 1) |
| N-b-15 | NC2 | N-b-3 | CHO1 | Me | Me | Me | H | 5-Ind | C | | 323 (M⁺ + 1) |
| N-b-16 | NA | N-b-15 | | Me | Me | H | H | 5-Ind | C | | 309 (M⁺ + 1) |
| N-b-17 | NC2 | N-b-5 | CHO1 | Me | Me | Me | H | 1Me-5-Ind | C | | 337 (M⁺ + 1) |
| N-b-18 | NA | N-b-17 | | Me | Me | H | H | 1Me-5-Ind | C | | 323 (M⁺ + 1) |
| N-b-19 | NC2 | N-b-9 | CHO1 | Me | Me | Me | H | 1Me-5-1HIdz | C | | 338 (M⁺ + 1) |
| N-b-20 | NA | N-b-19 | | Me | Me | H | H | 1Me-5-1HIdz | C | | 324 (M⁺ + 1) |
| N-b-21 | NB1 | Intn-12 | BRA1 | Et | H | Me | H | 2-Nap | C | | 334 (M⁺ + 1) |
| N-b-22 | NA | N-b-21 | | Et | H | H | H | 2-Nap | C | | 320 (M⁺ + 1) |
| N-b-23 | NB1 | Int.n-12 | BRA2 | Et | H | me | H | 5-Ind | C | | 323 (M⁺ + 1) |
| N-b-24 | NA | N-b-23 | | Et | H | H | H | 5-Ind | C | | 309 (M⁺ + 1) |
| N-b-25 | NB1 | Int.n-12 | BRA3 | Et | H | me | H | 1Me-5-Ind | C | | 337 (M⁺ + 1) |
| N-b-26 | NA | N-b-25 | | Et | H | H | H | 1Me-5-Ind | C | | 323 (M⁺ + 1) |
| N-b-27 | NB1 | Int.n-12 | BRA4 | Et | H | me | H | 1Et-5-Ind | C | | 351 (M⁺ + 1) |
| N-b-28 | NA | N-b-27 | | Et | H | H | H | 1Et-5-Ind | C | | 337 (M⁺ + 1) |
| N-b-29 | NB1 | Int.n-12 | BRA5 | Et | H | Me | H | 5-1HIdz | C | | 324 (M⁺ + 1) |
| N-b-30 | NA | N-b-29 | | Et | H | H | H | 5-1HIdz | C | | 310 (M⁺ + 1) |
| N-b-31 | NB1 | Int.n-12 | BRA6 | Et | H | Me | H | 1Me-5-1HIdz | C | | 338 (M⁺ + 1) |
| N-b-32 | NA | N-b-31 | | Et | H | H | H | 1Me-5-1HIdz | C | | 324 (M⁺ + 1) |
| N-b-33 | NB1 | Int.n-12 | BRA7 | Et | H | Me | H | 1Et-5-Idz | C | | 352 (M⁺ + 1) |
| N-b-34 | NA | N-b-33 | | Et | H | H | H | 1Et-5-Idz | C | | 338 (M⁺ + 1) |
| N-b-35 | NB1 | Int.n-12 | BRA8 | Et | H | Me | H | 2Me-5-Idz | C | | 338 (M⁺ + 1) |
| N-b-36 | NA | N-b-35 | | Et | H | H | H | 2Me-5-Idz | C | | 324 (M⁺ + 1) |
| N-b-37 | NB1 | Int.n-12 | BRA9 | Et | H | Me | H | 5-Bzt | C | | 341 (M⁺ + 1) |
| N-b-38 | NA | N-b-37 | | Et | H | H | H | 5-Bzt | C | | 327 (M⁺ + 1) |
| N-b-39 | NB1 | Int.n-12 | BRA10 | Et | H | Me | H | 3-Qu | C | | 335 (M⁺ + 1) |
| N-b-40 | NA | N-b-39 | | Et | H | H | H | 3-Qu | C | | 321 (M⁺ + 1) |
| N-b-41 | NB1 | Int.n-12 | BRA11 | Et | H | Me | H | 6-Qu | C | | 335 (M⁺ + 1) |
| N-b-42 | NA | N-b-41 | | Et | H | H | H | 6-Qu | C | | 321 (M⁺ + 1) |
| N-b-43 | NC2 | N-b-21 | CHO2 | Et | Et | me | H | 2-Nap | C | | 362 (M⁺ + 1) |
| N-b-44 | NA | N-b-43 | | Et | Et | H | H | 2-Nap | C | | 348 (M⁺ + 1) |

TABLE N-B-2

| Exp. | Syn. | SM1 | SM2 | Rz | Ry | Y | Zx | AR | LCMS method | RTime | Mass |
|---|---|---|---|---|---|---|---|---|---|---|---|
| N-b-45 | NC2 | N-b-25 | CHO2 | Et | Et | Me | H | 1Me-5-Ind | C | | 365 (M⁺ + 1) |
| N-b-46 | NA | N-b-45 | | Et | Et | H | H | 1Me-5-Ind | C | | 351 (M⁺ + 1) |
| N-b-47 | NB1 | Int.n-13 | | nPr | H | Me | H | 5-Ind | C | | 337 (M⁺ + 1) |
| N-b-48 | NA | N-b-47 | | nPr | H | H | H | 5-Ind | C | | 323 (M⁺ + 1) |
| N-b-49 | NB1 | Int.n-13 | | nPr | H | Me | H | 1Me-5-Ind | C | | 351 (M⁺ + 1) |
| N-b-50 | NA | N-b-49 | | nPr | H | H | H | 1Me-5-Ind | C | | 337 (M⁺ + 1) |
| N-b-51 | NB1 | Int.n-13 | | nPr | H | Me | H | 5-1HIdz | C | | 338 (M⁺ + 1) |
| N-b-52 | NA | N-b-51 | | nPr | H | H | H | 5-1HIdz | C | | 324 (M⁺ + 1) |
| N-b-53 | NB1 | Int.n-13 | | nPr | H | Me | H | 1Me-5-1HIdz | C | | 352 (M⁺ + 1) |

TABLE N-B-2-continued

| Exp. | Syn. | SM1 | SM2 | Rz | Ry | Y | Zx | AR | LCMS method | RTime | Mass |
|---|---|---|---|---|---|---|---|---|---|---|---|
| N-b-54 | NA | N-b-53 | | nPr | H | H | H | 1Me-5-1HIdz | C | | 338 (M⁺ + 1) |
| N-b-55 | NC2 | N-b-47 | CHO1 | nPr | Me | Me | H | 5-Ind | C | | 351 (M⁺ + 1) |
| N-b-56 | NA | N-b-55 | | nPr | Me | H | H | 5-Ind | C | | 337 (M⁺ + 1) |
| N-b-57 | NC2 | N-b-49 | CHO1 | nPr | Me | Me | H | 1Me-5-Ind | C | | 365 (M⁺ + 1) |
| N-b-58 | NA | N-b-57 | | nPr | Me | H | H | 1Me-5-Ind | C | | 351 (M⁺ + 1) |
| N-b-59 | NC2 | N-b-51 | CHO1 | nPr | Me | Me | H | 5-1HIdz | C | | 352 (M⁺ + 1) |
| N-b-60 | NA | N-b-59 | | nPr | Me | H | H | 5-1HIdz | C | | 338 (M⁺ + 1) |
| N-b-61 | NC2 | N-b-53 | CHO1 | nPr | Me | Me | H | 1Me-5-1HIdz | C | | 366 (M⁺ + 1) |
| N-b-62 | NA | N-b-61 | | nPr | Me | H | H | 1Me-5-1HIdz | C | | 352 (M⁺ + 1) |
| N-b-63 | NB1 | Int.n-14 | BRA2 | iPr | H | Me | H | 5-Ind | C | | 337 (M⁺ + 1) |
| N-b-64 | NA | N-b-63 | | iPr | H | H | H | 5-Ind | C | | 323 (M⁺ + 1) |
| N-b-65 | NB1 | Int.n-14 | BRA3 | iPr | H | Me | H | 1Me-5-Ind | C | | 351 (M⁺ + 1) |
| N-b-66 | NA | N-b-65 | | iPr | H | H | H | 1Me-5-Ind | C | | 337 (M⁺ + 1) |
| N-b-67 | NB1 | Int.n-14 | BRA5 | iPr | H | Me | H | 5-1HIdz | C | | 338 (M⁺ + 1) |
| N-b-68 | NA | N-b-67 | | iPr | H | H | H | 5-1HIdz | C | | 324 (M⁺ + 1) |
| N-b-69 | NB1 | Int.n-14 | BRA6 | iPr | H | Me | H | 1Me-5-1HIdz | C | | 352 (M⁺ + 1) |
| N-b-70 | NA | N-b-69 | | iPr | H | H | H | 1Me-5-1HIdz | C | | 338 (M⁺ + 1) |
| N-b-71 | NC2 | N-b-63 | CHO1 | iPr | Me | Me | H | 5-Ind | C | | 351 (M⁺ + 1) |
| N-b-72 | NA | N-b-71 | | iPr | Me | H | H | 5-Ind | C | | 337 (M⁺ + 1) |
| N-b-73 | NC2 | N-b-65 | CHO1 | iPr | Me | Me | H | 1Me-5-Ind | C | | 365 (M⁺ + 1) |
| N-b-74 | NA | N-b-73 | | iPr | Me | H | H | 1Me-5-Ind | C | | 351 (M⁺ + 1) |
| N-b-75 | NC1 | N-b-67 | CHO1 | iPr | Me | Me | H | 5-1HIdz | C | | 352 (M⁺ + 1) |
| N-b-76 | NA | N-b-75 | | iPr | Me | H | H | 5-1HIdz | C | | 338 (M⁺ + 1) |
| N-b-77 | NC1 | N-b-69 | CHO1 | iPr | Me | Me | H | 1Me-5-1HIdz | C | | 366 (M⁺ + 1) |
| N-b-78 | NA | N-b-77 | | iPr | Me | H | H | 1Me-5-1HIdz | C | | 352 (M⁺ + 1) |
| N-b-79 | NB1 | Int.n-7 | BRA1 | nBu | H | Me | H | 2-Nap | C | | 362 (M⁺ + 1) |
| N-b-80 | NA | N-b-79 | | nBu | H | H | H | 2-Nap | C | | 348 (M⁺ + 1) |
| N-b-81 | NB1 | Int.n-8 | BRA2 | nBu | H | Me | H | 5-Ind | C | | 351 (M⁺ + 1) |
| N-b-82 | NA | N-b-81 | | nBu | H | H | H | 5-Ind | C | | 337 (M⁺ + 1) |
| N-b-83 | NB1 | Int.n-10 | BRA5 | nBu | H | Me | H | 5-1HIdz | C | | 352 (M⁺ + 1) |
| N-b-84 | NA | N-b-83 | | nBu | H | H | H | 5-1HIdz | C | | 338 (M⁺ + 1) |
| N-b-85 | NB1 | Int.n-11 | BRA6 | nBu | H | Me | H | 1Me-5-1HIdz | C | | 366 (M⁺ + 1) |
| N-b-86 | NA | N-b-85 | | nBu | H | H | H | 1Me-5-1HIdz | C | | 352 (M⁺ + 1) |
| N-b-87 | NC1 | N-b-79 | CHO1 | nBu | Me | Me | H | 2-Nap | C | | 376 (M⁺ + 1) |
| N-b-88 | NA | N-b-87 | | nBu | Me | H | H | 2-Nap | C | | 351 (M⁺ + 1) |
| N-b-89 | NC1 | N-b-81 | CHO1 | nBu | Me | Me | H | 5-Ind | C | | 365 (M⁺ + 1) |
| N-b-90 | NA | N-b-89 | | nBu | Me | H | H | 5-Ind | C | | 351 (M⁺ + 1) |

TABLE N-B-3

| Exp. | Syn | SM1 | SM2 | Rz | Ry | Y | Zx | AR | LCMS method | RTime | Mass |
|---|---|---|---|---|---|---|---|---|---|---|---|
| N-b-91 | NC1 | N-b-83 | CHO1 | nBu | Me | Me | H | 5-1HIdz | C | | 366 (M⁺ + 1) |
| N-b-92 | NA | N-b-91 | | nBu | Me | H | H | 5-1HIdz | C | | 352 (M⁺ + 1) |
| N-b-93 | NC1 | N-b-85 | CHO1 | nBu | Me | Me | H | 1Me-5-1HIdz | C | | 380 (M⁺ + 1) |
| N-b-94 | NA | N-b-93 | | nBu | Me | H | H | 1Me-5-1HIdz | C | | 366 (M⁺ + 1) |
| N-b-95 | NC2 | N-b-81 | CHO2 | nBu | Et | Me | H | 5-Ind | C | | 379 (M⁺ + 1) |
| N-b-96 | NA | N-b-95 | | nBu | Et | H | H | 5-Ind | C | | 365 (M⁺ + 1) |
| N-b-97 | NC2 | N-b-85 | CHO2 | nBu | Et | Me | H | 1Me-5-1HIdz | C | | 394 (M⁺ + 1) |
| N-b-98 | NA | N-b-97 | | nBu | Et | H | H | 1Me-5-1HIdz | C | | 380 (M⁺ + 1) |
| N-b-99 | NC2 | Int.n-9 | CHO7 | iBu | H | Me | H | 1Me-5-Ind | C | | 365 (M⁺ + 1) |
| N-b-100 | NA | N-b-99 | | iBu | H | H | H | 1Me-5-Ind | C | | 351 (M⁺ + 1) |
| N-b-101 | NC2 | Int.n-10 | CHO7 | iBu | H | Me | H | 5-1HIdz | C | | 352 (M⁺ + 1) |
| N-b-102 | NA | N-b-101 | | iBu | H | H | H | 5-1HIdz | C | | 338 (M⁺ + 1) |
| N-b-103 | NC2 | Int.n-11 | CHO7 | iBu | H | Me | H | 1Me-5-1HIdz | C | | 366 (M⁺ + 1) |
| N-b-104 | NA | N-b-103 | | iBu | H | H | H | 1Me-5-1HIdz | C | | 352 (M⁺ + 1) |
| N-b-105 | NC2 | Int.n-15 | BRA11 | iBu | H | Me | H | 6-Qu | C | | 363 (M⁺ + 1) |
| N-b-106 | NA | N-b-105 | | iBu | H | H | H | 6-Qu | C | | 349 (M⁺ + 1) |
| N-b-107 | NC1 | N-b-99 | CHO1 | iBu | Me | Me | H | 1Me-5-Ind | C | | 379 (M⁺ + 1) |
| N-b-108 | NA | N-b-107 | | iBu | Me | H | H | 1Me-5-Ind | C | | 365 (M⁺ + 1) |
| N-b-109 | NC1 | N-b-103 | CHO1 | iBu | Me | Me | H | 1Me-5-1HIdz | C | | 380 (M⁺ + 1) |
| N-b-110 | NA | N-b-109 | | iBu | Me | H | H | 1Me-5-1HIdz | C | | 366 (M⁺ + 1) |
| N-b-111 | NC1 | N-b-105 | CHO1 | iBu | Me | Me | H | 6-Qu | C | | 377 (M⁺ + 1) |
| N-b-112 | NA | N-b-111 | | iBu | Me | H | H | 6-Qu | C | | 363 (M⁺ + 1) |
| N-b-113 | NC2 | N-b-99 | CHO2 | iBu | Et | Me | H | 1Me-5-Ind | C | | 393 (M⁺ + 1) |
| N-b-114 | NA | N-b-113 | | iBu | Et | H | H | 1Me-5-Ind | C | | 379 (M⁺ + 1) |
| N-b-115 | NC2 | N-b-101 | CHO2 | iBu | Et | Me | H | 5-1HIdz | C | | 380 (M⁺ + 1) |
| N-b-116 | NA | N-b-115 | | iBu | Et | H | H | 5-1HIdz | C | | 366 (M⁺ + 1) |
| N-b-117 | NC2 | N-b-103 | CHO2 | iBu | Et | Me | H | 1Me-5-1HIdz | C | | 394 (M⁺ + 1) |
| N-b-118 | NA | N-b-117 | | iBu | Et | H | H | 1Me-5-1HIdz | C | | 380 (M⁺ + 1) |

TABLE N-B-3-continued

| Exp. | Syn | SM1 | SM2 | Rz | Ry | Y | Zx | AR | LCMS method | RTime | Mass |
|---|---|---|---|---|---|---|---|---|---|---|---|
| N-b-119 | NB1 | Int.n-16 | BRA1 | cPen | H | Me | H | 2-Nap | C | | 374 (M⁺ + 1) |
| N-b-120 | NA | N-b-119 | | cPen | H | H | H | 2-Nap | C | | 360 (M⁺ + 1) |
| N-b-121 | NB1 | Int.n-16 | BRA2 | cPen | H | Me | H | 5-Ind | C | | 363 (M⁺ + 1) |
| N-b-122 | NA | N-b-121 | | cPen | H | H | H | 5-Ind | C | | 349 (M⁺ + 1) |
| N-b-123 | NB1 | Int.n-9 | BRA3 | cPen | H | Me | H | 1Me-5-Ind | C | | 377 (M⁺ + 1) |
| N-b-124 | NA | N-b-123 | | cPen | H | H | H | 1Me-5-Ind | C | | 363 (M⁺ + 1) |
| N-b-125 | NB1 | Int.n-16 | BRA5 | cPen | H | Me | H | 5-1HIdz | C | | 364 (M⁺ + 1) |
| N-b-126 | NA | N-b-125 | | cPen | H | H | H | 5-1HIdz | C | | 350 (M⁺ + 1) |
| N-b-127 | NB1 | Int.n-11 | BRA6 | cPen | H | Me | H | 1Me-5-1HIdz | C | | 378 (M⁺ + 1) |
| N-b-128 | NA | N-b-127 | | cPen | H | H | H | 1Me-5-1HIdz | C | | 364 (M⁺ + 1) |
| N-b-129 | NB1 | Int.n-16 | BRA11 | cPen | H | Me | H | 6-Qu | C | | 375 (M⁺ + 1) |
| N-b-130 | NA | N-b-129 | | cPen | H | H | H | 6-Qu | C | | 361 (M⁺ + 1) |
| N-b-131 | NB1 | Int.n-16 | BRA9 | cPen | H | Me | H | 5-Bzt | C | | 381 (M⁺ + 1) |
| N-b-132 | NA | N-b-131 | | cPen | H | H | H | 5-Bzt | C | | 367 (M⁺ + 1) |
| N-b-133 | NC1 | N-b-121 | CHO1 | cPen | Me | Me | H | 5-Ind | C | | 377 (M⁺ + 1) |
| N-b-134 | NA | N-b-133 | | cPen | Me | H | H | 5-Ind | C | | 363 (M⁺ + 1) |
| N-b-135 | NC1 | N-b-123 | CHO1 | cPen | Me | Me | H | 1Me-5-Ind | C | | 391 (M⁺ + 1) |
| N-b-136 | NA | N-b-135 | | cPen | Me | H | H | 1Me-5-Ind | C | | 377 (M⁺ + 1) |

TABLE N-B-4

| Exp. | Syn. | SM1 | SM2 | Rz | Ry | Y | Zx | AR | LCMS method | RTime | Mass |
|---|---|---|---|---|---|---|---|---|---|---|---|
| N-b-137 | NC1 | N-b-127 | CHO1 | cPen | Me | Me | H | 1Me-5-1HIdz | C | | 392 (M⁺ + 1) |
| N-b-138 | NA | N-b-137 | | cPen | Me | H | H | 1Me-5-1HIdz | C | | 378 (M⁺ + 1) |
| N-b-139 | NC2 | N-b-123 | CHO2 | cPen | Et | Me | H | 1Me-5-Ind | C | | 405 (M⁺ + 1) |
| N-b-140 | NA | N-b-139 | | cPen | Et | H | H | 1Me-5-Ind | C | | 391 (M⁺ + 1) |
| N-b-141 | NC2 | N-b-131 | CHO2 | cPen | Et | Me | H | 5-Bzt | C | | 409 (M⁺ + 1) |
| N-b-142 | NA | N-b-141 | | cPen | Et | H | H | 5-Bzt | C | | 395 (M⁺ + 1) |
| N-b-143 | NB1 | Int.n-17 | BRA1 | cHex | H | Me | H | 2-Nap | C | | 388 (M⁺ + 1) |
| N-b-144 | NA | N-b-143 | | cHex | H | H | H | 2-Nap | C | | 374 (M⁺ + 1) |
| N-b-145 | NB1 | Int.n-17 | BRA2 | cHex | H | Me | H | 5-Ind | C | | 377 (M⁺ + 1) |
| N-b-146 | NA | N-b-145 | | cHex | H | H | H | 5-Ind | C | | 363 (M⁺ + 1) |
| N-b-147 | NB1 | Int.n-9 | BRA3 | cHex | H | Me | H | 1Me-5-Ind | C | | 391 (M⁺ + 1) |
| N-b-148 | NA | N-b-147 | | cHex | H | H | H | 1Me-5-Ind | C | | 377 (M⁺ + 1) |
| N-b-149 | NB1 | Int.n-17 | BRA5 | cHex | H | Me | H | 5-1HIdz | C | | 378 (M⁺ + 1) |
| N-b-150 | NA | N-b-149 | | cHex | H | H | H | 5-1HIdz | C | | 364 (M⁺ + 1) |
| N-b-151 | NB1 | Int.n-17 | BRA6 | cHex | H | Me | H | 1Me-5-1HIdz | C | | 392 (M⁺ + 1) |
| N-b-152 | NA | N-b-151 | | cHex | H | H | H | 1Me-5-1HIdz | C | | 378 (M⁺ + 1) |
| N-b-153 | NB1 | Int.n-17 | BRA10 | cHex | H | Me | H | 3-Qu | C | | 389 (M⁺ + 1) |
| N-b-154 | NA | N-b-153 | | cHex | H | H | H | 3-Qu | C | | 375 (M⁺ + 1) |
| N-b-155 | NC1 | N-b-143 | CHO1 | cHex | Me | Me | H | 2-Nap | C | | 402 (M⁺ + 1) |
| N-b-156 | NA | N-b-155 | | cHex | Me | H | H | 2-Nap | C | | 388 (M⁺ + 1) |
| N-b-157 | NC1 | N-b-147 | CHO1 | cHex | Me | Me | H | 1Me-5-Ind | C | | 405 (M⁺ + 1) |
| N-b-158 | NA | N-b-157 | | cHex | Me | H | H | 1Me-5-Ind | C | | 391 (M⁺ + 1) |
| N-b-159 | NC1 | N-b-149 | CHO1 | cHex | Me | Me | H | 5-1HIdz | C | | 392 (M⁺ + 1) |
| N-b-160 | NA | N-b-159 | | cHex | Me | H | H | 5-1HIdz | C | | 378 (M⁺ + 1) |
| N-b-161 | NC1 | N-b-151 | CHO1 | cHex | Me | Me | H | 1Me-5-1HIdz | C | | 406 (M⁺ + 1) |
| N-b-162 | NA | N-b-161 | | cHex | Me | H | H | 1Me-5-1HIdz | C | | 392 (M⁺ + 1) |
| N-b-163 | NC2 | N-b-143 | CHO2 | cHex | Et | Me | H | 2-Nap | C | | 416 (M⁺ + 1) |
| N-b-164 | NA | N-b-163 | | cHex | Et | H | H | 2-Nap | C | | 402 (M⁺ + 1) |
| N-b-165 | NC2 | N-b-153 | CHO2 | cHex | Et | Me | H | 3-Qu | C | | 417 (M⁺ + 1) |
| N-b-166 | NA | N-b-165 | | cHex | Et | H | H | 3-Qu | C | | 403 (M⁺ + 1) |
| N-b-167 | NB1 | Int.n-18 | BRA2 | 2(Me)cHex | H | Me | H | 5-Ind | C | | 391 (M⁺ + 1) |
| N-b-168 | NA | N-b-167 | | 2(Me)cHex | H | H | H | 5-Ind | C | | 377 (M⁺ + 1) |
| N-b-169 | NB1 | Int.n-18 | BRA3 | 2(Me)cHex | H | Me | H | 1Me-5-Ind | C | | 405 (M⁺ + 1) |
| N-b-170 | NA | N-b-169 | | 2(Me)cHex | H | H | H | 1Me-5-Ind | C | | 391 (M⁺ + 1) |
| N-b-171 | NB1 | Int.n-18 | BRA5 | 2(Me)cHex | H | Me | H | 5-1HIdz | C | | 392 (M⁺ + 1) |
| N-b-172 | NA | N-b-171 | | 2(Me)cHex | H | H | H | 5-1HIdz | C | | 378 (M⁺ + 1) |
| N-b-173 | NB1 | Int.n-18 | BRA6 | 2(Me)cHex | H | Me | H | 1Me-5-1HIdz | C | | 406 (M⁺ + 1) |
| N-b-174 | NA | N-b-173 | | 2(Me)cHex | H | H | H | 1Me-5-1HIdz | C | | 392 (M⁺ + 1) |
| N-b-175 | NC2 | Int.n-8 | CHO25 | 2-Indane | H | Me | H | 5-Ind | C | | 411 (M⁺ + 1) |
| N-b-176 | NA | N-b-175 | | 2-Indane | H | H | H | 5-Ind | C | | 397 (M⁺ + 1) |
| N-b-177 | NC2 | Int.n-9 | CHO25 | 2-Indane | H | Me | H | 1Me-5-Ind | C | | 425 (M⁺ + 1) |
| N-b-178 | NA | N-b-177 | | 2-Indane | H | H | H | 1Me-5-Ind | C | | 411 (M⁺ + 1) |
| N-b-179 | NC2 | Int.n-10 | CHO25 | 2-Indane | H | Me | H | 5-1HIdz | C | | 412 (M⁺ + 1) |
| N-b-180 | NA | N-b-179 | | 2-Indane | H | H | H | 5-1HIdz | C | | 398 (M⁺ + 1) |
| N-b-181 | NC2 | Int.n-11 | CHO25 | 2-Indane | H | Me | H | 1Me-5-1HIdz | C | | 426 (M⁺ + 1) |
| N-b-182 | NA | N-b-181 | | 2-Indane | H | H | H | 1Me-5-1HIdz | C | | 412 (M⁺ + 1) |

TABLE N-B-5

| Exp. | Syn | SM1 | SM2 | Rz | Ry | Y | Zx | AR | LCMS method | RTime | Mass |
|---|---|---|---|---|---|---|---|---|---|---|---|
| N-b-183 | NF | N-b-1 | AcCl | Me | Ac | Me | H | 2-Nap | C | | 364 (M$^+$ + 1) |
| N-b-184 | NA | N-b-183 | | Me | Ac | H | H | 2-Nap | C | | 350 (M$^+$ + 1) |
| N-b-185 | NF | N-b-5 | AcCl | Me | Ac | Me | H | 1Me-5-Ind | C | | 367 (M$^+$ + 1) |
| N-b-186 | NA | N-b-185 | | Me | Ac | H | H | 1Me-5-Ind | C | | 353 (M$^+$ + 1) |
| N-b-187 | NF | N-b-11 | AcCl | Me | Ac | Me | H | 1Me-5-1HIdz | C | | 368 (M$^+$ + 1) |
| N-b-188 | NA | N-b-187 | | Me | Ac | H | H | 1Me-5-1HIdz | C | | 354 (M$^+$ + 1) |
| N-b-189 | NF | Int.n-11 | AcCl | Ac | Ac | me | H | 1Me-5-1HIdz | C | | 394 (M$^+$ + 1) |
| N-b-190 | NA | N-b-189 | | Ac | Ac | H | H | 1Me-5-1HIdz | C | | 380 (M$^+$ + 1) |
| N-b-191 | NF | Int.n-18 | MeOCOCl | Me | MeOC(O) | Me | H | 2-Nap | C | | 380 (M$^+$ + 1) |
| N-b-192 | NA | N-b-167 | | Me | MeOC(O) | H | H | 2-Nap | C | | 366 (M$^+$ + 1) |
| N-b-193 | NF | Int.n-18 | MeOCOCl | Me | MeOC(O) | Me | H | 1Me-5-Ind | C | | 383 (M$^+$ + 1) |
| N-b-194 | NA | N-b-169 | | Me | MeOC(O) | H | H | 1Me-5-Ind | C | | 369 (M$^+$ + 1) |
| N-b-195 | NF | Int.n-18 | MeOCOCl | Me | MeOC(O) | Me | H | 1Me-5-1HIdz | C | | 384 (M$^+$ + 1) |
| N-b-196 | NA | N-b-171 | | Me | MeOC(O) | H | H | 1Me-5-1HIdz | C | | 370 (M$^+$ + 1) |
| N-b-197 | NF-NA | N-b-1 | BzCl | Me | Bz | H | H | 2-Nap | C | | 396 (M$^+$ + 1) |
| N-b-198 | NF-NA | N-b-3 | BzCl | Me | Bz | H | H | 5-Ind | C | | 399 (M$^+$ + 1) |
| N-b-199 | NF-NA | N-b-5 | BzCl | Me | Bz | H | H | 1Me-5-Ind | C | | 399 (M$^+$ + 1) |
| N-b-200 | NF-NA | N-b-9 | BzCl | Me | Bz | H | H | 5-1HIdz | C | | 386 (M$^+$ + 1) |
| N-b-201 | NF-NA | N-b-11 | BzCl | Me | Bz | H | H | 1Me-5-1HIdz | C | | 400 (M$^+$ + 1) |
| N-b-202 | NF-NA | N-b-1 | PhOCOCl | Me | PhOC(O)C(Me)₂– | H | H | 2-Nap | C | | 412 (M$^+$ + 1) |
| N-b-203 | NF-NA | N-b-5 | PhOCOCl | Me | PhOC(O)C(Me)₂– | H | H | 1Me-5-Ind | C | | 415 (M$^+$ + 1) |
| N-b-204 | NF-NA | N-b-1 | cPenCH2COCl | Me | cPenCH₂-C(O)-C(Me)₃ | H | H | 2-Nap | C | | 402 (M$^+$ + 1) |
| N-b-205 | NF-NA | N-b-3 | cPenCH2COCl | Me | cPenCH₂-C(O)-C(Me)₃ | H | H | 1Me-5-Ind | C | | 405 (M$^+$ + 1) |
| N-b-206 | NF-NA | N-b-1 | piperidine-2-COCl | Me | piperidin-2-yl-C(O)-C(Me)₃ | H | H | 2-Nap | C | | 403 (M$^+$ + 1) |
| N-b-207 | NF-NA | N-b-5 | piperidine-2-COCl | Me | piperidin-2-yl-C(O)-C(Me)₃ | H | H | 1Me-5-Ind | C | | 406 (M$^+$ + 1) |
| N-b-208 | NF-NA | N-b-1 | PhNCO | Me | PhNHC(O) | H | H | 2-Nap | C | | 411 (M$^+$ + 1) |
| N-b-209 | NF-NA | N-b-5 | PhNCO | Me | PhNHC(O) | H | H | 1Me-5-Ind | C | | 414 (M$^+$ + 1) |
| N-b-210 | NF-NA | N-b-1 | cHexNCO | Me | cHexNHC(O) | H | H | 2-Nap | C | | 417 (M$^+$ + 1) |
| N-b-211 | NF-NA | N-b-5 | cHexNCO | Me | cHexNHC(O) | H | H | 1Me-5-Ind | C | | 420 (M$^+$ + 1) |
| N-b-212 | NF-NA | N-b-1 | cHexNCS | Me | PhNHC(S) | H | H | 2-Nap | C | | 430 (M$^+$ + 1) |

Example N-c-51
Synthesis of ethyl 3-[4-(imidazol-1-yl)-3-(naphthalen-2-yl)phenyl]acrylate (Compound No. N-c-51) (Synthesis method NB1)

According to the procedure described in the synthesis method of the compound of Example N-a-1 (Synthesis method NB1) provided that the reaction was carried out for 16 hours, and the column chromatography was performed with chloroform:methanol=100:1, Intermediate n-33 (300.4 mg), 2-naphthaleneboronic acid (208.3 mg), 2 M aqueous sodium carbonate (900 μl) and $(Ph_3P)_4Pd$ (108.3 mg) were reacted and treated to obtain the title compound (Intermediate N-c-51, 304.2 mg).

Example N-c-52
Synthesis of 3-[4-(imidazol-1-yl)-3-(naphthalen-2-yl)phenyl]acrylic acid (Compound No. N-c-51) (Synthesis method NA)

According to the procedure described in the synthesis method of the compound of Example N-a-2 (Synthesis method NA) provided that the reaction was carried out for 2 hours, the compound of Example N-c-51 (301.2 mg) and 2 N aqueous sodium hydroxide (980 μl) were reacted and treated to obtain the title compound (Compound No. N-c-52, 286.4 mg).

Examples N-c-1 to N-c-64

Typical examples of the compounds of the present invention that can be obtained by reacting and treating corresponding starting compounds using any of the methods described in the present specification including the examples described above are shown in Table-N-C-1 to Table-N-C-3. In the tables, the compound numbers are mentioned in the columns indicated as "Exp.". In the tables, used methods among the aforementioned synthesis methods are shown in the columns of "Syn" with symbols, the starting compounds 1 are mentioned in the columns of "SM1", and the starting compounds 2 are mentioned in the columns of "SM2".

TABLE N-C-1

| Exp. | Syn | SM1 | SM2 | NRzRy | Y | Zx | AR | LCMS method | RTime | Mass |
|---|---|---|---|---|---|---|---|---|---|---|
| N-c-1 | NB1 | Int.n-36 | BRA1 |  | Me | H | 2-Nap | C | | 358 ($M^+$ + 1) |
| N-c-2 | NA | N-c-1 | |  | H | H | 2-Nap | C | | 344 ($M^+$ + 1) |
| N-c-3 | NB1 | Int.n-36 | BRA2 |  | Me | H | 5-Ind | C | | 347 ($M^+$ + 1) |
| N-c-4 | NA | N-c-3 | |  | H | H | 5-Ind | C | | 333 ($M^+$ + 1) |
| N-c-5 | NB1 | Int.n-36 | BRA3 |  | Me | H | 1Me-5-Ind | C | | 361 ($M^+$ + 1) |
| N-c-6 | NA | N-c-5 | |  | H | H | 1Me-5-Ind | C | | 347 ($M^+$ + 1) |
| N-c-7 | NB1 | Int.n-37 | BRA5 |  | Me | H | 5-1HIdz | C | | 348 ($M^+$ + 1) |
| N-c-8 | NA | N-c-7 | | | H | H | 5-1HIdz | C | | 334 ($M^+$ + 1) |

TABLE N-C-1-continued

| Exp. | Syn | SM1 | SM2 | NRzRy | Y | Zx | AR | LCMS method | RTime | Mass |
|---|---|---|---|---|---|---|---|---|---|---|
| N-c-9 | NB1 | Int.n-36 | BRA6 | pyrrolidine | Me | H | 1Me-51HIdz | C | | 362 (M$^+$ + 1) |
| N-c-10 | NA | N-c-9 | | pyrrolidine | H | H | 1Me-5-1HIdz | C | | 348 (M$^+$ + 1) |
| N-c-11 | NB1 | Int.n-36 | BRA9 | pyrrolidine | Me | H | 5-Bzt | C | | 365 (M$^+$ + 1) |
| N-c-12 | NA | N-c-11 | | pyrrolidine | H | H | 5-Bzt | C | | 351 (M$^+$ + 1) |
| N-c-13 | NB1 | Int.n-36 | BRA10 | pyrrolidine | Me | H | 3-Qu | C | | 359 (M$^+$ + 1) |
| N-c-14 | NA | N-c-13 | | pyrrolidine | H | H | 3-Qu | C | | 345 (M$^+$ + 1) |
| N-c-15 | NB1 | Int.n-36 | BRA11 | pyrrolidine | Me | H | 6-Qu | C | | 359 (M$^+$ + 1) |
| N-c-16 | NA | N-c-15 | | pyrrolidine | H | H | 6-Qu | C | | 345 (M$^+$ + 1) |
| N-c-17 | NB1 | Int.n-37 | BRA1 | morpholine | Me | H | 2-Nap | C | | 374 (M$^+$ + 1) |
| N-c-18 | NA | N-c-17 | | morpholine | H | H | 2-Nap | C | | 360 (M$^+$ + 1) |
| N-c-19 | NB1 | Int.n-37 | BRA2 | morpholine | Me | H | 5-Ind | C | | 363 (M$^+$ + 1) |
| N-c-20 | NA | N-c-19 | | morpholine | H | H | 5-Ind | C | | 349 (M$^+$ + 1) |
| N-c-21 | NB1 | Int.n-37 | BRA3 | morpholine | Me | H | 1Me-5-Ind | C | | 377 (M$^+$ + 1) |

TABLE N-C-1-continued

| Exp. | Syn | SM1 | SM2 | NRzRy | Y | Zx | AR | LCMS method | RTime | Mass |
|---|---|---|---|---|---|---|---|---|---|---|
| N-c-22 | NA | N-c-21 | | morpholine | H | H | 1Me-5-Ind | C | | 363 (M⁺ + 1) |

TABLE N-C-2

| Exp. | Syn. | SM1 | SM2 | NRzRy | Y | Zx | AR | LCMS method | RTime | Mass |
|---|---|---|---|---|---|---|---|---|---|---|
| N-c-23 | NB1 | Int.n-37 | BRA5 | morpholine | Me | H | 5-1HIdz | C | | 364 (M⁺ + 1) |
| N-c-24 | NA | N-c-23 | | morpholine | H | H | 5-1HIdz | C | | 350 (M⁺ + 1) |
| N-c-25 | NB1 | Int.n-37 | BRA6 | morpholine | Me | H | 1Me-5-1HIdz | C | | 378 (M⁺ + 1) |
| N-c-26 | NA | N-c-25 | | morpholine | H | H | 1Me-5-1HIdz | C | | 364 (M⁺ + 1) |
| N-c-27 | NB1 | Int.n-26 | BRA1 | piperidine | Me | H | 2-Nap | C | | 372 (M⁺ + 1) |
| N-c-28 | NA | N-c-27 | | piperidine | H | H | 2-Nap | C | | 358 (M⁺ + 1) |
| N-c-29 | NB1 | Int.n-26 | BRA2 | piperidine | Me | H | 5-Ind | C | | 361 (M⁺ + 1) |
| N-c-30 | NA | N-c-29 | | piperidine | H | H | 5-Ind | C | | 347 (M⁺ + 1) |
| N-c-31 | NB1 | Int.n-26 | BRA3 | piperidine | Me | H | 1Me-5-Ind | C | | 375 (M⁺ + 1) |
| N-c-32 | NA | N-c-31 | | piperidine | H | H | 1Me-5-Ind | C | | 361 (M⁺ + 1) |

TABLE N-C-2-continued

| Exp. | Syn. | SM1 | SM2 | NRzRy | Y | Zx | AR | LCMS method | RTime | Mass |
|---|---|---|---|---|---|---|---|---|---|---|
| N-c-33 | NB1 | Int.n-26 | BRA5 | piperidine | Me | H | 5-1HIdz | C | | 362 (M⁺ + 1) |
| N-c-34 | NA | N-c-33 | | piperidine | H | H | 5-1HIdz | C | | 348 (M⁺ + 1) |
| N-c-35 | NB1 | Int.n-26 | BRA6 | piperidine | Me | H | 1Me-5-1HIdz | C | | 376 (M⁺ + 1) |
| N-c-36 | NA | N-c-35 | | piperidine | H | H | 1Me-5-1HIdz | C | | 362 (M⁺ + 1) |
| N-c-37 | NB1 | Int.n-28 | BRA1 | 4-Me-piperidine | Me | H | 2-Nap | C | | 386 (M⁺ + 1) |
| N-c-38 | NA | N-c-37 | | 4-Me-piperidine | H | H | 2-Nap | C | | 372 (M⁺ + 1) |
| N-c-39 | NB1 | Int.n-28 | BRA3 | 4-Me-piperidine | Me | H | 1Me-5-Ind | C | | 389 (M⁺ + 1) |
| N-c-40 | NA | N-c-39 | | 4-Me-piperidine | H | H | 1Me-5-Ind | C | | 375 (M⁺ + 1) |
| N-c-41 | NB1 | Int.n-28 | BRA5 | 4-Me-piperidine | Me | H | 5-1HIdz | C | | 376 (M⁺ + 1) |
| N-c-42 | NA | N-c-41 | | 4-Me-piperidine | H | H | 5-1HIdz | C | | 362 (M⁺ + 1) |
| N-c-43 | NB1 | Int.n-28 | BRA6 | 4-Me-piperidine | Me | H | 1Me-5-1HIdz | C | | 390 (M⁺ + 1) |
| N-c-44 | NA | N-c-43 | | 4-Me-piperidine | H | H | 1Me-5-1HIdz | C | | 376 (M⁺ + 1) |

TABLE N-C-3

| Exp. | Syn | SM1 | SM2 | NRzRy | Y | Zx | AR | LCMS method | RTime | Mass |
|---|---|---|---|---|---|---|---|---|---|---|
| N-c-45 | NB1 | Int.n-30 | BRA3 | azepane | Me | H | 1Me-5-Ind | C | | 3389 (M⁺ + 1) |

TABLE N-C-3-continued

| Exp. | Syn | SM1 | SM2 | NRzRy | Y | Zx | AR | LCMS method | RTime | Mass |
|---|---|---|---|---|---|---|---|---|---|---|
| N-c-46 | NA | N-c-45 | | 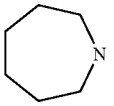 | H | H | 1Me-5-Ind | C | | 375 (M+ + 1) |
| N-c-47 | NB1 | Int.n-30 | BRA5 | 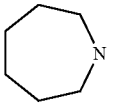 | Me | H | 5-1HIdz | C | | 376 (M+ + 1) |
| N-c-48 | NA | N-c-47 | | 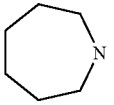 | H | H | 5-1HIdz | C | | 362 (M+ + 1) |
| N-c-49 | NB1 | Int.n-30 | BRA6 | 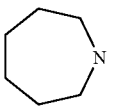 | Me | H | 1Me-5-1HIdz | C | | 390 (M+ + 1) |
| N-c-50 | NA | N-c-49 | | 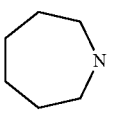 | H | H | 1Me-5-1HIdz | C | | 376 (M+ + 1) |
| N-c-51 | NB1 | Int.n-33 | BRA1 | 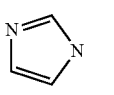 | Et | H | 2-Nap | C | | 369 (M+ + 1) |
| N-c-52 | NA | N-c-51 | | 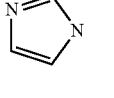 | H | H | 2-Nap | C | | 341 (M+ + 1) |
| N-c-53 | NB1 | Int.n-33 | BRA33 | 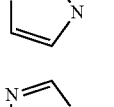 | Et | H | 1Me-5-Ind | C | | 372 (M+ + 1) |
| N-c-54 | NA | N-c-53 | | 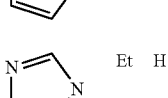 | H | H | 1Me-5-Ind | C | | 344 (M+ + 1) |
| N-c-55 | NB1 | Int.n-33 | BRA6 | 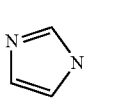 | Et | H | 1Me-5-1HIdz | C | | 373 (M+ + 1) |
| N-c-56 | NA | N-c-55 | | 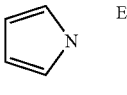 | H | H | 1Me-5-1HIdz | C | | 345 (M+ + 1) |
| N-c-57 | NB1 | Int.n-35 | BRA1 | 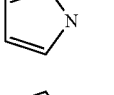 | Et | H | 2-Nap | C | | 368 (M+ + 1) |
| N-c-58 | NA | N-c-57 | | 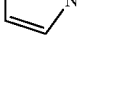 | H | H | 2-Nap | C | | 340 (M+ + 1) |
| N-c-59 | NB1 | Int.n-35 | BRA3 |  | Et | H | 1Me-5-Ind | C | | 371 (M+ + 1) |

TABLE N-C-3-continued

| Exp. | Syn | SM1 | SM2 | NRzRy | Y | Zx | AR | LCMS method | RTime | Mass |
|---|---|---|---|---|---|---|---|---|---|---|
| N-c-60 | NA | N-c-59 | |  | H | H | 1Me-5-Ind | C | | 343 (M$^+$ + 1) |
| N-c-61 | NB1 | Int.n35 | BRA5 |  | Et | H | 5-1HIdz | C | | 358 (M$^+$ + 1) |
| N-c-62 | NA | N-c-61 | |  | H | H | 5-1HIdz | C | | 330 (M$^+$ + 1) |
| N-c-63 | NB1 | Int.n-35 | BRA6 |  | Et | H | 1Me-5-1HIdz | C | | 372 (M$^+$ + 1) |
| N-c-64 | NA | N-c-63 | |  | H | H | 1Me-5-1HIdz | C | | 344 (M$^+$ + 1) |

Example N-d-61

Synthesis of ethyl 3-[4-(imidazol-1-yl)-3-(naphthalen-2-yl)phenyl]propionate (Compound No. N-d-51) (Synthesis method ND1)

According to the procedure described in the synthesis method of Intermediate n-7 (Synthesis method ND1) provided that the reaction was carried out for 6 hours, the compound of Example N-c-51 (301.5 mg) and 10% palladium/carbon (67.3 mg) were reacted and treated to obtain the title compound (Compound No. N-d-61, 143.5 mg).

Example N-d-62

Synthesis of 3-[4-(imidazol-1-yl)-3-(naphthalen-2-yl)phenyl]propionic acid (Compound No. N-d-62) (Synthesis method NA)

According to the procedure described in the synthesis method of the compound of Example N-a-2 (Synthesis method NA) provided that the reaction was carried out for 3 hours, the compound of Example N-d-61 (140.3 mg) and 2 N aqueous sodium hydroxide (600 µl) were reacted and treated to obtain the title compound (Compound No. N-d-62, 100.4 mg).

Examples N-d-1 to N-d-74

Typical examples of the compounds of the present invention that can be obtained by reacting and treating corresponding starting compounds using any of the methods described in the present specification including the examples described above are shown in Table-N-D-1 to Table-N-D-4. In the tables, the compound numbers are mentioned in the columns indicated as "Exp.". In the tables, used methods among the aforementioned synthesis methods are shown in the columns of "Syn" with symbols, the starting compounds 1 are mentioned in the columns of "SM1", and the starting compounds 2 are mentioned in the columns of "SM2".

TABLE N-D-1

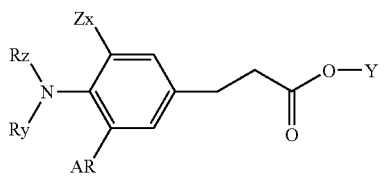

| Exp. | Syn | SM1 | SM2 | NRzRy | Y | Zx | AR | LCMS method | RTime | Mass |
|---|---|---|---|---|---|---|---|---|---|---|
| N-d-1 | NB1 | Int.n-21 | BRA1 |  | Me | H | 2-Nap | C | | 360 (M$^+$ + 1) |

TABLE N-D-1-continued

| Exp. | Syn | SM1 | SM2 | NRzRy | Y | Zx | AR | LCMS method | RTime | Mass |
|---|---|---|---|---|---|---|---|---|---|---|
| N-d-2 | NA | N-d-1 | |  | H | H | 2-Nap | C | | 346 (M⁺ + 1) |
| N-d-3 | NB1 | Int.n-21 | BRA2 |  | Me | H | 5-Ind | D | 4.79 | 349 (M⁺ + 1) |
| N-d-4 | NA | N-d-3 | |  | H | H | 5-Ind | D | 3.54 | 335 (M⁺ + 1) |
| N-d-5 | NB1 | Int.n-21 | BRA3 |  | Me | H | 1Me-5-Ind | D | 5.72 | 363 (M⁺ + 1) |
| N-d-6 | NA | N-d-5 | |  | H | H | 1Me-5-Ind | D | 4.31 | 349 (M⁺ + 1) |
| N-d-7 | NB1 | Int.n-21 | BRA5 |  | Me | H | 5-1HIdz | C | | 350 (M⁺ + 1) |
| N-d-8 | NA | N-d-7 | |  | H | H | 5-1HIdz | C | | 336 (M⁺ + 1) |
| N-d-9 | NB1 | Int.n-21 | BRA6 |  | Me | H | 1Me-5-1HIdz | C | | 364 (M⁺ + 1) |
| N-d-10 | NA | N-d-9 | |  | H | H | 1Me-5-1HIdz | C | | 350 (M⁺ + 1) |
| N-d-11 | NB1 | Int.n-21 | BRA9 |  | Me | H | 5-Bzt | C | | 367 (M⁺ + 1) |
| N-d-12 | NA | N-d-11 | |  | H | H | 5-Bzt | C | | 353 (M⁺ + 1) |
| N-d-13 | NB1 | Int.n-21 | BRA10 |  | Me | H | 3-Qu | C | | 361 (M⁺ + 1) |
| N-d-14 | NA | N-d-13 | |  | H | H | 3-Qu | C | | 347 (M⁺ + 1) |
| N-d-15 | NB1 | Int.n-21 | BRA11 |  | Me | H | 6-Qu | C | | 361 (M⁺ + 1) |

TABLE N-D-1-continued

| Exp. | Syn | SM1 | SM2 | NRzRy | Y | Zx | AR | LCMS method | RTime | Mass |
|---|---|---|---|---|---|---|---|---|---|---|
| N-d-16 | NA | N-d-15 | | pyrrolidine | H | H | 6-Qu | C | | 347 (M$^+$ + 1) |
| N-d-17 | NB1 | Int.n-24 | BRA1 | morpholine | Me | H | 2-Nap | C | | 376 (M$^+$ + 1) |
| N-d-18 | NA | N-d-17 | | morpholine | H | H | 2-Nap | C | | 362 (M$^+$ + 1) |
| N-d-19 | NB1 | Int.n-24 | BRA2 | morpholine | Me | H | 5-Ind | C | | 365 (M$^+$ + 1) |
| N-d-20 | NA | N-d-19 | | morpholine | H | H | 5-Ind | C | | 351 (M$^+$ + 1) |
| N-d-21 | NB1 | Int.n-24 | BRA3 | morpholine | Me | H | 1Me-5-Ind | C | | 379 (M$^+$ + 1) |
| N-d-22 | NA | N-d-21 | | morpholine | H | H | 1Me-5-Ind | C | | 365 (M$^+$ + 1) |

TABLE N-D-2

| Exp. | Syn | SM1 | SM2 | NRzRy | Y | Zx | AR | LCMS method | RTime | Mass |
|---|---|---|---|---|---|---|---|---|---|---|
| N-d-23 | NB1 | Int.n-24 | BRA5 | morpholine | Me | H | 5-1HIdz | C | | 366 (M$^+$ + 1) |
| N-d-24 | NA | N-d-23 | | morpholine | H | H | 5-1HIdz | C | | 352 (M$^+$ + 1) |
| N-d-25 | NB1 | Int.n-24 | BRA6 | morpholine | Me | H | 1Me-5-1HIdz | C | | 380 (M$^+$ + 1) |
| N-d-26 | NA | N-d-25 | | morpholine | H | H | 1Me-5-1HIdz | C | | 366 (M$^+$ + 1) |
| N-d-27 | NB1 | Int.n-24 | BRA9 | morpholine | Me | H | 5-Bzt | C | | 383 (M$^+$ + 1) |

TABLE N-D-2-continued

| Exp. | Syn | SM1 | SM2 | NRzRy | Y | Zx | AR | LCMS method | RTime | Mass |
|---|---|---|---|---|---|---|---|---|---|---|
| N-d-28 | NA | N-d-27 | |  | H | H | 5-Bzt | C | | 369 (M⁺ + 1) |
| N-d-29 | NB1 | Int.n-24 | BRA11 |  | Me | H | 6-Qu | C | | 377 (M⁺ + 1) |
| N-d-30 | NA | N-d-29 | |  | H | H | 6-Qu | C | | 363 (M⁺ + 1) |
| N-d-31 | NB1 | Int.n-27 | BRA1 | 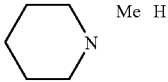 | Me | H | 2-Nap | C | | 374 (M⁺ + 1) |
| N-d-32 | NA | N-d-31 | | 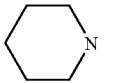 | H | H | 2-Nap | C | | 360 (M⁺ + 1) |
| N-d-33 | NB1 | Int.n-27 | BRA2 | 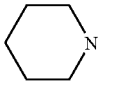 | Me | H | 5-Ind | C | | 363 (M⁺ + 1) |
| N-d-34 | NA | N-d-33 | |  | H | H | 5-Ind | C | | 349 (M⁺ + 1) |
| N-d-35 | NB1 | Int.n-27 | BRA3 | 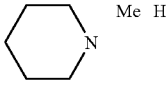 | Me | H | 1Me-5-Ind | C | | 377 (M⁺ + 1) |
| N-d-36 | NA | N-d-35 | | 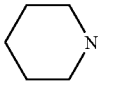 | H | H | 1Me-5-Ind | C | | 363 (M⁺ + 1) |
| N-d-37 | NB1 | Int.n-27 | BRA5 | 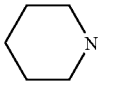 | Me | H | 5-1HIdz | C | | 364 (M⁺+ 1) |
| N-d-38 | NA | N-d-37 | | 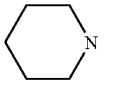 | H | H | 5-1HIdz | C | | 350 (M⁺ + 1) |
| N-d-39 | NB1 | Int.n-27 | BRA6 | 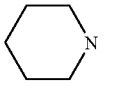 | Me | H | 1Me-5-1HIdz | C | | 378 (M⁺ + 1) |
| N-d-40 | NA | N-d-39 | | 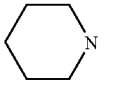 | H | H | 1Me-5-1HIdz | C | | 364 (M⁺+ 1) |
| N-d-41 | NB1 | Int.n-27 | BRA11 | 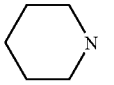 | Me | H | 6-Qu | C | | 375 (M⁺ + 1) |
| N-d-42 | NA | N-d-41 | | 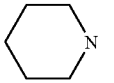 | H | H | 6-Qu | C | | 361 (M⁺ + 1) |

TABLE N-D-2-continued

| Exp. | Syn | SM1 | SM2 | NRzRy | Y | Zx | AR | LCMS method | RTime | Mass |
|---|---|---|---|---|---|---|---|---|---|---|
| N-d-43 | NB1 | Int.n-27 | BRA9 | piperidine | Me | H | 5-Bzt | C | | 381 (M⁺ + 1) |
| N-d-44 | NA | N-d-43 | | piperidine | H | H | 5-Bzt | C | | 367 (M⁺ + 1) |

TABLE N-D-3

| Exp. | Syn | SM1 | SM2 | NRzRy | Y | Zx | AR | LCMS method | RTime | Mass |
|---|---|---|---|---|---|---|---|---|---|---|
| N-d-45 | NB1 | Int.n-29 | BRA1 | 4-Me-piperidine | Me | H | 2-Nap | C | | 388 (M⁺ + 1) |
| N-d-46 | NA | N-d-45 | | 4-Me-piperidine | H | H | 2-Nap | C | | 374 (M⁺+ 1) |
| N-d-47 | NB1 | Int.n-29 | BRA3 | 4-Me-piperidine | Me | H | 1Me-5-Ind | C | | 391 (M⁺ + 1) |
| N-d-48 | NA | N-d-47 | | 4-Me-piperidine | H | H | 1Me-5-Ind | C | | 377 (M⁺ + 1) |
| N-d-49 | NB1 | Int.n-29 | BRA5 | 4-Me-piperidine | Me | H | 5-1Idz | C | | 378 (M⁺ + 1) |
| N-d-50 | NA | N-d-49 | | 4-Me-piperidine | H | H | 5-1Idz | C | | 364 (M⁺ + 1) |
| N-d-51 | NB1 | Int.n-29 | BRA6 | 4-Me-piperidine | Me | H | 1Me-5-1HIdz | C | | 392 (M⁺ + 1) |
| N-d-52 | NA | N-d-51 | | 4-Me-piperidine | H | H | 1Me-5-1HIdz | C | | 378 (M⁺ + 1) |
| N-d-53 | NB1 | Int.n-29 | BRA10 | 4-Me-piperidine | Me | H | 3-Qu | C | | 389 (M⁺ + 1) |
| N-d-54 | NA | N-d-53 | | 4-Me-piperidine | H | H | 3-Qu | C | | 375 (M⁺ + 1) |
| N-d-55 | NB1 | Int.n-31 | BRA3 | azepane | Me | H | 1Me-5-Ind | C | | 391 (M⁺ + 1) |

TABLE N-D-3-continued

| Exp. | Syn | SM1 | SM2 | NRzRy | Y | Zx | AR | LCMS method | RTime | Mass |
|---|---|---|---|---|---|---|---|---|---|---|
| N-d-56 | NA | N-d-55 | | 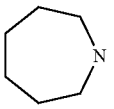 | H | H | 1Me-5-Ind | C | | 377 (M⁺ + 1) |
| N-d-57 | NB1 | Int.n-31 | BRA5 | 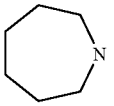 | Me | H | 5-1Idz | C | | 378 (M⁺ + 1) |
| N-d-58 | NA | N-d-57 | | 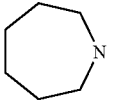 | H | H | 5-1Idz | C | | 364 (M⁺ + 1) |
| N-d-59 | NB1 | Int.n-31 | BRA6 | 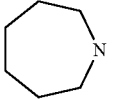 | Me | H | 1Me-5-1HIdz | C | | 392 (M⁺ + 1) |
| N-d-60 | NA | N-d-59 | | 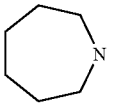 | H | H | 1Me-5-1HIdz | C | | 378 (M⁺ + 1) |
| N-d-61 | ND1 | N-c-51 | | 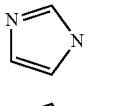 | Et | H | 2-Nap | C | | 371 (M⁺ + 1) |
| N-d-62 | NA | N-d-61 | | 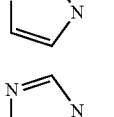 | H | H | 2-Nap | C | | 343 (M⁺ + 1) |
| N-d-63 | ND1 | N-c-53 | | 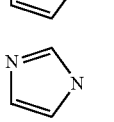 | Et | H | 1Me-5-Ind | C | | 374 (M⁺ + 1) |
| N-d-64 | NA | N-d-63 | | 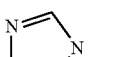 | H | H | 1Me-5-Ind | C | | 346 (M⁺ + 1) |
| N-d-65 | ND1 | N-c-55 | | 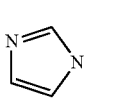 | Et | H | 1Me-5-1HIdz | C | | 375 (M⁺ + 1) |
| N-d-66 | NA | N-d-65 | |  | H | H | 1Me-5-1HIdz | C | | 347 (M⁺ + 1) |

TABLE N-D-4

| Exp. | Syn. | SM1 | SM2 | NRzRy | Y | Zx | AR | LCMS method | RTime | Mass |
|---|---|---|---|---|---|---|---|---|---|---|
| N-d-67 | ND1 | N-c-57 | |  | Et | H | 2-Nap | C | | 370 (M⁺ + 1) |
| N-d-68 | NA | N-d-45 | |  | H | H | 2-Nap | C | | 342 (M⁺ + 1) |

TABLE N-D-4-continued

| Exp. | Syn. | SM1 | SM2 | NRzRy | Y | Zx | AR | LCMS method | RTime | Mass |
|---|---|---|---|---|---|---|---|---|---|---|
| N-d-69 | ND1 | N-c-59 | |  | Et | H | 1Me-5-Ind | C | | 373 (M⁺ + 1) |
| N-d-70 | NA | N-d-47 | |  | H | H | 1Me-5-Ind | C | | 345 (M⁺ + 1) |
| N-d-71 | ND1 | N-c-61 | |  | Et | H | 5-1Idz | C | | 360 (M⁺ + 1) |
| N-d-72 | NA | N-d-49 | |  | H | H | 5-1Idz | C | | 332 (M⁺ + 1) |
| N-d-73 | ND1 | N-c-63 | |  | Et | H | 1Me-5-1HIdz | C | | 374 (M⁺ + 1) |
| N-d-74 | NA | N-d-51 | |  | H | H | 1Me-5-1HIdz | C | | 346 (M⁺ + 1) |

Examples N-e-1 to N-e-204

Typical examples of the compounds of the present invention that can be obtained by reacting and treating corresponding starting compounds using any of the methods described in the present specification are shown in Table-N-E-1 to Table-N-E-7. In the tables, the compound numbers are mentioned in the columns indicated as "Exp.". In the tables, corresponding methods among the aforementioned synthesis methods are shown in the columns of "Syn" with symbols, the starting compounds 1 are mentioned in the columns of "SM1", and the starting compounds 2 are mentioned in the columns of "SM2".

TABLE N-E-1

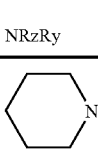

| Exp. | Syn | SM1 | SM2 | NRzRy | Y | AR | LCMS method | RTime | Mass |
|---|---|---|---|---|---|---|---|---|---|
| N-e-1 | NB1 | Int.n-48 | BRA1 | 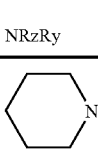 | Et | 2-Nap | C | | 389 (M⁺ + 1) |
| N-e-2 | NA | N-e-1 | |  | H | 2-Nap | C | | 375 (M⁺ + 1) |
| N-e-3 | NB1 | Int.n-48 | BRA2 |  | Et | 5-Ind | C | | 378 (M⁺ + 1) |
| N-e-4 | NA | N-e-3 | |  | H | 5-Ind | C | | 364 (M⁺ + 1) |

TABLE N-E-1-continued
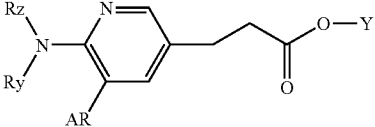
| Exp. | Syn | SM1 | SM2 | NRzRy | Y | AR | LCMS method | RTime | Mass |
|---|---|---|---|---|---|---|---|---|---|
| N-e-5 | NB1 | Int.n-48 | BRA3 | 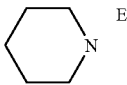 | Et | 1Me-5-Ind | C | | 392 (M⁺ + 1) |
| N-e-6 | NA | N-e-5 | | 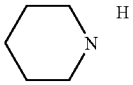 | H | 1Me-5-Ind | C | | 378 (M⁺ + 1) |
| N-e-7 | NB1 | Int.n-48 | BRA5 | 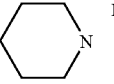 | Et | 5-1HIdz | C | | 379 (M⁺ + 1) |
| N-e-8 | NA | N-e-7 | | 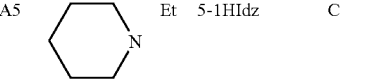 | H | 5-1HIdz | C | | 365 (M⁺ + 1) |
| N-e-9 | NB1 | Int.n-48 | BRA6 | 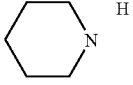 | Et | 1Me-5-1HIdz | C | | 393 (M⁺ + 1) |
| N-e-10 | NA | N-e-9 | | 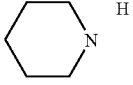 | H | 1Me-5-1HIdz | C | | 379 (M⁺ + 1) |
| N-e-11 | NB1 | Int.n-48 | BRA10 | 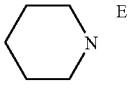 | Et | 3-Qu | C | | 390 (M⁺ + 1) |
| N-e-12 | NA | N-e-11 | |  | H | 3-Qu | C | | 376 (M⁺ + 1) |
| N-e-13 | NB1 | Int.n-48 | BRA11 | 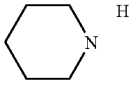 | Et | 6-Qu | C | | 390 (M⁺ + 1) |
| N-e-14 | NA | N-e-13 | | 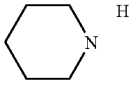 | H | 6-Qu | C | | 376 (M⁺ + 1) |
| N-e-15 | NB1 | Int.n-48 | BRA12 | 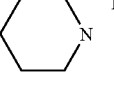 | Et | 6-IQ | C | | 390 (M⁺ + 1) |
| N-e-16 | NA | N-e-15 | | 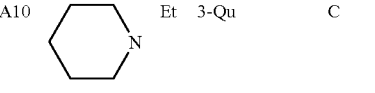 | H | 6-IQ | C | | 376 (M⁺ + 1) |
| N-e-17 | NB1 | Int.n-49 | BRA1 | 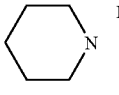 | Et | 2Nap | C | | 375 (M⁺ + 1) |
| N-e-18 | NA | N-e-17 | | 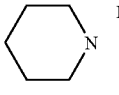 | H | 2Nap | C | | 361 (M⁺ + 1) |

TABLE N-E-1-continued

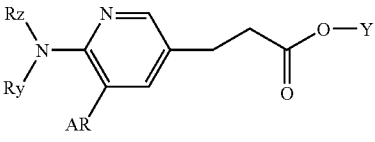

| Exp. | Syn | SM1 | SM2 | NRzRy | Y | AR | LCMS method | RTime | Mass |
|---|---|---|---|---|---|---|---|---|---|
| N-e-19 | NB1 | Int.n-49 | BRA2 |  | Et | 5-Ind | C | | 364 (M⁺ + 1) |
| N-e-20 | NA | N-e-19 | |  | H | 5-Ind | C | | 350 (M⁺ + 1) |
| N-e-21 | NB1 | Int.n-49 | BRA3 |  | Et | 1Me-5-Ind | C | | 378 (M⁺ + 1) |
| N-e-22 | NA | N-e-21 | |  | H | 1Me-5-Ind | C | | 364 (M⁺ + 1) |

TABLE N-E-2

| Exp. | Syn | SM1 | SM2 | NRzRy | Y | Ar | LCMS method | RTime | Mass |
|---|---|---|---|---|---|---|---|---|---|
| N-e-23 | NB1 | Int.n-49 | BRA5 |  | Et | 5-1HIdz | C | | 365 (M⁺ + 1) |
| N-e-24 | NA | N-e-23 | |  | H | 5-1HIdz | C | | 351 (M⁺ + 1) |
| N-e-25 | NB1 | Int.n-49 | BRA6 |  | Et | 1Me-5-1HIdz | C | | 379 (M⁺ + 1) |
| N-e-26 | NA | N-e-25 | |  | H | 1Me-5-1HIdz | C | | 365 (M⁺ + 1) |
| N-e-27 | NB1 | Int.n-50 | BRA1 |  | Et | 2-Nap | C | | 403 (M⁺ + 1) |
| N-e-28 | NA | N-e-27 | |  | H | 2-Nap | C | | 389 (M⁺ + 1) |
| N-e-29 | NB1 | Int.n-50 | BRA2 |  | Et | 5-Ind | C | | 392 (M⁺ + 1) |
| N-e-30 | NA | N-e-29 | | | H | 5-Ind | C | | 378 (M⁺ + 1) |

TABLE N-E-2-continued

| Exp. | Syn | SM1 | SM2 | NRzRy | Y | Ar | LCMS method | RTime | Mass |
|---|---|---|---|---|---|---|---|---|---|
| N-e-31 | NB1 | Int.n-50 | BRA3 | 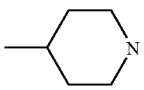 | Et | 1Me-5-Ind | C | | 406 (M$^+$ + 1) |
| N-e-32 | NA | N-e-31 | | 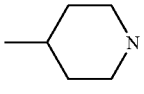 | H | 1Me-5-Ind | C | | 392 (M$^+$ + 1) |
| N-e-33 | NB1 | Int.n-50 | BRA5 | 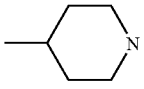 | Et | 5-1HIdz | C | | 393 (M$^+$ + 1) |
| N-e-34 | NA | N-e-33 | | 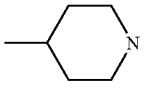 | H | 5-1HIdz | C | | 379 (M$^+$ + 1) |
| N-e-35 | NB1 | Int.n-50 | BRA6 | 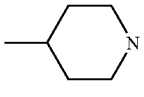 | Et | 1Me-5-iHIdz | C | | 407 (M$^+$ + 1) |
| N-e-36 | NA | N-e-35 | | 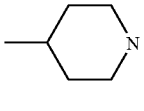 | H | 1Me-5-1HIdz | C | | 393 (M$^+$ + 1) |
| N-e-37 | NB1 | Int.n-51 | BRA1 | 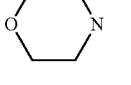 | Et | 2-Nap | C | | 391 (M$^+$ + 1) |
| N-e-38 | NA | N-e-37 | | 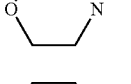 | H | 2-Nap | C | | 377 (M$^+$ + 1) |
| N-e-39 | NB1 | Int.n-51 | BRA3 | 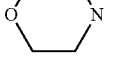 | Et | 1Me-5-Ind | C | | 394 (M$^+$ + 1) |
| N-e-40 | NA | N-e-39 | | 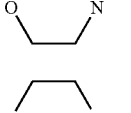 | H | 1Me-5-Ind | C | | 380 (M$^+$ + 1) |
| N-e-41 | NB1 | Int.n-51 | BRA5 | 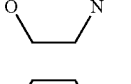 | Et | 5-1HIdz | C | | 381 (M$^+$ + 1) |
| N-e-42 | NA | N-e-41 | | 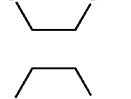 | H | 5-1HIdz | C | | 367 (M$^+$ + 1) |
| N-e-43 | NB1 | Int.n-51 | BRA6 | 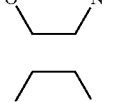 | Et | 1Me-5-1HIdz | C | | 395 (M$^+$ + 1) |
| N-e-44 | NA | N-e-43 | | 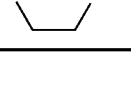 | H | 1Me-5-1HIdz | C | | 381 (M$^+$ + 1) |

TABLE N-E-3

| Exp. | Syn | SM1 | SM2 | NRzRy | Y | AR | LCMS method | RTime | Mass |
|---|---|---|---|---|---|---|---|---|---|
| N-e-45 | NB1 | Int.n-52 | BRA1 |  | Et | 2-Nap | C | | 403 (M⁺ + 1) |
| N-e-46 | NA | N-e-45 | |  | H | 2-Nap | C | | 389 (M⁺ + 1) |
| N-e-47 | NB1 | Int.n-52 | BRA3 |  | Et | 1Me-5-Ind | C | | 406 (M⁺ + 1) |
| N-e-48 | NA | N-e-47 | |  | H | 1Me-5-Ind | C | | 392 (M⁺ + 1) |
| N-e-49 | NB1 | Int.n-52 | BRA5 |  | Et | 5-1HIdz | C | | 393 (M⁺ + 1) |
| N-e-50 | NA | N-e-49 | |  | H | 5-1HIdz | C | | 379 (M⁺ + 1) |
| N-e-51 | NB1 | Int.n-52 | BRA6 |  | Et | 1Me-5-1HIdz | C | | 393 (M⁺ + 1) |
| N-e-52 | NA | N-e-51 | |  | H | 1Me-5-1HIdz | C | | 393 (M⁺ + 1) |

TABLE N-E-4

| Exp. | Syn | SM1 | SM2 | Rz | Ry | Y | AR | LCMS method | RTime | Mass |
|---|---|---|---|---|---|---|---|---|---|---|
| N-e-53 | NB1 | Int.n-53 | BRA1 | Et | Me | Et | 2-Nap | C | | 363 (M⁺ + 1) |
| N-e-54 | NA | N-e-53 | | Et | Me | H | 2-Nap | C | | 335 (M⁺ + 1) |
| N-e-55 | NB1 | Int.n-53 | NRA2 | Et | Me | Et | 5-Ind | C | | 352 (M⁺ + 1) |
| N-e-56 | NA | N-e-55 | | Et | Me | H | 5-Ind | C | | 324 (M⁺ + 1) |
| N-e-57 | NB1 | Int.n-53 | BRA3 | Et | Me | Et | 1Me-5-Ind | C | | 366 (M⁺ + 1) |
| N-e-58 | NA | N-e-57 | | Et | Me | H | 1Me-5-Ind | C | | 338 (M⁺ + 1) |
| N-e-59 | NB1 | Int.n-53 | BRA5 | Et | Me | Et | 5-1HIdz | C | | 353 (M⁺ + 1) |
| N-e-60 | NA | N-e-59 | | Et | Me | H | 5-1HIdz | C | | 325 (M⁺ + 1) |
| N-e-61 | NB1 | Int.n-53 | BRA6 | Et | Me | Et | 1Me-5-1HIdz | C | | 367 (M⁺ + 1) |
| N-e-62 | NA | N-e-61 | | Et | Me | H | 1Me-5-1HIdz | C | | 339 (M⁺ + 1) |
| N-e-63 | NB1 | Int.n-54 | BRA1 | Et | Et | Et | 2-Nap | C | | 377 (M⁺ + 1) |
| N-e-64 | NA | N-b-63 | | Et | Et | H | 2-Nap | C | | 349 (M⁺ + 1) |

TABLE N-E-4-continued

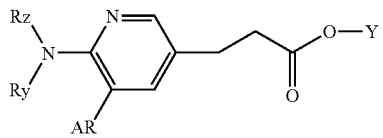

| Exp. | Syn | SM1 | SM2 | Rz | Ry | Y | AR | LCMS method | RTime | Mass |
|---|---|---|---|---|---|---|---|---|---|---|
| N-e-65 | NB1 | Int.n-54 | BRA2 | Et | Et | Et | 5-Ind | C | | 366 (M$^+$ + 1) |
| N-e-66 | NA | N-b-65 | | Et | Et | H | 5-Ind | C | | 338 (M$^+$ + 1) |
| N-e-67 | NB1 | Int.n-54 | BRA3 | Et | Et | Et | 1Me-5-Ind | C | | 380 (M$^+$ + 1) |
| N-e-68 | NA | N-b-67 | | Et | Et | H | 1Me-5-Ind | C | | 352 (M$^+$ + 1) |
| N-e-69 | NB1 | Int.n-54 | BRA5 | Et | Et | Et | 5-1HIdz | C | | 367 (M$^+$ + 1) |
| N-e-70 | NA | N-b-69 | | Et | Et | H | 5-1HIdz | C | | 339 (M$^+$ + 1) |
| N-e-71 | NB1 | Int.n-54 | BRA6 | Et | Et | Et | 1Me-5-1HIdz | C | | 381 (M$^+$ + 1) |
| N-e-72 | NA | N-b-71 | | Et | Et | H | 1Me-5-1HIdz | C | | 353 (M$^+$ + 1) |
| N-e-73 | NB1 | Int.n-55 | BRA1 | nPr | Me | Et | 2-Nap | C | | 377 (M$^+$ + 1) |
| N-e-74 | NA | N-b-73 | | nPr | Me | H | 2-Nap | C | | 349 (M$^+$ + 1) |
| N-e-75 | NB1 | Int.n-55 | BRA2 | nPr | Me | Et | 5-Ind | C | | 366 (M$^+$ + 1) |
| N-e-76 | NA | N-b-75 | | nPr | Me | H | 5-Ind | C | | 338 (M$^+$ + 1) |
| N-e-77 | NB1 | Int.n-55 | BRA5 | nPr | Me | Et | 1Me-5-Ind | C | | 380 (M$^+$ + 1) |
| N-e-78 | NA | N-b-77 | | nPr | Me | H | 1Me-5-Ind | C | | 352 (M$^+$ + 1) |
| N-e-79 | NB1 | Int.n-55 | BRA5 | nPr | Me | Et | 5-1HIdz | C | | 367 (M$^+$ + 1) |
| N-e-80 | NA | N-b-79 | | nPr | Me | H | 5-1HIdz | C | | 339 (M$^+$ + 1) |
| N-e-81 | NB1 | Int.n-55 | BRA6 | nPr | Me | Et | 1Me-5-1HIdz | C | | 381 (M$^+$ + 1) |
| N-e-82 | NA | N-b-81 | | nPr | Me | H | 1Me-5-1HIdz | C | | 353 (M$^+$ + 1) |
| N-e-83 | NB1 | Int.n-56 | BRA1 | iPr | Me | Et | 2-Nap | C | | 377 (M$^+$ + 1) |
| N-e-84 | NA | N-b-83 | | iPr | Me | H | 2-Nap | C | | 349 (M$^+$ + 1) |
| N-e-85 | NB1 | Int.n-56 | BRA2 | iPr | Me | Et | 5-Ind | C | | 366 (M$^+$ + 1) |
| N-e-86 | NA | N-b-85 | | iPr | Me | H | 5-Ind | C | | 338 (M$^+$ + 1) |
| N-e-87 | NB1 | Int.n-56 | BRA3 | iPr | Me | Et | 1Me-5-Ind | C | | 380 (M$^+$ + 1) |
| N-e-88 | NA | N-b-87 | | ipr | Me | H | 1Me-5-Ind | C | | 352 (M$^+$ + 1) |
| N-e-89 | NB1 | Int.n-56 | BRA5 | iPr | Me | Et | 5-1HIdz | C | | 367 (M$^+$ + 1) |
| N-e-90 | NA | N-b-89 | | iPr | Me | H | 5-1HIdz | C | | 339 (M$^+$ + 1) |
| N-e-91 | NB1 | Int.n-56 | BRA6 | iPr | Me | Et | 1Me-5-1HIdz | C | | 381 (M$^+$ + 1) |
| N-e-92 | NA | N-b-91 | | iPr | Me | H | 1Me-5-1HIdz | C | | 353 (M$^+$ + 1) |
| N-e-93 | NB1 | Int.n-57 | BRA1 | nBu | Me | Et | 2-Nap | C | | 391 (M$^+$ + 1) |
| N-e-94 | NA | N-b-93 | | nBu | Me | H | 2-Nap | C | | 363 (M$^+$ + 1) |
| N-e-95 | NB1 | Int.n-57 | BRA2 | nBu | Me | Et | 5-Ind | C | | 380 (M$^+$ + 1) |
| N-e-96 | NA | N-b-95 | | nBu | Me | H | 5-Ind | C | | 352 (M$^+$ + 1) |

TABLE N-E-5

| Exp. | Syn | SM1 | SM2 | Rz | Ry | Y | AR | LCMS method | RTime | Mass |
|---|---|---|---|---|---|---|---|---|---|---|
| N-e-97 | NB1 | Int.n-57 | BRA3 | nBu | Me | Et | 1Me-5-Ind | C | | 394 (M$^+$ + 1) |
| N-e-98 | NA | N-e-97 | | nBu | Me | H | 1Me-5-Ind | C | | 366 (M$^+$ + 1) |
| N-e-99 | NB1 | Int.n-57 | BRA5 | nBu | Me | Et | 5-1HIdz | C | | 381 (M$^+$ + 1) |
| N-e-100 | NA | N-e-99 | | nBu | Me | H | 5-1HIdz | C | | 353 (M$^+$ + 1) |
| N-e-101 | NB1 | Int.n-57 | BRA6 | nBu | Me | Et | 1Me-5-1HIdz | C | | 395 (M$^+$ + 1) |
| N-e-102 | NA | N-e-101 | | nBu | Me | H | 1Me-5-1HIdz | C | | 367 (M$^+$ + 1) |
| N-e-103 | NB1 | Int.n-58 | BRA1 | iBu | Me | Et | 2-Nap | C | | 391 (M$^+$ + 1) |
| N-e-104 | NA | N-e-103 | | iBu | Me | H | 2-Nap | C | | 363 (M$^+$ + 1) |
| N-e-105 | NB1 | Int.n-58 | BRA2 | iBu | Me | Et | 5-Ind | C | | 380 (M$^+$ + 1) |
| N-e-106 | NA | N-e-105 | | iBu | Me | H | 5-Ind | C | | 352 (M$^+$ + 1) |
| N-e-107 | NB1 | Int.n-58 | BRA3 | iBu | Me | Et | 1Me-5-Ind | C | | 394 (M$^+$ + 1) |
| N-e-108 | NA | N-e-107 | | iBu | Me | H | 1Me-5-Ind | C | | 366 (M$^+$ + 1) |
| N-e-109 | NB1 | Int.n-58 | BRA5 | iBu | Me | Et | 5-1HIdz | C | | 381 (M$^+$ + 1) |
| N-e-110 | NA | N-e-109 | | iBu | Me | H | 5-1HIdz | C | | 353 (M$^+$ + 1) |
| N-e-111 | NB1 | Int.n-58 | BRA6 | iBu | Me | Et | 1Me-5-1HIdz | C | | 395 (M$^+$ + 1) |
| N-e-112 | NA | N-e-111 | | iBu | Me | H | 1Me-5-1HIdz | C | | 367 (M$^+$ + 1) |
| N-e-113 | NB1 | Int.n-62 | BRA1 | Bn | H | Et | 2-Nap | C | | 411 (M$^+$ + 1) |
| N-e-114 | NA | N-e-113 | | Bn | H | H | 2-Nap | C | | 383 (M$^+$ + 1) |
| N-e-115 | NB1 | Int.n-62 | BRA2 | Bn | H | Et | 5-Ind | C | | 400 (M$^+$ + 1) |
| N-e-116 | NA | N-e-115 | | Bn | H | H | 5-Ind | C | | 372 (M$^+$ + 1) |
| N-e-117 | NB1 | Int.n-62 | BRA3 | Bn | H | Et | 1Me-5-Ind | C | | 414 (M$^+$ + 1) |
| N-e-118 | NA | N-e-117 | | Bn | H | H | 1Me-5-Ind | C | | 386 (M$^+$ + 1) |
| N-e-119 | NB1 | Int.n-62 | BRA5 | Bn | H | Et | 5-1HIdz | C | | 401 (M$^+$ + 1) |
| N-e-120 | NA | N-e-119 | | Bn | H | H | 5-1HIdz | C | | 373 (M$^+$ + 1) |
| N-e-121 | NB1 | Int.n-62 | BRA6 | Bn | H | Et | 1Me-5-1HIdz | C | | 415 (M$^+$ + 1) |
| N-e-122 | NA | N-e-121 | | Bn | H | H | 1Me-5-1HIdz | C | | 387 (M$^+$ + 1) |

TABLE N-E-5-continued

| Exp. | Syn | SM1 | SM2 | Rz | Ry | Y | AR | LCMS method | RTime | Mass |
|---|---|---|---|---|---|---|---|---|---|---|
| N-e-123 | NB1 | Int.n-63 | BRA1 | 4MeBn | H | Et | 2-Nap | C | | 425 (M⁺ + 1) |
| N-e-124 | NA | N-e-123 | | 4MeBn | H | H | 2-Nap | C | | 397 (M⁺ + 1) |
| N-e-125 | NB1 | Int.n-63 | BRA2 | 4MeBn | Me | Et | 5-Ind | C | | 414 (M⁺ + 1) |
| N-e-126 | NA | N-e-125 | | 4MeBn | Me | H | 5-Ind | C | | 386 (M⁺ + 1) |
| N-e-127 | NB1 | Int.n-63 | BRA5 | 4MeBn | Me | Et | 5-1HIdz | C | | 415 (M⁺ + 1) |
| N-e-128 | NA | N-e-127 | | 4MeBn | Me | H | 5-1HIdz | C | | 387 (M⁺ + 1) |
| N-e-129 | NB1 | Int.n-64 | BRA2 | 3MeBn | Me | Et | 5-Ind | C | | 414 (M⁺ + 1) |
| N-e-130 | NA | N-e-129 | | 3MeBn | Me | H | 5-Ind | C | | 386 (M⁺ + 1) |
| N-e-131 | NB1 | Int.n-64 | BRA3 | 3MeBn | Me | Et | 1Me-5-Ind | C | | 428 (M⁺ + 1) |
| N-e-132 | NA | N-e-131 | | 3MeBn | Me | H | 1Me-5-Ind | C | | 400 (M⁺ + 1) |
| N-e-133 | NB1 | Int.n-64 | BRA5 | 3MeBn | Me | Et | 5-1HIdz | C | | 415 (M⁺ + 1) |
| N-e-134 | NA | N-e-133 | | 3MeBn | Me | H | 5-1HIdz | C | | 387 (M⁺ + 1) |
| N-e-135 | NB1 | Int.n-65 | BRA1 | 2MeBn | Me | Et | 2-Nap | C | | 425 (M⁺ + 1) |
| N-e-136 | NA | N-e-135 | | 2MeBn | Me | H | 2-Nap | C | | 397 (M⁺ + 1) |
| N-e-137 | NB1 | Int.n-65 | BRA3 | 2MeBn | Me | Et | 1Me-5-Ind | C | | 428 (M⁺ + 1) |
| N-e-138 | NA | N-e-137 | | 2MeBn | Me | H | 1Me-5-Ind | C | | 400 (M⁺ + 1) |
| N-e-139 | NB1 | Int.n-65 | BRA6 | 2MeBn | Me | Et | 1Me-5-1HIdz | C | | 429 (M⁺ + 1) |
| N-e-140 | NA | N-e-139 | | 2MeBn | Me | H | 1Me-5-1HIdz | C | | 401 (M⁺ + 1) |

TABLE N-E-6

| Exp. | Syn | SM1 | SM2 | Rz | Ry | Y | AR | LCMS method | RTime | Mass |
|---|---|---|---|---|---|---|---|---|---|---|
| N-e-141 | NB1 | Int.n-66 | BRA1 | 4FBn | H | Et | 2-Nap | C | | 429 (M⁺ + 1) |
| N-e-142 | NA | N-e-141 | | 4FBn | H | H | 2-Nap | C | | 401 (M⁺ + 1) |
| N-e-143 | NB1 | Int.n-66 | BRA3 | 4FBn | H | Et | 1Me-5-Ind | C | | 432 (M⁺ + 1) |
| N-e-144 | NA | N-e-143 | | 4FBn | H | H | 1Me-5-Ind | C | | 404 (M⁺ + 1) |
| N-e-145 | NB1 | Int.n-66 | BRA6 | 4FBn | H | Et | 1Me-5-1HIdz | C | | 433 (M⁺ + 1) |
| N-e-146 | NA | N-e-145 | | 4FBn | H | H | 1Me-5-1HIdz | C | | 405 (M⁺ + 1) |
| N-e-147 | NB1 | Int.n-67 | BRA1 | 3FBn | H | Et | 2-Nap | C | | 429 (M⁺ + 1) |
| N-e-148 | NA | N-e-147 | | 3FBn | H | H | 2-Nap | C | | 401 (M⁺ + 1) |
| N-e-149 | NB1 | Int.n-67 | BRA2 | 3FBn | H | Et | 5-Ind | C | | 418 (M⁺ + 1) |
| N-e-150 | NA | N-e-149 | | 3FBn | H | H | 5-Ind | C | | 390 (M⁺ + 1) |
| N-e-151 | NB1 | Int.n-67 | BRA3 | 3FBn | H | Et | 1Me-5-Ind | C | | 432 (M⁺ + 1) |
| N-e-152 | NA | N-e-151 | | 3FBn | H | H | 1Me-5-Ind | C | | 404 (M⁺ + 1) |
| N-e-153 | NB1 | Int.n-68 | BRA3 | 2FBn | H | Et | 1Me-5-Ind | C | | 432 (M⁺ + 1) |
| N-e-154 | NA | N-e-153 | | 2FBn | H | H | 1Me-5-Ind | C | | 404 (M⁺ + 1) |
| N-e-155 | NB1 | Int.n-68 | BRA5 | 2FBn | H | Et | 5-1HIdz | C | | 419 (M⁺ + 1) |
| N-e-156 | NA | N-e-155 | | 2FBn | H | H | 5-1HIdz | C | | 391 (M⁺ + 1) |
| N-e-157 | NB1 | Int.n-68 | BRA6 | 2FBn | H | Et | 1Me-5-1HIdz | C | | 433 (M⁺ + 1) |
| N-e-158 | NA | N-e-157 | | 2FBn | H | H | 1Me-5-1HIdz | C | | 405 (M⁺ + 1) |
| N-e-159 | NB1 | Int.n-69 | BRA1 | 4MeOPh | H | Et | 2-Nap | C | | 427 (M⁺ + 1) |
| N-e-160 | NA | N-e-159 | | 4MeOPh | H | H | 2-Nap | C | | 399 (M⁺ + 1) |
| N-e-161 | NB1 | Int.n-69 | BRA2 | 4MeOPh | H | Et | 5-Ind | C | | 416 (M⁺ + 1) |
| N-e-162 | NA | N-e-161 | | 4MeOPh | H | H | 5-Ind | C | | 388 (M⁺ + 1) |
| N-e-163 | NB1 | Int.n-69 | BRA3 | 4MeOPh | H | Et | 1Me-5-Ind | C | | 430 (M⁺ + 1) |
| N-e-164 | NA | N-e-163 | | 4MeOPh | H | H | 1Me-5-Ind | C | | 402 (M⁺ + 1) |
| N-e-165 | NB1 | Int.n-69 | BRA5 | 4MeOPh | H | Et | 5-1HIdz | C | | 417 (M⁺ + 1) |
| N-e-166 | NA | N-e-165 | | 4MeOPh | H | H | 5-1HIdz | C | | 389 (M⁺ + 1) |
| N-e-167 | NB1 | Int.n-70 | BRA1 | 3MeOPh | H | Et | 2-Nap | C | | 427 (M⁺ + 1) |
| N-e-168 | NA | N-e-167 | | 3MeOPh | H | H | 2-Nap | C | | 399 (M⁺ + 1) |
| N-e-169 | NB1 | Int.n-70 | BRA3 | 3MeOPh | H | Et | 1Me-5-Ind | C | | 430 (M⁺ + 1) |
| N-e-170 | NA | N-e-169 | | 3MeOPh | H | H | 1Me-5-Ind | C | | 402 (M⁺ + 1) |
| N-e-171 | NB1 | Int.n-70 | BRA6 | 3MeOPh | H | Et | 1Me-5-1HIdz | C | | 431 (M⁺ + 1) |
| N-e-172 | NA | N-e-171 | | 3MeOPh | H | H | 1Me-5-1HIdz | C | | 403 (M⁺ + 1) |
| N-e-173 | NB1 | Int.n-71 | BRA5 | 2MeOPh | H | Et | 5-1HIdz | C | | 417 (M⁺ + 1) |
| N-e-174 | NA | N-e-173 | | 2MeOPh | H | H | 5-1HIdz | C | | 389 (M⁺ + 1) |
| N-e-175 | NB1 | Int.n-71 | BRA6 | 2MeOPh | H | Et | 1Me-5-1HIdz | C | | 431 (M⁺ + 1) |
| N-e-176 | NA | N-e-175 | | 2MeOPh | H | H | 1Me-5-1HIdz | C | | 403 (M⁺ + 1) |
| N-e-177 | NB1 | Int.n-71 | BRA11 | 2MeOPh | H | Et | 6-Qu | C | | 428 (M⁺ + 1) |
| N-e-178 | NA | N-e-177 | | 2MeOPh | H | H | 6-Qu | C | | 400 (M⁺ + 1) |
| N-e-179 | NB1 | Int.n-72 | BRA1 | 4CF3Ph | H | Et | 2-Nap | C | | 465 (M⁺ + 1) |
| N-e-180 | NA | N-e-179 | | 4CF3Ph | H | H | 2-Nap | C | | 437 (M⁺ + 1) |
| N-e-181 | NB1 | Int.n-72 | BRA3 | 4CF3Ph | H | Et | 1Me-5-Ind | C | | 468 (M⁺ + 1) |
| N-e-182 | NA | N-e-181 | | 4CF3Ph | H | H | 1Me-5-Ind | C | | 440 (M⁺ + 1) |
| N-e-183 | NB1 | Int.n-72 | BRA5 | 4CF3Ph | H | Et | 5-1HIdz | C | | 455 (M⁺ + 1) |
| N-e-184 | NA | N-e-183 | | 4CF3Ph | H | H | 5-1HIdz | C | | 427 (M⁺ + 1) |
| N-e-185 | NB1 | Int.n-72 | BRA6 | 4CF3Ph | H | Et | 1Me-5-1HIdz | C | | 469 (M⁺ + 1) |
| N-e-186 | NA | N-e-185 | | 4CF3Ph | H | H | 1Me-5-1HIdz | C | | 441 (M⁺ + 1) |

TABLE N-E-7

| Exp. | Syn | SM1 | SM2 | Rz | Ry | Y | AR | LCMS method | RTime | Mass |
|---|---|---|---|---|---|---|---|---|---|---|
| N-e-187 | NB1 | Int.n-73 | BRA1 | 2EtOPh | H | Et | 2-Nap | C | | 441 ($M^+ + 1$) |
| N-e-188 | NA | N-e-187 | | 2EtOPh | H | H | 2-Nap | C | | 413 ($M^+ + 1$) |
| N-e-189 | NB1 | Int.n-73 | BRA3 | 2EtOPh | H | Et | 1Me-5-Ind | C | | 444 ($M^+ + 1$) |
| N-e-190 | NA | N-e-189 | | 2EtOPh | H | H | 1Me-5-Ind | C | | 416 ($M^+ + 1$) |
| N-e-191 | NB1 | Int.n-73 | BRA6 | 2EtOPh | H | Et | 1Me-5-1HIdz | C | | 445 ($M^+ + 1$) |
| N-e-192 | NA | N-e-191 | | 2EtOPh | H | H | 1Me-5-1HIdz | C | | 417 ($M^+ + 1$) |
| N-e-193 | NB1 | Int.n-74 | BRA1 | 3iPrOPh | H | Et | 2-Nap | C | | 455 ($M^+ + 1$) |
| N-e-194 | NA | N-e-193 | | 3iPrOPh | H | H | 2-Nap | C | | 427 ($M^+ + 1$) |
| N-e-195 | NB1 | Int.n-74 | BRA2 | 3iPrOPh | H | Et | 5-Ind | C | | 444 ($M^+ + 1$) |
| N-e-196 | NA | N-e-195 | | 3iPrOPh | H | H | 5-Ind | C | | 416 ($M^+ + 1$) |
| N-e-197 | NB1 | Int.n-74 | BRA3 | 3iPrOPh | H | Et | 1Me-5-Ind | C | | 458 ($M^+ + 1$) |
| N-e-198 | NA | N-b-197 | | 3iPrOPh | H | H | 1Me-5-Ind | C | | 430 ($M^+ + 1$) |
| N-e-199 | NB1 | Int.n-75 | BRA3 | 3,5DFPh | H | Et | 1Me-5-Ind | C | | 436 ($M^+ + 1$) |
| N-e-200 | NA | N-b-199 | | 3,5DFPh | H | H | 1Me-5-Ind | C | | 408 ($M^+ + 1$) |
| N-e-201 | NB1 | Int.n-75 | BRA5 | 3,5DFPh | H | Et | 5-1HIdz | C | | 423 ($M^+ + 1$) |
| N-e-202 | NA | N-b-201 | | 3,5DFPh | H | H | 5-1HIdz | C | | 395 ($M^+ + 1$) |
| N-e-203 | NB1 | Int.n-75 | BRA6 | 3.5DFPh | H | Et | 1Me-5-1HIdz | C | | 437 ($M^+ + 1$) |
| N-e-204 | NA | N-b-203 | | 3,5DFPh | H | H | 1Me-5-1HIdz | C | | 409 ($M^+ + 1$) |

Example N-f-1

Synthesis of methyl 3-[3-(naphthalen-2-yl)-4-(N-phenylamino)phenyl]propionate (Compound No. N-f-1) (Synthesis method NB2)

A solution of Intermediate n-7 (306.1 mg) in dehydrated toluene (1 ml) was added with aniline (1 ml, TCI), palladium acetate (20.2 mg, WAKO), 2-(di-t-butylphosphine)biphenyl (39 mg, Across) and cesium carbonate (863.4 mg, WAKO), and stirred at 90° C. for 18 hours. The reaction mixture was added with ethyl acetate (40 ml), and washed successively with saturated aqueous sodium hydrogencarbonate, saturated aqueous ammonium chloride and saturated brine. The organic layer was dried, and then the solvent was evaporated under reduced pressure. The residue was purified by column chromatography (Quad, hexane:ethyl acetate=4:1) to obtain the title compound (Compound No. N-f-1, 101.4 mg).

Examples N-f-1 to N-f-92

Typical examples of the compounds of the present invention that can be obtained by reacting and treating corresponding starting compounds using any of the methods described in the present specification including the examples described above are shown in Table-N-F-1 and Table-N-F-2. In the tables, the compound numbers are mentioned in the columns indicated as "Exp.". In the tables, corresponding methods among the aforementioned synthesis methods are shown in the columns of "Syn" with symbols, the starting compounds 1 are mentioned in the columns of "SM1", and the starting compounds 2 are mentioned in the columns of "SM2".

TABLE N-F-1

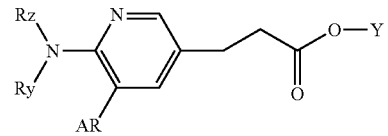

| Exp. | Syn | SM1 | SM2 | Rz | Ry | Y | AR | LCMS method | RTime | Mass |
|---|---|---|---|---|---|---|---|---|---|---|
| N-f-1 | NB2 | Int.n-7 | BRA14 | Ph | H | Me | 2-Nap | C | | 383 ($M^+ + 1$) |
| N-f-2 | NA | N-f-1 | | Ph | H | H | 2-Nap | C | | 369 ($M^+ + 1$) |
| N-f-3 | NB2 | Int.n-8 | BRA14 | Ph | H | Me | 5-Ind | C | | 372 ($M^+ + 1$) |
| N-f-4 | NA | N-f-3 | | Ph | H | H | 5-Ind | C | | 358 ($M^+ + 1$) |
| N-f-5 | NB2 | Int.n-9 | BRA14 | Ph | H | Me | 1Me-5-Ind | C | | 386 ($M^+ + 1$) |
| N-f-6 | NA | N-f-5 | | Ph | H | H | 1Me-5-Ind | C | | 372 ($M^+ + 1$) |
| N-f-7 | NB2 | Int.n-10 | BRA14 | Ph | H | Me | 5-1HIdz | C | | 373 ($M^+ + 1$) |
| N-f-8 | NA | N-f-7 | | Ph | H | H | 5-1HIdz | C | | 359 ($M^+ + 1$) |
| N-f-9 | NB2 | Int.n-11 | BRA14 | Ph | H | Me | 1Me-5-1HIdz | C | | 387 ($M^+ + 1$) |
| N-f-10 | NA | N-f-9 | | Ph | H | H | 1Me-5-1HIdz | C | | 373 ($M^+ + 1$) |
| N-f-11 | NB2 | N-f-1 | CHO1 | Ph | Me | Me | 2-Nap | C | | 397 ($M^+ + 1$) |
| N-f-12 | NA | N-f-11 | | Ph | Me | H | 2-Nap | C | | 383 ($M^+ + 1$) |
| N-f-13 | NB2 | N-f-3 | CHO1 | Ph | Me | Me | 1Me-5-Ind | C | | 400 ($M^+ + 1$) |
| N-f-14 | NA | N-f-13 | | Ph | Me | H | 1Me-5-Ind | C | | 386 ($M^+ + 1$) |
| N-f-15 | NB2 | N-f-5 | CHO1 | Ph | Me | Me | 1Me-5-1HIdz | C | | 401 ($M^+ + 1$) |
| N-f-16 | NA | N-f-15 | | Ph | Me | H | 1Me-5-1HIdz | C | | 387 ($M^+ + 1$) |
| N-f-17 | NB2 | Int.n-7 | BRA29 | 4MePh | H | Me | 2-Nap | C | | 397 ($M^+ + 1$) |
| N-f-18 | NA | N-f-17 | | 4MePh | H | H | 2-Nap | C | | 383 ($M^+ + 1$) |

TABLE N-F-1-continued

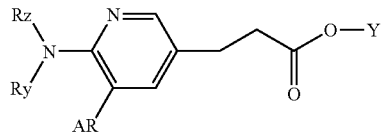

| Exp. | Syn | SM1 | SM2 | Rz | Ry | Y | AR | LCMS method | RTime | Mass |
|---|---|---|---|---|---|---|---|---|---|---|
| N-f-19 | NB2 | Int.n-9 | BRA29 | 4MePh | H | Me | 1Me-5-Ind | C | | 400 (M$^+$ + 1) |
| N-f-20 | NA | N-f-19 | | 4MePh | H | H | 1Me-5-Ind | C | | 386 (M$^+$ + 1) |
| N-f-21 | NB2 | Int.n-11 | BRA29 | 4MePh | H | Me | 1Me-5-1HIdz | C | | 401 (M$^+$ + 1) |
| N-f-22 | NA | N-f-21 | | 4MePh | H | H | 1Me-5-1HIdz | C | | 387 (M$^+$ + 1) |
| N-f-23 | NB2 | Int.n-7 | BRA60 | 3MePh | H | Me | 2-Nap | C | | 397 (M$^+$ + 1) |
| N-f-24 | NA | N-f-23 | | 3MePh | H | H | 2Nap | C | | 383 (M$^+$ + 1) |
| N-f-25 | NB2 | Int.n-9 | BRA60 | 3MePh | H | Me | 1Me-5-Ind | C | | 400 (M$^+$ + 1) |
| N-f-26 | NA | N-f-25 | | 3MePh | H | H | 1Me-5-Ind | C | | 386 (M$^+$ + 1) |
| N-f-27 | NB2 | Int.n-11 | BRA60 | 3MePh | H | Me | 1Me-5-1HIdz | C | | 401 (M$^+$ + 1) |
| N-f-28 | NA | N-f-27 | | 3MePh | H | H | 1Me-5-1HIdz | C | | 387 (M$^+$ + 1) |
| N-f-29 | NB2 | Int.n-7 | BRA59 | 2MePh | H | Me | 2-Nap | C | | 397 (M$^+$ + 1) |
| N-f-30 | NA | N-f-29 | | 2MePh | H | H | 2Nap | C | | 383 (M$^+$ + 1) |
| N-f-31 | NB2 | Int.n-8 | BRA59 | 2MePh | H | Me | 5-Ind | C | | 386 (M$^+$ + 1) |
| N-f-32 | NA | N-f-31 | | 2MePh | H | H | 5-Ind | C | | 372 (M$^+$ + 1) |
| N-f-33 | NB2 | Int.n-10 | BRA59 | 2MePh | H | Me | 5-1HIdz | C | | 387 (M$^+$ + 1) |
| N-f-34 | NA | N-f-33 | | 2MePh | H | H | 5-1HIdz | C | | 373 (M$^+$ + 1) |
| N-f-35 | NB2 | Int.n-7 | BRA22 | 4FPh | H | Me | 2-Nap | C | | 401 (M$^+$ + 1) |
| N-f-36 | NA | N-f-35 | | 4FPh | H | H | 2-Nap | C | | 387 (M$^+$ + 1) |
| N-f-37 | NB2 | Int.n-8 | BRA22 | 4FPh | H | Me | 5-Ind | C | | 390 (M$^+$ + 1) |
| N-f-38 | NA | N-f-37 | | 4FPh | H | H | 5-Ind | C | | 376 (M$^+$ + 1) |
| N-f-39 | NB2 | Int.n-9 | BRA22 | 4FPh | H | Me | 1Me-5-Ind | C | | 404 (M$^+$ + 1) |
| N-f-40 | NA | N-f-39 | | 4FPh | H | H | 1Me-5-Ind | C | | 390 (M$^+$ + 1) |
| N-f-41 | NB2 | Int.n-7 | BRA33 | 3FPh | H | Me | 2-Nap | C | | 401 (M$^+$ + 1) |
| N-f-42 | NA | N-f-41 | | 3FPh | H | H | 2-Nap | C | | 387 (M$^+$ + 1) |
| N-f-43 | NB2 | Int.n-10 | BRA33 | 3FPh | H | Me | 5-1HIdz | C | | 391 (M$^+$ + 1) |
| N-f-44 | NA | N-f-43 | | 3FPh | H | H | 5-1HIdz | C | | 377 (M$^+$ + 1) |
| N-f-45 | NB2 | Int.n-11 | BRA33 | 3FPh | H | Me | 1Me-5-1HIdz | C | | 405 (M$^+$ + 1) |
| N-f-46 | NA | N-f-45 | | 3FPh | H | H | 1Me-5-1HIdz | C | | 391 (M$^+$ + 1) |

TABLE N-F-2

| Exp. | Syn | SM1 | SM2 | Rz | Ry | Y | AR | LCMS method | RTime | Mass |
|---|---|---|---|---|---|---|---|---|---|---|
| N-f-47 | NB2 | Int.n-7 | BRA32 | 2FPh | H | Me | 2-Nap | C | | 401 (M$^+$ + 1) |
| N-f-48 | NA | N-f-47 | | 2FPh | H | H | 2-Nap | C | | 387 (M$^+$ + 1) |
| N-f-49 | NB2 | Int.n-8 | BRA32 | 2FPh | H | Me | 5-Ind | C | | 390 (M$^+$ + 1) |
| N-f-50 | NA | N-f-49 | | 2FPh | H | H | 5-Ind | C | | 376 (M$^+$ + 1) |
| N-f-51 | NB2 | Int.n-11 | BRA32 | 2FPh | H | Me | 1Me-5-1HIdz | C | | 405 (M$^+$ + 1) |
| N-f-52 | NA | N-f-51 | | 2FPh | H | H | 1Me-5-1HIdz | C | | 391 (M$^+$ + 1) |
| N-f-53 | NB2 | Int.n-8 | BRA19 | 4MeOPh | H | Me | 5-Ind | C | | 402 (M$^+$ + 1) |
| N-f-54 | NA | N-f-53 | | 4MeOPh | H | H | 5-Ind | C | | 388 (M$^+$ + 1) |
| N-f-55 | NB2 | Int.n-10 | BRA19 | 4MeOPh | H | Me | 5-1HIdz | C | | 403 (M$^+$ + 1) |
| N-f-56 | NA | N-f-55 | | 4MeOPh | H | H | 5-1HIdz | C | | 389 (M$^+$ + 1) |
| N-f-57 | NB2 | Int.n-11 | BRA19 | 4MeOPh | Me | Me | 1Me-5-1HIdz | C | | 417 (M$^+$ + 1) |
| N-f-58 | NA | N-f-57 | | 4MeOPh | Me | H | 1Me-5-1HIdz | C | | 403 (M$^+$ + 1) |
| N-f-59 | NB2 | Int.n-9 | BRA37 | 3MeOPh | Me | Me | 1Me-5-Ind | C | | 416 (M$^+$ + 1) |
| N-f-60 | NA | N-f-59 | | 3MeOPh | Me | H | 1Me-5-Ind | C | | 402 (M$^+$ + 1) |
| N-f-61 | NB2 | Int.n-10 | BRA37 | 3MeOPh | Me | Me | 5-1HIdz | C | | 403 (M$^+$ + 1) |
| N-f-62 | NA | N-f-61 | | 3MeOPh | Me | H | 5-1HIdz | C | | 389 (M$^+$ + 1) |
| N-f-63 | NB2 | Int.n-11 | BRA37 | 3MeOPh | H | Me | 1Me-5-1HIdz | C | | 417 (M$^+$ + 1) |
| N-f-64 | NA | N-f-63 | | 3MeOPh | H | H | 1Me-5-1HIdz | C | | 403 (M$^+$ + 1) |

TABLE N-F-2-continued

| Exp. | Syn | SM1 | SM2 | Rz | Ry | Y | AR | LCMS method | RTime | Mass |
|---|---|---|---|---|---|---|---|---|---|---|
| N-f-65 | NB2 | Int.n-7 | BRA38 | 2MeOPh | H | Me | 2-Nap | C | | 413 ($M^+ + 1$) |
| N-f-66 | NA | N-f-65 | | 2MeOPh | H | H | 2-Nap | C | | 399 ($M^+ + 1$) |
| N-f-67 | NB2 | Int.n-8 | BRA38 | 2MeOPh | H | Me | 5-Ind | C | | 402 ($M^+ + 1$) |
| N-f-68 | NA | N-f-67 | | 2MeOPh | H | H | 5-Ind | C | | 388 ($M^+ + 1$) |
| N-f-69 | NB2 | Int.n-11 | BRA38 | 2MeOPh | H | Me | 1Me-5-1HIdz | C | | 417 ($M^+ + 1$) |
| N-f-70 | NA | N-f-69 | | 2MeOPh | H | H | 1Me-5-1HIdz | C | | 403 ($M^+ + 1$) |
| N-f-71 | NB2 | Int.n-7 | BRA41 | 4CF3Ph | H | Me | 2-Nap | C | | 451 ($M^+ + 1$) |
| N-f-72 | NA | N-f-71 | | 4CF3Ph | H | H | 2-Nap | C | | 437 ($M^+ + 1$) |
| N-f-73 | NB2 | Int.n-9 | BRA41 | 4CF3Ph | H | Me | 1Me-5-Ind | C | | 454 ($M^+ + 1$) |
| N-f-74 | NA | N-f-73 | | 4CF3Ph | H | H | 1Me-5-Ind | C | | 440 ($M^+ + 1$) |
| N-f-75 | NB2 | Int.n-11 | BRA41 | 4CF3Ph | H | Me | 1Me-5-1HIdz | C | | 455 ($M^+ + 1$) |
| N-f-76 | NA | N-f-75 | | 4CF3Ph | H | H | 1Me-5-1HIdz | C | | 441 ($M^+ + 1$) |
| N-f-77 | NB2 | Int.n-8 | BRA88 | 4PhOPh | H | Me | 5-Ind | C | | 464 ($M^+ + 1$) |
| N-f-78 | NA | N-f-77 | | 4PhOPh | H | H | 5-Ind | C | | 450 ($M^+ + 1$) |
| N-f-79 | NB2 | Int.n-9 | BRA88 | 4PhOPh | H | Me | 1Me-5-Ind | C | | 478 ($M^+ + 1$) |
| N-f-80 | NA | N-f-79 | | 4PhOPh | H | H | 1Me-5-Ind | C | | 464 ($M^+ + 1$) |
| N-f-81 | NB2 | Int.n-10 | BRA88 | 4PhOPh | H | Me | 5-1HIdz | C | | 465 ($M^+ + 1$) |
| N-f-82 | NA | N-f-81 | | 4PhOPh | H | H | 5-1HIdz | C | | 451 ($M^+ + 1$) |
| N-f-83 | NB2 | Int.n-7 | BRA61 | 2ClPh | H | Me | 2-Nap | C | | 417 ($M^+ + 1$) |
| N-f-84 | NA | N-f-83 | | 2ClPh | H | H | 2-Nap | C | | 403 ($M^+ + 1$) |
| N-f-85 | NB2 | Int.n-9 | BRA61 | 2ClPh | H | Me | 1Me-5-Ind | C | | 420 ($M^+ + 1$) |
| N-f-86 | NA | N-f-85 | | 2ClPh | H | H | 1Me-5-Ind | C | | 406 ($M^+ + 1$) |
| N-f-87 | NB2 | Int.n-10 | BRA61 | 2ClPh | H | Me | 5-1HIdz | C | | 407 ($M^+ + 1$) |
| N-f-88 | NA | N-f-87 | | 2ClPh | H | H | 5-1HIdz | C | | 393 ($M^+ + 1$) |
| N-f-89 | NB2 | Int.n-7 | BRA73 | 3,5DMePh | H | Me | 2-Nap | C | | 411 ($M^+ + 1$) |
| N-f-90 | NA | N-f-89 | | 3,5DMePh | H | H | 2-Nap | C | | 397 ($M^+ + 1$) |
| N-f-91 | NB2 | Int.n-9 | BRA73 | 3,5DMePh | H | Me | 1Me-5-Ind | C | | 414 ($M^+ + 1$) |
| N-f-92 | NA | N-f-91 | | 3,5DMePh | H | H | 1Me-5-Ind | C | | 400 ($M^+ + 1$) |

Example N-g-33

Synthesis of methyl 3-[4-cyclopentylamino-3-methyl-5-(naphthalen-2-yl)phenyl]propionate (Compound No. N-e-33) (Synthesis method NB1)

According to the procedure described in the synthesis method of the compound of Example N-a-1 (Synthesis method NB) provided that the reaction was carried out for 18 hours, and the column chromatography was performed with hexane:ethyl acetate=4:1), the compound of Example N-g-1 (91.6 mg), methyl boronate (140.0 mg, Ald), 2 M aqueous sodium carbonate (300 μl) and (Ph₃P)₄Pd (75.5 mg) were reacted and treated to obtain the title compound (Compound-No. N-g-33, 41.3 mg).

Example N-g-251

Synthesis of methyl 3-[4-(N-methyl-N-cyclopentylamino)-3-(N-methylamino)-5-(naphthalen-2-yl) phenyl]propionate (Compound No. N-g-251) (Synthesis method NN1)

A solution of Compound No. N-g-131 (102 mg) in DMF (3 ml) was added with 60% sodium hydride (7 mg) under ice cooling, and stirred for 10 minutes. This reaction mixture was added with methyl iodide (17 μl), stirred for 10 minutes, then warmed to room temperature, and further stirred for 2 hours. The reaction mixture was poured into water, and added with ethyl acetate (30 ml) for extraction. The organic layer was washed successively with saturated aqueous sodium hydrogencarbonate, saturated aqueous ammonium chloride and saturated brine, and dried, and then the solvent was evaporated under reduced pressure. The residue was purified by column chromatography (Quad, hexane:ethyl acetate=3:1) to obtain the title compound (Compound No. N-g-251, 30 mg).

Example N-g-285

Synthesis of methyl 3-[3-(N-dimethylamino)-4-(N-methyl-N-cyclopentylamino)-5-(naphthalen-2-yl) phenyl]propionate (Compound No. N-g-285) (Synthesis method NN2)

A solution of Compound No. N-g-131 (102 mg) in DMF (3 ml) was added with 60% sodium hydride (20 mg) under ice cooling, and stirred for 10 minutes. This reaction mixture was added dropwise with methyl iodide (100 μl), stirred for 10 minutes, then warmed to room temperature, and further stirred for 16 hours. The reaction mixture was poured into water, and added with ethyl acetate (30 ml) for extraction. The organic layer was washed successively with saturated aqueous sodium hydrogencarbonate, saturated aqueous ammonium chloride and saturated brine, and dried, and then the solvent was evaporated under reduced pressure. The residue was purified by column chromatography (Quad, hexane:ethyl acetate=3:1) to obtain the title compound (Compound No. N-g-285, 80 mg).

Examples N-g-1 to N-g-318

Typical examples of the compounds of the present invention that can be obtained by reacting and treating corresponding starting compounds using any of the methods described in the present specification including the examples described above are shown in Table-N-G-1 to Table-N-G-7. In the tables, the compound numbers are mentioned in the columns indicated as "Exp.". In the tables, used methods among the aforementioned synthesis methods are shown in the columns of "Syn" with symbols, the starting compounds 1 are mentioned in the columns of "SM1", and the starting compounds 2 are mentioned in the columns of "SM2".

TABLE N-G-1

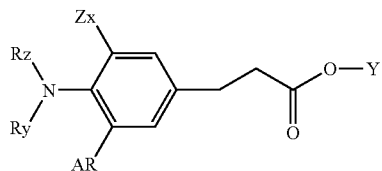

| Exp. | Syn | SM1 | SM2 | Rz | Ry | Y | Zx | AR | LCMS method | RTime | Mass |
|---|---|---|---|---|---|---|---|---|---|---|---|
| N-g-1 | NB1 | Int.n-39 | BRA1 | cPen | H | Me | Br | 2-Nap | C | | 452 (M$^+$) |
| N-g-2 | NA | N-g-1 | | cPen | H | H | Br | 2-Nap | C | | 438 (M$^+$) |
| N-g-3 | NB1 | Int.n-39 | BRA2 | cPen | H | Me | Br | 5-Ind | C | | 441 (M$^+$) |
| N-g-4 | NA | N-g-3 | | cPen | H | H | Br | 5-Ind | C | | 427 (M$^+$) |
| N-g-5 | NB1 | Int.n-39 | BRA3 | cPen | H | Me | Br | 1Me-5-Ind | C | | 455 (M$^+$) |
| N-g-6 | NA | N-g-5 | | cPen | H | H | Br | 1Me-5-Ind | C | | 441 (M$^+$) |
| N-g-7 | NB1 | Int.n-39 | BRA5 | cPen | H | Me | Br | 5-1HIdz | C | | 442 (M$^+$) |
| N-g-8 | NA | N-g-7 | | cPen | H | H | Br | 5-1HIdz | C | | 428 (M$^+$) |
| N-g-9 | NB1 | Int.n-39 | BRA6 | cPen | H | Me | Br | 1Me-5-1HIdz | C | | 456 (M$^+$) |
| N-g-10 | NA | N-g-9 | | cPen | H | H | Br | 1Me-5-1HIdz | C | | 442 (M$^+$) |
| N-g-11 | NB1 | Int.n-39 | BRA11 | cPen | H | Me | Br | 6-Qu | C | | 453 (M$^+$) |
| N-g-12 | NA | N-g-11 | | cPen | H | H | Br | 6-Qu | C | | 439 (M$^+$) |
| N-g-13 | NC2 | N-g-1 | CHO1 | cPen | Me | Me | Br | 2-Nap | C | | 466 (M$^+$) |
| N-g-14 | NA | N-g-13 | | cPen | Me | H | Br | 2-Nap | C | | 452 (M$^+$) |
| N-g-15 | NC2 | N-g-5 | CHO1 | cPen | Me | Me | Br | 1Me-5-Ind | C | | 455 (M$^+$) |
| N-g-16 | NA | N-g-15 | | cPen | Me | H | Br | 1Me-5-Ind | C | | 441 (M$^+$) |
| N-g-17 | NB1 | Int.n-41 | BRA2 | nPr | H | Me | Br | 5-Ind | C | | 415 (M$^+$) |
| N-g-18 | NA | N-g-17 | | nPr | H | H | Br | 5-Ind | C | | 401 (M$^+$) |
| N-g-19 | NB1 | Int.n-41 | BRA3 | nPr | H | Me | Br | 1Me-5-Ind | C | | 429 (M$^+$) |
| N-g-20 | NA | N-g-19 | | nPr | H | H | Br | 1Me-5-Ind | C | | 415 (M$^+$) |
| N-g-21 | NB1 | Int.n-41 | BRA5 | nPr | H | Me | Br | 5-1HIdz | C | | 416 (M$^+$) |
| N-g-22 | NA | N-g-21 | | nPr | H | H | Br | 5-1HIdz | C | | 402 (M$^+$) |
| N-g-23 | NB1 | Int.n-41 | BRA11 | nPr | H | Me | Br | 6-Qu | C | | 427 (M$^+$) |
| N-g-24 | NA | N-g-23 | | nPr | H | H | Br | 6-Qu | C | | 413 (M$^+$) |
| N-g-25 | NB1 | Int.n-43 | BRA1 | iPr | H | Me | Br | 2-Nap | C | | 426 (M$^+$) |
| N-g-26 | NA | N-g-25 | | iPr | H | H | Br | 2-Nap | C | | 412 (M$^+$) |
| N-g-27 | NB1 | Int.n-43 | BRA2 | iPr | H | Me | Br | 5-Ind | C | | 415 (M$^+$) |
| N-g-28 | NA | N-g-27 | | iPr | H | H | Br | 5-Ind | C | | 401 (M$^+$) |
| N-g-29 | NB1 | Int.n-43 | BRA6 | iPr | H | Me | Br | 1Me-5-1HIdz | C | | 430 (M$^+$) |
| N-g-30 | NA | N-g-29 | | iPr | H | H | Br | 1Me-5-1HIdz | C | | 416 (M$^+$) |
| N-g-31 | NB1 | Int.n-43 | BRA10 | iPr | H | Me | Br | 3-Qu | C | | 427 (M$^+$) |
| N-g-32 | NA | N-g-31 | | iPr | H | H | Br | 3-Qu | C | | 413 (M$^+$) |
| N-g-33 | NB1 | N-g-1 | BRA13 | cPen | H | Me | Me | 2-Nap | C | | 388 (M$^+$ + 1) |
| N-g-34 | NA | N-g-33 | | cPen | H | H | Me | 2-Nap | C | | 374 (M$^+$ + 1) |
| N-g-35 | NB1 | N-g-3 | BRA13 | cPen | H | Me | Me | 5-Ind | C | | 377 (M$^+$ + 1) |
| N-g-36 | NA | N-g-35 | | cPen | H | H | Me | 5-Ind | C | | 363 (M$^+$ + 1) |
| N-g-37 | NB1 | N-g-5 | BRA13 | cPen | H | Me | Me | 1Me-5-Ind | C | | 391 (M$^+$ + 1) |
| N-g-38 | NA | N-g-37 | | cPen | H | H | Me | 1Me-5-Ind | C | | 377 (M$^+$ + 1) |
| N-g-39 | NB1 | N-g-7 | BRA13 | cPen | H | Me | Me | 5-1HIdz | C | | 378 (M$^+$ + 1) |
| N-g-40 | NA | N-g-39 | | cPen | H | H | Me | 5-1HIdz | C | | 364 (M$^+$ + 1) |
| N-g-41 | NB1 | N-g-9 | BRA13 | cPen | H | Me | Me | 1Me-5-1HIdz | C | | 392 (M$^+$ + 1) |
| N-g-42 | NA | N-g-41 | | cPen | H | H | Me | 1Me-5-1HIdz | C | | 378 (M$^+$ + 1) |
| N-g-43 | NC2 | N-g-37 | CHO1 | cPen | Me | Me | Me | 1Me-5-Ind | C | | 405 (M$^+$ + 1) |
| N-g-44 | NA | N-g-43 | | cPen | Me | H | Me | 1Me-5-Ind | C | | 391 (M$^+$ + 1) |

TABLE N-G-2

| Exp. | Syn | SM1 | SM2 | Rz | Ry | Y | Zx | AR | LCMS method | RTime | Mass |
|---|---|---|---|---|---|---|---|---|---|---|---|
| N-g-45 | NB1 | Int.n-77 | BRA1 | cPen | H | Me | NO2 | 2-Nap | C | | 419 (M$^+$ + 1) |
| N-g-46 | NA | N-g-45 | | cPen | H | H | NO2 | 2-Nap | C | | 405 (M$^+$ + 1) |
| N-g-47 | NB1 | Int.n-77 | BRA2 | cPen | H | Me | NO2 | 5-Ind | C | | 408 (M$^+$ + 1) |
| N-g-48 | NA | N-g-47 | | cPen | H | H | NO2 | 5-Ind | C | | 394 (M$^+$ + 1) |
| N-g-49 | NB1 | Int.n-77 | BRA3 | cPen | H | Me | NO2 | 1Me-5-Ind | C | | 422 (M$^+$ + 1) |
| N-g-50 | NA | N-g-49 | | cPen | H | H | NO2 | 1Me-5-Ind | C | | 408 (M$^+$ + 1) |
| N-g-51 | NB1 | Int.n-77 | BRA5 | cPen | H | Me | NO2 | 5-1HIdz | C | | 409 (M$^+$ + 1) |
| N-g-52 | NA | N-g-51 | | cPen | H | H | NO2 | 5-1HIdz | C | | 395 (M$^+$ + 1) |
| N-g-53 | NB1 | Int.n-77 | BRA6 | cPen | H | Me | NO2 | 1Me-5-1HIdz | C | | 423 (M$^+$ + 1) |
| N-g-54 | NA | N-g-53 | | cPen | H | H | NO2 | 1Me-5-1HIdz | C | | 409 (M$^+$ + 1) |
| N-g-55 | NB1 | Int.n-78 | BRA1 | nPr | H | Me | NO2 | 2-Nap | C | | 393 (M$^+$ + 1) |
| N-g-56 | NA | N-g-55 | | nPr | H | H | NO2 | 2-Nap | C | | 379 (M$^+$ + 1) |

TABLE N-G-2-continued

| Exp. | Syn | SM1 | SM2 | Rz | Ry | Y | Zx | AR | LCMS method | RTime | Mass |
|---|---|---|---|---|---|---|---|---|---|---|---|
| N-g-57 | NB1 | Int.n-78 | BRA2 | nPr | H | Me | NO2 | 5-Ind | C | | 382 (M$^+$ + 1) |
| N-g-58 | NA | N-g-57 | | nPr | H | H | NO2 | 5-Ind | C | | 368 (M$^+$ + 1) |
| N-g-59 | NB1 | Int.n-78 | BRA3 | nPr | H | Me | NO2 | 1Me-5-Ind | C | | 396 (M$^+$ + 1) |
| N-g-60 | NA | N-g-59 | | nPr | H | H | NO2 | 1Me-5-Ind | C | | 382 (M$^+$ + 1) |
| N-g-61 | NB1 | Int.n-78 | BRA5 | nPr | H | Me | NO2 | 5-1HIdz | C | | 383 (M$^+$ + 1) |
| N-g-62 | NA | N-g-61 | | nPr | H | H | NO2 | 5-1HIdz | C | | 369 (M$^+$ + 1) |
| N-g-63 | NB1 | Int.n-78 | BRA6 | nPr | H | Me | NO2 | 1Me-5-1HIdz | C | | 397 (M$^+$ + 1) |
| N-g-64 | NA | N-g-63 | | nPr | H | H | NO2 | 1Me-5-1HIdz | C | | 383 (M$^+$ + 1) |
| N-g-65 | NB1 | Int.n-79 | BRA1 | iPr | H | Me | NO2 | 2-Nap | C | | 393 (M$^+$ + 1) |
| N-g-66 | NA | N-g-65 | | iPr | H | H | NO2 | 2-Nap | C | | 379 (M$^+$ + 1) |
| N-g-67 | NB1 | Int.n-79 | BRA2 | iPr | H | Me | NO2 | 5-Ind | C | | 382 (M$^+$ + 1) |
| N-g-68 | NA | N-g-67 | | iPr | H | H | NO2 | 5-Ind | C | | 368 (M$^+$ + 1) |
| N-g-69 | NB1 | Int.n-79 | BRA3 | iPr | H | Me | NO2 | 1Me-5-Ind | C | | 396 (M$^+$ + 1) |
| N-g-70 | NA | N-g-69 | | iPr | H | H | NO2 | 1Me-5-Ind | C | | 382 (M$^+$ + 1) |
| N-g-71 | NB1 | Int.n-79 | BRA5 | iPr | H | Me | NO2 | 5-1HIdz | C | | 383 (M$^+$ + 1) |
| N-g-72 | NA | N-g-71 | | iPr | H | H | NO2 | 5-1HIdz | C | | 369 (M$^+$ + 1) |
| N-g-73 | NB1 | Int.n-79 | BRA6 | iPr | H | Me | NO2 | 1Me-5-1HIdz | C | | 397 (M$^+$ + 1) |
| N-g-74 | NA | N-g-73 | | iPr | H | H | NO2 | 1Me-5-1HIdz | C | | 383 (M$^+$ + 1) |
| N-g-75 | NB1 | Int.n-83 | BRA1 | cPen | Me | Me | NO2 | 2-Nap | C | | 433 (M$^+$ + 1) |
| N-g-76 | NA | N-g-75 | | cPen | Me | H | NO2 | 2-Nap | C | | 419 (M$^+$ + 1) |
| N-g-77 | NB1 | Int.n-83 | BRA3 | cPen | Me | Me | NO2 | 1Me-5-Ind | C | | 436 (M$^+$ + 1) |
| N-g-78 | NA | N-g-77 | | cPen | Me | H | NO2 | 1Me-5-Ind | C | | 422 (M$^+$ + 1) |
| N-g-79 | NB1 | Int.n-83 | BRA6 | cPen | Me | Me | NO2 | 1Me-5-1HIdz | C | | 437 (M$^+$ + 1) |
| N-g-80 | NA | N-g-79 | | cPen | Me | H | NO2 | 1Me-5-1HIdz | C | | 423 (M$^+$ + 1) |
| N-g-81 | NB1 | Int.n-84 | BRA1 | nPr | Me | Me | NO2 | 2-Nap | C | | 407 (M$^+$ + 1) |
| N-g-82 | NA | N-g-81 | | nPr | Me | H | NO2 | 2-Nap | C | | 393 (M$^+$ + 1) |
| N-g-83 | NB1 | Int.n-84 | BRA2 | nPr | Me | Me | NO2 | 5-Ind | C | | 396 (M$^+$ + 1) |
| N-g-84 | NA | N-g-83 | | nPr | Me | H | NO2 | 5-Ind | C | | 382 (M$^+$ + 1) |
| N-g-85 | NB1 | Int.n-84 | BRA3 | nPr | Me | Me | NO2 | 1Me-5-Ind | C | | 410 (M$^+$ + 1) |
| N-g-86 | NA | N-g-85 | | nPr | Me | H | NO2 | 1Me-5-Ind | C | | 396 (M$^+$ + 1) |
| N-g-87 | NB1 | Int.n-84 | BRA5 | nPr | Me | Me | NO2 | 5-1HIdz | C | | 397 (M$^+$ + 1) |
| N-g-88 | NA | N-g-87 | | nPr | Me | H | NO2 | 5-1HIdz | C | | 383 (M$^+$ + 1) |
| N-g-89 | NB1 | Int.n-84 | BRA6 | nPr | Me | Me | NO2 | 1Me-5-1HIdz | C | | 411 (M$^+$ + 1) |
| N-g-90 | NA | N-g-89 | | nPr | Me | H | NO2 | 1Me-5-1HIdz | C | | 397 (M$^+$ + 1) |
| N-g-91 | NB1 | Int.n-85 | BRA1 | iPr | Me | Me | NO2 | 2-Nap | C | | 407 (M$^+$ + 1) |
| N-g-92 | NA | N-g-91 | | iPr | Me | H | NO2 | 2-Nap | C | | 393 (M$^+$ + 1) |

TABLE N-G-3

| Exp. | Syn | SM1 | SM2 | Rz | Ry | Y | Zx | AR | LCMS method | RTime | Mass |
|---|---|---|---|---|---|---|---|---|---|---|---|
| N-g-93 | NB1 | Int.n-85 | BRA2 | iPr | Me | Me | NO2 | 5-Ind | C | | 396 (M$^+$ + 1) |
| N-g-94 | NA | N-g-93 | | iPr | Me | H | NO2 | 5-Ind | C | | 382 (M$^+$ + 1) |
| N-g-95 | NB1 | Int.n-85 | BRA3 | iPr | Me | Me | NO2 | 1Me-5-Ind | C | | 410 (M$^+$ + 1) |
| N-g-96 | NA | N-g-95 | | iPr | Me | H | NO2 | 1Me-5-Ind | C | | 396 (M$^+$ + 1) |
| N-g-97 | NB1 | Int.n-85 | BRA5 | iPr | Me | Me | NO2 | 5-1HIdz | C | | 397 (M$^+$ + 1) |
| N-g-98 | NA | N-g-97 | | iPr | Me | H | NO2 | 5-1HIdz | C | | 383 (M$^+$ + 1) |
| N-g-99 | NB1 | Int.n-85 | BRA6 | iPr | Me | Me | NO2 | 1Me-5-1HIdz | C | | 411 (M$^+$ + 1) |
| N-g-100 | NA | N-g-99 | | iPr | Me | H | NO2 | 1Me-5-1HIdz | C | | 397 (M$^+$ + 1) |
| N-g-101 | ND1 | N-g-45 | | cPen | H | Me | NH2 | 2-Nap | C | | 389 (M$^+$ + 1) |
| N-g-102 | NA | N-g-101 | | cPen | H | H | NH2 | 2-Nap | C | | 375 (M$^+$ + 1) |
| N-g-103 | ND1 | N-g-47 | | cPen | H | Me | NH2 | 5-Ind | C | | 378 (M$^+$ + 1) |
| N-g-104 | NA | N-g-103 | | cPen | H | H | NH2 | 5-Ind | C | | 364 (M$^+$ + 1) |
| N-g-105 | ND1 | N-g-49 | | cPen | H | Me | NH2 | 1Me-5-Ind | C | | 392 (M$^+$ + 1) |
| N-g-106 | NA | N-g-105 | | cPen | H | H | NH2 | 1Me-5-Ind | C | | 378 (M$^+$ + 1) |
| N-g-107 | ND1 | N-g-51 | | cPen | H | Me | NH2 | 5-1HIdz | C | | 379 (M$^+$ + 1) |
| N-g-108 | NA | N-g-107 | | cPen | H | H | NH2 | 5-1HIdz | C | | 365 (M$^+$ + 1) |
| N-g-109 | ND1 | N-g-53 | | cPen | H | Me | NH2 | 1Me-5-1HIdz | C | | 393 (M$^+$ + 1) |
| N-g-110 | NA | N-g-109 | | cPen | H | H | NH2 | 1Me-5-1HIdz | C | | 379 (M$^+$ + 1) |
| N-g-111 | ND1 | N-g-55 | | nPr | H | Me | NH2 | 2-Nap | C | | 363 (M$^+$ + 1) |
| N-g-112 | NA | N-g-111 | | nPr | H | H | NH2 | 2-Nap | C | | 349 (M$^+$ + 1) |
| N-g-113 | ND1 | N-g-57 | | nPr | H | Me | NH2 | 5-Ind | C | | 352 (M$^+$ + 1) |
| N-g-114 | NA | N-g-113 | | nPr | H | H | NH2 | 5-Ind | C | | 338 (M$^+$ + 1) |
| N-g-115 | ND1 | N-g-59 | | nPr | H | Me | NH2 | 1Me-5-Ind | C | | 366 (M$^+$ + 1) |
| N-g-116 | NA | N-g-115 | | nPr | H | H | NH2 | 1Me-5-Ind | C | | 352 (M$^+$ + 1) |
| N-g-117 | ND1 | N-g-61 | | nPr | H | Me | NH2 | 5-1HIdz | C | | 353 (M$^+$ + 1) |
| N-g-118 | NA | N-g-117 | | nPr | H | H | NH2 | 5-1HIdz | C | | 339 (M$^+$ + 1) |
| N-g-119 | ND1 | N-g-63 | | nPr | H | Me | NH2 | 1Me-5-1HIdz | C | | 367 (M$^+$ + 1) |
| N-g-120 | NA | N-g-119 | | nPr | H | H | NH2 | 1Me-5-1HIdz | C | | 353 (M$^+$ + 1) |
| N-g-121 | ND1 | N-g-65 | | iPr | H | Me | NH2 | 2-Nap | C | | 363 (M$^+$ + 1) |

TABLE N-G-3-continued

| | | | | | | | | | LCMS | |
|---|---|---|---|---|---|---|---|---|---|---|
| Exp. | Syn | SM1 | SM2 | Rz | Ry | Y | Zx | AR | method | RTime Mass |
| N-g-122 | NA | N-g-121 | | iPr | H | H | NH2 | 2-Nap | C | 349 (M+ + 1) |
| N-g-123 | ND1 | N-g-67 | | iPr | H | Me | NH2 | 5-Ind | C | 352 (M+ + 1) |
| N-g-124 | NA | N-g-123 | | iPr | H | H | NH2 | 5-Ind | C | 338 (M+ + 1) |
| N-g-125 | ND1 | N-g-69 | | iPr | H | Me | NH2 | 1Me-5-Ind | C | 336 (M+ + 1) |
| N-g-126 | NA | N-g-125 | | iPr | H | H | NH2 | 1Me-5-Ind | C | 352 (M+ + 1) |
| N-g-127 | ND1 | N-g-71 | | iPr | H | Me | NH2 | 5-1HIdz | C | 353 (M+ + 1) |
| N-g-128 | NA | N-g-127 | | iPr | H | H | NH2 | 5-1HIdz | C | 339 (M+ + 1) |
| N-g-129 | ND1 | N-g-73 | | iPr | H | Me | NH2 | 1Me-5-1HIdz | C | 367 (M+ + 1) |
| N-g-130 | NA | N-g-129 | | iPr | H | H | NH2 | 1Me-5-1HIdz | C | 353 (M+ + 1) |
| N-g-131 | NC1 | N-g-75 | | cPen | Me | Me | NH2 | 2-Nap | C | 389 (M+ + 1) |
| N-g-132 | NA | N-g-131 | | cPen | Me | H | NH2 | 2-Nap | C | 375 (M+ + 1) |
| N-g-133 | NC1 | N-g-77 | | cPen | Me | Me | NH2 | 1Me-5-Ind | C | 392 (M+ + 1) |
| N-g-134 | NA | N-g-133 | | cPen | Me | H | NH2 | 1Me-5-Ind | C | 378 (M+ + 1) |
| N-g-135 | NC1 | N-g-79 | | cPen | Me | Me | NH2 | 5-1HIdz | C | 379 (M+ + 1) |
| N-g-136 | NA | N-g-135 | | cPen | Me | H | NH2 | 5-1HIdz | C | 365 (M+ + 1) |
| N-g-137 | NC1 | N-g-81 | | cPen | Me | Me | NH2 | 1Me-5-1HIdz | C | 393 (M+ + 1) |
| N-g-138 | NA | N-g-137 | | cPen | Me | H | NH2 | 1Me-5-1HIdz | C | 379 (M+ + 1) |

TABLE N-G-4

| | | | | | | | | | LCMS | |
|---|---|---|---|---|---|---|---|---|---|---|
| Exp. | Syn | SM1 | SM2 | Rz | Ry | Y | Zx | AR | method | RTime Mass |
| N-g-139 | ND1 | N-g-83 | | nPr | Me | Me | NH2 | 2-Nap | C | 363 (M+ + 1) |
| N-g-140 | NA | N-g-139 | | nPr | Me | H | NH2 | 2-Nap | C | 349 (M+ + 1) |
| N-g-141 | ND1 | N-g-85 | | nPr | Me | Me | NH2 | 5-Ind | C | 352 (M+ + 1) |
| N-g-142 | NA | N-g-141 | | nPr | Me | H | NH2 | 5-Ind | C | 338 (M+ + 1) |
| N-g-143 | ND1 | N-g-87 | | nPr | Me | Me | NH2 | 1Me-5-Ind | C | 366 (M+ + 1) |
| N-g-144 | NA | N-g-143 | | nPr | Me | H | NH2 | 1Me-5-Ind | C | 352 (M+ + 1) |
| N-g-145 | ND1 | N-g-89 | | nPr | Me | Me | NH2 | 5-1HIdz | C | 353 (M+ + 1) |
| N-g-146 | NA | N-g-145 | | nPr | Me | H | NH2 | 5-1HIdz | C | 339 (M+ + 1) |
| N-g-147 | ND1 | N-g-91 | | nPr | Me | Me | NH2 | 1Me-5-1HIdz | C | 367 (M+ + 1) |
| N-g-148 | NA | N-g-147 | | nPr | Me | H | NH2 | 1Me-5-1HIdz | C | 353 (M+ + 1) |
| N-g-149 | ND1 | N-g-93 | | iPr | Me | Me | NH2 | 2-Nap | C | 363 (M+ + 1) |
| N-g-150 | NA | N-g-149 | | iPr | Me | H | NH2 | 2-Nap | C | 349 (M+ + 1) |
| N-g-151 | ND1 | N-g-95 | | iPr | Me | Me | NH2 | 1Me-5-Ind | C | 366 (M+ + 1) |
| N-g-152 | NA | N-g-151 | | iPr | Me | H | NH2 | 1Me-5-Ind | C | 352 (M+ + 1) |
| N-g-153 | ND1 | N-g-97 | | iPr | Me | Me | NH2 | 5-1HIdz | C | 353 (M+ + 1) |
| N-g-154 | NA | N-g-153 | | iPr | Me | H | NH2 | 5-1HIdz | C | 339 (M+ + 1) |
| N-g-155 | ND1 | N-g-99 | | iPr | Me | Me | NH2 | 1Me-5-1HIdz | C | 367 (M+ + 1) |
| N-g-156 | NA | N-g-155 | | iPr | Me | H | NH2 | 1Me-5-1HIdz | C | 353 (M+ + 1) |
| N-g-157 | NB1 | Int.n-80 | BRA1 | 2-Indane | H | Me | NO2 | 2-Nap | C | 467 (M+ + 1) |
| N-g-158 | NA | N-g-157 | | 2-Indane | H | H | NO2 | 2-Nap | C | 453 (M+ + 1) |
| N-g-159 | NB1 | Int.n-80 | BRA2 | 2-Indane | H | Me | NO2 | 5-Ind | C | 456 (M+ + 1) |
| N-g-160 | NA | N-g-159 | | 2-Indane | H | H | NO2 | 5-Ind | C | 442 (M+ + 1) |
| N-g-161 | NB1 | Int.n-80 | BRA3 | 2-Indane | H | Me | NO2 | 1Me-5-Ind | C | 470 (M+ + 1) |
| N-g-162 | NA | N-g-161 | | 2-Indane | H | H | NO2 | 1Me-5-Ind | C | 456 (M+ + 1) |
| N-g-163 | NB1 | Int.n-80 | BRA5 | 2-Indane | H | Me | NO2 | 5-1HIdz | C | 457 (M+ + 1) |
| N-g-164 | NA | N-g-163 | | 2-Indane | H | H | NO2 | 5-1HIdz | C | 443 (M+ + 1) |
| N-g-165 | NB1 | Int.n-80 | BRA6 | 2-Indane | H | Me | NO2 | 1Me-5-1HIdz | C | 471 (M+ + 1) |
| N-g-166 | NA | N-g-165 | | 2-Indane | H | H | NO2 | 1Me-5-1HIdz | C | 457 (M+ + 1) |
| N-g-167 | NB1 | Int.n-81 | BRA2 | cHex | H | Me | NO2 | 5-Ind | C | 422 (M+ + 1) |
| N-g-168 | NA | N-g-167 | | cHex | H | H | NO2 | 5-Ind | C | 408 (M+ + 1) |
| N-g-169 | NB1 | Int.n-81 | BRA3 | cHex | H | Me | NO2 | 1Me-5-Ind | C | 436 (M+ + 1) |
| N-g-170 | NA | N-g-169 | | cHex | H | H | NO2 | 1Me-5-Ind | C | 422 (M+ + 1) |
| N-g-171 | NB1 | Int.n-81 | BRA5 | cHex | H | Me | NO2 | 5-1HIdz | C | 423 (M+ + 1) |
| N-g-172 | NA | N-g-171 | | cHex | H | H | NO2 | 5-1HIdz | C | 409 (M+ + 1) |
| N-g-173 | NB1 | Int.n-81 | BRA6 | cHex | H | Me | NO2 | 1Me-5-1HIdz | C | 437 (M+ + 1) |
| N-g-174 | NA | N-g-173 | | cHex | H | H | NO2 | 1Me-5-1HIdz | C | 423 (M+ + 1) |
| N-g-175 | NB1 | Int.n-82 | BRA1 | 2(Me)cHex | H | Me | NO2 | 2-Nap | C | 447 (M+ + 1) |
| N-g-176 | NA | N-g-175 | | 2(Me)cHex | H | H | NO2 | 2-Nap | C | 433 (M+ + 1) |
| N-g-177 | NB1 | Int.n-82 | BRA2 | 2(Me)cHex | H | Me | NO2 | 5-Ind | C | 436 (M+ + 1) |
| N-g-178 | NA | N-g-177 | | 2(Me)cHex | H | H | NO2 | 5-Ind | C | 422 (M+ + 1) |
| N-g-179 | NB1 | Int.n-82 | BRA3 | 2(Me)cHex | H | Me | NO2 | 1Me-5-Ind | C | 450 (M+ + 1) |
| N-g-180 | NA | N-g-179 | | 2(Me)cHex | H | H | NO2 | 1Me-5-Ind | C | 436 (M+ + 1) |
| N-g-181 | NB1 | Int.n-82 | BRA5 | 2(Me)cHex | H | Me | NO2 | 5-1HIdz | C | 437 (M+ + 1) |
| N-g-182 | NA | N-g-181 | | 2(Me)cHex | H | H | NO2 | 5-1HIdz | C | 423 (M+ + 1) |
| N-g-183 | NB1 | Int.n-82 | BRA6 | 2(Me)cHex | H | Me | NO2 | 1Me-5-1HIdz | C | 451 (M+ + 1) |
| N-g-184 | NA | N-g-183 | | 2(Me)cHex | H | H | NO2 | 1Me-5-1HIdz | C | 437 (M+ + 1) |

TABLE N-G-5

| Exp. | Syn | SM1 | SM2 | Rz | Ry | Y | Zx | AR | LCMS method | RTime | Mass |
|---|---|---|---|---|---|---|---|---|---|---|---|
| N-g-185 | NB1 | Int.n-86 | BRA1 | 2-Indane | Me | Me | NO2 | 2-Nap | C | | 481 (M⁺ + 1) |
| N-g-186 | NA | N-g-185 | | 2-Indane | Me | H | NO2 | 2-Nap | C | | 467 (M⁺ + 1) |
| N-g-187 | NB1 | Int.n-86 | BRA3 | 2-Indane | Me | Me | NO2 | 1Me-5-Ind | C | | 484 (M⁺ + 1) |
| N-g-188 | NA | N-g-187 | | 2-Indane | Me | H | NO2 | 1Me-5-Ind | C | | 470 (M⁺ + 1) |
| N-g-189 | NB1 | Int.n-86 | BRA5 | 2-Indane | Me | Me | NO2 | 5-1HIdz | C | | 471 (M⁺ + 1) |
| N-g-190 | NA | N-g-189 | | 2-Indane | Me | H | NO2 | 5-1HIdz | C | | 457 (M⁺ + 1) |
| N-g-191 | NB1 | Int.n-86 | BRA6 | 2-Indane | Me | Me | NO2 | 1Me-5-1HIdz | C | | 485 (M⁺ + 1) |
| N-g-192 | NA | N-g-191 | | 2-Indane | Me | H | NO2 | 1Me-5-1HIdz | C | | 471 (M⁺ + 1) |
| N-g-193 | NB1 | Int.n-87 | BRA1 | cHex | Me | Me | NO2 | 2-Nap | C | | 447 (M⁺ + 1) |
| N-g-194 | NA | N-g-193 | | cHex | Me | H | NO2 | 2-Nap | C | | 433 (M⁺ + 1) |
| N-g-195 | NB1 | Int.n-87 | BRA3 | cHex | Me | Me | NO2 | 1Me-5-Ind | C | | 450 (M⁺ + 1) |
| N-g-196 | NA | N-g-195 | | cHex | Me | H | NO2 | 1Me-5-Ind | C | | 436 (M⁺ + 1) |
| N-g-197 | NB1 | Int.n-87 | BRA5 | cHex | Me | Me | NO2 | 5-1HIdz | C | | 437 (M⁺ + 1) |
| N-g-198 | NA | N-g-197 | | cHex | Me | H | NO2 | 5-1HIdz | C | | 423 (M⁺ + 1) |
| N-g-199 | NB1 | Int.n-87 | BRA6 | cHex | Me | Me | NO2 | 1Me-5-1HIdz | C | | 451 (M⁺ + 1) |
| N-g-200 | NA | N-g-199 | | cHex | Me | H | NO2 | 1Me-5-1HIdz | C | | 437 (M⁺ + 1) |
| N-g-201 | NB1 | Int.n-88 | BRA1 | 4(Me)cHex | Me | Me | NO2 | 2-Nap | C | | 461 (M⁺ + 1) |
| N-g-202 | NA | N-g-201 | | 4(Me)cHex | Me | H | NO2 | 2-Nap | C | | 447 (M⁺ + 1) |
| N-g-203 | NB1 | Int.n-88 | BRA3 | 4(Me)cHex | Me | Me | NO2 | 1Me-5-Ind | C | | 464 (M⁺ + 1) |
| N-g-204 | NA | N-g-203 | | 4(Me)cHex | Me | H | NO2 | 1Me-5-Ind | C | | 450 (M⁺ + 1) |
| N-g-205 | NB1 | Int.n-88 | BRA6 | 4(Me)cHex | Me | Me | NO2 | 1Me-5-1HIdz | C | | 465 (M⁺ + 1) |
| N-g-206 | NA | N-g-205 | | 4(Me)cHex | Me | H | NO2 | 1Me-5-1HIdz | C | | 451 (M⁺ + 1) |
| N-g-207 | ND1 | N-g-159 | | 2-Indane | H | Me | NH2 | 5-Ind | C | | 426 (M⁺ + 1) |
| N-g-208 | NA | N-g-207 | | 2-Indane | H | H | NH2 | 5-Ind | C | | 412 (M⁺ + 1) |
| N-g-209 | ND1 | N-g-161 | | 2-Indane | H | Me | NH2 | 1Me-5-Ind | C | | 440 (M⁺ + 1) |
| N-g-210 | NA | N-g-209 | | 2-Indane | H | H | NH2 | 1Me-5-Ind | C | | 426 (M⁺ + 1) |
| N-g-211 | ND1 | N-g-163 | | 2-Indane | H | Me | NH2 | 5-1HIdz | C | | 427 (M⁺ + 1) |
| N-g-212 | NA | N-g-211 | | 2-Indane | H | H | NH2 | 5-1HIdz | C | | 413 (M⁺ + 1) |
| N-g-213 | ND1 | N-g-165 | | 2-Indane | H | Me | NH2 | 1Me-5-1HIdz | C | | 441 (M⁺ + 1) |
| N-g-214 | NA | N-g-213 | | 2-Indane | H | H | NH2 | 1Me-5-1HIdz | C | | 427 (M⁺ + 1) |
| N-g-215 | ND1 | N-g-167 | | cHex | H | Me | NH2 | 5-Ind | C | | 392 (M⁺ + 1) |
| N-g-216 | NA | N-g-215 | | cHex | H | H | NH2 | 5-Ind | C | | 378 (M⁺ + 1) |
| N-g-217 | ND1 | N-g-169 | | cHex | H | Me | NH2 | 1Me-5-Ind | C | | 406 (M⁺ + 1) |
| N-g-218 | NA | N-g-217 | | cHex | H | H | NH2 | 1Me-5-Ind | C | | 392 (M⁺ + 1) |
| N-g-219 | ND1 | N-g-171 | | cHex | H | Me | NH2 | 5-1HIdz | C | | 393 (M⁺ + 1) |
| N-g-220 | NA | N-g-219 | | cHex | H | H | NH2 | 5-1HIdz | C | | 379 (M⁺ + 1) |
| N-g-221 | ND1 | N-g-173 | | cHex | H | Me | NH2 | 1Me-5-1HIdz | C | | 407 (M⁺ + 1) |
| N-g-222 | NA | N-g-221 | | cHex | H | H | NH2 | 1Me-5-1HIdz | C | | 393 (M⁺ + 1) |
| N-g-223 | ND1 | N-g-177 | | 4(Me)cHex | H | Me | NH2 | 5-Ind | C | | 406 (M⁺ + 1) |
| N-g-224 | NA | N-g-223 | | 4(Me)cHex | H | H | NH2 | 5-Ind | C | | 392 (M⁺ + 1) |
| N-g-225 | ND1 | N-g-179 | | 4(Me)cHex | H | Me | NH2 | 1Me-5-Ind | C | | 420 (M⁺ + 1) |
| N-g-226 | NA | N-g-225 | | 4(Me)cHex | H | H | NH2 | 1Me-5-Ind | C | | 406 (M⁺ + 1) |
| N-g-227 | ND1 | N-g-181 | | 4(Me)cHex | H | Me | NH2 | 5-1HIdz | C | | 407 (M⁺ + 1) |
| N-g-228 | NA | N-g-227 | | 4(Me)cHex | H | H | NH2 | 5-1HIdz | C | | 393 (M⁺ + 1) |
| N-g-229 | ND1 | N-g-183 | | 4(Me)cHex | H | Me | NH2 | 1Me-5-1HIdz | C | | 421 (M⁺ + 1) |
| N-g-230 | NA | N-g-229 | | 4(Me)cHex | H | H | NH2 | 1Me-5-1HIdz | C | | 407 (M⁺ + 1) |

TABLE N-G-6

| Exp. | Syn | SM1 | SM2 | Rz | Ry | Y | Zx | AR | LCMS method | RTime | Mass |
|---|---|---|---|---|---|---|---|---|---|---|---|
| N-g-231 | ND1 | N-g-185 | | 2-Indane | Me | Me | NH2 | 2-Nap | C | | 451 (M⁺ + 1) |
| N-g-232 | NA | N-g-231 | | 2-Indane | Me | H | NH2 | 2-Nap | C | | 437 (M⁺ + 1) |
| N-g-233 | ND1 | N-g-187 | | 2-Indane | Me | Me | NH2 | 1Me-5-Ind | C | | 454 (M⁺ + 1) |
| N-g-234 | NA | N-g-233 | | 2-Indane | Me | H | NH2 | 1Me-5-Ind | C | | 440 (M⁺ + 1) |
| N-g-235 | ND1 | N-g-191 | | 2-Indane | Me | Me | NH2 | 1Me-5-1HIdz | C | | 455 (M⁺ + 1) |
| N-g-236 | NA | N-g-235 | | 2-Indane | Me | H | NH2 | 1Me-5-1HIdz | C | | 441 (M⁺ + 1) |
| N-g-237 | ND1 | N-g-193 | | cHex | Me | Me | NH2 | 2-Nap | C | | 417 (M⁺ + 1) |
| N-g-238 | NA | N-g-237 | | cHex | Me | H | NH2 | 2-Nap | C | | 403 (M⁺ + 1) |
| N-g-239 | ND1 | N-g-195 | | cHex | Me | Me | NH2 | 1Me-5-Ind | C | | 420 (M⁺ + 1) |
| N-g-240 | NA | N-g-239 | | cHex | Me | H | NH2 | 1Me-5-Ind | C | | 406 (M⁺ + 1) |
| N-g-241 | ND1 | N-g-197 | | cHex | Me | Me | NH2 | 5-1HIdz | C | | 407 (M⁺ + 1) |
| N-g-242 | NA | N-g-241 | | cHex | Me | H | NH2 | 5-1HIdz | C | | 393 (M⁺ + 1) |
| N-g-243 | ND1 | N-g-199 | | cHex | Me | Me | NH2 | 1Me-5-1HIdz | C | | 421 (M⁺ + 1) |
| N-g-244 | NA | N-g-243 | | cHex | Me | H | NH2 | 1Me-5-1HIdz | C | | 407 (M⁺ + 1) |
| N-g-245 | ND1 | N-g-201 | | 4(Me)cHex | Me | Me | NH2 | 2-Nap | C | | 431 (M⁺ + 1) |
| N-g-246 | NA | N-g-245 | | 4(Me)cHex | Me | H | NH2 | 2-Nap | C | | 417 (M⁺ + 1) |
| N-g-247 | ND1 | N-g-203 | | 4(Me)cHex | Me | Me | NH2 | 1Me-5-Ind | C | | 434 (M⁺ + 1) |
| N-g-248 | NA | N-g-247 | | 4(Me)cHex | Me | H | NH2 | 1Me-5-Ind | C | | 420 (M⁺ + 1) |
| N-g-249 | ND1 | N-g-205 | | 4(Me)cHex | Me | Me | NH2 | 1Me-5-1HIdz | C | | 435 (M⁺ + 1) |

TABLE N-G-6-continued

| Exp. | Syn | SM1 | SM2 | Rz | Ry | Y | Zx | AR | LCMS method | RTime | Mass |
|---|---|---|---|---|---|---|---|---|---|---|---|
| N-g-250 | NA | N-g-249 | | 4(Me)cHex | Me | H | NH2 | 1Me-5-1HIdz | C | | 421 (M⁺ + 1) |
| N-g-251 | NN1 | N-g-131 | CH₃I | cPen | Me | Me | NHMe | 2-Nap | C | | 417 (M⁺ + 1) |
| N-g-252 | NA | N-g-251 | | cPen | Me | H | NHMe | 2-Nap | C | | 403 (M⁺ + 1) |
| N-g-253 | NN1 | N-g-133 | CH₃I | cPen | Me | Me | NHMe | 1Me-5-Ind | C | | 420 (M⁺ + 1) |
| N-g-254 | NA | N-g-253 | | cPen | Me | H | NHMe | 1Me-5-Ind | C | | 406 (M⁺ + 1) |
| N-g-255 | NN1 | N-g-137 | CH₃I | cPen | Me | Me | NHMe | 1Me-5-1HIdz | C | | 421 (M⁺ + 1) |
| N-g-256 | NA | N-g-255 | | cPen | Me | H | NHMe | 1Me-5-1HIdz | C | | 407 (M⁺ + 1) |
| N-g-257 | NN1 | N-g-139 | CH₃I | nPr | Me | Me | NHMe | 2-Nap | C | | 391 (M⁺ + 1) |
| N-g-258 | NA | N-g-257 | | nPr | Me | H | NHMe | 2-Nap | C | | 377 (M⁺ + 1) |
| N-g-259 | NN1 | N-g-143 | CH₃I | nPr | Me | Me | NHMe | 1Me-5-Ind | C | | 394 (M⁺ + 1) |
| N-g-260 | NA | N-g-259 | | nPr | Me | H | NHMe | 1Me-5-Ind | C | | 380 (M⁺ + 1) |
| N-g-261 | NN1 | N-g-147 | CH₃I | nPr | Me | Me | NHMe | 1Me-5-1HIdz | C | | 395 (M⁺ + 1) |
| N-g-262 | NA | N-g-261 | | nPr | Me | H | NHMe | 1Me-5-1HIdz | C | | 381 (M⁺ + 1) |
| N-g-263 | NN1 | N-g-149 | CH₃I | iPr | Me | Me | NHMe | 2-Nap | C | | 391 (M⁺ + 1) |
| N-g-264 | NA | N-g-263 | | iPr | Me | H | NHMe | 2-Nap | C | | 377 (M⁺ + 1) |
| N-g-265 | NN1 | N-g-151 | CH₃I | iPr | Me | Me | NHMe | 1Me-5-Ind | C | | 394 (M⁺ + 1) |
| N-g-266 | NA | N-g-265 | | iPr | Me | H | NHMe | 1Me-5-Ind | C | | 380 (M⁺ + 1) |
| N-g-267 | NN1 | N-g-155 | CH₃I | iPr | Me | Me | NHMe | 1Me-5-1HIdz | C | | 395 (M⁺ + 1) |
| N-g-268 | NA | N-g-267 | | iPr | Me | H | NHMe | 1Me-5-1HIdz | C | | 381 (M⁺ + 1) |
| N-g-269 | NN1 | N-g-231 | CH₃I | 2-Indane | Me | Me | NHMe | 2-Nap | C | | 465 (M⁺ + 1) |
| N-g-270 | NA | N-g-269 | | 2-Indane | Me | H | NHMe | 2-Nap | C | | 451 (M⁺ + 1) |
| N-g-271 | NN1 | N-g-233 | CH₃I | 2-Indane | Me | Me | NHMe | 1Me-5-Ind | C | | 468 (M⁺ + 1) |
| N-g-272 | NA | N-g-271 | | 2-Indane | Me | H | NHMe | 1Me-5-Ind | C | | 454 (M⁺ + 1) |
| N-g-273 | NN1 | N-g-235 | CH₃I | 2-Indane | Me | Me | NHMe | 1Me-5-1HIdz | C | | 469 (M⁺ + 1) |
| N-g-274 | NA | N-g-273 | | 2-Indane | Me | H | NHMe | 1Me-5-1HIdz | C | | 455 (M⁺ + 1) |
| N-g-275 | NN1 | N-g-237 | CH₃I | cHex | Me | Me | NHMe | 2-Nap | C | | 431 (M⁺ + 1) |
| N-g-276 | NA | N-g-275 | | cHex | Me | H | NHMe | 2-Nap | C | | 417 (M⁺ + 1) |

TABLE N-G-7

| Exp. | Syn | SM1 | SM2 | Rz | Ry | Y | Zx | AR | LCMS method | RTime | Mass |
|---|---|---|---|---|---|---|---|---|---|---|---|
| N-g-277 | NN1 | N-g-239 | CH₃I | cHex | Me | Me | NHMe | 1Me-5-Ind | C | | 434 (M⁺ + 1) |
| N-g-278 | NA | N-g-277 | | cHex | Me | H | NHMe | 1Me-5-Ind | C | | 420 (M⁺ + 1) |
| N-g-279 | NN1 | N-g-245 | CH₃I | 4Me-cHex | Me | Me | NHMe | 2-Nap | C | | 445 (M⁺ + 1) |
| N-g-280 | NA | N-g-279 | | 4Me-cHex | Me | H | NHMe | 2-Nap | C | | 431 (M⁺ + 1) |
| N-g-281 | NN2 | N-g-247 | CH₃I | 4Me-cHex | Me | Me | NMe₂ | 1Me-5-Ind | C | | 448 (M⁺ + 1) |
| N-g-282 | NA | N-g-281 | | 4Me-cHex | Me | H | NMe₂ | 1Me-5-Ind | C | | 434 (M⁺ + 1) |
| N-g-283 | NN2 | N-g-249 | CH₃I | 4Me-cHex | Me | Me | NMe₂ | 1Me-5-1HIdz | C | | 449 (M⁺ + 1) |
| N-g-284 | NA | N-g-283 | | 4Me-cHex | Me | H | NMe₂ | 1Me-5-1HIdz | C | | 435 (M⁺ + 1) |
| N-g-285 | NN2 | N-g-131 | CH₃I | cPen | Me | Me | NMe₂ | 2-Nap | C | | 431 (M⁺ + 1) |
| N-g-286 | NA | N-g-285 | | cPen | Me | H | NMe₂ | 2-Nap | C | | 417 (M⁺ + 1) |
| N-g-287 | NN2 | N-g-133 | CH₃I | cPen | Me | Me | NMe₂ | 1Me-5-Ind | C | | 434 (M⁺ + 1) |
| N-g-288 | NA | N-g-287 | | cPen | Me | H | NMe₂ | 1Me-5-Ind | C | | 420 (M⁺ + 1) |
| N-g-289 | NN2 | N-g-137 | CH₃I | cPen | Me | Me | NMe₂ | 1Me-5-1HIdz | C | | 435 (M⁺ + 1) |
| N-g-290 | NA | N-g-289 | | cPen | Me | H | NMe₂ | 1Me-5-1HIdz | C | | 421 (M⁺ + 1) |
| N-g-291 | NN2 | N-g-139 | CH₃I | nPr | Me | Me | NMe₂ | 2-Nap | C | | 405 (M⁺ + 1) |
| N-g-292 | NA | N-g-291 | | nPr | Me | H | NMe₂ | 2-Nap | C | | 391 (M⁺ + 1) |
| N-g-293 | NN2 | N-g-143 | CH₃I | nPr | Me | Me | NMe₂ | 1Me-5-Ind | C | | 408 (M⁺ + 1) |
| N-g-294 | NA | N-g-293 | | nPr | Me | H | NMe₂ | 1Me-5-Ind | C | | 394 (M⁺ + 1) |
| N-g-295 | NN2 | N-g-147 | CH₃I | nPr | Me | Me | NMe₂ | 1Me-5-1HIdz | C | | 409 (M⁺ + 1) |
| N-g-296 | NA | N-g-295 | | nPr | Me | H | NMe₂ | 1Me-5-1HIdz | C | | 395 (M⁺ + 1) |
| N-g-297 | NN2 | N-g-149 | CH₃I | iPr | Me | Me | NMe₂ | 2-Nap | C | | 405 (M⁺ + 1) |
| N-g-298 | NA | N-g-297 | | iPr | Me | H | NMe₂ | 2-Nap | C | | 391 (M⁺ + 1) |
| N-g-299 | NN2 | N-g-151 | CH₃I | iPr | Me | Me | NMe₂ | 1Me-5-Ind | C | | 408 (M⁺ + 1) |
| N-g-300 | NA | N-g-299 | | iPr | Me | H | NMe₂ | 1Me-5-Ind | C | | 394 (M⁺ + 1) |
| N-g-301 | NN2 | N-g-155 | CH₃I | iPr | Me | Me | NMe₂ | 1Me-5-1HIdz | C | | 409 (M⁺ + 1) |
| N-g-302 | NA | N-g-301 | | iPr | Me | H | NMe₂ | 1Me-5-1HIdz | C | | 395 (M⁺ + 1) |
| N-g-303 | NN2 | N-g-231 | CH₃I | 2Indane | Me | Me | NMe₂ | 2-Nap | C | | 479 (M⁺ + 1) |
| N-g-304 | NA | N-g-303 | | 2Indane | Me | H | NMe₂ | 2-Nap | C | | 465 (M⁺ + 1) |
| N-g-305 | NN2 | N-g-233 | CH₃I | 2Indane | Me | Me | NMe₂ | 1Me-5-Ind | C | | 482 (M⁺ + 1) |
| N-g-306 | NA | N-g-305 | | 2Indane | Me | H | NMe₂ | 1Me-5-Ind | C | | 468 (M⁺ + 1) |
| N-g-307 | NN2 | N-g-235 | CH₃I | 2Indane | Me | Me | NMe₂ | 1Me-5-1HIdz | C | | 483 (M⁺ + 1) |
| N-g-308 | NA | N-g-307 | | 2Indane | Me | H | NMe₂ | 1Me-5-1HIdz | C | | 469 (M⁺ + 1) |
| N-g-309 | NN2 | N-g-237 | CH₃I | cHex | Me | Me | NMe₂ | 2-Nap | C | | 445 (M⁺ + 1) |
| N-g-310 | NA | N-g-265 | | cHex | Me | H | NMe₂ | 2-Nap | C | | 431 (M⁺ + 1) |
| N-g-311 | NN2 | N-g-239 | CH₃I | cHex | Me | Me | NMe₂ | 1Me-5-Ind | C | | 448 (M⁺ + 1) |
| N-g-312 | NA | N-g-267 | | cHex | Me | H | NMe₂ | 1Me-5-Ind | C | | 434 (M⁺ + 1) |
| N-g-313 | NN2 | N-g-245 | CH₃I | 4Me-cHex | Me | Me | NMe₂ | 2-Nap | C | | 459 (M⁺ + 1) |
| N-g-314 | NA | N-g-269 | | 4Me-cHex | Me | H | NMe₂ | 2-Nap | C | | 445 (M⁺ + 1) |

TABLE N-G-7-continued

| Exp. | Syn | SM1 | SM2 | Rz | Ry | Y | Zx | AR | LCMS method | RTime | Mass |
|---|---|---|---|---|---|---|---|---|---|---|---|
| N-g-315 | NN2 | N-g-247 | CH₃I | 4Me-cHex | Me | Me | NMe₂ | 1Me-5-Ind | C | | 462 (M⁺ + 1) |
| N-g-316 | NA | N-g-271 | | 4Me-cHex | Me | H | NMe₂ | 1Me-5-Ind | C | | 448 (M⁺ + 1) |
| N-g-317 | NN2 | N-g-249 | CH₃I | 4Me-cHex | Me | Me | NMe₂ | 1Me-5-1HIdz | C | | 463 (M⁺ + 1) |
| N-g-318 | NA | N-g-273 | | 4Me-cHex | Me | H | NMe₂ | 1Me-5-1HIdz | C | | 449 (M⁺ + 1) |

Examples N-h-1 to N-h-458

Typical examples of the compounds of the present invention that can be obtained by reacting and treating corresponding starting compounds using any of the methods described in the present specification are shown in Table-N-H-1 to Table-N-H-10. In the tables, the compound numbers are mentioned in the columns indicated as "Exp.". In the tables, corresponding methods among the aforementioned synthesis methods are shown in the columns of "Syn" with symbols, the starting compounds 1 are mentioned in the columns of "SM1", and the starting compounds 2 are mentioned in the columns of "SM2".

TABLE N-H-1

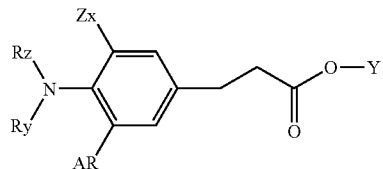

| Exp. | Syn | SM1 | SM2 | Rz | Ry | Y | Zx | AR | LCMS method | RTime | Mass |
|---|---|---|---|---|---|---|---|---|---|---|---|
| N-h-1 | NB1 | Int.n-89 | BRA1 | Bn | H | Me | NO2 | 2-Nap | C | | 441 (M⁺ + 1) |
| N-h-2 | NA | N-h-1 | | Bn | H | H | NO2 | 2-Nap | C | | 427 (M⁺ + 1) |
| N-h-3 | NB1 | Int.n-89 | BRA2 | Bn | H | Me | NO2 | 5-Ind | C | | 430 (M⁺ + 1) |
| N-h-4 | NA | N-h-3 | | Bn | H | H | NO2 | 5-Ind | C | | 416 (M⁺ + 1) |
| N-h-5 | NB1 | Int.n-89 | BRA3 | Bn | H | Me | NO2 | 1Me-5-Ind | C | | 444 (M⁺ + 1) |
| N-h-6 | NA | N-h-5 | | Bn | H | H | NO2 | 1Me-5-Ind | C | | 430 (M⁺ + 1) |
| N-h-7 | NB1 | Int.n-89 | BRA5 | Bn | H | Me | NO2 | 5-1HIdz | C | | 431 (M⁺ + 1) |
| N-h-8 | NA | N-h-7 | | Bn | H | H | NO2 | 5-1HIdz | C | | 417 (M⁺ + 1) |
| N-h-9 | NB1 | Int.n-89 | BRA6 | Bn | H | Me | NO2 | 1Me-5-1HIdz | C | | 445 (M⁺ + 1) |
| N-h-10 | NA | N-h-9 | | Bn | H | H | NO2 | 1Me-5-1HIdz | C | | 431 (M⁺ + 1) |
| N-h-11 | NB1 | Int.n-89 | BRA10 | Bn | H | Me | NO2 | 3-Qu | C | | 442 (M⁺ + 1) |
| N-h-12 | NA | N-h-11 | | Bn | H | H | NO2 | 3-Qu | C | | 428 (M⁺ + 1) |
| N-h-13 | NB1 | Int.n-89 | BRA11 | Bn | H | Me | NO2 | 6-Qu | C | | 442 (M⁺ + 1) |
| N-h-14 | NA | N-h-13 | | Bn | H | H | NO2 | 6-Qu | C | | 428 (M⁺ + 1) |
| N-h-15 | NB1 | Int.n-89 | BRA12 | Bn | H | Me | NO2 | 6-IQ | C | | 442 (M⁺ + 1) |
| N-h-16 | NA | N-h-15 | | Bn | H | H | NO2 | 6-IQ | C | | 428 (M⁺ + 1) |
| N-h-17 | NB1 | Int.n-90 | BRA1 | 4FBn | H | Me | NO2 | 2-Nap | C | | 459 (M⁺ + 1) |
| N-h-18 | NA | N-h-17 | | 4FBn | H | H | NO2 | 2-Nap | C | | 445 (M⁺ + 1) |
| N-h-19 | NB1 | Int.n-90 | BRA2 | 4FBn | H | Me | NO2 | 5-Ind | C | | 448 (M⁺) |
| N-h-20 | NA | N-h-19 | | 4FBn | H | H | NO2 | 5-Ind | C | | 434 (M⁺ + 1) |
| N-h-21 | NB1 | Int.n-90 | BRA3 | 4FBn | H | Me | NO2 | 1Me-5-Ind | C | | 462 (M⁺ + 1) |
| N-h-22 | NA | N-h-21 | | 4FBn | H | H | NO2 | 1Me-5-Ind | C | | 448 (M⁺ + 1) |
| N-h-23 | NB1 | Int.n-90 | BRA5 | 4FBn | H | Me | NO2 | 5-1HIdz | C | | 449 (M⁺ + 1) |
| N-h-24 | NA | N-h-23 | | 4FBn | H | H | NO2 | 5-1HIdz | C | | 435 (M⁺ + 1) |
| N-h-25 | NB1 | Int.n-90 | BRA6 | 4FBn | H | Me | NO2 | 1Me-5-1HIdz | C | | 463 (M⁺ + 1) |
| N-h-26 | NA | N-h-25 | | 4FBn | H | H | NO2 | 1Me-5-1HIdz | C | | 449 (M⁺ + 1) |
| N-h-27 | NB1 | Int.n-91 | BRA2 | 2FBn | H | Me | NO2 | 5-Ind | C | | 448 (M⁺ + 1) |
| N-h-28 | NA | N-h-27 | | 2FBn | H | H | NO2 | 5-Ind | C | | 434 (M⁺ + 1) |
| N-h-29 | NB1 | Int.n-91 | BRA3 | 2FBn | H | Me | NO2 | 1Me-5-Ind | C | | 462 (M⁺ + 1) |
| N-h-30 | NA | N-h-29 | | 2FBn | H | H | NO2 | 1Me-5-Ind | C | | 448 (M⁺ + 1) |
| N-h-31 | NB1 | Int.n-91 | BRA5 | 2FBn | H | Me | NO2 | 5-1HIdz | C | | 449 (M⁺ + 1) |
| N-h-32 | NA | N-h-31 | | 2FBn | H | H | NO2 | 5-1HIdz | C | | 435 (M⁺ + 1) |
| N-h-33 | NB1 | Int.n-91 | BRA6 | 2FBn | H | Me | NO2 | 1Me-5-1HIdz | C | | 463 (M⁺ + 1) |
| N-h-34 | NA | N-h-33 | | 2FBn | H | H | NO2 | 1Me-5-1HIdz | C | | 449 (M⁺ + 1) |
| N-h-35 | NB1 | Int.n-92 | BRA2 | 3FBn | H | Me | NO2 | 5-Ind | C | | 448 (M⁺ + 1) |
| N-h-36 | NA | N-h-35 | | 3FBn | H | H | NO2 | 5-Ind | C | | 434 (M⁺ + 1) |
| N-h-37 | NB1 | Int.n-91 | BRA3 | 3FBn | H | Me | NO2 | 1Me-5-Ind | C | | 462 (M⁺ + 1) |
| N-h-38 | NA | N-h-37 | | 3FBn | H | H | NO2 | 1Me-5-Ind | C | | 448 (M⁺ + 1) |
| N-h-39 | NB1 | Int.n-92 | BRA5 | 3FBn | H | Me | NO2 | 5-1HIdz | C | | 449 (M⁺ + 1) |
| N-h-40 | NA | N-h-39 | | 3FBn | H | H | NO2 | 5-1HIdz | C | | 435 (M⁺ + 1) |
| N-h-41 | NB1 | Int.n-92 | BRA6 | 3FBn | H | Me | NO2 | 1Me-5-1HIdz | C | | 463 (M⁺ + 1) |
| N-h-42 | NA | N-h-41 | | 3FBn | H | H | NO2 | 1Me-5-1HIdz | C | | 449 (M⁺ + 1) |

TABLE N-H-1-continued

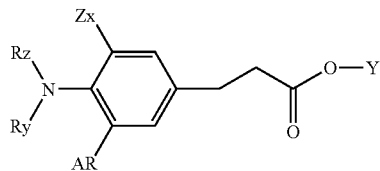

| | | | | | | | | | LCMS | |
|---|---|---|---|---|---|---|---|---|---|---|
| Exp. | Syn | SM1 | SM2 | Rz | Ry | Y | Zx | AR | method | RTime | Mass |
| N-h-43 | NB1 | Int.n-93 | BRA1 | 2,3DFBn | H | Me | NO2 | 2-Nap | C | | 477 (M⁺ + 1) |
| N-h-44 | NA | N-h-43 | | 2,3DFBn | H | H | NO2 | 2-Nap | C | | 463 (M⁺ + 1) |
| N-h-45 | NB1 | Int.n-93 | BRA3 | 2,3DFBn | H | Me | NO2 | 1Me-5-Ind | C | | 480 (M⁺ + 1) |
| N-h-46 | NA | N-h-45 | | 2,3DFBn | H | H | NO2 | 1Me-5-Ind | C | | 466 (M⁺ + 1) |

TABLE N-H-2

| | | | | | | | | | LCMS | | |
|---|---|---|---|---|---|---|---|---|---|---|---|
| Exp. | Syn | SM1 | SM2 | Rz | Ry | Y | Zx | AR | method | RTime | Mass |
| N-h-47 | NB1 | Int.n-93 | BRA5 | 2,3DFBn | H | Me | NO2 | 5-1HIdz | C | | 467 (M⁺ + 1) |
| N-h-48 | NA | N-h-47 | | 2,3DFBn | H | H | NO2 | 5-1HIdz | C | | 453 (M⁺ + 1) |
| N-h-49 | NB1 | Int.n-93 | BRA6 | 2,3DFBn | H | Me | NO2 | 1Me-5-1HIdz | C | | 481 (M⁺ + 1) |
| N-h-50 | NA | N-h-49 | | 2,3DFBn | H | H | NO2 | 1Me-5-1HIdz | C | | 467 (M⁺ + 1) |
| N-h-51 | NB1 | Int.n-94 | BRA2 | 3,4DFBn | H | Me | NO2 | 5-Ind | C | | 466 (M⁺ + 1) |
| N-h-52 | NA | N-h-51 | | 3,4DFBn | H | H | NO2 | 5-Ind | C | | 452 (M⁺ + 1) |
| N-h-53 | NB1 | Int.n-94 | BRA3 | 3,4DFBn | H | Me | NO2 | 1Me-5-Ind | C | | 480 (M⁺ + 1) |
| N-h-54 | NA | N-h-53 | | 3,4DFBn | H | H | NO2 | 1Me-5-Ind | C | | 466 (M⁺ + 1) |
| N-h-55 | NB1 | Int.n-94 | BRA6 | 3,4DFBn | H | Me | NO2 | 1Me-5-1HIdz | C | | 481 (M⁺ + 1) |
| N-h-56 | NA | N-h-55 | | 3,4DFBn | H | H | NO2 | 1Me-5-1HIdz | C | | 467 (M⁺ + 1) |
| N-h-57 | NB1 | Int.n-95 | BRA1 | 4PhBn | H | Me | NO2 | 2-Nap | C | | 517 (M⁺ + 1) |
| N-h-58 | NA | N-h-57 | | 4PhBn | H | H | NO2 | 2-Nap | C | | 503 (M⁺ + 1) |
| N-h-59 | NB1 | Int.n-95 | BRA2 | 4PhBn | H | Me | NO2 | 5-Ind | C | | 506 (M⁺ + 1) |
| N-h-60 | NA | N-h-59 | | 4PhBn | H | H | NO2 | 5-Ind | C | | 492 (M⁺ + 1) |
| N-h-61 | NB1 | Int.n-95 | BRA3 | 4PhBn | H | Me | NO2 | 1Me-5-Ind | C | | 520 (M⁺ + 1) |
| N-h-62 | NA | N-h-61 | | 4PhBn | H | H | NO2 | 1Me-5-Ind | C | | 506 (M⁺ + 1) |
| N-h-63 | NB1 | Int.n-95 | BRA5 | 4PhBn | H | Me | NO2 | 5-1HIdz | C | | 507 (M⁺ + 1) |
| N-h-64 | NA | N-h-63 | | 4PhBn | H | H | NO2 | 5-1HIdz | C | | 493 (M⁺ + 1) |
| N-h-65 | NB1 | Int.n-96 | BRA1 | 2CF3Bn | H | Me | NO2 | 2-Nap | C | | 509 (M⁺ + 1) |
| N-h-66 | NA | N-h-65 | | 2CF3Bn | H | H | NO2 | 2-Nap | C | | 495 (M⁺ + 1) |
| N-h-67 | NB1 | Int.n-96 | BRA2 | 2CF3Bn | H | Me | NO2 | 5-Ind | C | | 498 (M⁺ + 1) |
| N-h-68 | NA | N-h-67 | | 2CF3Bn | H | H | NO2 | 5-Ind | C | | 484 (M⁺ + 1) |
| N-h-69 | NB1 | Int.n-96 | BRA3 | 2CF3Bn | H | Me | NO2 | 1Me-5-Ind | C | | 512 (M⁺ + 1) |
| N-h-70 | NA | N-h-69 | | 2CF3Bn | H | H | NO2 | 1Me-5-Ind | C | | 498 (M⁺ + 1) |
| N-h-71 | NB1 | Int.n-96 | BRA5 | 2CF3Bn | H | Me | NO2 | 5-1HIdz | C | | 499 (M⁺ + 1) |
| N-h-72 | NA | N-h-71 | | 2CF3Bn | H | H | NO2 | 5-1HIdz | C | | 485 (M⁺ + 1) |
| N-h-73 | NB1 | Int.n-97 | BRA2 | 2-TF | H | Me | NO2 | 5-Ind | C | | 436 (M⁺ + 1) |
| N-h-74 | NA | N-h-73 | | 2-TF | H | H | NO2 | 5-Ind | C | | 422 (M⁺ + 1) |
| N-h-75 | NB1 | Int.n-97 | BRA3 | 2-TF | H | Me | NO2 | 1Me-5-Ind | C | | 450 (M⁺ + 1) |
| N-h-76 | NA | N-h-75 | | 2-TF | H | H | NO2 | 1Me-5-Ind | C | | 436 (M⁺ + 1) |
| N-h-77 | NB1 | Int.n-97 | BRA6 | 2-TF | H | Me | NO2 | 1Me-5-1HIdz | C | | 451 (M⁺ + 1) |
| N-h-78 | NA | N-h-77 | | 2-TF | H | H | NO2 | 1Me-5-1HIdz | C | | 437 (M⁺ + 1) |
| N-h-79 | NB1 | Int.n-98 | BRA2 | 3-TF | H | Me | NO2 | 5-Ind | C | | 436 (M⁺ + 1) |
| N-h-80 | NA | N-h-79 | | 3-TF | H | H | NO2 | 5-Ind | C | | 422 (M⁺ + 1) |
| N-h-81 | NB1 | Int.n-98 | BRA3 | 3-TF | H | Me | NO2 | 1Me-5-Ind | C | | 450 (M⁺ + 1) |
| N-h-82 | NA | N-h-81 | | 3-TF | H | H | NO2 | 1Me-5-Ind | C | | 436 (M⁺ + 1) |
| N-h-83 | NB1 | Int.n-98 | BRA5 | 3-TF | H | Me | NO2 | 5-1HIdz | C | | 437 (M⁺ + 1) |
| N-h-84 | NA | N-h-83 | | 3-TF | H | H | NO2 | 5-1HIdz | C | | 423 (M⁺ + 1) |
| N-h-85 | NB1 | Int.n-98 | BRA6 | 3-TF | H | Me | NO2 | 1Me-5-1HIdz | C | | 451 (M⁺ + 1) |
| N-h-86 | NA | N-h-85 | | 3-TF | H | H | NO2 | 1Me-5-1HIdz | C | | 437 (M⁺ + 1) |
| N-h-87 | NB1 | Int.n-99 | BRA1 | 2-FR | H | Me | NO2 | 2Nap | C | | 459 (M⁺ + 1) |
| N-h-88 | NA | N-h-87 | | 2-FR | H | H | NO2 | 2Nap | C | | 445 (M⁺ + 1) |
| N-h-89 | NB1 | Int.n-99 | BRA2 | 2-FR | H | Me | NO2 | 5-Ind | C | | 420 (M⁺ + 1) |
| N-h-90 | NA | N-h-89 | | 2-FR | H | H | NO2 | 5-Ind | C | | 406 (M⁺ + 1) |
| N-h-91 | NB1 | Int.n-99 | BRA6 | 2-FR | H | Me | NO2 | 1Me-5-1HIdz | C | | 434 (M⁺ + 1) |
| N-h-92 | NA | N-h-91 | | 2-FR | H | H | NO2 | 1Me-5-1HIdz | C | | 420 (M⁺ + 1) |

TABLE N-H-3

| Exp. | Syn | SM1 | SM2 | Rz | Ry | Y | Zx | AR | LCMS method | RTime | Mass |
|---|---|---|---|---|---|---|---|---|---|---|---|
| N-h-93 | NB1 | Int.n-100 | BRA1 | Bn | Me | Me | NO2 | 2-Nap | C | | 455 (M⁺+1) |
| N-h-94 | NA | N-h-93 | | Bn | Me | H | NO2 | 2-Nap | C | | 427 (M⁺+1) |
| N-h-95 | NB1 | Int.n-100 | BRA2 | Bn | Me | Me | NO2 | 5-Ind | C | | 430 (M⁺+1) |
| N-h-96 | NA | N-h-95 | | Bn | Me | H | NO2 | 5-Ind | C | | 416 (M⁺+1) |
| N-h-97 | NB1 | Int.n-100 | BRA3 | Bn | Me | Me | NO2 | 1Me-5-Ind | C | | 444 (M⁺+1) |
| N-h-98 | NA | N-h-97 | | Bn | Me | H | NO2 | 1Me-5-Ind | C | | 430 (M⁺+1) |
| N-h-99 | NB1 | Int.n-100 | BRA5 | Bn | Me | Me | NO2 | 5-1HIdz | C | | 431 (M⁺+1) |
| N-h-100 | NA | N-h-99 | | Bn | Me | H | NO2 | 5-1HIdz | C | | 417 (M⁺+1) |
| N-h-101 | NB1 | Int.n-100 | BRA6 | Bn | Me | Me | NO2 | 1Me-5-1HIdz | C | | 445 (M⁺+1) |
| N-h-102 | NA | N-h-101 | | Bn | Me | H | NO2 | 1Me-5-1HIdz | C | | 431 (M⁺+1) |
| N-h-103 | NB1 | Int.n-100 | BRA10 | Bn | Me | Me | NO2 | 3-Qu | C | | 442 (M⁺+1) |
| N-h-104 | NA | N-h-103 | | Bn | Me | H | NO2 | 3-Qu | C | | 428 (M⁺+1) |
| N-h-105 | NB1 | Int.n-100 | BRA11 | Bn | Me | Me | NO2 | 6-Qu | C | | 442 (M⁺+1) |
| N-h-106 | NA | N-h-105 | | Bn | Me | H | NO2 | 6-Qu | C | | 428 (M⁺+1) |
| N-h-107 | NB1 | Int.n-100 | BRA12 | Bn | Me | Me | NO2 | 6-IQ | C | | 442 (M⁺+1) |
| N-h-108 | NA | N-h-107 | | Bn | Me | H | NO2 | 6-IQ | C | | 428 (M⁺+1) |
| N-h-109 | NB1 | Int.n-101 | BRA1 | 4FBn | Me | Me | NO2 | 2-Nap | C | | 459 (M⁺+1) |
| N-h-110 | NA | N-h-109 | | 4FBn | Me | H | NO2 | 2-Nap | C | | 445 (M⁺+1) |
| N-h-111 | NB1 | Int.n-101 | BRA2 | 4FBn | Me | Me | NO2 | 5-Ind | C | | 448 (M⁺+1) |
| N-h-112 | NA | N-h-111 | | 4FBn | Me | H | NO2 | 5-Ind | C | | 434 (M⁺+1) |
| N-h-113 | NB1 | Int.n-101 | BRA3 | 4FBn | Me | Me | NO2 | 1Me-5-Ind | C | | 462 (M⁺+1) |
| N-h-114 | NA | N-h-113 | | 4FBn | Me | H | NO2 | 1Me-5-Ind | C | | 448 (M⁺+1) |
| N-h-115 | NB1 | Int.n-101 | BRA5 | 4FBn | Me | Me | NO2 | 5-1HIdz | C | | 449 (M⁺+1) |
| N-h-116 | NA | N-h-115 | | 4FBn | Me | H | NO2 | 5-1HIdz | C | | 435 (M⁺+1) |
| N-h-117 | NB1 | Int.n-101 | BRA6 | 4FBn | Me | Me | NO2 | 1Me-5-1HIdz | C | | 463 (M⁺+1) |
| N-h-118 | NA | N-h-117 | | 4FBn | Me | H | NO2 | 1Me-5-1HIdz | C | | 449 (M⁺+1) |
| N-h-119 | NB1 | Int.n-102 | BRA1 | 2FBn | Me | Me | NO2 | 2-Nap | C | | 448 (M⁺+1) |
| N-h-120 | NA | N-h-119 | | 2FBn | Me | H | NO2 | 2-Nap | C | | 434 (M⁺+1) |
| N-h-121 | NB1 | Int.n-102 | BRA3 | 2FBn | Me | Me | NO2 | 1Me-5-Ind | C | | 462 (M⁺+1) |
| N-h-122 | NA | N-h-121 | | 2FBn | Me | H | NO2 | 1Me-5-Ind | C | | 448 (M⁺+1) |
| N-h-123 | NB1 | Int.n-102 | BRA5 | 2FBn | Me | Me | NO2 | 5-1HIdz | C | | 449 (M⁺+1) |
| N-h-124 | NA | N-h-123 | | 2FBn | Me | H | NO2 | 5-1HIdz | C | | 435 (M⁺+1) |
| N-h-125 | NB1 | Int.n-102 | BRA6 | 2FBn | Me | Me | NO2 | 1Me-5-1HIdz | C | | 463 (M⁺+1) |
| N-h-126 | NA | N-h-125 | | 2FBn | Me | H | NO2 | 1Me-5-1HIdz | C | | 449 (M⁺+1) |
| N-h-127 | NB1 | Int.n-103 | BRA1 | 3FBn | Me | Me | NO2 | 2-Nap | C | | 448 (M⁺+1) |
| N-h-128 | NA | N-h-127 | | 3FBn | Me | H | NO2 | 2-Nap | C | | 434 (M⁺+1) |
| N-h-129 | NB1 | Int.n-103 | BRA3 | 3FBn | Me | Me | NO2 | 1Me-5-Ind | C | | 462 (M⁺+1) |
| N-h-130 | NA | N-h-129 | | 3FBn | Me | H | NO2 | 1Me-5-Ind | C | | 448 (M⁺+1) |
| N-h-131 | NB1 | Int.n-103 | BRA5 | 3FBn | Me | Me | NO2 | 5-1HIdz | C | | 449 (M⁺+1) |
| N-h-132 | NA | N-h-131 | | 3FBn | Me | H | NO2 | 5-1HIdz | C | | 435 (M⁺+1) |
| N-h-133 | NB1 | Int.n-103 | BRA6 | 3FBn | Me | Me | NO2 | 1Me-5-1HIdz | C | | 463 (M⁺+1) |
| N-h-134 | NA | N-h-133 | | 3FBn | Me | H | NO2 | 1Me-5-1HIdz | C | | 449 (M⁺+1) |
| N-h-135 | NB1 | Int.n-104 | BRA1 | 2,3DFBn | Me | Me | NO2 | 2-Nap | C | | 477 (M⁺+1) |
| N-h-136 | NA | N-h-135 | | 2,3DFBn | Me | H | NO2 | 2-Nap | C | | 463 (M⁺+1) |
| N-h-137 | NB1 | Int.n-104 | BRA3 | 2,3DFBn | Me | Me | NO2 | 1Me-5-Ind | C | | 480 (M⁺+1) |
| N-h-138 | NA | N-h-137 | | 2,3DFBn | Me | H | NO2 | 1Me-5-Ind | C | | 466 (M⁺+1) |

TABLE N-H-4

| Exp. | Syn | SM1 | SM2 | Rz | Ry | Y | Zx | AR | LCMS method | RTime | Mass |
|---|---|---|---|---|---|---|---|---|---|---|---|
| N-h-139 | NB1 | Int.n-104 | BRA5 | 2,3DFBn | Me | Me | NO2 | 5-1HIdz | C | | 481 (M⁺+1) |
| N-h-140 | NA | N-h-139 | | 2,3DFBn | Me | H | NO2 | 5-1HIdz | C | | 467 (M⁺+1) |
| N-h-141 | NB1 | Int.n-104 | BRA6 | 2,3DFBn | Me | Me | NO2 | 1Me-5-1HIdz | C | | 495 (M⁺+1) |
| N-h-142 | NA | N-h-141 | | 2,3DFBn | Me | H | NO2 | 1Me-5-1HIdz | C | | 481 (M⁺+1) |
| N-h-143 | NB1 | Int.n-105 | BRA1 | 3,4DFBn | Me | Me | NO2 | 2-Nap | C | | 480 (M⁺+1) |
| N-h-144 | NA | N-h-143 | | 3,4DFBn | Me | H | NO2 | 2-Nap | C | | 466 (M⁺+1) |
| N-h-145 | NB1 | Int.n-105 | BRA3 | 3,4DFBn | Me | Me | NO2 | 1Me-5-Ind | C | | 494 (M⁺+1) |
| N-h-146 | NA | N-h-145 | | 3,4DFBn | Me | H | NO2 | 1Me-5-Ind | C | | 480 (M⁺+1) |
| N-h-147 | NB1 | Int.n-105 | BRA6 | 3,4DFBn | Me | Me | NO2 | 1Me-5-1HIdz | C | | 495 (M⁺+1) |
| N-h-148 | NA | N-h-147 | | 3,4DFBn | Me | H | NO2 | 1Me-5-1HIdz | C | | 481 (M⁺+1) |
| N-h-149 | NB1 | Int.n-106 | BRA1 | 4PhBn | Me | Me | NO2 | 2-Nap | C | | 531 (M⁺+1) |
| N-h-150 | NA | N-h-149 | | 4PhBn | Me | H | NO2 | 2-Nap | C | | 517 (M⁺+1) |
| N-h-151 | NB1 | Int.n-106 | BRA2 | 4PhBn | Me | Me | NO2 | 5-Ind | C | | 520 (M⁺+1) |
| N-h-152 | NA | N-h-151 | | 4PhBn | Me | H | NO2 | 5-Ind | C | | 506 (M⁺+1) |
| N-h-153 | NB1 | Int.n-106 | BRA3 | 4PhBn | Me | Me | NO2 | 1Me-5-Ind | C | | 534 (M⁺+1) |
| N-h-154 | NA | N-h-153 | | 4PhBn | Me | H | NO2 | 1Me-5-Ind | C | | 520 (M⁺+1) |
| N-h-155 | NB1 | Int.n-106 | BRA6 | 4PhBn | Me | Me | NO2 | 1Me-5-1HIdz | C | | 521 (M⁺+1) |
| N-h-156 | NA | N-h-155 | | 4PhBn | Me | H | NO2 | 1Me-5-1HIdz | C | | 507 (M⁺+1) |
| N-h-157 | NB1 | Int.n-107 | BRA1 | 2CF3Bn | Me | Me | NO2 | 2-Nap | C | | 523 (M⁺+1) |

TABLE N-H-4-continued

| Exp. | Syn | SM1 | SM2 | Rz | Ry | Y | Zx | AR | LCMS method | RTime | Mass |
|---|---|---|---|---|---|---|---|---|---|---|---|
| N-h-158 | NA | N-h-157 | | 2CF3Bn | Me | H | NO2 | 2-Nap | C | | 509 (M$^+$ + 1) |
| N-h-159 | NB1 | Int.n-107 | BRA2 | 2CF3Bn | Me | Me | NO2 | 5-Ind | C | | 512 (M$^+$ + 1) |
| N-h-160 | NA | N-h-159 | | 2CF3Bn | Me | H | NO2 | 5-Ind | C | | 498 (M$^+$ + 1) |
| N-h-161 | NB1 | Int.n-107 | BRA3 | 2CF3Bn | Me | Me | NO2 | 1Me-5-Ind | C | | 526 (M$^+$ + 1) |
| N-h-162 | NA | N-h-161 | | 2CF3Bn | Me | H | NO2 | 1Me-5-Ind | C | | 512 (M$^+$ + 1) |
| N-h-163 | NB1 | Int.n-107 | BRA5 | 2CF3Bn | Me | Me | NO2 | 5-1HIdz | C | | 513 (M$^+$ + 1) |
| N-h-164 | NA | N-h-163 | | 2CF3Bn | Me | H | NO2 | 5-1HIdz | C | | 499 (M$^+$ + 1) |
| N-h-165 | NB1 | Int.n-108 | BRA1 | 2-TF | Me | Me | NO2 | 2-Nap | C | | 450 (M$^+$ + 1) |
| N-h-166 | NA | N-h-165 | | 2-TF | Me | H | NO2 | 2-Nap | C | | 436 (M$^+$ + 1) |
| N-h-167 | NB1 | Int.n-108 | BRA3 | 2-TF | Me | Me | NO2 | 1Me-5-Ind | C | | 464 (M$^+$ + 1) |
| N-h-168 | NA | N-h-167 | | 2-TF | Me | H | NO2 | 1Me-5-Ind | C | | 450 (M$^+$ + 1) |
| N-h-169 | NB1 | Int.n-108 | BRA6 | 2-TF | Me | Me | NO2 | 1Me-5-1HIdz | C | | 465 (M$^+$ + 1) |
| N-h-170 | NA | N-h-169 | | 2-TF | Me | H | NO2 | 1Me-5-1HIdz | C | | 451 (M$^+$ + 1) |
| N-h-171 | NB1 | Int.n-109 | BRA1 | 3-TF | Me | Me | NO2 | 2-Nap | C | | 450 (M$^+$ + 1) |
| N-h-172 | NA | N-h-171 | | 3-TF | Me | H | NO2 | 2-Nap | C | | 436 (M$^+$ + 1) |
| N-h-173 | NB1 | Int.n-109 | BRA2 | 3-TF | Me | Me | NO2 | 5-Ind | C | | 464 (M$^+$ + 1) |
| N-h-174 | NA | N-h-173 | | 3-TF | Me | H | NO2 | 5-Ind | C | | 450 (M$^+$ + 1) |
| N-h-175 | NB1 | Int.n-109 | BRA3 | 3-TF | Me | Me | NO2 | 1Me-5-Ind | C | | 451 (M$^+$ + 1) |
| N-h-176 | NA | N-h-175 | | 3-TF | Me | H | NO2 | 1Me-5-Ind | C | | 437 (M$^+$ + 1) |
| N-h-177 | NB1 | Int.n-110 | BRA6 | 3-TF | Me | Me | NO2 | 1Me-5-1HIdz | C | | 465 (M$^+$ + 1) |
| N-h-178 | NA | N-h-177 | | 3-TF | Me | H | NO2 | 1Me-5-1HIdz | C | | 451 (M$^+$ + 1) |
| N-h-179 | NB1 | Int.n-110 | BRA1 | 2-FR | Me | Me | NO2 | 2-Nap | C | | 473 (M$^+$ + 1) |
| N-h-180 | NA | N-h-179 | | 2-FR | Me | H | NO2 | 2-Nap | C | | 459 (M$^+$ + 1) |
| N-h-181 | NB1 | Int.n-110 | BRA2 | 2-FR | Me | Me | NO2 | 5-Ind | C | | 434 (M$^+$ + 1) |
| N-h-182 | NA | N-h-181 | | 2-FR | Me | H | NO2 | 5-Ind | C | | 420 (M$^+$ + 1) |
| N-h-183 | NB1 | Int.n-109 | BRA6 | 2-FR | Me | Me | NO2 | 1Me-5-1HIdz | C | | 448 (M$^+$ + 1) |
| N-h-184 | NA | N-h-183 | | 2-FR | Me | H | NO2 | 1Me-5-1HIdz | C | | 434 (M$^+$ + 1) |

TABLE N-H-5

| Exp. | Syn | SM1 | SM2 | Rz | Ry | Y | Zx | AR | LCMS method | RTime | Mass |
|---|---|---|---|---|---|---|---|---|---|---|---|
| N-h-185 | ND1 | N-h-1 | | Bn | H | Me | NH2 | 2-Nap | C | | 411 (M$^+$ + 1) |
| N-h-186 | NA | N-h-185 | | Bn | H | H | NH2 | 2-Nap | C | | 397 (M$^+$ + 1) |
| N-h-187 | ND1 | N-h-3 | | Bn | H | Me | NH2 | 5-Ind | C | | 400 (M$^+$ + 1) |
| N-h-188 | NA | N-h-187 | | Bn | H | H | NH2 | 5-Ind | C | | 386 (M$^+$ + 1) |
| N-h-189 | ND1 | N-h-5 | | Bn | H | Me | NH2 | 1Me-5-Ind | C | | 414 (M$^+$ + 1) |
| N-h-190 | NA | N-h-189 | | Bn | H | H | NH2 | 1Me-5-Ind | C | | 400 (M$^+$ + 1) |
| N-h-191 | ND1 | N-h-7 | | Bn | H | Me | NH2 | 5-1HIdz | C | | 401 (M$^+$ + 1) |
| N-h-192 | NA | N-h-191 | | Bn | H | H | NH2 | 5-1HIdz | C | | 387 (M$^+$ + 1) |
| N-h-193 | ND1 | N-h-9 | | Bn | H | Me | NH2 | 1Me-5-1HIdz | C | | 415 (M$^+$ + 1) |
| N-h-194 | NA | N-h-193 | | Bn | H | H | NH2 | 1Me-5-1HIdz | C | | 401 (M$^+$ + 1) |
| N-h-195 | ND1 | N-h-11 | | Bn | H | Me | NH2 | 3-Qu | C | | 412 (M$^+$ + 1) |
| N-h-196 | NA | N-h-195 | | Bn | H | H | NH2 | 3-Qu | C | | 398 (M$^+$ + 1) |
| N-h-197 | ND1 | N-h-13 | | Bn | H | Me | NH2 | 6-Qu | C | | 412 (M$^+$ + 1) |
| N-h-198 | NA | N-h-197 | | Bn | H | H | NH2 | 6-Qu | C | | 398 (M$^+$ + 1) |
| N-h-199 | ND1 | N-h-17 | | 4FBn | H | Me | NH2 | 2-Nap | C | | 429 (M$^+$ + 1) |
| N-h-200 | NA | N-h-199 | | 4FBn | H | H | NH2 | 2-Nap | C | | 415 (M$^+$ + 1) |
| N-h-201 | ND1 | N-h-19 | | 4FBn | H | Me | NH2 | 5-Ind | C | | 418 (M$^+$ + 1) |
| N-h-202 | NA | N-h-201 | | 4FBn | H | H | NH2 | 5-Ind | C | | 404 (M$^+$ + 1) |
| N-h-203 | ND1 | N-h-21 | | 4FBn | H | Me | NH2 | 1Me-5-Ind | C | | 432 (M$^+$ + 1) |
| N-h-204 | NA | N-h-203 | | 4FBn | H | H | NH2 | 1Me-5-Ind | C | | 418 (M$^+$ + 1) |
| N-h-205 | ND1 | N-h-23 | | 4FBn | H | Me | NH2 | 5-1HIdz | C | | 419 (M$^+$ + 1) |
| N-h-206 | NA | N-h-205 | | 4FBn | H | H | NH2 | 5-1HIdz | C | | 405 (M$^+$ + 1) |
| N-h-207 | ND1 | N-h-25 | | 4FBn | H | Me | NH2 | 1Me-5-1HIdz | C | | 433 (M$^+$ + 1) |
| N-h-208 | NA | N-h-207 | | 4FBn | H | H | NH2 | 1Me-5-1HIdz | C | | 419 (M$^+$ + 1) |
| N-h-209 | ND1 | N-h-27 | | 2FBn | H | Me | NH2 | 5-Ind | C | | 418 (M$^+$ + 1) |
| N-h-210 | NA | N-h-209 | | 2FBn | H | H | NH2 | 5-Ind | C | | 404 (M$^+$ + 1) |
| N-h-211 | ND1 | N-h-29 | | 2FBn | H | Me | NH2 | 1Me-5-Ind | C | | 432 (M$^+$ + 1) |
| N-h-212 | NA | N-h-211 | | 2FBn | H | H | NH2 | 1Me-5-Ind | C | | 418 (M$^+$ + 1) |
| N-h-213 | ND1 | N-h-31 | | 2FBn | H | Me | NH2 | 5-1HIdz | C | | 419 (M$^+$ + 1) |
| N-h-214 | NA | N-h-213 | | 2FBn | H | H | NH2 | 5-1HIdz | C | | 405 (M$^+$ + 1) |
| N-h-215 | ND1 | N-h-33 | | 2FBn | H | Me | NH2 | 1Me-5-1HIdz | C | | 433 (M$^+$ + 1) |
| N-h-216 | NA | N-h-215 | | 2FBn | H | H | NH2 | 1Me-5-1HIdz | C | | 419 (M$^+$ + 1) |
| N-h-217 | ND1 | N-h-35 | | 3FBn | H | Me | NH2 | 5-Ind | C | | 418 (M$^+$ + 1) |
| N-h-218 | NA | N-h-217 | | 3FBn | H | H | NH2 | 5-Ind | C | | 404 (M$^+$ + 1) |
| N-h-219 | ND1 | N-h-37 | | 3FBn | H | Me | NH2 | 1Me-5-Ind | C | | 432 (M$^+$ + 1) |
| N-h-220 | NA | N-h-219 | | 3FBn | H | H | NH2 | 1Me-5-Ind | C | | 418 (M$^+$ + 1) |
| N-h-221 | ND1 | N-h-39 | | 3FBn | H | Me | NH2 | 5-1HIdz | C | | 419 (M$^+$ + 1) |
| N-h-222 | NA | N-h-221 | | 3FBn | H | H | NH2 | 5-1HIdz | C | | 405 (M$^+$ + 1) |

TABLE N-H-5-continued

| Exp. | Syn | SM1 | SM2 | Rz | Ry | Y | Zx | AR | LCMS method | RTime | Mass |
|---|---|---|---|---|---|---|---|---|---|---|---|
| N-h-223 | ND1 | N-h-41 | | 3FBn | H | Me | NH2 | 1Me-5-1HIdz | C | | 433 (M⁺ + 1) |
| N-h-224 | NA | N-h-223 | | 3FBn | H | H | NH2 | 1Me-5-1HIdz | C | | 419 (M⁺ + 1) |
| N-h-225 | ND1 | N-h-43 | | 2,3DFBn | H | Me | NH2 | 2-Nap | C | | 447 (M⁺ + 1) |
| N-h-226 | NA | N-h-225 | | 2,3DFBn | H | H | NH2 | 2-Nap | C | | 433 (M⁺ + 1) |
| N-h-227 | ND1 | N-h-45 | | 2,3DFBn | H | Me | NH2 | 1Me-5-Ind | C | | 450 (M⁺ + 1) |
| N-h-228 | NA | N-h-227 | | 2,3DFBn | H | H | NH2 | 1Me-5-Ind | C | | 436 (M⁺ + 1) |
| N-h-229 | ND1 | N-h-47 | | 2,3DFBn | H | Me | NH2 | 5-1HIdz | C | | 437 (M⁺ + 1) |
| N-h-230 | NA | N-h-229 | | 2,3DFBn | H | H | NH2 | 5-1HIdz | C | | 423 (M⁺ + 1) |

TABLE N-H-6

| Exp. | Syn | SM1 | SM2 | Rz | Ry | Y | Zx | AR | LCMS method | RTime | Mass |
|---|---|---|---|---|---|---|---|---|---|---|---|
| N-h-231 | ND1 | N-h-49 | | 2,3DFBn | H | Me | NH2 | 1Me-5-1HIdz | C | | 451 (M⁺ + 1) |
| N-h-232 | NA | N-h-231 | | 2,3DFBn | H | H | NH2 | 1Me-5-1HIdz | C | | 437 (M⁺ + 1) |
| N-h-233 | ND1 | N-h-51 | | 3,4DFBn | H | Me | NH2 | 5-Ind | C | | 436 (M⁺ + 1) |
| N-h-234 | NA | N-h-233 | | 3,4DFBn | H | H | NH2 | 5-Ind | C | | 422 (M⁺ + 1) |
| N-h-235 | ND1 | N-h-53 | | 3,4DFBn | H | Me | NH2 | 1Me-5-Ind | C | | 450 (M⁺ + 1) |
| N-h-236 | NA | N-h-235 | | 3,4DFBn | H | H | NH2 | 1Me-5-Ind | C | | 436 (M⁺ + 1) |
| N-h-237 | ND1 | N-h-55 | | 3,4DFBn | H | Me | NH2 | 1Me-5-1HIdz | C | | 451 (M⁺ + 1) |
| N-h-238 | NA | N-h-237 | | 3,4DFBn | H | H | NH2 | 1Me-5-1HIdz | C | | 437 (M⁺ + 1) |
| N-h-239 | ND1 | N-h-57 | | 4PhBn | H | Me | NH2 | 2-Nap | C | | 487 (M⁺ + 1) |
| N-h-240 | NA | N-h-239 | | 4PhBn | H | H | NH2 | 2-Nap | C | | 473 (M⁺ + 1) |
| N-h-241 | ND1 | N-h-59 | | 4PhBn | H | Me | NH2 | 5-Ind | C | | 476 (M⁺ + 1) |
| N-h-242 | NA | N-h-241 | | 4PhBn | H | H | NH2 | 5-Ind | C | | 462 (M⁺ + 1) |
| N-h-243 | ND1 | N-h-61 | | 4PhBn | H | Me | NH2 | 1Me-5-Ind | C | | 490 (M⁺ + 1) |
| N-h-244 | NA | N-h-243 | | 4PhBn | H | H | NH2 | 1Me-5-Ind | C | | 476 (M⁺ + 1) |
| N-h-245 | ND1 | N-h-63 | | 4PhBn | H | Me | NH2 | 5-1HIdz | C | | 477 (M⁺ + 1) |
| N-h-246 | NA | N-h-245 | | 4PhBn | H | H | NH2 | 5-1HIdz | C | | 463 (M⁺ + 1) |
| N-h-247 | ND1 | N-h-65 | | 2CF3Bn | H | Me | NH2 | 2-Nap | C | | 479 (M⁺ + 1) |
| N-h-248 | NA | N-h-247 | | 2CF3Bn | H | H | NH2 | 2-Nap | C | | 465 (M⁺ + 1) |
| N-h-249 | ND1 | N-h-67 | | 2CF3Bn | H | Me | NH2 | 5-Ind | C | | 468 (M⁺ + 1) |
| N-h-250 | NA | N-h-249 | | 2CF3Bn | H | H | NH2 | 5-Ind | C | | 454 (M⁺ + 1) |
| N-h-251 | ND1 | N-h-69 | | 2CF3Bn | H | Me | NH2 | 1Me-5-Ind | C | | 482 (M⁺ + 1) |
| N-h-252 | NA | N-h-251 | | 2CF3Bn | H | H | NH2 | 1Me-5-Ind | C | | 468 (M⁺ + 1) |
| N-h-253 | ND1 | N-h-71 | | 2CF3Bn | H | Me | NH2 | 5-1HIdz | C | | 469 (M⁺ + 1) |
| N-h-254 | NA | N-h-253 | | 2CF3Bn | H | H | NH2 | 5-1HIdz | C | | 455 (M⁺ + 1) |
| N-h-255 | ND1 | N-h-73 | | 2-TF | H | Me | NH2 | 5-Ind | C | | 406 (M⁺ + 1) |
| N-h-256 | NA | N-h-255 | | 2-TF | H | H | NH2 | 5-Ind | C | | 392 (M⁺ + 1) |
| N-h-257 | ND1 | N-h-75 | | 2-TF | H | Me | NH2 | 1Me-5-Ind | C | | 420 (M⁺ + 1) |
| N-h-258 | NA | N-h-257 | | 2-TF | H | H | NH2 | 1Me-5-Ind | C | | 406 (M⁺ + 1) |
| N-h-259 | ND1 | N-h-77 | | 2-TF | H | Me | NH2 | 1Me-5-1HIdz | C | | 421 (M⁺ + 1) |
| N-h-260 | NA | N-h-259 | | 2-TF | H | H | NH2 | 1Me-5-1HIdz | C | | 407 (M⁺ + 1) |
| N-h-261 | ND1 | N-h-79 | | 3-TF | H | Me | NH2 | 5-Ind | C | | 406 (M⁺ + 1) |
| N-h-262 | NA | N-h-261 | | 3-TF | H | H | NH2 | 5-Ind | C | | 392 (M⁺ + 1) |
| N-h-263 | ND1 | N-h-81 | | 3-TF | H | Me | NH2 | 1Me-5-Ind | C | | 420 (M⁺ + 1) |
| N-h-264 | NA | N-h-263 | | 3-TF | H | H | NH2 | 1Me-5-Ind | C | | 406 (M⁺ + 1) |
| N-h-265 | ND1 | N-h-83 | | 3-TF | H | Me | NH2 | 5-1HIdz | C | | 407 (M⁺ + 1) |
| N-h-266 | NA | N-h-265 | | 3-TF | H | H | NH2 | 5-1HIdz | C | | 393 (M⁺ + 1) |
| N-h-267 | ND1 | N-h-85 | | 3-TF | H | Me | NH2 | 1Me-5-1HIdz | C | | 421 (M⁺ + 1) |
| N-h-268 | NA | N-h-267 | | 3-TF | H | H | NH2 | 1Me-5-1HIdz | C | | 407 (M⁺ + 1) |
| N-h-269 | ND1 | N-h-87 | | 2-FR | H | Me | NH2 | 2Nap | C | | 401 (M⁺ + 1) |
| N-h-270 | NA | N-h-269 | | 2-FR | H | H | NH2 | 2Nap | C | | 387 (M⁺ + 1) |
| N-h-271 | ND1 | N-h-89 | | 2-FR | H | Me | NH2 | 5-Ind | C | | 390 (M⁺ + 1) |
| N-h-272 | NA | N-h-271 | | 2-FR | H | H | NH2 | 5-Ind | C | | 376 (M⁺ + 1) |
| N-h-273 | ND1 | N-h-91 | | 2-FR | H | Me | NH2 | 1Me-5-1HIdz | C | | 405 (M⁺ + 1) |
| N-h-274 | NA | N-h-273 | | 2-FR | H | H | NH2 | 1Me-5-1HIdz | C | | 391 (M⁺ + 1) |

TABLE N-H-7

| Exp. | Syn | SM1 | SM2 | Rz | Ry | Y | Zx | AR | LCMS method | RTime | Mass |
|---|---|---|---|---|---|---|---|---|---|---|---|
| N-h-275 | ND1 | N-h-93 | | Bn | Me | Me | NH2 | 2-Nap | C | | 425 (M⁺ + 1) |
| N-h-276 | NA | N-h-275 | | Bn | Me | H | NH2 | 2-Nap | C | | 411 (M⁺ + 1) |
| N-h-277 | ND1 | N-h-95 | | Bn | Me | Me | NH2 | 5-Ind | C | | 414 (M⁺ + 1) |
| N-h-278 | NA | N-h-277 | | Bn | Me | H | NH2 | 5-Ind | C | | 400 (M⁺ + 1) |

TABLE N-H-7-continued

| Exp. | Syn | SM1 | SM2 | Rz | Ry | Y | Zx | AR | LCMS method | RTime | Mass |
|---|---|---|---|---|---|---|---|---|---|---|---|
| N-h-279 | ND1 | N-h-97 | | Bn | Me | Me | NH2 | 1Me-5-Ind | C | | 428 (M⁺ + 1) |
| N-h-280 | NA | N-h-279 | | Bn | Me | H | NH2 | 1Me-5-Ind | C | | 414 (M⁺ + 1) |
| N-h-281 | ND1 | N-h-99 | | Bn | Me | Me | NH2 | 5-1HIdz | C | | 415 (M⁺ + 1) |
| N-h-282 | NA | N-h-281 | | Bn | Me | H | NH2 | 5-1HIdz | C | | 401 (M⁺ + 1) |
| N-h-283 | ND1 | N-h-101 | | Bn | Me | Me | NH2 | 1Me-5-1HIdz | C | | 429 (M⁺ + 1) |
| N-h-284 | NA | N-h-283 | | Bn | Me | H | NH2 | 1Me-5-1HIdz | C | | 415 (M⁺ + 1) |
| N-h-285 | ND1 | N-h-103 | | Bn | Me | Me | NH2 | 3-Qu | C | | 426 (M⁺ + 1) |
| N-h-286 | NA | N-h-285 | | Bn | Me | H | NH2 | 3-Qu | C | | 412 (M⁺ + 1) |
| N-h-287 | ND1 | N-h-105 | | Bn | Me | Me | NH2 | 6-Qu | C | | 426 (M⁺ + 1) |
| N-h-288 | NA | N-h-287 | | Bn | Me | H | NH2 | 6-Qu | C | | 412 (M⁺ + 1) |
| N-h-289 | ND1 | N-h-107 | | Bn | Me | Me | NH2 | 6-IQ | C | | 426 (M⁺ + 1) |
| N-h-290 | NA | N-h-289 | | Bn | Me | H | NH2 | 6-IQ | C | | 412 (M⁺ + 1) |
| N-h-291 | ND1 | N-h-109 | | 4FBn | Me | Me | NH2 | 2-Nap | C | | 443 (M⁺ + 1) |
| N-h-292 | NA | N-h-291 | | 4FBn | Me | H | NH2 | 2-Nap | C | | 429 (M⁺ + 1) |
| N-h-293 | ND1 | N-h-111 | | 4FBn | Me | Me | NH2 | 5-Ind | C | | 432 (M⁺ + 1) |
| N-h-294 | NA | N-h-293 | | 4FBn | Me | H | NH2 | 5-Ind | C | | 418 (M⁺ + 1) |
| N-h-295 | ND1 | N-h-113 | | 4FBn | Me | Me | NH2 | 1Me-5-Ind | C | | 446 (M⁺ + 1) |
| N-h-296 | NA | N-h-295 | | 4FBn | Me | H | NH2 | 1Me-5-Ind | C | | 432 (M⁺ + 1) |
| N-h-297 | ND1 | N-h-115 | | 4FBn | Me | Me | NH2 | 5-1HIdz | C | | 433 (M⁺ + 1) |
| N-h-298 | NA | N-h-297 | | 4FBn | Me | H | NH2 | 5-1HIdz | C | | 419 (M⁺ + 1) |
| N-h-299 | ND1 | N-h-117 | | 4FBn | Me | Me | NH2 | 1Me-5-1HIdz | C | | 447 (M⁺ + 1) |
| N-h-300 | NA | N-h-299 | | 4FBn | Me | H | NH2 | 1Me-5-1HIdz | C | | 433 (M⁺ + 1) |
| N-h-301 | ND1 | N-h-119 | | 2FBn | Me | Me | NH2 | 2-Nap | C | | 443 (M⁺ + 1) |
| N-h-302 | NA | N-h-301 | | 2FBn | Me | H | NH2 | 2-Nap | C | | 429 (M⁺ + 1) |
| N-h-303 | ND1 | N-h-121 | | 2FBn | Me | Me | NH2 | 1Me-5-Ind | C | | 446 (M⁺ + 1) |
| N-h-304 | NA | N-h-303 | | 2FBn | Me | H | NH2 | 1Me-5-Ind | C | | 432 (M⁺ + 1) |
| N-h-305 | ND1 | N-h-123 | | 2FBn | Me | Me | NH2 | 5-1HIdz | C | | 433 (M⁺ + 1) |
| N-h-306 | NA | N-h-305 | | 2FBn | Me | H | NH2 | 5-1HIdz | C | | 419 (M⁺ + 1) |
| N-h-307 | ND1 | N-h-125 | | 2FBn | Me | Me | NH2 | 1Me-5-1HIdz | C | | 447 (M⁺ + 1) |
| N-h-308 | NA | N-h-307 | | 2FBn | Me | H | NH2 | 1Me-5-1HIdz | C | | 433 (M⁺ + 1) |
| N-h-309 | ND1 | N-h-127 | | 3FBn | Me | Me | NH2 | 2-Nap | C | | 443 (M⁺ + 1) |
| N-h-310 | NA | N-h-309 | | 3FBn | Me | H | NH2 | 2-Nap | C | | 429 (M⁺ + 1) |
| N-h-311 | ND1 | N-h-129 | | 3FBn | Me | Me | NH2 | 1Me-5-Ind | C | | 446 (M⁺ + 1) |
| N-h-312 | NA | N-h-311 | | 3FBn | Me | H | NH2 | 1Me-5-Ind | C | | 432 (M⁺ + 1) |
| N-h-313 | ND1 | N-h-131 | | 3FBn | Me | Me | NH2 | 5-1HIdz | C | | 433 (M⁺ + 1) |
| N-h-314 | NA | N-h-313 | | 3FBn | Me | H | NH2 | 5-1HIdz | C | | 419 (M⁺ + 1) |
| N-h-315 | ND1 | N-h-133 | | 3FBn | Me | Me | NH2 | 1Me-5-1HIdz | C | | 447 (M⁺ + 1) |
| N-h-316 | NA | N-h-315 | | 3FBn | Me | H | NH2 | 1Me-5-1HIdz | C | | 433 (M⁺ + 1) |
| N-h-317 | ND1 | N-h-135 | | 2,3DFBn | Me | Me | NH2 | 2-Nap | C | | 461 (M⁺ + 1) |
| N-h-318 | NA | N-h-317 | | 2,3DFBn | Me | H | NH2 | 2-Nap | C | | 447 (M⁺ + 1) |
| N-h-319 | ND1 | N-h-137 | | 2,3DFBn | Me | Me | NH2 | 1Me-5-Ind | C | | 464 (M⁺ + 1) |
| N-h-320 | NA | N-h-319 | | 2,3DFBn | Me | H | NH2 | 1Me-5-Ind | C | | 450 (M⁺ + 1) |

TABLE N-H-8

| Exp. | Syn | SM1 | SM2 | Rz | Ry | Y | Zx | AR | LCMS method | RTime | Mass |
|---|---|---|---|---|---|---|---|---|---|---|---|
| N-h-321 | ND1 | N-h-139 | | 2,3DFBn | Me | Me | NH2 | 5-1HIdz | C | | 451 (M⁺ + 1) |
| N-h-322 | NA | N-h-321 | | 2,3DFBn | Me | H | NH2 | 5-1HIdz | C | | 437 (M⁺ + 1) |
| N-h-323 | ND1 | N-h-141 | | 2,3DFBn | Me | Me | NH2 | 1Me-5-1HIdz | C | | 465 (M⁺ + 1) |
| N-h-324 | NA | N-h-323 | | 2,3DFBn | Me | H | NH2 | 1Me-5-1HIdz | C | | 451 (M⁺ + 1) |
| N-h-325 | ND1 | N-h-143 | | 3,4DFBn | Me | Me | NH2 | 2-Nap | C | | 461 (M⁺ + 1) |
| N-h-326 | NA | N-h-325 | | 3,4DFBn | Me | H | NH2 | 2-Nap | C | | 447 (M⁺ + 1) |
| N-h-327 | ND1 | N-h-145 | | 3,4DFBn | Me | Me | NH2 | 1Me-5-Ind | C | | 464 (M⁺ + 1) |
| N-h-328 | NA | N-h-327 | | 3,4DFBn | Me | H | NH2 | 1Me-5-Ind | C | | 450 (M⁺ + 1) |
| N-h-329 | ND1 | N-h-147 | | 3,4DFBn | Me | Me | NH2 | 1Me-5-1HIdz | C | | 465 (M⁺ + 1) |
| N-h-330 | NA | N-h-329 | | 3,4DFBn | Me | H | NH2 | 1Me-5-1HIdz | C | | 451 (M⁺ + 1) |
| N-h-331 | ND1 | N-h-149 | | 4PhBn | Me | Me | NH2 | 2-Nap | C | | 501 (M⁺ + 1) |
| N-h-332 | NA | N-h-331 | | 4PhBn | Me | H | NH2 | 2-Nap | C | | 487 (M⁺ + 1) |
| N-h-333 | ND1 | N-h-151 | | 4PhBn | Me | Me | NH2 | 5-Ind | C | | 490 (M⁺ + 1) |
| N-h-334 | NA | N-h-333 | | 4PhBn | Me | H | NH2 | 5-Ind | C | | 476 (M⁺ + 1) |
| N-h-335 | ND1 | N-h-153 | | 4PhBn | Me | Me | NH2 | 1Me-5-Ind | C | | 504 (M⁺ + 1) |
| N-h-336 | NA | N-h-335 | | 4PhBn | Me | H | NH2 | 1Me-5-Ind | C | | 490 (M⁺ + 1) |
| N-h-337 | ND1 | N-h-155 | | 4PhBn | Me | Me | NH2 | 1Me-5-1HIdz | C | | 505 (M⁺ + 1) |
| N-h-338 | NA | N-h-337 | | 4PhBn | Me | H | NH2 | 1Me-5-1HIdz | C | | 491 (M⁺ + 1) |
| N-h-339 | ND1 | N-h-157 | | 2CF3Bn | Me | Me | NH2 | 2-Nap | C | | 493 (M⁺ + 1) |
| N-h-340 | NA | N-h-339 | | 2CF3Bn | Me | H | NH2 | 2-Nap | C | | 479 (M⁺ + 1) |
| N-h-341 | ND1 | N-h-159 | | 2CF3Bn | Me | Me | NH2 | 5-Ind | C | | 482 (M⁺ + 1) |
| N-h-342 | NA | N-h-341 | | 2CF3Bn | Me | H | NH2 | 5-Ind | C | | 468 (M⁺ + 1) |
| N-h-343 | ND1 | N-h-161 | | 2CF3Bn | Me | Me | NH2 | 1Me-5-Ind | C | | 496 (M⁺ + 1) |

TABLE N-H-8-continued

| Exp. | Syn | SM1 | SM2 | Rz | Ry | Y | Zx | AR | LCMS method | RTime | Mass |
|---|---|---|---|---|---|---|---|---|---|---|---|
| N-h-344 | NA | N-h-343 | | 2CF3Bn | Me | H | NH2 | 1Me-5-Ind | C | | 482 (M+ + 1) |
| N-h-345 | ND1 | N-h-163 | | 2CF3Bn | Me | Me | NH2 | 5-1HIdz | C | | 483 (M+ + 1) |
| N-h-346 | NA | N-h-345 | | 2CF3Bn | Me | H | NH2 | 5-1HIdz | C | | 469 (M+ + 1) |
| N-h-347 | ND1 | N-h-165 | | 2-TF | Me | Me | NH2 | 2-Nap | C | | 431 (M+ + 1) |
| N-h-348 | NA | N-h-347 | | 2-TF | Me | H | NH2 | 2-Nap | C | | 417 (M+ + 1) |
| N-h-349 | ND1 | N-h-167 | | 2-TF | Me | Me | NH2 | 1Me-5-Ind | C | | 434 (M+ + 1) |
| N-h-350 | NA | N-h-349 | | 2-TF | Me | H | NH2 | 1Me-5-Ind | C | | 420 (M+ + 1) |
| N-h-351 | ND1 | N-h-169 | | 2-TF | Me | Me | NH2 | 1Me-5-1HIdz | C | | 435 (M+ + 1) |
| N-h-352 | NA | N-h-351 | | 2-TF | Me | H | NH2 | 1Me-5-1HIdz | C | | 421 (M+ + 1) |
| N-h-353 | ND1 | N-h-171 | | 3-TF | Me | Me | NH2 | 2-Nap | C | | 431 (M+ + 1) |
| N-h-354 | NA | N-h-353 | | 3-TF | Me | H | NH2 | 2-Nap | C | | 417 (M+ + 1) |
| N-h-355 | ND1 | N-h-173 | | 3-TF | Me | Me | NH2 | 5-Ind | C | | 420 (M+ + 1) |
| N-h-356 | NA | N-h-355 | | 3-TF | Me | H | NH2 | 5-Ind | C | | 406 (M+ + 1) |
| N-h-357 | ND1 | N-h-175 | | 3-TF | Me | Me | NH2 | 1Me-5-Ind | C | | 434 (M+ + 1) |
| N-h-358 | NA | N-h-357 | | 3-TF | Me | H | NH2 | 1Me-5-Ind | C | | 420 (M+ + 1) |
| N-h-359 | ND1 | N-h-177 | | 3-TF | Me | Me | NH2 | 1Me-5-1HIdz | C | | 435 (M+ + 1) |
| N-h-360 | NA | N-h-359 | | 3-TF | Me | H | NH2 | 1Me-5-1HIdz | C | | 421 (M+ + 1) |
| N-h-361 | ND1 | N-h-179 | | 2-FR | Me | Me | NH2 | 2-Nap | C | | 415 (M+ + 1) |
| N-h-362 | NA | N-h-361 | | 2-FR | Me | H | NH2 | 2-Nap | C | | 401 (M+ + 1) |
| N-h-363 | ND1 | N-h-181 | | 2-FR | Me | Me | NH2 | 5-Ind | C | | 404 (M+ + 1) |
| N-h-364 | NA | N-h-363 | | 2-FR | Me | H | NH2 | 5-Ind | C | | 390 (M+ + 1) |
| N-h-365 | ND1 | N-h-183 | | 2-FR | Me | Me | NH2 | 1Me-5-1HIdz | C | | 419 (M+ + 1) |
| N-h-366 | NA | N-h-365 | | 2-FR | Me | H | NH2 | 1Me-5-1HIdz | C | | 405 (M+ + 1) |

TABLE N-H-9

| Exp. | Syn | SM1 | SM2 | Rz | Ry | Y | Zx | AR | LCMS method | RTime | Mass |
|---|---|---|---|---|---|---|---|---|---|---|---|
| N-h-367 | NN1 | N-h-275 | CH3I | Bn | Me | Me | NHMe | 2-Nap | C | | 439 (M+ + 1) |
| N-h-368 | NA | N-h-367 | | Bn | Me | H | NHMe | 2-Nap | C | | 425 (M+ + 1) |
| N-h-369 | NN1 | N-h-279 | CH3I | Bn | Me | Me | NHMe | 1Me-5-Ind | C | | 442 (M+ + 1) |
| N-h-370 | NA | N-h-369 | | Bn | Me | H | NHMe | 1Me-5-Ind | C | | 428 (M+ + 1) |
| N-h-371 | NN1 | N-h-283 | CH3I | Bn | Me | Me | NHMe | 1Me-5-1HIdz | C | | 443 (M+ + 1) |
| N-h-372 | NA | N-h-371 | | Bn | Me | H | NHMe | 1Me-5-1HIdz | C | | 429 (M+ + 1) |
| N-h-373 | NN1 | N-h-285 | CH3I | Bn | Me | Me | NHMe | 3-Qu | C | | 440 (M+ + 1) |
| N-h-374 | NA | N-h-373 | | Bn | Me | H | NHMe | 3-Qu | C | | 426 (M+ + 1) |
| N-h-375 | NN1 | N-h-289 | CH3I | Bn | Me | Me | NHMe | 6-IQ | C | | 440 (M+ + 1) |
| N-h-376 | NA | N-h-375 | | Bn | Me | H | NHMe | 6-IQ | C | | 426 (M+ + 1) |
| N-h-377 | NN1 | N-h-291 | CH3I | 4FBn | Me | Me | NHMe | 2-Nap | C | | 457 (M+ + 1) |
| N-h-378 | NA | N-h-377 | | 4FBn | Me | H | NHMe | 2-Nap | C | | 443 (M+ + 1) |
| N-h-379 | NN1 | N-h-295 | CH3I | 4FBn | Me | Me | NHMe | 1Me-5-Ind | C | | 460 (M+ + 1) |
| N-h-380 | NA | N-h-379 | | 4FBn | Me | H | NHMe | 1Me-5-Ind | C | | 446 (M+ + 1) |
| N-h-381 | NN1 | N-h-299 | CH3I | 4FBn | Me | Me | NHMe | 1Me-5-1HIdz | C | | 461 (M+ + 1) |
| N-h-382 | NA | N-h-381 | | 4FBn | Me | H | NHMe | 1Me-5-1HIdz | C | | 447 (M+ + 1) |
| N-h-383 | NN1 | N-h-301 | CH3I | 2FBn | Me | Me | NHMe | 2-Nap | C | | 457 (M+ + 1) |
| N-h-384 | NA | N-h-383 | | 2FBn | Me | H | NHMe | 2-Nap | C | | 443 (M+ + 1) |
| N-h-385 | NN1 | N-h-303 | CH3I | 2FBn | Me | Me | NHMe | 1Me-5-Ind | C | | 460 (M+ + 1) |
| N-h-386 | NA | N-h-385 | | 2FBn | Me | H | NHMe | 1Me-5-Ind | C | | 446 (M+ + 1) |
| N-h-387 | NN1 | N-h-307 | CH3I | 2FBn | Me | Me | NHMe | 1Me-5-1HIdz | C | | 461 (M+ + 1) |
| N-h-388 | NA | N-h-387 | | 2FBn | Me | H | NHMe | 1Me-5-1HIdz | C | | 447 (M+ + 1) |
| N-h-389 | NN1 | N-h-309 | CH3I | 3FBn | Me | Me | NHMe | 2-Nap | C | | 457 (M+ + 1) |
| N-h-390 | NA | N-h-389 | | 3FBn | Me | H | NHMe | 2-Nap | C | | 443 (M+ + 1) |
| N-h-391 | NN1 | N-h-311 | CH3I | 3FBn | Me | Me | NHMe | 1Me-5-Ind | C | | 460 (M+ + 1) |
| N-h-392 | NA | N-h-391 | | 3FBn | Me | H | NHMe | 1Me-5-Ind | C | | 446 (M+ + 1) |
| N-h-393 | NN1 | N-h-317 | CH3I | 2,3DFBn | Me | Me | NHMe | 2-Nap | C | | 475 (M+ + 1) |
| N-h-394 | NA | N-h-393 | | 2,3DFBn | Me | H | NHMe | 2-Nap | C | | 461 (M+ + 1) |
| N-h-395 | NN1 | N-h-323 | CH3I | 2,3DFBn | Me | Me | NHMe | 1Me-5-1HIdz | C | | 479 (M+ + 1) |
| N-h-396 | NA | N-h-395 | | 2,3DFBn | Me | H | NHMe | 1Me-5-1HIdz | C | | 465 (M+ + 1) |
| N-h-397 | NN1 | N-h-327 | CH3I | 3,4DFBn | Me | Me | NHMe | 1Me-5-Ind | C | | 478 (M+ + 1) |
| N-h-398 | NA | N-h-397 | | 3,4DFBn | Me | H | NHMe | 1Me-5-Ind | C | | 464 (M+ + 1) |
| N-h-399 | NN1 | N-h-331 | CH3I | 4PhBn | Me | Me | NHMe | 2-Nap | C | | 515 (M+ + 1) |
| N-h-400 | NA | N-h-399 | | 4PhBn | Me | H | NHMe | 2-Nap | C | | 501 (M+ + 1) |
| N-h-401 | NN1 | N-h-337 | CH3I | 4PhBn | Me | Me | NHMe | 1Me-5-1HIdz | C | | 519 (M+ + 1) |
| N-h-402 | NA | N-h-401 | | 4PhBn | Me | H | NHMe | 1Me-5-1HIdz | C | | 505 (M+ + 1) |
| N-h-403 | NN1 | N-h-339 | CH3I | 2CF3Bn | Me | Me | NHMe | 2-Nap | C | | 507 (M+ + 1) |
| N-h-404 | NA | N-h-403 | | 2CF3Bn | Me | H | NHMe | 2-Nap | C | | 493 (M+ + 1) |
| N-h-405 | NN1 | N-h-343 | CH3I | 2CF3Bn | Me | Me | NHMe | 1Me-5-Ind | C | | 510 (M+ + 1) |
| N-h-406 | NA | N-h-405 | | 2CF3Bn | Me | H | NHMe | 1Me-5-Ind | C | | 496 (M+ + 1) |
| N-h-407 | NN1 | N-h-347 | CH3I | 2-TF | Me | Me | NHMe | 2-Nap | C | | 445 (M+ + 1) |
| N-h-408 | NA | N-h-407 | | 2-TF | Me | H | NHMe | 2-Nap | C | | 431 (M+ + 1) |

TABLE N-H-9-continued

| | | | | | | | | | LCMS | |
|---|---|---|---|---|---|---|---|---|---|---|
| Exp. | Syn | SM1 | SM2 | Rz | Ry | Y | Zx | AR | method | RTime | Mass |
| N-h-409 | NN1 | N-h-357 | CH$_3$I | 3-TF | Me | Me | NHMe | 1Me-5-Ind | C | | 448 (M$^+$ + 1) |
| N-h-410 | NA | N-h-409 | | 3-TF | Me | H | NHMe | 1Me-5-Ind | C | | 434 (M$^+$ + 1) |
| N-h-411 | NN1 | N-h-365 | CH$_3$I | 2-FR | Me | Me | NHMe | 1Me-5-1HIdz | C | | 433 (M$^+$ + 1) |
| N-h-412 | NA | N-h-411 | | 2-FR | Me | H | NHMe | 1Me-5-1HIdz | C | | 419 (M$^+$ + 1) |

TABLE N-H-10

| | | | | | | | | | LCMS | |
|---|---|---|---|---|---|---|---|---|---|---|
| Exp. | Syn | SM1 | SM2 | Rz | Ry | Y | Zx | AR | method | RTime | Mass |
| N-h-413 | NN2 | N-h-275 | CH$_3$I | Bn | Me | Me | NMe2 | 2-Nap | C | | 453 (M$^+$ + 1) |
| N-h-414 | NA | N-h-413 | | Bn | Me | H | NMe2 | 2-Nap | C | | 439 (M$^+$ + 1) |
| N-h-415 | NN2 | N-h-279 | CH$_3$I | Bn | Me | Me | NMe2 | 1Me-5-Ind | C | | 456 (M$^+$ + 1) |
| N-h-416 | NA | N-h-415 | | Bn | Me | H | NMe2 | 1Me-5-Ind | C | | 442 (M$^+$ + 1) |
| N-h-417 | NN2 | N-h-283 | CH$_3$I | Bn | Me | Me | NMe2 | 1Me-5-1HIdz | C | | 457 (M$^+$ + 1) |
| N-h-418 | NA | N-h-417 | | Bn | Me | H | NMe2 | 1Me-5-1HIdz | C | | 443 (M$^+$ + 1) |
| N-h-419 | NN2 | N-h-285 | CH$_3$I | Bn | Me | Me | NMe2 | 3-Qu | C | | 454 (M$^+$ + 1) |
| N-h-420 | NA | N-h-419 | | Bn | Me | H | NMe2 | 3-Qu | C | | 440 (M$^+$ + 1) |
| N-h-421 | NN2 | N-h-289 | CH$_3$I | Bn | Me | Me | NMe2 | 6-IQ | C | | 454 (M$^+$ + 1) |
| N-h-422 | NA | N-h-421 | | Bn | Me | H | NMe2 | 6-IQ | C | | 440 (M$^+$ + 1) |
| N-h-423 | NN2 | N-h-291 | CH$_3$I | 4FBn | Me | Me | NMe2 | 2-Nap | C | | 471 (M$^+$ + 1) |
| N-h-424 | NA | N-h-423 | | 4FBn | Me | H | NMe2 | 2-Nap | C | | 457 (M$^+$ + 1) |
| N-h-425 | NN2 | N-h-295 | CH$_3$I | 4FBn | Me | Me | NMe2 | 1Me-5-Ind | C | | 474 (M$^+$ + 1) |
| N-h-426 | NA | N-h-425 | | 4FBn | Me | H | NMe2 | 1Me-5-Ind | C | | 460 (M$^+$ + 1) |
| N-h-427 | NN2 | N-h-299 | CH$_3$I | 4FBn | Me | Me | NMe2 | 1Me-5-1HIdz | C | | 475 (M$^+$ + 1) |
| N-h-428 | NA | N-h-427 | | 4FBn | Me | H | NMe2 | 1Me-5-1HIdz | C | | 461 (M$^+$ + 1) |
| N-h-429 | NN2 | N-h-301 | CH$_3$I | 2FBn | Me | Me | NMe2 | 2-Nap | C | | 471 (M$^+$ + 1) |
| N-h-430 | NA | N-h-429 | | 2FBn | Me | H | NMe2 | 2-Nap | C | | 457 (M$^+$ + 1) |
| N-h-431 | NN2 | N-h-303 | CH$_3$I | 2FBn | Me | Me | NMe2 | 1Me-5-Ind | C | | 474 (M$^+$ + 1) |
| N-h-432 | NA | N-h-431 | | 2FBn | Me | H | NMe2 | 1Me-5-Ind | C | | 460 (M$^+$ + 1) |
| N-h-433 | NN2 | N-h-307 | CH$_3$I | 2FBn | Me | Me | NMe2 | 1Me-5-1HIdz | C | | 475 (M$^+$ + 1) |
| N-h-434 | NA | N-h-433 | | 2FBn | Me | H | NMe2 | 1Me-5-1HIdz | C | | 461 (M$^+$ + 1) |
| N-h-435 | NN2 | N-h-309 | CH$_3$I | 3FBn | Me | Me | NMe2 | 2-Nap | C | | 471 (M$^+$ + 1) |
| N-h-436 | NA | N-h-435 | | 3FBn | Me | H | NMe2 | 2-Nap | C | | 457 (M$^+$ + 1) |
| N-h-437 | NN2 | N-h-311 | CH$_3$I | 3FBn | Me | Me | NMe2 | 1Me-5-Ind | C | | 474 (M$^+$ + 1) |
| N-h-438 | NA | N-h-437 | | 3FBn | Me | H | NMe2 | 1Me-5-Ind | C | | 460 (M$^+$ + 1) |
| N-h-439 | NN2 | N-h-317 | CH$_3$I | 2,3DFBn | Me | Me | NMe2 | 2-Nap | C | | 489 (M$^+$ + 1) |
| N-h-440 | NA | N-h-439 | | 2,3DFBn | Me | H | NMe2 | 2-Nap | C | | 475 (M$^+$ + 1) |
| N-h-441 | NN2 | N-h-323 | CH$_3$I | 2,3DFBn | Me | Me | NMe2 | 1Me-5-1HIdz | C | | 493 (M$^+$ + 1) |
| N-h-442 | NA | N-h-441 | | 2,3DFBn | Me | H | NMe2 | 1Me-5-1HIdz | C | | 479 (M$^+$ + 1) |
| N-h-443 | NN2 | N-h-327 | CH$_3$I | 3,4DFBn | Me | Me | NMe2 | 1Me-5-Ind | C | | 492 (M$^+$ + 1) |
| N-h-444 | NA | N-h-443 | | 3,4DFBn | Me | H | NMe2 | 1Me-5-Ind | C | | 478 (M$^+$ + 1) |
| N-h-445 | NN2 | N-h-331 | CH$_3$I | 4PhBn | Me | Me | NMe2 | 2-Nap | C | | 529 (M$^+$ + 1) |
| N-h-446 | NA | N-h-445 | | 4PhBn | Me | H | NMe2 | 2-Nap | C | | 515 (M$^+$ + 1) |
| N-h-447 | NN2 | N-h-337 | CH$_3$I | 4PhBn | Me | Me | NMe2 | 1Me-5-1HIdz | C | | 533 (M$^+$ + 1) |
| N-h-448 | NA | N-h-447 | | 4PhBn | Me | H | NMe2 | 1Me-5-1HIdz | C | | 519 (M$^+$ + 1) |
| N-h-449 | NN2 | N-h-339 | CH$_3$I | 2CF3Bn | Me | Me | NMe2 | 2-Nap | C | | 521 (M$^+$ + 1) |
| N-h-450 | NA | N-h-449 | | 2CF3Bn | Me | H | NMe2 | 2-Nap | C | | 507 (M$^+$ + 1) |
| N-h-451 | NN2 | N-h-343 | CH$_3$I | 2CF3Bn | Me | Me | NMe2 | 1Me-5-Ind | C | | 524 (M$^+$ + 1) |
| N-h-452 | NA | N-h-451 | | 2CF3Bn | Me | H | NMe2 | 1Me-5-Ind | C | | 510 (M$^+$ + 1) |
| N-h-453 | NN2 | N-h-347 | CH$_3$I | 2-TF | Me | Me | NMe2 | 2-Nap | C | | 459 (M$^+$ + 1) |
| N-h-454 | NA | N-h-453 | | 2-TF | Me | H | NMe2 | 2-Nap | C | | 445 (M$^+$ + 1) |
| N-h-455 | NN2 | N-h-357 | CH$_3$I | 3-TF | Me | Me | NMe2 | 1Me-5-Ind | C | | 462 (M$^+$ + 1) |
| N-h-456 | NA | N-h-455 | | 3-TF | Me | H | NMe2 | 1Me-5-Ind | C | | 448 (M$^+$ + 1) |
| N-h-457 | NN2 | N-h-365 | CH$_3$I | 2-FR | Me | Me | NMe2 | 1Me-5-1HIdz | C | | 447 (M$^+$ + 1) |
| N-h-458 | NA | N-h-457 | | 2-FR | Me | H | NMe2 | 1Me-5-1HIdz | C | | 433 (M$^+$ + 1) |

Examples N-1 to N-i138

Typical examples of the compounds of the present invention that can be obtained by reacting and treating corresponding starting compounds using any of the methods described in the present specification are shown in Table-N-I-1 to Table-N-I-8. In the tables, the compound numbers are mentioned in the columns indicated as "Exp.". In the tables, used methods among the aforementioned synthesis methods are shown in the columns of "Syn" with symbols, the starting compounds 1 are mentioned in the columns of "SM1", and the starting compounds 2 are mentioned in the columns of "SM2".

TABLE N-I-1

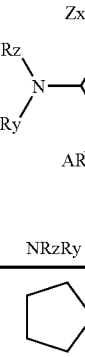

| Exp. | Syn | SM1 | SM2 | NRzRy | Y | Zx | AR | LCMS method | RTime | Mass |
|---|---|---|---|---|---|---|---|---|---|---|
| N-i-1 | NB1 | Int.n-111 | BRA1 |  | Me | NO2 | 2-Nap | C | | 405 (M+ + 1) |
| N-i-2 | NA | N-i-1 | |  | H | NO2 | 2-Nap | C | | 391 (M+ + 1) |
| N-i-3 | NB1 | Int.n-111 | BRA2 |  | Me | NO2 | 5-1Ind | C | | 394 (M+ + 1) |
| N-i-4 | NA | N-i-3 | |  | H | NO2 | 5-1Ind | C | | 380 (M+ + 1) |
| N-i-5 | NB1 | Int.n-111 | BRA3 |  | Me | NO2 | 1Me-5-Ind | C | | 408 (M+ + 1) |
| N-i-6 | NA | N-i-5 | |  | H | NO2 | 1Me-5-Ind | C | | 394 (M+ + 1) |
| N-i-7 | NB1 | Int.n-111 | BRA5 |  | Me | NO2 | 5-1HIdz | C | | 395 (M+ + 1) |
| N-i-8 | NA | N-i-7 | |  | H | NO2 | 5-1HIdz | C | | 381 (M+ + 1) |
| N-i-9 | NB1 | Int.n-111 | BRA6 |  | Me | NO2 | 1Me-5-1HIdz | C | | 409 (M+ + 1) |
| N-i-10 | NA | N-i-9 | |  | H | NO2 | 1Me-5-1HIdz | C | | 395 (M+ + 1) |
| N-i-11 | NB1 | Int.n-111 | BRA9 |  | Me | NO2 | 5-Bzt | C | | 412 (M+ + 1) |
| N-i-12 | NA | N-i-11 | | | H | NO2 | 5-Bzt | C | | 398 (M+ + 1) |

TABLE N-I-1-continued

Structure: Ar-N(Rz)(Ry) with Zx, AR substituents on phenyl ring bearing CH2CH2C(O)O-Y group

| Exp. | Syn | SM1 | SM2 | NRzRy | Y | Zx | AR | LCMS method | RTime | Mass |
|---|---|---|---|---|---|---|---|---|---|---|
| N-i-13 | NB1 | Int.n-111 | BRA 10 | pyrrolidine | Me | NO2 | 3-Qu | C | | 406 (M⁺ + 1) |
| N-i-14 | NA | N-i-13 | | pyrrolidine | H | NO2 | 3-Qu | C | | 392 (M⁺ + 1) |
| N-i-15 | NB1 | Int.n-111 | BRA 11 | pyrrolidine | Me | NO2 | 6-Qu | C | | 406 (M⁺ + 1) |
| N-i-16 | NA | N-i-15 | | pyrrolidine | H | NO2 | 6-Qu | C | | 392 (M⁺ + 1) |
| N-i-17 | NB1 | Int.n-112 | BRA1 | morpholine | Me | NO2 | 2-Nap | C | | 421 (M⁺ + 1) |
| N-i-18 | NA | N-i-17 | | morpholine | H | NO2 | 2-Nap | C | | 407 (M⁺ + 1) |
| N-i-19 | NB1 | Int.n-112 | BRA2 | morpholine | Me | NO2 | 5-1Ind | C | | 410 (M⁺ + 1) |
| N-i-20 | NA | N-i-19 | | morpholine | H | NO2 | 5-1Ind | C | | 396 (M⁺ + 1) |
| N-i-21 | NB1 | Int.n-112 | BRA3 | morpholine | Me | NO2 | 1Me-5-Ind | C | | 424 (M⁺ + 1) |
| N-i-22 | NA | N-i-21 | | morpholine | H | NO2 | 1Me-5-Ind | C | | 410 (M⁺ + 1) |

TABLE N-I-2

| Exp. | Syn | SM1 | SM2 | NRzRy | Y | Zx | AR | LCMS method | RTime | Mass |
|---|---|---|---|---|---|---|---|---|---|---|
| N-i-23 | NB1 | Int.n-112 | BRA5 | morpholine | Me | NO2 | 5-1HIdz | C | | 411 (M⁺ + 1) |
| N-i-24 | NA | N-i-23 | | morpholine | H | NO2 | 5-1HIdz | C | | 397 (M⁺ + 1) |

TABLE N-I-2-continued

| Exp. | Syn | SM1 | SM2 | NRzRy | Y | Zx | AR | LCMS method | RTime | Mass |
|---|---|---|---|---|---|---|---|---|---|---|
| N-i-25 | NB1 | Int.n-112 | BRA6 | 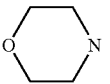 | Me | NO2 | 1Me-5-1HIdz | C | | 425 (M⁺ + 1) |
| N-i-26 | NA | N-i-25 | | 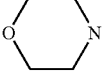 | H | NO2 | 1Me-5-1HIdz | C | | 411 (M⁺ + 1) |
| N-i-27 | NB1 | Int.n-113 | BRA1 | 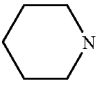 | Me | NO2 | 2-Nap | C | | 419 (M⁺ + 1) |
| N-i-28 | NA | N-i-27 | | 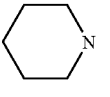 | H | NO2 | 2-Nap | C | | 405 (M⁺ + 1) |
| N-i-29 | NB1 | Int.n-113 | BRA2 | 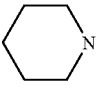 | Me | NO2 | 5-1Ind | C | | 408 (M⁺ + 1) |
| N-i-30 | NA | N-i-29 | | 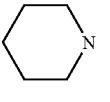 | H | NO2 | 5-1Ind | C | | 394 (M⁺ + 1) |
| N-i-31 | NB1 | Int.n-113 | BRA3 | 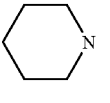 | Me | NO2 | 1Me-5-Ind | C | | 422 (M⁺ + 1) |
| N-i-32 | NA | N-i-31 | | 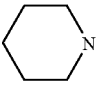 | H | NO2 | 1Me-5-Ind | C | | 408 (M⁺ + 1) |
| N-i-33 | NB1 | Int.n-113 | BRA5 | 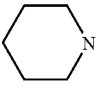 | Me | NO2 | 5-1HIdz | C | | 409 (M⁺ + 1) |
| N-i-34 | NA | N-i-33 | | 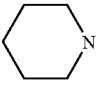 | H | NO2 | 5-1HIdz | C | | 395 (M⁺ + 1) |
| N-i-35 | NB1 | Int.n-113 | BRA6 | 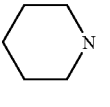 | Me | NO2 | 1Me-5-1HIdz | C | | 423 (M⁺ + 1) |
| N-i-36 | NA | N-i-35 | | 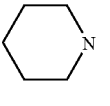 | H | NO2 | 1Me-5-1HIdz | C | | 409 (M⁺ + 1) |
| N-i-37 | NB1 | Int.n-113 | BRA11 | 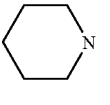 | Me | NO2 | 6-Qu | C | | 420 (M⁺ + 1) |
| N-i-38 | NA | N-i-37 | | 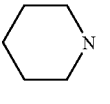 | H | NO2 | 6-Qu | C | | 406 (M⁺ + 1) |
| N-i-39 | NB1 | Int.n-114 | BRA1 | 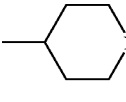 | Me | NO2 | 2-Nap | C | | 433 (M⁺ + 1) |

TABLE N-I-2-continued

| Exp. | Syn | SM1 | SM2 | NRzRy | Y | Zx | AR | LCMS method | RTime | Mass |
|---|---|---|---|---|---|---|---|---|---|---|
| N-i-40 | NA | N-i-39 | | 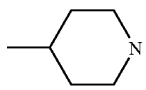 | H | NO2 | 2-Nap | C | | 419 (M$^+$ + 1) |
| N-i-41 | NB1 | Int.n-114 | BRA3 | 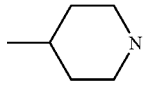 | Me | NO2 | 1Me-5-Ind | C | | 437 (M$^+$ + 1) |
| N-i-42 | NA | N-i-41 | | 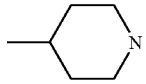 | H | NO2 | 1Me-5-Ind | C | | 423 (M$^+$ + 1) |
| N-i-43 | NB1 | Int.n-114 | BRA5 | 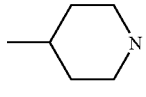 | Me | NO2 | 5-1HIdz | C | | 423 (M$^+$ + 1) |
| N-i-44 | NA | N-i-43 | | 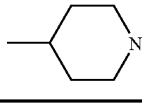 | H | NO2 | 5-1HIdz | C | | 409 (M$^+$ + 1) |

TABLE N-I-3

| Exp. | Syn | SM1 | SM2 | NRzRy | Y | Zx | AR | LCMS method | RTime | Mass |
|---|---|---|---|---|---|---|---|---|---|---|
| N-i-45 | NB1 | Int.n-114 | BRA6 | 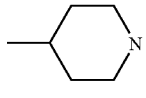 | Me | NO2 | 1Me-5-1HIdz | C | | 437 (M$^+$ + 1) |
| N-i-46 | NA | N-i-45 | | 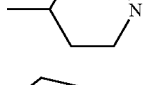 | H | NO2 | 1Me-5-1HIdz | C | | 423 (M$^+$ + 1) |
| N-i-47 | NB1 | Int.n-115 | BRA3 | 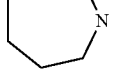 | Me | NO2 | 1Me-5-Ind | C | | 436 (M$^+$ + 1) |
| N-i-48 | NA | N-i-47 | | 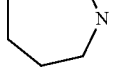 | H | NO2 | 1Me-5-Ind | C | | 422 (M$^+$ + 1) |
| N-i-49 | NB1 | Int.n-115 | BRA5 | 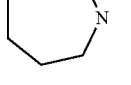 | Me | NO2 | 5-1HIdz | C | | 423 (M$^+$ + 1) |
| N-i-50 | NA | N-i-49 | | 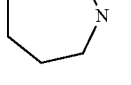 | H | NO2 | 5-1HIdz | C | | 409 (M$^+$ + 1) |
| N-i-51 | NB1 | Int.n-115 | BRA6 | 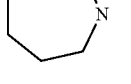 | Me | NO2 | 1Me-5-1HIdz | C | | 437 (M$^+$ + 1) |

TABLE N-I-3-continued

| Exp. | Syn | SM1 | SM2 | NRzRy | Y | Zx | AR | LCMS method | RTime | Mass |
|---|---|---|---|---|---|---|---|---|---|---|
| N-i-52 | NA | N-i-51 | |  | H | NO2 | 1Me-5-1HIdz | C | | 423 (M⁺ + 1) |
| N-i-53 | ND1 | N-i-1 | |  | Me | NH2 | 2-Nap | C | | 375 (M⁺ + 1) |
| N-i-54 | NA | N-i-53 | |  | H | NH2 | 2-Nap | C | | 361 (M⁺ + 1) |
| N-i-55 | ND1 | N-i-3 | |  | Me | NH2 | 5-1Ind | C | | 364 (M⁺ + 1) |
| N-i-56 | NA | N-i-55 | |  | H | NH2 | 5-1Ind | C | | 350 (M⁺ + 1) |
| N-i-57 | ND1 | N-i-5 | |  | Me | NH2 | 1Me-5-Ind | C | | 378 (M⁺ + 1) |
| N-i-58 | NA | N-i-57 | |  | H | NH2 | 1Me-5-Ind | C | | 364 (M⁺ + 1) |
| N-i-59 | ND1 | N-i-7 | |  | Me | NH2 | 5-1HIdz | C | | 365 (M⁺ + 1) |
| N-i-60 | NA | N-i-59 | |  | H | NH2 | 5-1HIdz | C | | 351 (M⁺ + 1) |
| N-i-61 | ND1 | N-i-9 | |  | Me | NH2 | 1Me-5-1HIdz | C | | 379 (M⁺ + 1) |
| N-i-62 | NA | N-i-61 | |  | H | NH2 | 1Me-5-1HIdz | C | | 365 (M⁺ + 1) |
| N-i-63 | ND1 | N-i-11 | |  | Me | NH2 | 5-Bzt | C | | 382 (M⁺ + 1) |
| N-i-64 | NA | N-i-63 | |  | H | NH2 | 5-Bzt | C | | 368 (M⁺+ 1) |
| N-i-65 | ND1 | N-i-13 | |  | Me | NH2 | 3-Qu | C | | 376 (M⁺ + 1) |
| N-i-66 | NA | N-i-65 | |  | H | NH2 | 3-Qu | C | | 362 (M⁺ + 1) |

TABLE N-I-4

| Exp. | Syn | SM1 | SM2 | NRzRy | Y | Zx | AR | LCMS method | RTime | Mass |
|---|---|---|---|---|---|---|---|---|---|---|
| N-i-67 | ND1 | N-i-15 | | pyrrolidine | Me | NH2 | 6-Qu | C | | 376 (M+ + 1) |
| N-i-68 | NA | N-i-67 | | pyrrolidine | H | NH2 | 6-Qu | C | | 362 (M+ + 1) |
| N-i-69 | ND1 | N-i-17 | | morpholine | Me | NH2 | 2-Nap | C | | 391 (M + + 1) |
| N-i-70 | NA | N-i-69 | | morpholine | H | NH2 | 2-Nap | C | | 377 (M+ + 1) |
| N-i-71 | ND1 | N-i-19 | | morpholine | Me | NH2 | 5-1Ind | C | | 380 (M+ + 1) |
| N-i-72 | NA | N-i-71 | | morpholine | H | NH2 | 5-1Ind | C | | 366 (M+ + 1) |
| N-i-73 | ND1 | N-i-21 | | morpholine | Me | NH2 | 1Me-5-Ind | C | | 394 (M+ + 1) |
| N-i-74 | NA | N-i-73 | | morpholine | H | NH2 | 1Me-5-Ind | C | | 380 (M+ + 1) |
| N-i-75 | ND1 | N-i-23 | | morpholine | Me | NH2 | 5-1HIdz | C | | 381 (M+ + 1) |
| N-i-76 | NA | N-i-75 | | morpholine | H | NH2 | 5-1HIdz | C | | 367 (M+ + 1) |
| N-i-77 | ND1 | N-i-25 | | morpholine | Me | NH2 | 1Me-5-1HIdz | C | | 395 (M+ + 1) |
| N-i-78 | NA | N-i-77 | | morpholine | H | NH2 | 1Me-5-1HIdz | C | | 381 (M+ + 1) |
| N-i-79 | ND1 | N-i-27 | | piperidine | Me | NH2 | 2-Nap | C | | 389 (M+ + 1) |
| N-i-80 | NA | N-i-79 | | piperidine | H | NH2 | 2-Nap | C | | 375 (M+ + 1) |
| N-i-81 | ND1 | N-i-29 | | piperidine | Me | NH2 | 5-1Ind | C | | 378 (M+ + 1) |

TABLE N-I-4-continued

| Exp. | Syn | SM1 | SM2 | NRzRy | Y | Zx | AR | LCMS method | RTime | Mass |
|---|---|---|---|---|---|---|---|---|---|---|
| N-i-82 | NA | N-i-81 | |  | H | NH2 | 5-1Ind | C | | 364 (M⁺ + 1) |
| N-i-83 | ND1 | N-i-31 | |  | Me | NH2 | 1Me-5-Ind | C | | 392 (M⁺ + 1) |
| N-i-84 | NA | N-i-83 | |  | H | NH2 | 1Me-5-Ind | C | | 378 (M⁺ + 1) |
| N-i-85 | ND1 | N-i-33 | |  | Me | NH2 | 5-1HIdz | C | | 379 (M⁺ + 1) |
| N-i-86 | NA | N-i-85 | |  | H | NH2 | 5-1HIdz | C | | 365 (M⁺ + 1) |
| N-i-87 | ND1 | N-i-35 | |  | Me | NH2 | 1Me-5-1HIdz | C | | 393 (M⁺ + 1) |
| N-i-88 | NA | N-i-87 | |  | H | NH2 | 1Me-5-1HIdz | C | | 379 (M⁺ + 1) |

TABLE N-I-5

| Exp. | Syn | SM1 | SM2 | NRzRy | Y | Zx | AR | LCMS method | RTime | Mass |
|---|---|---|---|---|---|---|---|---|---|---|
| N-i-89 | ND1 | N-i-37 | |  | Me | NH2 | 6-Qu | C | | 390 (M⁺ + 1) |
| N-i-90 | NA | N-i-89 | |  | H | NH2 | 6-Qu | C | | 376 (M⁺ + 1) |
| N-i-91 | ND1 | N-i-39 | |  | Me | NH2 | 2-Nap | C | | 403 (M⁺ + 1) |
| N-i-92 | NA | N-i-91 | |  | H | NH2 | 2-Nap | C | | 389 (M⁺ + 1) |
| N-i-93 | ND1 | N-i-41 | |  | Me | NH2 | 1Me-5-Ind | C | | 406 (M⁺ + 1) |
| N-i-94 | NA | N-i-93 | |  | H | NH2 | 1Me-5-Ind | C | | 392 (M⁺ + 1) |

TABLE N-I-5-continued

| Exp. | Syn | SM1 | SM2 | NRzRy | Y | Zx | AR | LCMS method | RTime | Mass |
|---|---|---|---|---|---|---|---|---|---|---|
| N-i-95 | ND1 | N-i-43 | | 4-Me-piperidine | Me | NH2 | 5-1Idz | C | | 393 (M$^+$ + 1) |
| N-i-96 | NA | N-i-95 | | 4-Me-piperidine | H | NH2 | 5-1Idz | C | | 379 (M$^+$ +1) |
| N-i-97 | ND1 | N-i-45 | | 4-Me-piperidine | Me | NH2 | 1Me-5-1HIdz | C | | 407 (M$^+$ + 1) |
| N-i-98 | NA | N-i-97 | | 4-Me-piperidine | H | NH2 | 1Me-5-1HIdz | C | | 393 (M$^+$ + 1) |
| N-i-99 | ND1 | N-i-47 | | azepane | Me | NH2 | 1Me-5-Ind | C | | 406 (M$^+$ + 1) |
| N-i-100 | NA | N-i-99 | | azepane | H | NH2 | 1Me-5-Ind | C | | 392 (M$^+$ + 1) |
| N-i-101 | ND1 | N-i-49 | | azepane | Me | NH2 | 5-1Idz | C | | 393 (M$^+$ + 1) |
| N-i-102 | NA | N-i-101 | | azepane | H | NH2 | 5-1Idz | C | | 379 (M$^+$ + 1) |
| N-i-103 | ND1 | N-i-51 | | azepane | Me | NH2 | 1Me-5-1HIdz | C | | 407 (M$^+$ + 1) |
| N-i-104 | NA | N-i-103 | | azepane | H | NH2 | 1Me-5-1HIdz | C | | 393 (M$^+$ + 1) |
| N-i-105 | NN1 | N-i-53 | CH$_3$I | pyrrolidine | Me | NHMe | 2-Nap | C | | 389 (M$^+$ + 1) |
| N-i-106 | NA | N-i-105 | | pyrrolidine | H | NHMe | 2-Nap | C | | 375 (M$^+$ + 1) |
| N-i-107 | NN1 | N-i-57 | CH$_3$I | pyrrolidine | Me | NHMe | 1Me-5-Ind | C | | 392 (M$^+$ + 1) |
| N-i-108 | NA | N-i-107 | | pyrrolidine | H | NHMe | 1Me-5-Ind | C | | 378 (M$^+$+ 1) |

TABLE N-I-5-continued

| Exp. | Syn | SM1 | SM2 | NRzRy | Y | Zx | AR | LCMS method | RTime | Mass |
|---|---|---|---|---|---|---|---|---|---|---|
| N-i-109 | NN1 | N-i-61 | CH₃I | pyrrolidine | Me | NHMe | 1Me-5-1HIdz | C | | 393 (M⁺+1) |
| N-i-110 | NA | N-i-109 | | pyrrolidine | H | NHMe | 1Me-5-1HIdz | C | | 379 (M⁺+1) |

TABLE N-I-6

| Exp. | Syn | SM1 | SM2 | NRzRy | Y | Zx | AR | LCMS method | RTime | Mass |
|---|---|---|---|---|---|---|---|---|---|---|
| N-i-111 | NN1 | N-i-63 | CH₃I | pyrrolidine | Me | NHMe | 5-Bzt | C | | 396 (M⁺+1) |
| N-i-112 | NA | N-i-111 | | pyrrolidine | H | NHMe | 5-Bzt | C | | 382 (M⁺+1) |
| N-i-113 | NN1 | N-i-65 | CH₃I | pyrrolidine | Me | NHMe | 3-Qu | C | | 390 (M⁺+1) |
| N-i-114 | NA | N-i-113 | | pyrrolidine | H | NHMe | 3-Qu | C | | 376 (M⁺+1) |
| N-i-115 | NN1 | N-i-67 | CH₃I | pyrrolidine | Me | NHMe | 6-Qu | C | | 390 (M⁺+1) |
| N-i-116 | NA | N-i-115 | | pyrrolidine | H | NHMe | 6-Qu | C | | 376 (M⁺+1) |
| N-i-117 | NN1 | N-i-69 | CH₃I | morpholine | Me | NHMe | 2-Nap | C | | 405 (M⁺+1) |
| N-i-118 | NA | N-i-117 | | morpholine | H | NHMe | 2-Nap | C | | 391 (M⁺+1) |
| N-i-119 | NN1 | N-i-73 | CH₃I | morpholine | Me | NHMe | 1Me-5-Ind | C | | 408 (M⁺+1) |
| N-i-120 | NA | N-i-119 | | morpholine | H | NHMe | 1Me-5-Ind | C | | 394 (M⁺+1) |
| N-i-121 | NN1 | N-i-77 | CH₃I | morpholine | Me | NHMe | 1Me-5-1HIdz | C | | 409 (M⁺+1) |
| N-i-122 | NA | N-i-121 | | morpholine | H | NHMe | 1Me-5-1HIdz | C | | 395 (M⁺+1) |

TABLE N-I-6-continued

| Exp. | Syn | SM1 | SM2 | NRzRy | Y | Zx | AR | LCMS method | RTime | Mass |
|---|---|---|---|---|---|---|---|---|---|---|
| N-i-123 | NN1 | N-i-79 | CH₃I |  | Me | NHMe | 2-Nap | C | | 403 (M⁺ + 1) |
| N-i-124 | NA | N-i-123 | |  | H | NHMe | 2-Nap | C | | 389 (M⁺ + 1) |
| N-i-125 | NN1 | N-i-83 | CH₃I | 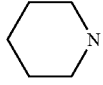 | Me | NHMe | 1Me-5-Ind | C | | 406 (M⁺ + 1) |
| N-i-126 | NA | N-i-125 | | 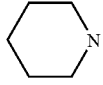 | H | NHMe | 1Me-5-Ind | C | | 392 (M⁺ + 1) |
| N-i-127 | NN1 | N-i-87 | CH₃I | 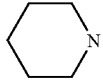 | Me | NHMe | 1Me-5-1HIdz | C | | 407 (M⁺+ 1) |
| N-i-128 | NA | N-i-127 | | 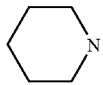 | H | NHMe | 1Me-5-1HIdz | C | | 393 (M⁺ + 1) |
| N-i-129 | NN1 | N-i-91 | CH₃I | 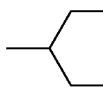 | Me | NHMe | 2-Nap | C | | 417 (M⁺+ 1) |
| N-i-130 | NA | N-i-129 | | 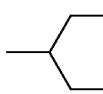 | H | NHMe | 2-Nap | C | | 403 (M⁺ + 1) |
| N-i-131 | NN1 | N-i-93 | CH₃I | 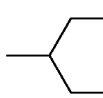 | Me | NHMe | 1Me-5-Ind | C | | 420 (M⁺ + 1) |
| N-i-132 | NA | N-i-131 | | 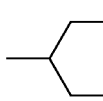 | H | NHMe | 1Me-5-Ind | C | | 406 (M⁺+ 1) |

TABLE N-I-7

| Exp. | Syn | SM1 | SM2 | NRzRy | Y | Zx | AR | LCMS method | RTime | Mass |
|---|---|---|---|---|---|---|---|---|---|---|
| N-i-133 | NN1 | N-i-97 | CH₃I | 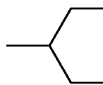 | Me | NHMe | 1Me-5-1HIdz | C | | 421 (M⁺ + 1) |
| N-i-134 | NA | N-i-133 | | 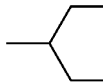 | H | NHMe | 1Me-5-1HIdz | C | | 407 (M⁺ + 1) |
| N-i-135 | NN1 | N-i-99 | CH₃I | 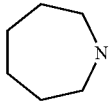 | Me | NHMe | 1Me-5-Ind | C | | 420 (M⁺ + 1) |

TABLE N-I-7-continued

| Exp. | Syn | SM1 | SM2 | NRzRy | Y | Zx | AR | LCMS method | RTime | Mass |
|---|---|---|---|---|---|---|---|---|---|---|
| N-i-136 | NA | N-i-135 | | 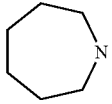 | H | NHMe | 1Me-5-Ind | C | | 406 (M⁺ + 1) |
| N-i-137 | NN1 | N-i-103 | CH₃I | 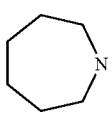 | Me | NHMe | 1Me-5-1HIdz | C | | 421 (M⁺ + 1) |
| N-i-138 | NA | N-i-137 | | 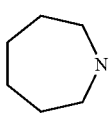 | H | NHMe | 1Me-5-1HIdz | C | | 407 (M⁺ + 1) |
| N-i-139 | NN2 | N-i-53 | CH₃I | 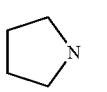 | Me | NMe2 | 2-Nap | C | | 403 (M⁺ + 1) |
| N-i-140 | NA | N-i-139 | | 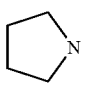 | H | NMe2 | 2-Nap | C | | 389 (M⁺ + 1) |
| N-i-141 | NN2 | N-i-57 | CH₃I | 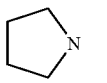 | Me | NMe2 | 1Me-5-Ind | C | | 406 (M⁺ + 1) |
| N-i-142 | NA | N-i-141 | | 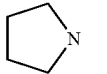 | H | NMe2 | 1Me-5-Ind | C | | 392 (M⁺ + 1) |
| N-i-143 | NN2 | N-i-61 | CH₃I | 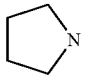 | Me | NMe2 | 1Me-5-1HIdz | C | | 407 (M⁺ + 1) |
| N-i-144 | NA | N-i-143 | | 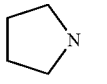 | H | NMe2 | 1Me-5-1HIdz | C | | 393 (M⁺ + 1) |
| N-i-145 | NN2 | N-i-63 | CH₃I | 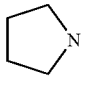 | Me | NMe2 | 5-Bzt | C | | 410 (M⁺ + 1) |
| N-i-146 | NA | N-i-145 | | 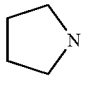 | H | NMe2 | 5-Bzt | C | | 396 (M⁺ + 1) |
| N-i-147 | NN2 | N-i-65 | CH₃I | 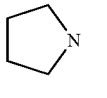 | Me | NMe2 | 3-Qu | C | | 404 (M⁺ + 1) |
| N-i-148 | NA | N-i-147 | | 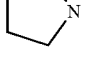 | H | NMe2 | 3-Qu | C | | 390 (M⁺ + 1) |
| N-i-149 | NN2 | N-i-67 | CH₃I | 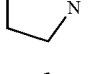 | Me | NMe2 | 6-Qu | C | | 404 (M⁺ + 1) |
| N-i-150 | NA | N-i-149 | | 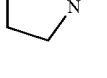 | H | NMe2 | 6-Qu | C | | 390 (M⁺ + 1) |

TABLE N-I-7-continued

| Exp. | Syn | SM1 | SM2 | NRzRy | Y | Zx | AR | LCMS method | RTime | Mass |
|---|---|---|---|---|---|---|---|---|---|---|
| N-i-151 | NN2 | N-i-69 | CH$_3$I | morpholine | Me | NMe2 | 2-Nap | C | | 419 (M$^+$ + 1) |
| N-i-152 | NA | N-i-151 | | morpholine | H | NMe2 | 2-Nap | C | | 405 (M$^+$ + 1) |
| N-i-153 | NN2 | N-i-73 | CH$_3$I | morpholine | Me | NMe2 | 1Me-5-Ind | C | | 422 (M$^+$ + 1) |
| N-i-154 | NA | N-i-153 | | morpholine | H | NMe2 | 1Me-5-Ind | C | | 408 (M$^+$ + 1) |

TABLE N-I-8

| Exp. | Syn | SM1 | SM2 | NRzRy | Y | Zx | AR | LCMS method | RTime | Mass |
|---|---|---|---|---|---|---|---|---|---|---|
| N-i-121 | NN2 | N-i-77 | CH$_3$I | morpholine | Me | NMe2 | 1Me-5-1HIdz | C | | 423 (M$^+$ + 1) |
| N-i-122 | NA | N-i-121 | | morpholine | H | NMe2 | 1Me-5-1HIdz | C | | 409 (M$^+$ + 1) |
| N-i-123 | NN2 | N-i-79 | CH$_3$I | piperidine | Me | NMe2 | 2-Nap | C | | 417 (M$^+$ + 1) |
| N-i-124 | NA | N-i-123 | | piperidine | H | NMe2 | 2-Nap | C | | 403 (M$^+$ + 1) |
| N-i-125 | NN2 | N-i-83 | CH$_3$I | piperidine | Me | NMe2 | 1Me-5-Ind | C | | 420 (M$^+$ + 1) |
| N-i-126 | NA | N-i-125 | | piperidine | H | NMe2 | 1Me-5-Ind | C | | 406 (M$^+$ + 1) |
| N-i-127 | NN2 | N-i-87 | CH$_3$I | piperidine | Me | NMe2 | 1Me-5-1HIdz | C | | 421 (M$^+$ + 1) |
| N-i-128 | NA | N-i-127 | | piperidine | H | NMe2 | 1Me-5-1HIdz | C | | 407 (M$^+$ + 1) |
| N-i-129 | NN2 | N-i-91 | CH$_3$I | 4-Me-piperidine | Me | NMe2 | 2-Nap | C | | 431 (M$^+$ + 1) |

TABLE N-I-8-continued

| Exp. | Syn | SM1 | SM2 | NRzRy | Y | Zx | AR | LCMS method | RTime | Mass |
|---|---|---|---|---|---|---|---|---|---|---|
| N-i-130 | NA | N-i-129 | | 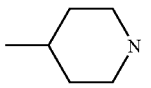 | H | NMe2 | 2-Nap | C | | 417 (M⁺+ 1) |
| N-i-131 | NN2 | N-i-93 | CH₃I | 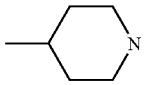 | Me | NMe2 | 1Me-5-Ind | C | | 434 (M⁺ + 1) |
| N-i-132 | NA | N-i-131 | | 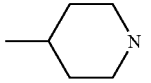 | H | NMe2 | 1Me-5-Ind | C | | 420 (M⁺ + 1) |
| N-i-133 | NN2 | N-i-97 | CH₃I | 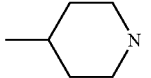 | Me | NMe2 | 1Me-5-1HIdz | C | | 435 (M⁺ + 1) |
| N-i-134 | NA | N-i-133 | | 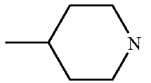 | H | NMe2 | 1Me-5-1HIdz | C | | 421 (M⁺ + 1) |
| N-i-135 | NN2 | N-i-99 | CH₃I | 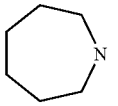 | Me | NMe2 | 2-Nap | C | | 431 (M⁺+ 1) |
| N-i-136 | NA | N-i-135 | | 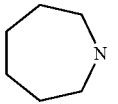 | H | NMe2 | 2-Nap | C | | 417 (M⁺ + 1) |
| N-i-137 | NN2 | N-i-103 | CH₃I | 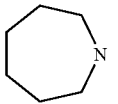 | Me | NMe2 | 1Me-5-1HIdz | C | | 435 (M⁺ + 1) |
| N-i-138 | NA | N-i-137 | | 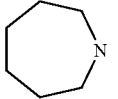 | H | NMe2 | 1Me-5-1HIdz | C | | 421 (M⁺ + 1) |

Test Examples

1. Suppressing Action on $PGE_2$ Production from IL-1β-Stimulated Mg-63 Cells (1) Method for Measurement An action of suppressing $PGE_2$ production caused by interleukin (IL) 1β as an inflammatory stimulant was studied by the following method. Cells of MG-63, which is a human osteosarcoma cell line (purchased from Dainippon Pharmaceutical), were suspended in EMEM medium (GIBCO) containing 10% fetal bovine serum (BioFluid), and then inoculated to each well of 96-well culture plate at a density of 2×10⁴ cells/well and cultured overnight. The medium was changed to EMEM medium containing 0.5% fetal bovine serum, and then a test compound was added to each well. Human interleukin-1β (ENDOGEN) was further added as an inflammatory stimulant at a final concentration of 1 ng/ml. The cells were further cultured for 18 hours. Then, the culture supernatant was collected, and the $PGE_2$ concentration in the culture supernatant was measured by using EIA kit (CAYMAN). By using a well which was not added with the stimulant as a negative control and a well which was added only with the stimulant as a positive control, suppression ratio on $PGE_2$ production was calculated from the produced amount of $PGE_2$ in the well added with the test compound using the following equation.

$PGE_2$ production suppression ratio=$[1-(C-B)/(A-B)]\times 100$  [Equation 1]

A: $PGE_2$ production amount of positive control
B: $PGE_2$ production amount of negative control
C: $PGE_2$ production amount in well added with test compound Further, cytotoxicity of the compounds was studied by using the cells after the collection of the supernatant according to the methylene blue uptake method. Specifically, the cells remained after the collection of the supernatant were fixed with glutaraldehyde and stained with a 0.05% methylene blue solution, then methylene blue taken up by the cells was extracted with 0.3 N hydrochloric acid, and absorbance of the extract was measured at 670 nm. The absorbance of the well of the aforementioned positive control was taken as 100%, and a test compound that gave absorbance in well of less than 80% was judged to be positive in cytotoxicity.

(2) Measurement Results

The test compounds (Compound Nos. G-1 to G-121, H-1 to H-32, J-1 to J-92, K-1 to K-40, L-1 to L-95, M-1 to M-32, N-1 to N-74, P-1 to P-50, Q-1 to Q-52, S-1 to S-73, T-1 to T-61, U-1 to U-18, V-1 to V-109, and W-1 to W-13) suppressed the $PGE_2$ production caused by IL-1β by 50% or more at 1.0 µM. Moreover, all the test compounds did not exhibit cytotoxicity at that concentration.

The test compounds (Compound Nos. Ca-1 to Ca-203) suppressed the $PGE_2$ production caused by IL-1β by 50% or more at 1.0 µM. None of the test compounds exhibited cytotoxicity at that concentration.

The test compounds (Compound Nos. S-a-1 to S-a-24, S-b-1 to S-b-138, and S-c-1 to S-c-138) suppressed the $PGE_2$ production caused by IL-1β by 50% or more at 1.0 µM. None of the test compounds exhibited cytotoxicity at that concentration.

Further, the test compounds (Compound Nos. N-a-1 to N-a-142, N-b-1 to N-b-182, N-c-1 to N-c-64, N-d-1 to N-d-74, N-e-1 to N-e-186 and N-g-1 to N-g-44) suppressed the $PGE_2$ production caused by IL-1β by 50% or more at 1.0 µM. None of the test compounds exhibited cytotoxicity at that concentration.

Therefore, the novel substituted phenylalkanoic acid derivatives or salts thereof according to the present invention are useful as agents for suppressing inflammatory prostaglandin production.

2. Suppressing Action on $PGD_2$ and $LTB_4$ Production from IgE-Stimulated RBL-2H3 Cells (1) Method for Measurement Suppressing action on $PGD_2$ and $LTB_4$ production caused by IgE as an allergic stimulant was investigated by the following method. Cells of RBL-2H3, which is a rat mastocytoma cell line (purchased from ATCC), were suspended in DEMEM medium (GIBCO) containing 10% fetal bovine serum (BioFluid), inoculated to each well of 48-well culture plate at a density of $2\times10^4$ cells/well and cultured overnight. Then, IgE antiserum directed to dinitrophenylated BSA (hereinafter abbreviated as "DNP-BSA") was further added to each well, and the cells were cultured for 30 minutes. Then, the medium was changed to DEMEM medium containing 0.5% fetal bovine serum, a test compound was added to each well, and DNP-BSA was further added at a final concentration of 100 ng/ml as a stimulant. Ten minutes after the stimulant was added, the culture supernatant was collected, and the $PGD_2$ concentration and $LTB_4$ concentration in the culture supernatant were measured by using EIA kit (CAYMAN). By using a well which was not added with the stimulant as a negative control and a well which was added only with the stimulant as a positive control, suppressing ratios on mediator production were calculated from the production amounts of the mediators in the well added with the test compound using the following equation 2.

$PGD_2$ or $LTB_4$ production suppression ratio=[1−(C−B)/(A−B)]×100     [Equation 2]

A: $PGD_2$ or $LTB_4$ production amount of positive control
B: $PGD_2$ or $LTB_4$ production amount of negative control
C: $PGD_2$ or $LTB_4$ production amount in well added with test compound Cytotoxicity of the compounds was studied in the same manner as those described above, by using the cells after the collection of the supernatant according to the methylene blue uptake method.

(2) Measurement Results

Representative compounds of the objective Compounds (I) described in the specification suppressed the $PGD_2$ and $LTB_4$ production caused by IgE stimulation by 50% or more at 1.0 µM. Moreover, all the test compounds did not exhibit cytotoxicity at that concentration. Thus, the novel substituted phenylalkanoic acid derivatives or salts thereof according to the present invention exhibit suppressing action on the allergic prostaglandin and leukotriene production, and are useful as suppressing agents for the production thereof.

3. Suppressing Effect on Mouse Zymosan-Stimulated Footpad Edema Reaction (1) Method for Measurement A suppressing effect on footpad edema caused by zymosan as an inflammatory stimulant was studied by the following method. Groups of ICR female mice (6- to 7-week old) each consisting of eight mice were used for the test. A test compound was suspended or dissolved in purified water containing 0.5% methylcellulose and orally administered to the test animals at 0.1 to 500 mg/10 ml/kg. To the control group, purified water containing 0.5% methylcellulose was administered in a similar manner, which was not added with a test compound. One hour after the administration of the test compound, 0.02 ml of a suspension of zymosan suspended in physiological saline (Otsuka Pharmaceutical) at 1 mg/ml was subcutaneously administered to right hind leg footpad of each mouse. One and two hours after the administration of the zymosan suspension, volume of the right hind leg footpad was measured by using an apparatus for measuring a volume of mouse hind leg footpad edema (Unicom). A difference of the volume of footpad measured above and the footpad volume before the administration of the test compound measured beforehand was regarded as a volume of the edema.

For the volume of the edema at 1 hour or 2 hours after the zymosan administration, a graph was prepared by indicating time in abscissa and the edema volume in ordinate, and an edema volume AUC (area under the curve) was obtained up to 2 hours by calculation using the following equation.

Edema volume $AUC$(µl·hour)=½×1×$A$+1×($A$+$B$)/2     [Equation 3]

A: Edema volume 1 hour after zymosan administration
B: Edema volume 2 hour after zymosan administration A suppression ratio on edema of test compound was obtained by calculation using the following equation.

Edema suppression ratio (%)=[1−$B$/$A$]×100     [Equation 4]

A: Edema volume AUC of positive control
B: Edema volume AUC of test compound administered group (2) Measurement Results Representative compounds of the objective Compounds (I) described in the specification more effectively suppressed footpad edema caused by subcutaneous administration of zymosan compared with the positive control group by oral administration at 0.1 to 500 mg/kg.

Therefore, the novel substituted phenylalkanoic acid derivatives or salts thereof according to the present invention exhibit a suppressing action on footpad edema caused by zymosan as an inflammatory stimulant, and thus they are useful as agents for prophylactic and/or therapeutic drugs for inflammatory diseases.

4. Suppressing Effect on Mouse IgE-Stimulated Footpad Edema Reaction (1) Method for Measurement Suppression on footpad edema caused by IgE antibody as an allergic stimulant was studied by the following method. Groups of C57BL/6 male mice (9- to 11-week old) each consisting of five mice were used for the test. Anti-DNP-BSA IgE serum was subcutaneously administered in a volume of 20 µl to right hind leg footpad of each mouse one day before the test. A test compound was suspended or dissolved in purified water containing 0.5% methylcellulose and orally administered to the test animals at 0.1 to 500 mg/10 ml/kg. To the control group, purified water containing 0.5% methylcellulose was administered in a similar manner, which was not added with any test compound. Two hours after the administration of the test compound, 0.2 ml of a solution of DNP-BSA dissolved in physiological saline (Otsuka Pharmaceutical) at 2.5 µg/ml was intravenously administered. The thickness of right hind leg footpad was measured by using a digital thickness gauge (MITSUTOYO) 10, 15, 20, and 30 minutes after the administration of DNP-BSA. A difference of the thickness of footpad measured above and the thickness before the administration of the test compound measured beforehand was regarded as a thickness of edema.

For the thickness of the edema at 10, 15, 20 and 30 minutes after the DNP-BSA administration, a graph was prepared indicating time in abscissa and the edema thickness in ordinate, and edema thickness AUC up to 2 hours was obtained by calculation according to the following equation.

$$\text{Edema thickness } AUC(\text{mm·minute}) = \frac{1}{2} \times 10 \times A + 5 \times (A+B)/2 + 5 \times (B+C)/2 + 10 \times (C+D)/2 \quad \text{[Equation 5]}$$

A: Edema thickness 10 minutes after DNP-BSA administration

B: Edema thickness 15 minutes after DNP-BSA administration

C: Edema thickness 20 minutes after DNP-BSA administration

D: Edema thickness 30 minutes after DNP-BSA administration

A suppressing ratio on edema of a test compound was obtained by calculation in accordance with the following equation.

$$\text{Edema suppression ratio}(\%) = [1 - B/A] \times 100 \quad \text{[Equation 6]}$$

A: Edema thickness AUC of positive control

B: Edema thickness AUC of test compound administered group (2) Measurement Results Representative compounds of the objective Compounds (I) described in the specification suppressed the footpad edema caused by IgE stimulation, i.e., footpad edema observed when DNP-BSA was administered to the mice sensitized with the anti-DNP-BSA IgE serum, compared with the positive control group by oral administration of 0.1 to 500 mg/kg.

Therefore, the novel substituted phenylalkanoic acid derivatives or salts thereof according to the present invention exhibit suppressing action on footpad edema caused by IgE antibody, which is an allergic stimulant, and thus they are useful as prophylactic and/or therapeutic drugs for allergic diseases.

5. Suppressing Effect on Mouse Acetic Acid Writhing Reaction (1) Method for Measurement A suppressing effect on acetic acid writhing reaction, which is an acute pain model, was studied by the following method. Groups of ICR female mice (6-week old) each consisting of eight mice were used for the test. A test compound was suspended or dissolved in purified water containing 0.5% methylcellulose and orally administered to the test animals at 0.1 to 500 mg/10 ml/kg. To the control group, purified water containing 0.5% methylcellulose was administered in a similar manner, which was not added with any test compound. One hour after the administration of the test compound, 0.9% aqueous acetic acid was intraperitoneally administered to the mice in a volume of 5 ml/kg, and number of writhing reactions during 15 minutes immediately after the administration of acetic acid was counted. Suppression ratio relative to the control group was obtained by calculation according to the following equation.

$$\text{Writhing suppression ratio}(\%) = [1 - B/A] \times 100 \quad \text{[Equation 7]}$$

A: Writhing number of positive control group

B: Writhing number of test compound administered group (2) Measurement Results

The representative compounds of the objective Compounds (I) described in the specification suppressed writhing caused by administration of aqueous acetic acid compared with the positive control group at oral administration of 0.1 to 500 mg/kg.

It has been elucidated that a writhing reaction caused by intraperitoneal administration of acetic acid is caused due to production of prostaglandin [Matsumoto et al., European Journal of Pharmacology (Eur. J. Pharmacol), 1998, vol. 352, p.47; Ueno et al., Biochemical Pharmacology (Biochem. Pharmacol), 2001, vol. 15, p.157].

Therefore, the novel substituted phenylalkanoic acid derivatives or salts thereof according to the present invention are useful as prophylactic and/or therapeutic agents for acute pain caused by prostaglandins.

6. Prophylactic and Therapeutic Effects for Rat Adjuvant Arthritis (1) Method for Measurement A suppressing effect on footpad edema observed in rat adjuvant arthritis, which is a disease model of rheumatoid arthritis as being one of autoimmune diseases and also a chronic inflammatory disease, was studied by the following method. Groups of Lewis female rats (8-week old) each consisting of six mice were used for the test. The test animals were immunized by subcutaneously administering, to right hind leg footpads, 50 µl of liquid paraffin containing 10 mg/ml of M. tuberculosis H37 RA (DIFCO) as an adjuvant. A test compound was suspended or dissolved in purified water containing 0.5% methylcellulose and orally administered to the test animals at 0.1 to 500 mg/5 ml/kg. The test compound was administered twice a day for 14 days, from the 12th day after the immunization. To the control group, purified water containing 0.5% methylcellulose was administered in a similar manner, which was not added with any test compound. Every 2 or 3 days after the administration of adjuvant, volume of left hind leg footpad, which was not administered with the adjuvant, was measured by using an apparatus for measuring a volume of edema of a rat hind leg footpad (Unicom). A suppression ratio on edema was obtained by calculation using the following equation.

Edema suppression ratio(%)={1−[(D−C)/C]/[(B−A)/A]}×100 [Equation 8]

A: Left hind leg footpad volume of positive control immediately before administration of adjuvant B: Left hind leg footpad volume of positive control on each measurement day C: Left hind leg footpad volume of test compound administered group immediately before administration of adjuvant D: Left hind leg footpad volume of test compound administered group on each measurement day (2) Measurement Results The representative compounds of the objective Compound (I) described in the specification suppressed footpad edema in adjuvant arthritis compared with the positive control group.

Therefore, the novel substituted phenylalkanoic acid derivatives or salts thereof according to the present invention are useful as agents for prophylactic and/or therapeutic drugs for rheumatoid arthritis and autoimmune diseases.

7. Effect on Rat Pulmonary Fibrosis (1) Method for Measurement

A suppressing effect on pulmonary fibrosing in a bleomycin-induced rat pulmonary fibrosis model, which is a pathological model of pulmonary fibrosis, was studied by the following method. Groups of BN female rats (7-week old) each consisting of seven rats were used for the test. The test animals were anesthetized with ketamine and xylazine, and the tracheae were exposed. Then, a 125 μg/0.1 ml solution of bleomycin (Nippon Kayaku) dissolved in physiological saline (Ohtsuka Pharmaceutical Factory) was injected into the tracheae by using a syringe. The negative control group was administered with 0.1 ml of saline into the tracheae.

Each test compound was suspended or dissolved in purified water containing 0.5% methylcellulose, and orally administered to the test animals at doses of 10, 30, 100 and 300 mg/5 ml/kg. The administration of the test compounds was started from the day of the bleomycin administration and performed once or twice a day for 21 days. The positive control group was administered with purified water containing 0.5% methylcellulose not added with any test compound in a similar manner. On the 21st day after the administration of bleomycin, the rats were sacrificed, and lungs were fixed with neutral buffered formalin to prepare histopathological samples. Staining of the histopathological samples was performed by the Azan method.

The histopathological samples of lungs were examined, and degree of fibrosing was represented with the following scores on the basis of formation of granulation tissues and proliferation of collagen fibers as indicators, i.e., −: no abnormality, ±: extremely mild change, +: mild change, ++: moderate change, and +++: significant change.

(2) Measurement Results

The fibrosing score of the negative control group was minus (−), and no pulmonary fibrosing was observed. The median of the fibrosing score of the positive control group was from ++ to +++, and pulmonary fibrosing was observed. The medians of the fibrosing score of the groups of rats administered with the test compounds (Compound Nos. G-2, G-4 and V-40) were from ± to +, and thus the fibrosing was milder compared with the positive control group. The median of the fibrosing score of the group administered with the other test compounds (Compound Nos. G118 and V-59) was from ± to +, and thus pulmonary fibrosing was milder that that observed in the positive control group. Accordingly, the compounds of the present invention are useful as a prophylactic and/or therapeutic agent for pulmonary fibrosis, and type 4 $PLA_2$ inhibitor compounds are useful as a prophylactic and/or therapeutic agent (including a progression-preventing agent) for pulmonary fibrosis.

Further, known $cPLA_2$ inhibitory compounds, arachidonyl trifluoromethyl ketone, 4-(1-benzhydryl-6-chloro-1H-indol-3-ylmethyl)-3-methoxybenzoic acid, N-{1-[2-(2,4-difluorobenzoyl)benzoyl]-4-tritylsulfanylpyrrolidin-2-ylmethyl}-4-(2,4-dioxothiazolidin-5-ylidenemethyl)benzoic acid amide and 4-{4-[2-(2-[bis(4-chlorophenyl)methoxy]ethylsulfonyl)ethoxy]phenyl}-1,1,1-trifluoro-2-butanone, are intraperitoneally or orally administered in a similar manner. Fibrosing is mild also in the groups administered with these known type 4 $PLA_2$ inhibitory compounds.

INDUSTRIAL APPLICABILITY

The compounds of the present invention have superior suppressing action on prostaglandin production and leukotriene production, and they are useful as active ingredients of medicaments for prophylactic and/or therapeutic treatment of various inflammatory diseases, autoimmune diseases, allergic diseases, pain, fibrosis and the like caused by these lipid mediators.

The invention claimed is:

1. A compound represented by the formula (I):

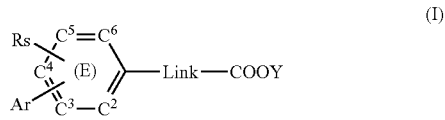

wherein in the formula, Link represents a saturated or unsaturated straight hydrocarbon chain having 1 to 3 carbon atoms, $C^2$, $C^3$, $C^4$, $C^5$, and $C^6$ in the aromatic ring (E) independently represent a ring-constituting carbon atom, one of the ring-constituting carbon atoms to which Rs and AR do not bind may be replaced with V, V represents nitrogen atom, or carbon atom substituted with Zx, Zx represents a linear or branched saturated alkyl group having 1 to 4 carbon atoms, fluorine atom, chlorine atom, bromine atom, nitro group, —$OR^9$, or —$N(Rn^1)(Rn^2)$, $R^9$ represents hydrogen atom, a lower alkyl group having 1 to 4 carbon atoms, or -$A^6$-Qp, wherein $A^6$ represents a single bond or methylene, Qp represents phenyl group, and the phenyl group may be substituted with one of $T^1$ or two or more of the same or different $T^1$, $T^1$ represents a linear or branched saturated alkyl group having 1 to 4 carbon atoms, hydroxyl group, fluorine atom, chlorine atom, bromine atom, trifluoromethyl group, nitro group, an alkoxy group having 1 to 4 carbon atoms, or a mono- or dialkylamino group having 1 to 4 carbon atoms, $Rn^1$ represents hydrogen atom or a linear or branched saturated alkyl group having 1 to 4 carbon atoms, $Rn^2$ has the same meaning as $Rn^1$, or represents —$COR^{23}$ or —$SO_2R^{24}$, or binds to $Rn^1$ to form a 3- to 6-membered ring together with the nitrogen atom to which they bind to form a saturated nitrogen-containing cycloalkyl group or morpholino group, $R^{23}$ represents hydrogen atom, a lower alkyl group having 1 to 4 carbon atoms, a lower alkoxy group having 1 to 4 carbon atoms, —O-$A^6$-Qp, or —$N(R^{25})(R^{26})$, $R^{25}$ represents hydrogen atom, or a linear or branched saturated alkyl group having 1 to 4 carbon atoms, $R^{26}$ has the same meaning as $R^{25}$, or binds to $R^{25}$ to form a 3- to 6-membered ring together with the nitrogen atom to which they bind to form a saturated nitrogen-containing cycloalkyl group or morpholino group, $R^{24}$ represents a lower alkyl group having 1 to 4 carbon atoms, amino group, or a mono- or dialkylamino group having 1 to 4 carbon atoms, Rs represents -D-Rx or —N(Ry)(Rz), D represents a single bond, oxygen atom, sulfur atom, —S(O)—, —S(O)$_2$—, or —C(O)—, Rx represents a linear or branched saturated alkyl group having 3 to 8 carbon atoms, Ra represented by the following formula:

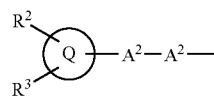
(Ra)

Rb represented by the following formula:

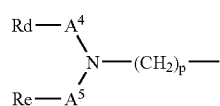
(Rb)

or Rc represented by the following formula:

Rd—A$^4$
   \
    N—(CH$_2$)$_p$—
   /
Re—A$^5$
(Rc)

symbol k in Ra represents 0 or an integer of 1 to 3, $R^1$ represents a saturated cyclic alkyl group having 3 to 7 carbon atoms, or a condensed saturated cyclic alkyl group having 6 to 8 carbon atoms, and $R^1$ may be substituted with one of lower alkyl group having 1 to 4 carbon atoms or two or more of the same or different lower alkyl groups having 1 to 4 carbon atoms, Q in Rb represents a partially unsaturated or completely unsaturated monocyclic or condensed bicyclic carbon ring or a heterocyclic ring (q), and binds to $A^2$ at an arbitrary position on the ring, the heterocyclic ring (q) contains the same or different 1 to 4 ring-constituting heteroatoms selected from the group consisting of nitrogen atom, oxygen atom, and sulfur atom, $A^1$ represents a single bond or an alkylene (a) having 1 to 3 carbon atoms, and the alkylene (a) may be substituted with a lower alkyl group having 1 to 4 carbon atoms or phenyl group, $A^2$ represents a single bond, oxygen atom, sulfur atom, —S(O)—, —S(O)$_2$—, or —N(R$^4$)— (provided that when $A^2$ represents oxygen atom, sulfur atom, —S(O)—, —S(O)$_2$— or —N(R$^4$)—, $A^1$ represents ethylene or trimethylene), $R^2$ and $R^3$ independently represent hydrogen atom, a linear or branched saturated alkyl group having 1 to 4 carbon atoms, oxo group, thioxo group, fluorine atom, chlorine atom, bromine atom, trifluoromethyl group, —OR$^5$, —N(R$^6$)(R$^{6'}$), —NHCOR$^7$, —NHSO$_2$R$^8$, or -A$^6$-Qa, or they bind to each other to represent methylenedioxy group, Qa represents a partially unsaturated or completely unsaturated monocyclic or condensed bicyclic carbon ring or a heterocyclic ring (qa), binds to $A^6$ at an arbitrary position on the ring, and may be substituted with one of $T^1$ or two or more of the same or different $T^1$, the heterocyclic ring (qa) contains the same or different 1 to 4 ring-constituting heteroatoms selected from the group consisting of nitrogen atom, oxygen atom, and sulfur atom, $R^4$ and $R^6$ independently represent hydrogen atom or a lower alkyl group having 1 to 4 carbon atoms, $R^5$ and $R^7$ independently represent hydrogen atom, a lower alkyl group having 1 to 4 carbon atoms, or -A$^6$-Qa, $R^8$ represents a lower alkyl group having 1 to 4 carbon atoms, $R^{6'}$ has the same meaning as $R^6$, or binds to $R^6$ to form a 3- to 6-membered ring together with the nitrogen atom to which they bind to represent a saturated nitrogen-containing cycloalkyl group or morpholino group, symbol p in Rc represents an integer of 2 to 4, $A^4$ represents a single bond, methylene, or ethylene, $A^5$ represents —C(O)—, —C(S)—, or —S(O)$_2$—, Rd represents hydrogen atom, an alkyl group having 1 to 8 carbon atoms, or Qa, Re represents an alkyl group having 1 to 8 carbon atoms, -A$^6$-Qa, —(CH$_2$)$_i$R$^{14}$, —OR$^{28}$, —SR$^{28}$, or —N(R$^{29}$)(R$^{30}$), symbol i represents an integer of 1 to 3, $R^{14}$ represents hydroxyl group, an alkoxy group having 1 to 4 carbon atoms, carboxyl group, or an N,N-dialkylcarbamoyl group having 1 to 4 carbon atoms, $R^{28}$ represents an alkyl group having 1 to 8 carbon atoms, or -A$^6$-Qa, $R^{29}$ represents an alkyl group having 1 to 8 carbon atoms, an alkoxycarbonyl group having 1 to 4 carbon atoms, or -A$^6$-Qa, $R^{30}$ represents hydrogen atom or a lower alkyl group having 1 to 4 carbon atoms, or binds to $R^{29}$ to form a 3- to 6-membered ring together with the nitrogen atom to which they bind to represent a saturated nitrogen-containing cycloalkyl group or morpholino group, Rz has the same meaning as Rx, or Rz represents methyl group, ethyl group, or -A$^5$-Re, Ry represents hydrogen atom, an alkyl group having 1 to 8 carbon atoms, or -A$^6$-Qp, or Ry may bind to Rz to form, together with a nitrogen atom to which they bind, a saturated or unsaturated 3 to 7-membered nitrogen-containing cyclic group, wherein said nitrogen-containing cyclic group may optionally be substituted with one or two lower alkyl groups having 1 to 4 carbon atoms wherein said two alkyl groups may be the same or different, AR represents a partially unsaturated or completely unsaturated condensed bicyclic carbon ring or a heterocyclic ring (ar), and may be substituted with one of Xa or two or more of the same or different Xa, the heterocyclic ring (ar) contains the same or different 1 to 4 ring-constituting heteroatoms selected from the group consisting of nitrogen atom, oxygen atom, and sulfur atom, Xa represents a linear or branched saturated alkyl group having 1 to 4 carbon atoms, a saturated cyclic alkyl group having 3 to 7 carbon atoms, oxo group, thioxo group, fluorine atom, chlorine atom, trifluoromethyl group, —(CH$_2$)$_i$R$^{14}$, —OR$^{10}$, —N(R$^{11}$)(R$^{12}$), —SO$_2$R$^{13}$, or —COR$^{27}$, $R^{10}$ represents hydrogen atom, a lower alkyl group having 1 to 4 carbon atoms, or —(CH$_2$)$_i$R$^{14}$, $R^{11}$ represents hydrogen atom or a lower alkyl group having 1 to 4 carbon atoms, $R^{12}$ represents hydrogen atom, a lower alkyl group having 1 to 4 carbon atoms, a hydroxyalkyl group having 2 to 4 carbon atoms, —COR$^{15}$, or —SO$_2$R$^{16}$, or binds to $R^{11}$ to form a 3- to 6-membered ring together with the nitrogen atom to which they bind to represent a saturated nitrogen-containing cycloalkyl group or morpholino group, $R^{15}$ represents a lower alkyl group having 1 to 4 carbon atoms, a hydroxyalkyl group having 2 to 4 carbon atoms, amino group, a mono- or dialkylamino group having 1 to 4 carbon atoms, or -A$^6$-Qa, $R^{13}$ and $R^{16}$ independently represent a lower alkyl group having 1 to 4 carbon atoms, amino group, or a mono- or dialkylamino group having 1 to 4 carbon atoms, $R^{27}$ represents hydrogen atom, hydroxyl group, an alkoxy group having 1 to 4 carbon atoms, a lower alkyl group having 1 to 4 carbon atoms, amino group, or a mono- or dialkylamino group having 1 to 4 carbon atoms, Y represents hydrogen atom, a lower alkyl group having 1 to 4 carbon atoms, —(CH$_2$)$_m$N(R$^{18}$)(R$^{19}$), or —C(R$^{20}$)$_2$OC(O)A$^3$R$^{21}$, symbol m represents an integer of 2 or 3, R$^{18}$ is the same as R$^{19}$, or binds to R$^{19}$ to form a 3- to 6-membered ring together with the nitrogen atom to which they bind to represent a saturated nitrogen-containing cycloalkyl group or morpholino group, R$^{19}$ represents methyl group, ethyl group, or propyl group, R$^{20}$ represents hydrogen atom, methyl group, ethyl group, or propyl group, R$^{21}$ represents a lower alkyl group having 1 to 4 carbon atoms, a cyclic saturated alkyl group having 3 to 6 carbon atoms, or phenyl group, and A$^3$ represents a single bond, or oxygen atom, or a salt thereof.

2. The compound or salt thereof according to claim 1, which comprises the combination according to general formula (I), wherein in the formula, Link represents a saturated or unsaturated straight hydrocarbon chain having 1 to 3 carbon atoms, C$^2$, C$^3$, C$^4$, C$^5$, and C$^6$ in the aromatic ring (E) independently represent a ring-constituting carbon atom, one of the ring-constituting carbon atoms to which Rs and AR do not bind may be replaced with V, V represents nitrogen atom, or carbon atom substituted with Zx, Zx represents a linear or branched saturated alkyl group having 1 to 4 carbon atoms, fluorine atom, chlorine atom, bromine atom, nitro group, —OR$^9$, or —N(Rn$^1$)(Rn$^2$), R$^9$ represents hydrogen atom, a lower alkyl group having 1 to 4 carbon atoms, or -A$^6$-Qp, wherein A$^6$ represents a single bond or methylene, Qp represents phenyl group, and the phenyl group may be substituted with one of T$^1$ or two or more of the same or different T$^1$, T$^1$ represents a linear or branched saturated alkyl group having 1 to 4 carbon atoms, hydroxyl group, fluorine atom, chlorine atom, bromine atom, trifluoromethyl group, nitro group, an alkoxy group having 1 to 4 carbon atoms, or a mono- or dialkylamino group having 1 to 4 carbon atoms, Rn$^1$ represents hydrogen atom or a linear or branched saturated alkyl group having 1 to 4 carbon atoms, Rn$^2$ has the same meaning as Rn$^1$, or represents —COR$^{23}$ or —SO$_2$R$^{24}$, or binds to Rn$^1$ to form a 3- to 6-membered ring together with the nitrogen atom to which they bind to form a saturated nitrogen-containing cycloalkyl group or morpholino group, R$^{23}$ represents hydrogen atom, a lower alkyl group having 1 to 4 carbon atoms, a lower alkoxy group having 1 to 4 carbon atoms, —O-A$^6$-Qp, or —N(R$^{25}$)(R$^{26}$), R$^{25}$ represents hydrogen atom, or a linear or branched saturated alkyl group having 1 to 4 carbon atoms, R$^{26}$ has the same meaning as R$^{25}$, or binds to R$^{25}$ to form a 3- to 6-membered ring together with the nitrogen atom to which they bind to form a saturated nitrogen-containing cycloalkyl group or morpholino group, R$^{24}$ represents a lower alkyl group having 1 to 4 carbon atoms, amino group, or a mono- or dialkylamino group having 1 to 4 carbon atoms, Rs represents -D-Rx or —N(Ry)(Rz), D represents a single bond, oxygen atom, sulfur atom, —S(O)—, —S(O)$_2$—, or —C(O)—, Rx represents a linear or branched saturated alkyl group having 3 to 8 carbon atoms, or represents Ra, Rb, or Rc, wherein symbol k in Ra represents 0 or an integer of 1 to 3, R$^1$ represents a saturated cyclic alkyl group having 3 to 7 carbon atoms, or a condensed saturated cyclic alkyl group having 6 to 8 carbon atoms, and R$^1$ may be substituted with one of lower alkyl group having 1 to 4 carbon atoms or two or more of the same or different lower alkyl groups having 1 to 4 carbon atoms, Q in Rb represents a partially unsaturated or completely unsaturated monocyclic or condensed bicyclic carbon ring or a heterocyclic ring (q), and binds to A$^2$ at an arbitrary position on the ring, the heterocyclic ring (q) contains the same or different 1 to 4 ring-constituting heteroatoms selected from the group consisting of nitrogen atom, oxygen atom, and sulfur atom, A$^1$ represents a single bond or an alkylene (a) having 1 to 3 carbon atoms, and the alkylene (a) may be substituted with a lower alkyl group having 1 to 4 carbon atoms or phenyl group, A$^2$ represents a single bond, oxygen atom, sulfur atom, —S(O)—, —S(O)$_2$—, or —N(R$^4$)— (provided that when A$^2$ represents oxygen atom, sulfur atom, —S(O)—, —S(O)$_2$— or —N(R$^4$)—, A$^1$ represents ethylene or trimethylene), R$^2$ and R$^3$ independently represent hydrogen atom, a linear or branched saturated alkyl group having 1 to 4 carbon atoms, oxo group, thioxo group, fluorine atom, chlorine atom, bromine atom, trifluoromethyl group, —OR$^5$, —N(R$^6$)(R$^{6'}$), —NH-COR$^7$, —NHSO$_2$R$^8$, or -A$^6$-Qa, or they bind to each other to represent methylenedioxy group, Qa represents a partially unsaturated or completely unsaturated monocyclic or condensed bicyclic carbon ring or a heterocyclic ring (qa), binds to A$^6$ at an arbitrary position on the ring, and may be substituted with one of T$^1$ or two or more of the same or different T$^1$, the heterocyclic ring (qa) contains the same or different 1 to 4 ring-constituting heteroatoms selected from the group consisting of nitrogen atom, oxygen atom, and sulfur atom, R$^4$ and R$^6$ independently represent hydrogen atom or a lower alkyl group having 1 to 4 carbon atoms, R$^5$ and R$^7$ independently represent hydrogen atom, a lower alkyl group having 1 to 4 carbon atoms, or -A$^6$-Qa, R$^8$ represents a lower alkyl group having 1 to 4 carbon atoms, R$^{6'}$ has the same meaning as R$^6$, or binds to R$^6$ to form a 3- to 6-membered ring together with the nitrogen atom to which they bind to represent a saturated nitrogen-containing cycloalkyl group or morpholino group, symbol p in Rc represents an integer of 2 to 4, A$^4$ represents a single bond, methylene, or ethylene, A$^5$ represents —C(O)—, —C(S)—, or —S(O)$_2$—, Rd represents hydrogen atom, an alkyl group having 1 to 8 carbon atoms, or Qa, Re represents an alkyl group having 1 to 8 carbon atoms, -A$^6$-Qa, —(CH$_2$)$_i$R$^{14}$, —OR$^{28}$, —SR$^{28}$, or —N(R$^{29}$)(R$^{30}$), symbol i represents an integer of 1 to 3, R$^{14}$ represents hydroxyl group, an alkoxy group having 1 to 4 carbon atoms, carboxyl group, or an N,N-dialkylcarbamoyl group having 1 to 4 carbon atoms, R$^{28}$ represents an alkyl group having 1 to 8 carbon atoms, or -A$^6$-Qa, R$^{29}$ represents an alkyl group having 1 to 8 carbon atoms, an alkoxycarbonyl group having 1 to 4 carbon atoms, or -A$^6$-Qa, R$^{30}$ represents hydrogen atom or a lower alkyl group having 1 to 4 carbon atoms, or binds to R$^{29}$ to form a 3- to 6-membered ring together with the nitrogen atom to which they bind to represent a saturated nitrogen-containing cycloalkyl group or morpholino group, Rz has the same meaning as Rx, or Rz represents methyl group, ethyl group, or -A$^5$-Re, Ry represents hydrogen atom, an alkyl group having 1 to 8 carbon atoms, or -A$^6$-Qp, or Ry may bind to Rz to form, together with a nitrogen atom to which they bind, a saturated or unsaturated 3 to 7-membered nitrogen-containing cyclic group, wherein said nitrogen-containing cyclic group may optionally be substituted with one or two lower alkyl groups having 1 to 4 carbon atoms wherein said two alkyl groups may be the same or different, AR is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthalidin-3-yl group, [1,8]naphthalidin-4-yl group, [1,5]naphthalidin-3-yl group, [1,5]naphthalidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizine-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group, wherein the aforementioned groups may be substituted with one of Xa or two or more of the same or different Xa, Xa represents a linear or branched saturated alkyl group having 1 to 4 carbon atoms, a saturated cyclic alkyl group having 3 to 7 carbon atoms, oxo group, thioxo group, fluorine atom, chlorine atom, trifluoromethyl group, —(CH$_2$)$_r$R$^{14}$, —OR$^{10}$, —N(R$^{11}$)(R$^{12}$), —SO$_2$R$^{13}$, or —COR$^{27}$, R$^{10}$ represents hydrogen atom, a lower alkyl group having 1 to 4 carbon atoms, or —(CH$_2$)$_r$R$^{14}$, R$^{11}$ represents hydrogen atom or a lower alkyl group having 1 to 4 carbon atoms, R$^{12}$ represents hydrogen atom, a lower alkyl group having 1 to 4 carbon atoms, a hydroxyalkyl group having 2 to 4 carbon atoms, —COR$^{15}$, or —SO$_2$R$^{16}$, or binds to R$^{11}$ to form a 3- to 6-membered ring together with the nitrogen atom to which they bind to represent a saturated nitrogen-containing cycloalkyl group or morpholino group, R$^{15}$ represents a lower alkyl group having 1 to 4 carbon atoms, a hydroxyalkyl group having 2 to 4 carbon atoms, amino group, a mono- or dialkylamino group having 1 to 4 carbon atoms, or -A$^6$-Qa, R$^{13}$ and R$^{16}$ independently represent a lower alkyl group having 1 to 4 carbon atoms, amino group, or a mono- or dialkylamino group having 1 to 4 carbon atoms, R$^{27}$ represents hydrogen atom, hydroxyl group, an alkoxy group having 1 to 4 carbon atoms, a lower alkyl group having 1 to 4 carbon atoms, amino group, or a mono- or dialkylamino group having 1 to 4 carbon atoms, Y represents hydrogen atom, a lower alkyl group having 1 to 4 carbon atoms, —(CH$_2$)$_m$N(R$^{18}$)(R$^{19}$), or —C(R$^{20}$)$_2$OC(O)A$^3$R$^{21}$, symbol m represents an integer of 2 or 3, R$^{18}$ is the same as R$^{19}$, or binds to R$^{19}$ to form a 3- to 6-membered ring together with the nitrogen atom to which they bind to represent a saturated nitrogen-containing cycloalkyl group or morpholino group, R$^{19}$ represents methyl group, ethyl group, or propyl group, R$^{20}$ represents hydrogen atom, methyl group, ethyl group, or propyl group, R$^{21}$ represents a lower alkyl group having 1 to 4 carbon atoms, a cyclic saturated alkyl group having 3 to 6 carbon atoms, or phenyl group, and A$^3$ represents a single bond, or oxygen atom, provided that the following compounds are excluded:

the compound wherein AR is a residue of naphthalene, benzofuran, benzo[b]thiophene, indole, benzothiazole, dihydro-3H-benzothiazole, quinoline, dihydro-1H-quinoline, benzo[d]isothiazole, 1H-indazole, benzo[c]isothiazole, 2H-indazole, imidazo[1,2-a]pyridine, 1H-pyrrolo[2,3-b]pyridine, isoquinoline, or dihydro-2H-isoquinoline, wherein the aforementioned residue may be substituted with one of Xa or two or more of the same or different Za;

the compound wherein Link is —(CH$_2$)$_n$—, AR binds to C$^3$ in the aromatic ring (E), Rs binds to C$^4$ in the aromatic ring (E), C$^5$ is a ring-constituting carbon atom substituted with Zx, or an unsubstituted ring-constituting carbon atom, C$^2$ and C$^6$ are unsubstituted ring-constituting atoms, Rx is —O—Rx, and Rx is a linear or branched saturated alkyl group having 3 to 8 carbon atoms, or Rx is Ra or Rb.

3. The compound or salt thereof according to claim 2, wherein Link is —(CH$_2$)$_n$—, n is an integer of 1 to 3, Rz has the same meaning as that of Rx or represents -$A^5$-Re when Rs is —N(Ry)(Rz), and Ry is hydrogen atom, an alkyl group having 1 to 8 carbon atoms, or $A^6$-Qp, or Ry binds to Rz to form, together with a nitrogen atom to which they bind, a saturated or unsaturated 3 to 7-membered nitrogen-containing cyclic group.

4. The compound or salt thereof according to claim 3, wherein Rs is -D-Rx or —N(Ry)(Rz), D is a single bond, oxygen atom, sulfur atom, —S(O)—, —S(O)$_2$—, or —C(O)—, Rx is a linear or branched saturated alkyl group having 3 to 8 carbon atoms, or Ra, Rb, or Rc, k in Ra is 0 or an integer of 1 to 3, $R^1$ is a saturated cycloalkyl group having 3 to 7 carbon atoms or a condensed saturated cycloalkyl group having 6 to 8 carbon atoms, $R^1$ may be substituted with one of lower alkyl group having 1 to 4 carbon atoms or two or more of the same or different lower alkyl groups having 1 to 4 carbon atoms, Q in Rb is phenyl group, thienyl group, furyl group, pyrrolyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, tetrahydronaphthyl group, indanyl group, indenyl group, quinolyl group, isoquinolyl group, indolyl group, benzofuryl group, benzothienyl group, benzimidazolyl group, benzoxazolyl group, benzothiazolyl group, indazolyl group, 4H-chromenyl group, dihydrobenzodioxyl group, benzoisoxazolyl group, pyrrolopyridinyl group, pyrazolopyridinyl group, triazolopyridinyl group, thienopyridinyl group, thienopyrazolyl group, 1,3-dihydrobenzimidazole group, dihydro-3H-benzoxazole group, or dihydro-3H-benzothiazole group (the aforementioned groups bond to $A^2$ at an arbitrary position on the rings), $A^1$ is a single bond or an alkylene (a) having 1 to 3 carbon atoms, the alkylene (a) may be substituted with a lower alkyl group having 1 to 4 carbon atoms or phenyl group, $A^2$ is a single bond, oxygen atom, sulfur atom, —S(O)—, —S(O)$_2$—, or —N($R^4$)— (provided that when $A^2$ represents oxygen atom, sulfur atom, —S(O)—, —S(O)$_2$—, or —N($R^4$)—, $A^1$ represents ethylene or trimethylene), $R^2$ and $R^3$ independently represent hydrogen atom, a linear or branched saturated alkyl group having 1 to 4 carbon atoms, oxo group, thioxo group, fluorine atom, chlorine atom, bromine atom, trifluoromethyl group, —$OR^5$, —N($R^6$)($R^{6'}$), —NHCO$R^7$, —NHSO$_2R^8$, or -$A^6$-Qa, or they bind to each other to represent methylenedioxy group, Qa is phenyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, indanyl group, indenyl group, quinolyl group, isoquinolyl group, indolyl group, benzofuryl group, benzothienyl group, benzimidazolyl group, benzoxazolyl group, benzothiazolyl group, or indazolyl group wherein the aforementioned groups may be substituted with one of $T^1$ or two or more of the same or different $T^1$, and bind to $A^6$ at an arbitrary position on the rings, $R^4$ and $R^6$ independently represent hydrogen atom or a lower alkyl group having 1 to 4 carbon atoms, $R^5$ and $R^7$ independently represent hydrogen atom, a lower alkyl group having 1 to 4 carbon atoms, or -$A^6$-Qa, $R^8$ is a lower alkyl group having 1 to 4 carbon atoms, $R^{6'}$ has the same meaning as $R^6$, or binds to $R^6$ to form a 3- to 6-membered ring together with the nitrogen atom to which they bind to form a saturated nitrogen-containing cycloalkyl group or morpholino group, p in Rc is an integer of 2 to 4, $A^4$ is a single bond or methylene or ethylene, $A^5$ is —C(O)—, —C(S)—, or —S(O)$_2$—, Rd is hydrogen atom, an alkyl group having 1 to 8 carbon atoms, or Qa, Re is an alkyl group having 1 to 8 carbon atoms, -$A^6$-Qa, —(CH$_2$)$_i$$R^{14}$, —OR$^{28}$, —SR$^{28}$, or —N($R^{29}$)($R^{30}$), i is an integer of 1 to 3, $R^{14}$ is hydroxyl group, an alkoxy group having 1 to 4 carbon atoms, carboxyl group, or an N,N-dialkylcarbamoyl group having 1 to 4 carbon atoms, $R^{28}$ is an alkyl group having 1 to 8 carbon atoms or -$A^6$-Qa, $R^{29}$ is an alkyl group having 1 to 8 carbon atoms, an alkoxycarbonyl group having 1 to 4 carbon atoms, or -$A^6$-Qa group, $R^{30}$ is hydrogen atom or a lower alkyl group having 1 to 4 carbon atoms, or binds to $R^{29}$ to form a 3- to 6-membered ring together with the nitrogen atom to which they bind to form a saturated nitrogen-containing cycloalkyl group or morpholino group, Rz has the same meaning as Rx, or is -$A^5$-Re, and Ry is hydrogen atom, an alkyl group having 1 to 8 carbon atoms, or -$A^6$-Qp, or binds to Rz to form a saturated or unsaturated nitrogen-containing cyclic substituent having 3 to 7 atoms together with nitrogen atom to which they bind.

5. The compound or salt thereof according to claim 3, wherein Rs is —O—Rx.

6. The compound or salt thereof according to claim 3, wherein AR binds to $C^3$ in the aromatic ring (E), and Rs binds to one of the ring-constituting carbon atoms $C^4$, $C^5$, and $C^6$.

7. The compound or salt thereof according to claim 3, wherein AR binds to $C^2$ in the aromatic ring (E), and Rs binds to one of the ring-constituting carbon atoms $C^3$, $C^4$, and $C^5$.

8. The compound or salt thereof according to claim 6, wherein Rs is —O—Rx, and all of $C^2$, $C^3$, $C^4$, $C^5$, and $C^6$ in the aromatic ring (E) are not replaced with V.

9. The compound or salt thereof according to claim 7, wherein n is an integer of 2, and Y is hydrogen atom or a lower alkyl group having 1 to 4 carbon atoms.

10. The compound or salt thereof according to claim 6, wherein Rs binds to the ring-constituting carbon atom $C^5$ or $C^6$ in the aromatic ring (E).

11. The compound or salt thereof according to claim 10, wherein Rs is —O—Rx, and all of $C^2$, $C^3$, $C^4$, $C^5$, and $C^6$ in the aromatic ring (E) are not replaced with V.

12. The compound or salt thereof according to claim 11, wherein n is an integer of 2, and Y is hydrogen atom or a lower alkyl group having 1 to 4 carbon atoms.

13. The compound or salt thereof according to claim 6, wherein Rs binds to $C^4$ in the aromatic ring (E), and $C^6$ is replaced with V.

14. The compound or salt thereof according to claim 13, wherein n is an integer of 2, V is carbon atom substituted with Zx, D is oxygen atom, and Y is hydrogen atom or a lower alkyl group having 1 to 4 carbon atoms.

15. The compound or salt thereof according to claim 6, wherein Rs binds to $C^4$ in the aromatic ring (E), $C^5$ is nitrogen atom, and $C^2$ and $C^6$ are unsubstituted ring-constituting carbon atoms, or wherein Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, and Rs is —N(Ry)(Rz), or wherein Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, Rs is -D-Rx, and D is a single bond, sulfur atom, —S(O)—, —S(O)$_2$—, or —C(O)—.

16. The compound or salt thereof according to claim 15, wherein Rs binds to $C^4$ in the aromatic ring (E), $C^5$ is nitrogen atom, and $C^2$ and $C^6$ are unsubstituted ring-constituting carbon atoms.

17. The compound or salt thereof according to claim 16, wherein n is an integer of 2, Rs is —O—Rx, and Y is hydrogen atom or a lower alkyl group having 1 to 4 carbon atoms.

18. The compound or salt thereof according to claim 15, wherein Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, and Rs is —N(Ry)(Rz).

19. The compound or salt thereof according to claim 2, wherein Link is —$(CH_2)_n$—, n is an integer of 1 to 3, $C^2$ and $C^6$ in the aromatic ring (E) are unsubstituted ring-constituting carbon atoms, AR binds to $C^3$ in the aromatic ring (E), and Rs is —N(Ry)(Rz) and binds to $C^4$ in the aromatic ring (E).

20. The compound or salt thereof according to claim 19, wherein n is 2, and $C^5$ is carbon atom substituted with Zx or unsubstituted ring-constituting carbon atom.

21. The compound or salt thereof according to claim 19, wherein Rz is a linear or branched saturated alkyl group having 1 to 8 carbon atoms, or Rz is Ra, Rb, or Rc, k in Ra is 0 or an integer of 1 to 3, $R^1$ is a saturated cyclic alkyl group having 3 to 7 carbon atoms or a condensed saturated cyclic alkyl group having 6 to 8 carbon atoms, $R^1$ may be substituted with one of lower alkyl group having 1 to 4 carbon atoms or two or more of the same or different lower alkyl groups having 1 to 4 carbon atoms, Q in Rb is phenyl group, thienyl group, furyl group, pyrrolyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, tetrahydronaphthyl group, indanyl group, indenyl group, quinolyl group, isoquinolyl group, indolyl group, benzofuryl group, benzothienyl group, benzimidazolyl group, benzoxazolyl group, benzothiazolyl group, indazolyl group, 4H-chromenyl group, dihydrobenzodioxyl group, benzoisoxazolyl group, pyrrolopyridinyl group, pyrazolopyridinyl group, triazolopyridinyl group, thienopyridinyl group, thienopyrazolyl group, 1,3-dihydrobenzimidazole group, dihydro-3H-benzoxazole group, or dihydro-3H-benzothiazole group, wherein the aforementioned groups binds to $A^2$ at an arbitrary position, $A^1$ is a single bond or an alkylene (a) having 1 to 3 carbon atoms, the alkylene (a) may be substituted with a lower alkyl group having 1 to 4 carbon atoms or phenyl group, $A^2$ is a single bond, oxygen atom, sulfur atom, —S(O)—, —S(O)$_2$—, or —N($R^4$)—, provided that when $A^2$ represents oxygen atom, sulfur atom, —S(O)—, —S(O)$_2$—, or —N($R^4$)—, $A^1$ represents ethylene or trimethylene, $R^2$ and $R^3$ independently represent hydrogen atom, a linear or branched saturated alkyl group having 1 to 4 carbon atoms, oxo group, thioxo group, fluorine atom, chlorine atom, bromine atom, trifluoromethyl group, —$OR^5$, —N($R^6$)($R^{6'}$), —$NHCOR^7$, —$NHSO_2R^8$, or -$A^6$-Qa, or they bind to each other to represent methylenedioxy group, Qa is phenyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, indanyl group, indenyl group, quinolyl group, isoquinolyl group, indolyl group, benzofuryl group, benzothienyl group, benzimidazolyl group, benzoxazolyl group, benzothiazolyl group, or indazolyl group, wherein these groups may be substituted with one of $T^1$ or two or more of the same or different $T^1$, and bind to $A^6$ at an arbitrary position on the ring, $R^4$ and $R^6$ independently represent hydrogen atom or a lower alkyl group having 1 to 4 carbon atoms, $R^5$ and $R^7$ independently represent hydrogen atom, a lower alkyl group having 1 to 4 carbon atoms, or -$A^6$-Qa, $R^8$ is a lower alkyl group having 1 to 4 carbon atoms, $R^{6'}$ has the same meaning as $R^6$, or binds to $R^6$ to form a 3- to 6-membered ring together with the nitrogen atom to which they bind to form a saturated nitrogen-containing cycloalkyl group or morpholino group, p in Rc is an integer of 2 to 4, $A^4$ is a single bond or methylene or ethylene, $A^5$ is —C(O)—, —C(S)—, or —S(O)$_2$—, Rd is hydrogen atom, an alkyl group having 1 to 8 carbon atoms, or Qa, Re is an alkyl group having 1 to 8 carbon atoms, -$A^6$-Qa, —$(CH_2)_iR^{14}$, —$OR^{28}$, —$SR^{28}$, or —N($R^{29}$)($R^{30}$), i is an integer of 1 to 3, $R^{14}$ is hydroxyl group, an alkoxy group having 1 to 4 carbon atoms, carboxyl group, or an N,N-dialkylcarbamoyl group having 1 to 4 carbon atoms, $R^{28}$ is an alkyl group having 1 to 8 carbon atoms or -$A^6$-Qa, $R^{29}$ is an alkyl group having 1 to 8 carbon atoms, an alkoxycarbonyl group having 1 to 4 carbon atoms, or -$A^6$-Qa group, $R^{30}$ is hydrogen atom or a lower alkyl group having 1 to 4 carbon atoms, or binds to $R^{29}$ to form a 3- to 6-membered ring together with the nitrogen atom to which they bind to form a saturated nitrogen-containing cycloalkyl group or morpholino group, and Ry is hydrogen atom, an alkyl group having 1 to 8 carbon atoms, or binds to Rz to form a saturated or unsaturated nitrogen-containing cyclic substituent having 3 to 7 atoms together with nitrogen atom to which they binds and said nitrogen-containing cyclic substituent may be substituted with one or two lower alkyl groups having 1 to 4 carbon atoms wherein said two alkyl groups may be the same or different.

22. The compound or salt thereof according to claim 15, wherein Rs binds to $C^4$ in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, Rs is -D-Rx, and D is a single bond, sulfur atom, —S(O)—, —S(O)$_2$—, or —C(O)—.

23. The compound or salt thereof according to claim 6, wherein AR binds to C3 in the aromatic ring (E), $C^5$ is a ring-constituting carbon atom substituted with Zx, or an unsubstituted ring-constituting carbon atom, $C^2$ and $C^6$ are unsubstituted ring-constituting carbon atoms, Rs is -D-Rx, and D is a single bond, sulfur atom, —S(O)—, —S(O)$_2$—, or C(O)—.

24. The compound or salt thereof according to claim 22, wherein Rs is -D-Rx, and D is a single bond.

25. The compound or salt thereof according to claim 22, wherein n is an integer of 2, and Y is hydrogen atom or a lower alkyl group having 1 to 4 carbon atoms.

26. The compound or salt thereof according to claim 6, wherein Link is —$(CH_2)_n$—, n is an integer of 2, AR binds $C^3$ in the aromatic ring (E), Rs binds to $C^4$ in the aromatic ring (E), $C^5$ is a ring-constituting carbon atom substituted with the substituent Zx, or an unsubstituted ring-constituting carbon atom, $C^2$ and $C^6$ are unsubstituted ring-constituting carbon atoms, Rs is -D-Rx, D is a single bond, sulfur atom, S(O)—, —S(O)$_2$—, or C(O)—, and Y is hydrogen atom or a lower alkyl group having 1 to 4 carbon atoms.

27. The compound or salt thereof according to claim 6, wherein Link is —$(CH_2)_n$—, n is an integer of 2, AR binds $C^3$ in the aromatic ring (E), Rs binds to $C^4$ in the aromatic ring (E), $C^5$ may be replaced with V, $C^2$ and $C^6$ are unsubstituted ring-constituting carbon atoms, Rs is -D-Rx, D is a single bond, sulfur atom, S(O)—, —S(O)$_2$—, or C(O)—, and Y is hydrogen atom or a lower alkyl group having 1 to 4 carbon atoms.

28. The compound or salt thereof according to claim 6, wherein n is an integer of 2, Rs binds to $C^4$ in the aromatic ring (E), $C^5$ is a carbon atom substituted with —N($Rn_1$)($Rn_2$), provided that one of $Rn_1$ and $Rn_2$ is a substituent other than hydrogen atom, $C^2$ and $C^6$ are unsubstituted ring-constituting carbon atoms, Rs is —O—Rx, and Y is hydrogen atom or a lower alkyl group having 1 to 4 carbon atoms.

29. The compound or salt thereof according to claim 6, wherein n is an integer of 2, Rs binds to $C^4$ in the aromatic ring (E), $C^5$ is a ring-constituting carbon atom substituted with the substituent Zx, or an unsubstituted ring-constituting carbon atom, $C^2$ and $C^6$ are unsubstituted ring-constituting carbon atoms, Rs is —O—Rc, and Y is hydrogen atom or a lower alkyl group having 1 to 4 carbon atoms.

30. A medicament containing the compound according to claim 3 or a pharmacologically acceptable salt thereof as an active ingredient together with a pharmaceutically acceptable carrier.

31. A medicament containing the compound according to claim 15 or a pharmacologically acceptable salt thereof as an active ingredient together with a pharmaceutically acceptable carrier.

32. An agent for inhibiting production of a prostaglandin and/or leukotriene, which comprises the compound according to claim 3 or a pharmacologically acceptable salt thereof as an active ingredient together with a pharmaceutically acceptable carrier.

33. An agent for inhibiting production of a prostaglandin and/or leukotriene, which comprises the compound according to claim 15 or a pharmacologically acceptable salt thereof as an active ingredient together with a pharmaceutically acceptable carrier.

34. An agent for therapeutic treatment of pulmonary fibrosis which comprises the compound according to claim 1 or a pharmacologically acceptable salt thereof as an active ingredient together with a pharmaceutically acceptable carrier.

35. The compound or salt according to claim 23, wherein Rs is -D-Rx and D is a single bond.

36. The compound or salt thereof according to claim 23, wherein n is an integer of 2, and Y is hydrogen atom or lower alkyl group having 1 to 4 carbon atoms.

* * * * *